United States Patent
Liu et al.

(10) Patent No.: US 11,993,661 B2
(45) Date of Patent: May 28, 2024

(54) CONSTRUCTS TARGETING PROSTATE-SPECIFIC MEMBRANE ANTIGEN (PSMA) AND USES THEREOF

(71) Applicant: EUREKA THERAPEUTICS, INC., Emeryville, CA (US)

(72) Inventors: Hong Liu, El Sobrante, CA (US); Hongruo Yun, San Francisco, CA (US); Xiaomei Ge, Foster City, CA (US); Zhiyuan Yang, Albany, CA (US); Lianxing Liu, San Francisco, CA (US); Pengbo Zhang, Fremont, CA (US); Yixiang Xu, Pearland, TX (US); Shan Li, Emeryville, CA (US); Lucas Horan, Emeryville, CA (US)

(73) Assignee: EUREKA THERAPEUTICS, INC., Emeryville, CA (US)

( * ) Notice: Subject to any disclaimer, the term of this patent is extended or adjusted under 35 U.S.C. 154(b) by 677 days.

(21) Appl. No.: 17/253,589

(22) PCT Filed: Jun. 17, 2019

(86) PCT No.: PCT/US2019/037534
§ 371 (c)(1),
(2) Date: Dec. 17, 2020

(87) PCT Pub. No.: WO2019/245991
PCT Pub. Date: Dec. 26, 2019

(65) Prior Publication Data
US 2022/0185910 A1    Jun. 16, 2022

Related U.S. Application Data

(60) Provisional application No. 62/686,605, filed on Jun. 18, 2018.

(51) Int. Cl.
| | | |
|---|---|---|
| *C07K 16/00* | (2006.01) | |
| *A61P 35/00* | (2006.01) | |
| *C07H 21/04* | (2006.01) | |
| *C07K 14/705* | (2006.01) | |
| *C07K 14/725* | (2006.01) | |
| *C07K 16/28* | (2006.01) | |
| *C07K 16/30* | (2006.01) | |
| *C07K 16/46* | (2006.01) | |
| *C12N 5/02* | (2006.01) | |
| *C12N 15/00* | (2006.01) | |
| *G01N 33/574* | (2006.01) | |

(52) U.S. Cl.
CPC .......... *C07K 16/3069* (2013.01); *A61P 35/00* (2018.01); *C07K 14/7051* (2013.01); *C07K 14/70521* (2013.01); *C07K 16/2809* (2013.01); *G01N 33/57434* (2013.01); *C07K 2317/21* (2013.01); *C07K 2317/31* (2013.01); *C07K 2317/622* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell |
| 4,676,980 A | 6/1987 | Segal |
| 4,816,567 A | 3/1989 | Cabilly |
| 4,975,278 A | 12/1990 | Senter |
| 4,994,560 A | 2/1991 | Kruper, Jr. |
| 5,208,020 A | 5/1993 | Chari |
| 5,229,275 A | 7/1993 | Goroff |
| 5,274,119 A | 12/1993 | Frazier |
| 5,342,604 A | 8/1994 | Wilson |
| 5,350,674 A | 9/1994 | Boenisch |
| 5,399,346 A | 3/1995 | Anderson |
| 5,428,139 A | 6/1995 | Kiefer |
| 5,435,990 A | 7/1995 | Cheng |
| 5,489,425 A | 2/1996 | Kruper, Jr. |
| 5,500,362 A | 3/1996 | Robinson |
| 5,505,931 A | 4/1996 | Pribish |
| 5,545,806 A | 8/1996 | Lonberg |
| 5,545,807 A | 8/1996 | Surani |
| 5,567,610 A | 10/1996 | Borrebaeck |
| 5,569,825 A | 10/1996 | Lonberg |
| 5,580,859 A | 12/1996 | Felgner |
| 5,585,362 A | 12/1996 | Wilson |
| 5,589,466 A | 12/1996 | Felgner |

(Continued)

FOREIGN PATENT DOCUMENTS

| | | |
|---|---|---|
| CN | 104853766 A | 8/2015 |
| EP | 0308936 A2 | 3/1989 |

(Continued)

OTHER PUBLICATIONS

Slovin et al. Chimeric antigen Receptor (CAR+) modified T cells targeting prostate-specific membrane antigen (PSMA) in patients (pts) with castrate metastatic prostate caner (CMPC). Journal of Clinical Oncology, 31(6), Abstract #72 (Year: 2013).*

Zhong et al. Chimeric Antigen Receptors Combining 4-1BB and CD28 Signaling Domains Augment PI3kinase/AKT/Bcl-XL Activation and CD8+ T Cell-mediated Tumor Eradication. Molecular Therapy vol. 18 No. 2, 413-420 Feb. 2010 (Year: 2010).*

(Continued)

*Primary Examiner* — Maher M Haddad
(74) *Attorney, Agent, or Firm* — MORRISON & FOERSTER LLP

(57) ABSTRACT

The present application provides constructs comprising an antibody moiety that specifically binds to PSMA (e.g., PSMA expressed on the surface of a cell). Also provided are methods of making and using these constructs.

25 Claims, 9 Drawing Sheets
Specification includes a Sequence Listing.

(56) References Cited

U.S. PATENT DOCUMENTS

| | | |
|---|---|---|
| 5,591,669 A | 1/1997 | Krimpenfort et al. |
| 5,625,126 A | 4/1997 | Lonberg |
| 5,633,425 A | 5/1997 | Lonberg |
| 5,648,260 A | 7/1997 | Winter |
| 5,652,361 A | 7/1997 | Simon |
| 5,661,016 A | 8/1997 | Lonberg |
| 5,674,821 A | 10/1997 | Cook et al. |
| 5,696,239 A | 12/1997 | Wilson |
| 5,714,631 A | 2/1998 | Wilson |
| 5,731,168 A | 3/1998 | Carter |
| 5,750,373 A | 5/1998 | Garrard |
| 5,756,065 A | 5/1998 | Wilson |
| 5,808,003 A | 9/1998 | Subramanian |
| 5,821,337 A | 10/1998 | Carter |
| 5,858,358 A | 1/1999 | June et al. |
| 5,883,223 A | 3/1999 | Gray |
| 6,194,551 B1 | 2/2001 | Idusogie |
| 6,326,193 B1 | 12/2001 | Liu |
| 6,352,694 B1 | 3/2002 | June |
| 6,534,055 B1 | 3/2003 | June |
| 6,602,684 B1 | 8/2003 | Umana |
| 6,692,964 B1 | 2/2004 | June |
| 6,737,056 B1 | 5/2004 | Presta |
| 6,797,514 B2 | 9/2004 | Berenson |
| 6,867,041 B2 | 3/2005 | Berenson |
| 6,887,466 B2 | 5/2005 | June |
| 6,905,680 B2 | 6/2005 | June |
| 6,905,681 B1 | 6/2005 | June |
| 6,905,874 B2 | 6/2005 | Berenson |
| 7,067,318 B2 | 6/2006 | June |
| 7,144,575 B2 | 12/2006 | June |
| 7,172,869 B2 | 2/2007 | June |
| 7,175,843 B2 | 2/2007 | June |
| 7,232,566 B2 | 6/2007 | June |
| 7,332,581 B2 | 2/2008 | Presta |
| 7,371,826 B2 | 5/2008 | Presta |
| 7,521,541 B2 | 4/2009 | Eigenbrot |
| 2002/0164328 A1 | 11/2002 | Shinkawa |
| 2003/0115614 A1 | 6/2003 | Kanda |
| 2003/0157108 A1 | 8/2003 | Presta |
| 2004/0033229 A1 | 2/2004 | Maddon et al. |
| 2004/0093621 A1 | 5/2004 | Shitara |
| 2004/0109865 A1 | 6/2004 | Niwa |
| 2004/0110282 A1 | 6/2004 | Kanda |
| 2004/0110704 A1 | 6/2004 | Yamane |
| 2004/0132140 A1 | 7/2004 | Satoh |
| 2005/0014934 A1 | 1/2005 | Hinton |
| 2005/0079574 A1 | 4/2005 | Bond |
| 2005/0119455 A1 | 6/2005 | Fuh |
| 2005/0123546 A1 | 6/2005 | Umana |
| 2005/0266000 A1 | 12/2005 | Bond |
| 2006/0121005 A1 | 6/2006 | Berenson |
| 2007/0117126 A1 | 5/2007 | Sidhu |
| 2007/0160598 A1 | 7/2007 | Dennis |
| 2007/0237764 A1 | 10/2007 | Birtalan |
| 2007/0292936 A1 | 12/2007 | Barthelemy |
| 2008/0286284 A1 | 11/2008 | Maddon et al. |
| 2009/0002360 A1 | 1/2009 | Chen, III |

FOREIGN PATENT DOCUMENTS

| | | |
|---|---|---|
| EP | 0308936 A3 | 2/1990 |
| EP | 0404097 A2 | 12/1990 |
| EP | 1391213 A1 | 2/2004 |
| JP | 2015535689 A | 12/2018 |
| WO | 199100360 A1 | 1/1991 |
| WO | 199220373 A1 | 11/1992 |
| WO | 199308829 A1 | 5/1993 |
| WO | 199311161 A1 | 6/1993 |
| WO | 199321232 A1 | 10/1993 |
| WO | 199411026 A2 | 5/1994 |
| WO | 199411026 A3 | 8/1994 |
| WO | 199429351 A2 | 12/1994 |
| WO | 199429351 A3 | 2/1995 |
| WO | 199704801 A1 | 2/1997 |
| WO | 199717852 A1 | 5/1997 |
| WO | 1997030087 A1 | 8/1997 |
| WO | 9735616 A1 | 10/1997 |
| WO | 199856418 A1 | 12/1998 |
| WO | 1998058964 A1 | 12/1998 |
| WO | 1999022764 A1 | 5/1999 |
| WO | 9947554 A1 | 9/1999 |
| WO | 199951642 A1 | 10/1999 |
| WO | 200042072 A2 | 7/2000 |
| WO | 200061739 A1 | 10/2000 |
| WO | 200042072 A3 | 11/2000 |
| WO | 200129246 A1 | 4/2001 |
| WO | 2001029058 A1 | 4/2001 |
| WO | 200196584 A2 | 12/2001 |
| WO | 2003011878 A2 | 2/2003 |
| WO | 2003048731 A2 | 6/2003 |
| WO | 2003084570 A1 | 10/2003 |
| WO | 2003085107 A1 | 10/2003 |
| WO | 2003011878 A3 | 11/2003 |
| WO | 2003048731 A3 | 1/2004 |
| WO | 2002031140 A1 | 2/2004 |
| WO | 2004056312 A2 | 7/2004 |
| WO | 2005035586 A1 | 4/2005 |
| WO | 2004056312 A3 | 5/2005 |
| WO | 2003085119 A1 | 8/2005 |
| WO | 2005100402 A1 | 10/2005 |
| WO | 2006029879 A2 | 3/2006 |
| WO | 2006029879 A3 | 9/2006 |
| WO | 2005035778 A1 | 12/2006 |
| WO | 2005053742 A1 | 6/2007 |
| WO | 2008077546 A1 | 7/2008 |
| WO | 2009067800 A1 | 6/2009 |
| WO | 2009089004 A1 | 7/2009 |
| WO | 2010037837 A2 | 4/2010 |
| WO | 2011056983 A1 | 5/2011 |
| WO | 2011133886 A2 | 10/2011 |
| WO | 2011133886 A3 | 12/2011 |
| WO | 2014055668 A1 | 4/2014 |
| WO | 2016054520 A2 | 4/2016 |
| WO | 2017029512 A1 | 2/2017 |
| WO | 2017070608 A1 | 4/2017 |
| WO | WO-2017180713 A1 * | 10/2017 ......... A61K 47/6803 |
| WO | 2018200582 A1 | 11/2018 |
| WO | 2019245991 A1 | 12/2019 |

OTHER PUBLICATIONS

Abhinandan, K.R. et al. (Aug. 2008, e-pub. Jul. 9, 2008). "Analysis and Improvements To Kabat and Structurally Correct Numbering Of Antibody Variable Domain," Molecular Immunology 45(14):3832-3839.

Afshar-Oromieh, A. et al. (Oct. 1, 2016). "The Rise Of PSMA Ligands For Diagnosis And Therapy Of Prostate Cancer," Journal of Nuclear Medicine 57(Supplement 3):79S-89S.

Al-Lazikani, B. et al. (1997). "Standard Conformations for the Canonical Structures of Immunoglobulins," J. Mol. Biol. 273:927-948.

Baldwin, R.W. et al. (Mar. 15, 1986). "Monoclonal Antibodies in Cancer Treatment," Lancet 1(8481):603-605.

Berg, I.J.M, et al. (Dec. 1998) "Selective Expansion Of A Peripheral Blood CD8+ Memory T Cell Subset Expressing Both Granzyme B And L-Selectin During Primary Viral Infection In Renal Allograft Recipients," Transplant Proc. 30(8):3975-3977.

Boerner, P. et al. (Jul. 1, 1991). "Production of a Antigen-Specific Human Monoclonal Antibodies from In Vitro-Primed Human Splenocytes," J. Immunol. 147(1):86-95.

Brischwein, K. et al. (Mar. 1, 2006, e-pub. Sep. 1, 2005). "MT110: A Novel Bispecific Single-Chain Antibody Construct With High Efficacy In Eradicating Established Tumors," Molecular Immunology 43(8):1129-1143.

Brüggemann, M. et al. (1993). "Designer Mice: The Production of Human Antibody Repertoires in Transgenic Animals," Year in Immuno. 7:33-40.

Brüggemann, M. et al. (Nov. 1, 1987). "Comparison of the Effector Functions of Human Immunoglobulins Using a Matched Set of Chimeric Antibodies," J. Exp. Med. 166:1351-1361.

(56) References Cited

OTHER PUBLICATIONS

Burton, D.R. (1985). "Immunoglobulin G: Functional Sites," Molec. Immunol. 22(3):161-206.
Capel, P.J. et al. (Feb. 1994). "Heterogeneity of Human IgG Fc Receptors," Immunomethods 4(1):25-34.
Chari, R.V.J. et al. (Jan. 1, 1992). "Immunoconjugates Containing Noveal Maytansinoids: Promising Anticancer Drugs," Cancer Res. 52:127-131.
Chmielewski, M. (Sep. 2011; e-pub. Jul. 8, 2011). "IL-12 Release by Engineered T Cells Expressing Chimeric Antigen Receptors Can Effectively Muster an Antigen-Independent Macrophage Response on Tumor Cells That Have Shut Down Tumor Antigen Expression," Cancer Research 71(17):5697-5706.
Chothia, C. et al. (Aug. 20, 1987). "Canonical Structures for the Hypervariable Regions of Immunoglobulins," J. Mol. Biol. 196(4):901-917.
Chothia, C. et al. (Dec. 1989). "Conformations of Immunoglobulin Hypervariable Regions," Nature 342(6252):877-883.
Chothia, C. et al. (Dec. 5, 1985). "Domain Association In Immunoglobulin Molecules. The Packing Of Variable Domains," J. Mol. Biol. 186(3):651-663.
Chowdhury, P.S. (2008). "Engineering Hot Spots for Affinity Enhancement of Antibodies," Methods Mol. Biol. 207:179-196.
Clackson, T. et al. (Aug. 15, 1991). "Making Antibody Fragments Using Phage Display Libraries," Nature 352:624-628.
Clipstone, N.A. et al. (Jun. 25, 1992). "Identification Of Calcineurin As A Key Signalling Enzyme In T-Lymphocyte Activation," Nature 357(6380):695-697.
Clynes, R. et al. (Jan. 1998). "Fc Receptors are Required in Passive and Active Immunity to Melanoma," Proc. Natl. Acad. Sci. U.S.A. 95:652-656.
Colcher, D. et al. (Jan. 1986). "Use Of Monoclonal Antibodies As Radiopharmaceuticals For The Localization Of Human Carcinoma Xenografts In Athymic Mice," Methods Enzymol. 121:802-816.
Cole et al. (1985). "The EBV-Hybridoma Technique And Its Application To Human Lung Cancer," Monolclonal Antibodies and Cancer Therapy 27:77-96.
Cragg, M.S. et al. (Apr. 1, 2004). "Antibody Specificity Controls In Vivo Effector Mechanisms Of Anti-CD20 Reagents," Blood 103(7):2738-2743.
Cragg, M.S. et al. (Feb. 1, 2003). "Complement-Mediated Lysis By Anti-CD20 Mab Correlates With Segregation Into Lipid Rafts," Blood 101(3):1045-1052.
David, G.S. et al. (1974). "Protein Iodination With Solid State Lactoperoxidase," Biochemistry 13(5):1014-1021.
Daeron, M. (1997). "Fc Receptor Biology," Ann. Rev. Immunol. 15:203-234.
De Haas, M. et al. (Oct. 1995). "Fcγ Receptors of Phagocytes," J. Lab. Clin. Med. 126(4):330-341.
Duncan, A.R. et al. (Apr. 21, 1988). "The Binding Site for C1q on IgG," Nature 322:738-740.
Durand, D. B. et al. (Apr. 1988). "Characterization Of Antigen Receptor Response Elements Within The Interleukin-2 Enhancer," Molecular And Cellular Biology 8(2):1715-1724.
Edgar, R.C. (2004, e-pub. Mar. 19, 2004). "MUSCLE: Multiple Sequence Alignment With High Accuracy And High Throughput," Nucleic Acids Research 32(5):1792-1797.
Edgar, R.C. (Aug. 19, 2004). "MUSCLE: A Multiple Sequence Alignment Method With Reduced Time And Space Complexity," BMC Bioinformatics 5(113):1-19.
Eisenhauer, E.A. et al. (2009) "New Response Evaluation Criteria in Solid Tumors: Revised RECIST Guideline (version 1.1)." Eur. J. Cancer 45:228-247.
Fellouse, F.A. et al. (Aug. 24, 2004). "Synthetic Antibodies from a Four-Amino-Acid Code: A Dominant Role for Tyrosine in Antigen Recognition," Proc. Natl. Acad. Sci. USA 101(34):12467-12472.
Ferrara, C. et al. (2006, e-pub. Jan. 24, 2006). "Modulation of Therapeutic Antibody Effector Functions by Glycosylation Engineering: Influence of Golgi Enzyme Localization Domain and Co-Expression of Heterologous β1,4-N-Acetylglucosaminyltransferase III and Golgi α-Mannosidase II," Biotechnology and Bioengineering 93(5):851-861.
Fishwild, D.M. et al. (Jul. 1996). "High-Avidity Human IgGK Monoclonal Antibodies from a Novel Strain of Minilocus Transgenic Mice," Nature Biotechnol. 14:845-851.
Fraker, P.J. et al. (Feb. 28, 1978). "Protein and Cell Membrane Iodinations With a Sparingly Soluble Chloroamide, 1,3,4,6-Tetrachloro-3a,6a-Diphenylglycoluril," Biochem. Biophys. Res. Commun. 80(4):849-857.
Garland, R.J. et al. (Jul. 1999) "The Use Of Teflon Cell Culture Bags To Expand Functionally Active CD8+ Cytotoxic T Lymphocytes," J. Immunol Meth. 227(1-2):53-63.
Gazzano-Santoro, H. et al. (1996). "A Non-Radioactive Complement-Dependent Cytotoxicity Assay Anti-CD20 Monoclonal Antibody," J. Immunol. Methods 202:163-171.
Ghetie, V. et al. (2000). "Multiple Roles For The Major Histocompatibility Complex Class I-Related Receptor FCRN," Annu. Rev. Immunol. 18:739-766.
Griffiths, A.D. et al. (1993). "Human Anti-Self Antibodies with High Specificity from Phage Display Libraries," EMBO J. 12(2):725-734.
Gu, J. et al. (Jan. 1, 2012). "Generation Of Dual-Variable-Domain Immunoglobulin Molecules For Dual-Specific Targeting," Methods In Enzymology 502:25-41.
Guyer, R.L. et al. (Aug. 1976). "Immunoglobulin Binding By Mouse Intestinal Epithelial Cell Receptors," J. Immunol. 117(2):587-593.
Haanen, J.B. et al. (Nov. 1, 1999). "Selective Expansion Of Cross-Reactive CD8+ Memory T Cells By Viral Variants." The Journal of Experimental Medicine 190(9):1319-1328.
Hellstrom, I. et al. (Mar. 1985). "Strong Antitumor Activities of IgG3 Antibodies to a Human Melanoma-associated Ganglioside," Proc. Natl. Acad. Sci. USA 82:1499-1502.
Hellstrom, I. et al. (Sep. 1986). "Antitumor Effects of L6, an IgG2a Antibody That Reacts With Most Human Carcinomas," Proc. Natl. Acad. Sci. USA 83:7059-7063.
Hinman, L.M. et al. (Jul. 15, 1993). "Preparation and Characterization of Monoclonal Antibody Conjugates of the Calicheamicins: A Novel and Potent Family of Antitumor Antibiotics," Cancer Research 53:3336-3342.
Hoet, R.M. et al. (Mar. 2005), "Generation Of High-Affinity Human Antibodies By Combining Donor-Derived and Synthetic Complementarity-Determining-Region Diversity," Nat Biotechnol, 23(3):344-348.
Holliger, P. et al. (Jul. 1993). "Diabodies": Small Bivalent and Bispecific Antibody Fragments, Proceedings of the National Academy of Sciences USA 90:6444-6448.
Honegger, A. et al. (Jun. 8, 2001). "Yet Another Numbering Scheme For Immunoglobulin Variable Domains: An Automatic Modeling And Analysis Tool," J. Mol. Biol. 309:657-670.
Hoogenboom, H.R. et al. (2001). "Overview of Antibody Phage-Display Technology and Its Applications," Chapter 1 in Methods in Molecular Biology, O'Brien et al. ed., Humana Press, Totowa, NJ, 178:1-37.
Hoogenboom, H.R. et al. (Sep. 20, 1992). "By-Passing Immunisation Human Antibodies From Synthetic Repertoires Of Germline VH Gene Segments Rearranged In Vitro," J. Mol. Biol. 227(2):381-388.
Hunter, W.M. et al. (May 5, 1962). "Preparation Iodine-131 Labelled Human Growth Hormone of High Specific Activiey," Nature 194:495-496.
Idusogie, E.E. et al. (2000). "Mapping of the C1q Binding Site on Rituxan, a Chimeric Antibody With a Human IgG1 Fc," J. Immunol. 164:4178-4184.
International Preliminary Report on Patentability dated Dec. 30, 2020, dated Dec. 22, 2020, for International Patent Application No. PCT/US2019/037534, filed Jun. 17, 2019, 7 pages.
International Search Report and The Written Opinion of the International Searching Authority dated Sep. 18, 2019, for Patent Application No. PCT/US2019/037534, filed Jun. 17, 2019, 9 pages.

(56) References Cited

OTHER PUBLICATIONS

Jakobovits, A. et al. (Mar. 18, 1993). "Germ-Line Transmission And Expression Of A Human-Derived Yeast Artificial Chromosome," Nature 362(6417):255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90(6):2551-2555.
Jones, P. et al. (May 29, 1986). "Replacing The Complementarity-Determining Regions In A Human Antibody With Those From A Mouse," Nature 321:522-525.
Junghans, R.P. et al. (Oct. 2016). "Phase I Trial Of Anti-Psma Designer Car-T Cells In Prostate Cancer: Possible Role For Interacting Interleukin 2-T Cell Pharmacodynamics As A Determinant Of Clinical Response," The Prostate 76(14):1257-1270, 27 pages.
Kabat, E.A. (1991). Sequences of Proteins of Immunological Interest, 5th ed., Public Health Service, National Institutes of Health, Bethesda, MD, pp. 647-723.
Kabat, E.A. et al. (Oct. 10, 1977). "Unusual Distributions Of Amino Acids In Complementarity-Determining (Hypervariable) Segments Of Heavy And Light Chains Of Immunoglobulins And Their Possible Roles In Specificity Of Antibody-Combining Sites," J. Biol. Chem. 252(19):6609-6616.
Kam, N.W.S. et al. (Aug. 16, 2005). "Carbon Nanotubes as Multifunctional Biological Transporters and Near-Infrared Agents for Selective Cancer Cell Destruction," PNAS 102(33):11600-11605, 6 pages.
Kanda, Y. et al. (Jul. 5, 2006, e-pub. Apr. 11, 2006). "Comparison of Cell Line for Stable Production of Fucose-Negative Antibodies with Enhanced ADCC," Biotechnol. Bioeng. 94(4):680-688.
Kim, J-K. et al. (1994). "Localization of the Site of the Murine IgG1 Molecule That is Involved in Binding to the Murine Intestinal Fc Receptor," Eur. J. Immunol. 24:2429-2434.
Kohler, G. et al. (Aug. 7, 1975) "Continuous Cultures Of Fused Cells Secreting Antibody Of Predefined Specificity," Nature 256:495-497.
Kostelny, S.A. et al. (Mar. 1, 1992). "Formation of a Bispecific Antibody By The Use of Leucine Zippers," J. Immunol. 148(5):1547-1553.
Kozbor, D. (Dec. 1984). "A Human Hybrid Myeloma for Production of Human Monoclonal Antibodies," J. Immunol. 133(6):3001-3005.
Labrijn, A.F. et al. (Mar. 26, 2013). "Efficient Generation of stable Bispecific IgG1 by Controlled Fab-arm Exchange," Proc. Natl. Acad. Sci. USA 110(13):5145-5150.
Lee, C.V. et al. (2004). "Bivalent Antibody Phage Display Mimics Natural Immunoglobulin," J. Immunol. Methods 284(1-2):119-132.
Lee, C.V. et al. (2004). "High-Affinity Human Antibodies From Phage-Displayed Synthetic Fab Libraries With A Single Framework Scaffold," J. Mol. Biol. 340:1073-1093.
Lefranc, M.P. et al. (Jan. 2003). "IMGT Unique Numbering For Immunoglobulin And T Cell Receptor Variable Domains And Ig Superfamily V-Like Domains," Dev. Comp. Immunol. 27(1):55-77.
Lindhofer, H. et al., "Preferential Species-Restricted Heavy/Light Chain Pairing In Rat/Mouse Quadromas. Implications For A Single-Step Purification Of Bispecific Antibodies," J Immunol (1995) 55(1):219-225.
Liu, C. et al. (Aug. 1996). "Eradication of Large Colon Tumor Xenografts by Targeted Delivery of Maytansinoids," Proc. Natl. Acad. Sci. USA 93:8618-8623.
Liu, H. et al. (Sep. 1, 1997). "Monoclonal Antibodies To The Extracellular Domain Of Prostate-Specific Membrane Antigen Also React With Tumor Vascular Endothelium," Cancer Research 57(17):3629-3634.
Lode, H.N. et al. (Jul. 15, 1998). "Targeted Therapy with a Novel Enediyene Antibiotic Calicheamicin 011 Effectively Suppresses Growth and Dissemination of Liver Metastases in a Syngeneic Model of Murine Neuroblastoma," Cancer Res. 58:2925-2928.
Lonberg, N. et al. (1995, e-pub. Jul. 10, 2009). "Human Antibodies From Transgenic Mice," Int. Rev. Immunol. 13(1):65-93.

Lonberg, N. et al. (Apr. 28, 1994). "Antigen-Specific Human Antibodies From Mice Comprising Four Distinct Genetic Modifications," Nature 368(6474):856-859.
MacCallum, R.M. et al. (Oct. 1996). "Antibody-Antigen Interactions: Contact Analysis and Binding Site Topography," J. Mol. Biol. 262(5):732-745.
Mack, M. et al. (Jul. 1995). "A Small Bispecific Antibody Construct Expressed as a Functional Single-Chain Molecule With High Tumor Cell Cytotoxicity," Proc. Natl. Acad. Sci. USA 92:7021-7025.
Mandler, R. et al. (2000). "Synthesis and Evaluation of Antiproliferative Activity of a Geldanamycin-Herceptin TM Immunoconjugate," Bioorganic & Med. Chem. Letters 10:1025-1028.
Mandler, R. et al. (2002, e-pub. Jun. 19, 2002). "Modifications in Synthesis Strategy Improve the Yield and Efficacy of Geldanamycin-Herceptin Immunoconjugates," Bioconjugate Chem. 13:786-791.
Mandler, R. et al. (Oct. 2000). "Immunoconjugates of Geldanamycin and Anti-HER2 Monoclonal Antibodies: Antiproliferative Activity on Human Breast Carcinoma Cell Lines," J. Nat. Cancer Inst. 92(19):1573-1581.
Marks, J.D. et al. (1991). "By-Passing Immunization Human Antibodies from V-gene Libraries Displayed on Phage," J. Mol. Biol. 222:581-597.
Marks, J.D. et al. (2004) "Selection of Human Antibodies from Phage Display Libraries," Chapter 8 in Methods in Molecular Biology, LO, B.K.C. (ed.), Humana Press Inc., Totowa, NJ, 248:161-176, 29 pages.
Marks, J.D. et al. (Jul. 1992). "By-Passing Immunization: Building High Affinity Human Antibodies by Chain Shuffling," Bio/Technology 10:779-783.
McCafferty, J. et al. (Dec. 6, 1990). "Phage Antibodies: Filamentous Phage Displaying Antibody Variable Domains," Nature 348:552-554.
Milone, M.C. et al. (e-pub. Apr. 21, 2009). "Chimeric Receptors Containing CD137 Signal Transduction Domains Mediate Enhanced Survival Of T Cells And Increased Antileukemic Efficacy In Vivo," Molecular Therapy: The Journal Of The American Society Of Gene Therapy 17(8):1453-1464.
Milstein, C. et al. (Oct. 6, 1983). "Hybrid Hybridomas and Their Use in Immunohistochemistry," Nature 305:537-539.
Morrison, S.C. et al. (Nov. 1984). "Chimeric Human Antibody Molecules: Mouse Antigen-Binding Domains With Human Constant Region Domains," Proc. Natl. Acad. Sci. USA 81:6851-6855.
Morrison, S.L. (Apr. 28, 1994). "Success in Specification," Nature 368:812-813.
Munson, P.J. et al. (1980). "Ligand: A Versatile Computerized Approach for Characterization of Ligand-Binding Systems," Anal. Biochem. 107:220-239.
Muthumani, K. et al. (Dec. 2017). "Novel Prostate Cancer Immunotherapy With A Dna-Encoded Anti-Prostate-Specific Membrane Antigen Monoclonal Antibody," Cancer Immunology, Immunotherapy 66(12):1577-1588.
Neuberger, M. (Jul. 1996). "Generating High-Avidity Human Mabs in Mice," Nature Biotechnology 14:826.
Neuberger, M.S. et al. (Dec. 13, 1984). "Recombinant Antibodies Processing Novel Effector Functions," Nature 312:604-608.
Niculesu-Duvaz, I. et al. (1997). "Antibody-Directed Enzyme Prodrug Therapy (ADEPT): A Review," Adv. Drug Del. Rev. 26:151-172.
Nygren, H. (May 1982). "Conjugation of Horseradish Peroxidase To Fab Fragments With Different Homobifunctional and Heterobifunctional Cross-Linking Reagents. A Comparative Study," J. Histochem. and Cytochem. 30(5):407-412.
Okazaki, A. et al. (Mar. 5, 2004). "Fucose Depletion From Human IgG1 Oligosaccharide Enhances Binding Enthalpy And Association Rate Between IgG1 and FcγRIIIa," J. Mol. Biol. 336(5):1239-1249.
Pain, D. et al. (1981). "Preparation of Protein A-Peroxidase Monoconjugate Using a Heterobifunctional Reagent, and Its Use in Enzyme Immunoassays," J. Immunol. Methods 40:219-230.
Perambakam, S. et al. (2010, e-pub Jan. 5, 2011). "Long-Term Follow-Up Of HLA-A2+ Patients With High-Risk, Hormone-Sensitive Prostate Cancer Vaccinated With The Prostate Specific Antigen Peptide Homologue (PSA146-154)," Clinical & Developmental Immunology 473453:11 pages.

(56) References Cited

OTHER PUBLICATIONS

Petkova, S.B. et al. (2006, e-pub. Oct. 31, 2006). "Enhanced Half-Life of Genetically Engineered Human IgG1 Antibodies in a Humanized FcRn Mouse Model: Potential Application in Humorally Mediated Autoimmune Disease," Int'l. Immunol. 18(12):1759-1769.
Plückthun, A. (1994). "Antibodies from *Escherichia coli*," in Chapter 11 The Pharmacology of Monoclonal Antibodies, vol. 113, Rosenburg and Moore eds., Springer-Verlag, New York, pp. 269-315, 48 pages.
Presta, L.G. (1992). "Antibody Engineering," Current Opinion in Structural Biology 2:593-596.
Pullarkat, V. et al. (Apr. 1, 1999). "A Phase I Study Of A HER2/Neu Bispecific Antibody With Granulocyte-Colony-Stimulating Factor In Patients With Metastatic Breast Cancer That Overexpresses HER2/Neu," Cancer Immunology, Immunotherapy 48(1):9-21.
Ravetch, J.V. et al. (1991). "Fc Receptors," Annu. Rev. Immunol. 9:457-492.
Ridgway, J.B.B. et al. (1996). "Knobs-Into-Holes' Engineering of Antibody CH3 Domains for Heavy Chain Heterodimerization," Protein Engineering 9(7):617-621.
Riechmann, L. et al. (Mar. 24, 1988). "Reshaping Human Antibodies for Therapy," Nature 332:323-329.
Ripka, J. et al. (Sep. 1986). "Two Chinese Hamster Ovary Glycosylation Mutants Affected in the Conversion of GDP-Mannose to GDP-Fucose," Arch Biochem Biophys. 249(2):533-545.
Rosenberg, S.A. et al. (Dec. 22, 1988). "Use of Tumor-Infiltrating Lymphocytes and Interleukin-2 in the Immunotherapy of Patients with Metastatic Melanoma—A preliminary Report," The New England Journal of Medicine 319:1676-1680.
Rossi, E.A. et al. (May 2, 2006). "Stably Tethered Multifunctional Structures Of Defined Composition Made By The Dock And Lock Method For Use In Cancer Targeting," Proceedings Of The National Academy Of Sciences 103(18):6841-6846.
Rowland, G.F. et al. (1986). "Drug Localisation And Growth Inhibition Studies of Vindesine-Monoclonal Anti-CEA Conjugates in a Human Tumour Xenograft," Cancer Immunol. Immunother. 21:183-187.
Sergeeva, A. et al. (Apr. 21, 2011, e-pub. Feb. 4, 2011). "An Anti-PR1/HLA-A2 T-Cell Receptor-Like Antibody Mediates Complement-Dependent Cytotoxicity Against Acute Myeloid Leukemia Progenitor Cells," Blood 117(16):4262-4272.
Shields, R.L. et al. (Mar. 2, 2001). "High Resolution Mapping of the Binding Site on Human IgG1 for FcγRI, FcγRII, FcγRIII, and FcRn and Design of IgG1 Variants With Improved Binding to the FcγR," J. Biol.Chem. 276(9):6591-6604.
Sidhu, S.S. et al. (2004). "Phage-Displayed Antibody Libraries of Synthetic Heavy Chain Complementarity Determining Regions," J. Mol. Biol. 338(2):299-310.
Syrigos, K. et al. (1999). "Antibody Directed Enzyme Prodrug Therapy (ADEPT): A Review of the Experimental and Clinical Considerations," Anticancer Research 19:605-614.
Therasse, P. et al. (Feb. 2, 2000). "New Guidelines to Evaluate the Response to Treatment in Solid Tumors," J. Natl. Cancer Inst. 92(3):205-216.
Thorpe, (1985). "Antibody Carriers Of Cytotoxic Agents In Cancer Therapy: A Review," in Monoclonal Antibodies '84: Biological And Clinical Applications, Pinchera et al. (eds.), pp. 475-506.
Tomimatsu, K. et al. (2009, e-pub. Jul. 7, 2009). "Production of Human Monoclonal Antibodies against FcεRIα by a Method Combining in Vitro Immunization with Phage Display," Biosci. Biotechnol. Biochem. 73(7):1465-1469.
Traunecker, A. et al. (1991). "Bispecific Single Chain Molecules (Janusins) Target Cytotoxic Lymphocytes on HIV Infected Cells," EMBO J. 10(12):3655-3659.
Tutt, A. et al. (Jul. 1, 1991) "Trispecific F(ab')3 Derivatives that use Cooperative Signaling Via the TCR/CD3 Complex and CD2 to Activate and Redirect Resting Cytotoxic T Cells," J. Immunol. 147(1):60-69.
Ui-Tel, K. et al. (2000). "Sensitive Assay of RNA Interference in *Drosophila* and Chinese Hamster Cultured Cells Using Firefly Luciferase Gene As Target," FEBS Letters 479:79-82.
Verhoeyen, M. et al. (Oct. 23, 1987) "Reshaping Human Antibodies: Grafting an Antilysozyme Activity," Science 239:1534-1536.
Veri, M.-C. et al. (Jul. 2010). "Therapeutic Control of B Cell Activation via Recruitment of Fcγ Receptor IIb (CD32B) Inhibitory Function With a Novel Bispecific Antibody Scaffold," Arthritis & Rheumatism, 62(7):1933-1943.
Vitetta, E.S. et al. (Nov. 20, 1987). "Redesigning Nature's Poisons to Create Anti-Tumor Reagents," Science 238:1098-1104.
Winter, G. el al. (1994). "Making Antibodies by Phage Display Technology," Ann. Rev. Immunol. 12:433-455.
Wright, A. et al. (Jan. 1997). "Effect of Glycosylation on Antibody Function: Implications for Genetics Engineering," Trends Biotechnol. 15:26-32.
Wu, J. et al. (Jul. 2019, e-pub. May 2, 2019). "A Novel Fully Human Antibody Targeting Extracellular Domain of PSMA inhibits Tumor Growth in Prostate Cancer," Mol. Cancer Therapeutics 18(7):1289-1301.
Yamane-Ohnuki, N. et al. (Sep. 5, 2004, e-pub Aug. 6, 2004). "Establishment Of FUT8 Knockout Chinese Hamster Ovary Cells: An Ideal Host Cell Line For Producing Completely Defucosylated Antibodies With Enhanced Antibody-Dependent Cellular Cytotoxicity," Biotechnology and Bioengineering 87(5):614-622.
Zhang, L. et al. (Apr. 2011). "Improving Adoptive T Cell Therapy By Targeting And Controlling IL-12 Expression To The Tumor Environment," Molecular Therapy 19(4):751-759.
European Search Report dated Mar. 28, 2022, for European Patent Application No. 19822284.6, filed on Jan. 15, 2021, 8 pages.

* cited by examiner

SEQUENCE LISTING

```
<160> NUMBER OF SEQ ID NOS: 186

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Gly Tyr Ser Phe Thr Ser Tyr Trp
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Gly Tyr Asn Phe Ala Ser Tyr Trp
1               5

<210> SEQ ID NO 3
<211> LENGTH: 8
<212> TYPE: PRT
<213> ORGANISM: Artificial Sequence
```

```
<220> FEATURE:
<223> OTHER INFORMATION: Synthetic Construct

<400> SEQUENCE: 3

Ile Tyr Pro Gly Asp Ser Asp Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct

<400> SEQUENCE: 4

Ile Tyr Pro Asp Asp Ser Asp Thr
1               5

<210> SEQ ID NO 5
<211> LENGTH: 14
<212> TYPE: PRT
<213> ORGANISM: Artificial Sequence
<220> FEATURE:
<223> OTHER INFORMATION: Synthetic Construct

<400> SEQUENCE: 5

Ala Arg Ser Met Gly Ser Ser Leu Tyr Ala Ser Ser Asp Val
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

<400> SEQUENCE: 6

Ala Arg Asp Ser Tyr Tyr Gly Ile Asp Val
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Ser Ser Asn Ile Gly Ala Gly Tyr Asp
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Construct

<400> SEQUENCE: 8

Ser Ser Asn Ile Gly Ser Asn Thr
1               5

<210> SEQ ID NO 9
<211> LENGTH: 11
<212> TYPE: PRT
<213> ORGANISM: Artificial Sequence
<220> FEATURE:
```

```
<223> OTHER INFORMATION: Synthetic Construct

<400> SEQUENCE: 9

Gln Ser Tyr Asp Ser Ser Leu Ser Gly Tyr Val
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic Construct

<400> SEQUENCE: 10

Ala Ala Trp Asp Asp Ser Leu Asn Gly Tyr Val
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = S or N
<220> FEATURE:
<221> NAME/KEY: VARIANT
<222> LOCATION: 5
<223> OTHER INFORMATION: Xaa = T or A

<400> SEQUENCE: 11

Gly Tyr Xaa Phe Xaa Ser Tyr Trp
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = G or D

<400> SEQUENCE: 12

Ile Tyr Pro Xaa Asp Ser Asp Thr
1               5

<210> SEQ ID NO 13
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = S or absent
<220> FEATURE:
<221> NAME/KEY: VARIANT
<222> LOCATION: 4
<223> OTHER INFORMATION: Xaa = M or absent
<220> FEATURE:
<221> NAME/KEY: VARIANT
<222> LOCATION: 5
<223> OTHER INFORMATION: Xaa = G or absent
<220> FEATURE:
<221> NAME/KEY: VARIANT
```

```
<222> LOCATION: 6
<223> OTHER INFORMATION: Xaa = S or absent
<220> FEATURE:
<221> NAME/KEY: VARIANT
<222> LOCATION: 7
<223> OTHER INFORMATION: Xaa = S or D
<220> FEATURE:
<221> NAME/KEY: VARIANT
<222> LOCATION: 8
<223> OTHER INFORMATION: Xaa = L or S
<220> FEATURE:
<221> NAME/KEY: VARIANT
<222> LOCATION: 10
<223> OTHER INFORMATION: Xaa = A or Y
<220> FEATURE:
<221> NAME/KEY: VARIANT
<222> LOCATION: 11
<223> OTHER INFORMATION: Xaa = S or G
<220> FEATURE:
<221> NAME/KEY: VARIANT
<222> LOCATION: 12
<223> OTHER INFORMATION: Xaa = S or I

<400> SEQUENCE: 13

Ala Arg Xaa Xaa Xaa Xaa Xaa Xaa Tyr Xaa Xaa Xaa Asp Val
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = A or S
<220> FEATURE:
<221> NAME/KEY: VARIANT
<222> LOCATION: 7
<223> OTHER INFORMATION: Xaa = G or N
<220> FEATURE:
<221> NAME/KEY: VARIANT
<222> LOCATION: 8
<223> OTHER INFORMATION: Xaa = Y or T
<220> FEATURE:
<221> NAME/KEY: VARIANT
<222> LOCATION: 9
<223> OTHER INFORMATION: Xaa = D or absent

<400> SEQUENCE: 14

Ser Ser Asn Ile Gly Xaa Xaa Xaa Xaa
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Q or A
<220> FEATURE:
<221> NAME/KEY: VARIANT
<222> LOCATION: 2
<223> OTHER INFORMATION: Xaa = S or A
<220> FEATURE:
<221> NAME/KEY: VARIANT
<222> LOCATION: 3
<223> OTHER INFORMATION: Xaa = Y or W
<220> FEATURE:
<221> NAME/KEY: VARIANT
<222> LOCATION: 5
```

```
<223> OTHER INFORMATION: Xaa = S or D
<220> FEATURE:
<221> NAME/KEY: VARIANT
<222> LOCATION: 8
<223> OTHER INFORMATION: Xaa = S or N

<400> SEQUENCE: 15

Xaa Xaa Xaa Asp Xaa Ser Leu Xaa Gly Tyr Val
1               5                   10

<210> SEQ ID NO 16
<211> LENGTH: 121
<212> TYPE: PRT
<213> ORGANISM: Artificial Sequence
<220> FEATURE:
<223> OTHER INFORMATION: Synthetic Construct

<400> SEQUENCE: 16

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Met Gly Ser Ser Leu Tyr Ala Ser Ser Asp Val Trp Gly
            100                 105                 110

Gln Gly Thr Leu Val Thr Val Ser Ser
            115                 120

<210> SEQ ID NO 17
<211> LENGTH: 117
<212> TYPE: PRT
<213> ORGANISM: Artificial Sequence
<220> FEATURE:
<223> OTHER INFORMATION: Synthetic Construct

<400> SEQUENCE: 17

Glu Val Gln Leu Val Gln Ser Gly Ala Glu Met Lys Lys Pro Gly Glu
1               5                   10                  15

Ser Leu Lys Ile Ser Cys Lys Gly Ser Gly Tyr Asn Phe Ala Ser Tyr
                20                  25                  30

Trp Val Gly Trp Val Arg Gln Met Pro Gly Lys Gly Leu Glu Trp Met
            35                  40                  45

Gly Thr Ile Tyr Pro Asp Asp Ser Asp Thr Arg Tyr Gly Pro Ala Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Ser Tyr Tyr Gly Ile Asp Val Trp Gly Gln Gly Thr Leu
            100                 105                 110

Val Thr Val Ser Ser
            115
```

<210> SEQ ID NO 18
<211> LENGTH: 112
<212> TYPE: PRT
<213> ORGANISM: Artificial Sequence
<220> FEATURE:
<223> OTHER INFORMATION: Synthetic Construct

<400> SEQUENCE: 18

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110
```

<210> SEQ ID NO 19
<211> LENGTH: 111
<212> TYPE: PRT
<213> ORGANISM: Artificial Sequence
<220> FEATURE:
<223> OTHER INFORMATION: Synthetic Construct

<400> SEQUENCE: 19

```
Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Met Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly
            100                 105                 110
```

<210> SEQ ID NO 20
<211> LENGTH: 254
<212> TYPE: PRT
<213> ORGANISM: Artificial Sequence
<220> FEATURE:
<223> OTHER INFORMATION: Synthetic Construct

<400> SEQUENCE: 20

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
```

```
              35                  40                  45
Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Tyr Val Phe Gly Thr Gly Thr Lys Val Thr Val Leu Gly
                100                 105                 110

Ser Arg Gly Gly Gly Gly Ser Gly Gly Gly Ser Gly Gly Gly Gly
                115                 120                 125

Ser Leu Glu Met Ala Glu Val Gln Leu Val Gln Ser Gly Ala Glu Val
                130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
                180                 185                 190

Tyr Ser Pro Ser Phe Gln Gly Gln Val Thr Ile Ser Ala Asp Lys Ser
                195                 200                 205

Ile Ser Thr Ala Tyr Leu Gln Trp Ser Ser Leu Lys Ala Ser Asp Thr
210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser
                245                 250

<210> SEQ ID NO 21
<211> LENGTH: 249
<212> TYPE: PRT
<213> ORGANISM: Artificial Sequence
<220> FEATURE:
<223> OTHER INFORMATION: Synthetic Construct

<400> SEQUENCE: 21

Gln Ala Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
                 20                  25                  30

Thr Val Asn Trp Tyr Gln Gln Leu Pro Gly Thr Ala Pro Lys Leu Leu
             35                  40                  45

Met Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Tyr Val Phe Gly Thr Gly Thr Lys Val Thr Val Leu Gly Ser
                100                 105                 110

Arg Gly Gly Gly Gly Ser Gly Gly Gly Ser Gly Gly Gly Gly Ser
                115                 120                 125

Leu Glu Met Ala Glu Val Gln Leu Val Gln Ser Gly Ala Glu Met Lys
                130                 135                 140

Lys Pro Gly Glu Ser Leu Lys Ile Ser Cys Lys Gly Ser Gly Tyr Asn
```

```
                145                 150                 155                 160
        Phe Ala Ser Tyr Trp Val Gly Trp Val Arg Gln Met Pro Gly Lys Gly
                        165                 170                 175

Leu Glu Trp Met Gly Thr Ile Tyr Pro Asp Asp Ser Asp Thr Arg Tyr
                        180                 185                 190

Gly Pro Ala Phe Gln Gly Gln Val Thr Ile Ser Ala Asp Lys Ser Ile
                        195                 200                 205

Ser Thr Ala Tyr Leu Gln Trp Ser Ser Leu Lys Ala Ser Asp Thr Ala
                210                 215                 220

Met Tyr Tyr Cys Ala Arg Asp Ser Tyr Tyr Gly Ile Asp Val Trp Gly
        225                 230                 235                 240

Gln Gly Thr Leu Val Thr Val Ser Ser
                        245

<210> SEQ ID NO 22
<211> LENGTH: 222
<212> TYPE: PRT
<213> ORGANISM: Artificial Sequence
<220> FEATURE:
<223> OTHER INFORMATION: Synthetic Construct

<400> SEQUENCE: 22

Ala Ala Ala Ile Glu Val Met Tyr Pro Pro Pro Tyr Leu Asp Asn Glu
        1               5                   10                  15

Lys Ser Asn Gly Thr Ile Ile His Val Lys Gly Lys His Leu Cys Pro
                        20                  25                  30

Ser Pro Leu Phe Pro Gly Pro Ser Lys Pro Phe Trp Val Leu Val Val
                        35                  40                  45

Val Gly Gly Val Leu Ala Cys Tyr Ser Leu Leu Val Thr Val Ala Phe
                50                  55                  60

Ile Ile Phe Trp Val Arg Ser Lys Arg Ser Arg Leu Leu His Ser Asp
        65                  70                  75                  80

Tyr Met Asn Met Thr Pro Arg Arg Pro Gly Pro Thr Arg Lys His Tyr
                        85                  90                  95

Gln Pro Tyr Ala Pro Pro Arg Asp Phe Ala Ala Tyr Arg Ser Arg Val
                        100                 105                 110

Lys Phe Ser Arg Ser Ala Asp Ala Pro Ala Tyr Gln Gln Gly Gln Asn
                        115                 120                 125

Gln Leu Tyr Asn Glu Leu Asn Leu Gly Arg Arg Glu Glu Tyr Asp Val
                130                 135                 140

Leu Asp Lys Arg Arg Gly Arg Asp Pro Glu Met Gly Gly Lys Pro Arg
        145                 150                 155                 160

Arg Lys Asn Pro Gln Glu Gly Leu Tyr Asn Glu Leu Gln Lys Asp Lys
                        165                 170                 175

Met Ala Glu Ala Tyr Ser Glu Ile Gly Met Lys Gly Glu Arg Arg Arg
                        180                 185                 190

Gly Lys Gly His Asp Gly Leu Tyr Gln Gly Leu Ser Thr Ala Thr Lys
                        195                 200                 205

Asp Thr Tyr Asp Ala Leu His Met Gln Ala Leu Pro Pro Arg
                210                 215                 220

<210> SEQ ID NO 23
<211> LENGTH: 225
<212> TYPE: PRT
<213> ORGANISM: Artificial Sequence
<220> FEATURE:
<223> OTHER INFORMATION: Synthetic Construct
```

<400> SEQUENCE: 23

```
Thr Gly Thr Thr Thr Pro Ala Pro Arg Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
        35                  40                  45

Tyr Ile Trp Ala Pro Leu Ala Gly Thr Cys Gly Val Leu Leu Leu Ser
    50                  55                  60

Leu Val Ile Thr Leu Tyr Cys Lys Arg Gly Arg Lys Lys Leu Leu Tyr
65                  70                  75                  80

Ile Phe Lys Gln Pro Phe Met Arg Pro Val Gln Thr Thr Gln Glu Glu
                85                  90                  95

Asp Gly Cys Ser Cys Arg Phe Pro Glu Glu Glu Glu Gly Gly Cys Glu
            100                 105                 110

Leu Arg Val Lys Phe Ser Arg Ser Ala Asp Ala Pro Ala Tyr Gln Gln
            115                 120                 125

Gly Gln Asn Gln Leu Tyr Asn Glu Leu Asn Leu Gly Arg Arg Glu Glu
        130                 135                 140

Tyr Asp Val Leu Asp Lys Arg Arg Gly Arg Asp Pro Glu Met Gly Gly
145                 150                 155                 160

Lys Pro Arg Arg Lys Asn Pro Gln Glu Gly Leu Tyr Asn Glu Leu Gln
                165                 170                 175

Lys Asp Lys Met Ala Glu Ala Tyr Ser Glu Ile Gly Met Lys Gly Glu
            180                 185                 190

Arg Arg Arg Gly Lys Gly His Asp Gly Leu Tyr Gln Gly Leu Ser Thr
        195                 200                 205

Ala Thr Lys Asp Thr Tyr Asp Ala Leu His Met Gln Ala Leu Pro Pro
    210                 215                 220

Arg
225
```

<210> SEQ ID NO 24
<211> LENGTH: 21
<212> TYPE: PRT
<213> ORGANISM: Artificial Sequence
<220> FEATURE:
<223> OTHER INFORMATION: Synthetic Construct

<400> SEQUENCE: 24

```
Ser Arg Gly Gly Gly Gly Ser Gly Gly Gly Ser Gly Gly Gly Gly
1               5                   10                  15

Ser Leu Glu Met Ala
            20
```

<210> SEQ ID NO 25
<211> LENGTH: 510
<212> TYPE: PRT
<213> ORGANISM: Artificial Sequence
<220> FEATURE:
<223> OTHER INFORMATION: Synthetic Construct

<400> SEQUENCE: 25

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30
```

```
Tyr Asp Val His Trp Tyr Gln Gln Leu Pro Gly Thr Ala Pro Lys Leu
         35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Tyr Val Phe Gly Thr Gly Thr Lys Val Thr Val Leu Gly
                100                 105                 110

Ser Arg Gly Gly Gly Ser Gly Gly Gly Ser Gly Gly Gly Gly
                115                 120                 125

Ser Leu Glu Met Ala Glu Val Gln Leu Val Gln Ser Gly Ala Glu Val
        130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
            195                 200                 205

Ile Ser Thr Ala Tyr Leu Gln Trp Ser Ser Leu Lys Ala Ser Asp Thr
        210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Thr Ser
                245                 250                 255

Gly Gly Gly Gly Ser Asp Val Gln Leu Val Gln Ser Gly Ala Glu Val
            260                 265                 270

Lys Lys Pro Gly Ala Ser Val Lys Val Ser Cys Lys Ala Ser Gly Tyr
            275                 280                 285

Thr Phe Thr Arg Tyr Thr Met His Trp Val Arg Gln Ala Pro Gly Gln
        290                 295                 300

Gly Leu Glu Trp Ile Gly Tyr Ile Asn Pro Ser Arg Gly Tyr Thr Asn
305                 310                 315                 320

Tyr Ala Asp Ser Val Lys Gly Arg Phe Thr Ile Thr Thr Asp Lys Ser
                325                 330                 335

Thr Ser Thr Ala Tyr Met Glu Leu Ser Ser Leu Arg Ser Glu Asp Thr
            340                 345                 350

Ala Thr Tyr Tyr Cys Ala Arg Tyr Tyr Asp Asp His Tyr Cys Leu Asp
        355                 360                 365

Tyr Trp Gly Gln Gly Thr Thr Val Thr Val Ser Ser Gly Glu Gly Thr
370                 375                 380

Ser Thr Gly Ser Gly Gly Ser Gly Gly Ser Gly Gly Ala Asp Asp Ile
385                 390                 395                 400

Val Leu Thr Gln Ser Pro Ala Thr Leu Ser Leu Ser Pro Gly Glu Arg
                405                 410                 415

Ala Thr Leu Ser Cys Arg Ala Ser Gln Ser Val Ser Tyr Met Asn Trp
            420                 425                 430

Tyr Gln Gln Lys Pro Gly Lys Ala Pro Lys Arg Trp Ile Tyr Asp Thr
        435                 440                 445
```

```
Ser Lys Val Ala Ser Gly Val Pro Ala Arg Phe Ser Gly Ser Gly Ser
    450                 455                 460
Gly Thr Asp Tyr Ser Leu Thr Ile Asn Ser Leu Glu Ala Glu Asp Ala
465                 470                 475                 480
Ala Thr Tyr Tyr Cys Gln Gln Trp Ser Ser Asn Pro Leu Thr Phe Gly
                485                 490                 495
Gly Gly Thr Lys Val Glu Ile Lys His His His His His His
                500                 505                 510

<210> SEQ ID NO 26
<211> LENGTH: 504
<212> TYPE: PRT
<213> ORGANISM: Artificial Sequence
<220> FEATURE:
<223> OTHER INFORMATION: Synthetic Construct

<400> SEQUENCE: 26

Gln Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ala Gly
            20                  25                  30
Tyr Asp Val His Trp Tyr Gln Gln Leu Pro Gly Thr Ala Pro Lys Leu
        35                  40                  45
Leu Ile Tyr Gly Asn Ser Asn Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Gln Ser Tyr Asp Ser Ser
                85                  90                  95
Leu Ser Gly Tyr Val Phe Gly Thr Gly Thr Lys Val Thr Val Leu Gly
            100                 105                 110
Ser Arg Gly Gly Gly Gly Ser Gly Gly Gly Gly Ser Gly Gly Gly Gly
        115                 120                 125
Ser Leu Glu Met Ala Glu Val Gln Leu Val Gln Ser Gly Ala Glu Val
    130                 135                 140
Lys Lys Pro Gly Glu Ser Leu Lys Ile Ser Cys Lys Gly Ser Gly Tyr
145                 150                 155                 160
Ser Phe Thr Ser Tyr Trp Ile Gly Trp Val Arg Gln Met Pro Gly Lys
                165                 170                 175
Gly Leu Glu Trp Met Gly Ile Ile Tyr Pro Gly Asp Ser Asp Thr Arg
            180                 185                 190
Tyr Ser Pro Ser Phe Gln Gly Gln Val Thr Ile Ser Ala Asp Lys Ser
        195                 200                 205
Ile Ser Thr Ala Tyr Leu Gln Trp Ser Ser Leu Lys Ala Ser Asp Thr
    210                 215                 220
Ala Met Tyr Tyr Cys Ala Arg Ser Met Gly Ser Ser Leu Tyr Ala Ser
225                 230                 235                 240
Ser Asp Val Trp Gly Gln Gly Thr Leu Val Thr Val Ser Ser Thr Ser
                245                 250                 255
Gly Gly Gly Gly Ser Asp Val Gln Leu Val Gln Ser Gly Ala Glu Val
            260                 265                 270
Lys Lys Pro Gly Ala Ser Val Lys Val Ser Cys Lys Ala Ser Gly Tyr
        275                 280                 285
Thr Phe Thr Arg Tyr Thr Met His Trp Val Arg Gln Ala Pro Gly Gln
    290                 295                 300
```

Gly Leu Glu Trp Ile Gly Tyr Ile Asn Pro Ser Arg Gly Tyr Thr Asn
305                 310                 315                 320

Tyr Ala Asp Ser Val Lys Gly Arg Phe Thr Ile Thr Asp Lys Ser
            325                 330                 335

Thr Ser Thr Ala Tyr Met Glu Leu Ser Ser Leu Arg Ser Glu Asp Thr
                340                 345                 350

Ala Thr Tyr Tyr Cys Ala Arg Tyr Tyr Asp Asp His Tyr Cys Leu Asp
            355                 360                 365

Tyr Trp Gly Gln Gly Thr Thr Val Thr Val Ser Ser Gly Glu Gly Thr
        370                 375                 380

Ser Thr Gly Ser Gly Gly Ser Gly Gly Ser Gly Gly Ala Asp Asp Ile
385                 390                 395                 400

Val Leu Thr Gln Ser Pro Ala Thr Leu Ser Leu Ser Pro Gly Glu Arg
                405                 410                 415

Ala Thr Leu Ser Cys Arg Ala Ser Gln Ser Val Ser Tyr Met Asn Trp
            420                 425                 430

Tyr Gln Gln Lys Pro Gly Lys Ala Pro Lys Arg Trp Ile Tyr Asp Thr
        435                 440                 445

Ser Lys Val Ala Ser Gly Val Pro Ala Arg Phe Ser Gly Ser Gly Ser
450                 455                 460

Gly Thr Asp Tyr Ser Leu Thr Ile Asn Ser Leu Glu Ala Glu Asp Ala
465                 470                 475                 480

Ala Thr Tyr Tyr Cys Gln Gln Trp Ser Ser Asn Pro Leu Thr Phe Gly
            485                 490                 495

Gly Gly Thr Lys Val Glu Ile Lys
            500

<210> SEQ ID NO 27
<211> LENGTH: 505
<212> TYPE: PRT
<213> ORGANISM: Artificial Sequence
<220> FEATURE:
<223> OTHER INFORMATION: Synthetic Construct

<400> SEQUENCE: 27

Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Met Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Met Lys
    130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175

Leu Glu Trp Met Gly Thr Ile Tyr Pro Asp Ser Asp Thr Arg Tyr
        180                 185                 190

Gly Pro Ala Phe Gln Gly Gln Val Thr Ile Ser Ala Asp Lys Ser Ile
            195                 200                 205

Ser Thr Ala Tyr Leu Gln Trp Ser Ser Leu Lys Ala Ser Asp Thr Ala
    210                 215                 220

Met Tyr Tyr Cys Ala Arg Asp Ser Tyr Tyr Gly Ile Asp Val Trp Gly
225                 230                 235                 240

Gln Gly Thr Leu Val Thr Val Ser Ser Thr Ser Gly Gly Gly Ser
                245                 250                 255

Asp Val Gln Leu Val Gln Ser Gly Ala Glu Val Lys Lys Pro Gly Ala
                260                 265                 270

Ser Val Lys Val Ser Cys Lys Ala Ser Gly Tyr Thr Phe Thr Arg Tyr
            275                 280                 285

Thr Met His Trp Val Arg Gln Ala Pro Gly Gln Gly Leu Glu Trp Ile
            290                 295                 300

Gly Tyr Ile Asn Pro Ser Arg Gly Tyr Thr Asn Tyr Ala Asp Ser Val
305                 310                 315                 320

Lys Gly Arg Phe Thr Ile Thr Thr Asp Lys Ser Thr Ser Thr Ala Tyr
                325                 330                 335

Met Glu Leu Ser Ser Leu Arg Ser Glu Asp Thr Ala Thr Tyr Tyr Cys
            340                 345                 350

Ala Arg Tyr Tyr Asp Asp His Tyr Cys Leu Asp Tyr Trp Gly Gln Gly
        355                 360                 365

Thr Thr Val Thr Val Ser Ser Gly Glu Gly Thr Ser Thr Gly Ser Gly
370                 375                 380

Gly Ser Gly Gly Ser Gly Ala Asp Asp Ile Val Leu Thr Gln Ser
385                 390                 395                 400

Pro Ala Thr Leu Ser Leu Ser Pro Gly Glu Arg Ala Thr Leu Ser Cys
            405                 410                 415

Arg Ala Ser Gln Ser Val Ser Tyr Met Asn Trp Tyr Gln Gln Lys Pro
        420                 425                 430

Gly Lys Ala Pro Lys Arg Trp Ile Tyr Asp Thr Ser Lys Val Ala Ser
        435                 440                 445

Gly Val Pro Ala Arg Phe Ser Gly Ser Gly Ser Gly Thr Asp Tyr Ser
    450                 455                 460

Leu Thr Ile Asn Ser Leu Glu Ala Glu Asp Ala Ala Thr Tyr Tyr Cys
465                 470                 475                 480

Gln Gln Trp Ser Ser Asn Pro Leu Thr Phe Gly Gly Gly Thr Lys Val
                485                 490                 495

Glu Ile Lys His His His His His His
            500                 505

<210> SEQ ID NO 28
<211> LENGTH: 499
<212> TYPE: PRT
<213> ORGANISM: Artificial Sequence
<220> FEATURE:
<223> OTHER INFORMATION: Synthetic Construct

<400> SEQUENCE: 28

Gln Ala Val Leu Thr Gln Pro Pro Ser Ala Ser Gly Thr Pro Gly Gln
1               5                   10                  15

-continued

```
Arg Val Thr Ile Ser Cys Ser Gly Ser Ser Asn Ile Gly Ser Asn
             20                  25                  30

Thr Val Asn Trp Tyr Gln Gln Leu Pro Gly Thr Ala Pro Lys Leu Leu
             35                  40                  45

Met Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
             85                  90                  95

Asn Gly Tyr Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
            115                 120                 125

Leu Glu Met Ala Glu Val Gln Leu Val Gln Ser Gly Ala Glu Met Lys
            130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175

Leu Glu Trp Met Gly Thr Ile Tyr Pro Asp Asp Ser Asp Thr Arg Tyr
            180                 185                 190

Gly Pro Ala Phe Gln Gly Gln Val Thr Ile Ser Ala Asp Lys Ser Ile
            195                 200                 205

Ser Thr Ala Tyr Leu Gln Trp Ser Ser Leu Lys Ala Ser Asp Thr Ala
210                 215                 220

Met Tyr Tyr Cys Ala Arg Asp Ser Tyr Gly Ile Asp Val Trp Gly
225                 230                 235                 240

Gln Gly Thr Leu Val Thr Val Ser Ser Thr Ser Gly Gly Gly Gly Ser
                245                 250                 255

Asp Val Gln Leu Val Gln Ser Gly Ala Glu Val Lys Lys Pro Gly Ala
            260                 265                 270

Ser Val Lys Val Ser Cys Lys Ala Ser Gly Tyr Thr Phe Thr Arg Tyr
            275                 280                 285

Thr Met His Trp Val Arg Gln Ala Pro Gly Gln Gly Leu Glu Trp Ile
            290                 295                 300

Gly Tyr Ile Asn Pro Ser Arg Gly Tyr Thr Asn Tyr Ala Asp Ser Val
305                 310                 315                 320

Lys Gly Arg Phe Thr Ile Thr Thr Asp Lys Ser Thr Ser Thr Ala Tyr
                325                 330                 335

Met Glu Leu Ser Ser Leu Arg Ser Glu Asp Thr Ala Thr Tyr Tyr Cys
            340                 345                 350

Ala Arg Tyr Tyr Asp Asp His Tyr Cys Leu Asp Tyr Trp Gly Gln Gly
            355                 360                 365

Thr Thr Val Thr Val Ser Ser Gly Glu Gly Thr Ser Thr Gly Ser Gly
            370                 375                 380

Gly Ser Gly Gly Ser Gly Gly Ala Asp Asp Ile Val Leu Thr Gln Ser
385                 390                 395                 400

Pro Ala Thr Leu Ser Leu Ser Pro Gly Glu Arg Ala Thr Leu Ser Cys
                405                 410                 415

Arg Ala Ser Gln Ser Val Ser Tyr Met Asn Trp Tyr Gln Gln Lys Pro
            420                 425                 430

Gly Lys Ala Pro Lys Arg Trp Ile Tyr Asp Thr Ser Lys Val Ala Ser
```

```
                    435                 440                 445
Gly Val Pro Ala Arg Phe Ser Gly Ser Gly Ser Gly Thr Asp Tyr Ser
        450                 455                 460

Leu Thr Ile Asn Ser Leu Glu Ala Glu Asp Ala Ala Thr Tyr Tyr Cys
465                 470                 475                 480

Gln Gln Trp Ser Ser Asn Pro Leu Thr Phe Gly Gly Gly Thr Lys Val
                485                 490                 495

Glu Ile Lys

<210> SEQ ID NO 29
<211> LENGTH: 486
<212> TYPE: PRT
<213> ORGANISM: Artificial Sequence
<220> FEATURE:
<223> OTHER INFORMATION: Synthetic Construct: Clone A-CAR

<400> SEQUENCE: 29

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Gly Ser Gly Gly Gly Gly
            115                 120                 125

Ser Leu Glu Met Ala Glu Val Gln Leu Val Gln Ser Gly Ala Glu Val
            130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205

Ile Ser Thr Ala Tyr Leu Gln Trp Ser Ser Leu Lys Ala Ser Asp Thr
210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Glu Gln
                245                 250                 255

Lys Leu Ile Ser Glu Glu Asp Leu Ala Ala Ile Glu Val Met Tyr
            260                 265                 270

Pro Pro Pro Tyr Leu Asp Asn Glu Lys Ser Asn Gly Thr Ile Ile His
        275                 280                 285

Val Lys Gly Lys His Leu Cys Pro Ser Pro Leu Phe Pro Gly Pro Ser
290                 295                 300
```

```
Lys Pro Phe Trp Val Leu Val Val Gly Gly Val Leu Ala Cys Tyr
305                 310                 315                 320

Ser Leu Leu Val Thr Val Ala Phe Ile Ile Phe Trp Val Arg Ser Lys
            325                 330                 335

Arg Ser Arg Leu Leu His Ser Asp Tyr Met Asn Met Thr Pro Arg Arg
        340                 345                 350

Pro Gly Pro Thr Arg Lys His Tyr Gln Pro Tyr Ala Pro Pro Arg Asp
    355                 360                 365

Phe Ala Ala Tyr Arg Ser Arg Val Lys Phe Ser Arg Ser Ala Asp Ala
370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
                420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 30
<211> LENGTH: 481
<212> TYPE: PRT
<213> ORGANISM: Artificial Sequence
<220> FEATURE:
<223> OTHER INFORMATION: Synthetic Construct: Clone B-CAR

<400> SEQUENCE: 30

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Met Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
                100                 105                 110

Arg Gly Gly Gly Gly Ser Gly Gly Gly Ser Gly Gly Gly Gly Ser
            115                 120                 125

Leu Glu Met Ala Glu Val Gln Leu Val Gln Ser Gly Ala Glu Met Lys
        130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175
```

```
Leu Glu Trp Met Gly Thr Ile Tyr Pro Asp Asp Ser Asp Thr Arg Tyr
            180                 185                 190

Gly Pro Ala Phe Gln Gly Gln Val Thr Ile Ser Ala Asp Lys Ser Ile
            195                 200                 205

Ser Thr Ala Tyr Leu Gln Trp Ser Ser Leu Lys Ala Ser Asp Thr Ala
    210                 215                 220

Met Tyr Tyr Cys Ala Arg Asp Ser Tyr Gly Ile Asp Val Trp Gly
225                 230                 235                 240

Gln Gly Thr Leu Val Thr Val Ser Ser Glu Gln Lys Leu Ile Ser Glu
            245                 250                 255

Glu Asp Leu Ala Ala Ile Glu Val Met Tyr Pro Pro Pro Tyr Leu
            260                 265                 270

Asp Asn Glu Lys Ser Asn Gly Thr Ile Ile His Val Lys Gly Lys His
            275                 280                 285

Leu Cys Pro Ser Pro Leu Phe Pro Gly Pro Ser Lys Pro Phe Trp Val
            290                 295                 300

Leu Val Val Val Gly Gly Val Leu Ala Cys Tyr Ser Leu Leu Val Thr
305                 310                 315                 320

Val Ala Phe Ile Ile Phe Trp Val Arg Ser Lys Arg Ser Arg Leu Leu
            325                 330                 335

His Ser Asp Tyr Met Asn Met Thr Pro Arg Arg Pro Gly Pro Thr Arg
            340                 345                 350

Lys His Tyr Gln Pro Tyr Ala Pro Pro Arg Asp Phe Ala Ala Tyr Arg
            355                 360                 365

Ser Arg Val Lys Phe Ser Arg Ser Ala Asp Ala Pro Ala Tyr Gln Gln
            370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Gly Arg Asp Pro Glu Met Gly Gly
            405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
            435                 440                 445

Arg Arg Arg Gly Lys Gly His Asp Gly Leu Tyr Gln Gly Leu Ser Thr
            450                 455                 460

Ala Thr Lys Asp Thr Tyr Asp Ala Leu His Met Gln Ala Leu Pro Pro
465                 470                 475                 480

Arg

<210> SEQ ID NO 31
<211> LENGTH: 292
<212> TYPE: PRT
<213> ORGANISM: Artificial Sequence
<220> FEATURE:
<223> OTHER INFORMATION: Synthetic Construct

<400> SEQUENCE: 31

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
            35                  40                  45
```

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Met Gly Ser Ser Leu Tyr Ala Ser Ser Asp Val Trp Gly
            100                 105                 110

Gln Gly Thr Leu Val Thr Val Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
210                 215                 220

Glu Val Lys Thr Asp Ser Thr Asp His Val Lys Pro Lys Glu Thr Glu
225                 230                 235                 240

Asn Thr Lys Gln Pro Ser Lys Ser Cys His Lys Pro Lys Ala Ile Val
                245                 250                 255

His Thr Glu Lys Val Asn Met Met Ser Leu Thr Val Leu Gly Leu Arg
            260                 265                 270

Met Leu Phe Ala Lys Thr Val Ala Val Asn Phe Leu Leu Thr Ala Lys
            275                 280                 285

Leu Phe Phe Leu
    290

<210> SEQ ID NO 32
<211> LENGTH: 284
<212> TYPE: PRT
<213> ORGANISM: Artificial Sequence
<220> FEATURE:
<223> OTHER INFORMATION: Synthetic Construct

<400> SEQUENCE: 32

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

```
Gln Pro Lys Ala Asn Pro Thr Val Thr Leu Phe Pro Pro Ser Ser Glu
            115                 120                 125

Glu Leu Gln Ala Asn Lys Ala Thr Leu Val Cys Leu Ile Ser Asp Phe
        130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser Pro Ile Lys Thr Asp Val Ile
    210                 215                 220

Thr Met Asp Pro Lys Asp Asn Cys Ser Lys Asp Ala Asn Asp Thr Leu
225                 230                 235                 240

Leu Leu Gln Leu Thr Asn Thr Ser Ala Tyr Tyr Met Tyr Leu Leu Leu
                245                 250                 255

Leu Leu Lys Ser Val Val Tyr Phe Ala Ile Ile Thr Cys Cys Leu Leu
            260                 265                 270

Arg Arg Thr Ala Phe Cys Cys Asn Gly Glu Lys Ser
        275                 280

<210> SEQ ID NO 33
<211> LENGTH: 648
<212> TYPE: PRT
<213> ORGANISM: Artificial Sequence
<220> FEATURE:
<223> OTHER INFORMATION: Synthetic Construct: Anti-PSMA caTCR #1
      (a.k.a. Anti-PSMA Clone A caTCR, "Ax1-caTCR", or "Clone A-caTCR")

<400> SEQUENCE: 33

Met Glu Thr Asp Thr Leu Leu Leu Trp Val Leu Leu Leu Trp Val Pro
1               5                   10                  15

Gly Ser Thr Gly Glu Val Gln Leu Val Gln Ser Gly Ala Glu Val Lys
            20                  25                  30

Lys Pro Gly Glu Ser Leu Lys Ile Ser Cys Lys Gly Ser Gly Tyr Ser
        35                  40                  45

Phe Thr Ser Tyr Trp Ile Gly Trp Val Arg Gln Met Pro Gly Lys Gly
    50                  55                  60

Leu Glu Trp Met Gly Ile Ile Tyr Pro Gly Asp Ser Asp Thr Arg Tyr
65                  70                  75                  80

Ser Pro Ser Phe Gln Gly Gln Val Thr Ile Ser Ala Asp Lys Ser Ile
                85                  90                  95

Ser Thr Ala Tyr Leu Gln Trp Ser Ser Leu Lys Ala Ser Asp Thr Ala
            100                 105                 110

Met Tyr Tyr Cys Ala Arg Ser Met Gly Ser Ser Leu Tyr Ala Ser Ser
        115                 120                 125

Asp Val Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190
```

```
Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
210                 215                 220

Asn Val Asn His Lys Pro Ser Asn Thr Lys Val Asp Lys Arg Val Glu
225                 230                 235                 240

Pro Lys Ser Cys Glu Val Lys Thr Asp Ser Thr Asp His Val Lys Pro
                245                 250                 255

Lys Glu Thr Glu Asn Thr Lys Gln Pro Ser Lys Ser Cys His Lys Pro
                260                 265                 270

Lys Ala Ile Val His Thr Glu Lys Val Asn Met Met Ser Leu Thr Val
            275                 280                 285

Leu Gly Leu Arg Met Leu Phe Ala Lys Thr Val Ala Val Asn Phe Leu
            290                 295                 300

Leu Thr Ala Lys Leu Phe Phe Leu Arg Ala Lys Arg Ser Gly Ser Gly
305                 310                 315                 320

Ala Pro Val Lys Gln Thr Leu Asn Phe Asp Leu Leu Lys Leu Ala Gly
                325                 330                 335

Asp Val Glu Ser Asn Pro Gly Pro Met Glu Thr Asp Thr Leu Leu Leu
                340                 345                 350

Trp Val Leu Leu Leu Trp Val Pro Gly Ser Thr Gly Gln Ser Val Leu
            355                 360                 365

Thr Gln Pro Pro Ser Val Ser Gly Ala Pro Gly Gln Arg Val Thr Ile
            370                 375                 380

Ser Cys Thr Gly Ser Ser Ser Asn Ile Gly Ala Gly Tyr Asp Val His
385                 390                 395                 400

Trp Tyr Gln Gln Leu Pro Gly Thr Ala Pro Lys Leu Leu Ile Tyr Gly
                405                 410                 415

Asn Ser Asn Arg Pro Ser Gly Val Pro Asp Arg Phe Ser Gly Ser Lys
                420                 425                 430

Ser Gly Thr Ser Ala Ser Leu Ala Ile Thr Gly Leu Gln Ala Glu Asp
            435                 440                 445

Glu Ala Asp Tyr Tyr Cys Gln Ser Tyr Asp Ser Ser Leu Ser Gly Tyr
            450                 455                 460

Val Phe Gly Thr Gly Thr Lys Val Thr Val Leu Gly Gln Pro Lys Ala
465                 470                 475                 480

Asn Pro Thr Val Thr Leu Phe Pro Pro Ser Ser Glu Glu Leu Gln Ala
                485                 490                 495

Asn Lys Ala Thr Leu Val Cys Leu Ile Ser Asp Phe Tyr Pro Gly Ala
                500                 505                 510

Val Thr Val Ala Trp Lys Ala Asp Gly Ser Pro Val Lys Ala Gly Val
            515                 520                 525

Glu Thr Thr Lys Pro Ser Lys Gln Ser Asn Asn Lys Tyr Ala Ala Ser
            530                 535                 540

Ser Tyr Leu Ser Leu Thr Pro Glu Gln Trp Lys Ser His Arg Ser Tyr
545                 550                 555                 560

Ser Cys Gln Val Thr His Glu Gly Ser Thr Val Glu Lys Thr Val Ala
                565                 570                 575

Pro Thr Glu Cys Ser Pro Ile Lys Thr Asp Val Ile Thr Met Asp Pro
                580                 585                 590

Lys Asp Asn Cys Ser Lys Asp Ala Asn Asp Thr Leu Leu Leu Gln Leu
            595                 600                 605
```

```
Thr Asn Thr Ser Ala Tyr Tyr Met Tyr Leu Leu Leu Leu Lys Ser
    610                 615                 620

Val Val Tyr Phe Ala Ile Ile Thr Cys Cys Leu Leu Arg Arg Thr Ala
625                 630                 635                 640

Phe Cys Cys Asn Gly Glu Lys Ser
                645

<210> SEQ ID NO 34
<211> LENGTH: 288
<212> TYPE: PRT
<213> ORGANISM: Artificial Sequence
<220> FEATURE:
<223> OTHER INFORMATION: Synthetic Construct

<400> SEQUENCE: 34

Glu Val Gln Leu Val Gln Ser Gly Ala Glu Met Lys Lys Pro Gly Glu
1               5                   10                  15

Ser Leu Lys Ile Ser Cys Lys Gly Ser Gly Tyr Asn Phe Ala Ser Tyr
                20                  25                  30

Trp Gly Trp Val Arg Gln Met Pro Gly Lys Gly Leu Glu Trp Met
            35                  40                  45

Gly Thr Ile Tyr Pro Asp Asp Ser Asp Thr Arg Tyr Gly Pro Ala Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Ser Tyr Tyr Gly Ile Asp Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Glu Val Lys Thr
    210                 215                 220

Asp Ser Thr Asp His Val Lys Pro Lys Glu Thr Glu Asn Thr Lys Gln
225                 230                 235                 240

Pro Ser Lys Ser Cys His Lys Pro Lys Ala Ile Val His Thr Glu Lys
                245                 250                 255

Val Asn Met Met Ser Leu Thr Val Leu Gly Leu Arg Met Leu Phe Ala
            260                 265                 270

Lys Thr Val Ala Val Asn Phe Leu Leu Thr Ala Lys Leu Phe Phe Leu
        275                 280                 285

<210> SEQ ID NO 35
<211> LENGTH: 283
<212> TYPE: PRT
<213> ORGANISM: Artificial Sequence
<220> FEATURE:
```

<223> OTHER INFORMATION: Synthetic Construct

<400> SEQUENCE: 35

```
Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Met Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser Pro Ile Lys Thr Asp Val Ile Thr
    210                 215                 220

Met Asp Pro Lys Asp Asn Cys Ser Lys Asp Ala Asn Asp Thr Leu Leu
225                 230                 235                 240

Leu Gln Leu Thr Asn Thr Ser Ala Tyr Tyr Met Tyr Leu Leu Leu Leu
                245                 250                 255

Leu Lys Ser Val Val Tyr Phe Ala Ile Ile Thr Cys Cys Leu Leu Arg
            260                 265                 270

Arg Thr Ala Phe Cys Cys Asn Gly Glu Lys Ser
        275                 280
```

<210> SEQ ID NO 36
<211> LENGTH: 643
<212> TYPE: PRT
<213> ORGANISM: Artificial Sequence
<220> FEATURE:
<223> OTHER INFORMATION: Synthetic Construct: Anti-PSMA caTCR #2 (a.k.a.
      Anti-PSMA Clone B caTCR, "Bx1-caTCR", or "Clone B-caTCR")

<400> SEQUENCE: 36

```
Met Glu Thr Asp Thr Leu Leu Leu Trp Val Leu Leu Leu Trp Val Pro
1               5                   10                  15

Gly Ser Thr Gly Glu Val Gln Leu Val Gln Ser Gly Ala Glu Met Lys
            20                  25                  30

Lys Pro Gly Glu Ser Leu Lys Ile Ser Cys Lys Gly Ser Gly Tyr Asn
        35                  40                  45

Phe Ala Ser Tyr Trp Val Gly Trp Val Arg Gln Met Pro Gly Lys Gly
```

```
                50                  55                  60
Leu Glu Trp Met Gly Thr Ile Tyr Pro Asp Asp Ser Asp Thr Arg Tyr
 65                  70                  75                  80

Gly Pro Ala Phe Gln Gly Gln Val Thr Ile Ser Ala Asp Lys Ser Ile
                 85                  90                  95

Ser Thr Ala Tyr Leu Gln Trp Ser Ser Leu Lys Ala Ser Asp Thr Ala
                100                 105                 110

Met Tyr Tyr Cys Ala Arg Asp Ser Tyr Tyr Gly Ile Asp Val Trp Gly
                115                 120                 125

Gln Gly Thr Leu Val Thr Val Ser Ser Ala Ser Thr Lys Gly Pro Ser
                130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
                195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Arg Val Glu Pro Lys Ser Cys
225                 230                 235                 240

Glu Val Lys Thr Asp Ser Thr Asp His Val Lys Pro Lys Glu Thr Glu
                245                 250                 255

Asn Thr Lys Gln Pro Ser Lys Ser Cys His Lys Pro Lys Ala Ile Val
                260                 265                 270

His Thr Glu Lys Val Asn Met Met Ser Leu Thr Val Leu Gly Leu Arg
                275                 280                 285

Met Leu Phe Ala Lys Thr Val Ala Val Asn Phe Leu Leu Thr Ala Lys
                290                 295                 300

Leu Phe Phe Leu Arg Ala Lys Arg Ser Gly Ser Gly Ala Pro Val Lys
305                 310                 315                 320

Gln Thr Leu Asn Phe Asp Leu Leu Lys Leu Ala Gly Asp Val Glu Ser
                325                 330                 335

Asn Pro Gly Pro Met Glu Thr Asp Thr Leu Leu Leu Trp Val Leu Leu
                340                 345                 350

Leu Trp Val Pro Gly Ser Thr Gly Gln Ala Val Leu Thr Gln Pro Pro
                355                 360                 365

Ser Ala Ser Gly Thr Pro Gly Gln Arg Val Thr Ile Ser Cys Ser Gly
370                 375                 380

Ser Ser Ser Asn Ile Gly Ser Asn Thr Val Asn Trp Tyr Gln Gln Leu
385                 390                 395                 400

Pro Gly Thr Ala Pro Lys Leu Leu Met Tyr Ser Asn Asn Gln Arg Pro
                405                 410                 415

Ser Gly Val Pro Asp Arg Phe Ser Gly Ser Lys Ser Gly Thr Ser Ala
                420                 425                 430

Ser Leu Ala Ile Ser Gly Leu Gln Ser Glu Asp Glu Ala Asp Tyr Tyr
                435                 440                 445

Cys Ala Ala Trp Asp Asp Ser Leu Asn Gly Tyr Val Phe Gly Thr Gly
                450                 455                 460

Thr Lys Val Thr Val Leu Gly Gln Pro Lys Ala Asn Pro Thr Val Thr
465                 470                 475                 480
```

```
Leu Phe Pro Pro Ser Ser Glu Glu Leu Gln Ala Asn Lys Ala Thr Leu
                485                 490                 495

Val Cys Leu Ile Ser Asp Phe Tyr Pro Gly Ala Val Thr Val Ala Trp
            500                 505                 510

Lys Ala Asp Gly Ser Pro Val Lys Ala Gly Val Glu Thr Thr Lys Pro
        515                 520                 525

Ser Lys Gln Ser Asn Asn Lys Tyr Ala Ala Ser Ser Tyr Leu Ser Leu
    530                 535                 540

Thr Pro Glu Gln Trp Lys Ser His Arg Ser Tyr Ser Cys Gln Val Thr
545                 550                 555                 560

His Glu Gly Ser Thr Val Glu Lys Thr Val Ala Pro Thr Glu Cys Ser
                565                 570                 575

Pro Ile Lys Thr Asp Val Ile Thr Met Asp Pro Lys Asp Asn Cys Ser
            580                 585                 590

Lys Asp Ala Asn Asp Thr Leu Leu Leu Gln Leu Thr Asn Thr Ser Ala
        595                 600                 605

Tyr Tyr Met Tyr Leu Leu Leu Leu Lys Ser Val Val Tyr Phe Ala
    610                 615                 620

Ile Ile Thr Cys Cys Leu Leu Arg Arg Thr Ala Phe Cys Cys Asn Gly
625                 630                 635                 640

Glu Lys Ser

<210> SEQ ID NO 37
<211> LENGTH: 364
<212> TYPE: PRT
<213> ORGANISM: Artificial Sequence
<220> FEATURE:
<223> OTHER INFORMATION: Synthetic Construct

<400> SEQUENCE: 37

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Gly Ser Gly Gly Gly Gly
        115                 120                 125

Ser Leu Glu Met Ala Glu Val Gln Leu Val Gln Ser Gly Ala Glu Val
    130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190
```

```
Tyr Ser Pro Ser Phe Gln Gly Gln Val Thr Ile Ser Ala Asp Lys Ser
            195                 200                 205

Ile Ser Thr Ala Tyr Leu Gln Trp Ser Ser Leu Lys Ala Ser Asp Thr
    210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Ala Ala
                245                 250                 255

Ala Ile Glu Val Met Tyr Pro Pro Tyr Leu Asp Asn Glu Lys Ser
            260                 265                 270

Asn Gly Thr Ile Ile His Val Lys Gly Lys His Leu Cys Pro Ser Pro
            275                 280                 285

Leu Phe Pro Gly Pro Ser Lys Pro Phe Trp Val Leu Val Val Val Gly
            290                 295                 300

Gly Val Leu Ala Cys Tyr Ser Leu Leu Val Thr Val Ala Phe Ile Ile
305                 310                 315                 320

Phe Trp Val Arg Ser Lys Arg Ser Arg Leu Leu His Ser Asp Tyr Met
                325                 330                 335

Asn Met Thr Pro Arg Arg Pro Gly Pro Thr Arg Lys His Tyr Gln Pro
            340                 345                 350

Tyr Ala Pro Pro Arg Asp Phe Ala Ala Tyr Arg Ser
            355                 360

<210> SEQ ID NO 38
<211> LENGTH: 359
<212> TYPE: PRT
<213> ORGANISM: Artificial Sequence
<220> FEATURE:
<223> OTHER INFORMATION: Synthetic Construct

<400> SEQUENCE: 38

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
                35                  40                  45

Met Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
                100                 105                 110

Arg Gly Gly Gly Ser Gly Gly Gly Gly Ser Gly Gly Gly Gly Ser
            115                 120                 125

Leu Glu Met Ala Glu Val Gln Leu Val Gln Ser Gly Ala Glu Met Lys
            130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175

Leu Glu Trp Met Gly Thr Ile Tyr Pro Asp Asp Ser Asp Thr Arg Tyr
                180                 185                 190
```

```
Gly Pro Ala Phe Gln Gly Gln Val Thr Ile Ser Ala Asp Lys Ser Ile
            195                 200                 205

Ser Thr Ala Tyr Leu Gln Trp Ser Ser Leu Lys Ala Ser Asp Thr Ala
        210                 215                 220

Met Tyr Tyr Cys Ala Arg Asp Ser Tyr Gly Ile Asp Val Trp Gly
225                 230                 235                 240

Gln Gly Thr Leu Val Thr Val Ser Ser Ala Ala Ile Glu Val Met
                245                 250                 255

Tyr Pro Pro Pro Tyr Leu Asp Asn Glu Lys Ser Asn Gly Thr Ile Ile
            260                 265                 270

His Val Lys Gly Lys His Leu Cys Pro Ser Pro Leu Phe Pro Gly Pro
        275                 280                 285

Ser Lys Pro Phe Trp Val Leu Val Val Gly Gly Val Leu Ala Cys
    290                 295                 300

Tyr Ser Leu Leu Val Thr Val Ala Phe Ile Ile Phe Trp Val Arg Ser
305                 310                 315                 320

Lys Arg Ser Arg Leu Leu His Ser Asp Tyr Met Asn Met Thr Pro Arg
                325                 330                 335

Arg Pro Gly Pro Thr Arg Lys His Tyr Gln Pro Tyr Ala Pro Pro Arg
            340                 345                 350

Asp Phe Ala Ala Tyr Arg Ser
            355

<210> SEQ ID NO 39
<211> LENGTH: 451
<212> TYPE: PRT
<213> ORGANISM: Artificial Sequence
<220> FEATURE:
<223> OTHER INFORMATION: Synthetic Construct

<400> SEQUENCE: 39

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Met Gly Ser Ser Leu Tyr Ala Ser Ser Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 40
<211> LENGTH: 217
<212> TYPE: PRT
<213> ORGANISM: Artificial Sequence
<220> FEATURE:
<223> OTHER INFORMATION: Synthetic Construct

<400> SEQUENCE: 40

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

```
Leu Ser Gly Tyr Val Phe Gly Thr Gly Thr Lys Val Thr Val Leu Gly
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
                195                 200                 205

Lys Thr Val Ala Pro Thr Glu Cys Ser
            210                 215

<210> SEQ ID NO 41
<211> LENGTH: 447
<212> TYPE: PRT
<213> ORGANISM: Artificial Sequence
<220> FEATURE:
<223> OTHER INFORMATION: Synthetic Construct

<400> SEQUENCE: 41

Glu Val Gln Leu Val Gln Ser Gly Ala Glu Met Lys Lys Pro Gly Glu
1               5                   10                  15

Ser Leu Lys Ile Ser Cys Lys Gly Ser Gly Tyr Asn Phe Ala Ser Tyr
                20                  25                  30

Trp Val Gly Trp Val Arg Gln Met Pro Gly Lys Gly Leu Glu Trp Met
            35                  40                  45

Gly Thr Ile Tyr Pro Asp Asp Ser Asp Thr Arg Tyr Gly Pro Ala Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Ser Tyr Tyr Gly Ile Asp Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
            210                 215                 220

Thr Cys Pro Pro Cys Pro Ala Pro Glu Leu Leu Gly Gly Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
                435                 440                 445

<210> SEQ ID NO 42
<211> LENGTH: 216
<212> TYPE: PRT
<213> ORGANISM: Artificial Sequence
<220> FEATURE:
<223> OTHER INFORMATION: Synthetic Construct

<400> SEQUENCE: 42

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
                35                  40                  45

Met Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Gln
                100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160
```

```
Ala Gly Val Glu Thr Thr Lys Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
210                 215

<210> SEQ ID NO 43
<211> LENGTH: 750
<212> TYPE: PRT
<213> ORGANISM: Artificial Sequence
<220> FEATURE:
<223> OTHER INFORMATION: Synthetic Construct

<400> SEQUENCE: 43

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
            85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
130                 135                 140

Glu Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
            165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
        210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
            245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
        290                 295                 300
```

```
Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
            325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
            355                 360                 365

Asp Arg Tyr Val Ile Leu Gly His Arg Asp Ser Trp Val Phe Gly
            370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
            405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
            485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
            530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
            565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
            610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
            645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
```

```
                    725                 730                 735

Phe Thr Val Gln Ala Ala Glu Thr Leu Ser Glu Val Ala
            740                 745                 750

<210> SEQ ID NO 44
<211> LENGTH: 707
<212> TYPE: PRT
<213> ORGANISM: Artificial Sequence
<220> FEATURE:
<223> OTHER INFORMATION: Synthetic Construct

<400> SEQUENCE: 44

Lys Ser Ser Asn Glu Ala Thr Asn Ile Thr Pro Lys His Asn Met Lys
1               5                   10                  15

Ala Phe Leu Asp Glu Leu Lys Ala Glu Asn Ile Lys Lys Phe Leu Tyr
            20                  25                  30

Asn Phe Thr Gln Ile Pro His Leu Ala Gly Thr Glu Gln Asn Phe Gln
        35                  40                  45

Leu Ala Lys Gln Ile Gln Ser Gln Trp Lys Glu Phe Gly Leu Asp Ser
    50                  55                  60

Val Glu Leu Ala His Tyr Asp Val Leu Leu Ser Tyr Pro Asn Lys Thr
65                  70                  75                  80

His Pro Asn Tyr Ile Ser Ile Asn Glu Asp Gly Asn Glu Ile Phe
                85                  90                  95

Asn Thr Ser Leu Phe Glu Pro Pro Pro Gly Tyr Glu Asn Val Ser
            100                 105                 110

Asp Ile Val Pro Pro Phe Ser Ala Phe Ser Pro Gln Gly Met Pro Glu
        115                 120                 125

Gly Asp Leu Val Tyr Val Asn Tyr Ala Arg Thr Glu Asp Phe Phe Lys
    130                 135                 140

Leu Glu Arg Asp Met Lys Ile Asn Cys Ser Gly Lys Ile Val Ile Ala
145                 150                 155                 160

Arg Tyr Gly Lys Val Phe Arg Gly Asn Lys Val Lys Asn Ala Gln Leu
                165                 170                 175

Ala Gly Ala Lys Gly Val Ile Leu Tyr Ser Asp Pro Ala Asp Tyr Phe
            180                 185                 190

Ala Pro Gly Val Lys Ser Tyr Pro Asp Gly Trp Asn Leu Pro Gly Gly
        195                 200                 205

Gly Val Gln Arg Gly Asn Ile Leu Asn Leu Asn Gly Ala Gly Asp Pro
    210                 215                 220

Leu Thr Pro Gly Tyr Pro Ala Asn Glu Tyr Ala Tyr Arg Arg Gly Ile
225                 230                 235                 240

Ala Glu Ala Val Gly Leu Pro Ser Ile Pro Val His Pro Ile Gly Tyr
                245                 250                 255

Tyr Asp Ala Gln Lys Leu Leu Glu Lys Met Gly Gly Ser Ala Pro Pro
            260                 265                 270

Asp Ser Ser Trp Arg Gly Ser Leu Lys Val Pro Tyr Asn Val Gly Pro
        275                 280                 285

Gly Phe Thr Gly Asn Phe Ser Thr Gln Lys Val Lys Met His Ile His
    290                 295                 300

Ser Thr Asn Glu Val Thr Arg Ile Tyr Asn Val Ile Gly Thr Leu Arg
305                 310                 315                 320

Gly Ala Val Glu Pro Asp Arg Tyr Val Ile Leu Gly Gly His Arg Asp
                325                 330                 335

Ser Trp Val Phe Gly Gly Ile Asp Pro Gln Ser Gly Ala Ala Val Val
```

340                 345                 350
His Glu Ile Val Arg Ser Phe Gly Thr Leu Lys Lys Glu Gly Trp Arg
                355                 360                 365

Pro Arg Arg Thr Ile Leu Phe Ala Ser Trp Asp Ala Glu Glu Phe Gly
370                 375                 380

Leu Leu Gly Ser Thr Glu Trp Ala Glu Glu Asn Ser Arg Leu Leu Gln
385                 390                 395                 400

Glu Arg Gly Val Ala Tyr Ile Asn Ala Asp Ser Ser Ile Glu Gly Asn
                405                 410                 415

Tyr Thr Leu Arg Val Asp Cys Thr Pro Leu Met Tyr Ser Leu Val His
                420                 425                 430

Asn Leu Thr Lys Glu Leu Lys Ser Pro Asp Glu Gly Phe Glu Gly Lys
                435                 440                 445

Ser Leu Tyr Glu Ser Trp Thr Lys Lys Ser Pro Ser Pro Glu Phe Ser
                450                 455                 460

Gly Met Pro Arg Ile Ser Lys Leu Gly Ser Gly Asn Asp Phe Glu Val
465                 470                 475                 480

Phe Phe Gln Arg Leu Gly Ile Ala Ser Gly Arg Ala Arg Tyr Thr Lys
                485                 490                 495

Asn Trp Glu Thr Asn Lys Phe Ser Gly Tyr Pro Leu Tyr His Ser Val
                500                 505                 510

Tyr Glu Thr Tyr Glu Leu Val Glu Lys Phe Tyr Asp Pro Met Phe Lys
                515                 520                 525

Tyr His Leu Thr Val Ala Gln Val Arg Gly Gly Met Val Phe Glu Leu
                530                 535                 540

Ala Asn Ser Ile Val Leu Pro Phe Asp Cys Arg Asp Tyr Ala Val Val
545                 550                 555                 560

Leu Arg Lys Tyr Ala Asp Lys Ile Tyr Ser Ile Ser Met Lys His Pro
                565                 570                 575

Gln Glu Met Lys Thr Tyr Ser Val Ser Phe Asp Ser Leu Phe Ser Ala
                580                 585                 590

Val Lys Asn Phe Thr Glu Ile Ala Ser Lys Phe Ser Glu Arg Leu Gln
                595                 600                 605

Asp Phe Asp Lys Ser Asn Pro Ile Val Leu Arg Met Met Asn Asp Gln
                610                 615                 620

Leu Met Phe Leu Glu Arg Ala Phe Ile Asp Pro Leu Gly Leu Pro Asp
625                 630                 635                 640

Arg Pro Phe Tyr Arg His Val Ile Tyr Ala Pro Ser Ser His Asn Lys
                645                 650                 655

Tyr Ala Gly Glu Ser Phe Pro Gly Ile Tyr Asp Ala Leu Phe Asp Ile
                660                 665                 670

Glu Ser Lys Val Asp Pro Ser Lys Ala Trp Gly Glu Val Lys Arg Gln
                675                 680                 685

Ile Tyr Val Ala Ala Phe Thr Val Gln Ala Ala Glu Thr Leu Ser
                690                 695                 700

Glu Val Ala
705

<210> SEQ ID NO 45
<211> LENGTH: 476
<212> TYPE: PRT
<213> ORGANISM: Artificial Sequence
<220> FEATURE:
<223> OTHER INFORMATION: Synthetic Construct: Clone A-CAR

```
<400> SEQUENCE: 45

Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
            115                 120                 125

Ser Leu Glu Met Ala Glu Val Gln Leu Val Gln Ser Gly Ala Glu Val
    130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205

Ile Ser Thr Ala Tyr Leu Gln Trp Ser Ser Leu Lys Ala Ser Asp Thr
    210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Ala Ala
                245                 250                 255

Ala Ile Glu Val Met Tyr Pro Pro Pro Tyr Leu Asp Asn Glu Lys Ser
            260                 265                 270

Asn Gly Thr Ile Ile His Val Lys Gly Lys His Leu Cys Pro Ser Pro
        275                 280                 285

Leu Phe Pro Gly Pro Ser Lys Pro Phe Trp Val Leu Val Val Val Gly
    290                 295                 300

Gly Val Leu Ala Cys Tyr Ser Leu Leu Val Thr Val Ala Phe Ile Ile
305                 310                 315                 320

Phe Trp Val Arg Ser Lys Arg Ser Arg Leu Leu His Ser Asp Tyr Met
                325                 330                 335

Asn Met Thr Pro Arg Arg Pro Gly Pro Thr Arg Lys His Tyr Gln Pro
            340                 345                 350

Tyr Ala Pro Pro Arg Asp Phe Ala Ala Tyr Arg Ser Arg Val Lys Phe
        355                 360                 365

Ser Arg Ser Ala Asp Ala Pro Ala Tyr Gln Gln Gly Gln Asn Gln Leu
    370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Arg Arg Lys
                405                 410                 415
```

```
Asn Pro Gln Glu Gly Leu Tyr Asn Glu Leu Gln Lys Asp Lys Met Ala
                420                 425                 430

Glu Ala Tyr Ser Glu Ile Gly Met Lys Gly Glu Arg Arg Arg Gly Lys
            435                 440                 445

Gly His Asp Gly Leu Tyr Gln Gly Leu Ser Thr Ala Thr Lys Asp Thr
        450                 455                 460

Tyr Asp Ala Leu His Met Gln Ala Leu Pro Pro Arg
465                 470                 475

<210> SEQ ID NO 46
<211> LENGTH: 471
<212> TYPE: PRT
<213> ORGANISM: Artificial Sequence
<220> FEATURE:
<223> OTHER INFORMATION: Synthetic Construct: Clone B-CAR

<400> SEQUENCE: 46

Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Met Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
            100                 105                 110

Arg Gly Gly Gly Gly Ser Gly Gly Gly Ser Gly Gly Gly Gly Ser
        115                 120                 125

Leu Glu Met Ala Glu Val Gln Leu Val Gln Ser Gly Ala Glu Met Lys
    130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175

Leu Glu Trp Met Gly Thr Ile Tyr Pro Asp Asp Ser Asp Thr Arg Tyr
            180                 185                 190

Gly Pro Ala Phe Gln Gly Gln Val Thr Ile Ser Ala Asp Lys Ser Ile
        195                 200                 205

Ser Thr Ala Tyr Leu Gln Trp Ser Ser Leu Lys Ala Ser Asp Thr Ala
    210                 215                 220

Met Tyr Tyr Cys Ala Arg Asp Ser Tyr Gly Ile Asp Val Trp Gly
225                 230                 235                 240

Gln Gly Thr Leu Val Thr Val Ser Ser Ala Ala Ala Ile Glu Val Met
                245                 250                 255

Tyr Pro Pro Pro Tyr Leu Asp Asn Glu Lys Ser Asn Gly Thr Ile Ile
            260                 265                 270

His Val Lys Gly Lys His Leu Cys Pro Ser Pro Leu Phe Pro Gly Pro
        275                 280                 285

Ser Lys Pro Phe Trp Val Leu Val Val Val Gly Gly Val Leu Ala Cys
    290                 295                 300
```

```
Tyr Ser Leu Leu Val Thr Val Ala Phe Ile Ile Phe Trp Val Arg Ser
305                 310                 315                 320

Lys Arg Ser Arg Leu Leu His Ser Asp Tyr Met Asn Met Thr Pro Arg
                325                 330                 335

Arg Pro Gly Pro Thr Arg Lys His Tyr Gln Pro Tyr Ala Pro Pro Arg
            340                 345                 350

Asp Phe Ala Ala Tyr Arg Ser Arg Val Lys Phe Ser Arg Ser Ala Asp
        355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470

<210> SEQ ID NO 47
<211> LENGTH: 907
<212> TYPE: PRT
<213> ORGANISM: Artificial Sequence
<220> FEATURE:
<223> OTHER INFORMATION: Synthetic Construct: Bivalent Anti-PSMA Clone
      A caTCR with 1 scFv and 1 Fab (a.k.a. "Ax2-caTCR-1" or "Bivalent
      Clone A caTCR-1")

<400> SEQUENCE: 47

Met Glu Thr Asp Thr Leu Leu Leu Trp Val Leu Leu Leu Trp Val Pro
1               5                   10                  15

Gly Ser Thr Gly Gln Ser Val Leu Thr Gln Pro Pro Ser Val Ser Gly
            20                  25                  30

Ala Pro Gly Gln Arg Val Thr Ile Ser Cys Thr Gly Ser Ser Ser Asn
        35                  40                  45

Ile Gly Ala Gly Tyr Asp Val His Trp Tyr Gln Gln Leu Pro Gly Thr
    50                  55                  60

Ala Pro Lys Leu Leu Ile Tyr Gly Asn Ser Asn Arg Pro Ser Gly Val
65                  70                  75                  80

Pro Asp Arg Phe Ser Gly Ser Lys Ser Gly Thr Ser Ala Ser Leu Ala
                85                  90                  95

Ile Thr Gly Leu Gln Ala Glu Asp Glu Ala Asp Tyr Tyr Cys Gln Ser
            100                 105                 110

Tyr Asp Ser Ser Leu Ser Gly Tyr Val Phe Gly Thr Gly Thr Lys Val
        115                 120                 125

Thr Val Leu Gly Ser Arg Gly Gly Gly Ser Gly Gly Gly Gly Ser
    130                 135                 140

Gly Gly Gly Gly Ser Leu Glu Met Ala Glu Val Gln Leu Val Gln Ser
145                 150                 155                 160

Gly Ala Glu Val Lys Lys Pro Gly Glu Ser Leu Lys Ile Ser Cys Lys
                165                 170                 175
```

```
Gly Ser Gly Tyr Ser Phe Thr Ser Tyr Trp Ile Trp Val Arg Gln
            180                 185                 190

Met Pro Gly Lys Gly Leu Glu Trp Met Gly Ile Ile Tyr Pro Gly Asp
            195                 200                 205

Ser Asp Thr Arg Tyr Ser Pro Ser Phe Gln Gly Gln Val Thr Ile Ser
            210                 215                 220

Ala Asp Lys Ser Ile Ser Thr Ala Tyr Leu Gln Trp Ser Ser Leu Lys
225                 230                 235                 240

Ala Ser Asp Thr Ala Met Tyr Tyr Cys Ala Arg Ser Met Gly Ser Ser
            245                 250                 255

Leu Tyr Ala Ser Ser Asp Val Trp Gly Gln Gly Thr Leu Val Thr Val
            260                 265                 270

Ser Ser Gly Gly Gly Gly Ser Glu Val Gln Leu Val Gln Ser Gly Ala
            275                 280                 285

Glu Val Lys Lys Pro Gly Glu Ser Leu Lys Ile Ser Cys Lys Gly Ser
            290                 295                 300

Gly Tyr Ser Phe Thr Ser Tyr Trp Ile Gly Trp Val Arg Gln Met Pro
305                 310                 315                 320

Gly Lys Gly Leu Glu Trp Met Gly Ile Ile Tyr Pro Gly Asp Ser Asp
            325                 330                 335

Thr Arg Tyr Ser Pro Ser Phe Gln Gly Gln Val Thr Ile Ser Ala Asp
            340                 345                 350

Lys Ser Ile Ser Thr Ala Tyr Leu Gln Trp Ser Ser Leu Lys Ala Ser
            355                 360                 365

Asp Thr Ala Met Tyr Tyr Cys Ala Arg Ser Met Gly Ser Ser Leu Tyr
            370                 375                 380

Ala Ser Ser Asp Val Trp Gly Gln Gly Thr Leu Val Thr Val Ser Ser
385                 390                 395                 400

Ala Ser Thr Lys Gly Pro Ser Val Phe Pro Leu Ala Pro Ser Ser Lys
            405                 410                 415

Ser Thr Ser Gly Gly Thr Ala Ala Leu Gly Cys Leu Val Lys Asp Tyr
            420                 425                 430

Phe Pro Glu Pro Val Thr Val Ser Trp Asn Ser Gly Ala Leu Thr Ser
            435                 440                 445

Gly Val His Thr Phe Pro Ala Val Leu Gln Ser Ser Gly Leu Tyr Ser
            450                 455                 460

Leu Ser Ser Val Val Thr Val Pro Ser Ser Ser Leu Gly Thr Gln Thr
465                 470                 475                 480

Tyr Ile Cys Asn Val Asn His Lys Pro Ser Asn Thr Lys Val Asp Lys
            485                 490                 495

Arg Val Glu Pro Lys Ser Cys Glu Val Lys Thr Asp Ser Thr Asp His
            500                 505                 510

Val Lys Pro Lys Glu Thr Glu Asn Thr Lys Gln Pro Ser Lys Ser Cys
            515                 520                 525

His Lys Pro Lys Ala Ile Val His Thr Glu Lys Val Asn Met Met Ser
            530                 535                 540

Leu Thr Val Leu Gly Leu Arg Met Leu Phe Ala Lys Thr Val Ala Val
545                 550                 555                 560

Asn Phe Leu Leu Thr Ala Lys Leu Phe Phe Leu Arg Ala Lys Arg Ser
            565                 570                 575

Gly Ser Gly Ala Pro Val Lys Gln Thr Leu Asn Phe Asp Leu Leu Lys
            580                 585                 590

Leu Ala Gly Asp Val Glu Ser Asn Pro Gly Pro Met Glu Thr Asp Thr
```

```
                595                 600                 605
Leu Leu Leu Trp Val Leu Leu Trp Val Pro Gly Ser Thr Gly Gln
        610                 615                 620

Ser Val Leu Thr Gln Pro Pro Ser Val Ser Gly Ala Pro Gly Gln Arg
625                 630                 635                 640

Val Thr Ile Ser Cys Thr Gly Ser Ser Asn Ile Gly Ala Gly Tyr
                645                 650                 655

Asp Val His Trp Tyr Gln Gln Leu Pro Gly Thr Ala Pro Lys Leu Leu
                660                 665                 670

Ile Tyr Gly Asn Ser Asn Arg Pro Ser Gly Val Pro Asp Arg Phe Ser
        675                 680                 685

Gly Ser Lys Ser Gly Thr Ser Ala Ser Leu Ala Ile Thr Gly Leu Gln
        690                 695                 700

Ala Glu Asp Glu Ala Asp Tyr Tyr Cys Gln Ser Tyr Asp Ser Ser Leu
705                 710                 715                 720

Ser Gly Tyr Val Phe Gly Thr Gly Thr Lys Val Thr Val Leu Gly Gln
                725                 730                 735

Pro Lys Ala Asn Pro Thr Val Thr Leu Phe Pro Pro Ser Ser Glu Glu
            740                 745                 750

Leu Gln Ala Asn Lys Ala Thr Leu Val Cys Leu Ile Ser Asp Phe Tyr
        755                 760                 765

Pro Gly Ala Val Thr Val Ala Trp Lys Ala Asp Gly Ser Pro Val Lys
770                 775                 780

Ala Gly Val Glu Thr Thr Lys Pro Ser Lys Gln Ser Asn Asn Lys Tyr
785                 790                 795                 800

Ala Ala Ser Ser Tyr Leu Ser Leu Thr Pro Glu Gln Trp Lys Ser His
                805                 810                 815

Arg Ser Tyr Ser Cys Gln Val Thr His Glu Gly Ser Thr Val Glu Lys
            820                 825                 830

Thr Val Ala Pro Thr Glu Cys Ser Pro Ile Lys Thr Asp Val Ile Thr
                835                 840                 845

Met Asp Pro Lys Asp Asn Cys Ser Lys Asp Ala Asn Asp Thr Leu Leu
850                 855                 860

Leu Gln Leu Thr Asn Thr Ser Ala Tyr Tyr Met Tyr Leu Leu Leu Leu
865                 870                 875                 880

Leu Lys Ser Val Val Tyr Phe Ala Ile Ile Thr Cys Cys Leu Leu Arg
                885                 890                 895

Arg Thr Ala Phe Cys Cys Asn Gly Glu Lys Ser
            900                 905

<210> SEQ ID NO 48
<211> LENGTH: 901
<212> TYPE: PRT
<213> ORGANISM: Artificial Sequence
<220> FEATURE:
<223> OTHER INFORMATION: Synthetic Construct: Bivalent Anti-PSMA Clone
      A caTCR with 2 Fabs (a.k.a. "Ax2-caTCR-2" or "Bivalent Clone A
      caTCR-2")

<400> SEQUENCE: 48

Met Glu Thr Asp Thr Leu Leu Leu Trp Val Leu Leu Leu Trp Val Pro
1               5                   10                  15

Gly Ser Thr Gly Glu Val Gln Leu Val Gln Ser Gly Ala Glu Val Lys
            20                  25                  30

Lys Pro Gly Glu Ser Leu Lys Ile Ser Cys Lys Gly Ser Gly Tyr Ser
        35                  40                  45
```

-continued

```
Phe Thr Ser Tyr Trp Ile Gly Trp Val Arg Gln Met Pro Gly Lys Gly
     50                  55                  60
Leu Glu Trp Met Gly Ile Ile Tyr Pro Gly Asp Ser Asp Thr Arg Tyr
65                  70                  75                  80
Ser Pro Ser Phe Gln Gly Gln Val Thr Ile Ser Ala Asp Lys Ser Ile
                 85                  90                  95
Ser Thr Ala Tyr Leu Gln Trp Ser Ser Leu Lys Ala Ser Asp Thr Ala
                100                 105                 110
Met Tyr Tyr Cys Ala Arg Ser Met Gly Ser Ser Leu Tyr Ala Ser Ser
             115                 120                 125
Asp Val Trp Gly Gln Gly Thr Leu Val Thr Val Ser Ser Gly Gly Gly
         130                 135                 140
Gly Ser Gly Gly Gly Gly Ser Glu Val Gln Leu Val Gln Ser Gly Ala
145                 150                 155                 160
Glu Val Lys Lys Pro Gly Glu Ser Leu Lys Ile Ser Cys Lys Gly Ser
                 165                 170                 175
Gly Tyr Ser Phe Thr Ser Tyr Trp Ile Gly Trp Val Arg Gln Met Pro
                180                 185                 190
Gly Lys Gly Leu Glu Trp Met Gly Ile Ile Tyr Pro Gly Asp Ser Asp
             195                 200                 205
Thr Arg Tyr Ser Pro Ser Phe Gln Gly Gln Val Thr Ile Ser Ala Asp
         210                 215                 220
Lys Ser Ile Ser Thr Ala Tyr Leu Gln Trp Ser Ser Leu Lys Ala Ser
225                 230                 235                 240
Asp Thr Ala Met Tyr Tyr Cys Ala Arg Ser Met Gly Ser Ser Leu Tyr
                 245                 250                 255
Ala Ser Ser Asp Val Trp Gly Gln Gly Thr Leu Val Thr Val Ser Ser
                260                 265                 270
Ala Ser Thr Lys Gly Pro Ser Val Phe Pro Leu Ala Pro Ser Ser Lys
             275                 280                 285
Ser Thr Ser Gly Gly Thr Ala Ala Leu Gly Cys Leu Val Lys Asp Tyr
         290                 295                 300
Phe Pro Glu Pro Val Thr Val Ser Trp Asn Ser Gly Ala Leu Thr Ser
305                 310                 315                 320
Gly Val His Thr Phe Pro Ala Val Leu Gln Ser Ser Gly Leu Tyr Ser
                 325                 330                 335
Leu Ser Ser Val Val Thr Val Pro Ser Ser Ser Leu Gly Thr Gln Thr
                340                 345                 350
Tyr Ile Cys Asn Val Asn His Lys Pro Ser Asn Thr Lys Val Asp Lys
             355                 360                 365
Arg Val Glu Pro Lys Ser Cys Glu Val Lys Thr Asp Ser Thr Asp His
         370                 375                 380
Val Lys Pro Lys Glu Thr Glu Asn Thr Lys Gln Pro Ser Lys Ser Cys
385                 390                 395                 400
His Lys Pro Lys Ala Ile Val His Thr Glu Lys Val Asn Met Met Ser
                 405                 410                 415
Leu Thr Val Leu Gly Leu Arg Met Leu Phe Ala Lys Thr Val Ala Val
                420                 425                 430
Asn Phe Leu Leu Thr Ala Lys Leu Phe Phe Leu Arg Ala Lys Arg Ser
             435                 440                 445
Gly Ser Gly Ala Pro Val Lys Gln Thr Leu Asn Phe Asp Leu Leu Lys
         450                 455                 460
```

```
Leu Ala Gly Asp Val Glu Ser Asn Pro Gly Pro Met Glu Thr Asp Thr
465                 470                 475                 480

Leu Leu Leu Trp Val Leu Leu Trp Val Pro Gly Ser Thr Gly Gln
            485                 490                 495

Ser Val Leu Thr Gln Pro Pro Ser Val Ser Gly Ala Pro Gly Gln Arg
            500                 505                 510

Val Thr Ile Ser Cys Thr Gly Ser Ser Ser Asn Ile Gly Ala Gly Tyr
            515                 520                 525

Asp Val His Trp Tyr Gln Gln Leu Pro Gly Thr Ala Pro Lys Leu Leu
            530                 535                 540

Ile Tyr Gly Asn Ser Asn Arg Pro Ser Gly Val Pro Asp Arg Phe Ser
545                 550                 555                 560

Gly Ser Lys Ser Gly Thr Ser Ala Ser Leu Ala Ile Thr Gly Leu Gln
            565                 570                 575

Ala Glu Asp Glu Ala Asp Tyr Tyr Cys Gln Ser Tyr Asp Ser Ser Leu
            580                 585                 590

Ser Gly Tyr Val Phe Gly Thr Gly Thr Lys Val Thr Val Leu Gly Gly
            595                 600                 605

Gly Gly Gly Ser Gly Gly Gly Gly Ser Gln Ser Val Leu Thr Gln Pro
            610                 615                 620

Pro Ser Val Ser Gly Ala Pro Gly Gln Arg Val Thr Ile Ser Cys Thr
625                 630                 635                 640

Gly Ser Ser Ser Asn Ile Gly Ala Gly Tyr Asp Val His Trp Tyr Gln
                    645                 650                 655

Gln Leu Pro Gly Thr Ala Pro Lys Leu Leu Ile Tyr Gly Asn Ser Asn
            660                 665                 670

Arg Pro Ser Gly Val Pro Asp Arg Phe Ser Gly Ser Lys Ser Gly Thr
            675                 680                 685

Ser Ala Ser Leu Ala Ile Thr Gly Leu Gln Ala Glu Asp Glu Ala Asp
            690                 695                 700

Tyr Tyr Cys Gln Ser Tyr Asp Ser Ser Leu Ser Gly Tyr Val Phe Gly
705                 710                 715                 720

Thr Gly Thr Lys Val Thr Val Leu Gly Gln Pro Lys Ala Asn Pro Thr
            725                 730                 735

Val Thr Leu Phe Pro Pro Ser Ser Glu Glu Leu Gln Ala Asn Lys Ala
            740                 745                 750

Thr Leu Val Cys Leu Ile Ser Asp Phe Tyr Pro Gly Ala Val Thr Val
            755                 760                 765

Ala Trp Lys Ala Asp Gly Ser Pro Val Lys Ala Gly Val Glu Thr Thr
            770                 775                 780

Lys Pro Ser Lys Gln Ser Asn Asn Lys Tyr Ala Ala Ser Ser Tyr Leu
785                 790                 795                 800

Ser Leu Thr Pro Glu Gln Trp Lys Ser His Arg Ser Tyr Ser Cys Gln
            805                 810                 815

Val Thr His Glu Gly Ser Thr Val Glu Lys Thr Val Ala Pro Thr Glu
            820                 825                 830

Cys Ser Pro Ile Lys Thr Asp Val Ile Thr Met Asp Pro Lys Asp Asn
            835                 840                 845

Cys Ser Lys Asp Ala Asn Asp Thr Leu Leu Gln Leu Thr Asn Thr
            850                 855                 860

Ser Ala Tyr Tyr Met Tyr Leu Leu Leu Leu Lys Ser Val Val Tyr
865                 870                 875                 880

Phe Ala Ile Ile Thr Cys Cys Leu Leu Arg Arg Thr Ala Phe Cys Cys
```

```
                        885                 890                 895

Asn Gly Glu Lys Ser
            900

<210> SEQ ID NO 49
<211> LENGTH: 897
<212> TYPE: PRT
<213> ORGANISM: Artificial Sequence
<220> FEATURE:
<223> OTHER INFORMATION: Synthetic Construct: Bivalent Anti-PSMA Clone
      B caTCR with 1 scFv and 1 Fab (a.k.a. "Bx2-caTCR-1" or "Bivalent
      Clone B caTCR-1")

<400> SEQUENCE: 49

Met Glu Thr Asp Thr Leu Leu Leu Trp Val Leu Leu Leu Trp Val Pro
1               5                   10                  15

Gly Ser Thr Gly Gln Ala Val Leu Thr Gln Pro Pro Ser Ala Ser Gly
            20                  25                  30

Thr Pro Gly Gln Arg Val Thr Ile Ser Cys Ser Gly Ser Ser Ser Asn
        35                  40                  45

Ile Gly Ser Asn Thr Val Asn Trp Tyr Gln Gln Leu Pro Gly Thr Ala
    50                  55                  60

Pro Lys Leu Leu Met Tyr Ser Asn Asn Gln Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Gln Ser Glu Asp Glu Ala Asp Tyr Tyr Cys Ala Ala Trp
            100                 105                 110

Asp Asp Ser Leu Asn Gly Tyr Val Phe Gly Thr Gly Thr Lys Val Thr
        115                 120                 125

Val Leu Gly Ser Arg Gly Gly Gly Ser Gly Gly Gly Gly Ser Gly
    130                 135                 140

Gly Gly Gly Ser Leu Glu Met Ala Glu Val Gln Leu Val Gln Ser Gly
145                 150                 155                 160

Ala Glu Met Lys Lys Pro Gly Glu Ser Leu Lys Ile Ser Cys Lys Gly
                165                 170                 175

Ser Gly Tyr Asn Phe Ala Ser Tyr Trp Val Gly Trp Val Arg Gln Met
            180                 185                 190

Pro Gly Lys Gly Leu Glu Trp Met Gly Thr Ile Tyr Pro Asp Asp Ser
        195                 200                 205

Asp Thr Arg Tyr Gly Pro Ala Phe Gln Gly Gln Val Thr Ile Ser Ala
    210                 215                 220

Asp Lys Ser Ile Ser Thr Ala Tyr Leu Gln Trp Ser Ser Leu Lys Ala
225                 230                 235                 240

Ser Asp Thr Ala Met Tyr Tyr Cys Ala Arg Asp Ser Tyr Tyr Gly Ile
                245                 250                 255

Asp Val Trp Gly Gln Gly Thr Leu Val Thr Val Ser Ser Gly Gly Gly
            260                 265                 270

Gly Ser Glu Val Gln Leu Val Gln Ser Gly Ala Glu Met Lys Lys Pro
        275                 280                 285

Gly Glu Ser Leu Lys Ile Ser Cys Lys Gly Ser Gly Tyr Asn Phe Ala
    290                 295                 300

Ser Tyr Trp Val Gly Trp Val Arg Gln Met Pro Gly Lys Gly Leu Glu
305                 310                 315                 320

Trp Met Gly Thr Ile Tyr Pro Asp Asp Ser Asp Thr Arg Tyr Gly Pro
                325                 330                 335
```

```
Ala Phe Gln Gly Gln Val Thr Ile Ser Ala Asp Lys Ser Ile Ser Thr
                340                 345                 350

Ala Tyr Leu Gln Trp Ser Ser Leu Lys Ala Ser Asp Thr Ala Met Tyr
                355                 360                 365

Tyr Cys Ala Arg Asp Ser Tyr Tyr Gly Ile Asp Val Trp Gly Gln Gly
                370                 375                 380

Thr Leu Val Thr Val Ser Ser Ala Ser Thr Lys Gly Pro Ser Val Phe
385                 390                 395                 400

Pro Leu Ala Pro Ser Ser Lys Ser Thr Ser Gly Gly Thr Ala Ala Leu
                405                 410                 415

Gly Cys Leu Val Lys Asp Tyr Phe Pro Glu Pro Val Thr Val Ser Trp
                420                 425                 430

Asn Ser Gly Ala Leu Thr Ser Gly Val His Thr Phe Pro Ala Val Leu
                435                 440                 445

Gln Ser Ser Gly Leu Tyr Ser Leu Ser Ser Val Val Thr Val Pro Ser
                450                 455                 460

Ser Ser Leu Gly Thr Gln Thr Tyr Ile Cys Asn Val Asn His Lys Pro
465                 470                 475                 480

Ser Asn Thr Lys Val Asp Lys Arg Val Glu Pro Lys Ser Cys Glu Val
                485                 490                 495

Lys Thr Asp Ser Thr Asp His Val Lys Pro Lys Glu Thr Glu Asn Thr
                500                 505                 510

Lys Gln Pro Ser Lys Ser Cys His Lys Pro Lys Ala Ile Val His Thr
                515                 520                 525

Glu Lys Val Asn Met Met Ser Leu Thr Val Leu Gly Leu Arg Met Leu
                530                 535                 540

Phe Ala Lys Thr Val Ala Val Asn Phe Leu Leu Thr Ala Lys Leu Phe
545                 550                 555                 560

Phe Leu Arg Ala Lys Arg Ser Gly Ser Gly Ala Pro Val Lys Gln Thr
                565                 570                 575

Leu Asn Phe Asp Leu Leu Lys Leu Ala Gly Asp Val Glu Ser Asn Pro
                580                 585                 590

Gly Pro Met Glu Thr Asp Thr Leu Leu Leu Trp Val Leu Leu Leu Trp
                595                 600                 605

Val Pro Gly Ser Thr Gly Gln Ala Val Leu Thr Gln Pro Pro Ser Ala
                610                 615                 620

Ser Gly Thr Pro Gly Gln Arg Val Thr Ile Ser Cys Ser Gly Ser Ser
625                 630                 635                 640

Ser Asn Ile Gly Ser Asn Thr Val Asn Trp Tyr Gln Gln Leu Pro Gly
                645                 650                 655

Thr Ala Pro Lys Leu Leu Met Tyr Ser Asn Asn Gln Arg Pro Ser Gly
                660                 665                 670

Val Pro Asp Arg Phe Ser Gly Ser Lys Ser Gly Thr Ser Ala Ser Leu
                675                 680                 685

Ala Ile Ser Gly Leu Gln Ser Glu Asp Glu Ala Asp Tyr Tyr Cys Ala
                690                 695                 700

Ala Trp Asp Asp Ser Leu Asn Gly Tyr Val Phe Gly Thr Gly Thr Lys
705                 710                 715                 720

Val Thr Val Leu Gly Gln Pro Lys Ala Asn Pro Thr Val Thr Leu Phe
                725                 730                 735

Pro Pro Ser Ser Glu Glu Leu Gln Ala Asn Lys Ala Thr Leu Val Cys
                740                 745                 750
```

-continued

```
Leu Ile Ser Asp Phe Tyr Pro Gly Ala Val Thr Val Ala Trp Lys Ala
        755                 760                 765

Asp Gly Ser Pro Val Lys Ala Gly Val Glu Thr Thr Lys Pro Ser Lys
    770                 775                 780

Gln Ser Asn Asn Lys Tyr Ala Ala Ser Ser Tyr Leu Ser Leu Thr Pro
785                 790                 795                 800

Glu Gln Trp Lys Ser His Arg Ser Tyr Ser Cys Gln Val Thr His Glu
                805                 810                 815

Gly Ser Thr Val Glu Lys Thr Val Ala Pro Thr Glu Cys Ser Pro Ile
                820                 825                 830

Lys Thr Asp Val Ile Thr Met Asp Pro Lys Asp Asn Cys Ser Lys Asp
            835                 840                 845

Ala Asn Asp Thr Leu Leu Leu Gln Leu Thr Asn Thr Ser Ala Tyr Tyr
850                 855                 860

Met Tyr Leu Leu Leu Leu Leu Lys Ser Val Val Tyr Phe Ala Ile Ile
865                 870                 875                 880

Thr Cys Cys Leu Leu Arg Arg Thr Ala Phe Cys Cys Asn Gly Glu Lys
                885                 890                 895

Ser
```

<210> SEQ ID NO 50
<211> LENGTH: 891
<212> TYPE: PRT
<213> ORGANISM: Artificial Sequence
<220> FEATURE:
<223> OTHER INFORMATION: Synthetic Construct: Bivalent Anti-PSMA Clone
      B caTCR with 2 Fabs (a.k.a. "Bx2-caTCR-2" or "Bivalent Clone B
      caTCR-2")

<400> SEQUENCE: 50

```
Met Glu Thr Asp Thr Leu Leu Leu Trp Val Leu Leu Leu Trp Val Pro
1               5                   10                  15

Gly Ser Thr Gly Glu Val Gln Leu Val Gln Ser Gly Ala Glu Met Lys
                20                  25                  30

Lys Pro Gly Glu Ser Leu Lys Ile Ser Cys Lys Gly Ser Gly Tyr Asn
            35                  40                  45

Phe Ala Ser Tyr Trp Val Gly Trp Val Arg Gln Met Pro Gly Lys Gly
    50                  55                  60

Leu Glu Trp Met Gly Thr Ile Tyr Pro Asp Asp Ser Asp Thr Arg Tyr
65                  70                  75                  80

Gly Pro Ala Phe Gln Gly Gln Val Thr Ile Ser Ala Asp Lys Ser Ile
                85                  90                  95

Ser Thr Ala Tyr Leu Gln Trp Ser Ser Leu Lys Ala Ser Asp Thr Ala
                100                 105                 110

Met Tyr Tyr Cys Ala Arg Asp Ser Tyr Gly Ile Asp Val Trp Gly
            115                 120                 125

Gln Gly Thr Leu Val Thr Val Ser Ser Gly Gly Gly Ser Gly Gly
        130                 135                 140

Gly Gly Ser Glu Val Gln Leu Val Gln Ser Gly Ala Glu Met Lys Lys
145                 150                 155                 160

Pro Gly Glu Ser Leu Lys Ile Ser Cys Lys Gly Ser Gly Tyr Asn Phe
                165                 170                 175

Ala Ser Tyr Trp Val Gly Trp Val Arg Gln Met Pro Gly Lys Gly Leu
            180                 185                 190

Glu Trp Met Gly Thr Ile Tyr Pro Asp Asp Ser Asp Thr Arg Tyr Gly
        195                 200                 205
```

```
Pro Ala Phe Gln Gly Gln Val Thr Ile Ser Ala Asp Lys Ser Ile Ser
    210                 215                 220
Thr Ala Tyr Leu Gln Trp Ser Ser Leu Lys Ala Ser Asp Thr Ala Met
225                 230                 235                 240
Tyr Tyr Cys Ala Arg Asp Ser Tyr Tyr Gly Ile Asp Val Trp Gly Gln
                245                 250                 255
Gly Thr Leu Val Thr Val Ser Ser Ala Ser Thr Lys Gly Pro Ser Val
                260                 265                 270
Phe Pro Leu Ala Pro Ser Ser Lys Ser Thr Ser Gly Gly Thr Ala Ala
                275                 280                 285
Leu Gly Cys Leu Val Lys Asp Tyr Phe Pro Glu Pro Val Thr Val Ser
    290                 295                 300
Trp Asn Ser Gly Ala Leu Thr Ser Gly Val His Thr Phe Pro Ala Val
305                 310                 315                 320
Leu Gln Ser Ser Gly Leu Tyr Ser Leu Ser Ser Val Val Thr Val Pro
                325                 330                 335
Ser Ser Ser Leu Gly Thr Gln Thr Tyr Ile Cys Asn Val Asn His Lys
                340                 345                 350
Pro Ser Asn Thr Lys Val Asp Lys Arg Val Glu Pro Lys Ser Cys Glu
                355                 360                 365
Val Lys Thr Asp Ser Thr Asp His Val Lys Pro Lys Glu Thr Glu Asn
    370                 375                 380
Thr Lys Gln Pro Ser Lys Ser Cys His Lys Pro Lys Ala Ile Val His
385                 390                 395                 400
Thr Glu Lys Val Asn Met Met Ser Leu Thr Val Leu Gly Leu Arg Met
                405                 410                 415
Leu Phe Ala Lys Thr Val Ala Val Asn Phe Leu Leu Thr Ala Lys Leu
                420                 425                 430
Phe Phe Leu Arg Ala Lys Arg Ser Gly Ser Gly Ala Pro Val Lys Gln
                435                 440                 445
Thr Leu Asn Phe Asp Leu Leu Lys Leu Ala Gly Asp Val Glu Ser Asn
    450                 455                 460
Pro Gly Pro Met Glu Thr Asp Thr Leu Leu Leu Trp Val Leu Leu Leu
465                 470                 475                 480
Trp Val Pro Gly Ser Thr Gly Gln Ala Val Leu Thr Gln Pro Pro Ser
                485                 490                 495
Ala Ser Gly Thr Pro Gly Gln Arg Val Thr Ile Ser Cys Ser Gly Ser
                500                 505                 510
Ser Ser Asn Ile Gly Ser Asn Thr Val Asn Trp Tyr Gln Gln Leu Pro
                515                 520                 525
Gly Thr Ala Pro Lys Leu Leu Met Tyr Ser Asn Asn Gln Arg Pro Ser
    530                 535                 540
Gly Val Pro Asp Arg Phe Ser Gly Ser Lys Ser Gly Thr Ser Ala Ser
545                 550                 555                 560
Leu Ala Ile Ser Gly Leu Gln Ser Glu Asp Glu Ala Asp Tyr Tyr Cys
                565                 570                 575
Ala Ala Trp Asp Asp Ser Leu Asn Gly Tyr Val Phe Gly Thr Gly Thr
                580                 585                 590
Lys Val Thr Val Leu Gly Gly Gly Gly Ser Gly Gly Gly Gly Ser
                595                 600                 605
Gln Ala Val Leu Thr Gln Pro Pro Ser Ala Ser Gly Thr Pro Gly Gln
    610                 615                 620
```

Arg Val Thr Ile Ser Cys Ser Gly Ser Ser Ser Asn Ile Gly Ser Asn
625                 630                 635                 640

Thr Val Asn Trp Tyr Gln Gln Leu Pro Gly Thr Ala Pro Lys Leu Leu
            645                 650                 655

Met Tyr Ser Asn Asn Gln Arg Pro Ser Gly Val Pro Asp Arg Phe Ser
        660                 665                 670

Gly Ser Lys Ser Gly Thr Ser Ala Ser Leu Ala Ile Ser Gly Leu Gln
    675                 680                 685

Ser Glu Asp Glu Ala Asp Tyr Tyr Cys Ala Ala Trp Asp Asp Ser Leu
690                 695                 700

Asn Gly Tyr Val Phe Gly Thr Gly Thr Lys Val Thr Val Leu Gly Gln
705                 710                 715                 720

Pro Lys Ala Asn Pro Thr Val Thr Leu Phe Pro Pro Ser Ser Glu Glu
            725                 730                 735

Leu Gln Ala Asn Lys Ala Thr Leu Val Cys Leu Ile Ser Asp Phe Tyr
        740                 745                 750

Pro Gly Ala Val Thr Val Ala Trp Lys Ala Asp Gly Ser Pro Val Lys
    755                 760                 765

Ala Gly Val Glu Thr Thr Lys Pro Ser Lys Gln Ser Asn Asn Lys Tyr
770                 775                 780

Ala Ala Ser Ser Tyr Leu Ser Leu Thr Pro Glu Gln Trp Lys Ser His
785                 790                 795                 800

Arg Ser Tyr Ser Cys Gln Val Thr His Glu Gly Ser Thr Val Glu Lys
            805                 810                 815

Thr Val Ala Pro Thr Glu Cys Ser Pro Ile Lys Thr Asp Val Ile Thr
        820                 825                 830

Met Asp Pro Lys Asp Asn Cys Ser Lys Asp Ala Asn Asp Thr Leu Leu
    835                 840                 845

Leu Gln Leu Thr Asn Thr Ser Ala Tyr Tyr Met Tyr Leu Leu Leu Leu
850                 855                 860

Leu Lys Ser Val Val Tyr Phe Ala Ile Ile Thr Cys Cys Leu Leu Arg
865                 870                 875                 880

Arg Thr Ala Phe Cys Cys Asn Gly Glu Lys Ser
            885                 890

<210> SEQ ID NO 51
<211> LENGTH: 394
<212> TYPE: PRT
<213> ORGANISM: Artificial Sequence
<220> FEATURE:
<223> OTHER INFORMATION: Synthetic Construct

<400> SEQUENCE: 51

Met Glu Thr Asp Thr Leu Leu Leu Trp Val Leu Leu Leu Trp Val Pro
1               5                   10                  15

Gly Ser Thr Gly Gln Ser Val Leu Thr Gln Pro Pro Ser Val Ser Gly
            20                  25                  30

Ala Pro Gly Gln Arg Val Thr Ile Ser Cys Thr Gly Ser Ser Ser Asn
        35                  40                  45

Ile Gly Ala Gly Tyr Asp Val His Trp Tyr Gln Gln Leu Pro Gly Thr
    50                  55                  60

Ala Pro Lys Leu Leu Ile Tyr Gly Asn Ser Asn Arg Pro Ser Gly Val
65                  70                  75                  80

Pro Asp Arg Phe Ser Gly Ser Lys Ser Gly Thr Ser Ala Ser Leu Ala
                85                  90                  95

Ile Thr Gly Leu Gln Ala Glu Asp Glu Ala Asp Tyr Tyr Cys Gln Ser
            100                 105                 110

Tyr Asp Ser Ser Leu Ser Gly Tyr Val Phe Gly Thr Gly Thr Lys Val
        115                 120                 125

Thr Val Leu Gly Ser Arg Gly Gly Gly Ser Gly Gly Gly Gly Ser
    130                 135                 140

Gly Gly Gly Gly Ser Leu Glu Met Ala Glu Val Gln Leu Val Gln Ser
145                 150                 155                 160

Gly Ala Glu Val Lys Lys Pro Gly Glu Ser Leu Lys Ile Ser Cys Lys
                165                 170                 175

Gly Ser Gly Tyr Ser Phe Thr Ser Tyr Trp Ile Gly Trp Val Arg Gln
            180                 185                 190

Met Pro Gly Lys Gly Leu Glu Trp Met Gly Ile Ile Tyr Pro Gly Asp
        195                 200                 205

Ser Asp Thr Arg Tyr Ser Pro Ser Phe Gln Gly Gln Val Thr Ile Ser
    210                 215                 220

Ala Asp Lys Ser Ile Ser Thr Ala Tyr Leu Gln Trp Ser Ser Leu Lys
225                 230                 235                 240

Ala Ser Asp Thr Ala Met Tyr Tyr Cys Ala Arg Ser Met Gly Ser Ser
                245                 250                 255

Leu Tyr Ala Ser Ser Asp Val Trp Gly Gln Gly Thr Leu Val Thr Val
            260                 265                 270

Ser Ser Glu Gln Lys Leu Ile Ser Glu Glu Asp Leu Ala Ala Ala Ile
        275                 280                 285

Glu Val Met Tyr Pro Pro Tyr Leu Asp Asn Glu Lys Ser Asn Gly
    290                 295                 300

Thr Ile Ile His Val Lys Gly Lys His Leu Cys Pro Ser Pro Leu Phe
305                 310                 315                 320

Pro Gly Pro Ser Lys Pro Phe Trp Val Leu Val Val Val Gly Gly Val
                325                 330                 335

Leu Ala Cys Tyr Ser Leu Leu Val Thr Val Ala Phe Ile Ile Phe Trp
            340                 345                 350

Val Arg Ser Lys Arg Ser Arg Leu Leu His Ser Asp Tyr Met Asn Met
        355                 360                 365

Thr Pro Arg Arg Pro Gly Pro Thr Arg Lys His Tyr Gln Pro Tyr Ala
    370                 375                 380

Pro Pro Arg Asp Phe Ala Ala Tyr Arg Ser
385                 390

<210> SEQ ID NO 52
<211> LENGTH: 384
<212> TYPE: PRT
<213> ORGANISM: Artificial Sequence
<220> FEATURE:
<223> OTHER INFORMATION: Synthetic Construct

<400> SEQUENCE: 52

Met Glu Thr Asp Thr Leu Leu Leu Trp Val Leu Leu Leu Trp Val Pro
1               5                   10                  15

Gly Ser Thr Gly Gln Ser Val Leu Thr Gln Pro Pro Ser Val Ser Gly
            20                  25                  30

Ala Pro Gly Gln Arg Val Thr Ile Ser Cys Thr Gly Ser Ser Ser Asn
        35                  40                  45

Ile Gly Ala Gly Tyr Asp Val His Trp Tyr Gln Gln Leu Pro Gly Thr
    50                  55                  60

Ala Pro Lys Leu Leu Ile Tyr Gly Asn Ser Asn Arg Pro Ser Gly Val
65                  70                  75                  80

Pro Asp Arg Phe Ser Gly Ser Lys Ser Gly Thr Ser Ala Ser Leu Ala
                85                  90                  95

Ile Thr Gly Leu Gln Ala Glu Asp Glu Ala Asp Tyr Tyr Cys Gln Ser
            100                 105                 110

Tyr Asp Ser Ser Leu Ser Gly Tyr Val Phe Gly Thr Gly Thr Lys Val
        115                 120                 125

Thr Val Leu Gly Ser Arg Gly Gly Gly Ser Gly Gly Gly Gly Ser
    130                 135                 140

Gly Gly Gly Gly Ser Leu Glu Met Ala Glu Val Gln Leu Val Gln Ser
145                 150                 155                 160

Gly Ala Glu Val Lys Lys Pro Gly Glu Ser Leu Lys Ile Ser Cys Lys
                165                 170                 175

Gly Ser Gly Tyr Ser Phe Thr Ser Tyr Trp Ile Gly Trp Val Arg Gln
            180                 185                 190

Met Pro Gly Lys Gly Leu Glu Trp Met Gly Ile Ile Tyr Pro Gly Asp
        195                 200                 205

Ser Asp Thr Arg Tyr Ser Pro Ser Phe Gln Gly Gln Val Thr Ile Ser
    210                 215                 220

Ala Asp Lys Ser Ile Ser Thr Ala Tyr Leu Gln Trp Ser Ser Leu Lys
225                 230                 235                 240

Ala Ser Asp Thr Ala Met Tyr Tyr Cys Ala Arg Ser Met Gly Ser Ser
                245                 250                 255

Leu Tyr Ala Ser Ser Asp Val Trp Gly Gln Gly Thr Leu Val Thr Val
            260                 265                 270

Ser Ser Ala Ala Ala Ile Glu Val Met Tyr Pro Pro Tyr Leu Asp
        275                 280                 285

Asn Glu Lys Ser Asn Gly Thr Ile Ile His Val Lys Gly Lys His Leu
    290                 295                 300

Cys Pro Ser Pro Leu Phe Pro Gly Pro Ser Lys Pro Phe Trp Val Leu
305                 310                 315                 320

Val Val Val Gly Gly Val Leu Ala Cys Tyr Ser Leu Leu Val Thr Val
                325                 330                 335

Ala Phe Ile Ile Phe Trp Val Arg Ser Lys Arg Ser Arg Leu Leu His
            340                 345                 350

Ser Asp Tyr Met Asn Met Thr Pro Arg Arg Pro Gly Pro Thr Arg Lys
        355                 360                 365

His Tyr Gln Pro Tyr Ala Pro Pro Arg Asp Phe Ala Ala Tyr Arg Ser
    370                 375                 380

<210> SEQ ID NO 53
<211> LENGTH: 389
<212> TYPE: PRT
<213> ORGANISM: Artificial Sequence
<220> FEATURE:
<223> OTHER INFORMATION: Synthetic Construct

<400> SEQUENCE: 53

Met Glu Thr Asp Thr Leu Leu Leu Trp Val Leu Leu Leu Trp Val Pro
1               5                   10                  15

Gly Ser Thr Gly Gln Ala Val Leu Thr Gln Pro Pro Ser Ala Ser Gly
            20                  25                  30

Thr Pro Gly Gln Arg Val Thr Ile Ser Cys Ser Gly Ser Ser Ser Asn
        35                  40                  45

```
Ile Gly Ser Asn Thr Val Asn Trp Tyr Gln Gln Leu Pro Gly Thr Ala
 50                  55                  60

Pro Lys Leu Leu Met Tyr Ser Asn Asn Gln Arg Pro Ser Gly Val Pro
 65                  70                  75                  80

Asp Arg Phe Ser Gly Ser Lys Ser Gly Thr Ser Ala Ser Leu Ala Ile
                 85                  90                  95

Ser Gly Leu Gln Ser Glu Asp Glu Ala Asp Tyr Tyr Cys Ala Ala Trp
                100                 105                 110

Asp Asp Ser Leu Asn Gly Tyr Val Phe Gly Thr Gly Thr Lys Val Thr
            115                 120                 125

Val Leu Gly Ser Arg Gly Gly Gly Ser Gly Gly Gly Ser Gly
130                 135                 140

Gly Gly Gly Ser Leu Glu Met Ala Glu Val Gln Leu Val Gln Ser Gly
145                 150                 155                 160

Ala Glu Met Lys Lys Pro Gly Glu Ser Leu Lys Ile Ser Cys Lys Gly
                165                 170                 175

Ser Gly Tyr Asn Phe Ala Ser Tyr Trp Val Gly Trp Val Arg Gln Met
            180                 185                 190

Pro Gly Lys Gly Leu Glu Trp Met Gly Thr Ile Tyr Pro Asp Asp Ser
            195                 200                 205

Asp Thr Arg Tyr Gly Pro Ala Phe Gln Gly Gln Val Thr Ile Ser Ala
210                 215                 220

Asp Lys Ser Ile Ser Thr Ala Tyr Leu Gln Trp Ser Ser Leu Lys Ala
225                 230                 235                 240

Ser Asp Thr Ala Met Tyr Tyr Cys Ala Arg Asp Ser Tyr Tyr Gly Ile
                245                 250                 255

Asp Val Trp Gly Gln Gly Thr Leu Val Thr Val Ser Ser Glu Gln Lys
            260                 265                 270

Leu Ile Ser Glu Glu Asp Leu Ala Ala Ala Ile Glu Val Met Tyr Pro
            275                 280                 285

Pro Pro Tyr Leu Asp Asn Glu Lys Ser Asn Gly Thr Ile Ile His Val
            290                 295                 300

Lys Gly Lys His Leu Cys Pro Ser Pro Leu Phe Pro Gly Pro Ser Lys
305                 310                 315                 320

Pro Phe Trp Val Leu Val Val Val Gly Gly Val Leu Ala Cys Tyr Ser
                325                 330                 335

Leu Leu Val Thr Val Ala Phe Ile Ile Phe Trp Val Arg Ser Lys Arg
            340                 345                 350

Ser Arg Leu Leu His Ser Asp Tyr Met Asn Met Thr Pro Arg Arg Pro
            355                 360                 365

Gly Pro Thr Arg Lys His Tyr Gln Pro Tyr Ala Pro Pro Arg Asp Phe
370                 375                 380

Ala Ala Tyr Arg Ser
385

<210> SEQ ID NO 54
<211> LENGTH: 379
<212> TYPE: PRT
<213> ORGANISM: Artificial Sequence
<220> FEATURE:
<223> OTHER INFORMATION: Synthetic Construct

<400> SEQUENCE: 54

Met Glu Thr Asp Thr Leu Leu Leu Trp Val Leu Leu Leu Trp Val Pro
 1               5                  10                  15
```

Gly Ser Thr Gly Gln Ala Val Leu Thr Gln Pro Ser Ala Ser Gly
            20                  25                  30

Thr Pro Gly Gln Arg Val Thr Ile Ser Cys Ser Gly Ser Ser Asn
        35                  40                  45

Ile Gly Ser Asn Thr Val Asn Trp Tyr Gln Gln Leu Pro Gly Thr Ala
50                  55                  60

Pro Lys Leu Leu Met Tyr Ser Asn Asn Gln Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Gln Ser Glu Asp Glu Ala Asp Tyr Tyr Cys Ala Ala Trp
            100                 105                 110

Asp Asp Ser Leu Asn Gly Tyr Val Phe Gly Thr Gly Thr Lys Val Thr
            115                 120                 125

Val Leu Gly Ser Arg Gly Gly Gly Gly Ser Gly Gly Gly Gly Ser Gly
    130                 135                 140

Gly Gly Gly Ser Leu Glu Met Ala Glu Val Gln Leu Val Gln Ser Gly
145                 150                 155                 160

Ala Glu Met Lys Lys Pro Gly Glu Ser Leu Lys Ile Ser Cys Lys Gly
                165                 170                 175

Ser Gly Tyr Asn Phe Ala Ser Tyr Trp Val Gly Trp Val Arg Gln Met
            180                 185                 190

Pro Gly Lys Gly Leu Glu Trp Met Gly Thr Ile Tyr Pro Asp Asp Ser
        195                 200                 205

Asp Thr Arg Tyr Gly Pro Ala Phe Gln Gly Gln Val Thr Ile Ser Ala
210                 215                 220

Asp Lys Ser Ile Ser Thr Ala Tyr Leu Gln Trp Ser Ser Leu Lys Ala
225                 230                 235                 240

Ser Asp Thr Ala Met Tyr Tyr Cys Ala Arg Asp Ser Tyr Tyr Gly Ile
                245                 250                 255

Asp Val Trp Gly Gln Gly Thr Leu Val Thr Val Ser Ser Ala Ala Ala
            260                 265                 270

Ile Glu Val Met Tyr Pro Pro Tyr Leu Asp Asn Glu Lys Ser Asn
        275                 280                 285

Gly Thr Ile Ile His Val Lys Gly Lys His Leu Cys Pro Ser Pro Leu
    290                 295                 300

Phe Pro Gly Pro Ser Lys Pro Phe Trp Val Leu Val Val Val Gly Gly
305                 310                 315                 320

Val Leu Ala Cys Tyr Ser Leu Leu Val Thr Val Ala Phe Ile Ile Phe
                325                 330                 335

Trp Val Arg Ser Lys Arg Ser Arg Leu Leu His Ser Asp Tyr Met Asn
            340                 345                 350

Met Thr Pro Arg Arg Pro Gly Pro Thr Arg Lys His Tyr Gln Pro Tyr
        355                 360                 365

Ala Pro Pro Arg Asp Phe Ala Ala Tyr Arg Ser
        370                 375

<210> SEQ ID NO 55
<211> LENGTH: 374
<212> TYPE: PRT
<213> ORGANISM: Artificial Sequence
<220> FEATURE:
<223> OTHER INFORMATION: Synthetic Construct

<400> SEQUENCE: 55

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly Gly
        115                 120                 125

Ser Leu Glu Met Ala Glu Val Gln Leu Val Gln Ser Gly Ala Glu Val
    130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
            165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205

Ile Ser Thr Ala Tyr Leu Gln Trp Ser Ser Leu Lys Ala Ser Asp Thr
    210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Glu Gln
            245                 250                 255

Lys Leu Ile Ser Glu Glu Asp Leu Ala Ala Ala Ile Glu Val Met Tyr
            260                 265                 270

Pro Pro Pro Tyr Leu Asp Asn Glu Lys Ser Asn Gly Thr Ile Ile His
        275                 280                 285

Val Lys Gly Lys His Leu Cys Pro Ser Pro Leu Phe Pro Gly Pro Ser
    290                 295                 300

Lys Pro Phe Trp Val Leu Val Val Val Gly Gly Val Leu Ala Cys Tyr
305                 310                 315                 320

Ser Leu Leu Val Thr Val Ala Phe Ile Ile Phe Trp Val Arg Ser Lys
            325                 330                 335

Arg Ser Arg Leu Leu His Ser Asp Tyr Met Asn Met Thr Pro Arg Arg
        340                 345                 350

Pro Gly Pro Thr Arg Lys His Tyr Gln Pro Tyr Ala Pro Pro Arg Asp
    355                 360                 365

Phe Ala Ala Tyr Arg Ser
    370

<210> SEQ ID NO 56
<211> LENGTH: 363
<212> TYPE: PRT
<213> ORGANISM: Artificial Sequence
<220> FEATURE:
<223> OTHER INFORMATION: Synthetic Construct

<400> SEQUENCE: 56

Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
            115                 120                 125

Ser Leu Glu Met Ala Glu Val Gln Leu Val Gln Ser Gly Ala Glu Val
130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
            165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205

Ile Ser Thr Ala Tyr Leu Gln Trp Ser Ser Leu Lys Ala Ser Asp Thr
210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Glu Gln
            245                 250                 255

Lys Leu Ile Ser Glu Glu Asp Leu Ala Ala Ala Thr Gly Pro Ala Asp
            260                 265                 270

Leu Ser Pro Gly Ala Ser Ser Val Thr Pro Ala Pro Ala Arg Glu
        275                 280                 285

Pro Gly His Ser Pro Gln Ile Ile Ser Phe Phe Leu Ala Leu Thr Ser
        290                 295                 300

Thr Ala Leu Leu Phe Leu Leu Phe Phe Leu Thr Leu Arg Phe Ser Val
305                 310                 315                 320

Val Lys Arg Gly Arg Lys Lys Leu Leu Tyr Ile Phe Lys Gln Pro Phe
            325                 330                 335

Met Arg Pro Val Gln Thr Thr Gln Glu Glu Asp Gly Cys Ser Cys Arg
            340                 345                 350

Phe Pro Glu Glu Glu Glu Gly Gly Cys Glu Leu
        355                 360

<210> SEQ ID NO 57
<211> LENGTH: 353
<212> TYPE: PRT
<213> ORGANISM: Artificial Sequence
<220> FEATURE:
<223> OTHER INFORMATION: Synthetic Construct

<400> SEQUENCE: 57

Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
            115                 120                 125

Ser Leu Glu Met Ala Glu Val Gln Leu Val Gln Ser Gly Ala Glu Val
130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205

Ile Ser Thr Ala Tyr Leu Gln Trp Ser Ser Leu Lys Ala Ser Asp Thr
210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Ala Ala
                245                 250                 255

Ala Thr Gly Pro Ala Asp Leu Ser Pro Gly Ala Ser Ser Val Thr Pro
            260                 265                 270

Pro Ala Pro Ala Arg Glu Pro Gly His Ser Pro Gln Ile Ile Ser Phe
        275                 280                 285

Phe Leu Ala Leu Thr Ser Thr Ala Leu Leu Phe Leu Leu Phe Phe Leu
290                 295                 300

Thr Leu Arg Phe Ser Val Val Lys Arg Gly Arg Lys Lys Leu Leu Tyr
305                 310                 315                 320

Ile Phe Lys Gln Pro Phe Met Arg Pro Val Gln Thr Thr Gln Glu Glu
                325                 330                 335

Asp Gly Cys Ser Cys Arg Phe Pro Glu Glu Glu Gly Gly Cys Glu
            340                 345                 350

Leu

<210> SEQ ID NO 58
<211> LENGTH: 388
<212> TYPE: PRT
<213> ORGANISM: Artificial Sequence
<220> FEATURE:
<223> OTHER INFORMATION: Synthetic Construct

<400> SEQUENCE: 58

```
Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
            115                 120                 125

Ser Leu Glu Met Ala Glu Val Gln Leu Val Gln Ser Gly Ala Glu Val
130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
            165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205

Ile Ser Thr Ala Tyr Leu Gln Trp Ser Ser Leu Lys Ala Ser Asp Thr
    210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Glu Gln
            245                 250                 255

Lys Leu Ile Ser Glu Glu Asp Leu Ala Ala Ala Thr Gly Pro Thr His
            260                 265                 270

Leu Pro Tyr Val Ser Glu Met Leu Glu Ala Arg Thr Ala Gly His Met
        275                 280                 285

Gln Thr Leu Ala Asp Phe Arg Gln Leu Pro Ala Arg Thr Leu Ser Thr
    290                 295                 300

His Trp Pro Pro Gln Arg Ser Leu Cys Ser Ser Asp Phe Ile Arg Ile
305                 310                 315                 320

Leu Val Ile Phe Ser Gly Met Phe Leu Val Phe Thr Leu Ala Gly Ala
            325                 330                 335

Leu Phe Leu His Gln Arg Arg Lys Tyr Arg Ser Asn Lys Gly Glu Ser
            340                 345                 350

Pro Val Glu Pro Ala Glu Pro Cys Arg Tyr Ser Cys Pro Arg Glu Glu
        355                 360                 365

Glu Gly Ser Thr Ile Pro Ile Gln Glu Asp Tyr Arg Lys Pro Glu Pro
    370                 375                 380

Ala Cys Ser Pro
385
```

<210> SEQ ID NO 59

<211> LENGTH: 378
<212> TYPE: PRT
<213> ORGANISM: Artificial Sequence
<220> FEATURE:
<223> OTHER INFORMATION: Synthetic Construct

<400> SEQUENCE: 59

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Ser Gly Gly Gly Ser Gly Gly Gly Gly
        115                 120                 125

Ser Leu Glu Met Ala Glu Val Gln Leu Val Gln Ser Gly Ala Glu Val
    130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205

Ile Ser Thr Ala Tyr Leu Gln Trp Ser Ser Leu Lys Ala Ser Asp Thr
    210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Ala Ala
                245                 250                 255

Ala Thr Gly Pro Thr His Leu Pro Tyr Val Ser Glu Met Leu Glu Ala
            260                 265                 270

Arg Thr Ala Gly His Met Gln Thr Leu Ala Asp Phe Arg Gln Leu Pro
        275                 280                 285

Ala Arg Thr Leu Ser Thr His Trp Pro Pro Gln Arg Ser Leu Cys Ser
    290                 295                 300

Ser Asp Phe Ile Arg Ile Leu Val Ile Phe Ser Gly Met Phe Leu Val
305                 310                 315                 320

Phe Thr Leu Ala Gly Ala Leu Phe Leu His Gln Arg Arg Lys Tyr Arg
                325                 330                 335

Ser Asn Lys Gly Glu Ser Pro Val Glu Pro Ala Glu Pro Cys Arg Tyr
            340                 345                 350

Ser Cys Pro Arg Glu Glu Glu Gly Ser Thr Ile Pro Ile Gln Glu Asp
        355                 360                 365

Tyr Arg Lys Pro Glu Pro Ala Cys Ser Pro
    370                 375

<210> SEQ ID NO 60
<211> LENGTH: 539
<212> TYPE: PRT
<213> ORGANISM: Artificial Sequence
<220> FEATURE:
<223> OTHER INFORMATION: Synthetic Construct

<400> SEQUENCE: 60

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
                100                 105                 110

Ser Arg Gly Gly Gly Gly Ser Gly Gly Gly Ser Gly Gly Gly Gly
            115                 120                 125

Ser Leu Glu Met Ala Glu Val Gln Leu Val Gln Ser Gly Ala Glu Val
        130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205

Ile Ser Thr Ala Tyr Leu Gln Trp Ser Ser Leu Lys Ala Ser Asp Thr
    210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Glu Gln
                245                 250                 255

Lys Leu Ile Ser Glu Glu Asp Leu Ala Ala Ala Thr Gly Ala Pro Pro
            260                 265                 270

Leu Gly Thr Gln Pro Asp Cys Asn Pro Thr Pro Glu Asn Gly Glu Ala
        275                 280                 285

Pro Ala Ser Thr Ser Pro Thr Gln Ser Leu Leu Val Asp Ser Gln Ala
    290                 295                 300

Ser Lys Thr Leu Pro Ile Pro Thr Ser Ala Pro Val Ala Leu Ser Ser
305                 310                 315                 320

Thr Gly Lys Pro Val Leu Asp Ala Gly Pro Val Leu Phe Trp Val Ile
                325                 330                 335

Leu Val Leu Val Val Val Val Gly Ser Ser Ala Phe Leu Leu Cys His
            340                 345                 350

Arg Arg Ala Cys Arg Lys Arg Ile Arg Gln Lys Leu His Leu Cys Tyr
        355                 360                 365
```

Pro Val Gln Thr Ser Gln Pro Lys Leu Glu Leu Val Asp Ser Arg Pro
    370                 375                 380

Arg Arg Ser Ser Thr Gln Leu Arg Ser Gly Ala Ser Val Thr Glu Pro
385                 390                 395                 400

Val Ala Glu Glu Arg Gly Leu Met Ser Gln Pro Leu Met Glu Thr Cys
                405                 410                 415

His Ser Val Gly Ala Ala Tyr Leu Glu Ser Leu Pro Leu Gln Asp Ala
                420                 425                 430

Ser Pro Ala Gly Gly Pro Ser Ser Pro Arg Asp Leu Pro Glu Pro Arg
                435                 440                 445

Val Ser Thr Glu His Thr Asn Asn Lys Ile Glu Lys Ile Tyr Ile Met
    450                 455                 460

Lys Ala Asp Thr Val Ile Val Gly Thr Val Lys Ala Glu Leu Pro Glu
465                 470                 475                 480

Gly Arg Gly Leu Ala Gly Pro Ala Glu Pro Glu Leu Glu Glu Glu Leu
                485                 490                 495

Glu Ala Asp His Thr Pro His Tyr Pro Glu Gln Glu Thr Glu Pro Pro
                500                 505                 510

Leu Gly Ser Cys Ser Asp Val Met Leu Ser Val Glu Glu Glu Gly Lys
                515                 520                 525

Glu Asp Pro Leu Pro Thr Ala Ala Ser Gly Lys
    530                 535

<210> SEQ ID NO 61
<211> LENGTH: 529
<212> TYPE: PRT
<213> ORGANISM: Artificial Sequence
<220> FEATURE:
<223> OTHER INFORMATION: Synthetic Construct

<400> SEQUENCE: 61

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
        115                 120                 125

Ser Leu Glu Met Ala Glu Val Gln Leu Val Gln Ser Gly Ala Glu Val
    130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

```
Tyr Ser Pro Ser Phe Gln Gly Gln Val Thr Ile Ser Ala Asp Lys Ser
            195                 200                 205

Ile Ser Thr Ala Tyr Leu Gln Trp Ser Ser Leu Lys Ala Ser Asp Thr
        210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Ala Ala
            245                 250                 255

Ala Thr Gly Ala Pro Pro Leu Gly Thr Gln Pro Asp Cys Asn Pro Thr
            260                 265                 270

Pro Glu Asn Gly Glu Ala Pro Ala Ser Thr Ser Pro Thr Gln Ser Leu
            275                 280                 285

Leu Val Asp Ser Gln Ala Ser Lys Thr Leu Pro Ile Pro Thr Ser Ala
            290                 295                 300

Pro Val Ala Leu Ser Ser Thr Gly Lys Pro Val Leu Asp Ala Gly Pro
305                 310                 315                 320

Val Leu Phe Trp Val Ile Leu Val Leu Val Val Val Gly Ser Ser
            325                 330                 335

Ala Phe Leu Leu Cys His Arg Arg Ala Cys Arg Lys Arg Ile Arg Gln
            340                 345                 350

Lys Leu His Leu Cys Tyr Pro Val Gln Thr Ser Gln Pro Lys Leu Glu
            355                 360                 365

Leu Val Asp Ser Arg Pro Arg Arg Ser Ser Thr Gln Leu Arg Ser Gly
            370                 375                 380

Ala Ser Val Thr Glu Pro Val Ala Glu Glu Arg Gly Leu Met Ser Gln
385                 390                 395                 400

Pro Leu Met Glu Thr Cys His Ser Val Gly Ala Ala Tyr Leu Glu Ser
            405                 410                 415

Leu Pro Leu Gln Asp Ala Ser Pro Ala Gly Gly Pro Ser Ser Pro Arg
            420                 425                 430

Asp Leu Pro Glu Pro Arg Val Ser Thr Glu His Thr Asn Asn Lys Ile
            435                 440                 445

Glu Lys Ile Tyr Ile Met Lys Ala Asp Thr Val Ile Val Gly Thr Val
            450                 455                 460

Lys Ala Glu Leu Pro Glu Gly Arg Gly Leu Ala Gly Pro Ala Glu Pro
465                 470                 475                 480

Glu Leu Glu Glu Glu Leu Glu Ala Asp His Thr Pro His Tyr Pro Glu
            485                 490                 495

Gln Glu Thr Glu Pro Pro Leu Gly Ser Cys Ser Asp Val Met Leu Ser
            500                 505                 510

Val Glu Glu Glu Gly Lys Glu Asp Pro Leu Pro Thr Ala Ala Ser Gly
            515                 520                 525

Lys

<210> SEQ ID NO 62
<211> LENGTH: 379
<212> TYPE: PRT
<213> ORGANISM: Artificial Sequence
<220> FEATURE:
<223> OTHER INFORMATION: Synthetic Construct

<400> SEQUENCE: 62

Gln Ser Val Leu Thr Gln Pro Pro Ser Val Ser Gly Ala Pro Gly Gln
1               5                   10                  15
```

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
            115                 120                 125

Ser Leu Glu Met Ala Glu Val Gln Leu Val Gln Ser Gly Ala Glu Val
            130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
                195                 200                 205

Ile Ser Thr Ala Tyr Leu Gln Trp Ser Ser Leu Lys Ala Ser Asp Thr
210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Glu Gln
            245                 250                 255

Lys Leu Ile Ser Glu Glu Asp Leu Ala Ala Ala Thr Gly Asp Arg Asp
                260                 265                 270

Pro Pro Ala Thr Gln Pro Gln Glu Thr Gln Gly Pro Pro Ala Arg Pro
            275                 280                 285

Ile Thr Val Gln Pro Thr Glu Ala Trp Pro Arg Thr Ser Gln Gly Pro
            290                 295                 300

Ser Thr Arg Pro Val Glu Val Pro Gly Gly Arg Ala Val Ala Ala Ile
305                 310                 315                 320

Leu Gly Leu Gly Leu Val Leu Gly Leu Leu Gly Pro Leu Ala Ile Leu
            325                 330                 335

Leu Ala Leu Tyr Leu Leu Arg Arg Asp Gln Arg Leu Pro Pro Asp Ala
            340                 345                 350

His Lys Pro Pro Gly Gly Gly Ser Phe Arg Thr Pro Ile Gln Glu Glu
            355                 360                 365

Gln Ala Asp Ala His Ser Thr Leu Ala Lys Ile
            370                 375

<210> SEQ ID NO 63
<211> LENGTH: 369
<212> TYPE: PRT
<213> ORGANISM: Artificial Sequence
<220> FEATURE:
<223> OTHER INFORMATION: Synthetic Construct

<400> SEQUENCE: 63

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
            115                 120                 125

Ser Leu Glu Met Ala Glu Val Gln Leu Val Gln Ser Gly Ala Glu Val
130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205

Ile Ser Thr Ala Tyr Leu Gln Trp Ser Ser Leu Lys Ala Ser Asp Thr
    210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Ala Ala
                245                 250                 255

Ala Thr Gly Asp Arg Asp Pro Pro Ala Thr Gln Pro Gln Glu Thr Gln
            260                 265                 270

Gly Pro Pro Ala Arg Pro Ile Thr Val Gln Pro Thr Glu Ala Trp Pro
        275                 280                 285

Arg Thr Ser Gln Gly Pro Ser Thr Arg Pro Val Glu Val Pro Gly Gly
    290                 295                 300

Arg Ala Val Ala Ala Ile Leu Gly Leu Gly Leu Val Leu Gly Leu Leu
305                 310                 315                 320

Gly Pro Leu Ala Ile Leu Leu Ala Leu Tyr Leu Leu Arg Arg Asp Gln
                325                 330                 335

Arg Leu Pro Pro Asp Ala His Lys Pro Pro Gly Gly Ser Phe Arg
            340                 345                 350

Thr Pro Ile Gln Glu Gln Ala Asp Ala His Ser Thr Leu Ala Lys
        355                 360                 365

Ile

<210> SEQ ID NO 64
<211> LENGTH: 386
<212> TYPE: PRT
<213> ORGANISM: Artificial Sequence
<220> FEATURE:
<223> OTHER INFORMATION: Synthetic Construct

```
<400> SEQUENCE: 64

Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
            115                 120                 125

Ser Leu Glu Met Ala Glu Val Gln Leu Val Gln Ser Gly Ala Glu Val
130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205

Ile Ser Thr Ala Tyr Leu Gln Trp Ser Ser Leu Lys Ala Ser Asp Thr
    210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Glu Gln
                245                 250                 255

Lys Leu Ile Ser Glu Glu Asp Leu Ala Ala Ala Thr Gly Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Gln Arg Arg Lys Tyr Arg Ser Asn Lys Gly Glu Ser Pro Val
            340                 345                 350

Glu Pro Ala Glu Pro Cys Arg Tyr Ser Cys Pro Arg Glu Glu Glu Gly
        355                 360                 365

Ser Thr Ile Pro Ile Gln Glu Asp Tyr Arg Lys Pro Glu Pro Ala Cys
    370                 375                 380

Ser Pro
385

<210> SEQ ID NO 65
```

```
<211> LENGTH: 376
<212> TYPE: PRT
<213> ORGANISM: Artificial Sequence
<220> FEATURE:
<223> OTHER INFORMATION: Synthetic Construct

<400> SEQUENCE: 65

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
            115                 120                 125

Ser Leu Glu Met Ala Glu Val Gln Leu Val Gln Ser Gly Ala Glu Val
        130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205

Ile Ser Thr Ala Tyr Leu Gln Trp Ser Ser Leu Lys Ala Ser Asp Thr
    210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Ala Ala
                245                 250                 255

Ala Thr Gly Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Gln Arg Arg Lys Tyr Arg Ser Asn
                325                 330                 335

Lys Gly Glu Ser Pro Val Glu Pro Ala Glu Pro Cys Arg Tyr Ser Cys
            340                 345                 350

Pro Arg Glu Glu Glu Gly Ser Thr Ile Pro Ile Gln Glu Asp Tyr Arg
        355                 360                 365

Lys Pro Glu Pro Ala Cys Ser Pro
    370                 375
```

```
<210> SEQ ID NO 66
<211> LENGTH: 526
<212> TYPE: PRT
<213> ORGANISM: Artificial Sequence
<220> FEATURE:
<223> OTHER INFORMATION: Synthetic Construct

<400> SEQUENCE: 66
```

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
        115                 120                 125

Ser Leu Glu Met Ala Glu Val Gln Leu Val Gln Ser Gly Ala Glu Val
    130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205

Ile Ser Thr Ala Tyr Leu Gln Trp Ser Ser Leu Lys Ala Ser Asp Thr
    210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Glu Gln
                245                 250                 255

Lys Leu Ile Ser Glu Glu Asp Leu Ala Ala Ala Thr Gly Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys His Arg Arg Ala Cys Arg Lys Arg Ile Arg Gln Lys Leu His
            340                 345                 350

Leu Cys Tyr Pro Val Gln Thr Ser Gln Pro Lys Leu Glu Leu Val Asp
        355                 360                 365

```
Ser Arg Pro Arg Arg Ser Ser Thr Gln Leu Arg Ser Gly Ala Ser Val
        370                 375                 380

Thr Glu Pro Val Ala Glu Arg Gly Leu Met Ser Gln Pro Leu Met
385                 390                 395                 400

Glu Thr Cys His Ser Val Gly Ala Ala Tyr Leu Glu Ser Leu Pro Leu
                    405                 410                 415

Gln Asp Ala Ser Pro Ala Gly Gly Pro Ser Ser Pro Arg Asp Leu Pro
                420                 425                 430

Glu Pro Arg Val Ser Thr Glu His Thr Asn Asn Lys Ile Glu Lys Ile
        435                 440                 445

Tyr Ile Met Lys Ala Asp Thr Val Ile Val Gly Thr Val Lys Ala Glu
        450                 455                 460

Leu Pro Glu Gly Arg Gly Leu Ala Gly Pro Ala Glu Pro Glu Leu Glu
465                 470                 475                 480

Glu Glu Leu Glu Ala Asp His Thr Pro His Tyr Pro Glu Gln Glu Thr
                485                 490                 495

Glu Pro Pro Leu Gly Ser Cys Ser Asp Val Met Leu Ser Val Glu Glu
                500                 505                 510

Glu Gly Lys Glu Asp Pro Leu Pro Thr Ala Ala Ser Gly Lys
            515                 520                 525

<210> SEQ ID NO 67
<211> LENGTH: 516
<212> TYPE: PRT
<213> ORGANISM: Artificial Sequence
<220> FEATURE:
<223> OTHER INFORMATION: Synthetic Construct

<400> SEQUENCE: 67

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Gly Ser Gly Gly Gly Gly
        115                 120                 125

Ser Leu Glu Met Ala Glu Val Gln Leu Val Gln Ser Gly Ala Glu Val
    130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205
```

```
Ile Ser Thr Ala Tyr Leu Gln Trp Ser Ser Leu Lys Ala Ser Asp Thr
    210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Ala Ala
                245                 250                 255

Ala Thr Gly Thr Thr Thr Pro Ala Pro Arg Pro Pro Thr Pro Ala Pro
                260                 265                 270

Thr Ile Ala Ser Gln Pro Leu Ser Leu Arg Pro Glu Ala Cys Arg Pro
            275                 280                 285

Ala Ala Gly Gly Ala Val His Thr Arg Gly Leu Asp Phe Ala Cys Asp
        290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys His Arg Arg Ala Cys Arg Lys Arg
                325                 330                 335

Ile Arg Gln Lys Leu His Leu Cys Tyr Pro Val Gln Thr Ser Gln Pro
                340                 345                 350

Lys Leu Glu Leu Val Asp Ser Arg Pro Arg Arg Ser Thr Gln Leu
            355                 360                 365

Arg Ser Gly Ala Ser Val Thr Glu Pro Val Ala Glu Glu Arg Gly Leu
370                 375                 380

Met Ser Gln Pro Leu Met Glu Thr Cys His Ser Val Gly Ala Ala Tyr
385                 390                 395                 400

Leu Glu Ser Leu Pro Leu Gln Asp Ala Ser Pro Ala Gly Gly Pro Ser
                405                 410                 415

Ser Pro Arg Asp Leu Pro Glu Pro Arg Val Ser Thr Glu His Thr Asn
            420                 425                 430

Asn Lys Ile Glu Lys Ile Tyr Ile Met Lys Ala Asp Thr Val Ile Val
            435                 440                 445

Gly Thr Val Lys Ala Glu Leu Pro Glu Gly Arg Gly Leu Ala Gly Pro
            450                 455                 460

Ala Glu Pro Glu Leu Glu Glu Glu Leu Glu Ala Asp His Thr Pro His
465                 470                 475                 480

Tyr Pro Glu Gln Glu Thr Glu Pro Pro Leu Gly Ser Cys Ser Asp Val
                485                 490                 495

Met Leu Ser Val Glu Glu Glu Gly Lys Glu Asp Pro Leu Pro Thr Ala
            500                 505                 510

Ala Ser Gly Lys
        515

<210> SEQ ID NO 68
<211> LENGTH: 380
<212> TYPE: PRT
<213> ORGANISM: Artificial Sequence
<220> FEATURE:
<223> OTHER INFORMATION: Synthetic Construct

<400> SEQUENCE: 68

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45
```

```
Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Tyr Val Phe Gly Thr Gly Thr Lys Val Thr Val Leu Gly
            100                 105                 110

Ser Arg Gly Gly Gly Ser Gly Gly Gly Ser Gly Gly Gly Gly
        115                 120                 125

Ser Leu Glu Met Ala Glu Val Gln Leu Val Gln Ser Gly Ala Glu Val
130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205

Ile Ser Thr Ala Tyr Leu Gln Trp Ser Ser Leu Lys Ala Ser Asp Thr
210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Glu Gln
                245                 250                 255

Lys Leu Ile Ser Glu Glu Asp Leu Ala Ala Ala Thr Gly Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Ala Leu Tyr Leu Leu Arg Arg Asp Gln Arg Leu Pro Pro Asp
            340                 345                 350

Ala His Lys Pro Pro Gly Gly Gly Ser Phe Arg Thr Pro Ile Gln Glu
        355                 360                 365

Glu Gln Ala Asp Ala His Ser Thr Leu Ala Lys Ile
370                 375                 380

<210> SEQ ID NO 69
<211> LENGTH: 370
<212> TYPE: PRT
<213> ORGANISM: Artificial Sequence
<220> FEATURE:
<223> OTHER INFORMATION: Synthetic Construct

<400> SEQUENCE: 69

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                20                  25                  30
```

```
Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Ser Gly Gly Gly Ser Gly Gly Gly Gly
            115                 120                 125

Ser Leu Glu Met Ala Glu Val Gln Leu Val Gln Ser Gly Ala Glu Val
    130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205

Ile Ser Thr Ala Tyr Leu Gln Trp Ser Ser Leu Lys Ala Ser Asp Thr
    210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Ala Ala
                245                 250                 255

Ala Thr Gly Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Ala Leu Tyr Leu Arg Arg Asp
                325                 330                 335

Gln Arg Leu Pro Pro Asp Ala His Lys Pro Pro Gly Gly Gly Ser Phe
            340                 345                 350

Arg Thr Pro Ile Gln Glu Glu Gln Ala Asp Ala His Ser Thr Leu Ala
        355                 360                 365

Lys Ile
    370

<210> SEQ ID NO 70
<211> LENGTH: 369
<212> TYPE: PRT
<213> ORGANISM: Artificial Sequence
<220> FEATURE:
<223> OTHER INFORMATION: Synthetic Construct

<400> SEQUENCE: 70

Gln Ala Val Leu Thr Gln Pro Pro Ser Ala Ser Gly Thr Pro Gly Gln
 1               5                  10                  15
```

```
Arg Val Thr Ile Ser Cys Ser Gly Ser Ser Asn Ile Gly Ser Asn
             20                  25                  30

Thr Val Asn Trp Tyr Gln Gln Leu Pro Gly Thr Ala Pro Lys Leu Leu
         35                  40                  45

Met Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Tyr Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
            115                 120                 125

Leu Glu Met Ala Glu Val Gln Leu Val Gln Ser Gly Ala Glu Met Lys
130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175

Leu Glu Trp Met Gly Thr Ile Tyr Pro Asp Asp Ser Asp Thr Arg Tyr
            180                 185                 190

Gly Pro Ala Phe Gln Gly Gln Val Thr Ile Ser Ala Asp Lys Ser Ile
            195                 200                 205

Ser Thr Ala Tyr Leu Gln Trp Ser Ser Leu Lys Ala Ser Asp Thr Ala
210                 215                 220

Met Tyr Tyr Cys Ala Arg Asp Ser Tyr Tyr Gly Ile Asp Val Trp Gly
225                 230                 235                 240

Gln Gly Thr Leu Val Thr Val Ser Ser Glu Gln Lys Leu Ile Ser Glu
                245                 250                 255

Glu Asp Leu Ala Ala Ala Ile Glu Val Met Tyr Pro Pro Pro Tyr Leu
            260                 265                 270

Asp Asn Glu Lys Ser Asn Gly Thr Ile Ile His Val Lys Gly Lys His
            275                 280                 285

Leu Cys Pro Ser Pro Leu Phe Pro Gly Pro Ser Lys Pro Phe Trp Val
290                 295                 300

Leu Val Val Val Gly Gly Val Leu Ala Cys Tyr Ser Leu Leu Val Thr
305                 310                 315                 320

Val Ala Phe Ile Ile Phe Trp Val Arg Ser Lys Arg Ser Arg Leu Leu
                325                 330                 335

His Ser Asp Tyr Met Asn Met Thr Pro Arg Arg Pro Gly Pro Thr Arg
            340                 345                 350

Lys His Tyr Gln Pro Tyr Ala Pro Pro Arg Asp Phe Ala Ala Tyr Arg
            355                 360                 365

Ser

<210> SEQ ID NO 71
<211> LENGTH: 358
<212> TYPE: PRT
<213> ORGANISM: Artificial Sequence
<220> FEATURE:
<223> OTHER INFORMATION: Synthetic Construct

<400> SEQUENCE: 71
```

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Met Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
            115                 120                 125

Leu Glu Met Ala Glu Val Gln Leu Val Gln Ser Gly Ala Glu Met Lys
            130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175

Leu Glu Trp Met Gly Thr Ile Tyr Pro Asp Asp Ser Asp Thr Arg Tyr
            180                 185                 190

Gly Pro Ala Phe Gln Gly Gln Val Thr Ile Ser Ala Asp Lys Ser Ile
            195                 200                 205

Ser Thr Ala Tyr Leu Gln Trp Ser Ser Leu Lys Ala Ser Asp Thr Ala
210                 215                 220

Met Tyr Tyr Cys Ala Arg Asp Ser Tyr Tyr Gly Ile Asp Val Trp Gly
225                 230                 235                 240

Gln Gly Thr Leu Val Thr Val Ser Ser Glu Gln Lys Leu Ile Ser Glu
            245                 250                 255

Glu Asp Leu Ala Ala Ala Thr Gly Pro Ala Asp Leu Ser Pro Gly Ala
            260                 265                 270

Ser Ser Val Thr Pro Pro Ala Pro Ala Arg Glu Pro Gly His Ser Pro
            275                 280                 285

Gln Ile Ile Ser Phe Phe Leu Ala Leu Thr Ser Thr Ala Leu Leu Phe
            290                 295                 300

Leu Leu Phe Phe Leu Thr Leu Arg Phe Ser Val Val Lys Arg Gly Arg
305                 310                 315                 320

Lys Lys Leu Leu Tyr Ile Phe Lys Gln Pro Phe Met Arg Pro Val Gln
            325                 330                 335

Thr Thr Gln Glu Glu Asp Gly Cys Ser Cys Arg Phe Pro Glu Glu Glu
            340                 345                 350

Glu Gly Gly Cys Glu Leu
            355

<210> SEQ ID NO 72
<211> LENGTH: 348
<212> TYPE: PRT
<213> ORGANISM: Artificial Sequence
<220> FEATURE:
<223> OTHER INFORMATION: Synthetic Construct

<400> SEQUENCE: 72

```
Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Met Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
            115                 120                 125

Leu Glu Met Ala Glu Val Gln Leu Val Gln Ser Gly Ala Glu Met Lys
            130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175

Leu Glu Trp Met Gly Thr Ile Tyr Pro Asp Asp Ser Asp Thr Arg Tyr
            180                 185                 190

Gly Pro Ala Phe Gln Gly Gln Val Thr Ile Ser Ala Asp Lys Ser Ile
            195                 200                 205

Ser Thr Ala Tyr Leu Gln Trp Ser Ser Leu Lys Ala Ser Asp Thr Ala
210                 215                 220

Met Tyr Tyr Cys Ala Arg Asp Ser Tyr Tyr Gly Ile Asp Val Trp Gly
225                 230                 235                 240

Gln Gly Thr Leu Val Thr Val Ser Ser Ala Ala Ala Thr Gly Pro Ala
            245                 250                 255

Asp Leu Ser Pro Gly Ala Ser Ser Val Thr Pro Pro Ala Pro Ala Arg
            260                 265                 270

Glu Pro Gly His Ser Pro Gln Ile Ile Ser Phe Phe Leu Ala Leu Thr
            275                 280                 285

Ser Thr Ala Leu Leu Phe Leu Leu Phe Phe Leu Thr Leu Arg Phe Ser
            290                 295                 300

Val Val Lys Arg Gly Arg Lys Lys Leu Leu Tyr Ile Phe Lys Gln Pro
305                 310                 315                 320

Phe Met Arg Pro Val Gln Thr Thr Gln Glu Glu Asp Gly Cys Ser Cys
                325                 330                 335

Arg Phe Pro Glu Glu Glu Glu Gly Gly Cys Glu Leu
            340                 345
```

<210> SEQ ID NO 73
<211> LENGTH: 383
<212> TYPE: PRT
<213> ORGANISM: Artificial Sequence
<220> FEATURE:
<223> OTHER INFORMATION: Synthetic Construct

<400> SEQUENCE: 73

```
Gln Ala Val Leu Thr Gln Pro Pro Ser Ala Ser Gly Thr Pro Gly Gln
1               5                   10                  15
```

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Met Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Ser Leu
                85                  90                  95

Asn Gly Tyr Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
            115                 120                 125

Leu Glu Met Ala Glu Val Gln Leu Val Gln Ser Gly Ala Glu Met Lys
            130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175

Leu Glu Trp Met Gly Thr Ile Tyr Pro Asp Asp Ser Asp Thr Arg Tyr
            180                 185                 190

Gly Pro Ala Phe Gln Gly Gln Val Thr Ile Ser Ala Asp Lys Ser Ile
            195                 200                 205

Ser Thr Ala Tyr Leu Gln Trp Ser Ser Leu Lys Ala Ser Asp Thr Ala
210                 215                 220

Met Tyr Tyr Cys Ala Arg Asp Ser Tyr Tyr Gly Ile Asp Val Trp Gly
225                 230                 235                 240

Gln Gly Thr Leu Val Thr Val Ser Ser Glu Gln Lys Leu Ile Ser Glu
            245                 250                 255

Glu Asp Leu Ala Ala Ala Thr Gly Pro Thr His Leu Pro Tyr Val Ser
            260                 265                 270

Glu Met Leu Glu Ala Arg Thr Ala Gly His Met Gln Thr Leu Ala Asp
            275                 280                 285

Phe Arg Gln Leu Pro Ala Arg Thr Leu Ser Thr His Trp Pro Pro Gln
290                 295                 300

Arg Ser Leu Cys Ser Ser Asp Phe Ile Arg Ile Leu Val Ile Phe Ser
305                 310                 315                 320

Gly Met Phe Leu Val Phe Thr Leu Ala Gly Ala Leu Phe Leu His Gln
                325                 330                 335

Arg Arg Lys Tyr Arg Ser Asn Lys Gly Glu Ser Pro Val Glu Pro Ala
            340                 345                 350

Glu Pro Cys Arg Tyr Ser Cys Pro Arg Glu Glu Gly Ser Thr Ile
            355                 360                 365

Pro Ile Gln Glu Asp Tyr Arg Lys Pro Glu Pro Ala Cys Ser Pro
    370                 375                 380

<210> SEQ ID NO 74
<211> LENGTH: 373
<212> TYPE: PRT
<213> ORGANISM: Artificial Sequence
<220> FEATURE:
<223> OTHER INFORMATION: Synthetic Construct

<400> SEQUENCE: 74

```
Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Met Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
            115                 120                 125

Leu Glu Met Ala Glu Val Gln Leu Val Gln Ser Gly Ala Glu Met Lys
            130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175

Leu Glu Trp Met Gly Thr Ile Tyr Pro Asp Asp Ser Asp Thr Arg Tyr
            180                 185                 190

Gly Pro Ala Phe Gln Gly Gln Val Thr Ile Ser Ala Asp Lys Ser Ile
            195                 200                 205

Ser Thr Ala Tyr Leu Gln Trp Ser Ser Leu Lys Ala Ser Asp Thr Ala
210                 215                 220

Met Tyr Tyr Cys Ala Arg Asp Ser Tyr Tyr Gly Ile Asp Val Trp Gly
225                 230                 235                 240

Gln Gly Thr Leu Val Thr Val Ser Ser Ala Ala Thr Gly Pro Thr
            245                 250                 255

His Leu Pro Tyr Val Ser Glu Met Leu Glu Ala Arg Thr Ala Gly His
            260                 265                 270

Met Gln Thr Leu Ala Asp Phe Arg Gln Leu Pro Ala Arg Thr Leu Ser
    275                 280                 285

Thr His Trp Pro Pro Gln Arg Ser Leu Cys Ser Ser Asp Phe Ile Arg
    290                 295                 300

Ile Leu Val Ile Phe Ser Gly Met Phe Leu Val Phe Thr Leu Ala Gly
305                 310                 315                 320

Ala Leu Phe Leu His Gln Arg Arg Lys Tyr Arg Ser Asn Lys Gly Glu
                325                 330                 335

Ser Pro Val Glu Pro Ala Glu Pro Cys Arg Tyr Ser Cys Pro Arg Glu
            340                 345                 350

Glu Glu Gly Ser Thr Ile Pro Ile Gln Glu Asp Tyr Arg Lys Pro Glu
            355                 360                 365

Pro Ala Cys Ser Pro
    370

<210> SEQ ID NO 75
<211> LENGTH: 534
<212> TYPE: PRT
<213> ORGANISM: Artificial Sequence
<220> FEATURE:
<223> OTHER INFORMATION: Synthetic Construct
```

<400> SEQUENCE: 75

```
Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Met Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
            100                 105                 110

Arg Gly Gly Gly Gly Ser Gly Gly Gly Ser Gly Gly Gly Ser
            115                 120                 125

Leu Glu Met Ala Glu Val Gln Leu Val Gln Ser Gly Ala Glu Met Lys
            130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175

Leu Glu Trp Met Gly Thr Ile Tyr Pro Asp Asp Ser Asp Thr Arg Tyr
            180                 185                 190

Gly Pro Ala Phe Gln Gly Gln Val Thr Ile Ser Ala Asp Lys Ser Ile
            195                 200                 205

Ser Thr Ala Tyr Leu Gln Trp Ser Ser Leu Lys Ala Ser Asp Thr Ala
210                 215                 220

Met Tyr Tyr Cys Ala Arg Asp Ser Tyr Tyr Gly Ile Asp Val Trp Gly
225                 230                 235                 240

Gln Gly Thr Leu Val Thr Val Ser Ser Glu Gln Lys Leu Ile Ser Glu
                245                 250                 255

Glu Asp Leu Ala Ala Ala Thr Gly Ala Pro Pro Leu Gly Thr Gln Pro
            260                 265                 270

Asp Cys Asn Pro Thr Pro Glu Asn Gly Glu Ala Pro Ala Ser Thr Ser
            275                 280                 285

Pro Thr Gln Ser Leu Leu Val Asp Ser Gln Ala Ser Lys Thr Leu Pro
290                 295                 300

Ile Pro Thr Ser Ala Pro Val Ala Leu Ser Ser Thr Gly Lys Pro Val
305                 310                 315                 320

Leu Asp Ala Gly Pro Val Leu Phe Trp Val Ile Leu Val Leu Val Val
                325                 330                 335

Val Val Gly Ser Ser Ala Phe Leu Leu Cys His Arg Arg Ala Cys Arg
            340                 345                 350

Lys Arg Ile Arg Gln Lys Leu His Leu Cys Tyr Pro Val Gln Thr Ser
            355                 360                 365

Gln Pro Lys Leu Glu Leu Val Asp Ser Arg Pro Arg Arg Ser Ser Thr
            370                 375                 380

Gln Leu Arg Ser Gly Ala Ser Val Thr Glu Pro Val Ala Glu Glu Arg
385                 390                 395                 400

Gly Leu Met Ser Gln Pro Leu Met Glu Thr Cys His Ser Val Gly Ala
```

```
                    405                 410                 415

Ala Tyr Leu Glu Ser Leu Pro Leu Gln Asp Ala Ser Pro Ala Gly Gly
                420                 425                 430

Pro Ser Ser Pro Arg Asp Leu Pro Glu Pro Arg Val Ser Thr Glu His
            435                 440                 445

Thr Asn Asn Lys Ile Glu Lys Ile Tyr Ile Met Lys Ala Asp Thr Val
        450                 455                 460

Ile Val Gly Thr Val Lys Ala Glu Leu Pro Glu Gly Arg Gly Leu Ala
465                 470                 475                 480

Gly Pro Ala Glu Pro Glu Leu Glu Glu Leu Glu Ala Asp His Thr
                485                 490                 495

Pro His Tyr Pro Glu Gln Glu Thr Glu Pro Pro Leu Gly Ser Cys Ser
            500                 505                 510

Asp Val Met Leu Ser Val Glu Glu Glu Gly Lys Glu Asp Pro Leu Pro
        515                 520                 525

Thr Ala Ala Ser Gly Lys
    530

<210> SEQ ID NO 76
<211> LENGTH: 524
<212> TYPE: PRT
<213> ORGANISM: Artificial Sequence
<220> FEATURE:
<223> OTHER INFORMATION: Synthetic Construct

<400> SEQUENCE: 76

Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Met Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
            100                 105                 110

Arg Gly Gly Gly Gly Ser Gly Gly Gly Ser Gly Gly Gly Gly Ser
        115                 120                 125

Leu Glu Met Ala Glu Val Gln Leu Val Gln Ser Gly Ala Glu Met Lys
    130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175

Leu Glu Trp Met Gly Thr Ile Tyr Pro Asp Asp Ser Asp Thr Arg Tyr
            180                 185                 190

Gly Pro Ala Phe Gln Gly Gln Val Thr Ile Ser Ala Asp Lys Ser Ile
        195                 200                 205

Ser Thr Ala Tyr Leu Gln Trp Ser Ser Leu Lys Ala Ser Asp Thr Ala
    210                 215                 220

Met Tyr Tyr Cys Ala Arg Asp Ser Tyr Tyr Gly Ile Asp Val Trp Gly
```

```
225                 230                 235                 240
Gln Gly Thr Leu Val Thr Val Ser Ser Ala Ala Thr Gly Ala Pro
                245                 250                 255

Pro Leu Gly Thr Gln Pro Asp Cys Asn Pro Thr Pro Glu Asn Gly Glu
                260                 265                 270

Ala Pro Ala Ser Thr Ser Pro Thr Gln Ser Leu Leu Val Asp Ser Gln
                275                 280                 285

Ala Ser Lys Thr Leu Pro Ile Pro Thr Ser Ala Pro Val Ala Leu Ser
            290                 295                 300

Ser Thr Gly Lys Pro Val Leu Asp Ala Gly Pro Val Leu Phe Trp Val
305                 310                 315                 320

Ile Leu Val Leu Val Val Val Gly Ser Ala Phe Leu Leu Cys
                325                 330                 335

His Arg Arg Ala Cys Arg Lys Arg Ile Arg Gln Lys Leu His Leu Cys
                340                 345                 350

Tyr Pro Val Gln Thr Ser Gln Pro Lys Leu Glu Leu Val Asp Ser Arg
                355                 360                 365

Pro Arg Arg Ser Ser Thr Gln Leu Arg Ser Gly Ala Ser Val Thr Glu
            370                 375                 380

Pro Val Ala Glu Glu Arg Gly Leu Met Ser Gln Pro Leu Met Glu Thr
385                 390                 395                 400

Cys His Ser Val Gly Ala Ala Tyr Leu Glu Ser Leu Pro Leu Gln Asp
                405                 410                 415

Ala Ser Pro Ala Gly Gly Pro Ser Ser Pro Arg Asp Leu Pro Glu Pro
                420                 425                 430

Arg Val Ser Thr Glu His Thr Asn Asn Lys Ile Glu Lys Ile Tyr Ile
            435                 440                 445

Met Lys Ala Asp Thr Val Ile Val Gly Thr Val Lys Ala Glu Leu Pro
            450                 455                 460

Glu Gly Arg Gly Leu Ala Gly Pro Ala Glu Pro Glu Leu Glu Glu Glu
465                 470                 475                 480

Leu Glu Ala Asp His Thr Pro His Tyr Pro Glu Gln Glu Thr Glu Pro
                485                 490                 495

Pro Leu Gly Ser Cys Ser Asp Val Met Leu Ser Val Glu Glu Glu Gly
                500                 505                 510

Lys Glu Asp Pro Leu Pro Thr Ala Ala Ser Gly Lys
            515                 520

<210> SEQ ID NO 77
<211> LENGTH: 374
<212> TYPE: PRT
<213> ORGANISM: Artificial Sequence
<220> FEATURE:
<223> OTHER INFORMATION: Synthetic Construct

<400> SEQUENCE: 77

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Met Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
```

```
            65                  70                  75                  80
Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
            100                 105                 110

Arg Gly Gly Gly Gly Ser Gly Gly Gly Ser Gly Gly Gly Ser
            115                 120                 125

Leu Glu Met Ala Glu Val Gln Leu Val Gln Ser Gly Ala Glu Met Lys
            130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175

Leu Glu Trp Met Gly Thr Ile Tyr Pro Asp Asp Ser Asp Thr Arg Tyr
                180                 185                 190

Gly Pro Ala Phe Gln Gly Gln Val Thr Ile Ser Ala Asp Lys Ser Ile
                195                 200                 205

Ser Thr Ala Tyr Leu Gln Trp Ser Ser Leu Lys Ala Ser Asp Thr Ala
        210                 215                 220

Met Tyr Tyr Cys Ala Arg Asp Ser Tyr Tyr Gly Ile Asp Val Trp Gly
225                 230                 235                 240

Gln Gly Thr Leu Val Thr Val Ser Ser Glu Gln Lys Leu Ile Ser Glu
                245                 250                 255

Glu Asp Leu Ala Ala Ala Thr Gly Asp Arg Asp Pro Ala Thr Gln
            260                 265                 270

Pro Gln Glu Thr Gln Gly Pro Pro Ala Arg Pro Ile Thr Val Gln Pro
            275                 280                 285

Thr Glu Ala Trp Pro Arg Thr Ser Gln Gly Pro Ser Thr Arg Pro Val
            290                 295                 300

Glu Val Pro Gly Gly Arg Ala Val Ala Ala Ile Leu Gly Leu Gly Leu
305                 310                 315                 320

Val Leu Gly Leu Leu Gly Pro Leu Ala Ile Leu Leu Ala Leu Tyr Leu
                325                 330                 335

Leu Arg Arg Asp Gln Arg Leu Pro Pro Asp Ala His Lys Pro Pro Gly
                340                 345                 350

Gly Gly Ser Phe Arg Thr Pro Ile Gln Glu Glu Gln Ala Asp Ala His
                355                 360                 365

Ser Thr Leu Ala Lys Ile
            370

<210> SEQ ID NO 78
<211> LENGTH: 364
<212> TYPE: PRT
<213> ORGANISM: Artificial Sequence
<220> FEATURE:
<223> OTHER INFORMATION: Synthetic Construct

<400> SEQUENCE: 78

Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Met Tyr Ser Asn Asn Gln Arg Pro Ser Gly Val Pro Asp Arg Phe Ser
```

50                  55                  60
Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                     85                  90                  95

Asn Gly Tyr Val Phe Gly Thr Gly Thr Lys Val Thr Val Leu Gly Ser
                    100                 105                 110

Arg Gly Gly Gly Ser Gly Gly Gly Ser Gly Gly Gly Ser
            115                 120                 125

Leu Glu Met Ala Glu Val Gln Leu Val Gln Ser Gly Ala Glu Met Lys
            130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                    165                 170                 175

Leu Glu Trp Met Gly Thr Ile Tyr Pro Asp Asp Ser Asp Thr Arg Tyr
                180                 185                 190

Gly Pro Ala Phe Gln Gly Gln Val Thr Ile Ser Ala Asp Lys Ser Ile
                195                 200                 205

Ser Thr Ala Tyr Leu Gln Trp Ser Ser Leu Lys Ala Ser Asp Thr Ala
210                 215                 220

Met Tyr Tyr Cys Ala Arg Asp Ser Tyr Tyr Gly Ile Asp Val Trp Gly
225                 230                 235                 240

Gln Gly Thr Leu Val Thr Val Ser Ser Ala Ala Ala Thr Gly Asp Arg
                245                 250                 255

Asp Pro Pro Ala Thr Gln Pro Gln Glu Thr Gln Gly Pro Pro Ala Arg
                260                 265                 270

Pro Ile Thr Val Gln Pro Thr Glu Ala Trp Pro Arg Thr Ser Gln Gly
                275                 280                 285

Pro Ser Thr Arg Pro Val Glu Val Pro Gly Gly Arg Ala Val Ala Ala
                290                 295                 300

Ile Leu Gly Leu Gly Leu Val Leu Gly Leu Leu Gly Pro Leu Ala Ile
305                 310                 315                 320

Leu Leu Ala Leu Tyr Leu Leu Arg Arg Asp Gln Arg Leu Pro Pro Asp
                325                 330                 335

Ala His Lys Pro Pro Gly Gly Gly Ser Phe Arg Thr Pro Ile Gln Glu
                340                 345                 350

Glu Gln Ala Asp Ala His Ser Thr Leu Ala Lys Ile
            355                 360

<210> SEQ ID NO 79
<211> LENGTH: 381
<212> TYPE: PRT
<213> ORGANISM: Artificial Sequence
<220> FEATURE:
<223> OTHER INFORMATION: Synthetic Construct

<400> SEQUENCE: 79

Gln Ala Val Leu Thr Gln Pro Pro Ser Ala Ser Gly Thr Pro Gly Gln
  1               5                  10                  15

Arg Val Thr Ile Ser Cys Ser Gly Ser Ser Ser Asn Ile Gly Ser Asn
                 20                  25                  30

Thr Val Asn Trp Tyr Gln Gln Leu Pro Gly Thr Ala Pro Lys Leu Leu
             35                  40                  45

Met Tyr Ser Asn Asn Gln Arg Pro Ser Gly Val Pro Asp Arg Phe Ser

```
        50                  55                  60
Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Tyr Val Phe Gly Thr Gly Thr Lys Val Thr Val Leu Gly Ser
            100                 105                 110

Arg Gly Gly Gly Ser Gly Gly Gly Ser Gly Gly Gly Ser
        115                 120                 125

Leu Glu Met Ala Glu Val Gln Leu Val Gln Ser Gly Ala Glu Met Lys
    130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175

Leu Glu Trp Met Gly Thr Ile Tyr Pro Asp Asp Ser Asp Thr Arg Tyr
            180                 185                 190

Gly Pro Ala Phe Gln Gly Gln Val Thr Ile Ser Ala Asp Lys Ser Ile
        195                 200                 205

Ser Thr Ala Tyr Leu Gln Trp Ser Ser Leu Lys Ala Ser Asp Thr Ala
210                 215                 220

Met Tyr Tyr Cys Ala Arg Asp Ser Tyr Tyr Gly Ile Asp Val Trp Gly
225                 230                 235                 240

Gln Gly Thr Leu Val Thr Val Ser Ser Glu Gln Lys Leu Ile Ser Glu
                245                 250                 255

Glu Asp Leu Ala Ala Ala Thr Gly Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Gln Arg Arg
                325                 330                 335

Lys Tyr Arg Ser Asn Lys Gly Glu Ser Pro Val Glu Pro Ala Glu Pro
            340                 345                 350

Cys Arg Tyr Ser Cys Pro Arg Glu Glu Glu Gly Ser Thr Ile Pro Ile
        355                 360                 365

Gln Glu Asp Tyr Arg Lys Pro Glu Pro Ala Cys Ser Pro
    370                 375                 380

<210> SEQ ID NO 80
<211> LENGTH: 371
<212> TYPE: PRT
<213> ORGANISM: Artificial Sequence
<220> FEATURE:
<223> OTHER INFORMATION: Synthetic Construct

<400> SEQUENCE: 80

Gln Ala Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
```

```
                    35                  40                  45
Met Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Tyr Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Met Lys
    130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175

Leu Glu Trp Met Gly Thr Ile Tyr Pro Asp Asp Ser Asp Thr Arg Tyr
            180                 185                 190

Gly Pro Ala Phe Gln Gly Gln Val Thr Ile Ser Ala Asp Lys Ser Ile
        195                 200                 205

Ser Thr Ala Tyr Leu Gln Trp Ser Ser Leu Lys Ala Ser Asp Thr Ala
    210                 215                 220

Met Tyr Tyr Cys Ala Arg Asp Ser Tyr Tyr Gly Ile Asp Val Trp Gly
225                 230                 235                 240

Gln Gly Thr Leu Val Thr Val Ser Ser Ala Ala Thr Gly Thr Thr
                245                 250                 255

Thr Pro Ala Pro Arg Pro Pro Thr Pro Ala Pro Thr Ile Ala Ser Gln
            260                 265                 270

Pro Leu Ser Leu Arg Pro Glu Ala Cys Arg Pro Ala Ala Gly Gly Ala
        275                 280                 285

Val His Thr Arg Gly Leu Asp Phe Ala Cys Asp Ile Tyr Ile Trp Ala
    290                 295                 300

Pro Leu Ala Gly Thr Cys Gly Val Leu Leu Leu Ser Leu Val Ile Thr
305                 310                 315                 320

Leu Tyr Cys Gln Arg Arg Lys Tyr Arg Ser Asn Lys Gly Glu Ser Pro
                325                 330                 335

Val Glu Pro Ala Glu Pro Cys Arg Tyr Ser Cys Pro Arg Glu Glu Glu
            340                 345                 350

Gly Ser Thr Ile Pro Ile Gln Glu Asp Tyr Arg Lys Pro Glu Pro Ala
        355                 360                 365

Cys Ser Pro
    370

<210> SEQ ID NO 81
<211> LENGTH: 521
<212> TYPE: PRT
<213> ORGANISM: Artificial Sequence
<220> FEATURE:
<223> OTHER INFORMATION: Synthetic Construct

<400> SEQUENCE: 81

Gln Ala Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
```

```
            20                  25                  30
Thr Val Asn Trp Tyr Gln Gln Leu Pro Gly Thr Ala Pro Lys Leu Leu
             35                  40                  45
Met Tyr Ser Asn Asn Gln Arg Pro Ser Gly Val Pro Asp Arg Phe Ser
 50                  55                  60
Gly Ser Lys Ser Gly Thr Ser Ala Ser Leu Ala Ile Ser Gly Leu Gln
 65                  70                  75                  80
Ser Glu Asp Glu Ala Asp Tyr Tyr Cys Ala Ala Trp Asp Asp Ser Leu
                 85                  90                  95
Asn Gly Tyr Val Phe Gly Thr Gly Thr Lys Val Thr Val Leu Gly Ser
                100                 105                 110
Arg Gly Gly Gly Ser Gly Gly Gly Ser Gly Gly Gly Gly Ser
            115                 120                 125
Leu Glu Met Ala Glu Val Gln Leu Val Gln Ser Gly Ala Glu Met Lys
            130                 135                 140
Lys Pro Gly Glu Ser Leu Lys Ile Ser Cys Lys Gly Ser Gly Tyr Asn
145                 150                 155                 160
Phe Ala Ser Tyr Trp Val Gly Trp Val Arg Gln Met Pro Gly Lys Gly
                165                 170                 175
Leu Glu Trp Met Gly Thr Ile Tyr Pro Asp Asp Ser Asp Thr Arg Tyr
                180                 185                 190
Gly Pro Ala Phe Gln Gly Gln Val Thr Ile Ser Ala Asp Lys Ser Ile
            195                 200                 205
Ser Thr Ala Tyr Leu Gln Trp Ser Ser Leu Lys Ala Ser Asp Thr Ala
        210                 215                 220
Met Tyr Tyr Cys Ala Arg Asp Ser Tyr Tyr Gly Ile Asp Val Trp Gly
225                 230                 235                 240
Gln Gly Thr Leu Val Thr Val Ser Ser Glu Gln Lys Leu Ile Ser Glu
                245                 250                 255
Glu Asp Leu Ala Ala Ala Thr Gly Thr Thr Pro Ala Pro Arg Pro
            260                 265                 270
Pro Thr Pro Ala Pro Thr Ile Ala Ser Gln Pro Leu Ser Leu Arg Pro
        275                 280                 285
Glu Ala Cys Arg Pro Ala Ala Gly Gly Ala Val His Thr Arg Gly Leu
        290                 295                 300
Asp Phe Ala Cys Asp Ile Tyr Ile Trp Ala Pro Leu Ala Gly Thr Cys
305                 310                 315                 320
Gly Val Leu Leu Leu Ser Leu Val Ile Thr Leu Tyr Cys His Arg Arg
                325                 330                 335
Ala Cys Arg Lys Arg Ile Arg Gln Lys Leu His Leu Cys Tyr Pro Val
                340                 345                 350
Gln Thr Ser Gln Pro Lys Leu Glu Leu Val Asp Ser Arg Pro Arg Arg
            355                 360                 365
Ser Ser Thr Gln Leu Arg Ser Gly Ala Ser Val Thr Glu Pro Val Ala
        370                 375                 380
Glu Glu Arg Gly Leu Met Ser Gln Pro Leu Met Glu Thr Cys His Ser
385                 390                 395                 400
Val Gly Ala Ala Tyr Leu Glu Ser Leu Pro Leu Gln Asp Ala Ser Pro
                405                 410                 415
Ala Gly Gly Pro Ser Ser Pro Arg Asp Leu Pro Glu Pro Arg Val Ser
            420                 425                 430
Thr Glu His Thr Asn Asn Lys Ile Glu Lys Ile Tyr Ile Met Lys Ala
        435                 440                 445
```

```
Asp Thr Val Ile Val Gly Thr Val Lys Ala Glu Leu Pro Glu Gly Arg
    450                 455                 460

Gly Leu Ala Gly Pro Ala Glu Pro Glu Leu Glu Glu Leu Glu Ala
465                 470                 475                 480

Asp His Thr Pro His Tyr Pro Glu Gln Glu Thr Glu Pro Pro Leu Gly
                485                 490                 495

Ser Cys Ser Asp Val Met Leu Ser Val Glu Glu Gly Lys Glu Asp
                500                 505                 510

Pro Leu Pro Thr Ala Ala Ser Gly Lys
            515                 520

<210> SEQ ID NO 82
<211> LENGTH: 511
<212> TYPE: PRT
<213> ORGANISM: Artificial Sequence
<220> FEATURE:
<223> OTHER INFORMATION: Synthetic Construct

<400> SEQUENCE: 82

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
                35                  40                  45

Met Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
                100                 105                 110

Arg Gly Gly Gly Gly Ser Gly Gly Gly Gly Ser Gly Gly Gly Gly Ser
            115                 120                 125

Leu Glu Met Ala Glu Val Gln Leu Val Gln Ser Gly Ala Glu Met Lys
    130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175

Leu Glu Trp Met Gly Thr Ile Tyr Pro Asp Asp Ser Asp Thr Arg Tyr
                180                 185                 190

Gly Pro Ala Phe Gln Gly Gln Val Thr Ile Ser Ala Asp Lys Ser Ile
            195                 200                 205

Ser Thr Ala Tyr Leu Gln Trp Ser Ser Leu Lys Ala Ser Asp Thr Ala
    210                 215                 220

Met Tyr Tyr Cys Ala Arg Asp Ser Tyr Tyr Gly Ile Asp Val Trp Gly
225                 230                 235                 240

Gln Gly Thr Leu Val Thr Val Ser Ser Ala Ala Thr Gly Thr Thr
                245                 250                 255

Thr Pro Ala Pro Arg Pro Pro Thr Pro Ala Pro Thr Ile Ala Ser Gln
            260                 265                 270

Pro Leu Ser Leu Arg Pro Glu Ala Cys Arg Pro Ala Ala Gly Gly Ala
    275                 280                 285
```

Val His Thr Arg Gly Leu Asp Phe Ala Cys Asp Ile Tyr Ile Trp Ala
        290                 295                 300

Pro Leu Ala Gly Thr Cys Gly Val Leu Leu Leu Ser Leu Val Ile Thr
305                 310                 315                 320

Leu Tyr Cys His Arg Arg Ala Cys Arg Lys Arg Ile Arg Gln Lys Leu
                325                 330                 335

His Leu Cys Tyr Pro Val Gln Thr Ser Gln Pro Lys Leu Glu Leu Val
                340                 345                 350

Asp Ser Arg Pro Arg Arg Ser Ser Thr Gln Leu Arg Ser Gly Ala Ser
            355                 360                 365

Val Thr Glu Pro Val Ala Glu Arg Gly Leu Met Ser Gln Pro Leu
        370                 375                 380

Met Glu Thr Cys His Ser Val Gly Ala Ala Tyr Leu Glu Ser Leu Pro
385                 390                 395                 400

Leu Gln Asp Ala Ser Pro Ala Gly Gly Pro Ser Ser Pro Arg Asp Leu
                405                 410                 415

Pro Glu Pro Arg Val Ser Thr Glu His Thr Asn Asn Lys Ile Glu Lys
                420                 425                 430

Ile Tyr Ile Met Lys Ala Asp Thr Val Ile Val Gly Thr Val Lys Ala
            435                 440                 445

Glu Leu Pro Glu Gly Arg Gly Leu Ala Gly Pro Ala Glu Pro Glu Leu
450                 455                 460

Glu Glu Glu Leu Glu Ala Asp His Thr Pro His Tyr Pro Glu Gln Glu
465                 470                 475                 480

Thr Glu Pro Pro Leu Gly Ser Cys Ser Asp Val Met Leu Ser Val Glu
                485                 490                 495

Glu Glu Gly Lys Glu Asp Pro Leu Pro Thr Ala Ala Ser Gly Lys
            500                 505                 510

<210> SEQ ID NO 83
<211> LENGTH: 375
<212> TYPE: PRT
<213> ORGANISM: Artificial Sequence
<220> FEATURE:
<223> OTHER INFORMATION: Synthetic Construct

<400> SEQUENCE: 83

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Met Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
                100                 105                 110

Arg Gly Gly Gly Gly Ser Gly Gly Gly Gly Ser Gly Gly Gly Gly Ser
            115                 120                 125

Leu Glu Met Ala Glu Val Gln Leu Val Gln Ser Gly Ala Glu Met Lys
        130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
            165                 170                 175

Leu Glu Trp Met Gly Thr Ile Tyr Pro Asp Asp Ser Asp Thr Arg Tyr
        180                 185                 190

Gly Pro Ala Phe Gln Gly Gln Val Thr Ile Ser Ala Asp Lys Ser Ile
    195                 200                 205

Ser Thr Ala Tyr Leu Gln Trp Ser Ser Leu Lys Ala Ser Asp Thr Ala
210                 215                 220

Met Tyr Tyr Cys Ala Arg Asp Ser Tyr Tyr Gly Ile Asp Val Trp Gly
225                 230                 235                 240

Gln Gly Thr Leu Val Thr Val Ser Ser Glu Gln Lys Leu Ile Ser Glu
            245                 250                 255

Glu Asp Leu Ala Ala Ala Thr Gly Thr Thr Pro Ala Pro Arg Pro
        260                 265                 270

Pro Thr Pro Ala Pro Thr Ile Ala Ser Gln Pro Leu Ser Leu Arg Pro
    275                 280                 285

Glu Ala Cys Arg Pro Ala Ala Gly Gly Ala Val His Thr Arg Gly Leu
290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Ala Leu Tyr
            325                 330                 335

Leu Leu Arg Arg Asp Gln Arg Leu Pro Pro Asp Ala His Lys Pro Pro
        340                 345                 350

Gly Gly Gly Ser Phe Arg Thr Pro Ile Gln Glu Glu Gln Ala Asp Ala
    355                 360                 365

His Ser Thr Leu Ala Lys Ile
    370                 375

<210> SEQ ID NO 84
<211> LENGTH: 365
<212> TYPE: PRT
<213> ORGANISM: Artificial Sequence
<220> FEATURE:
<223> OTHER INFORMATION: Synthetic Construct

<400> SEQUENCE: 84

Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Met Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
            100                 105                 110

Arg Gly Gly Gly Gly Ser Gly Gly Gly Ser Gly Gly Gly Gly Ser
        115                 120                 125

```
Leu Glu Met Ala Glu Val Gln Leu Val Gln Ser Gly Ala Glu Met Lys
            130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175

Leu Glu Trp Met Gly Thr Ile Tyr Pro Asp Asp Ser Asp Thr Arg Tyr
            180                 185                 190

Gly Pro Ala Phe Gln Gly Gln Val Thr Ile Ser Ala Asp Lys Ser Ile
            195                 200                 205

Ser Thr Ala Tyr Leu Gln Trp Ser Ser Leu Lys Ala Ser Asp Thr Ala
            210                 215                 220

Met Tyr Tyr Cys Ala Arg Asp Ser Tyr Tyr Gly Ile Asp Val Trp Gly
225                 230                 235                 240

Gln Gly Thr Leu Val Thr Val Ser Ser Ala Ala Thr Gly Thr Thr
                245                 250                 255

Thr Pro Ala Pro Arg Pro Pro Thr Pro Ala Pro Thr Ile Ala Ser Gln
                260                 265                 270

Pro Leu Ser Leu Arg Pro Glu Ala Cys Arg Pro Ala Ala Gly Gly Ala
                275                 280                 285

Val His Thr Arg Gly Leu Asp Phe Ala Cys Asp Ile Tyr Ile Trp Ala
            290                 295                 300

Pro Leu Ala Gly Thr Cys Gly Val Leu Leu Leu Ser Leu Val Ile Thr
305                 310                 315                 320

Leu Tyr Cys Ala Leu Tyr Leu Leu Arg Arg Asp Gln Arg Leu Pro Pro
                325                 330                 335

Asp Ala His Lys Pro Pro Gly Gly Gly Ser Phe Arg Thr Pro Ile Gln
            340                 345                 350

Glu Glu Gln Ala Asp Ala His Ser Thr Leu Ala Lys Ile
            355                 360                 365

<210> SEQ ID NO 85
<211> LENGTH: 1064
<212> TYPE: PRT
<213> ORGANISM: Artificial Sequence
<220> FEATURE:
<223> OTHER INFORMATION: Synthetic Construct

<400> SEQUENCE: 85

Met Glu Thr Asp Thr Leu Leu Leu Trp Val Leu Leu Leu Trp Val Pro
1               5                   10                  15

Gly Ser Thr Gly Glu Val Gln Leu Val Gln Ser Gly Ala Glu Val Lys
            20                  25                  30

Lys Pro Gly Glu Ser Leu Lys Ile Ser Cys Lys Gly Ser Gly Tyr Ser
            35                  40                  45

Phe Thr Ser Tyr Trp Ile Gly Trp Val Arg Gln Met Pro Gly Lys Gly
        50                  55                  60

Leu Glu Trp Met Gly Ile Ile Tyr Pro Gly Asp Ser Asp Thr Arg Tyr
65                  70                  75                  80

Ser Pro Ser Phe Gln Gly Gln Val Thr Ile Ser Ala Asp Lys Ser Ile
                85                  90                  95

Ser Thr Ala Tyr Leu Gln Trp Ser Ser Leu Lys Ala Ser Asp Thr Ala
            100                 105                 110

Met Tyr Tyr Cys Ala Arg Ser Met Gly Ser Ser Leu Tyr Ala Ser Ser
            115                 120                 125
```

```
Asp Val Trp Gly Gln Gly Thr Leu Val Thr Val Ser Ser Ala Ser Thr
            130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
                180                 185                 190
Thr Phe Pro Ala Val Leu Gln Ser Ser Gly Leu Tyr Ser Leu Ser Ser
            195                 200                 205
Val Val Thr Val Pro Ser Ser Ser Leu Gly Thr Gln Thr Tyr Ile Cys
            210                 215                 220
Asn Val Asn His Lys Pro Ser Asn Thr Lys Val Asp Lys Arg Val Glu
225                 230                 235                 240
Pro Lys Ser Cys Glu Val Lys Thr Asp Ser Thr Asp His Val Lys Pro
                245                 250                 255
Lys Glu Thr Glu Asn Thr Lys Gln Pro Ser Lys Ser Cys His Lys Pro
                260                 265                 270
Lys Ala Ile Val His Thr Glu Lys Val Asn Met Met Ser Leu Thr Val
            275                 280                 285
Leu Gly Leu Arg Met Leu Phe Ala Lys Thr Val Ala Val Asn Phe Leu
290                 295                 300
Leu Thr Ala Lys Leu Phe Phe Leu Arg Ala Lys Arg Ser Gly Ser Gly
305                 310                 315                 320
Ala Pro Val Lys Gln Thr Leu Asn Phe Asp Leu Leu Lys Leu Ala Gly
                325                 330                 335
Asp Val Glu Ser Asn Pro Gly Pro Met Glu Thr Asp Thr Leu Leu Leu
            340                 345                 350
Trp Val Leu Leu Leu Trp Val Pro Gly Ser Thr Gly Gln Ser Val Leu
            355                 360                 365
Thr Gln Pro Pro Ser Val Ser Gly Ala Pro Gly Gln Arg Val Thr Ile
            370                 375                 380
Ser Cys Thr Gly Ser Ser Ser Asn Ile Gly Ala Gly Tyr Asp Val His
385                 390                 395                 400
Trp Tyr Gln Gln Leu Pro Gly Thr Ala Pro Lys Leu Leu Ile Tyr Gly
                405                 410                 415
Asn Ser Asn Arg Pro Ser Gly Val Pro Asp Arg Phe Ser Gly Ser Lys
                420                 425                 430
Ser Gly Thr Ser Ala Ser Leu Ala Ile Thr Gly Leu Gln Ala Glu Asp
            435                 440                 445
Glu Ala Asp Tyr Tyr Cys Gln Ser Tyr Asp Ser Ser Leu Ser Gly Tyr
            450                 455                 460
Val Phe Gly Thr Gly Thr Lys Val Thr Val Leu Gly Gln Pro Lys Ala
465                 470                 475                 480
Asn Pro Thr Val Thr Leu Phe Pro Pro Ser Glu Glu Leu Gln Ala
                485                 490                 495
Asn Lys Ala Thr Leu Val Cys Leu Ile Ser Asp Phe Tyr Pro Gly Ala
                500                 505                 510
Val Thr Val Ala Trp Lys Ala Asp Gly Ser Pro Val Lys Ala Gly Val
            515                 520                 525
Glu Thr Thr Lys Pro Ser Lys Gln Ser Asn Asn Lys Tyr Ala Ala Ser
530                 535                 540
```

-continued

```
Ser Tyr Leu Ser Leu Thr Pro Glu Gln Trp Lys Ser His Arg Ser Tyr
545                 550                 555                 560

Ser Cys Gln Val Thr His Glu Gly Ser Thr Val Glu Lys Thr Val Ala
                565                 570                 575

Pro Thr Glu Cys Ser Pro Ile Lys Thr Asp Val Ile Thr Met Asp Pro
            580                 585                 590

Lys Asp Asn Cys Ser Lys Asp Ala Asn Asp Thr Leu Leu Gln Leu
        595                 600                 605

Thr Asn Thr Ser Ala Tyr Tyr Met Tyr Leu Leu Leu Leu Lys Ser
    610                 615                 620

Val Val Tyr Phe Ala Ile Ile Thr Cys Leu Leu Arg Arg Thr Ala
625                 630                 635                 640

Phe Cys Cys Asn Gly Glu Lys Ser Gly Ser Gly Ala Thr Asn Phe Ser
                645                 650                 655

Leu Leu Lys Gln Ala Gly Asp Val Glu Glu Asn Pro Gly Pro Met Glu
                660                 665                 670

Thr Asp Thr Leu Leu Leu Trp Val Leu Leu Leu Trp Val Pro Gly Ser
            675                 680                 685

Thr Gly Gln Ser Val Leu Thr Gln Pro Pro Ser Val Ser Gly Ala Pro
690                 695                 700

Gly Gln Arg Val Thr Ile Ser Cys Thr Gly Ser Ser Asn Ile Gly
705                 710                 715                 720

Ala Gly Tyr Asp Val His Trp Tyr Gln Gln Leu Pro Gly Thr Ala Pro
                725                 730                 735

Lys Leu Leu Ile Tyr Gly Asn Ser Asn Arg Pro Ser Gly Val Pro Asp
            740                 745                 750

Arg Phe Ser Gly Ser Lys Ser Gly Thr Ser Ala Ser Leu Ala Ile Thr
        755                 760                 765

Gly Leu Gln Ala Glu Asp Glu Ala Asp Tyr Tyr Cys Gln Ser Tyr Asp
    770                 775                 780

Ser Ser Leu Ser Gly Tyr Val Phe Gly Thr Gly Thr Lys Val Thr Val
785                 790                 795                 800

Leu Gly Ser Arg Gly Gly Gly Gly Ser Gly Gly Gly Gly Ser Gly Gly
                805                 810                 815

Gly Gly Ser Leu Glu Met Ala Glu Val Gln Leu Val Gln Ser Gly Ala
            820                 825                 830

Glu Val Lys Lys Pro Gly Glu Ser Leu Lys Ile Ser Cys Lys Gly Ser
        835                 840                 845

Gly Tyr Ser Phe Thr Ser Tyr Trp Ile Gly Trp Val Arg Gln Met Pro
    850                 855                 860

Gly Lys Gly Leu Glu Trp Met Gly Ile Ile Tyr Pro Gly Asp Ser Asp
865                 870                 875                 880

Thr Arg Tyr Ser Pro Ser Phe Gln Gly Gln Val Thr Ile Ser Ala Asp
                885                 890                 895

Lys Ser Ile Ser Thr Ala Tyr Leu Gln Trp Ser Ser Leu Lys Ala Ser
            900                 905                 910

Asp Thr Ala Met Tyr Tyr Cys Ala Arg Ser Met Gly Ser Ser Leu Tyr
        915                 920                 925

Ala Ser Ser Asp Val Trp Gly Gln Gly Thr Leu Val Thr Val Ser Ser
    930                 935                 940

Glu Gln Lys Leu Ile Ser Glu Glu Asp Leu Ala Ala Ala Ile Glu Val
945                 950                 955                 960

Met Tyr Pro Pro Pro Tyr Leu Asp Asn Glu Lys Ser Asn Gly Thr Ile
```

```
              965                 970                 975
Ile His Val Lys Gly Lys His Leu Cys Pro Ser Pro Leu Phe Pro Gly
            980                 985                 990

Pro Ser Lys Pro Phe Trp Val Leu Val Val Gly Val Leu Ala
            995                 1000                1005

Cys Tyr Ser Leu Leu Val Thr Val Ala Phe Ile Ile Phe Trp Val Arg
    1010                1015                1020

Ser Lys Arg Ser Arg Leu Leu His Ser Asp Tyr Met Asn Met Thr Pro
1025                1030                1035                1040

Arg Arg Pro Gly Pro Thr Arg Lys His Tyr Gln Pro Tyr Ala Pro Pro
                1045                1050                1055

Arg Asp Phe Ala Ala Tyr Arg Ser
            1060

<210> SEQ ID NO 86
<211> LENGTH: 1059
<212> TYPE: PRT
<213> ORGANISM: Artificial Sequence
<220> FEATURE:
<223> OTHER INFORMATION: Synthetic Construct: PSMA Clone A caTCR + PSMA
      Clone B-CSR-1A (a.k.a. "Ax1-caTCR + B-CSR" or "Ax1-caTCR + B-CSR-
      1A")

<400> SEQUENCE: 86

Met Glu Thr Asp Thr Leu Leu Leu Trp Val Leu Leu Leu Trp Val Pro
1               5                   10                  15

Gly Ser Thr Gly Glu Val Gln Leu Val Gln Ser Gly Ala Glu Val Lys
            20                  25                  30

Lys Pro Gly Glu Ser Leu Lys Ile Ser Cys Lys Gly Ser Gly Tyr Ser
        35                  40                  45

Phe Thr Ser Tyr Trp Ile Gly Trp Val Arg Gln Met Pro Gly Lys Gly
    50                  55                  60

Leu Glu Trp Met Gly Ile Ile Tyr Pro Gly Asp Ser Asp Thr Arg Tyr
65                  70                  75                  80

Ser Pro Ser Phe Gln Gly Gln Val Thr Ile Ser Ala Asp Lys Ser Ile
                85                  90                  95

Ser Thr Ala Tyr Leu Gln Trp Ser Ser Leu Lys Ala Ser Asp Thr Ala
            100                 105                 110

Met Tyr Tyr Cys Ala Arg Ser Met Gly Ser Ser Leu Tyr Ala Ser Ser
        115                 120                 125

Asp Val Trp Gly Gln Gly Thr Leu Val Thr Val Ser Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Glu Val Lys Thr Asp Ser Thr Asp His Val Lys Pro
                245                 250                 255
```

```
Lys Glu Thr Glu Asn Thr Lys Gln Pro Ser Lys Ser Cys His Lys Pro
            260                 265                 270

Lys Ala Ile Val His Thr Glu Lys Val Asn Met Met Ser Leu Thr Val
            275                 280                 285

Leu Gly Leu Arg Met Leu Phe Ala Lys Thr Val Ala Val Asn Phe Leu
            290                 295                 300

Leu Thr Ala Lys Leu Phe Phe Leu Arg Ala Lys Arg Ser Gly Ser Gly
305                 310                 315                 320

Ala Pro Val Lys Gln Thr Leu Asn Phe Asp Leu Leu Lys Leu Ala Gly
            325                 330                 335

Asp Val Glu Ser Asn Pro Gly Pro Met Glu Thr Asp Thr Leu Leu Leu
            340                 345                 350

Trp Val Leu Leu Leu Trp Val Pro Gly Ser Thr Gly Gln Ser Val Leu
            355                 360                 365

Thr Gln Pro Pro Ser Val Ser Gly Ala Pro Gly Gln Arg Val Thr Ile
            370                 375                 380

Ser Cys Thr Gly Ser Ser Ser Asn Ile Gly Ala Gly Tyr Asp Val His
385                 390                 395                 400

Trp Tyr Gln Gln Leu Pro Gly Thr Ala Pro Lys Leu Leu Ile Tyr Gly
            405                 410                 415

Asn Ser Asn Arg Pro Ser Gly Val Pro Asp Arg Phe Ser Gly Ser Lys
            420                 425                 430

Ser Gly Thr Ser Ala Ser Leu Ala Ile Thr Gly Leu Gln Ala Glu Asp
            435                 440                 445

Glu Ala Asp Tyr Tyr Cys Gln Ser Tyr Asp Ser Ser Leu Ser Gly Tyr
            450                 455                 460

Val Phe Gly Thr Gly Thr Lys Val Thr Val Leu Gly Gln Pro Lys Ala
465                 470                 475                 480

Asn Pro Thr Val Thr Leu Phe Pro Pro Ser Ser Glu Glu Leu Gln Ala
            485                 490                 495

Asn Lys Ala Thr Leu Val Cys Leu Ile Ser Asp Phe Tyr Pro Gly Ala
            500                 505                 510

Val Thr Val Ala Trp Lys Ala Asp Gly Ser Pro Val Lys Ala Gly Val
            515                 520                 525

Glu Thr Thr Lys Pro Ser Lys Gln Ser Asn Asn Lys Tyr Ala Ala Ser
530                 535                 540

Ser Tyr Leu Ser Leu Thr Pro Glu Gln Trp Lys Ser His Arg Ser Tyr
545                 550                 555                 560

Ser Cys Gln Val Thr His Glu Gly Ser Thr Val Glu Lys Thr Val Ala
                565                 570                 575

Pro Thr Glu Cys Ser Pro Ile Lys Thr Asp Val Ile Thr Met Asp Pro
            580                 585                 590

Lys Asp Asn Cys Ser Lys Asp Ala Asn Asp Thr Leu Leu Leu Gln Leu
            595                 600                 605

Thr Asn Thr Ser Ala Tyr Tyr Met Tyr Leu Leu Leu Leu Lys Ser
            610                 615                 620

Val Val Tyr Phe Ala Ile Ile Thr Cys Cys Leu Leu Arg Arg Thr Ala
625                 630                 635                 640

Phe Cys Cys Asn Gly Glu Lys Ser Gly Ser Gly Ala Thr Asn Phe Ser
                645                 650                 655

Leu Leu Lys Gln Ala Gly Asp Val Glu Glu Asn Pro Gly Pro Met Glu
            660                 665                 670
```

Thr Asp Thr Leu Leu Leu Trp Val Leu Leu Trp Val Pro Gly Ser
            675                 680                 685

Thr Gly Gln Ala Val Leu Thr Gln Pro Pro Ser Ala Ser Gly Thr Pro
690                 695                 700

Gly Gln Arg Val Thr Ile Ser Cys Ser Gly Ser Ser Ser Asn Ile Gly
705                 710                 715                 720

Ser Asn Thr Val Asn Trp Tyr Gln Gln Leu Pro Gly Thr Ala Pro Lys
                725                 730                 735

Leu Leu Met Tyr Ser Asn Asn Gln Arg Pro Ser Gly Val Pro Asp Arg
            740                 745                 750

Phe Ser Gly Ser Lys Ser Gly Thr Ser Ala Ser Leu Ala Ile Ser Gly
        755                 760                 765

Leu Gln Ser Glu Asp Glu Ala Asp Tyr Tyr Cys Ala Ala Trp Asp Asp
    770                 775                 780

Ser Leu Asn Gly Tyr Val Phe Gly Thr Gly Thr Lys Val Thr Val Leu
785                 790                 795                 800

Gly Ser Arg Gly Gly Gly Gly Ser Gly Gly Gly Gly Ser Gly Gly Gly
                805                 810                 815

Gly Ser Leu Glu Met Ala Glu Val Gln Leu Val Gln Ser Gly Ala Glu
        820                 825                 830

Met Lys Lys Pro Gly Glu Ser Leu Lys Ile Ser Cys Lys Gly Ser Gly
    835                 840                 845

Tyr Asn Phe Ala Ser Tyr Trp Val Gly Trp Val Arg Gln Met Pro Gly
850                 855                 860

Lys Gly Leu Glu Trp Met Gly Thr Ile Tyr Pro Asp Asp Ser Asp Thr
865                 870                 875                 880

Arg Tyr Gly Pro Ala Phe Gln Gly Gln Val Thr Ile Ser Ala Asp Lys
                885                 890                 895

Ser Ile Ser Thr Ala Tyr Leu Gln Trp Ser Ser Leu Lys Ala Ser Asp
            900                 905                 910

Thr Ala Met Tyr Tyr Cys Ala Arg Asp Ser Tyr Tyr Gly Ile Asp Val
        915                 920                 925

Trp Gly Gln Gly Thr Leu Val Thr Val Ser Ser Glu Gln Lys Leu Ile
    930                 935                 940

Ser Glu Glu Asp Leu Ala Ala Ala Ile Glu Val Met Tyr Pro Pro Pro
945                 950                 955                 960

Tyr Leu Asp Asn Glu Lys Ser Asn Gly Thr Ile Ile His Val Lys Gly
                965                 970                 975

Lys His Leu Cys Pro Ser Pro Leu Phe Pro Gly Pro Ser Lys Pro Phe
            980                 985                 990

Trp Val Leu Val Val Val Gly Gly Val Leu Ala Cys Tyr Ser Leu Leu
        995                 1000                1005

Val Thr Val Ala Phe Ile Ile Phe Trp Val Arg Ser Lys Arg Ser Arg
    1010                1015                1020

Leu Leu His Ser Asp Tyr Met Asn Met Thr Pro Arg Arg Pro Gly Pro
1025                1030                1035                1040

Thr Arg Lys His Tyr Gln Pro Tyr Ala Pro Pro Arg Asp Phe Ala Ala
                1045                1050                1055

Tyr Arg Ser

<210> SEQ ID NO 87
<211> LENGTH: 1059
<212> TYPE: PRT
<213> ORGANISM: Artificial Sequence

```
<220> FEATURE:
<223> OTHER INFORMATION: Synthetic Construct: PSMA Clone B caTCR + PSMA
      Clone A-CSR-1A (a.k.a. "Bx1-caTCR + A-CSR" or "Bx1-caTCR + A-CSR-
      1A")

<400> SEQUENCE: 87

Met Glu Thr Asp Thr Leu Leu Leu Trp Val Leu Leu Trp Val Pro
1               5                   10                  15

Gly Ser Thr Gly Glu Val Gln Leu Val Gln Ser Gly Ala Glu Met Lys
            20                  25                  30

Lys Pro Gly Glu Ser Leu Lys Ile Ser Cys Lys Gly Ser Gly Tyr Asn
        35                  40                  45

Phe Ala Ser Tyr Trp Val Gly Trp Val Arg Gln Met Pro Gly Lys Gly
    50                  55                  60

Leu Glu Trp Met Gly Thr Ile Tyr Pro Asp Asp Ser Asp Thr Arg Tyr
65                  70                  75                  80

Gly Pro Ala Phe Gln Gly Gln Val Thr Ile Ser Ala Asp Lys Ser Ile
                85                  90                  95

Ser Thr Ala Tyr Leu Gln Trp Ser Ser Leu Lys Ala Ser Asp Thr Ala
            100                 105                 110

Met Tyr Tyr Cys Ala Arg Asp Ser Tyr Tyr Gly Ile Asp Val Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Glu Val Lys Thr Asp Ser Thr Asp His Val Lys Pro Lys Glu Thr Glu
                245                 250                 255

Asn Thr Lys Gln Pro Ser Lys Ser Cys His Lys Pro Lys Ala Ile Val
            260                 265                 270

His Thr Glu Lys Val Asn Met Met Ser Leu Thr Val Leu Gly Leu Arg
        275                 280                 285

Met Leu Phe Ala Lys Thr Val Ala Val Asn Phe Leu Leu Thr Ala Lys
    290                 295                 300

Leu Phe Phe Leu Arg Ala Lys Arg Ser Gly Ser Gly Ala Pro Val Lys
305                 310                 315                 320

Gln Thr Leu Asn Phe Asp Leu Leu Lys Leu Ala Gly Asp Val Glu Ser
                325                 330                 335

Asn Pro Gly Pro Met Glu Thr Asp Thr Leu Leu Leu Trp Val Leu Leu
            340                 345                 350

Leu Trp Val Pro Gly Ser Thr Gly Gln Ala Val Leu Thr Gln Pro Pro
        355                 360                 365

Ser Ala Ser Gly Thr Pro Gly Gln Arg Val Thr Ile Ser Cys Ser Gly
    370                 375                 380
```

```
Ser Ser Ser Asn Ile Gly Ser Asn Thr Val Asn Trp Tyr Gln Gln Leu
385                 390                 395                 400

Pro Gly Thr Ala Pro Lys Leu Leu Met Tyr Ser Asn Asn Gln Arg Pro
            405                 410                 415

Ser Gly Val Pro Asp Arg Phe Ser Gly Ser Lys Ser Gly Thr Ser Ala
            420                 425                 430

Ser Leu Ala Ile Ser Gly Leu Gln Ser Glu Asp Glu Ala Asp Tyr Tyr
            435                 440                 445

Cys Ala Ala Trp Asp Asp Ser Leu Asn Gly Tyr Val Phe Gly Thr Gly
450                 455                 460

Thr Lys Val Thr Val Leu Gly Gln Pro Lys Ala Asn Pro Thr Val Thr
465                 470                 475                 480

Leu Phe Pro Pro Ser Ser Glu Glu Leu Gln Ala Asn Lys Ala Thr Leu
            485                 490                 495

Val Cys Leu Ile Ser Asp Phe Tyr Pro Gly Ala Val Thr Val Ala Trp
            500                 505                 510

Lys Ala Asp Gly Ser Pro Val Lys Ala Gly Val Glu Thr Thr Lys Pro
515                 520                 525

Ser Lys Gln Ser Asn Asn Lys Tyr Ala Ala Ser Ser Tyr Leu Ser Leu
530                 535                 540

Thr Pro Glu Gln Trp Lys Ser His Arg Ser Tyr Ser Cys Gln Val Thr
545                 550                 555                 560

His Glu Gly Ser Thr Val Glu Lys Thr Val Ala Pro Thr Glu Cys Ser
            565                 570                 575

Pro Ile Lys Thr Asp Val Ile Thr Met Asp Pro Lys Asp Asn Cys Ser
            580                 585                 590

Lys Asp Ala Asn Asp Thr Leu Leu Leu Gln Leu Thr Asn Thr Ser Ala
            595                 600                 605

Tyr Tyr Met Tyr Leu Leu Leu Leu Lys Ser Val Val Tyr Phe Ala
            610                 615                 620

Ile Ile Thr Cys Cys Leu Leu Arg Arg Thr Ala Phe Cys Cys Asn Gly
625                 630                 635                 640

Glu Lys Ser Gly Ser Gly Ala Thr Asn Phe Ser Leu Leu Lys Gln Ala
            645                 650                 655

Gly Asp Val Glu Glu Asn Pro Gly Pro Met Glu Thr Asp Thr Leu Leu
            660                 665                 670

Leu Trp Val Leu Leu Leu Trp Val Pro Gly Ser Thr Gly Gln Ser Val
            675                 680                 685

Leu Thr Gln Pro Pro Ser Val Ser Gly Ala Pro Gly Gln Arg Val Thr
            690                 695                 700

Ile Ser Cys Thr Gly Ser Ser Ser Asn Ile Gly Ala Gly Tyr Asp Val
705                 710                 715                 720

His Trp Tyr Gln Gln Leu Pro Gly Thr Ala Pro Lys Leu Leu Ile Tyr
            725                 730                 735

Gly Asn Ser Asn Arg Pro Ser Gly Val Pro Asp Arg Phe Ser Gly Ser
            740                 745                 750

Lys Ser Gly Thr Ser Ala Ser Leu Ala Ile Thr Gly Leu Gln Ala Glu
            755                 760                 765

Asp Glu Ala Asp Tyr Tyr Cys Gln Ser Tyr Asp Ser Ser Leu Ser Gly
            770                 775                 780

Tyr Val Phe Gly Thr Gly Thr Lys Val Thr Val Leu Gly Ser Arg Gly
785                 790                 795                 800

Gly Gly Gly Ser Gly Gly Gly Gly Ser Gly Gly Gly Gly Ser Leu Glu
```

```
                    805                 810                 815
Met Ala Glu Val Gln Leu Val Gln Ser Gly Ala Glu Val Lys Lys Pro
            820                 825                 830

Gly Glu Ser Leu Lys Ile Ser Cys Lys Gly Ser Gly Tyr Ser Phe Thr
        835                 840                 845

Ser Tyr Trp Ile Gly Trp Val Arg Gln Met Pro Gly Lys Gly Leu Glu
    850                 855                 860

Trp Met Gly Ile Ile Tyr Pro Gly Asp Ser Asp Thr Arg Tyr Ser Pro
865                 870                 875                 880

Ser Phe Gln Gly Gln Val Thr Ile Ser Ala Asp Lys Ser Ile Ser Thr
                885                 890                 895

Ala Tyr Leu Gln Trp Ser Ser Leu Lys Ala Ser Asp Thr Ala Met Tyr
            900                 905                 910

Tyr Cys Ala Arg Ser Met Gly Ser Ser Leu Tyr Ala Ser Ser Asp Val
        915                 920                 925

Trp Gly Gln Gly Thr Leu Val Thr Val Ser Ser Glu Gln Lys Leu Ile
    930                 935                 940

Ser Glu Glu Asp Leu Ala Ala Ala Ile Glu Val Met Tyr Pro Pro Pro
945                 950                 955                 960

Tyr Leu Asp Asn Glu Lys Ser Asn Gly Thr Ile Ile His Val Lys Gly
                965                 970                 975

Lys His Leu Cys Pro Ser Pro Leu Phe Pro Gly Pro Ser Lys Pro Phe
            980                 985                 990

Trp Val Leu Val Val Val Gly Gly Val Leu Ala Cys Tyr Ser Leu Leu
        995                 1000                1005

Val Thr Val Ala Phe Ile Ile Phe Trp Val Arg Ser Lys Arg Ser Arg
    1010                1015                1020

Leu Leu His Ser Asp Tyr Met Asn Met Thr Pro Arg Arg Pro Gly Pro
1025                1030                1035                1040

Thr Arg Lys His Tyr Gln Pro Tyr Ala Pro Pro Arg Asp Phe Ala Ala
                1045                1050                1055

Tyr Arg Ser
```

<210> SEQ ID NO 88
<211> LENGTH: 1054
<212> TYPE: PRT
<213> ORGANISM: Artificial Sequence
<220> FEATURE:
<223> OTHER INFORMATION: Synthetic Construct: PSMA Clone B caTCR + PSMA Clone A-CSR-1A (a.k.a. "Bx1-caTCR + A-CSR" or "Bx1-caTCR + A-CSR-1A")

<400> SEQUENCE: 88

```
Met Glu Thr Asp Thr Leu Leu Leu Trp Val Leu Leu Leu Trp Val Pro
1               5                   10                  15

Gly Ser Thr Gly Glu Val Gln Leu Val Gln Ser Gly Ala Glu Met Lys
            20                  25                  30

Lys Pro Gly Glu Ser Leu Lys Ile Ser Cys Lys Gly Ser Gly Tyr Asn
        35                  40                  45

Phe Ala Ser Tyr Trp Val Gly Trp Val Arg Gln Met Pro Gly Lys Gly
    50                  55                  60

Leu Glu Trp Met Gly Thr Ile Tyr Pro Asp Ser Asp Thr Arg Tyr
65                  70                  75                  80

Gly Pro Ala Phe Gln Gly Gln Val Thr Ile Ser Ala Asp Lys Ser Ile
                85                  90                  95
```

```
Ser Thr Ala Tyr Leu Gln Trp Ser Ser Leu Lys Ala Ser Asp Thr Ala
            100                 105                 110

Met Tyr Tyr Cys Ala Arg Asp Ser Tyr Gly Ile Asp Val Trp Gly
    115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Glu Val Lys Thr Asp Ser Thr Asp His Val Lys Pro Lys Glu Thr Glu
                245                 250                 255

Asn Thr Lys Gln Pro Ser Lys Ser Cys His Lys Pro Lys Ala Ile Val
            260                 265                 270

His Thr Glu Lys Val Asn Met Met Ser Leu Thr Val Leu Gly Leu Arg
        275                 280                 285

Met Leu Phe Ala Lys Thr Val Ala Val Asn Phe Leu Leu Thr Ala Lys
    290                 295                 300

Leu Phe Phe Leu Arg Ala Lys Arg Ser Gly Ser Gly Ala Pro Val Lys
305                 310                 315                 320

Gln Thr Leu Asn Phe Asp Leu Leu Lys Leu Ala Gly Asp Val Glu Ser
                325                 330                 335

Asn Pro Gly Pro Met Glu Thr Asp Thr Leu Leu Leu Trp Val Leu Leu
            340                 345                 350

Leu Trp Val Pro Gly Ser Thr Gly Gln Ala Val Leu Thr Gln Pro Pro
    355                 360                 365

Ser Ala Ser Gly Thr Pro Gly Gln Arg Val Thr Ile Ser Cys Ser Gly
370                 375                 380

Ser Ser Ser Asn Ile Gly Ser Asn Thr Val Asn Trp Tyr Gln Gln Leu
385                 390                 395                 400

Pro Gly Thr Ala Pro Lys Leu Leu Met Tyr Ser Asn Asn Gln Arg Pro
                405                 410                 415

Ser Gly Val Pro Asp Arg Phe Ser Gly Ser Lys Ser Gly Thr Ser Ala
            420                 425                 430

Ser Leu Ala Ile Ser Gly Leu Gln Ser Glu Asp Glu Ala Asp Tyr Tyr
        435                 440                 445

Cys Ala Ala Trp Asp Asp Ser Leu Asn Gly Tyr Val Phe Gly Thr Gly
    450                 455                 460

Thr Lys Val Thr Val Leu Gly Gln Pro Lys Ala Asn Pro Thr Val Thr
465                 470                 475                 480

Leu Phe Pro Pro Ser Ser Glu Glu Leu Gln Ala Asn Lys Ala Thr Leu
                485                 490                 495

Val Cys Leu Ile Ser Asp Phe Tyr Pro Gly Ala Val Thr Val Ala Trp
            500                 505                 510

Lys Ala Asp Gly Ser Pro Val Lys Ala Gly Val Glu Thr Thr Lys Pro
```

```
            515                 520                 525
Ser Lys Gln Ser Asn Lys Tyr Ala Ala Ser Ser Tyr Leu Ser Leu
530                 535                 540

Thr Pro Glu Gln Trp Lys Ser His Arg Ser Tyr Ser Cys Gln Val Thr
545                 550                 555                 560

His Glu Gly Ser Thr Val Glu Lys Thr Val Ala Pro Thr Glu Cys Ser
                    565                 570                 575

Pro Ile Lys Thr Asp Val Ile Thr Met Asp Pro Lys Asp Asn Cys Ser
                580                 585                 590

Lys Asp Ala Asn Asp Thr Leu Leu Gln Leu Thr Asn Thr Ser Ala
                595                 600                 605

Tyr Tyr Met Tyr Leu Leu Leu Leu Lys Ser Val Val Tyr Phe Ala
610                 615                 620

Ile Ile Thr Cys Cys Leu Leu Arg Arg Thr Ala Phe Cys Cys Asn Gly
625                 630                 635                 640

Glu Lys Ser Gly Ser Gly Ala Thr Asn Phe Ser Leu Leu Lys Gln Ala
                645                 650                 655

Gly Asp Val Glu Glu Asn Pro Gly Pro Met Glu Thr Asp Thr Leu Leu
                660                 665                 670

Leu Trp Val Leu Leu Leu Trp Val Pro Gly Ser Thr Gly Gln Ala Val
                675                 680                 685

Leu Thr Gln Pro Pro Ser Ala Ser Gly Thr Pro Gly Gln Arg Val Thr
690                 695                 700

Ile Ser Cys Ser Gly Ser Ser Asn Ile Gly Ser Asn Thr Val Asn
705                 710                 715                 720

Trp Tyr Gln Gln Leu Pro Gly Thr Ala Pro Lys Leu Leu Met Tyr Ser
                725                 730                 735

Asn Asn Gln Arg Pro Ser Gly Val Pro Asp Arg Phe Ser Gly Ser Lys
                740                 745                 750

Ser Gly Thr Ser Ala Ser Leu Ala Ile Ser Gly Leu Gln Ser Glu Asp
                755                 760                 765

Glu Ala Asp Tyr Tyr Cys Ala Ala Trp Asp Asp Ser Leu Asn Gly Tyr
                770                 775                 780

Val Phe Gly Thr Gly Thr Lys Val Thr Val Leu Gly Ser Arg Gly Gly
785                 790                 795                 800

Gly Gly Ser Gly Gly Gly Ser Gly Gly Gly Ser Leu Glu Met
                805                 810                 815

Ala Glu Val Gln Leu Val Gln Ser Gly Ala Glu Met Lys Lys Pro Gly
                820                 825                 830

Glu Ser Leu Lys Ile Ser Cys Lys Gly Ser Gly Tyr Asn Phe Ala Ser
                835                 840                 845

Tyr Trp Val Gly Trp Val Arg Gln Met Pro Gly Lys Gly Leu Glu Trp
                850                 855                 860

Met Gly Thr Ile Tyr Pro Asp Asp Ser Asp Thr Arg Tyr Gly Pro Ala
865                 870                 875                 880

Phe Gln Gly Gln Val Thr Ile Ser Ala Asp Lys Ser Ile Ser Thr Ala
                885                 890                 895

Tyr Leu Gln Trp Ser Ser Leu Lys Ala Ser Asp Thr Ala Met Tyr Tyr
                900                 905                 910

Cys Ala Arg Asp Ser Tyr Tyr Gly Ile Asp Val Trp Gly Gln Gly Thr
                915                 920                 925

Leu Val Thr Val Ser Ser Glu Gln Lys Leu Ile Ser Glu Glu Asp Leu
                930                 935                 940
```

```
Ala Ala Ala Ile Glu Val Met Tyr Pro Pro Tyr Leu Asp Asn Glu
945                 950                 955                 960

Lys Ser Asn Gly Thr Ile Ile His Val Lys Gly Lys His Leu Cys Pro
                965                 970                 975

Ser Pro Leu Phe Pro Gly Pro Ser Lys Pro Phe Trp Val Leu Val Val
            980                 985                 990

Val Gly Gly Val Leu Ala Cys Tyr Ser Leu Leu Val Thr Val Ala Phe
        995                 1000                1005

Ile Ile Phe Trp Val Arg Ser Lys Arg Ser Arg Leu Leu His Ser Asp
    1010                1015                1020

Tyr Met Asn Met Thr Pro Arg Arg Pro Gly Pro Thr Arg Lys His Tyr
1025                1030                1035                1040

Gln Pro Tyr Ala Pro Pro Arg Asp Phe Ala Ala Tyr Arg Ser
            1045                1050

<210> SEQ ID NO 89
<211> LENGTH: 1318
<212> TYPE: PRT
<213> ORGANISM: Artificial Sequence
<220> FEATURE:
<223> OTHER INFORMATION: Synthetic Construct: Bivalent PSMA Clone A
      caTCR with 1 scFv and 1 Fab + PSMA Clone B-CSR-1A, to be called
      "Ax2-caTCR + B-CSR" in PCT figure.

<400> SEQUENCE: 89

Met Glu Thr Asp Thr Leu Leu Leu Trp Val Leu Leu Leu Trp Val Pro
1               5                   10                  15

Gly Ser Thr Gly Gln Ser Val Leu Thr Gln Pro Pro Ser Val Ser Gly
            20                  25                  30

Ala Pro Gly Gln Arg Val Thr Ile Ser Cys Thr Gly Ser Ser Ser Asn
        35                  40                  45

Ile Gly Ala Gly Tyr Asp Val His Trp Tyr Gln Gln Leu Pro Gly Thr
    50                  55                  60

Ala Pro Lys Leu Leu Ile Tyr Gly Asn Ser Asn Arg Pro Ser Gly Val
65                  70                  75                  80

Pro Asp Arg Phe Ser Gly Ser Lys Ser Gly Thr Ser Ala Ser Leu Ala
                85                  90                  95

Ile Thr Gly Leu Gln Ala Glu Asp Glu Ala Asp Tyr Tyr Cys Gln Ser
            100                 105                 110

Tyr Asp Ser Ser Leu Ser Gly Tyr Val Phe Gly Thr Gly Thr Lys Val
        115                 120                 125

Thr Val Leu Gly Ser Arg Gly Gly Gly Gly Ser Gly Gly Gly Gly Ser
    130                 135                 140

Gly Gly Gly Gly Ser Leu Glu Met Ala Glu Val Gln Leu Val Gln Ser
145                 150                 155                 160

Gly Ala Glu Val Lys Lys Pro Gly Glu Ser Leu Lys Ile Ser Cys Lys
                165                 170                 175

Gly Ser Gly Tyr Ser Phe Thr Ser Tyr Trp Ile Gly Trp Val Arg Gln
            180                 185                 190

Met Pro Gly Lys Gly Leu Glu Trp Met Gly Ile Ile Tyr Pro Gly Asp
        195                 200                 205

Ser Asp Thr Arg Tyr Ser Pro Ser Phe Gln Gly Gln Val Thr Ile Ser
    210                 215                 220

Ala Asp Lys Ser Ile Ser Thr Ala Tyr Leu Gln Trp Ser Ser Leu Lys
225                 230                 235                 240
```

```
Ala Ser Asp Thr Ala Met Tyr Tyr Cys Ala Arg Ser Met Gly Ser Ser
                245                 250                 255

Leu Tyr Ala Ser Ser Asp Val Trp Gly Gln Gly Thr Leu Val Thr Val
            260                 265                 270

Ser Ser Gly Gly Gly Gly Ser Glu Val Gln Leu Val Gln Ser Gly Ala
        275                 280                 285

Glu Val Lys Lys Pro Gly Glu Ser Leu Lys Ile Ser Cys Lys Gly Ser
290                 295                 300

Gly Tyr Ser Phe Thr Ser Tyr Trp Ile Gly Val Arg Gln Met Pro
305                 310                 315                 320

Gly Lys Gly Leu Glu Trp Met Gly Ile Ile Tyr Pro Gly Asp Ser Asp
                325                 330                 335

Thr Arg Tyr Ser Pro Ser Phe Gln Gly Gln Val Thr Ile Ser Ala Asp
            340                 345                 350

Lys Ser Ile Ser Thr Ala Tyr Leu Gln Trp Ser Ser Leu Lys Ala Ser
        355                 360                 365

Asp Thr Ala Met Tyr Tyr Cys Ala Arg Ser Met Gly Ser Ser Leu Tyr
370                 375                 380

Ala Ser Ser Asp Val Trp Gly Gln Gly Thr Leu Val Thr Val Ser Ser
385                 390                 395                 400

Ala Ser Thr Lys Gly Pro Ser Val Phe Pro Leu Ala Pro Ser Ser Lys
                405                 410                 415

Ser Thr Ser Gly Gly Thr Ala Ala Leu Gly Cys Leu Val Lys Asp Tyr
            420                 425                 430

Phe Pro Glu Pro Val Thr Val Ser Trp Asn Ser Gly Ala Leu Thr Ser
        435                 440                 445

Gly Val His Thr Phe Pro Ala Val Leu Gln Ser Ser Gly Leu Tyr Ser
    450                 455                 460

Leu Ser Ser Val Val Thr Val Pro Ser Ser Ser Leu Gly Thr Gln Thr
465                 470                 475                 480

Tyr Ile Cys Asn Val Asn His Lys Pro Ser Asn Thr Lys Val Asp Lys
                485                 490                 495

Arg Val Glu Pro Lys Ser Cys Glu Val Lys Thr Asp Ser Thr Asp His
            500                 505                 510

Val Lys Pro Lys Glu Thr Glu Asn Thr Lys Gln Pro Ser Lys Ser Cys
        515                 520                 525

His Lys Pro Lys Ala Ile Val His Thr Glu Lys Val Asn Met Met Ser
    530                 535                 540

Leu Thr Val Leu Gly Leu Arg Met Leu Phe Ala Lys Thr Val Ala Val
545                 550                 555                 560

Asn Phe Leu Leu Thr Ala Lys Leu Phe Phe Leu Arg Ala Lys Arg Ser
                565                 570                 575

Gly Ser Gly Ala Pro Val Lys Gln Thr Leu Asn Phe Asp Leu Leu Lys
            580                 585                 590

Leu Ala Gly Asp Val Glu Ser Asn Pro Gly Pro Met Glu Thr Asp Thr
        595                 600                 605

Leu Leu Leu Trp Val Leu Leu Leu Trp Val Pro Gly Ser Thr Gly Gln
    610                 615                 620

Ser Val Leu Thr Gln Pro Pro Ser Val Ser Gly Ala Pro Gly Gln Arg
625                 630                 635                 640

Val Thr Ile Ser Cys Thr Gly Ser Ser Ser Asn Ile Gly Ala Gly Tyr
                645                 650                 655

Asp Val His Trp Tyr Gln Gln Leu Pro Gly Thr Ala Pro Lys Leu Leu
```

```
              660                 665                 670
Ile Tyr Gly Asn Ser Asn Arg Pro Ser Gly Val Pro Asp Arg Phe Ser
            675                 680                 685

Gly Ser Lys Ser Gly Thr Ser Ala Ser Leu Ala Ile Thr Gly Leu Gln
        690                 695                 700

Ala Glu Asp Glu Ala Asp Tyr Tyr Cys Gln Ser Tyr Asp Ser Ser Leu
705                 710                 715                 720

Ser Gly Tyr Val Phe Gly Thr Gly Thr Lys Val Thr Val Leu Gly Gln
                725                 730                 735

Pro Lys Ala Asn Pro Thr Val Thr Leu Phe Pro Pro Ser Ser Glu Glu
            740                 745                 750

Leu Gln Ala Asn Lys Ala Thr Leu Val Cys Leu Ile Ser Asp Phe Tyr
        755                 760                 765

Pro Gly Ala Val Thr Val Ala Trp Lys Ala Asp Gly Ser Pro Val Lys
    770                 775                 780

Ala Gly Val Glu Thr Thr Lys Pro Ser Lys Gln Ser Asn Asn Lys Tyr
785                 790                 795                 800

Ala Ala Ser Ser Tyr Leu Ser Leu Thr Pro Glu Gln Trp Lys Ser His
                805                 810                 815

Arg Ser Tyr Ser Cys Gln Val Thr His Glu Gly Ser Thr Val Glu Lys
            820                 825                 830

Thr Val Ala Pro Thr Glu Cys Ser Pro Ile Lys Thr Asp Val Ile Thr
        835                 840                 845

Met Asp Pro Lys Asp Asn Cys Ser Lys Asp Ala Asn Asp Thr Leu Leu
    850                 855                 860

Leu Gln Leu Thr Asn Thr Ser Ala Tyr Tyr Met Tyr Leu Leu Leu Leu
865                 870                 875                 880

Leu Lys Ser Val Val Tyr Phe Ala Ile Ile Thr Cys Cys Leu Leu Arg
                885                 890                 895

Arg Thr Ala Phe Cys Cys Asn Gly Glu Lys Ser Gly Ser Gly Ala Thr
            900                 905                 910

Asn Phe Ser Leu Leu Lys Gln Ala Gly Asp Val Glu Glu Asn Pro Gly
        915                 920                 925

Pro Met Glu Thr Asp Thr Leu Leu Leu Trp Val Leu Leu Leu Trp Val
    930                 935                 940

Pro Gly Ser Thr Gly Gln Ala Val Leu Thr Gln Pro Pro Ser Ala Ser
945                 950                 955                 960

Gly Thr Pro Gly Gln Arg Val Thr Ile Ser Cys Ser Gly Ser Ser Ser
                965                 970                 975

Asn Ile Gly Ser Asn Thr Val Asn Trp Tyr Gln Gln Leu Pro Gly Thr
            980                 985                 990

Ala Pro Lys Leu Leu Met Tyr Ser Asn Asn Gln Arg Pro Ser Gly Val
        995                 1000                1005

Pro Asp Arg Phe Ser Gly Ser Lys Ser Gly Thr Ser Ala Ser Leu Ala
    1010                1015                1020

Ile Ser Gly Leu Gln Ser Glu Asp Glu Ala Asp Tyr Tyr Cys Ala Ala
1025                1030                1035                1040

Trp Asp Asp Ser Leu Asn Gly Tyr Val Phe Gly Thr Gly Thr Lys Val
                1045                1050                1055

Thr Val Leu Gly Ser Arg Gly Gly Gly Gly Ser Gly Gly Gly Gly Ser
            1060                1065                1070

Gly Gly Gly Gly Ser Leu Glu Met Ala Glu Val Gln Leu Val Gln Ser
        1075                1080                1085
```

Gly Ala Glu Met Lys Lys Pro Gly Glu Ser Leu Lys Ile Ser Cys Lys
            1090                1095                1100

Gly Ser Gly Tyr Asn Phe Ala Ser Tyr Trp Val Gly Trp Val Arg Gln
1105                1110                1115                1120

Met Pro Gly Lys Gly Leu Glu Trp Met Gly Thr Ile Tyr Pro Asp Asp
            1125                1130                1135

Ser Asp Thr Arg Tyr Gly Pro Ala Phe Gln Gly Gln Val Thr Ile Ser
            1140                1145                1150

Ala Asp Lys Ser Ile Ser Thr Ala Tyr Leu Gln Trp Ser Ser Leu Lys
            1155                1160                1165

Ala Ser Asp Thr Ala Met Tyr Tyr Cys Ala Arg Asp Ser Tyr Tyr Gly
            1170                1175                1180

Ile Asp Val Trp Gly Gln Gly Thr Leu Val Thr Val Ser Ser Glu Gln
1185                1190                1195                1200

Lys Leu Ile Ser Glu Glu Asp Leu Ala Ala Ala Ile Glu Val Met Tyr
            1205                1210                1215

Pro Pro Pro Tyr Leu Asp Asn Glu Lys Ser Asn Gly Thr Ile Ile His
            1220                1225                1230

Val Lys Gly Lys His Leu Cys Pro Ser Pro Leu Phe Pro Gly Pro Ser
            1235                1240                1245

Lys Pro Phe Trp Val Leu Val Val Val Gly Gly Val Leu Ala Cys Tyr
            1250                1255                1260

Ser Leu Leu Val Thr Val Ala Phe Ile Ile Phe Trp Val Arg Ser Lys
1265                1270                1275                1280

Arg Ser Arg Leu Leu His Ser Asp Tyr Met Asn Met Thr Pro Arg Arg
            1285                1290                1295

Pro Gly Pro Thr Arg Lys His Tyr Gln Pro Tyr Ala Pro Pro Arg Asp
            1300                1305                1310

Phe Ala Ala Tyr Arg Ser
            1315

<210> SEQ ID NO 90
<211> LENGTH: 1313
<212> TYPE: PRT
<213> ORGANISM: Artificial Sequence
<220> FEATURE:
<223> OTHER INFORMATION: Synthetic Construct

<400> SEQUENCE: 90

Met Glu Thr Asp Thr Leu Leu Leu Trp Val Leu Leu Leu Trp Val Pro
1               5                   10                  15

Gly Ser Thr Gly Gln Ala Val Leu Thr Gln Pro Pro Ser Ala Ser Gly
            20                  25                  30

Thr Pro Gly Gln Arg Val Thr Ile Ser Cys Ser Gly Ser Ser Ser Asn
            35                  40                  45

Ile Gly Ser Asn Thr Val Asn Trp Tyr Gln Gln Leu Pro Gly Thr Ala
            50                  55                  60

Pro Lys Leu Leu Met Tyr Ser Asn Asn Gln Arg Pro Ser Gly Val Pro
65                  70                  75                  80

Asp Arg Phe Ser Gly Ser Lys Ser Gly Thr Ser Ala Ser Leu Ala Ile
            85                  90                  95

Ser Gly Leu Gln Ser Glu Asp Glu Ala Asp Tyr Tyr Cys Ala Ala Trp
            100                 105                 110

Asp Asp Ser Leu Asn Gly Tyr Val Phe Gly Thr Gly Thr Lys Val Thr
            115                 120                 125

```
Val Leu Gly Ser Arg Gly Gly Gly Ser Gly Gly Gly Ser Gly
    130                 135                 140

Gly Gly Gly Ser Leu Glu Met Ala Glu Val Gln Leu Val Gln Ser Gly
145                 150                 155                 160

Ala Glu Met Lys Lys Pro Gly Glu Ser Leu Lys Ile Ser Cys Lys Gly
                165                 170                 175

Ser Gly Tyr Asn Phe Ala Ser Tyr Trp Val Gly Trp Val Arg Gln Met
                180                 185                 190

Pro Gly Lys Gly Leu Glu Trp Met Gly Thr Ile Tyr Pro Asp Asp Ser
            195                 200                 205

Asp Thr Arg Tyr Gly Pro Ala Phe Gln Gly Gln Val Thr Ile Ser Ala
    210                 215                 220

Asp Lys Ser Ile Ser Thr Ala Tyr Leu Gln Trp Ser Ser Leu Lys Ala
225                 230                 235                 240

Ser Asp Thr Ala Met Tyr Tyr Cys Ala Arg Asp Ser Tyr Tyr Gly Ile
                245                 250                 255

Asp Val Trp Gly Gln Gly Thr Leu Val Thr Val Ser Ser Gly Gly Gly
                260                 265                 270

Gly Ser Glu Val Gln Leu Val Gln Ser Gly Ala Glu Met Lys Lys Pro
            275                 280                 285

Gly Glu Ser Leu Lys Ile Ser Cys Lys Gly Ser Gly Tyr Asn Phe Ala
    290                 295                 300

Ser Tyr Trp Val Gly Trp Val Arg Gln Met Pro Gly Lys Gly Leu Glu
305                 310                 315                 320

Trp Met Gly Thr Ile Tyr Pro Asp Asp Ser Asp Thr Arg Tyr Gly Pro
                325                 330                 335

Ala Phe Gln Gly Gln Val Thr Ile Ser Ala Asp Lys Ser Ile Ser Thr
                340                 345                 350

Ala Tyr Leu Gln Trp Ser Ser Leu Lys Ala Ser Asp Thr Ala Met Tyr
            355                 360                 365

Tyr Cys Ala Arg Asp Ser Tyr Tyr Gly Ile Asp Val Trp Gly Gln Gly
    370                 375                 380

Thr Leu Val Thr Val Ser Ser Ala Ser Thr Lys Gly Pro Ser Val Phe
385                 390                 395                 400

Pro Leu Ala Pro Ser Ser Lys Ser Thr Ser Gly Gly Thr Ala Ala Leu
                405                 410                 415

Gly Cys Leu Val Lys Asp Tyr Phe Pro Glu Pro Val Thr Val Ser Trp
                420                 425                 430

Asn Ser Gly Ala Leu Thr Ser Gly Val His Thr Phe Pro Ala Val Leu
            435                 440                 445

Gln Ser Ser Gly Leu Tyr Ser Leu Ser Ser Val Val Thr Val Pro Ser
    450                 455                 460

Ser Ser Leu Gly Thr Gln Thr Tyr Ile Cys Asn Val Asn His Lys Pro
465                 470                 475                 480

Ser Asn Thr Lys Val Asp Lys Arg Val Glu Pro Lys Ser Cys Glu Val
                485                 490                 495

Lys Thr Asp Ser Thr Asp His Val Lys Pro Lys Glu Thr Glu Asn Thr
                500                 505                 510

Lys Gln Pro Ser Lys Ser Cys His Lys Pro Lys Ala Ile Val His Thr
            515                 520                 525

Glu Lys Val Asn Met Met Ser Leu Thr Val Leu Gly Leu Arg Met Leu
    530                 535                 540
```

```
Phe Ala Lys Thr Val Ala Val Asn Phe Leu Leu Thr Ala Lys Leu Phe
545                 550                 555                 560

Phe Leu Arg Ala Lys Arg Ser Gly Ser Gly Ala Pro Val Lys Gln Thr
                565                 570                 575

Leu Asn Phe Asp Leu Leu Lys Leu Ala Gly Asp Val Glu Ser Asn Pro
                580                 585                 590

Gly Pro Met Glu Thr Asp Thr Leu Leu Leu Trp Val Leu Leu Leu Trp
                595                 600                 605

Val Pro Gly Ser Thr Gly Gln Ala Val Leu Thr Gln Pro Pro Ser Ala
                610                 615                 620

Ser Gly Thr Pro Gly Gln Arg Val Thr Ile Ser Cys Ser Gly Ser Ser
625                 630                 635                 640

Ser Asn Ile Gly Ser Asn Thr Val Asn Trp Tyr Gln Gln Leu Pro Gly
                645                 650                 655

Thr Ala Pro Lys Leu Leu Met Tyr Ser Asn Asn Gln Arg Pro Ser Gly
                660                 665                 670

Val Pro Asp Arg Phe Ser Gly Ser Lys Ser Gly Thr Ser Ala Ser Leu
                675                 680                 685

Ala Ile Ser Gly Leu Gln Ser Glu Asp Glu Ala Asp Tyr Tyr Cys Ala
                690                 695                 700

Ala Trp Asp Asp Ser Leu Asn Gly Tyr Val Phe Gly Thr Gly Thr Lys
705                 710                 715                 720

Val Thr Val Leu Gly Gln Pro Lys Ala Asn Pro Thr Val Thr Leu Phe
                725                 730                 735

Pro Pro Ser Ser Glu Glu Leu Gln Ala Asn Lys Ala Thr Leu Val Cys
                740                 745                 750

Leu Ile Ser Asp Phe Tyr Pro Gly Ala Val Thr Val Ala Trp Lys Ala
                755                 760                 765

Asp Gly Ser Pro Val Lys Ala Gly Val Glu Thr Thr Lys Pro Ser Lys
                770                 775                 780

Gln Ser Asn Asn Lys Tyr Ala Ala Ser Ser Tyr Leu Ser Leu Thr Pro
785                 790                 795                 800

Glu Gln Trp Lys Ser His Arg Ser Tyr Ser Cys Gln Val Thr His Glu
                805                 810                 815

Gly Ser Thr Val Glu Lys Thr Val Ala Pro Thr Glu Cys Ser Pro Ile
                820                 825                 830

Lys Thr Asp Val Ile Thr Met Asp Pro Lys Asp Asn Cys Ser Lys Asp
                835                 840                 845

Ala Asn Asp Thr Leu Leu Leu Gln Leu Thr Asn Thr Ser Ala Tyr Tyr
850                 855                 860

Met Tyr Leu Leu Leu Leu Leu Lys Ser Val Val Tyr Phe Ala Ile Ile
865                 870                 875                 880

Thr Cys Cys Leu Leu Arg Arg Thr Ala Phe Cys Cys Asn Gly Glu Lys
                885                 890                 895

Ser Gly Ser Gly Ala Thr Asn Phe Ser Leu Leu Lys Gln Ala Gly Asp
                900                 905                 910

Val Glu Glu Asn Pro Gly Pro Met Glu Thr Asp Thr Leu Leu Leu Trp
                915                 920                 925

Val Leu Leu Leu Trp Val Pro Gly Ser Thr Gly Gln Ser Val Leu Thr
                930                 935                 940

Gln Pro Pro Ser Val Ser Gly Ala Pro Gly Gln Arg Val Thr Ile Ser
945                 950                 955                 960

Cys Thr Gly Ser Ser Ser Asn Ile Gly Ala Gly Tyr Asp Val His Trp
```

```
                    965                 970                 975

Tyr Gln Gln Leu Pro Gly Thr Ala Pro Lys Leu Leu Ile Tyr Gly Asn
            980                 985                 990

Ser Asn Arg Pro Ser Gly Val Pro Asp Arg Phe Ser Gly Ser Lys Ser
        995                1000                1005

Gly Thr Ser Ala Ser Leu Ala Ile Thr Gly Leu Gln Ala Glu Asp Glu
   1010                1015                1020

Ala Asp Tyr Tyr Cys Gln Ser Tyr Asp Ser Ser Leu Ser Gly Tyr Val
1025                1030                1035                1040

Phe Gly Thr Gly Thr Lys Val Thr Val Leu Gly Ser Arg Gly Gly Gly
            1045                1050                1055

Gly Ser Gly Gly Gly Gly Ser Gly Gly Gly Gly Ser Leu Glu Met Ala
        1060                1065                1070

Glu Val Gln Leu Val Gln Ser Gly Ala Glu Val Lys Lys Pro Gly Glu
   1075                1080                1085

Ser Leu Lys Ile Ser Cys Lys Gly Ser Gly Tyr Ser Phe Thr Ser Tyr
   1090                1095                1100

Trp Ile Gly Trp Val Arg Gln Met Pro Gly Lys Gly Leu Glu Trp Met
1105                1110                1115                1120

Gly Ile Ile Tyr Pro Gly Asp Ser Asp Thr Arg Tyr Ser Pro Ser Phe
            1125                1130                1135

Gln Gly Gln Val Thr Ile Ser Ala Asp Lys Ser Ile Ser Thr Ala Tyr
        1140                1145                1150

Leu Gln Trp Ser Ser Leu Lys Ala Ser Asp Thr Ala Met Tyr Tyr Cys
   1155                1160                1165

Ala Arg Ser Met Gly Ser Ser Leu Tyr Ala Ser Ser Asp Val Trp Gly
   1170                1175                1180

Gln Gly Thr Leu Val Thr Val Ser Ser Glu Gln Lys Leu Ile Ser Glu
1185                1190                1195                1200

Glu Asp Leu Ala Ala Ala Ile Glu Val Met Tyr Pro Pro Tyr Leu
            1205                1210                1215

Asp Asn Glu Lys Ser Asn Gly Thr Ile Ile His Val Lys Gly Lys His
        1220                1225                1230

Leu Cys Pro Ser Pro Leu Phe Pro Gly Pro Ser Lys Pro Phe Trp Val
   1235                1240                1245

Leu Val Val Val Gly Gly Val Leu Ala Cys Tyr Ser Leu Leu Val Thr
   1250                1255                1260

Val Ala Phe Ile Ile Phe Trp Val Arg Ser Lys Arg Ser Arg Leu Leu
1265                1270                1275                1280

His Ser Asp Tyr Met Asn Met Thr Pro Arg Arg Pro Gly Pro Thr Arg
            1285                1290                1295

Lys His Tyr Gln Pro Tyr Ala Pro Pro Arg Asp Phe Ala Ala Tyr Arg
        1300                1305                1310

Ser

<210> SEQ ID NO 91
<211> LENGTH: 902
<212> TYPE: PRT
<213> ORGANISM: Artificial Sequence
<220> FEATURE:
<223> OTHER INFORMATION: Synthetic Construct

<400> SEQUENCE: 91

Met Glu Thr Asp Thr Leu Leu Leu Trp Val Leu Leu Leu Trp Val Pro
1               5                   10                  15
```

```
Gly Ser Thr Gly Gln Ser Val Leu Thr Gln Pro Pro Ser Val Ser Gly
         20                  25                  30

Ala Pro Gly Gln Arg Val Thr Ile Ser Cys Thr Gly Ser Ser Ser Asn
         35                  40                  45

Ile Gly Ala Gly Tyr Asp Val His Trp Tyr Gln Gln Leu Pro Gly Thr
 50                  55                  60

Ala Pro Lys Leu Leu Ile Tyr Gly Asn Ser Asn Arg Pro Ser Gly Val
 65                  70                  75                  80

Pro Asp Arg Phe Ser Gly Ser Lys Ser Gly Thr Ser Ala Ser Leu Ala
             85                  90                  95

Ile Thr Gly Leu Gln Ala Glu Asp Glu Ala Asp Tyr Tyr Cys Gln Ser
            100                 105                 110

Tyr Asp Ser Ser Leu Ser Gly Tyr Val Phe Gly Thr Gly Thr Lys Val
            115                 120                 125

Thr Val Leu Gly Ser Arg Gly Gly Gly Ser Gly Gly Gly Gly Ser
130                 135                 140

Gly Gly Gly Gly Ser Leu Glu Met Ala Glu Val Gln Leu Val Gln Ser
145                 150                 155                 160

Gly Ala Glu Val Lys Lys Pro Gly Glu Ser Leu Lys Ile Ser Cys Lys
                165                 170                 175

Gly Ser Gly Tyr Ser Phe Thr Ser Tyr Trp Ile Gly Trp Val Arg Gln
            180                 185                 190

Met Pro Gly Lys Gly Leu Glu Trp Met Gly Ile Ile Tyr Pro Gly Asp
        195                 200                 205

Ser Asp Thr Arg Tyr Ser Pro Ser Phe Gln Gly Gln Val Thr Ile Ser
    210                 215                 220

Ala Asp Lys Ser Ile Ser Thr Ala Tyr Leu Gln Trp Ser Ser Leu Lys
225                 230                 235                 240

Ala Ser Asp Thr Ala Met Tyr Tyr Cys Ala Arg Ser Met Gly Ser Ser
                245                 250                 255

Leu Tyr Ala Ser Ser Asp Val Trp Gly Gln Gly Thr Leu Val Thr Val
            260                 265                 270

Ser Ser Gly Gly Gly Gly Ser Glu Val Gln Leu Val Gln Ser Gly Ala
        275                 280                 285

Glu Met Lys Lys Pro Gly Glu Ser Leu Lys Ile Ser Cys Lys Gly Ser
    290                 295                 300

Gly Tyr Asn Phe Ala Ser Tyr Trp Val Gly Trp Val Arg Gln Met Pro
305                 310                 315                 320

Gly Lys Gly Leu Glu Trp Met Gly Thr Ile Tyr Pro Asp Asp Ser Asp
                325                 330                 335

Thr Arg Tyr Gly Pro Ala Phe Gln Gly Gln Val Thr Ile Ser Ala Asp
            340                 345                 350

Lys Ser Ile Ser Thr Ala Tyr Leu Gln Trp Ser Ser Leu Lys Ala Ser
        355                 360                 365

Asp Thr Ala Met Tyr Tyr Cys Ala Arg Asp Ser Tyr Tyr Gly Ile Asp
    370                 375                 380

Val Trp Gly Gln Gly Thr Leu Val Thr Val Ser Ser Ala Ser Thr Lys
385                 390                 395                 400

Gly Pro Ser Val Phe Pro Leu Ala Pro Ser Ser Lys Ser Thr Ser Gly
                405                 410                 415

Gly Thr Ala Ala Leu Gly Cys Leu Val Lys Asp Tyr Phe Pro Glu Pro
            420                 425                 430
```

```
Val Thr Val Ser Trp Asn Ser Gly Ala Leu Thr Ser Gly Val His Thr
            435                 440                 445

Phe Pro Ala Val Leu Gln Ser Ser Gly Leu Tyr Ser Leu Ser Ser Val
    450                 455                 460

Val Thr Val Pro Ser Ser Ser Leu Gly Thr Gln Thr Tyr Ile Cys Asn
465                 470                 475                 480

Val Asn His Lys Pro Ser Asn Thr Lys Val Asp Lys Arg Val Glu Pro
                485                 490                 495

Lys Ser Cys Glu Val Lys Thr Asp Ser Thr Asp His Val Lys Pro Lys
            500                 505                 510

Glu Thr Glu Asn Thr Lys Gln Pro Ser Lys Ser Cys His Lys Pro Lys
            515                 520                 525

Ala Ile Val His Thr Glu Lys Val Asn Met Met Ser Leu Thr Val Leu
    530                 535                 540

Gly Leu Arg Met Leu Phe Ala Lys Thr Val Ala Val Asn Phe Leu Leu
545                 550                 555                 560

Thr Ala Lys Leu Phe Phe Leu Arg Ala Lys Arg Ser Gly Ser Gly Ala
                565                 570                 575

Pro Val Lys Gln Thr Leu Asn Phe Asp Leu Leu Lys Leu Ala Gly Asp
            580                 585                 590

Val Glu Ser Asn Pro Gly Pro Met Glu Thr Asp Thr Leu Leu Leu Trp
            595                 600                 605

Val Leu Leu Leu Trp Val Pro Gly Ser Thr Gly Gln Ala Val Leu Thr
    610                 615                 620

Gln Pro Pro Ser Ala Ser Gly Thr Pro Gly Gln Arg Val Thr Ile Ser
625                 630                 635                 640

Cys Ser Gly Ser Ser Ser Asn Ile Gly Ser Asn Thr Val Asn Trp Tyr
                645                 650                 655

Gln Gln Leu Pro Gly Thr Ala Pro Lys Leu Leu Met Tyr Ser Asn Asn
            660                 665                 670

Gln Arg Pro Ser Gly Val Pro Asp Arg Phe Ser Gly Ser Lys Ser Gly
            675                 680                 685

Thr Ser Ala Ser Leu Ala Ile Ser Gly Leu Gln Ser Glu Asp Glu Ala
    690                 695                 700

Asp Tyr Tyr Cys Ala Ala Trp Asp Asp Ser Leu Asn Gly Tyr Val Phe
705                 710                 715                 720

Gly Thr Gly Thr Lys Val Thr Val Leu Gly Gln Pro Lys Ala Asn Pro
                725                 730                 735

Thr Val Thr Leu Phe Pro Pro Ser Ser Glu Glu Leu Gln Ala Asn Lys
            740                 745                 750

Ala Thr Leu Val Cys Leu Ile Ser Asp Phe Tyr Pro Gly Ala Val Thr
    755                 760                 765

Val Ala Trp Lys Ala Asp Gly Ser Pro Val Lys Ala Gly Val Glu Thr
770                 775                 780

Thr Lys Pro Ser Lys Gln Ser Asn Asn Lys Tyr Ala Ala Ser Ser Tyr
                785                 790                 795                 800

Leu Ser Leu Thr Pro Glu Gln Trp Lys Ser His Arg Ser Tyr Ser Cys
            805                 810                 815

Gln Val Thr His Glu Gly Ser Thr Val Glu Lys Thr Val Ala Pro Thr
            820                 825                 830

Glu Cys Ser Pro Ile Lys Thr Asp Val Ile Thr Met Asp Pro Lys Asp
    835                 840                 845

Asn Cys Ser Lys Asp Ala Asn Asp Thr Leu Leu Leu Gln Leu Thr Asn
```

```
                    850                 855                 860
Thr Ser Ala Tyr Tyr Met Tyr Leu Leu Leu Leu Lys Ser Val Val
865                 870                 875                 880

Tyr Phe Ala Ile Ile Thr Cys Cys Leu Leu Arg Arg Thr Ala Phe Cys
                885                 890                 895

Cys Asn Gly Glu Lys Ser
            900

<210> SEQ ID NO 92
<211> LENGTH: 896
<212> TYPE: PRT
<213> ORGANISM: Artificial Sequence
<220> FEATURE:
<223> OTHER INFORMATION: Synthetic Construct

<400> SEQUENCE: 92

Met Glu Thr Asp Thr Leu Leu Leu Trp Val Leu Leu Leu Trp Val Pro
1               5                   10                  15

Gly Ser Thr Gly Glu Val Gln Leu Val Gln Ser Gly Ala Glu Val Lys
                20                  25                  30

Lys Pro Gly Glu Ser Leu Lys Ile Ser Cys Lys Gly Ser Gly Tyr Ser
            35                  40                  45

Phe Thr Ser Tyr Trp Ile Gly Trp Val Arg Gln Met Pro Gly Lys Gly
        50                  55                  60

Leu Glu Trp Met Gly Ile Ile Tyr Pro Gly Asp Ser Asp Thr Arg Tyr
65                  70                  75                  80

Ser Pro Ser Phe Gln Gly Gln Val Thr Ile Ser Ala Asp Lys Ser Ile
                85                  90                  95

Ser Thr Ala Tyr Leu Gln Trp Ser Ser Leu Lys Ala Ser Asp Thr Ala
            100                 105                 110

Met Tyr Tyr Cys Ala Arg Ser Met Gly Ser Ser Leu Tyr Ala Ser Ser
        115                 120                 125

Asp Val Trp Gly Gln Gly Thr Leu Val Thr Val Ser Ser Gly Gly Gly
    130                 135                 140

Gly Ser Gly Gly Gly Gly Ser Glu Val Gln Leu Val Gln Ser Gly Ala
145                 150                 155                 160

Glu Met Lys Lys Pro Gly Glu Ser Leu Lys Ile Ser Cys Lys Gly Ser
                165                 170                 175

Gly Tyr Asn Phe Ala Ser Tyr Trp Val Gly Trp Val Arg Gln Met Pro
            180                 185                 190

Gly Lys Gly Leu Glu Trp Met Gly Thr Ile Tyr Pro Asp Asp Ser Asp
        195                 200                 205

Thr Arg Tyr Gly Pro Ala Phe Gln Gly Gln Val Thr Ile Ser Ala Asp
    210                 215                 220

Lys Ser Ile Ser Thr Ala Tyr Leu Gln Trp Ser Ser Leu Lys Ala Ser
225                 230                 235                 240

Asp Thr Ala Met Tyr Tyr Cys Ala Arg Asp Ser Tyr Tyr Gly Ile Asp
                245                 250                 255

Val Trp Gly Gln Gly Thr Leu Val Thr Val Ser Ser Ala Ser Thr Lys
            260                 265                 270

Gly Pro Ser Val Phe Pro Leu Ala Pro Ser Ser Lys Ser Thr Ser Gly
        275                 280                 285

Gly Thr Ala Ala Leu Gly Cys Leu Val Lys Asp Tyr Phe Pro Glu Pro
    290                 295                 300

Val Thr Val Ser Trp Asn Ser Gly Ala Leu Thr Ser Gly Val His Thr
```

```
                305                 310                 315                 320
            Phe Pro Ala Val Leu Gln Ser Ser Gly Leu Tyr Ser Leu Ser Ser Val
                            325                 330                 335

Val Thr Val Pro Ser Ser Leu Gly Thr Gln Thr Tyr Ile Cys Asn
                            340                 345                 350

Val Asn His Lys Pro Ser Asn Thr Lys Val Asp Lys Arg Val Glu Pro
                            355                 360                 365

Lys Ser Cys Glu Val Lys Thr Asp Ser Thr His Val Lys Pro Lys
            370                 375                 380

Glu Thr Glu Asn Thr Lys Gln Pro Ser Lys Ser Cys His Lys Pro Lys
            385                 390                 395                 400

Ala Ile Val His Thr Glu Lys Val Asn Met Met Ser Leu Thr Val Leu
                            405                 410                 415

Gly Leu Arg Met Leu Phe Ala Lys Thr Val Ala Val Asn Phe Leu Leu
                            420                 425                 430

Thr Ala Lys Leu Phe Phe Leu Arg Ala Lys Arg Ser Gly Ser Gly Ala
                            435                 440                 445

Pro Val Lys Gln Thr Leu Asn Phe Asp Leu Leu Lys Leu Ala Gly Asp
                            450                 455                 460

Val Glu Ser Asn Pro Gly Pro Met Glu Thr Asp Thr Leu Leu Leu Trp
            465                 470                 475                 480

Val Leu Leu Leu Trp Val Pro Gly Ser Thr Gly Gln Ser Val Leu Thr
                            485                 490                 495

Gln Pro Pro Ser Val Ser Gly Ala Pro Gly Gln Arg Val Thr Ile Ser
                            500                 505                 510

Cys Thr Gly Ser Ser Ser Asn Ile Gly Ala Gly Tyr Asp Val His Trp
                            515                 520                 525

Tyr Gln Gln Leu Pro Gly Thr Ala Pro Lys Leu Leu Ile Tyr Gly Asn
                            530                 535                 540

Ser Asn Arg Pro Ser Gly Val Pro Asp Arg Phe Ser Gly Ser Lys Ser
            545                 550                 555                 560

Gly Thr Ser Ala Ser Leu Ala Ile Thr Gly Leu Gln Ala Glu Asp Glu
                            565                 570                 575

Ala Asp Tyr Tyr Cys Gln Ser Tyr Asp Ser Ser Leu Ser Gly Tyr Val
                            580                 585                 590

Phe Gly Thr Gly Thr Lys Val Thr Val Leu Gly Gly Gly Gly Ser
                            595                 600                 605

Gly Gly Gly Gly Ser Gln Ala Val Leu Thr Gln Pro Pro Ser Ala Ser
                            610                 615                 620

Gly Thr Pro Gly Gln Arg Val Thr Ile Ser Cys Ser Gly Ser Ser Ser
            625                 630                 635                 640

Asn Ile Gly Ser Asn Thr Val Asn Trp Tyr Gln Gln Leu Pro Gly Thr
                            645                 650                 655

Ala Pro Lys Leu Leu Met Tyr Ser Asn Asn Gln Arg Pro Ser Gly Val
                            660                 665                 670

Pro Asp Arg Phe Ser Gly Ser Lys Ser Gly Thr Ser Ala Ser Leu Ala
                            675                 680                 685

Ile Ser Gly Leu Gln Ser Glu Asp Glu Ala Asp Tyr Tyr Cys Ala Ala
                            690                 695                 700

Trp Asp Asp Ser Leu Asn Gly Tyr Val Phe Gly Thr Gly Thr Lys Val
            705                 710                 715                 720

Thr Val Leu Gly Gln Pro Lys Ala Asn Pro Thr Val Thr Leu Phe Pro
                            725                 730                 735
```

Pro Ser Ser Glu Glu Leu Gln Ala Asn Lys Ala Thr Leu Val Cys Leu
            740                 745                 750

Ile Ser Asp Phe Tyr Pro Gly Ala Val Thr Val Ala Trp Lys Ala Asp
        755                 760                 765

Gly Ser Pro Val Lys Ala Gly Val Glu Thr Thr Lys Pro Ser Lys Gln
    770                 775                 780

Ser Asn Asn Lys Tyr Ala Ala Ser Ser Tyr Leu Ser Leu Thr Pro Glu
785                 790                 795                 800

Gln Trp Lys Ser His Arg Ser Tyr Ser Cys Gln Val Thr His Glu Gly
                805                 810                 815

Ser Thr Val Glu Lys Thr Val Ala Pro Thr Glu Cys Ser Pro Ile Lys
            820                 825                 830

Thr Asp Val Ile Thr Met Asp Pro Lys Asp Asn Cys Ser Lys Asp Ala
        835                 840                 845

Asn Asp Thr Leu Leu Leu Gln Leu Thr Asn Thr Ser Ala Tyr Tyr Met
850                 855                 860

Tyr Leu Leu Leu Leu Lys Ser Val Val Tyr Phe Ala Ile Ile Thr
865                 870                 875                 880

Cys Cys Leu Leu Arg Arg Thr Ala Phe Cys Cys Asn Gly Glu Lys Ser
                885                 890                 895

<210> SEQ ID NO 93
<211> LENGTH: 633
<212> TYPE: PRT
<213> ORGANISM: Artificial Sequence
<220> FEATURE:
<223> OTHER INFORMATION: Synthetic Construct

<400> SEQUENCE: 93

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly Gly
        115                 120                 125

Ser Leu Glu Met Ala Glu Val Gln Leu Val Gln Ser Gly Ala Glu Val
    130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205

-continued

```
Ile Ser Thr Ala Tyr Leu Gln Trp Ser Ser Leu Lys Ala Ser Asp Thr
    210                 215                 220
Ala Met Tyr Tyr Cys Ala Arg Ser Met Gly Ser Ser Leu Tyr Ala Ser
225                 230                 235                 240
Ser Asp Val Trp Gly Gln Gly Thr Leu Val Thr Val Ser Ser Gly Gly
                245                 250                 255
Gly Gly Ser Gly Gly Gly Gly Ser Gln Ala Val Leu Thr Gln Pro Pro
                260                 265                 270
Ser Ala Ser Gly Thr Pro Gly Gln Arg Val Thr Ile Ser Cys Ser Gly
                275                 280                 285
Ser Ser Ser Asn Ile Gly Ser Asn Thr Val Asn Trp Tyr Gln Gln Leu
    290                 295                 300
Pro Gly Thr Ala Pro Lys Leu Leu Met Tyr Ser Asn Asn Gln Arg Pro
305                 310                 315                 320
Ser Gly Val Pro Asp Arg Phe Ser Gly Ser Lys Ser Gly Thr Ser Ala
                325                 330                 335
Ser Leu Ala Ile Ser Gly Leu Gln Ser Glu Asp Glu Ala Asp Tyr Tyr
                340                 345                 350
Cys Ala Ala Trp Asp Asp Ser Leu Asn Gly Tyr Val Phe Gly Thr Gly
                355                 360                 365
Thr Lys Val Thr Val Leu Gly Ser Arg Gly Gly Gly Gly Ser Gly Gly
    370                 375                 380
Gly Gly Ser Gly Gly Gly Gly Ser Leu Glu Met Ala Glu Val Gln Leu
385                 390                 395                 400
Val Gln Ser Gly Ala Glu Met Lys Lys Pro Gly Glu Ser Leu Lys Ile
                405                 410                 415
Ser Cys Lys Gly Ser Gly Tyr Asn Phe Ala Ser Tyr Trp Val Gly Trp
                420                 425                 430
Val Arg Gln Met Pro Gly Lys Gly Leu Glu Trp Met Gly Thr Ile Tyr
                435                 440                 445
Pro Asp Asp Ser Asp Thr Arg Tyr Gly Pro Ala Phe Gln Gly Gln Val
    450                 455                 460
Thr Ile Ser Ala Asp Lys Ser Ile Ser Thr Ala Tyr Leu Gln Trp Ser
465                 470                 475                 480
Ser Leu Lys Ala Ser Asp Thr Ala Met Tyr Tyr Cys Ala Arg Asp Ser
                485                 490                 495
Tyr Tyr Gly Ile Asp Val Trp Gly Gln Gly Thr Leu Val Thr Val Ser
                500                 505                 510
Ser Glu Gln Lys Leu Ile Ser Glu Glu Asp Leu Ala Ala Ala Ile Glu
    515                 520                 525
Val Met Tyr Pro Pro Tyr Leu Asp Asn Glu Lys Ser Asn Gly Thr
530                 535                 540
Ile Ile His Val Lys Gly Lys His Leu Cys Pro Ser Pro Leu Phe Pro
545                 550                 555                 560
Gly Pro Ser Lys Pro Phe Trp Val Leu Val Val Val Gly Gly Val Leu
                565                 570                 575
Ala Cys Tyr Ser Leu Leu Val Thr Val Ala Phe Ile Ile Phe Trp Val
                580                 585                 590
Arg Ser Lys Arg Ser Arg Leu Leu His Ser Asp Tyr Met Asn Met Thr
    595                 600                 605
Pro Arg Arg Pro Gly Pro Thr Arg Lys His Tyr Gln Pro Tyr Ala Pro
610                 615                 620
```

-continued

Pro Arg Asp Phe Ala Ala Tyr Arg Ser
625                 630

<210> SEQ ID NO 94
<211> LENGTH: 21
<212> TYPE: PRT
<213> ORGANISM: Artificial Sequence
<220> FEATURE:
<223> OTHER INFORMATION: Synthetic Construct

<400> SEQUENCE: 94

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 95
<211> LENGTH: 27
<212> TYPE: PRT
<213> ORGANISM: Artificial Sequence
<220> FEATURE:
<223> OTHER INFORMATION: Synthetic Construct

<400> SEQUENCE: 95

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 96
<211> LENGTH: 21
<212> TYPE: PRT
<213> ORGANISM: Artificial Sequence
<220> FEATURE:
<223> OTHER INFORMATION: Synthetic Construct

<400> SEQUENCE: 96

Ile Leu Val Ile Phe Ser Gly Met Phe Leu Val Phe Thr Leu Ala Gly
1               5                   10                  15

Ala Leu Phe Leu His
            20

<210> SEQ ID NO 97
<211> LENGTH: 27
<212> TYPE: PRT
<213> ORGANISM: Artificial Sequence
<220> FEATURE:
<223> OTHER INFORMATION: Synthetic Construct

<400> SEQUENCE: 97

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 98
<211> LENGTH: 28
<212> TYPE: PRT
<213> ORGANISM: Artificial Sequence
<220> FEATURE:
<223> OTHER INFORMATION: Synthetic Construct

<400> SEQUENCE: 98

Pro Val Leu Asp Ala Gly Pro Val Leu Phe Trp Val Ile Leu Val Leu
1               5                   10                  15

```
Val Val Val Val Gly Ser Ser Ala Phe Leu Leu Cys
            20                  25

<210> SEQ ID NO 99
<211> LENGTH: 21
<212> TYPE: PRT
<213> ORGANISM: Artificial Sequence
<220> FEATURE:
<223> OTHER INFORMATION: Synthetic Construct

<400> SEQUENCE: 99

Val Ala Ala Ile Leu Gly Leu Gly Leu Val Leu Gly Leu Gly Pro
1               5                   10                  15

Leu Ala Ile Leu Leu
            20

<210> SEQ ID NO 100
<211> LENGTH: 42
<212> TYPE: PRT
<213> ORGANISM: Artificial Sequence
<220> FEATURE:
<223> OTHER INFORMATION: Synthetic Construct

<400> SEQUENCE: 100

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 101
<211> LENGTH: 48
<212> TYPE: PRT
<213> ORGANISM: Artificial Sequence
<220> FEATURE:
<223> OTHER INFORMATION: Synthetic Construct

<400> SEQUENCE: 101

Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 102
<211> LENGTH: 41
<212> TYPE: PRT
<213> ORGANISM: Artificial Sequence
<220> FEATURE:
<223> OTHER INFORMATION: Synthetic Construct

<400> SEQUENCE: 102

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 103
```

```
<211> LENGTH: 42
<212> TYPE: PRT
<213> ORGANISM: Artificial Sequence
<220> FEATURE:
<223> OTHER INFORMATION: Synthetic Construct

<400> SEQUENCE: 103

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
        35                  40

<210> SEQ ID NO 104
<211> LENGTH: 120
<212> TYPE: PRT
<213> ORGANISM: Artificial Sequence
<220> FEATURE:
<223> OTHER INFORMATION: Synthetic Construct

<400> SEQUENCE: 104

Glu Gln Lys Leu Ile Ser Glu Glu Asp Leu Ala Ala Ala Ile Glu Val
1               5                   10                  15

Met Tyr Pro Pro Pro Tyr Leu Asp Asn Glu Lys Ser Asn Gly Thr Ile
            20                  25                  30

Ile His Val Lys Gly Lys His Leu Cys Pro Ser Pro Leu Phe Pro Gly
        35                  40                  45

Pro Ser Lys Pro Phe Trp Val Leu Val Val Val Gly Gly Val Leu Ala
    50                  55                  60

Cys Tyr Ser Leu Leu Val Thr Val Ala Phe Ile Ile Phe Trp Val Arg
65                  70                  75                  80

Ser Lys Arg Ser Arg Leu Leu His Ser Asp Tyr Met Asn Met Thr Pro
                85                  90                  95

Arg Arg Pro Gly Pro Thr Arg Lys His Tyr Gln Pro Tyr Ala Pro Pro
            100                 105                 110

Arg Asp Phe Ala Ala Tyr Arg Ser
        115                 120

<210> SEQ ID NO 105
<211> LENGTH: 107
<212> TYPE: PRT
<213> ORGANISM: Artificial Sequence
<220> FEATURE:
<223> OTHER INFORMATION: Synthetic Construct

<400> SEQUENCE: 105

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95
```

```
Ala Pro Pro Arg Asp Phe Ala Ala Tyr Arg Ser
            100                 105
```

<210> SEQ ID NO 106
<211> LENGTH: 109
<212> TYPE: PRT
<213> ORGANISM: Artificial Sequence
<220> FEATURE:
<223> OTHER INFORMATION: Synthetic Construct

<400> SEQUENCE: 106

```
Glu Gln Lys Leu Ile Ser Glu Glu Asp Leu Ala Ala Ala Thr Gly Pro
1               5                   10                  15

Ala Asp Leu Ser Pro Gly Ala Ser Ser Val Thr Pro Ala Pro Ala
            20                  25                  30

Arg Glu Pro Gly His Ser Pro Gln Ile Ile Ser Phe Phe Leu Ala Leu
            35                  40                  45

Thr Ser Thr Ala Leu Leu Phe Leu Leu Phe Phe Leu Thr Leu Arg Phe
        50                  55                  60

Ser Val Val Lys Arg Gly Arg Lys Lys Leu Leu Tyr Ile Phe Lys Gln
65                  70                  75                  80

Pro Phe Met Arg Pro Val Gln Thr Thr Gln Glu Glu Asp Gly Cys Ser
                85                  90                  95

Cys Arg Phe Pro Glu Glu Glu Glu Gly Gly Cys Glu Leu
            100                 105
```

<210> SEQ ID NO 107
<211> LENGTH: 94
<212> TYPE: PRT
<213> ORGANISM: Artificial Sequence
<220> FEATURE:
<223> OTHER INFORMATION: Synthetic Construct

<400> SEQUENCE: 107

```
Pro Ala Asp Leu Ser Pro Gly Ala Ser Ser Val Thr Pro Ala Pro
1               5                   10                  15

Ala Arg Glu Pro Gly His Ser Pro Gln Ile Ile Ser Phe Phe Leu Ala
            20                  25                  30

Leu Thr Ser Thr Ala Leu Leu Phe Leu Leu Phe Phe Leu Thr Leu Arg
        35                  40                  45

Phe Ser Val Val Lys Arg Gly Arg Lys Lys Leu Leu Tyr Ile Phe Lys
        50                  55                  60

Gln Pro Phe Met Arg Pro Val Gln Thr Thr Gln Glu Glu Asp Gly Cys
65                  70                  75                  80

Ser Cys Arg Phe Pro Glu Glu Glu Glu Gly Gly Cys Glu Leu
                85                  90
```

<210> SEQ ID NO 108
<211> LENGTH: 134
<212> TYPE: PRT
<213> ORGANISM: Artificial Sequence
<220> FEATURE:
<223> OTHER INFORMATION: Synthetic Construct

<400> SEQUENCE: 108

```
Glu Gln Lys Leu Ile Ser Glu Glu Asp Leu Ala Ala Ala Thr Gly Pro
1               5                   10                  15

Thr His Leu Pro Tyr Val Ser Glu Met Leu Glu Ala Arg Thr Ala Gly
            20                  25                  30

His Met Gln Thr Leu Ala Asp Phe Arg Gln Leu Pro Ala Arg Thr Leu
```

```
                    35                  40                  45
Ser Thr His Trp Pro Pro Gln Arg Ser Leu Cys Ser Ser Asp Phe Ile
 50                  55                  60

Arg Ile Leu Val Ile Phe Ser Gly Met Phe Leu Val Phe Thr Leu Ala
 65                  70                  75                  80

Gly Ala Leu Phe Leu His Gln Arg Arg Lys Tyr Arg Ser Asn Lys Gly
                 85                  90                  95

Glu Ser Pro Val Glu Pro Ala Glu Pro Cys Arg Tyr Ser Cys Pro Arg
                100                 105                 110

Glu Glu Glu Gly Ser Thr Ile Pro Ile Gln Glu Asp Tyr Arg Lys Pro
            115                 120                 125

Glu Pro Ala Cys Ser Pro
            130

<210> SEQ ID NO 109
<211> LENGTH: 119
<212> TYPE: PRT
<213> ORGANISM: Artificial Sequence
<220> FEATURE:
<223> OTHER INFORMATION: Synthetic Construct

<400> SEQUENCE: 109

Pro Thr His Leu Pro Tyr Val Ser Glu Met Leu Glu Ala Arg Thr Ala
 1               5                  10                  15

Gly His Met Gln Thr Leu Ala Asp Phe Arg Gln Leu Pro Ala Arg Thr
                 20                  25                  30

Leu Ser Thr His Trp Pro Pro Gln Arg Ser Leu Cys Ser Ser Asp Phe
             35                  40                  45

Ile Arg Ile Leu Val Ile Phe Ser Gly Met Phe Leu Val Phe Thr Leu
 50                  55                  60

Ala Gly Ala Leu Phe Leu His Gln Arg Arg Lys Tyr Arg Ser Asn Lys
 65                  70                  75                  80

Gly Glu Ser Pro Val Glu Pro Ala Glu Pro Cys Arg Tyr Ser Cys Pro
                 85                  90                  95

Arg Glu Glu Glu Gly Ser Thr Ile Pro Ile Gln Glu Asp Tyr Arg Lys
                100                 105                 110

Pro Glu Pro Ala Cys Ser Pro
            115

<210> SEQ ID NO 110
<211> LENGTH: 285
<212> TYPE: PRT
<213> ORGANISM: Artificial Sequence
<220> FEATURE:
<223> OTHER INFORMATION: Synthetic Construct

<400> SEQUENCE: 110

Glu Gln Lys Leu Ile Ser Glu Glu Asp Leu Ala Ala Ala Thr Gly Ala
 1               5                  10                  15

Pro Pro Leu Gly Thr Gln Pro Asp Cys Asn Pro Thr Pro Glu Asn Gly
                 20                  25                  30

Glu Ala Pro Ala Ser Thr Ser Pro Thr Gln Ser Leu Leu Val Asp Ser
             35                  40                  45

Gln Ala Ser Lys Thr Leu Pro Ile Pro Thr Ser Ala Pro Val Ala Leu
 50                  55                  60

Ser Ser Thr Gly Lys Pro Val Leu Asp Ala Gly Pro Val Leu Phe Trp
 65                  70                  75                  80
```

```
Val Ile Leu Val Leu Val Val Val Gly Ser Ser Ala Phe Leu Leu
         85                  90                  95

Cys His Arg Arg Ala Cys Arg Lys Arg Ile Arg Gln Lys Leu His Leu
        100                 105                 110

Cys Tyr Pro Val Gln Thr Ser Gln Pro Lys Leu Glu Leu Val Asp Ser
        115                 120                 125

Arg Pro Arg Ser Ser Thr Gln Leu Arg Ser Gly Ala Ser Val Thr
130                 135                 140

Glu Pro Val Ala Glu Glu Arg Gly Leu Met Ser Gln Pro Leu Met Glu
145                 150                 155                 160

Thr Cys His Ser Val Gly Ala Ala Tyr Leu Glu Ser Leu Pro Leu Gln
                165                 170                 175

Asp Ala Ser Pro Ala Gly Gly Pro Ser Ser Pro Arg Asp Leu Pro Glu
                180                 185                 190

Pro Arg Val Ser Thr Glu His Thr Asn Asn Lys Ile Glu Lys Ile Tyr
            195                 200                 205

Ile Met Lys Ala Asp Thr Val Ile Val Gly Thr Val Lys Ala Glu Leu
        210                 215                 220

Pro Glu Gly Arg Gly Leu Ala Gly Pro Ala Glu Pro Glu Leu Glu Glu
225                 230                 235                 240

Glu Leu Glu Ala Asp His Thr Pro His Tyr Pro Glu Gln Glu Thr Glu
                245                 250                 255

Pro Pro Leu Gly Ser Cys Ser Asp Val Met Leu Ser Val Glu Glu
                260                 265                 270

Gly Lys Glu Asp Pro Leu Pro Thr Ala Ala Ser Gly Lys
        275                 280                 285

<210> SEQ ID NO 111
<211> LENGTH: 270
<212> TYPE: PRT
<213> ORGANISM: Artificial Sequence
<220> FEATURE:
<223> OTHER INFORMATION: Synthetic Construct

<400> SEQUENCE: 111

Ala Pro Pro Leu Gly Thr Gln Pro Asp Cys Asn Pro Thr Pro Glu Asn
1               5                   10                  15

Gly Glu Ala Pro Ala Ser Thr Ser Pro Thr Gln Ser Leu Leu Val Asp
            20                  25                  30

Ser Gln Ala Ser Lys Thr Leu Pro Ile Pro Thr Ser Ala Pro Val Ala
        35                  40                  45

Leu Ser Ser Thr Gly Lys Pro Val Leu Asp Ala Gly Pro Val Leu Phe
    50                  55                  60

Trp Val Ile Leu Val Leu Val Val Val Gly Ser Ser Ala Phe Leu
65                  70                  75                  80

Leu Cys His Arg Arg Ala Cys Arg Lys Arg Ile Arg Gln Lys Leu His
                85                  90                  95

Leu Cys Tyr Pro Val Gln Thr Ser Gln Pro Lys Leu Glu Leu Val Asp
            100                 105                 110

Ser Arg Pro Arg Arg Ser Ser Thr Gln Leu Arg Ser Gly Ala Ser Val
        115                 120                 125

Thr Glu Pro Val Ala Glu Glu Arg Gly Leu Met Ser Gln Pro Leu Met
    130                 135                 140

Glu Thr Cys His Ser Val Gly Ala Ala Tyr Leu Glu Ser Leu Pro Leu
145                 150                 155                 160
```

Gln Asp Ala Ser Pro Ala Gly Gly Pro Ser Pro Arg Asp Leu Pro
                165                 170                 175

Glu Pro Arg Val Ser Thr Glu His Thr Asn Asn Lys Ile Glu Lys Ile
            180                 185                 190

Tyr Ile Met Lys Ala Asp Thr Val Ile Val Gly Thr Val Lys Ala Glu
            195                 200                 205

Leu Pro Glu Gly Arg Gly Leu Ala Gly Pro Ala Glu Pro Glu Leu Glu
            210                 215                 220

Glu Glu Leu Glu Ala Asp His Thr Pro His Tyr Pro Glu Gln Glu Thr
225                 230                 235                 240

Glu Pro Pro Leu Gly Ser Cys Ser Asp Val Met Leu Ser Val Glu Glu
            245                 250                 255

Glu Gly Lys Glu Asp Pro Leu Pro Thr Ala Ala Ser Gly Lys
            260                 265                 270

<210> SEQ ID NO 112
<211> LENGTH: 125
<212> TYPE: PRT
<213> ORGANISM: Artificial Sequence
<220> FEATURE:
<223> OTHER INFORMATION: Synthetic Construct

<400> SEQUENCE: 112

Glu Gln Lys Leu Ile Ser Glu Glu Asp Leu Ala Ala Ala Thr Gly Asp
1               5                   10                  15

Arg Asp Pro Pro Ala Thr Gln Pro Gln Glu Thr Gln Gly Pro Pro Ala
            20                  25                  30

Arg Pro Ile Thr Val Gln Pro Thr Glu Ala Trp Pro Arg Thr Ser Gln
        35                  40                  45

Gly Pro Ser Thr Arg Pro Val Glu Val Pro Gly Gly Arg Ala Val Ala
    50                  55                  60

Ala Ile Leu Gly Leu Gly Leu Val Leu Gly Leu Leu Gly Pro Leu Ala
65                  70                  75                  80

Ile Leu Leu Ala Leu Tyr Leu Leu Arg Arg Asp Gln Arg Leu Pro Pro
                85                  90                  95

Asp Ala His Lys Pro Pro Gly Gly Gly Ser Phe Arg Thr Pro Ile Gln
            100                 105                 110

Glu Glu Gln Ala Asp Ala His Ser Thr Leu Ala Lys Ile
        115                 120                 125

<210> SEQ ID NO 113
<211> LENGTH: 110
<212> TYPE: PRT
<213> ORGANISM: Artificial Sequence
<220> FEATURE:
<223> OTHER INFORMATION: Synthetic Construct

<400> SEQUENCE: 113

Asp Arg Asp Pro Pro Ala Thr Gln Pro Gln Glu Thr Gln Gly Pro Pro
1               5                   10                  15

Ala Arg Pro Ile Thr Val Gln Pro Thr Glu Ala Trp Pro Arg Thr Ser
            20                  25                  30

Gln Gly Pro Ser Thr Arg Pro Val Glu Val Pro Gly Gly Arg Ala Val
        35                  40                  45

Ala Ala Ile Leu Gly Leu Gly Leu Val Leu Gly Leu Leu Gly Pro Leu
    50                  55                  60

Ala Ile Leu Leu Ala Leu Tyr Leu Leu Arg Arg Asp Gln Arg Leu Pro
65                  70                  75                  80

```
Pro Asp Ala His Lys Pro Pro Gly Gly Gly Ser Phe Arg Thr Pro Ile
                85                  90                  95

Gln Glu Glu Gln Ala Asp Ala His Ser Thr Leu Ala Lys Ile
            100                 105                 110
```

<210> SEQ ID NO 114
<211> LENGTH: 132
<212> TYPE: PRT
<213> ORGANISM: Artificial Sequence
<220> FEATURE:
<223> OTHER INFORMATION: Synthetic Construct

<400> SEQUENCE: 114

```
Glu Gln Lys Leu Ile Ser Glu Glu Asp Leu Ala Ala Ala Thr Gly Thr
1               5                   10                  15

Thr Thr Pro Ala Pro Arg Pro Pro Thr Pro Ala Pro Thr Ile Ala Ser
                20                  25                  30

Gln Pro Leu Ser Leu Arg Pro Glu Ala Cys Arg Pro Ala Ala Gly Gly
            35                  40                  45

Ala Val His Thr Arg Gly Leu Asp Phe Ala Cys Asp Ile Tyr Ile Trp
    50                  55                  60

Ala Pro Leu Ala Gly Thr Cys Gly Val Leu Leu Leu Ser Leu Val Ile
65                  70                  75                  80

Thr Leu Tyr Cys Gln Arg Arg Lys Tyr Arg Ser Asn Lys Gly Glu Ser
                85                  90                  95

Pro Val Glu Pro Ala Glu Pro Cys Arg Tyr Ser Cys Pro Arg Glu Glu
            100                 105                 110

Glu Gly Ser Thr Ile Pro Ile Gln Glu Asp Tyr Arg Lys Pro Glu Pro
        115                 120                 125

Ala Cys Ser Pro
        130
```

<210> SEQ ID NO 115
<211> LENGTH: 117
<212> TYPE: PRT
<213> ORGANISM: Artificial Sequence
<220> FEATURE:
<223> OTHER INFORMATION: Synthetic Construct

<400> SEQUENCE: 115

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys Gln Arg Arg Lys Tyr Arg Ser Asn Lys Gly Glu
65                  70                  75                  80

Ser Pro Val Glu Pro Ala Glu Pro Cys Arg Tyr Ser Cys Pro Arg Glu
                85                  90                  95

Glu Glu Gly Ser Thr Ile Pro Ile Gln Glu Asp Tyr Arg Lys Pro Glu
            100                 105                 110

Pro Ala Cys Ser Pro
        115
```

```
<210> SEQ ID NO 116
<211> LENGTH: 272
<212> TYPE: PRT
<213> ORGANISM: Artificial Sequence
<220> FEATURE:
<223> OTHER INFORMATION: Synthetic Construct

<400> SEQUENCE: 116

Glu Gln Lys Leu Ile Ser Glu Asp Leu Ala Ala Thr Gly Thr
1               5                   10                  15

Thr Thr Pro Ala Pro Arg Pro Pro Thr Pro Ala Pro Thr Ile Ala Ser
                20                  25                  30

Gln Pro Leu Ser Leu Arg Pro Glu Ala Cys Arg Pro Ala Ala Gly Gly
            35                  40                  45

Ala Val His Thr Arg Gly Leu Asp Phe Ala Cys Asp Ile Tyr Ile Trp
50                  55                  60

Ala Pro Leu Ala Gly Thr Cys Gly Val Leu Leu Leu Ser Leu Val Ile
65                  70                  75                  80

Thr Leu Tyr Cys His Arg Arg Ala Cys Arg Lys Arg Ile Arg Gln Lys
                85                  90                  95

Leu His Leu Cys Tyr Pro Val Gln Thr Ser Gln Pro Lys Leu Glu Leu
            100                 105                 110

Val Asp Ser Arg Pro Arg Arg Ser Ser Thr Gln Leu Arg Ser Gly Ala
        115                 120                 125

Ser Val Thr Glu Pro Val Ala Glu Glu Arg Gly Leu Met Ser Gln Pro
130                 135                 140

Leu Met Glu Thr Cys His Ser Val Gly Ala Ala Tyr Leu Glu Ser Leu
145                 150                 155                 160

Pro Leu Gln Asp Ala Ser Pro Ala Gly Gly Pro Ser Ser Pro Arg Asp
                165                 170                 175

Leu Pro Glu Pro Arg Val Ser Thr Glu His Thr Asn Asn Lys Ile Glu
            180                 185                 190

Lys Ile Tyr Ile Met Lys Ala Asp Thr Val Ile Val Gly Thr Val Lys
        195                 200                 205

Ala Glu Leu Pro Glu Gly Arg Gly Leu Ala Gly Pro Ala Glu Pro Glu
210                 215                 220

Leu Glu Glu Glu Leu Glu Ala Asp His Thr Pro His Tyr Pro Glu Gln
225                 230                 235                 240

Glu Thr Glu Pro Pro Leu Gly Ser Cys Ser Asp Val Met Leu Ser Val
                245                 250                 255

Glu Glu Glu Gly Lys Glu Asp Pro Leu Pro Thr Ala Ala Ser Gly Lys
            260                 265                 270

<210> SEQ ID NO 117
<211> LENGTH: 257
<212> TYPE: PRT
<213> ORGANISM: Artificial Sequence
<220> FEATURE:
<223> OTHER INFORMATION: Synthetic Construct

<400> SEQUENCE: 117

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45
```

```
Trp Ala Pro Leu Ala Gly Thr Cys Gly Val Leu Leu Leu Ser Leu Val
         50                  55                  60

Ile Thr Leu Tyr Cys His Arg Ala Cys Arg Lys Arg Ile Arg Gln
 65                  70                  75                  80

Lys Leu His Leu Cys Tyr Pro Val Gln Thr Ser Gln Pro Lys Leu Glu
                 85                  90                  95

Leu Val Asp Ser Arg Pro Arg Ser Ser Thr Gln Leu Arg Ser Gly
             100                 105                 110

Ala Ser Val Thr Glu Pro Val Ala Glu Glu Arg Gly Leu Met Ser Gln
             115                 120                 125

Pro Leu Met Glu Thr Cys His Ser Val Gly Ala Ala Tyr Leu Glu Ser
            130                 135                 140

Leu Pro Leu Gln Asp Ala Ser Pro Ala Gly Gly Pro Ser Ser Pro Arg
145                 150                 155                 160

Asp Leu Pro Glu Pro Arg Val Ser Thr Glu His Thr Asn Asn Lys Ile
                165                 170                 175

Glu Lys Ile Tyr Ile Met Lys Ala Asp Thr Val Ile Val Gly Thr Val
            180                 185                 190

Lys Ala Glu Leu Pro Glu Gly Arg Gly Leu Ala Gly Pro Ala Glu Pro
195                 200                 205

Glu Leu Glu Glu Glu Leu Glu Ala Asp His Thr Pro His Tyr Pro Glu
    210                 215                 220

Gln Glu Thr Glu Pro Pro Leu Gly Ser Cys Ser Asp Val Met Leu Ser
225                 230                 235                 240

Val Glu Glu Glu Gly Lys Glu Asp Pro Leu Pro Thr Ala Ala Ser Gly
                245                 250                 255

Lys

<210> SEQ ID NO 118
<211> LENGTH: 126
<212> TYPE: PRT
<213> ORGANISM: Artificial Sequence
<220> FEATURE:
<223> OTHER INFORMATION: Synthetic Construct

<400> SEQUENCE: 118

Glu Gln Lys Leu Ile Ser Glu Glu Asp Leu Ala Ala Ala Thr Gly Thr
 1               5                  10                  15

Thr Thr Pro Ala Pro Arg Pro Pro Thr Pro Ala Pro Thr Ile Ala Ser
                 20                  25                  30

Gln Pro Leu Ser Leu Arg Pro Glu Ala Cys Arg Pro Ala Ala Gly Gly
             35                  40                  45

Ala Val His Thr Arg Gly Leu Asp Phe Ala Cys Asp Ile Tyr Ile Trp
 50                  55                  60

Ala Pro Leu Ala Gly Thr Cys Gly Val Leu Leu Leu Ser Leu Val Ile
 65                  70                  75                  80

Thr Leu Tyr Cys Ala Leu Tyr Leu Leu Arg Arg Asp Gln Arg Leu Pro
                 85                  90                  95

Pro Asp Ala His Lys Pro Pro Gly Gly Gly Ser Phe Arg Thr Pro Ile
                100                 105                 110

Gln Glu Glu Gln Ala Asp Ala His Ser Thr Leu Ala Lys Ile
            115                 120                 125

<210> SEQ ID NO 119
<211> LENGTH: 111
<212> TYPE: PRT
```

<213> ORGANISM: Artificial Sequence
<220> FEATURE:
<223> OTHER INFORMATION: Synthetic Construct

<400> SEQUENCE: 119

```
Thr Thr Thr Pro Ala Pro Arg Pro Pro Thr Pro Ala Pro Thr Ile Ala
1               5                   10                  15
Ser Gln Pro Leu Ser Leu Arg Pro Glu Ala Cys Arg Pro Ala Ala Gly
            20                  25                  30
Gly Ala Val His Thr Arg Gly Leu Asp Phe Ala Cys Asp Ile Tyr Ile
        35                  40                  45
Trp Ala Pro Leu Ala Gly Thr Cys Gly Val Leu Leu Leu Ser Leu Val
50                  55                  60
Ile Thr Leu Tyr Cys Ala Leu Tyr Leu Leu Arg Arg Asp Gln Arg Leu
65                  70                  75                  80
Pro Pro Asp Ala His Lys Pro Pro Gly Gly Gly Ser Phe Arg Thr Pro
                85                  90                  95
Ile Gln Glu Glu Gln Ala Asp Ala His Ser Thr Leu Ala Lys Ile
            100                 105                 110
```

<210> SEQ ID NO 120
<211> LENGTH: 126
<212> TYPE: PRT
<213> ORGANISM: Artificial Sequence
<220> FEATURE:
<223> OTHER INFORMATION: Synthetic Construct

<400> SEQUENCE: 120

```
Glu Gln Lys Leu Ile Ser Glu Glu Asp Leu Ala Ala Ala Thr Gly Thr
1               5                   10                  15
Thr Thr Pro Ala Pro Arg Pro Pro Thr Pro Ala Pro Thr Ile Ala Ser
            20                  25                  30
Gln Pro Leu Ser Leu Arg Pro Glu Ala Cys Arg Pro Ala Ala Gly Gly
        35                  40                  45
Ala Val His Thr Arg Gly Leu Asp Phe Ala Cys Asp Ile Tyr Ile Trp
50                  55                  60
Ala Pro Leu Ala Gly Thr Cys Gly Val Leu Leu Leu Ser Leu Val Ile
65                  70                  75                  80
Thr Leu Tyr Cys Lys Arg Gly Arg Lys Lys Leu Leu Tyr Ile Phe Lys
                85                  90                  95
Gln Pro Phe Met Arg Pro Val Gln Thr Thr Gln Glu Glu Asp Gly Cys
            100                 105                 110
Ser Cys Arg Phe Pro Glu Glu Glu Gly Gly Cys Glu Leu
        115                 120                 125
```

<210> SEQ ID NO 121
<211> LENGTH: 111
<212> TYPE: PRT
<213> ORGANISM: Artificial Sequence
<220> FEATURE:
<223> OTHER INFORMATION: Synthetic Construct

<400> SEQUENCE: 121

```
Thr Thr Thr Pro Ala Pro Arg Pro Pro Thr Pro Ala Pro Thr Ile Ala
1               5                   10                  15
Ser Gln Pro Leu Ser Leu Arg Pro Glu Ala Cys Arg Pro Ala Ala Gly
            20                  25                  30
Gly Ala Val His Thr Arg Gly Leu Asp Phe Ala Cys Asp Ile Tyr Ile
        35                  40                  45
```

```
Trp Ala Pro Leu Ala Gly Thr Cys Gly Val Leu Leu Leu Ser Leu Val
    50                  55                  60

Ile Thr Leu Tyr Cys Lys Arg Gly Arg Lys Leu Leu Tyr Ile Phe
65                  70                  75                  80

Lys Gln Pro Phe Met Arg Pro Val Gln Thr Thr Gln Glu Glu Asp Gly
                85                  90                  95

Cys Ser Cys Arg Phe Pro Glu Glu Glu Gly Gly Cys Glu Leu
                100                 105                 110

<210> SEQ ID NO 122
<211> LENGTH: 103
<212> TYPE: PRT
<213> ORGANISM: Artificial Sequence
<220> FEATURE:
<223> OTHER INFORMATION: Synthetic Construct

<400> SEQUENCE: 122

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys
            100

<210> SEQ ID NO 123
<211> LENGTH: 103
<212> TYPE: PRT
<213> ORGANISM: Artificial Sequence
<220> FEATURE:
<223> OTHER INFORMATION: Synthetic Construct

<400> SEQUENCE: 123

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Glu
    50                  55                  60

Leu Val Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys
            100

<210> SEQ ID NO 124
<211> LENGTH: 106
<212> TYPE: PRT
```

```
<213> ORGANISM: Artificial Sequence
<220> FEATURE:
<223> OTHER INFORMATION: Synthetic Construct

<400> SEQUENCE: 124

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 125
<211> LENGTH: 106
<212> TYPE: PRT
<213> ORGANISM: Artificial Sequence
<220> FEATURE:
<223> OTHER INFORMATION: Synthetic Construct

<400> SEQUENCE: 125

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 126
<211> LENGTH: 106
<212> TYPE: PRT
<213> ORGANISM: Artificial Sequence
<220> FEATURE:
<223> OTHER INFORMATION: Synthetic Construct

<400> SEQUENCE: 126

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
50                  55                  60
```

```
Tyr Ser Leu Leu Ser Ser Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 127
<211> LENGTH: 902
<212> TYPE: PRT
<213> ORGANISM: Artificial Sequence
<220> FEATURE:
<223> OTHER INFORMATION: Synthetic Construct

<400> SEQUENCE: 127

Met Glu Thr Asp Thr Leu Leu Leu Trp Val Leu Leu Leu Trp Val Pro
1               5                   10                  15

Gly Ser Thr Gly Gln Ser Val Leu Thr Gln Pro Pro Ser Val Ser Gly
            20                  25                  30

Ala Pro Gly Gln Arg Val Thr Ile Ser Cys Thr Gly Ser Ser Ser Asn
        35                  40                  45

Ile Gly Ala Gly Tyr Asp Val His Trp Tyr Gln Gln Leu Pro Gly Thr
50                  55                  60

Ala Pro Lys Leu Leu Ile Tyr Gly Asn Ser Asn Arg Pro Ser Gly Val
65                  70                  75                  80

Pro Asp Arg Phe Ser Gly Ser Lys Ser Gly Thr Ser Ala Ser Leu Ala
                85                  90                  95

Ile Thr Gly Leu Gln Ala Glu Asp Glu Ala Asp Tyr Tyr Cys Gln Ser
            100                 105                 110

Tyr Asp Ser Ser Leu Ser Gly Tyr Val Phe Gly Thr Gly Thr Lys Val
        115                 120                 125

Thr Val Leu Gly Ser Arg Gly Gly Gly Ser Gly Gly Gly Gly Ser
130                 135                 140

Gly Gly Gly Gly Ser Leu Glu Met Ala Glu Val Gln Leu Val Gln Ser
145                 150                 155                 160

Gly Ala Glu Val Lys Lys Pro Gly Glu Ser Leu Lys Ile Ser Cys Lys
                165                 170                 175

Gly Ser Gly Tyr Ser Phe Thr Ser Tyr Trp Ile Gly Trp Val Arg Gln
            180                 185                 190

Met Pro Gly Lys Gly Leu Glu Trp Met Gly Ile Ile Tyr Pro Gly Asp
        195                 200                 205

Ser Asp Thr Arg Tyr Ser Pro Ser Phe Gln Gly Gln Val Thr Ile Ser
    210                 215                 220

Ala Asp Lys Ser Ile Ser Thr Ala Tyr Leu Gln Trp Ser Ser Leu Lys
225                 230                 235                 240

Ala Ser Asp Thr Ala Met Tyr Tyr Cys Ala Arg Ser Met Gly Ser Ser
                245                 250                 255

Leu Tyr Ala Ser Ser Asp Val Trp Gly Gln Gly Thr Leu Val Thr Val
            260                 265                 270

Ser Ser Gly Gly Gly Gly Ser Glu Val Gln Leu Val Gln Ser Gly Ala
        275                 280                 285

Glu Met Lys Lys Pro Gly Glu Ser Leu Lys Ile Ser Cys Lys Gly Ser
    290                 295                 300

Gly Tyr Asn Phe Ala Ser Tyr Trp Val Gly Trp Val Arg Gln Met Pro
305                 310                 315                 320
```

```
Gly Lys Gly Leu Glu Trp Met Gly Thr Ile Tyr Pro Asp Ser Asp
            325                 330                 335

Thr Arg Tyr Gly Pro Ala Phe Gln Gly Gln Val Thr Ile Ser Ala Asp
            340                 345                 350

Lys Ser Ile Ser Thr Ala Tyr Leu Gln Trp Ser Ser Leu Lys Ala Ser
            355                 360                 365

Asp Thr Ala Met Tyr Tyr Cys Ala Arg Asp Ser Tyr Tyr Gly Ile Asp
        370                 375                 380

Val Trp Gly Gln Gly Thr Leu Val Thr Val Ser Ser Ala Ser Thr Lys
385                 390                 395                 400

Gly Pro Ser Val Phe Pro Leu Ala Pro Ser Ser Lys Ser Thr Ser Gly
                405                 410                 415

Gly Thr Ala Ala Leu Gly Cys Leu Val Lys Asp Tyr Phe Pro Glu Pro
            420                 425                 430

Val Thr Val Ser Trp Asn Ser Gly Ala Leu Thr Ser Gly Val His Thr
            435                 440                 445

Phe Pro Ala Val Leu Gln Ser Ser Gly Leu Tyr Ser Leu Ser Ser Val
        450                 455                 460

Val Thr Val Pro Ser Ser Ser Leu Gly Thr Gln Thr Tyr Ile Cys Asn
465                 470                 475                 480

Val Asn His Lys Pro Ser Asn Thr Lys Val Asp Lys Arg Val Glu Pro
                485                 490                 495

Lys Ser Cys Glu Val Lys Thr Asp Ser Thr Asp His Val Lys Pro Lys
            500                 505                 510

Glu Thr Glu Asn Thr Lys Gln Pro Ser Lys Ser Cys His Lys Pro Lys
        515                 520                 525

Ala Ile Val His Thr Glu Lys Val Asn Met Met Ser Leu Thr Val Leu
        530                 535                 540

Gly Leu Arg Met Leu Phe Ala Lys Thr Val Ala Val Asn Phe Leu Leu
545                 550                 555                 560

Thr Ala Lys Leu Phe Phe Leu Arg Ala Lys Arg Ser Gly Ser Gly Ala
                565                 570                 575

Pro Val Lys Gln Thr Leu Asn Phe Asp Leu Leu Lys Leu Ala Gly Asp
            580                 585                 590

Val Glu Ser Asn Pro Gly Pro Met Glu Thr Asp Thr Leu Leu Leu Trp
        595                 600                 605

Val Leu Leu Leu Trp Val Pro Gly Ser Thr Gly Gln Ala Val Leu Thr
610                 615                 620

Gln Pro Pro Ser Ala Ser Gly Thr Pro Gly Gln Arg Val Thr Ile Ser
625                 630                 635                 640

Cys Ser Gly Ser Ser Ser Asn Ile Gly Ser Asn Thr Val Asn Trp Tyr
                645                 650                 655

Gln Gln Leu Pro Gly Thr Ala Pro Lys Leu Leu Met Tyr Ser Asn Asn
            660                 665                 670

Gln Arg Pro Ser Gly Val Pro Asp Arg Phe Ser Gly Ser Lys Ser Gly
        675                 680                 685

Thr Ser Ala Ser Leu Ala Ile Ser Gly Leu Gln Ser Glu Asp Glu Ala
        690                 695                 700

Asp Tyr Tyr Cys Ala Ala Trp Asp Asp Ser Leu Asn Gly Tyr Val Phe
705                 710                 715                 720

Gly Thr Gly Thr Lys Val Thr Val Leu Gly Gln Pro Lys Ala Asn Pro
                725                 730                 735
```

```
Thr Val Thr Leu Phe Pro Pro Ser Glu Glu Leu Gln Ala Asn Lys
            740                 745                 750
Ala Thr Leu Val Cys Leu Ile Ser Asp Phe Tyr Pro Gly Ala Val Thr
        755                 760                 765
Val Ala Trp Lys Ala Asp Gly Ser Pro Val Lys Ala Gly Val Glu Thr
    770                 775                 780
Thr Lys Pro Ser Lys Gln Ser Asn Asn Lys Tyr Ala Ala Ser Ser Tyr
785                 790                 795                 800
Leu Ser Leu Thr Pro Glu Gln Trp Lys Ser His Arg Ser Tyr Ser Cys
                805                 810                 815
Gln Val Thr His Glu Gly Ser Thr Val Glu Lys Thr Val Ala Pro Thr
            820                 825                 830
Glu Cys Ser Pro Ile Lys Thr Asp Val Ile Thr Met Asp Pro Lys Asp
        835                 840                 845
Asn Cys Ser Lys Asp Ala Asn Asp Thr Leu Leu Gln Leu Thr Asn
    850                 855                 860
Thr Ser Ala Tyr Tyr Met Tyr Leu Leu Leu Leu Lys Ser Val Val
865                 870                 875                 880
Tyr Phe Ala Ile Ile Thr Cys Cys Leu Leu Arg Arg Thr Ala Phe Cys
                885                 890                 895
Cys Asn Gly Glu Lys Ser
            900
```

```
<210> SEQ ID NO 128
<211> LENGTH: 20
<212> TYPE: PRT
<213> ORGANISM: Artificial Sequence
<220> FEATURE:
<223> OTHER INFORMATION: Synthetic Construct

<400> SEQUENCE: 128

Met Glu Thr Asp Thr Leu Leu Leu Trp Val Leu Leu Leu Trp Val Pro
1               5                   10                  15
Gly Ser Thr Gly
            20

<210> SEQ ID NO 129
<211> LENGTH: 5
<212> TYPE: PRT
<213> ORGANISM: Artificial Sequence
<220> FEATURE:
<223> OTHER INFORMATION: Synthetic Construct

<400> SEQUENCE: 129

Arg Ala Lys Arg Ser
1               5

<210> SEQ ID NO 130
<211> LENGTH: 27
<212> TYPE: PRT
<213> ORGANISM: Artificial Sequence
<220> FEATURE:
<223> OTHER INFORMATION: Synthetic Construct

<400> SEQUENCE: 130

Gly Ser Gly Ala Pro Val Lys Gln Thr Leu Asn Phe Asp Leu Leu Lys
1               5                   10                  15
Leu Ala Gly Asp Val Glu Ser Asn Pro Gly Pro
            20                  25
```

```
<210> SEQ ID NO 131
<211> LENGTH: 32
<212> TYPE: PRT
<213> ORGANISM: Artificial Sequence
<220> FEATURE:
<223> OTHER INFORMATION: Synthetic Construct

<400> SEQUENCE: 131

Arg Ala Lys Arg Ser Gly Ser Gly Ala Pro Val Lys Gln Thr Leu Asn
1               5                   10                  15

Phe Asp Leu Leu Lys Leu Ala Gly Asp Val Glu Ser Asn Pro Gly Pro
            20                  25                  30

<210> SEQ ID NO 132
<211> LENGTH: 22
<212> TYPE: PRT
<213> ORGANISM: Artificial Sequence
<220> FEATURE:
<223> OTHER INFORMATION: Synthetic Construct

<400> SEQUENCE: 132

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 133
<211> LENGTH: 27
<212> TYPE: PRT
<213> ORGANISM: Artificial Sequence
<220> FEATURE:
<223> OTHER INFORMATION: Synthetic Construct

<400> SEQUENCE: 133

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25

<210> SEQ ID NO 134
<211> LENGTH: 68
<212> TYPE: PRT
<213> ORGANISM: Artificial Sequence
<220> FEATURE:
<223> OTHER INFORMATION: Synthetic Construct

<400> SEQUENCE: 134

Glu Val Lys Thr Asp Ser Thr Asp His Val Lys Pro Lys Glu Thr Glu
1               5                   10                  15

Asn Thr Lys Gln Pro Ser Lys Ser Cys His Lys Pro Lys Ala Ile Val
            20                  25                  30

His Thr Glu Lys Val Asn Met Met Ser Leu Thr Val Leu Gly Leu Arg
        35                  40                  45

Met Leu Phe Ala Lys Thr Val Ala Val Asn Phe Leu Thr Ala Lys
    50                  55                  60

Leu Phe Phe Leu
65

<210> SEQ ID NO 135
<211> LENGTH: 67
<212> TYPE: PRT
<213> ORGANISM: Artificial Sequence
<220> FEATURE:
<223> OTHER INFORMATION: Synthetic Construct
```

<400> SEQUENCE: 135

Pro Ile Lys Thr Asp Val Ile Thr Met Asp Pro Lys Asp Asn Cys Ser
1               5                   10                  15

Lys Asp Ala Asn Asp Thr Leu Leu Gln Leu Thr Asn Thr Ser Ala
            20                  25                  30

Tyr Tyr Met Tyr Leu Leu Leu Leu Lys Ser Val Val Tyr Phe Ala
        35                  40                  45

Ile Ile Thr Cys Cys Leu Leu Arg Arg Thr Ala Phe Cys Cys Asn Gly
    50                  55                  60

Glu Lys Ser
65

<210> SEQ ID NO 136
<211> LENGTH: 10
<212> TYPE: PRT
<213> ORGANISM: Artificial Sequence
<220> FEATURE:
<223> OTHER INFORMATION: Synthetic Construct

<400> SEQUENCE: 136

Glu Gln Lys Leu Ile Ser Glu Glu Asp Leu
1               5                   10

<210> SEQ ID NO 137
<211> LENGTH: 22
<212> TYPE: PRT
<213> ORGANISM: Artificial Sequence
<220> FEATURE:
<223> OTHER INFORMATION: Synthetic Construct

<400> SEQUENCE: 137

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 138
<211> LENGTH: 8
<212> TYPE: PRT
<213> ORGANISM: Artificial Sequence
<220> FEATURE:
<223> OTHER INFORMATION: Synthetic Construct

<400> SEQUENCE: 138

Asp Tyr Lys Asp Asp Asp Asp Lys
1               5

<210> SEQ ID NO 139
<211> LENGTH: 22
<212> TYPE: PRT
<213> ORGANISM: Artificial Sequence
<220> FEATURE:
<223> OTHER INFORMATION: Synthetic Construct

<400> SEQUENCE: 139

Gly Ser Arg Gly Gly Gly Ser Gly Gly Gly Ser Gly Gly Gly
1               5                   10                  15

Gly Ser Leu Glu Met Ala
            20

<210> SEQ ID NO 140
<211> LENGTH: 5

```
<212> TYPE: PRT
<213> ORGANISM: Artificial Sequence
<220> FEATURE:
<223> OTHER INFORMATION: Synthetic Construct

<400> SEQUENCE: 140

Gly Gly Gly Gly Ser
1               5

<210> SEQ ID NO 141
<211> LENGTH: 10
<212> TYPE: PRT
<213> ORGANISM: Artificial Sequence
<220> FEATURE:
<223> OTHER INFORMATION: Synthetic Construct

<400> SEQUENCE: 141

Gly Gly Gly Gly Ser Gly Gly Gly Gly Ser
1               5                   10

<210> SEQ ID NO 142
<211> LENGTH: 15
<212> TYPE: PRT
<213> ORGANISM: Artificial Sequence
<220> FEATURE:
<223> OTHER INFORMATION: Synthetic Construct

<400> SEQUENCE: 142

Gly Gly Gly Gly Ser Gly Gly Gly Gly Ser Gly Gly Gly Gly Ser
1               5                   10                  15

<210> SEQ ID NO 143
<211> LENGTH: 5
<212> TYPE: PRT
<213> ORGANISM: Artificial Sequence
<220> FEATURE:
<223> OTHER INFORMATION: Synthetic Construct

<400> SEQUENCE: 143

Ala Ala Ala Thr Gly
1               5

<210> SEQ ID NO 144
<211> LENGTH: 11
<212> TYPE: PRT
<213> ORGANISM: Artificial Sequence
<220> FEATURE:
<223> OTHER INFORMATION: Synthetic Construct

<400> SEQUENCE: 144

Thr Pro Leu Gly Asp Thr Thr His Thr Ser Gly
1               5                   10

<210> SEQ ID NO 145
<211> LENGTH: 3
<212> TYPE: PRT
<213> ORGANISM: Artificial Sequence
<220> FEATURE:
<223> OTHER INFORMATION: Synthetic Construct

<400> SEQUENCE: 145

Ala Ala Ala
1

<210> SEQ ID NO 146
<211> LENGTH: 4
<212> TYPE: PRT
```

```
<213> ORGANISM: Artificial Sequence
<220> FEATURE:
<223> OTHER INFORMATION: Synthetic Construct

<400> SEQUENCE: 146

Gly Gly Ser Gly
1

<210> SEQ ID NO 147
<211> LENGTH: 4
<212> TYPE: PRT
<213> ORGANISM: Artificial Sequence
<220> FEATURE:
<223> OTHER INFORMATION: Synthetic Construct

<400> SEQUENCE: 147

Ser Gly Gly Gly
1

<210> SEQ ID NO 148
<211> LENGTH: 4
<212> TYPE: PRT
<213> ORGANISM: Artificial Sequence
<220> FEATURE:
<223> OTHER INFORMATION: Synthetic Construct

<400> SEQUENCE: 148

Gly Ser Gly Ser
1

<210> SEQ ID NO 149
<211> LENGTH: 6
<212> TYPE: PRT
<213> ORGANISM: Artificial Sequence
<220> FEATURE:
<223> OTHER INFORMATION: Synthetic Construct

<400> SEQUENCE: 149

Gly Ser Gly Ser Gly Ser
1               5

<210> SEQ ID NO 150
<211> LENGTH: 8
<212> TYPE: PRT
<213> ORGANISM: Artificial Sequence
<220> FEATURE:
<223> OTHER INFORMATION: Synthetic Construct

<400> SEQUENCE: 150

Gly Ser Gly Ser Gly Ser Gly Ser
1               5

<210> SEQ ID NO 151
<211> LENGTH: 10
<212> TYPE: PRT
<213> ORGANISM: Artificial Sequence
<220> FEATURE:
<223> OTHER INFORMATION: Synthetic Construct

<400> SEQUENCE: 151

Gly Ser Gly Ser Gly Ser Gly Ser Gly Ser
1               5                   10

<210> SEQ ID NO 152
<211> LENGTH: 6
<212> TYPE: PRT
<213> ORGANISM: Artificial Sequence
```

```
<220> FEATURE:
<223> OTHER INFORMATION: Synthetic Construct

<400> SEQUENCE: 152

Gly Gly Ser Gly Gly Ser
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic Construct

<400> SEQUENCE: 153

Gly Gly Ser Gly Gly Ser Gly Gly Ser
1               5

<210> SEQ ID NO 154
<211> LENGTH: 12
<212> TYPE: PRT
<213> ORGANISM: Artificial Sequence
<220> FEATURE:
<223> OTHER INFORMATION: Synthetic Construct

<400> SEQUENCE: 154

Gly Gly Ser Gly Gly Ser Gly Gly Ser Gly Gly Ser
1               5                   10

<210> SEQ ID NO 155
<211> LENGTH: 4
<212> TYPE: PRT
<213> ORGANISM: Artificial Sequence
<220> FEATURE:
<223> OTHER INFORMATION: Synthetic Construct

<400> SEQUENCE: 155

Gly Gly Ser Gly
1

<210> SEQ ID NO 156
<211> LENGTH: 8
<212> TYPE: PRT
<213> ORGANISM: Artificial Sequence
<220> FEATURE:
<223> OTHER INFORMATION: Synthetic Construct

<400> SEQUENCE: 156

Gly Gly Ser Gly Gly Gly Ser Gly
1               5

<210> SEQ ID NO 157
<211> LENGTH: 12
<212> TYPE: PRT
<213> ORGANISM: Artificial Sequence
<220> FEATURE:
<223> OTHER INFORMATION: Synthetic Construct

<400> SEQUENCE: 157

Gly Gly Ser Gly Gly Gly Ser Gly Gly Gly Ser Gly
1               5                   10

<210> SEQ ID NO 158
<211> LENGTH: 6
<212> TYPE: PRT
<213> ORGANISM: Artificial Sequence
<220> FEATURE:
```

-continued

<223> OTHER INFORMATION: Synthetic Construct

<400> SEQUENCE: 158

His His His His His His
1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic Construct

<400> SEQUENCE: 159

Tyr Pro Tyr Asp Val Pro Asp Tyr Ala
1               5

<210> SEQ ID NO 160
<211> LENGTH: 10
<212> TYPE: PRT
<213> ORGANISM: Artificial Sequence
<220> FEATURE:
<223> OTHER INFORMATION: Synthetic Construct

<400> SEQUENCE: 160

Tyr Pro Tyr Asp Val Pro Asp Tyr Ala Ser
1               5                   10

<210> SEQ ID NO 161
<211> LENGTH: 1064
<212> TYPE: PRT
<213> ORGANISM: Artificial Sequence
<220> FEATURE:
<223> OTHER INFORMATION: Synthetic Construct

<400> SEQUENCE: 161

Met Glu Thr Asp Thr Leu Leu Leu Trp Val Leu Leu Leu Trp Val Pro
1               5                   10                  15

Gly Ser Thr Gly Gln Ser Val Leu Thr Gln Pro Pro Ser Val Ser Gly
            20                  25                  30

Ala Pro Gly Gln Arg Val Thr Ile Ser Cys Thr Gly Ser Ser Ser Asn
        35                  40                  45

Ile Gly Ala Gly Tyr Asp Val His Trp Tyr Gln Gln Leu Pro Gly Thr
    50                  55                  60

Ala Pro Lys Leu Leu Ile Tyr Gly Asn Ser Asn Arg Pro Ser Gly Val
65                  70                  75                  80

Pro Asp Arg Phe Ser Gly Ser Lys Ser Gly Thr Ser Ala Ser Leu Ala
                85                  90                  95

Ile Thr Gly Leu Gln Ala Glu Asp Glu Ala Asp Tyr Tyr Cys Gln Ser
            100                 105                 110

Tyr Asp Ser Ser Leu Ser Gly Tyr Val Phe Gly Thr Gly Thr Lys Val
        115                 120                 125

Thr Val Leu Gly Ser Arg Gly Gly Gly Gly Ser Gly Gly Gly Gly Ser
    130                 135                 140

Gly Gly Gly Gly Ser Leu Glu Met Ala Glu Val Gln Leu Val Gln Ser
145                 150                 155                 160

Gly Ala Glu Val Lys Lys Pro Gly Glu Ser Leu Lys Ile Ser Cys Lys
                165                 170                 175

Gly Ser Gly Tyr Ser Phe Thr Ser Tyr Trp Ile Gly Trp Val Arg Gln
            180                 185                 190

-continued

```
Met Pro Gly Lys Gly Leu Glu Trp Met Gly Ile Ile Tyr Pro Gly Asp
            195                 200                 205

Ser Asp Thr Arg Tyr Ser Pro Ser Phe Gln Gly Gln Val Thr Ile Ser
    210                 215                 220

Ala Asp Lys Ser Ile Ser Thr Ala Tyr Leu Gln Trp Ser Ser Leu Lys
225                 230                 235                 240

Ala Ser Asp Thr Ala Met Tyr Tyr Cys Ala Arg Ser Met Gly Ser Ser
                245                 250                 255

Leu Tyr Ala Ser Ser Asp Val Trp Gly Gln Gly Thr Leu Val Thr Val
            260                 265                 270

Ser Ser Glu Gln Lys Leu Ile Ser Glu Glu Asp Leu Ala Ala Ala Ile
    275                 280                 285

Glu Val Met Tyr Pro Pro Tyr Leu Asp Asn Glu Lys Ser Asn Gly
290                 295                 300

Thr Ile Ile His Val Lys Gly Lys His Leu Cys Pro Ser Pro Leu Phe
305                 310                 315                 320

Pro Gly Pro Ser Lys Pro Phe Trp Val Leu Val Val Val Gly Gly Val
                325                 330                 335

Leu Ala Cys Tyr Ser Leu Leu Val Thr Val Ala Phe Ile Ile Phe Trp
            340                 345                 350

Val Arg Ser Lys Arg Ser Arg Leu Leu His Ser Asp Tyr Met Asn Met
    355                 360                 365

Thr Pro Arg Arg Pro Gly Pro Thr Arg Lys His Tyr Gln Pro Tyr Ala
370                 375                 380

Pro Pro Arg Asp Phe Ala Ala Tyr Arg Ser Gly Ser Gly Ala Thr Asn
385                 390                 395                 400

Phe Ser Leu Leu Lys Gln Ala Gly Asp Val Glu Glu Asn Pro Gly Pro
                405                 410                 415

Met Glu Thr Asp Thr Leu Leu Leu Trp Val Leu Leu Leu Trp Val Pro
            420                 425                 430

Gly Ser Thr Gly Glu Val Gln Leu Val Gln Ser Gly Ala Glu Val Lys
    435                 440                 445

Lys Pro Gly Glu Ser Leu Lys Ile Ser Cys Lys Gly Ser Gly Tyr Ser
450                 455                 460

Phe Thr Ser Tyr Trp Ile Gly Trp Val Arg Gln Met Pro Gly Lys Gly
465                 470                 475                 480

Leu Glu Trp Met Gly Ile Ile Tyr Pro Gly Asp Ser Asp Thr Arg Tyr
                485                 490                 495

Ser Pro Ser Phe Gln Gly Gln Val Thr Ile Ser Ala Asp Lys Ser Ile
            500                 505                 510

Ser Thr Ala Tyr Leu Gln Trp Ser Ser Leu Lys Ala Ser Asp Thr Ala
    515                 520                 525

Met Tyr Tyr Cys Ala Arg Ser Met Gly Ser Ser Leu Tyr Ala Ser Ser
530                 535                 540

Asp Val Trp Gly Gln Gly Thr Leu Val Thr Val Ser Ser Ala Ser Thr
545                 550                 555                 560

Lys Gly Pro Ser Val Phe Pro Leu Ala Pro Ser Ser Lys Ser Thr Ser
                565                 570                 575

Gly Gly Thr Ala Ala Leu Gly Cys Leu Val Lys Asp Tyr Phe Pro Glu
            580                 585                 590

Pro Val Thr Val Ser Trp Asn Ser Gly Ala Leu Thr Ser Gly Val His
    595                 600                 605

Thr Phe Pro Ala Val Leu Gln Ser Ser Gly Leu Tyr Ser Leu Ser Ser
```

-continued

```
            610                 615                 620
Val Val Thr Val Pro Ser Ser Leu Gly Thr Gln Thr Tyr Ile Cys
625                 630                 635                 640

Asn Val Asn His Lys Pro Ser Asn Thr Lys Val Asp Lys Arg Val Glu
                645                 650                 655

Pro Lys Ser Cys Glu Val Lys Thr Asp Ser Thr Asp His Val Lys Pro
                660                 665                 670

Lys Glu Thr Glu Asn Thr Lys Gln Pro Ser Lys Ser Cys His Lys Pro
                675                 680                 685

Lys Ala Ile Val His Thr Glu Lys Val Asn Met Met Ser Leu Thr Val
                690                 695                 700

Leu Gly Leu Arg Met Leu Phe Ala Lys Thr Val Ala Val Asn Phe Leu
705                 710                 715                 720

Leu Thr Ala Lys Leu Phe Phe Leu Arg Ala Lys Arg Ser Gly Ser Gly
                725                 730                 735

Ala Pro Val Lys Gln Thr Leu Asn Phe Asp Leu Leu Lys Leu Ala Gly
                740                 745                 750

Asp Val Glu Ser Asn Pro Gly Pro Met Glu Thr Asp Thr Leu Leu Leu
                755                 760                 765

Trp Val Leu Leu Leu Trp Val Pro Gly Ser Thr Gly Gln Ser Val Leu
770                 775                 780

Thr Gln Pro Pro Ser Val Ser Gly Ala Pro Gly Gln Arg Val Thr Ile
785                 790                 795                 800

Ser Cys Thr Gly Ser Ser Ser Asn Ile Gly Ala Gly Tyr Asp Val His
                805                 810                 815

Trp Tyr Gln Gln Leu Pro Gly Thr Ala Pro Lys Leu Leu Ile Tyr Gly
                820                 825                 830

Asn Ser Asn Arg Pro Ser Gly Val Pro Asp Arg Phe Ser Gly Ser Lys
                835                 840                 845

Ser Gly Thr Ser Ala Ser Leu Ala Ile Thr Gly Leu Gln Ala Glu Asp
                850                 855                 860

Glu Ala Asp Tyr Tyr Cys Gln Ser Tyr Asp Ser Ser Leu Ser Gly Tyr
865                 870                 875                 880

Val Phe Gly Thr Gly Thr Lys Val Thr Val Leu Gly Gln Pro Lys Ala
                885                 890                 895

Asn Pro Thr Val Thr Leu Phe Pro Pro Ser Ser Glu Glu Leu Gln Ala
                900                 905                 910

Asn Lys Ala Thr Leu Val Cys Leu Ile Ser Asp Phe Tyr Pro Gly Ala
                915                 920                 925

Val Thr Val Ala Trp Lys Ala Asp Gly Ser Pro Val Lys Ala Gly Val
930                 935                 940

Glu Thr Thr Lys Pro Ser Lys Gln Ser Asn Asn Lys Tyr Ala Ala Ser
945                 950                 955                 960

Ser Tyr Leu Ser Leu Thr Pro Glu Gln Trp Lys Ser His Arg Ser Tyr
                965                 970                 975

Ser Cys Gln Val Thr His Glu Gly Ser Thr Val Glu Lys Thr Val Ala
                980                 985                 990

Pro Thr Glu Cys Ser Pro Ile Lys Thr Asp Val Ile Thr Met Asp Pro
                995                 1000                1005

Lys Asp Asn Cys Ser Lys Asp Ala Asn Asp Thr Leu Leu Leu Gln Leu
                1010                1015                1020

Thr Asn Thr Ser Ala Tyr Tyr Met Tyr Leu Leu Leu Leu Leu Lys Ser
1025                1030                1035                1040
```

Val Val Tyr Phe Ala Ile Ile Thr Cys Cys Leu Leu Arg Arg Thr Ala
            1045                1050                1055

Phe Cys Cys Asn Gly Glu Lys Ser
            1060

<210> SEQ ID NO 162
<211> LENGTH: 1059
<212> TYPE: PRT
<213> ORGANISM: Artificial Sequence
<220> FEATURE:
<223> OTHER INFORMATION: Synthetic Construct

<400> SEQUENCE: 162

Met Glu Thr Asp Thr Leu Leu Leu Trp Val Leu Leu Leu Trp Val Pro
1               5                   10                  15

Gly Ser Thr Gly Gln Ala Val Leu Thr Gln Pro Pro Ser Ala Ser Gly
            20                  25                  30

Thr Pro Gly Gln Arg Val Thr Ile Ser Cys Ser Gly Ser Ser Ser Asn
        35                  40                  45

Ile Gly Ser Asn Thr Val Asn Trp Tyr Gln Gln Leu Pro Gly Thr Ala
    50                  55                  60

Pro Lys Leu Leu Met Tyr Ser Asn Asn Gln Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Gln Ser Glu Asp Glu Ala Asp Tyr Tyr Cys Ala Ala Trp
            100                 105                 110

Asp Asp Ser Leu Asn Gly Tyr Val Phe Gly Thr Gly Thr Lys Val Thr
        115                 120                 125

Val Leu Gly Ser Arg Gly Gly Gly Gly Ser Gly Gly Gly Gly Ser Gly
    130                 135                 140

Gly Gly Ser Leu Glu Met Ala Glu Val Gln Leu Val Gln Ser Gly
145                 150                 155                 160

Ala Glu Met Lys Lys Pro Gly Glu Ser Leu Lys Ile Ser Cys Lys Gly
                165                 170                 175

Ser Gly Tyr Asn Phe Ala Ser Tyr Trp Val Gly Trp Val Arg Gln Met
            180                 185                 190

Pro Gly Lys Gly Leu Glu Trp Met Gly Thr Ile Tyr Pro Asp Asp Ser
        195                 200                 205

Asp Thr Arg Tyr Gly Pro Ala Phe Gln Gly Gln Val Thr Ile Ser Ala
    210                 215                 220

Asp Lys Ser Ile Ser Thr Ala Tyr Leu Gln Trp Ser Ser Leu Lys Ala
225                 230                 235                 240

Ser Asp Thr Ala Met Tyr Tyr Cys Ala Arg Asp Ser Tyr Tyr Gly Ile
                245                 250                 255

Asp Val Trp Gly Gln Gly Thr Leu Val Thr Val Ser Ser Glu Gln Lys
            260                 265                 270

Leu Ile Ser Glu Glu Asp Leu Ala Ala Ala Ile Glu Val Met Tyr Pro
        275                 280                 285

Pro Pro Tyr Leu Asp Asn Glu Lys Ser Asn Gly Thr Ile Ile His Val
    290                 295                 300

Lys Gly Lys His Leu Cys Pro Ser Pro Leu Phe Pro Gly Pro Ser Lys
305                 310                 315                 320

Pro Phe Trp Val Leu Val Val Val Gly Gly Val Leu Ala Cys Tyr Ser
                325                 330                 335

```
Leu Leu Val Thr Val Ala Phe Ile Ile Phe Trp Val Arg Ser Lys Arg
            340                 345                 350

Ser Arg Leu Leu His Ser Asp Tyr Met Asn Met Thr Pro Arg Arg Pro
            355                 360                 365

Gly Pro Thr Arg Lys His Tyr Gln Pro Tyr Ala Pro Pro Arg Asp Phe
            370                 375                 380

Ala Ala Tyr Arg Ser Gly Ser Gly Ala Thr Asn Phe Ser Leu Leu Lys
385                 390                 395                 400

Gln Ala Gly Asp Val Glu Asn Pro Gly Pro Met Glu Thr Asp Thr
            405                 410                 415

Leu Leu Leu Trp Val Leu Leu Leu Trp Val Pro Gly Ser Thr Gly Glu
            420                 425                 430

Val Gln Leu Val Gln Ser Gly Ala Glu Val Lys Lys Pro Gly Glu Ser
            435                 440                 445

Leu Lys Ile Ser Cys Lys Gly Ser Gly Tyr Ser Phe Thr Ser Tyr Trp
            450                 455                 460

Ile Gly Trp Val Arg Gln Met Pro Gly Lys Gly Leu Glu Trp Met Gly
465                 470                 475                 480

Ile Ile Tyr Pro Gly Asp Ser Asp Thr Arg Tyr Ser Pro Ser Phe Gln
            485                 490                 495

Gly Gln Val Thr Ile Ser Ala Asp Lys Ser Ile Ser Thr Ala Tyr Leu
            500                 505                 510

Gln Trp Ser Ser Leu Lys Ala Ser Asp Thr Ala Met Tyr Tyr Cys Ala
            515                 520                 525

Arg Ser Met Gly Ser Ser Leu Tyr Ala Ser Ser Asp Val Trp Gly Gln
            530                 535                 540

Gly Thr Leu Val Thr Val Ser Ser Ala Ser Thr Lys Gly Pro Ser Val
545                 550                 555                 560

Phe Pro Leu Ala Pro Ser Ser Lys Ser Thr Ser Gly Gly Thr Ala Ala
            565                 570                 575

Leu Gly Cys Leu Val Lys Asp Tyr Phe Pro Glu Pro Val Thr Val Ser
            580                 585                 590

Trp Asn Ser Gly Ala Leu Thr Ser Gly Val His Thr Phe Pro Ala Val
            595                 600                 605

Leu Gln Ser Ser Gly Leu Tyr Ser Leu Ser Ser Val Val Thr Val Pro
            610                 615                 620

Ser Ser Ser Leu Gly Thr Gln Thr Tyr Ile Cys Asn Val Asn His Lys
625                 630                 635                 640

Pro Ser Asn Thr Lys Val Asp Lys Arg Val Glu Pro Lys Ser Cys Glu
            645                 650                 655

Val Lys Thr Asp Ser Thr Asp His Val Lys Pro Lys Glu Thr Glu Asn
            660                 665                 670

Thr Lys Gln Pro Ser Lys Ser Cys His Lys Pro Lys Ala Ile Val His
            675                 680                 685

Thr Glu Lys Val Asn Met Met Ser Leu Thr Val Leu Gly Leu Arg Met
            690                 695                 700

Leu Phe Ala Lys Thr Val Ala Val Asn Phe Leu Leu Thr Ala Lys Leu
705                 710                 715                 720

Phe Phe Leu Arg Ala Lys Arg Ser Gly Ser Gly Ala Pro Val Lys Gln
            725                 730                 735

Thr Leu Asn Phe Asp Leu Leu Lys Leu Ala Gly Asp Val Glu Ser Asn
            740                 745                 750
```

```
Pro Gly Pro Met Glu Thr Asp Thr Leu Leu Leu Trp Val Leu Leu Leu
        755                 760                 765

Trp Val Pro Gly Ser Thr Gly Gln Ser Val Leu Thr Gln Pro Pro Ser
    770                 775                 780

Val Ser Gly Ala Pro Gly Gln Arg Val Thr Ile Ser Cys Thr Gly Ser
785                 790                 795                 800

Ser Ser Asn Ile Gly Ala Gly Tyr Asp Val His Trp Tyr Gln Gln Leu
                805                 810                 815

Pro Gly Thr Ala Pro Lys Leu Leu Ile Tyr Gly Asn Ser Asn Arg Pro
        820                 825                 830

Ser Gly Val Pro Asp Arg Phe Ser Gly Ser Lys Ser Gly Thr Ser Ala
    835                 840                 845

Ser Leu Ala Ile Thr Gly Leu Gln Ala Glu Asp Glu Ala Asp Tyr Tyr
850                 855                 860

Cys Gln Ser Tyr Asp Ser Ser Leu Ser Gly Tyr Val Phe Gly Thr Gly
865                 870                 875                 880

Thr Lys Val Thr Val Leu Gly Gln Pro Lys Ala Asn Pro Thr Val Thr
                885                 890                 895

Leu Phe Pro Pro Ser Ser Glu Glu Leu Gln Ala Asn Lys Ala Thr Leu
        900                 905                 910

Val Cys Leu Ile Ser Asp Phe Tyr Pro Gly Ala Val Thr Val Ala Trp
    915                 920                 925

Lys Ala Asp Gly Ser Pro Val Lys Ala Gly Val Glu Thr Thr Lys Pro
930                 935                 940

Ser Lys Gln Ser Asn Asn Lys Tyr Ala Ala Ser Ser Tyr Leu Ser Leu
945                 950                 955                 960

Thr Pro Glu Gln Trp Lys Ser His Arg Ser Tyr Ser Cys Gln Val Thr
                965                 970                 975

His Glu Gly Ser Thr Val Glu Lys Thr Val Ala Pro Thr Glu Cys Ser
        980                 985                 990

Pro Ile Lys Thr Asp Val Ile Thr Met Asp Pro Lys Asp Asn Cys Ser
    995                 1000                1005

Lys Asp Ala Asn Asp Thr Leu Leu Leu Gln Leu Thr Asn Thr Ser Ala
1010                1015                1020

Tyr Tyr Met Tyr Leu Leu Leu Leu Lys Ser Val Val Tyr Phe Ala
1025                1030                1035                1040

Ile Ile Thr Cys Cys Leu Leu Arg Arg Thr Ala Phe Cys Cys Asn Gly
                1045                1050                1055

Glu Lys Ser
```

<210> SEQ ID NO 163
<211> LENGTH: 1058
<212> TYPE: PRT
<213> ORGANISM: Artificial Sequence
<220> FEATURE:
<223> OTHER INFORMATION: Synthetic Construct

<400> SEQUENCE: 163

```
Met Glu Thr Asp Thr Leu Leu Leu Trp Val Leu Leu Leu Trp Val Pro
1               5                   10                  15

Gly Ser Thr Gly Gln Ser Val Leu Thr Gln Pro Pro Ser Val Ser Gly
                20                  25                  30

Ala Pro Gly Gln Arg Val Thr Ile Ser Cys Thr Gly Ser Ser Ser Asn
            35                  40                  45

Ile Gly Ala Gly Tyr Asp Val His Trp Tyr Gln Gln Leu Pro Gly Thr
```

```
            50                  55                  60
Ala Pro Lys Leu Leu Ile Tyr Gly Asn Ser Asn Arg Pro Ser Gly Val
 65                  70                  75                  80

Pro Asp Arg Phe Ser Gly Ser Lys Ser Gly Thr Ser Ala Ser Leu Ala
                     85                  90                  95

Ile Thr Gly Leu Gln Ala Glu Asp Glu Ala Asp Tyr Tyr Cys Gln Ser
                    100                 105                 110

Tyr Asp Ser Ser Leu Ser Gly Tyr Val Phe Gly Thr Gly Thr Lys Val
                115                 120                 125

Thr Val Leu Gly Ser Arg Gly Gly Gly Ser Gly Gly Gly Gly Ser
130                 135                 140

Gly Gly Gly Gly Ser Leu Glu Met Ala Glu Val Gln Leu Val Gln Ser
145                 150                 155                 160

Gly Ala Glu Val Lys Lys Pro Gly Glu Ser Leu Lys Ile Ser Cys Lys
                    165                 170                 175

Gly Ser Gly Tyr Ser Phe Thr Ser Tyr Trp Ile Gly Trp Val Arg Gln
                180                 185                 190

Met Pro Gly Lys Gly Leu Glu Trp Met Gly Ile Ile Tyr Pro Gly Asp
                195                 200                 205

Ser Asp Thr Arg Tyr Ser Pro Ser Phe Gln Gly Gln Val Thr Ile Ser
210                 215                 220

Ala Asp Lys Ser Ile Ser Thr Ala Tyr Leu Gln Trp Ser Ser Leu Lys
225                 230                 235                 240

Ala Ser Asp Thr Ala Met Tyr Tyr Cys Ala Arg Ser Met Gly Ser Ser
                245                 250                 255

Leu Tyr Ala Ser Ser Asp Val Trp Gly Gln Gly Thr Leu Val Thr Val
                260                 265                 270

Ser Ser Glu Gln Lys Leu Ile Ser Glu Glu Asp Leu Ala Ala Ala Ile
                275                 280                 285

Glu Val Met Tyr Pro Pro Tyr Leu Asp Asn Glu Lys Ser Asn Gly
                290                 295                 300

Thr Ile Ile His Val Lys Gly Lys His Leu Cys Pro Ser Pro Leu Phe
305                 310                 315                 320

Pro Gly Pro Ser Lys Pro Phe Trp Val Leu Val Val Val Gly Gly Val
                    325                 330                 335

Leu Ala Cys Tyr Ser Leu Leu Val Thr Val Ala Phe Ile Ile Phe Trp
                340                 345                 350

Val Arg Ser Lys Arg Ser Arg Leu Leu His Ser Asp Tyr Met Asn Met
                355                 360                 365

Thr Pro Arg Arg Pro Gly Pro Thr Arg Lys His Tyr Gln Pro Tyr Ala
370                 375                 380

Pro Pro Arg Asp Phe Ala Ala Tyr Arg Ser Gly Ser Gly Ala Thr Asn
385                 390                 395                 400

Phe Ser Leu Leu Lys Gln Ala Gly Asp Val Glu Glu Asn Pro Gly Met
                    405                 410                 415

Glu Thr Asp Thr Leu Leu Leu Trp Val Leu Leu Leu Trp Val Pro Gly
                420                 425                 430

Ser Thr Gly Glu Val Gln Leu Val Gln Ser Gly Ala Glu Met Lys Lys
                435                 440                 445

Pro Gly Glu Ser Leu Lys Ile Ser Cys Lys Gly Ser Gly Tyr Asn Phe
                450                 455                 460

Ala Ser Tyr Trp Val Gly Trp Val Arg Gln Met Pro Gly Lys Gly Leu
465                 470                 475                 480
```

-continued

Glu Trp Met Gly Thr Ile Tyr Pro Asp Asp Ser Asp Thr Arg Tyr Gly
                485                 490                 495

Pro Ala Phe Gln Gly Gln Val Thr Ile Ser Ala Asp Lys Ser Ile Ser
            500                 505                 510

Thr Ala Tyr Leu Gln Trp Ser Ser Leu Lys Ala Ser Asp Thr Ala Met
        515                 520                 525

Tyr Tyr Cys Ala Arg Asp Ser Tyr Tyr Gly Ile Asp Val Trp Gly Gln
    530                 535                 540

Gly Thr Leu Val Thr Val Ser Ser Ala Ser Thr Lys Gly Pro Ser Val
545                 550                 555                 560

Phe Pro Leu Ala Pro Ser Ser Lys Ser Thr Ser Gly Gly Thr Ala Ala
                565                 570                 575

Leu Gly Cys Leu Val Lys Asp Tyr Phe Pro Glu Pro Val Thr Val Ser
            580                 585                 590

Trp Asn Ser Gly Ala Leu Thr Ser Gly Val His Thr Phe Pro Ala Val
        595                 600                 605

Leu Gln Ser Ser Gly Leu Tyr Ser Leu Ser Ser Val Val Thr Val Pro
    610                 615                 620

Ser Ser Ser Leu Gly Thr Gln Thr Tyr Ile Cys Asn Val Asn His Lys
625                 630                 635                 640

Pro Ser Asn Thr Lys Val Asp Lys Arg Val Glu Pro Lys Ser Cys Glu
                645                 650                 655

Val Lys Thr Asp Ser Thr Asp His Val Lys Pro Lys Glu Thr Glu Asn
            660                 665                 670

Thr Lys Gln Pro Ser Lys Ser Cys His Lys Pro Lys Ala Ile Val His
        675                 680                 685

Thr Glu Lys Val Asn Met Met Ser Leu Thr Val Leu Gly Leu Arg Met
    690                 695                 700

Leu Phe Ala Lys Thr Val Ala Val Asn Phe Leu Leu Thr Ala Lys Leu
705                 710                 715                 720

Phe Phe Leu Arg Ala Lys Arg Ser Gly Ser Gly Ala Pro Val Lys Gln
                725                 730                 735

Thr Leu Asn Phe Asp Leu Leu Lys Leu Ala Gly Asp Val Glu Ser Asn
            740                 745                 750

Pro Gly Pro Met Glu Thr Asp Thr Leu Leu Leu Trp Val Leu Leu Leu
        755                 760                 765

Trp Val Pro Gly Ser Thr Gly Gln Ala Val Leu Thr Gln Pro Pro Ser
    770                 775                 780

Ala Ser Gly Thr Pro Gly Gln Arg Val Thr Ile Ser Cys Ser Gly Ser
785                 790                 795                 800

Ser Ser Asn Ile Gly Ser Asn Thr Val Asn Trp Tyr Gln Gln Leu Pro
                805                 810                 815

Gly Thr Ala Pro Lys Leu Leu Met Tyr Ser Asn Asn Gln Arg Pro Ser
            820                 825                 830

Gly Val Pro Asp Arg Phe Ser Gly Ser Lys Ser Gly Thr Ser Ala Ser
        835                 840                 845

Leu Ala Ile Ser Gly Leu Gln Ser Glu Asp Glu Ala Asp Tyr Tyr Cys
    850                 855                 860

Ala Ala Trp Asp Asp Ser Leu Asn Gly Tyr Val Phe Gly Thr Gly Thr
865                 870                 875                 880

Lys Val Thr Val Leu Gly Gln Pro Lys Ala Asn Pro Thr Val Thr Leu
                885                 890                 895

-continued

```
Phe Pro Pro Ser Ser Glu Glu Leu Gln Ala Asn Lys Ala Thr Leu Val
                900                 905                 910

Cys Leu Ile Ser Asp Phe Tyr Pro Gly Ala Val Thr Val Ala Trp Lys
            915                 920                 925

Ala Asp Gly Ser Pro Val Lys Ala Gly Val Glu Thr Thr Lys Pro Ser
        930                 935                 940

Lys Gln Ser Asn Asn Lys Tyr Ala Ala Ser Ser Tyr Leu Ser Leu Thr
945                 950                 955                 960

Pro Glu Gln Trp Lys Ser His Arg Ser Tyr Ser Cys Gln Val Thr His
                965                 970                 975

Glu Gly Ser Thr Val Glu Lys Thr Val Ala Pro Thr Glu Cys Ser Pro
            980                 985                 990

Ile Lys Thr Asp Val Ile Thr Met Asp Pro Lys Asp Asn Cys Ser Lys
        995                 1000                1005

Asp Ala Asn Asp Thr Leu Leu Leu Gln Leu Thr Asn Thr Ser Ala Tyr
    1010                1015                1020

Tyr Met Tyr Leu Leu Leu Leu Lys Ser Val Val Tyr Phe Ala Ile
1025                1030                1035                1040

Ile Thr Cys Cys Leu Leu Arg Arg Thr Ala Phe Cys Cys Asn Gly Glu
                1045                1050                1055

Lys Ser

<210> SEQ ID NO 164
<211> LENGTH: 1054
<212> TYPE: PRT
<213> ORGANISM: Artificial Sequence
<220> FEATURE:
<223> OTHER INFORMATION: Synthetic Construct

<400> SEQUENCE: 164

Met Glu Thr Asp Thr Leu Leu Leu Trp Val Leu Leu Leu Trp Val Pro
1               5                   10                  15

Gly Ser Thr Gly Gln Ala Val Leu Thr Gln Pro Pro Ser Ala Ser Gly
                20                  25                  30

Thr Pro Gly Gln Arg Val Thr Ile Ser Cys Ser Gly Ser Ser Ser Asn
            35                  40                  45

Ile Gly Ser Asn Thr Val Asn Trp Tyr Gln Gln Leu Pro Gly Thr Ala
        50                  55                  60

Pro Lys Leu Leu Met Tyr Ser Asn Asn Gln Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Gln Ser Glu Asp Glu Ala Asp Tyr Tyr Cys Ala Ala Trp
            100                 105                 110

Asp Asp Ser Leu Asn Gly Tyr Val Phe Gly Thr Gly Thr Lys Val Thr
        115                 120                 125

Val Leu Gly Ser Arg Gly Gly Gly Gly Ser Gly Gly Gly Ser
    130                 135                 140

Gly Gly Gly Ser Leu Glu Met Ala Glu Val Gln Leu Val Gln Ser Gly
145                 150                 155                 160

Ala Glu Met Lys Lys Pro Gly Glu Ser Leu Lys Ile Ser Cys Lys Gly
                165                 170                 175

Ser Gly Tyr Asn Phe Ala Ser Tyr Trp Val Gly Trp Val Arg Gln Met
            180                 185                 190

Pro Gly Lys Gly Leu Glu Trp Met Gly Thr Ile Tyr Pro Asp Asp Ser
```

```
            195                 200                 205
Asp Thr Arg Tyr Gly Pro Ala Phe Gln Gly Gln Val Thr Ile Ser Ala
210                 215                 220

Asp Lys Ser Ile Ser Thr Ala Tyr Leu Gln Trp Ser Ser Leu Lys Ala
225                 230                 235                 240

Ser Asp Thr Ala Met Tyr Tyr Cys Ala Arg Asp Ser Tyr Tyr Gly Ile
                    245                 250                 255

Asp Val Trp Gly Gln Gly Thr Leu Val Thr Val Ser Ser Glu Gln Lys
                260                 265                 270

Leu Ile Ser Glu Glu Asp Leu Ala Ala Ile Glu Val Met Tyr Pro
                275                 280                 285

Pro Pro Tyr Leu Asp Asn Glu Lys Ser Asn Gly Thr Ile Ile His Val
290                 295                 300

Lys Gly Lys His Leu Cys Pro Ser Pro Leu Phe Pro Gly Pro Ser Lys
305                 310                 315                 320

Pro Phe Trp Val Leu Val Val Val Gly Gly Val Leu Ala Cys Tyr Ser
                    325                 330                 335

Leu Leu Val Thr Val Ala Phe Ile Ile Phe Trp Val Arg Ser Lys Arg
                340                 345                 350

Ser Arg Leu Leu His Ser Asp Tyr Met Asn Met Thr Pro Arg Arg Pro
                355                 360                 365

Gly Pro Thr Arg Lys His Tyr Gln Pro Tyr Ala Pro Pro Arg Asp Phe
370                 375                 380

Ala Ala Tyr Arg Ser Gly Ser Gly Ala Thr Asn Phe Ser Leu Leu Lys
385                 390                 395                 400

Gln Ala Gly Asp Val Glu Glu Asn Pro Gly Pro Met Glu Thr Asp Thr
                    405                 410                 415

Leu Leu Leu Trp Val Leu Leu Leu Trp Val Pro Gly Ser Thr Gly Glu
                420                 425                 430

Val Gln Leu Val Gln Ser Gly Ala Glu Met Lys Lys Pro Gly Glu Ser
                435                 440                 445

Leu Lys Ile Ser Cys Lys Gly Ser Gly Tyr Asn Phe Ala Ser Tyr Trp
450                 455                 460

Val Gly Trp Val Arg Gln Met Pro Gly Lys Gly Leu Glu Trp Met Gly
465                 470                 475                 480

Thr Ile Tyr Pro Asp Asp Ser Asp Thr Arg Tyr Gly Pro Ala Phe Gln
                    485                 490                 495

Gly Gln Val Thr Ile Ser Ala Asp Lys Ser Ile Ser Thr Ala Tyr Leu
                500                 505                 510

Gln Trp Ser Ser Leu Lys Ala Ser Asp Thr Ala Met Tyr Tyr Cys Ala
                515                 520                 525

Arg Asp Ser Tyr Tyr Gly Ile Asp Val Trp Gly Gln Gly Thr Leu Val
                530                 535                 540

Thr Val Ser Ser Ala Ser Thr Lys Gly Pro Ser Val Phe Pro Leu Ala
545                 550                 555                 560

Pro Ser Ser Lys Ser Thr Ser Gly Gly Thr Ala Ala Leu Gly Cys Leu
                    565                 570                 575

Val Lys Asp Tyr Phe Pro Glu Pro Val Thr Val Ser Trp Asn Ser Gly
                580                 585                 590

Ala Leu Thr Ser Gly Val His Thr Phe Pro Ala Val Leu Gln Ser Ser
                595                 600                 605

Gly Leu Tyr Ser Leu Ser Ser Val Val Thr Val Pro Ser Ser Ser Leu
                610                 615                 620
```

```
Gly Thr Gln Thr Tyr Ile Cys Asn Val Asn His Lys Pro Ser Asn Thr
625                 630                 635                 640

Lys Val Asp Lys Arg Val Glu Pro Lys Ser Cys Glu Val Lys Thr Asp
            645                 650                 655

Ser Thr Asp His Val Lys Pro Lys Thr Glu Asn Thr Lys Gln Pro
                660                 665                 670

Ser Lys Ser Cys His Lys Pro Lys Ala Ile Val His Thr Glu Lys Val
            675                 680                 685

Asn Met Met Ser Leu Thr Val Leu Gly Leu Arg Met Leu Phe Ala Lys
690                 695                 700

Thr Val Ala Val Asn Phe Leu Leu Thr Ala Lys Leu Phe Phe Leu Arg
705                 710                 715                 720

Ala Lys Arg Ser Gly Ser Gly Ala Pro Val Lys Gln Thr Leu Asn Phe
                725                 730                 735

Asp Leu Leu Lys Leu Ala Gly Asp Val Glu Ser Asn Pro Gly Pro Met
            740                 745                 750

Glu Thr Asp Thr Leu Leu Leu Trp Val Leu Leu Trp Val Pro Gly
        755                 760                 765

Ser Thr Gly Gln Ala Val Leu Thr Gln Pro Pro Ser Ala Ser Gly Thr
770                 775                 780

Pro Gly Gln Arg Val Thr Ile Ser Cys Ser Gly Ser Ser Ser Asn Ile
785                 790                 795                 800

Gly Ser Asn Thr Val Asn Trp Tyr Gln Gln Leu Pro Gly Thr Ala Pro
                805                 810                 815

Lys Leu Leu Met Tyr Ser Asn Asn Gln Arg Pro Ser Gly Val Pro Asp
                820                 825                 830

Arg Phe Ser Gly Ser Lys Ser Gly Thr Ser Ala Ser Leu Ala Ile Ser
            835                 840                 845

Gly Leu Gln Ser Glu Asp Glu Ala Asp Tyr Tyr Cys Ala Ala Trp Asp
850                 855                 860

Asp Ser Leu Asn Gly Tyr Val Phe Gly Thr Gly Thr Lys Val Thr Val
865                 870                 875                 880

Leu Gly Gln Pro Lys Ala Asn Pro Thr Val Thr Leu Phe Pro Pro Ser
                885                 890                 895

Ser Glu Glu Leu Gln Ala Asn Lys Ala Thr Leu Val Cys Leu Ile Ser
            900                 905                 910

Asp Phe Tyr Pro Gly Ala Val Thr Val Ala Trp Lys Ala Asp Gly Ser
            915                 920                 925

Pro Val Lys Ala Gly Val Glu Thr Thr Lys Pro Ser Lys Gln Ser Asn
            930                 935                 940

Asn Lys Tyr Ala Ala Ser Ser Tyr Leu Ser Leu Thr Pro Glu Gln Trp
945                 950                 955                 960

Lys Ser His Arg Ser Tyr Ser Cys Gln Val Thr His Glu Gly Ser Thr
            965                 970                 975

Val Glu Lys Thr Val Ala Pro Thr Glu Cys Ser Pro Ile Lys Thr Asp
            980                 985                 990

Val Ile Thr Met Asp Pro Lys Asp Asn Cys Ser Lys Asp Ala Asn Asp
            995                 1000                1005

Thr Leu Leu Leu Gln Leu Thr Asn Thr Ser Ala Tyr Tyr Met Tyr Leu
        1010                1015                1020

Leu Leu Leu Leu Lys Ser Val Val Tyr Phe Ala Ile Ile Thr Cys Cys
1025                1030                1035                1040
```

-continued

Leu Leu Arg Arg Thr Ala Phe Cys Cys Asn Gly Glu Lys Ser
            1045                1050

<210> SEQ ID NO 165
<211> LENGTH: 551
<212> TYPE: PRT
<213> ORGANISM: Artificial Sequence
<220> FEATURE:
<223> OTHER INFORMATION: Synthetic Construct

<400> SEQUENCE: 165

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
            115                 120                 125

Ser Leu Glu Met Ala Glu Val Gln Leu Val Gln Ser Gly Ala Glu Val
        130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205

Ile Ser Thr Ala Tyr Leu Gln Trp Ser Ser Leu Lys Ala Ser Asp Thr
    210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Gly Gly
                245                 250                 255

Gly Gly Ser Glu Val Gln Leu Val Gln Ser Gly Ala Glu Val Lys Lys
            260                 265                 270

Pro Gly Glu Ser Leu Lys Ile Ser Cys Lys Gly Ser Gly Tyr Ser Phe
        275                 280                 285

Thr Ser Tyr Trp Ile Gly Trp Val Arg Gln Met Pro Gly Lys Gly Leu
    290                 295                 300

Glu Trp Met Gly Ile Ile Tyr Pro Gly Asp Ser Asp Thr Arg Tyr Ser
305                 310                 315                 320

Pro Ser Phe Gln Gly Gln Val Thr Ile Ser Ala Asp Lys Ser Ile Ser
                325                 330                 335

Thr Ala Tyr Leu Gln Trp Ser Ser Leu Lys Ala Ser Asp Thr Ala Met
            340                 345                 350

```
Tyr Tyr Cys Ala Arg Ser Met Gly Ser Ser Leu Tyr Ala Ser Ser Asp
            355                 360                 365

Val Trp Gly Gln Gly Thr Leu Val Thr Val Ser Ser Ala Ser Thr Lys
370                 375                 380

Gly Pro Ser Val Phe Pro Leu Ala Pro Ser Ser Lys Ser Thr Ser Gly
385                 390                 395                 400

Gly Thr Ala Ala Leu Gly Cys Leu Val Lys Asp Tyr Phe Pro Glu Pro
                405                 410                 415

Val Thr Val Ser Trp Asn Ser Gly Ala Leu Thr Ser Gly Val His Thr
                420                 425                 430

Phe Pro Ala Val Leu Gln Ser Ser Gly Leu Tyr Ser Leu Ser Ser Val
                435                 440                 445

Val Thr Val Pro Ser Ser Ser Leu Gly Thr Gln Thr Tyr Ile Cys Asn
            450                 455                 460

Val Asn His Lys Pro Ser Asn Thr Lys Val Asp Lys Arg Val Glu Pro
465                 470                 475                 480

Lys Ser Cys Glu Val Lys Thr Asp Ser Thr Asp His Val Lys Pro Lys
                485                 490                 495

Glu Thr Glu Asn Thr Lys Gln Pro Ser Lys Ser Cys His Lys Pro Lys
                500                 505                 510

Ala Ile Val His Thr Glu Lys Val Asn Met Met Ser Leu Thr Val Leu
                515                 520                 525

Gly Leu Arg Met Leu Phe Ala Lys Thr Val Ala Val Asn Phe Leu Leu
                530                 535                 540

Thr Ala Lys Leu Phe Phe Leu
545                 550

<210> SEQ ID NO 166
<211> LENGTH: 284
<212> TYPE: PRT
<213> ORGANISM: Artificial Sequence
<220> FEATURE:
<223> OTHER INFORMATION: Synthetic Construct

<400> SEQUENCE: 166

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
                35                  40                  45

Leu Ile Tyr Gly Asn Ser Asn Arg Pro Ser Gly Val Pro Asp Arg Phe
            50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
                100                 105                 110

Gln Pro Lys Ala Asn Pro Thr Val Thr Leu Phe Pro Pro Ser Ser Glu
                115                 120                 125

Glu Leu Gln Ala Asn Lys Ala Thr Leu Val Cys Leu Ile Ser Asp Phe
            130                 135                 140

Tyr Pro Gly Ala Val Thr Val Ala Trp Lys Ala Asp Gly Ser Pro Val
145                 150                 155                 160
```

```
Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser Pro Ile Lys Thr Asp Val Ile
210                 215                 220

Thr Met Asp Pro Lys Asp Asn Cys Ser Lys Asp Ala Asn Asp Thr Leu
225                 230                 235                 240

Leu Leu Gln Leu Thr Asn Thr Ser Ala Tyr Tyr Met Tyr Leu Leu Leu
                245                 250                 255

Leu Leu Lys Ser Val Val Tyr Phe Ala Ile Ile Thr Cys Cys Leu Leu
            260                 265                 270

Arg Arg Thr Ala Phe Cys Cys Asn Gly Glu Lys Ser
        275                 280

<210> SEQ ID NO 167
<211> LENGTH: 423
<212> TYPE: PRT
<213> ORGANISM: Artificial Sequence
<220> FEATURE:
<223> OTHER INFORMATION: Synthetic Construct

<400> SEQUENCE: 167

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Met Gly Ser Ser Leu Tyr Ala Ser Ser Asp Val Trp Gly
            100                 105                 110

Gln Gly Thr Leu Val Thr Val Ser Gly Gly Gly Ser Gly Gly
        115                 120                 125

Gly Gly Ser Glu Val Gln Leu Val Gln Ser Gly Ala Glu Val Lys Lys
130                 135                 140

Pro Gly Glu Ser Leu Lys Ile Ser Cys Lys Gly Ser Gly Tyr Ser Phe
145                 150                 155                 160

Thr Ser Tyr Trp Ile Gly Trp Val Arg Gln Met Pro Gly Lys Gly Leu
                165                 170                 175

Glu Trp Met Gly Ile Ile Tyr Pro Gly Asp Ser Asp Thr Arg Tyr Ser
            180                 185                 190

Pro Ser Phe Gln Gly Gln Val Thr Ile Ser Ala Asp Lys Ser Ile Ser
        195                 200                 205

Thr Ala Tyr Leu Gln Trp Ser Ser Leu Lys Ala Ser Asp Thr Ala Met
    210                 215                 220

Tyr Tyr Cys Ala Arg Ser Met Gly Ser Ser Leu Tyr Ala Ser Ser Asp
225                 230                 235                 240
```

```
Val Trp Gly Gln Gly Thr Leu Val Thr Val Ser Ser Ala Ser Thr Lys
                245                 250                 255

Gly Pro Ser Val Phe Pro Leu Ala Pro Ser Ser Lys Ser Thr Ser Gly
            260                 265                 270

Gly Thr Ala Ala Leu Gly Cys Leu Val Lys Asp Tyr Phe Pro Glu Pro
            275                 280                 285

Val Thr Val Ser Trp Asn Ser Gly Ala Leu Thr Ser Gly Val His Thr
    290                 295                 300

Phe Pro Ala Val Leu Gln Ser Ser Gly Leu Tyr Ser Leu Ser Ser Val
305                 310                 315                 320

Val Thr Val Pro Ser Ser Ser Leu Gly Thr Gln Thr Tyr Ile Cys Asn
            325                 330                 335

Val Asn His Lys Pro Ser Asn Thr Lys Val Asp Lys Arg Val Glu Pro
            340                 345                 350

Lys Ser Cys Glu Val Lys Thr Asp Ser Thr Asp His Val Lys Pro Lys
            355                 360                 365

Glu Thr Glu Asn Thr Lys Gln Pro Ser Lys Ser Cys His Lys Pro Lys
            370                 375                 380

Ala Ile Val His Thr Glu Lys Val Asn Met Met Ser Leu Thr Val Leu
385                 390                 395                 400

Gly Leu Arg Met Leu Phe Ala Lys Thr Val Ala Val Asn Phe Leu Leu
                405                 410                 415

Thr Ala Lys Leu Phe Phe Leu
            420

<210> SEQ ID NO 168
<211> LENGTH: 406
<212> TYPE: PRT
<213> ORGANISM: Artificial Sequence
<220> FEATURE:
<223> OTHER INFORMATION: Synthetic Construct

<400> SEQUENCE: 168

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Gly Gly Gly Gly Ser Gly Gly Gly Ser Gln Ser Val Leu Thr Gln
            115                 120                 125

Pro Pro Ser Val Ser Gly Ala Pro Gly Gln Arg Val Thr Ile Ser Cys
130                 135                 140

Thr Gly Ser Ser Ser Asn Ile Gly Ala Gly Tyr Asp Val His Trp Tyr
145                 150                 155                 160

Gln Gln Leu Pro Gly Thr Ala Pro Lys Leu Leu Ile Tyr Gly Asn Ser
                165                 170                 175
```

-continued

```
Asn Arg Pro Ser Gly Val Pro Asp Arg Phe Ser Gly Ser Lys Ser Gly
            180                 185                 190

Thr Ser Ala Ser Leu Ala Ile Thr Gly Leu Gln Ala Glu Asp Glu Ala
        195                 200                 205

Asp Tyr Tyr Cys Gln Ser Tyr Asp Ser Ser Leu Ser Gly Tyr Val Phe
    210                 215                 220

Gly Thr Gly Thr Lys Val Thr Val Leu Gly Gln Pro Lys Ala Asn Pro
225                 230                 235                 240

Thr Val Thr Leu Phe Pro Pro Ser Ser Glu Glu Leu Gln Ala Asn Lys
                245                 250                 255

Ala Thr Leu Val Cys Leu Ile Ser Asp Phe Tyr Pro Gly Ala Val Thr
            260                 265                 270

Val Ala Trp Lys Ala Asp Gly Ser Pro Val Lys Ala Gly Val Glu Thr
        275                 280                 285

Thr Lys Pro Ser Lys Gln Ser Asn Asn Lys Tyr Ala Ala Ser Ser Tyr
    290                 295                 300

Leu Ser Leu Thr Pro Glu Gln Trp Lys Ser His Arg Ser Tyr Ser Cys
305                 310                 315                 320

Gln Val Thr His Glu Gly Ser Thr Val Glu Lys Thr Val Ala Pro Thr
                325                 330                 335

Glu Cys Ser Pro Ile Lys Thr Asp Val Ile Thr Met Asp Pro Lys Asp
            340                 345                 350

Asn Cys Ser Lys Asp Ala Asn Asp Thr Leu Leu Gln Leu Thr Asn
        355                 360                 365

Thr Ser Ala Tyr Tyr Met Tyr Leu Leu Leu Leu Lys Ser Val Val
    370                 375                 380

Tyr Phe Ala Ile Ile Thr Cys Cys Leu Leu Arg Arg Thr Ala Phe Cys
385                 390                 395                 400

Cys Asn Gly Glu Lys Ser
                405

<210> SEQ ID NO 169
<211> LENGTH: 542
<212> TYPE: PRT
<213> ORGANISM: Artificial Sequence
<220> FEATURE:
<223> OTHER INFORMATION: Synthetic Construct

<400> SEQUENCE: 169

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Met Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
            100                 105                 110

Arg Gly Gly Gly Gly Ser Gly Gly Gly Ser Gly Gly Gly Gly Ser
        115                 120                 125
```

-continued

```
Leu Glu Met Ala Glu Val Gln Leu Val Gln Ser Gly Ala Glu Met Lys
    130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175

Leu Glu Trp Met Gly Thr Ile Tyr Pro Asp Asp Ser Asp Thr Arg Tyr
            180                 185                 190

Gly Pro Ala Phe Gln Gly Gln Val Thr Ile Ser Ala Asp Lys Ser Ile
        195                 200                 205

Ser Thr Ala Tyr Leu Gln Trp Ser Ser Leu Lys Ala Ser Asp Thr Ala
210                 215                 220

Met Tyr Tyr Cys Ala Arg Asp Ser Tyr Tyr Gly Ile Asp Val Trp Gly
225                 230                 235                 240

Gln Gly Thr Leu Val Thr Val Ser Ser Gly Gly Gly Ser Glu Val
                245                 250                 255

Gln Leu Val Gln Ser Gly Ala Glu Met Lys Lys Pro Gly Glu Ser Leu
        260                 265                 270

Lys Ile Ser Cys Lys Gly Ser Gly Tyr Asn Phe Ala Ser Tyr Trp Val
    275                 280                 285

Gly Trp Val Arg Gln Met Pro Gly Lys Gly Leu Glu Trp Met Gly Thr
290                 295                 300

Ile Tyr Pro Asp Asp Ser Asp Thr Arg Tyr Gly Pro Ala Phe Gln Gly
305                 310                 315                 320

Gln Val Thr Ile Ser Ala Asp Lys Ser Ile Ser Thr Ala Tyr Leu Gln
                325                 330                 335

Trp Ser Ser Leu Lys Ala Ser Asp Thr Ala Met Tyr Tyr Cys Ala Arg
            340                 345                 350

Asp Ser Tyr Tyr Gly Ile Asp Val Trp Gly Gln Gly Thr Leu Val Thr
        355                 360                 365

Val Ser Ser Ala Ser Thr Lys Gly Pro Ser Val Phe Pro Leu Ala Pro
370                 375                 380

Ser Ser Lys Ser Thr Ser Gly Gly Thr Ala Ala Leu Gly Cys Leu Val
385                 390                 395                 400

Lys Asp Tyr Phe Pro Glu Pro Val Thr Val Ser Trp Asn Ser Gly Ala
                405                 410                 415

Leu Thr Ser Gly Val His Thr Phe Pro Ala Val Leu Gln Ser Ser Gly
            420                 425                 430

Leu Tyr Ser Leu Ser Ser Val Val Thr Val Pro Ser Ser Ser Leu Gly
        435                 440                 445

Thr Gln Thr Tyr Ile Cys Asn Val Asn His Lys Pro Ser Asn Thr Lys
450                 455                 460

Val Asp Lys Arg Val Glu Pro Lys Ser Cys Glu Val Lys Thr Asp Ser
465                 470                 475                 480

Thr Asp His Val Lys Pro Lys Glu Thr Glu Asn Thr Lys Gln Pro Ser
                485                 490                 495

Lys Ser Cys His Lys Pro Lys Ala Ile Val His Thr Glu Lys Val Asn
            500                 505                 510

Met Met Ser Leu Thr Val Leu Gly Leu Arg Met Leu Phe Ala Lys Thr
        515                 520                 525

Val Ala Val Asn Phe Leu Leu Thr Ala Lys Leu Phe Phe Leu
530                 535                 540
```

-continued

```
<210> SEQ ID NO 170
<211> LENGTH: 283
<212> TYPE: PRT
<213> ORGANISM: Artificial Sequence
<220> FEATURE:
<223> OTHER INFORMATION: Synthetic Construct

<400> SEQUENCE: 170

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Met Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser Pro Ile Lys Thr Asp Val Ile Thr
    210                 215                 220

Met Asp Pro Lys Asp Asn Cys Ser Lys Asp Ala Asn Asp Thr Leu Leu
225                 230                 235                 240

Leu Gln Leu Thr Asn Thr Ser Ala Tyr Tyr Met Tyr Leu Leu Leu Leu
                245                 250                 255

Leu Lys Ser Val Val Tyr Phe Ala Ile Ile Thr Cys Cys Leu Leu Arg
            260                 265                 270

Arg Thr Ala Phe Cys Cys Asn Gly Glu Lys Ser
        275                 280

<210> SEQ ID NO 171
<211> LENGTH: 415
<212> TYPE: PRT
<213> ORGANISM: Artificial Sequence
<220> FEATURE:
<223> OTHER INFORMATION: Synthetic Construct

<400> SEQUENCE: 171

Glu Val Gln Leu Val Gln Ser Gly Ala Glu Met Lys Lys Pro Gly Glu
1               5                   10                  15

Ser Leu Lys Ile Ser Cys Lys Gly Ser Gly Tyr Asn Phe Ala Ser Tyr
                20                  25                  30
```

Trp Val Gly Trp Val Arg Gln Met Pro Gly Lys Gly Leu Glu Trp Met
            35                  40                  45

Gly Thr Ile Tyr Pro Asp Asp Ser Asp Thr Arg Tyr Gly Pro Ala Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Asp Ser Tyr Tyr Gly Ile Asp Val Trp Gly Gln Gly Thr Leu
            100                 105                 110

Val Thr Val Ser Ser Gly Gly Gly Ser Gly Gly Gly Ser Glu
            115                 120                 125

Val Gln Leu Val Gln Ser Gly Ala Glu Met Lys Lys Pro Gly Glu Ser
130                 135                 140

Leu Lys Ile Ser Cys Lys Gly Ser Gly Tyr Asn Phe Ala Ser Tyr Trp
145                 150                 155                 160

Val Gly Trp Val Arg Gln Met Pro Gly Lys Gly Leu Glu Trp Met Gly
                165                 170                 175

Thr Ile Tyr Pro Asp Asp Ser Asp Thr Arg Tyr Gly Pro Ala Phe Gln
            180                 185                 190

Gly Gln Val Thr Ile Ser Ala Asp Lys Ser Ile Ser Thr Ala Tyr Leu
        195                 200                 205

Gln Trp Ser Ser Leu Lys Ala Ser Asp Thr Ala Met Tyr Tyr Cys Ala
    210                 215                 220

Arg Asp Ser Tyr Tyr Gly Ile Asp Val Trp Gly Gln Gly Thr Leu Val
225                 230                 235                 240

Thr Val Ser Ser Ala Ser Thr Lys Gly Pro Ser Val Phe Pro Leu Ala
            245                 250                 255

Pro Ser Ser Lys Ser Thr Ser Gly Gly Thr Ala Ala Leu Gly Cys Leu
                260                 265                 270

Val Lys Asp Tyr Phe Pro Glu Pro Val Thr Val Ser Trp Asn Ser Gly
            275                 280                 285

Ala Leu Thr Ser Gly Val His Thr Phe Pro Ala Val Leu Gln Ser Ser
        290                 295                 300

Gly Leu Tyr Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
            325                 330                 335

Lys Val Asp Lys Arg Val Glu Pro Lys Ser Cys Glu Val Lys Thr Asp
                340                 345                 350

Ser Thr Asp His Val Lys Pro Lys Glu Thr Glu Asn Thr Lys Gln Pro
            355                 360                 365

Ser Lys Ser Cys His Lys Pro Lys Ala Ile Val His Thr Glu Lys Val
        370                 375                 380

Asn Met Met Ser Leu Thr Val Leu Gly Leu Arg Met Leu Phe Ala Lys
385                 390                 395                 400

Thr Val Ala Val Asn Phe Leu Leu Thr Ala Lys Leu Phe Phe Leu
                405                 410                 415

<210> SEQ ID NO 172
<211> LENGTH: 404
<212> TYPE: PRT
<213> ORGANISM: Artificial Sequence
<220> FEATURE:
<223> OTHER INFORMATION: Synthetic Construct

<400> SEQUENCE: 172

```
Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Met Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Gly
            100                 105                 110

Gly Gly Gly Ser Gly Gly Gly Ser Gln Ala Val Leu Thr Gln Pro
        115                 120                 125

Pro Ser Ala Ser Gly Thr Pro Gly Gln Arg Val Thr Ile Ser Cys Ser
130                 135                 140

Gly Ser Ser Ser Asn Ile Gly Ser Asn Thr Val Asn Trp Tyr Gln Gln
145                 150                 155                 160

Leu Pro Gly Thr Ala Pro Lys Leu Leu Met Tyr Ser Asn Asn Gln Arg
                165                 170                 175

Pro Ser Gly Val Pro Asp Arg Phe Ser Gly Ser Lys Ser Gly Thr Ser
            180                 185                 190

Ala Ser Leu Ala Ile Ser Gly Leu Gln Ser Glu Asp Glu Ala Asp Tyr
        195                 200                 205

Tyr Cys Ala Ala Trp Asp Asp Ser Leu Asn Gly Tyr Val Phe Gly Thr
    210                 215                 220

Gly Thr Lys Val Thr Val Leu Gly Gln Pro Lys Ala Asn Pro Thr Val
225                 230                 235                 240

Thr Leu Phe Pro Pro Ser Ser Glu Glu Leu Gln Ala Asn Lys Ala Thr
                245                 250                 255

Leu Val Cys Leu Ile Ser Asp Phe Tyr Pro Gly Ala Val Thr Val Ala
            260                 265                 270

Trp Lys Ala Asp Gly Ser Pro Val Lys Ala Gly Val Glu Thr Thr Lys
        275                 280                 285

Pro Ser Lys Gln Ser Asn Asn Lys Tyr Ala Ala Ser Ser Tyr Leu Ser
290                 295                 300

Leu Thr Pro Glu Gln Trp Lys Ser His Arg Ser Tyr Ser Cys Gln Val
305                 310                 315                 320

Thr His Glu Gly Ser Thr Val Glu Lys Thr Val Ala Pro Thr Glu Cys
                325                 330                 335

Ser Pro Ile Lys Thr Asp Val Ile Thr Met Asp Pro Lys Asp Asn Cys
            340                 345                 350

Ser Lys Asp Ala Asn Asp Thr Leu Leu Leu Gln Leu Thr Asn Thr Ser
        355                 360                 365

Ala Tyr Tyr Met Tyr Leu Leu Leu Leu Lys Ser Val Val Tyr Phe
    370                 375                 380

Ala Ile Ile Thr Cys Cys Leu Leu Arg Arg Thr Ala Phe Cys Cys Asn
385                 390                 395                 400

Gly Glu Lys Ser
```

```
<210> SEQ ID NO 173
<211> LENGTH: 547
<212> TYPE: PRT
<213> ORGANISM: Artificial Sequence
<220> FEATURE:
<223> OTHER INFORMATION: Synthetic Construct

<400> SEQUENCE: 173
```

Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
        115                 120                 125

Ser Leu Glu Met Ala Glu Val Gln Leu Val Gln Ser Gly Ala Glu Val
    130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205

Ile Ser Thr Ala Tyr Leu Gln Trp Ser Ser Leu Lys Ala Ser Asp Thr
    210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Gly Gly
                245                 250                 255

Gly Gly Ser Glu Val Gln Leu Val Gln Ser Gly Ala Glu Met Lys Lys
            260                 265                 270

Pro Gly Glu Ser Leu Lys Ile Ser Cys Lys Gly Ser Gly Tyr Asn Phe
        275                 280                 285

Ala Ser Tyr Trp Val Gly Trp Val Arg Gln Met Pro Gly Lys Gly Leu
    290                 295                 300

Glu Trp Met Gly Thr Ile Tyr Pro Asp Asp Ser Asp Thr Arg Tyr Gly
305                 310                 315                 320

Pro Ala Phe Gln Gly Gln Val Thr Ile Ser Ala Asp Lys Ser Ile Ser
                325                 330                 335

Thr Ala Tyr Leu Gln Trp Ser Ser Leu Lys Ala Ser Asp Thr Ala Met
            340                 345                 350

Tyr Tyr Cys Ala Arg Asp Ser Tyr Gly Ile Asp Val Trp Gly Gln
        355                 360                 365

```
Gly Thr Leu Val Thr Val Ser Ala Ser Thr Lys Gly Pro Ser Val
        370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
                405                 410                 415

Trp Asn Ser Gly Ala Leu Thr Ser Gly Val His Thr Phe Pro Ala Val
                420                 425                 430

Leu Gln Ser Ser Gly Leu Tyr Ser Leu Ser Ser Val Val Thr Val Pro
            435                 440                 445

Ser Ser Ser Leu Gly Thr Gln Thr Tyr Ile Cys Asn Val Asn His Lys
        450                 455                 460

Pro Ser Asn Thr Lys Val Asp Lys Arg Val Glu Pro Lys Ser Cys Glu
465                 470                 475                 480

Val Lys Thr Asp Ser Thr Asp His Val Lys Pro Lys Glu Thr Glu Asn
                485                 490                 495

Thr Lys Gln Pro Ser Lys Ser Cys His Lys Pro Lys Ala Ile Val His
                500                 505                 510

Thr Glu Lys Val Asn Met Met Ser Leu Thr Val Leu Gly Leu Arg Met
            515                 520                 525

Leu Phe Ala Lys Thr Val Ala Val Asn Phe Leu Leu Thr Ala Lys Leu
        530                 535                 540

Phe Phe Leu
545

<210> SEQ ID NO 174
<211> LENGTH: 283
<212> TYPE: PRT
<213> ORGANISM: Artificial Sequence
<220> FEATURE:
<223> OTHER INFORMATION: Synthetic Construct

<400> SEQUENCE: 174

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Met Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Gln
                100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175
```

```
Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser Pro Ile Lys Thr Asp Val Ile Thr
        210                 215                 220

Met Asp Pro Lys Asp Asn Cys Ser Lys Asp Ala Asn Asp Thr Leu Leu
225                 230                 235                 240

Leu Gln Leu Thr Asn Thr Ser Ala Tyr Tyr Met Tyr Leu Leu Leu Leu
                245                 250                 255

Leu Lys Ser Val Val Tyr Phe Ala Ile Ile Thr Cys Cys Leu Leu Arg
            260                 265                 270

Arg Thr Ala Phe Cys Cys Asn Gly Glu Lys Ser
            275                 280
```

<210> SEQ ID NO 175
<211> LENGTH: 284
<212> TYPE: PRT
<213> ORGANISM: Artificial Sequence
<220> FEATURE:
<223> OTHER INFORMATION: Synthetic Construct

<400> SEQUENCE: 175

```
Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Met Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser Glu Val Lys Thr Asp Ser Thr Asp
        210                 215                 220

His Val Lys Pro Lys Glu Thr Glu Asn Thr Lys Gln Pro Ser Lys Ser
225                 230                 235                 240

Cys His Lys Pro Lys Ala Ile Val His Thr Glu Lys Val Asn Met Met
                245                 250                 255
```

```
Ser Leu Thr Val Leu Gly Leu Arg Met Leu Phe Ala Lys Thr Val Ala
            260                 265                 270

Val Asn Phe Leu Leu Thr Ala Lys Leu Phe Phe Leu
            275                 280

<210> SEQ ID NO 176
<211> LENGTH: 546
<212> TYPE: PRT
<213> ORGANISM: Artificial Sequence
<220> FEATURE:
<223> OTHER INFORMATION: Synthetic Construct

<400> SEQUENCE: 176

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
            115                 120                 125

Ser Leu Glu Met Ala Glu Val Gln Leu Val Gln Ser Gly Ala Glu Val
            130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205

Ile Ser Thr Ala Tyr Leu Gln Trp Ser Ser Leu Lys Ala Ser Asp Thr
    210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Gly Gly
                245                 250                 255

Gly Gly Ser Glu Val Gln Leu Val Gln Ser Gly Ala Glu Met Lys Lys
            260                 265                 270

Pro Gly Glu Ser Leu Lys Ile Ser Cys Lys Gly Ser Gly Tyr Asn Phe
        275                 280                 285

Ala Ser Tyr Trp Val Gly Trp Val Arg Gln Met Pro Gly Lys Gly Leu
    290                 295                 300

Glu Trp Met Gly Thr Ile Tyr Pro Asp Ser Asp Thr Arg Tyr Gly
305                 310                 315                 320

Pro Ala Phe Gln Gly Gln Val Thr Ile Ser Ala Asp Lys Ser Ile Ser
                325                 330                 335
```

```
Thr Ala Tyr Leu Gln Trp Ser Ser Leu Lys Ala Ser Asp Thr Ala Met
                340                 345                 350

Tyr Tyr Cys Ala Arg Asp Ser Tyr Gly Ile Asp Val Trp Gly Gln
            355                 360                 365

Gly Thr Leu Val Thr Val Ser Ser Ala Ser Thr Lys Gly Pro Ser Val
        370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
                405                 410                 415

Trp Asn Ser Gly Ala Leu Thr Ser Gly Val His Thr Phe Pro Ala Val
                420                 425                 430

Leu Gln Ser Ser Gly Leu Tyr Ser Leu Ser Ser Val Val Thr Val Pro
            435                 440                 445

Ser Ser Ser Leu Gly Thr Gln Thr Tyr Ile Cys Asn Val Asn His Lys
450                 455                 460

Pro Ser Asn Thr Lys Val Asp Lys Arg Val Glu Pro Lys Ser Cys Pro
465                 470                 475                 480

Ile Lys Thr Asp Val Ile Thr Met Asp Pro Lys Asp Asn Cys Ser Lys
                485                 490                 495

Asp Ala Asn Asp Thr Leu Leu Leu Gln Leu Thr Asn Thr Ser Ala Tyr
            500                 505                 510

Tyr Met Tyr Leu Leu Leu Leu Lys Ser Val Val Tyr Phe Ala Ile
            515                 520                 525

Ile Thr Cys Cys Leu Leu Arg Arg Thr Ala Phe Cys Cys Asn Gly Glu
            530                 535                 540

Lys Ser
545

<210> SEQ ID NO 177
<211> LENGTH: 419
<212> TYPE: PRT
<213> ORGANISM: Artificial Sequence
<220> FEATURE:
<223> OTHER INFORMATION: Synthetic Construct

<400> SEQUENCE: 177

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Met Gly Ser Ser Leu Tyr Ala Ser Ser Asp Val Trp Gly
                100                 105                 110

Gln Gly Thr Leu Val Thr Val Ser Ser Gly Gly Gly Gly Ser Gly Gly
            115                 120                 125

Gly Gly Ser Glu Val Gln Leu Val Gln Ser Gly Ala Glu Met Lys Lys
130                 135                 140
```

-continued

```
Pro Gly Glu Ser Leu Lys Ile Ser Cys Lys Gly Ser Gly Tyr Asn Phe
145                 150                 155                 160

Ala Ser Tyr Trp Val Gly Trp Val Arg Gln Met Pro Gly Lys Gly Leu
                165                 170                 175

Glu Trp Met Gly Thr Ile Tyr Pro Asp Asp Ser Asp Thr Arg Tyr Gly
            180                 185                 190

Pro Ala Phe Gln Gly Gln Val Thr Ile Ser Ala Asp Lys Ser Ile Ser
                195                 200                 205

Thr Ala Tyr Leu Gln Trp Ser Ser Leu Lys Ala Ser Asp Thr Ala Met
            210                 215                 220

Tyr Tyr Cys Ala Arg Asp Ser Tyr Tyr Gly Ile Asp Val Trp Gly Gln
225                 230                 235                 240

Gly Thr Leu Val Thr Val Ser Ser Ala Ser Thr Lys Gly Pro Ser Val
                245                 250                 255

Phe Pro Leu Ala Pro Ser Ser Lys Ser Thr Ser Gly Gly Thr Ala Ala
            260                 265                 270

Leu Gly Cys Leu Val Lys Asp Tyr Phe Pro Glu Pro Val Thr Val Ser
                275                 280                 285

Trp Asn Ser Gly Ala Leu Thr Ser Gly Val His Thr Phe Pro Ala Val
            290                 295                 300

Leu Gln Ser Ser Gly Leu Tyr Ser Leu Ser Ser Val Val Thr Val Pro
305                 310                 315                 320

Ser Ser Ser Leu Gly Thr Gln Thr Tyr Ile Cys Asn Val Asn His Lys
                325                 330                 335

Pro Ser Asn Thr Lys Val Asp Lys Arg Val Glu Pro Lys Ser Cys Glu
            340                 345                 350

Val Lys Thr Asp Ser Thr Asp His Val Lys Pro Lys Glu Thr Glu Asn
                355                 360                 365

Thr Lys Gln Pro Ser Lys Ser Cys His Lys Pro Lys Ala Ile Val His
            370                 375                 380

Thr Glu Lys Val Asn Met Met Ser Leu Thr Val Leu Gly Leu Arg Met
385                 390                 395                 400

Leu Phe Ala Lys Thr Val Ala Val Asn Phe Leu Leu Thr Ala Lys Leu
                405                 410                 415

Phe Phe Leu

<210> SEQ ID NO 178
<211> LENGTH: 405
<212> TYPE: PRT
<213> ORGANISM: Artificial Sequence
<220> FEATURE:
<223> OTHER INFORMATION: Synthetic Construct

<400> SEQUENCE: 178

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80
```

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Gly Gly Gly Gly Ser Gly Gly Gly Gly Ser Gln Ala Val Leu Thr Gln
            115                 120                 125

Pro Pro Ser Ala Ser Gly Thr Pro Gly Gln Arg Val Thr Ile Ser Cys
    130                 135                 140

Ser Gly Ser Ser Ser Asn Ile Gly Ser Asn Thr Val Asn Trp Tyr Gln
145                 150                 155                 160

Gln Leu Pro Gly Thr Ala Pro Lys Leu Leu Met Tyr Ser Asn Asn Gln
                165                 170                 175

Arg Pro Ser Gly Val Pro Asp Arg Phe Ser Gly Ser Lys Ser Gly Thr
            180                 185                 190

Ser Ala Ser Leu Ala Ile Ser Gly Leu Gln Ser Glu Asp Glu Ala Asp
        195                 200                 205

Tyr Tyr Cys Ala Ala Trp Asp Asp Ser Leu Asn Gly Tyr Val Phe Gly
210                 215                 220

Thr Gly Thr Lys Val Thr Val Leu Gly Gln Pro Lys Ala Asn Pro Thr
225                 230                 235                 240

Val Thr Leu Phe Pro Pro Ser Ser Glu Glu Leu Gln Ala Asn Lys Ala
                245                 250                 255

Thr Leu Val Cys Leu Ile Ser Asp Phe Tyr Pro Gly Ala Val Thr Val
            260                 265                 270

Ala Trp Lys Ala Asp Gly Ser Pro Val Lys Ala Gly Val Glu Thr Thr
        275                 280                 285

Lys Pro Ser Lys Gln Ser Asn Asn Lys Tyr Ala Ala Ser Ser Tyr Leu
290                 295                 300

Ser Leu Thr Pro Glu Gln Trp Lys Ser His Arg Ser Tyr Ser Cys Gln
305                 310                 315                 320

Val Thr His Glu Gly Ser Thr Val Glu Lys Thr Val Ala Pro Thr Glu
                325                 330                 335

Cys Ser Pro Ile Lys Thr Asp Val Ile Thr Met Asp Pro Lys Asp Asn
            340                 345                 350

Cys Ser Lys Asp Ala Asn Asp Thr Leu Leu Leu Gln Leu Thr Asn Thr
        355                 360                 365

Ser Ala Tyr Tyr Met Tyr Leu Leu Leu Leu Lys Ser Val Val Tyr
370                 375                 380

Phe Ala Ile Ile Thr Cys Cys Leu Leu Arg Arg Thr Ala Phe Cys Cys
385                 390                 395                 400

Asn Gly Glu Lys Ser
            405

<210> SEQ ID NO 179
<211> LENGTH: 406
<212> TYPE: PRT
<213> ORGANISM: Artificial Sequence
<220> FEATURE:
<223> OTHER INFORMATION: Synthetic Construct

<400> SEQUENCE: 179

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
                35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
                100                 105                 110

Gly Gly Gly Gly Ser Gly Gly Gly Gly Ser Gln Ala Val Leu Thr Gln
            115                 120                 125

Pro Pro Ser Ala Ser Gly Thr Pro Gly Gln Arg Val Thr Ile Ser Cys
130                 135                 140

Ser Gly Ser Ser Ser Asn Ile Gly Ser Asn Thr Val Asn Trp Tyr Gln
145                 150                 155                 160

Gln Leu Pro Gly Thr Ala Pro Lys Leu Leu Met Tyr Ser Asn Asn Gln
                165                 170                 175

Arg Pro Ser Gly Val Pro Asp Arg Phe Ser Gly Ser Lys Ser Gly Thr
            180                 185                 190

Ser Ala Ser Leu Ala Ile Ser Gly Leu Gln Ser Glu Asp Glu Ala Asp
        195                 200                 205

Tyr Tyr Cys Ala Ala Trp Asp Asp Ser Leu Asn Gly Tyr Val Phe Gly
        210                 215                 220

Thr Gly Thr Lys Val Thr Val Leu Gly Gln Pro Lys Ala Asn Pro Thr
225                 230                 235                 240

Val Thr Leu Phe Pro Pro Ser Ser Glu Glu Leu Gln Ala Asn Lys Ala
                245                 250                 255

Thr Leu Val Cys Leu Ile Ser Asp Phe Tyr Pro Gly Ala Val Thr Val
                260                 265                 270

Ala Trp Lys Ala Asp Gly Ser Pro Val Lys Ala Gly Val Glu Thr Thr
            275                 280                 285

Lys Pro Ser Lys Gln Ser Asn Asn Lys Tyr Ala Ala Ser Ser Tyr Leu
290                 295                 300

Ser Leu Thr Pro Glu Gln Trp Lys Ser His Arg Ser Tyr Ser Cys Gln
305                 310                 315                 320

Val Thr His Glu Gly Ser Thr Val Glu Lys Thr Val Ala Pro Thr Glu
                325                 330                 335

Cys Ser Glu Val Lys Thr Asp Ser Thr Asp His Val Lys Pro Lys Glu
            340                 345                 350

Thr Glu Asn Thr Lys Gln Pro Ser Lys Ser Cys His Lys Pro Lys Ala
        355                 360                 365

Ile Val His Thr Glu Lys Val Asn Met Met Ser Leu Thr Val Leu Gly
        370                 375                 380

Leu Arg Met Leu Phe Ala Lys Thr Val Ala Val Asn Phe Leu Leu Thr
385                 390                 395                 400

Ala Lys Leu Phe Phe Leu
                405

<210> SEQ ID NO 180
<211> LENGTH: 418
<212> TYPE: PRT
<213> ORGANISM: Artificial Sequence
<220> FEATURE:
<223> OTHER INFORMATION: Synthetic Construct

<400> SEQUENCE: 180

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Met Gly Ser Ser Leu Tyr Ala Ser Ser Asp Val Trp Gly
            100                 105                 110

Gln Gly Thr Leu Val Thr Val Ser Ser Gly Gly Gly Ser Gly Gly
        115                 120                 125

Gly Gly Ser Glu Val Gln Leu Val Gln Ser Gly Ala Glu Met Lys Lys
130                 135                 140

Pro Gly Glu Ser Leu Lys Ile Ser Cys Lys Gly Ser Gly Tyr Asn Phe
145                 150                 155                 160

Ala Ser Tyr Trp Val Gly Trp Val Arg Gln Met Pro Gly Lys Gly Leu
                165                 170                 175

Glu Trp Met Gly Thr Ile Tyr Pro Asp Asp Ser Asp Thr Arg Tyr Gly
            180                 185                 190

Pro Ala Phe Gln Gly Gln Val Thr Ile Ser Ala Asp Lys Ser Ile Ser
        195                 200                 205

Thr Ala Tyr Leu Gln Trp Ser Ser Leu Lys Ala Ser Asp Thr Ala Met
    210                 215                 220

Tyr Tyr Cys Ala Arg Asp Ser Tyr Tyr Gly Ile Asp Val Trp Gly Gln
225                 230                 235                 240

Gly Thr Leu Val Thr Val Ser Ser Ala Ser Thr Lys Gly Pro Ser Val
                245                 250                 255

Phe Pro Leu Ala Pro Ser Ser Lys Ser Thr Ser Gly Gly Thr Ala Ala
            260                 265                 270

Leu Gly Cys Leu Val Lys Asp Tyr Phe Pro Glu Pro Val Thr Val Ser
        275                 280                 285

Trp Asn Ser Gly Ala Leu Thr Ser Gly Val His Thr Phe Pro Ala Val
    290                 295                 300

Leu Gln Ser Ser Gly Leu Tyr Ser Leu Ser Ser Val Val Thr Val Pro
305                 310                 315                 320

Ser Ser Ser Leu Gly Thr Gln Thr Tyr Ile Cys Asn Val Asn His Lys
                325                 330                 335

Pro Ser Asn Thr Lys Val Asp Lys Arg Val Glu Pro Lys Ser Cys Pro
            340                 345                 350

Ile Lys Thr Asp Val Ile Thr Met Asp Pro Lys Asp Asn Cys Ser Lys
        355                 360                 365

Asp Ala Asn Asp Thr Leu Leu Leu Gln Leu Thr Asn Thr Ser Ala Tyr
    370                 375                 380

Tyr Met Tyr Leu Leu Leu Leu Leu Lys Ser Val Val Tyr Phe Ala Ile
385                 390                 395                 400

Ile Thr Cys Cys Leu Leu Arg Arg Thr Ala Phe Cys Cys Asn Gly Glu

-continued

```
                    405                 410                 415

Lys Ser

<210> SEQ ID NO 181
<211> LENGTH: 902
<212> TYPE: PRT
<213> ORGANISM: Artificial Sequence
<220> FEATURE:
<223> OTHER INFORMATION: Synthetic Construct

<400> SEQUENCE: 181

Met Glu Thr Asp Thr Leu Leu Leu Trp Val Leu Leu Leu Trp Val Pro
1               5                   10                  15

Gly Ser Thr Gly Gln Ala Val Leu Thr Gln Pro Pro Ser Ala Ser Gly
            20                  25                  30

Thr Pro Gly Gln Arg Val Thr Ile Ser Cys Ser Gly Ser Ser Ser Asn
        35                  40                  45

Ile Gly Ser Asn Thr Val Asn Trp Tyr Gln Gln Leu Pro Gly Thr Ala
    50                  55                  60

Pro Lys Leu Leu Met Tyr Ser Asn Asn Gln Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Gln Ser Glu Asp Glu Ala Asp Tyr Tyr Cys Ala Ala Trp
            100                 105                 110

Asp Asp Ser Leu Asn Gly Tyr Val Phe Gly Thr Gly Thr Lys Val Thr
        115                 120                 125

Val Leu Gly Gln Pro Lys Ala Asn Pro Thr Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Gly
                165                 170                 175

Ser Pro Val Lys Ala Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser Pro Ile Lys Thr
225                 230                 235                 240

Asp Val Ile Thr Met Asp Pro Lys Asp Asn Cys Ser Lys Asp Ala Asn
                245                 250                 255

Asp Thr Leu Leu Leu Gln Leu Thr Asn Thr Ser Ala Tyr Tyr Met Tyr
            260                 265                 270

Leu Leu Leu Leu Lys Ser Val Val Tyr Phe Ala Ile Ile Thr Cys
        275                 280                 285

Cys Leu Leu Arg Arg Thr Ala Phe Cys Cys Asn Gly Glu Lys Ser Arg
    290                 295                 300

Ala Lys Arg Ser Gly Ser Gly Ala Pro Val Lys Gln Thr Leu Asn Phe
305                 310                 315                 320

Asp Leu Leu Lys Leu Ala Gly Asp Val Glu Ser Asn Pro Gly Pro Met
                325                 330                 335

Glu Thr Asp Thr Leu Leu Leu Trp Val Leu Leu Leu Trp Val Pro Gly
            340                 345                 350
```

Ser Thr Gly Gln Ser Val Leu Thr Gln Pro Ser Val Ser Gly Ala
                355                 360                 365

Pro Gly Gln Arg Val Thr Ile Ser Cys Thr Gly Ser Ser Asn Ile
    370                 375                 380

Gly Ala Gly Tyr Asp Val His Trp Tyr Gln Gln Leu Pro Gly Thr Ala
385                 390                 395                 400

Pro Lys Leu Leu Ile Tyr Gly Asn Ser Asn Arg Pro Ser Gly Val Pro
                405                 410                 415

Asp Arg Phe Ser Gly Ser Lys Ser Gly Thr Ser Ala Ser Leu Ala Ile
            420                 425                 430

Thr Gly Leu Gln Ala Glu Asp Glu Ala Asp Tyr Tyr Cys Gln Ser Tyr
        435                 440                 445

Asp Ser Ser Leu Ser Gly Tyr Val Phe Gly Thr Gly Thr Lys Val Thr
    450                 455                 460

Val Leu Gly Ser Arg Gly Gly Gly Ser Gly Gly Gly Ser Gly
465                 470                 475                 480

Gly Gly Gly Ser Leu Glu Met Ala Glu Val Gln Leu Val Gln Ser Gly
            485                 490                 495

Ala Glu Val Lys Lys Pro Gly Glu Ser Leu Lys Ile Ser Cys Lys Gly
            500                 505                 510

Ser Gly Tyr Ser Phe Thr Ser Tyr Trp Ile Gly Trp Val Arg Gln Met
        515                 520                 525

Pro Gly Lys Gly Leu Glu Trp Met Gly Ile Ile Tyr Pro Gly Asp Ser
    530                 535                 540

Asp Thr Arg Tyr Ser Pro Ser Phe Gln Gly Gln Val Thr Ile Ser Ala
545                 550                 555                 560

Asp Lys Ser Ile Ser Thr Ala Tyr Leu Gln Trp Ser Ser Leu Lys Ala
                565                 570                 575

Ser Asp Thr Ala Met Tyr Tyr Cys Ala Arg Ser Met Gly Ser Ser Leu
            580                 585                 590

Tyr Ala Ser Ser Asp Val Trp Gly Gln Gly Thr Leu Val Thr Val Ser
        595                 600                 605

Ser Gly Gly Gly Gly Ser Glu Val Gln Leu Val Gln Ser Gly Ala Glu
    610                 615                 620

Met Lys Lys Pro Gly Glu Ser Leu Lys Ile Ser Cys Lys Gly Ser Gly
625                 630                 635                 640

Tyr Asn Phe Ala Ser Tyr Trp Val Gly Trp Val Arg Gln Met Pro Gly
                645                 650                 655

Lys Gly Leu Glu Trp Met Gly Thr Ile Tyr Pro Asp Asp Ser Asp Thr
            660                 665                 670

Arg Tyr Gly Pro Ala Phe Gln Gly Gln Val Thr Ile Ser Ala Asp Lys
        675                 680                 685

Ser Ile Ser Thr Ala Tyr Leu Gln Trp Ser Ser Leu Lys Ala Ser Asp
    690                 695                 700

Thr Ala Met Tyr Tyr Cys Ala Arg Asp Ser Tyr Tyr Gly Ile Asp Val
705                 710                 715                 720

Trp Gly Gln Gly Thr Leu Val Thr Val Ser Ser Ala Ser Thr Lys Gly
                725                 730                 735

Pro Ser Val Phe Pro Leu Ala Pro Ser Ser Lys Ser Thr Ser Gly Gly
            740                 745                 750

Thr Ala Ala Leu Gly Cys Leu Val Lys Asp Tyr Phe Pro Glu Pro Val
        755                 760                 765

```
Thr Val Ser Trp Asn Ser Gly Ala Leu Thr Ser Gly Val His Thr Phe
            770                 775                 780

Pro Ala Val Leu Gln Ser Ser Gly Leu Tyr Ser Leu Ser Ser Val Val
785                 790                 795                 800

Thr Val Pro Ser Ser Ser Leu Gly Thr Gln Thr Tyr Ile Cys Asn Val
            805                 810                 815

Asn His Lys Pro Ser Asn Thr Lys Val Asp Lys Arg Val Glu Pro Lys
            820                 825                 830

Ser Cys Glu Val Lys Thr Asp Ser Thr Asp His Val Lys Pro Lys Glu
            835                 840                 845

Thr Glu Asn Thr Lys Gln Pro Ser Lys Ser Cys His Lys Pro Lys Ala
850                 855                 860

Ile Val His Thr Glu Lys Val Asn Met Met Ser Leu Thr Val Leu Gly
865                 870                 875                 880

Leu Arg Met Leu Phe Ala Lys Thr Val Ala Val Asn Phe Leu Leu Thr
            885                 890                 895

Ala Lys Leu Phe Phe Leu
            900
```

<210> SEQ ID NO 182
<211> LENGTH: 896
<212> TYPE: PRT
<213> ORGANISM: Artificial Sequence
<220> FEATURE:
<223> OTHER INFORMATION: Synthetic Construct

<400> SEQUENCE: 182

```
Met Glu Thr Asp Thr Leu Leu Leu Trp Val Leu Leu Leu Trp Val Pro
1               5                   10                  15

Gly Ser Thr Gly Gln Ser Val Leu Thr Gln Pro Pro Ser Val Ser Gly
            20                  25                  30

Ala Pro Gly Gln Arg Val Thr Ile Ser Cys Thr Gly Ser Ser Ser Asn
            35                  40                  45

Ile Gly Ala Gly Tyr Asp Val His Trp Tyr Gln Gln Leu Pro Gly Thr
50                  55                  60

Ala Pro Lys Leu Leu Ile Tyr Gly Asn Ser Asn Arg Pro Ser Gly Val
65                  70                  75                  80

Pro Asp Arg Phe Ser Gly Ser Lys Ser Gly Thr Ser Ala Ser Leu Ala
            85                  90                  95

Ile Thr Gly Leu Gln Ala Glu Asp Glu Ala Asp Tyr Tyr Cys Gln Ser
            100                 105                 110

Tyr Asp Ser Ser Leu Ser Gly Tyr Val Phe Gly Thr Gly Thr Lys Val
            115                 120                 125

Thr Val Leu Gly Gly Gly Gly Ser Gly Gly Gly Ser Gln Ala
            130                 135                 140

Val Leu Thr Gln Pro Pro Ser Ala Ser Gly Thr Pro Gly Gln Arg Val
145                 150                 155                 160

Thr Ile Ser Cys Ser Gly Ser Ser Ser Asn Ile Gly Ser Asn Thr Val
            165                 170                 175

Asn Trp Tyr Gln Gln Leu Pro Gly Thr Ala Pro Lys Leu Leu Met Tyr
            180                 185                 190

Ser Asn Asn Gln Arg Pro Ser Gly Val Pro Asp Arg Phe Ser Gly Ser
            195                 200                 205

Lys Ser Gly Thr Ser Ala Ser Leu Ala Ile Ser Gly Leu Gln Ser Glu
            210                 215                 220
```

-continued

```
Asp Glu Ala Asp Tyr Tyr Cys Ala Ala Trp Asp Ser Leu Asn Gly
225                 230                 235                 240

Tyr Val Phe Gly Thr Gly Thr Lys Val Thr Val Leu Gly Gln Pro Lys
            245                 250                 255

Ala Asn Pro Thr Val Thr Leu Phe Pro Pro Ser Ser Glu Glu Leu Gln
            260                 265                 270

Ala Asn Lys Ala Thr Leu Val Cys Leu Ile Ser Asp Phe Tyr Pro Gly
            275                 280                 285

Ala Val Thr Val Ala Trp Lys Ala Asp Gly Ser Pro Val Lys Ala Gly
            290                 295                 300

Val Glu Thr Thr Lys Pro Ser Lys Gln Ser Asn Asn Lys Tyr Ala Ala
305                 310                 315                 320

Ser Ser Tyr Leu Ser Leu Thr Pro Glu Gln Trp Lys Ser His Arg Ser
            325                 330                 335

Tyr Ser Cys Gln Val Thr His Glu Gly Ser Thr Val Glu Lys Thr Val
            340                 345                 350

Ala Pro Thr Glu Cys Ser Pro Ile Lys Thr Asp Val Ile Thr Met Asp
            355                 360                 365

Pro Lys Asp Asn Cys Ser Lys Asp Ala Asn Asp Thr Leu Leu Leu Gln
370                 375                 380

Leu Thr Asn Thr Ser Ala Tyr Tyr Met Tyr Leu Leu Leu Leu Leu Lys
385                 390                 395                 400

Ser Val Val Tyr Phe Ala Ile Ile Thr Cys Cys Leu Leu Arg Arg Thr
            405                 410                 415

Ala Phe Cys Cys Asn Gly Glu Lys Ser Arg Ala Lys Arg Ser Gly Ser
            420                 425                 430

Gly Ala Pro Val Lys Gln Thr Leu Asn Phe Asp Leu Leu Lys Leu Ala
            435                 440                 445

Gly Asp Val Glu Ser Asn Pro Gly Pro Met Glu Thr Asp Thr Leu Leu
            450                 455                 460

Leu Trp Val Leu Leu Leu Trp Val Pro Gly Ser Thr Gly Glu Val Gln
465                 470                 475                 480

Leu Val Gln Ser Gly Ala Glu Val Lys Lys Pro Gly Glu Ser Leu Lys
            485                 490                 495

Ile Ser Cys Lys Gly Ser Gly Tyr Ser Phe Thr Ser Tyr Trp Ile Gly
            500                 505                 510

Trp Val Arg Gln Met Pro Gly Lys Gly Leu Glu Trp Met Gly Ile Ile
            515                 520                 525

Tyr Pro Gly Asp Ser Asp Thr Arg Tyr Ser Pro Ser Phe Gln Gly Gln
            530                 535                 540

Val Thr Ile Ser Ala Asp Lys Ser Ile Ser Thr Ala Tyr Leu Gln Trp
545                 550                 555                 560

Ser Ser Leu Lys Ala Ser Asp Thr Ala Met Tyr Tyr Cys Ala Arg Ser
            565                 570                 575

Met Gly Ser Ser Leu Tyr Ala Ser Ser Asp Val Trp Gly Gln Gly Thr
            580                 585                 590

Leu Val Thr Val Ser Ser Gly Gly Gly Gly Ser Gly Gly Gly Gly Ser
            595                 600                 605

Glu Val Gln Leu Val Gln Ser Gly Ala Glu Met Lys Lys Pro Gly Glu
            610                 615                 620

Ser Leu Lys Ile Ser Cys Lys Gly Ser Gly Tyr Asn Phe Ala Ser Tyr
625                 630                 635                 640

Trp Val Gly Trp Val Arg Gln Met Pro Gly Lys Gly Leu Glu Trp Met
```

Gly Thr Ile Tyr Pro Asp Asp Ser Asp Thr Arg Tyr Gly Pro Ala Phe
            645                 650                 655
                660                 665                 670

Gln Gly Gln Val Thr Ile Ser Ala Asp Lys Ser Ile Ser Thr Ala Tyr
                675                 680                 685

Leu Gln Trp Ser Ser Leu Lys Ala Ser Asp Thr Ala Met Tyr Tyr Cys
            690                 695                 700

Ala Arg Asp Ser Tyr Tyr Gly Ile Asp Val Trp Gly Gln Gly Thr Leu
705                 710                 715                 720

Val Thr Val Ser Ser Ala Ser Thr Lys Gly Pro Ser Val Phe Pro Leu
                725                 730                 735

Ala Pro Ser Ser Lys Ser Thr Ser Gly Gly Thr Ala Ala Leu Gly Cys
                740                 745                 750

Leu Val Lys Asp Tyr Phe Pro Glu Pro Val Thr Val Ser Trp Asn Ser
            755                 760                 765

Gly Ala Leu Thr Ser Gly Val His Thr Phe Pro Ala Val Leu Gln Ser
770                 775                 780

Ser Gly Leu Tyr Ser Leu Ser Ser Val Val Thr Val Pro Ser Ser Ser
785                 790                 795                 800

Leu Gly Thr Gln Thr Tyr Ile Cys Asn Val Asn His Lys Pro Ser Asn
            805                 810                 815

Thr Lys Val Asp Lys Arg Val Glu Pro Lys Ser Cys Glu Val Lys Thr
            820                 825                 830

Asp Ser Thr Asp His Val Lys Pro Lys Glu Thr Glu Asn Thr Lys Gln
            835                 840                 845

Pro Ser Lys Ser Cys His Lys Pro Lys Ala Ile Val His Thr Glu Lys
            850                 855                 860

Val Asn Met Met Ser Leu Thr Val Leu Gly Leu Arg Met Leu Phe Ala
865                 870                 875                 880

Lys Thr Val Ala Val Asn Phe Leu Leu Thr Ala Lys Leu Phe Phe Leu
                885                 890                 895

<210> SEQ ID NO 183
<211> LENGTH: 188
<212> TYPE: PRT
<213> ORGANISM: Artificial Sequence
<220> FEATURE:
<223> OTHER INFORMATION: Synthetic Construct

<400> SEQUENCE: 183

His Arg Arg Ala Cys Arg Lys Arg Ile Arg Gln Lys Leu His Leu Cys
1               5                   10                  15

Tyr Pro Val Gln Thr Ser Gln Pro Lys Leu Glu Leu Val Asp Ser Arg
                20                  25                  30

Pro Arg Arg Ser Ser Thr Gln Leu Arg Ser Gly Ala Ser Val Thr Glu
            35                  40                  45

Pro Val Ala Glu Glu Arg Gly Leu Met Ser Gln Pro Leu Met Glu Thr
        50                  55                  60

Cys His Ser Val Gly Ala Ala Tyr Leu Glu Ser Leu Pro Leu Gln Asp
65                  70                  75                  80

Ala Ser Pro Ala Gly Gly Pro Ser Ser Pro Arg Asp Leu Pro Glu Pro
                85                  90                  95

Arg Val Ser Thr Glu His Thr Asn Asn Lys Ile Glu Lys Ile Tyr Ile
            100                 105                 110

Met Lys Ala Asp Thr Val Ile Val Gly Thr Val Lys Ala Glu Leu Pro

```
                115                 120                 125
Glu Gly Arg Gly Leu Ala Gly Pro Ala Glu Pro Glu Leu Glu Glu
        130                 135                 140

Leu Glu Ala Asp His Thr Pro His Tyr Pro Glu Gln Glu Thr Glu Pro
145                 150                 155                 160

Pro Leu Gly Ser Cys Ser Asp Val Met Leu Ser Val Glu Glu Glu Gly
                165                 170                 175

Lys Glu Asp Pro Leu Pro Thr Ala Ala Ser Gly Lys
            180                 185

<210> SEQ ID NO 184
<211> LENGTH: 623
<212> TYPE: PRT
<213> ORGANISM: Artificial Sequence
<220> FEATURE:
<223> OTHER INFORMATION: Synthetic Construct

<400> SEQUENCE: 184

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
                100                 105                 110

Ser Arg Gly Gly Gly Gly Ser Gly Gly Gly Ser Gly Gly Gly Gly
            115                 120                 125

Ser Leu Glu Met Ala Glu Val Gln Leu Val Gln Ser Gly Ala Glu Val
        130                 135                 140

Lys Lys Pro Gly Glu Ser Leu Lys Ile Ser Cys Lys Gly Ser Gly Tyr
145                 150                 155                 160

Ser Phe Thr Ser Tyr Trp Ile Gly Trp Val Arg Gln Met Pro Gly Lys
                165                 170                 175

Gly Leu Glu Trp Met Gly Ile Ile Tyr Pro Gly Asp Ser Asp Thr Arg
            180                 185                 190

Tyr Ser Pro Ser Phe Gln Gly Gln Val Thr Ile Ser Ala Asp Lys Ser
        195                 200                 205

Ile Ser Thr Ala Tyr Leu Gln Trp Ser Ser Leu Lys Ala Ser Asp Thr
    210                 215                 220

Ala Met Tyr Tyr Cys Ala Arg Ser Met Gly Ser Ser Leu Tyr Ala Ser
225                 230                 235                 240

Ser Asp Val Trp Gly Gln Gly Thr Leu Val Thr Val Ser Ser Gly Gly
                245                 250                 255

Gly Gly Ser Gly Gly Gly Gly Ser Gln Ala Val Leu Thr Gln Pro Pro
            260                 265                 270

Ser Ala Ser Gly Thr Pro Gly Gln Arg Val Thr Ile Ser Cys Ser Gly
        275                 280                 285

Ser Ser Ser Asn Ile Gly Ser Asn Thr Val Asn Trp Tyr Gln Gln Leu
```

```
                 290                 295                 300
Pro Gly Thr Ala Pro Lys Leu Leu Met Tyr Ser Asn Asn Gln Arg Pro
305                 310                 315                 320

Ser Gly Val Pro Asp Arg Phe Ser Gly Ser Lys Ser Gly Thr Ser Ala
                325                 330                 335

Ser Leu Ala Ile Ser Gly Leu Gln Ser Glu Asp Glu Ala Asp Tyr Tyr
            340                 345                 350

Cys Ala Ala Trp Asp Asp Ser Leu Asn Gly Tyr Val Phe Gly Thr Gly
            355                 360                 365

Thr Lys Val Thr Val Leu Gly Ser Arg Gly Gly Gly Gly Ser Gly Gly
        370                 375                 380

Gly Gly Ser Gly Gly Gly Ser Leu Glu Met Ala Glu Val Gln Leu
385                 390                 395                 400

Val Gln Ser Gly Ala Glu Met Lys Lys Pro Gly Glu Ser Leu Lys Ile
                405                 410                 415

Ser Cys Lys Gly Ser Gly Tyr Asn Phe Ala Ser Tyr Trp Val Gly Trp
            420                 425                 430

Val Arg Gln Met Pro Gly Lys Gly Leu Glu Trp Met Gly Thr Ile Tyr
        435                 440                 445

Pro Asp Asp Ser Asp Thr Arg Tyr Gly Pro Ala Phe Gln Gly Gln Val
    450                 455                 460

Thr Ile Ser Ala Asp Lys Ser Ile Ser Thr Ala Tyr Leu Gln Trp Ser
465                 470                 475                 480

Ser Leu Lys Ala Ser Asp Thr Ala Met Tyr Tyr Cys Ala Arg Asp Ser
                485                 490                 495

Tyr Tyr Gly Ile Asp Val Trp Gly Gln Gly Thr Leu Val Thr Val Ser
            500                 505                 510

Ser Ala Ala Ala Ile Glu Val Met Tyr Pro Pro Tyr Leu Asp Asn
        515                 520                 525

Glu Lys Ser Asn Gly Thr Ile Ile His Val Lys Gly Lys His Leu Cys
    530                 535                 540

Pro Ser Pro Leu Phe Pro Gly Pro Ser Lys Pro Phe Trp Val Leu Val
545                 550                 555                 560

Val Val Gly Gly Val Leu Ala Cys Tyr Ser Leu Leu Val Thr Val Ala
                565                 570                 575

Phe Ile Ile Phe Trp Val Arg Ser Lys Arg Ser Arg Leu Leu His Ser
            580                 585                 590

Asp Tyr Met Asn Met Thr Pro Arg Arg Pro Gly Pro Thr Arg Lys His
        595                 600                 605

Tyr Gln Pro Tyr Ala Pro Pro Arg Asp Phe Ala Ala Tyr Arg Ser
    610                 615                 620

<210> SEQ ID NO 185
<211> LENGTH: 633
<212> TYPE: PRT
<213> ORGANISM: Artificial Sequence
<220> FEATURE:
<223> OTHER INFORMATION: Synthetic Construct

<400> SEQUENCE: 185

Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
```

```
                35                  40                  45
Met Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Trp Asp Asp Ser Leu
                 85                  90                  95

Asn Gly Tyr Val Phe Gly Thr Gly Thr Lys Val Thr Val Leu Gly Ser
                100                 105                 110

Arg Gly Gly Gly Gly Ser Gly Gly Gly Gly Ser Gly Gly Gly Gly Ser
                115                 120                 125

Leu Glu Met Ala Glu Val Gln Leu Val Gln Ser Gly Ala Glu Met Lys
    130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175

Leu Glu Trp Met Gly Thr Ile Tyr Pro Asp Asp Ser Asp Thr Arg Tyr
                180                 185                 190

Gly Pro Ala Phe Gln Gly Gln Val Thr Ile Ser Ala Asp Lys Ser Ile
                195                 200                 205

Ser Thr Ala Tyr Leu Gln Trp Ser Ser Leu Lys Ala Ser Asp Thr Ala
210                 215                 220

Met Tyr Tyr Cys Ala Arg Asp Ser Tyr Tyr Gly Ile Asp Val Trp Gly
225                 230                 235                 240

Gln Gly Thr Leu Val Thr Val Ser Ser Gly Gly Gly Ser Gly Gly
                245                 250                 255

Gly Gly Ser Gln Ser Val Leu Thr Gln Pro Pro Ser Val Ser Gly Ala
                260                 265                 270

Pro Gly Gln Arg Val Thr Ile Ser Cys Thr Gly Ser Ser Ser Asn Ile
                275                 280                 285

Gly Ala Gly Tyr Asp Val His Trp Tyr Gln Gln Leu Pro Gly Thr Ala
                290                 295                 300

Pro Lys Leu Leu Ile Tyr Gly Asn Ser Asn Arg Pro Ser Gly Val Pro
305                 310                 315                 320

Asp Arg Phe Ser Gly Ser Lys Ser Gly Thr Ser Ala Ser Leu Ala Ile
                325                 330                 335

Thr Gly Leu Gln Ala Glu Asp Glu Ala Asp Tyr Tyr Cys Gln Ser Tyr
                340                 345                 350

Asp Ser Ser Leu Ser Gly Tyr Val Phe Gly Thr Gly Thr Lys Val Thr
                355                 360                 365

Val Leu Gly Ser Arg Gly Gly Gly Gly Ser Gly Gly Gly Gly Ser Gly
    370                 375                 380

Gly Gly Ser Leu Glu Met Ala Glu Val Gln Leu Val Gln Ser Gly
385                 390                 395                 400

Ala Glu Val Lys Lys Pro Gly Glu Ser Leu Lys Ile Ser Cys Lys Gly
                405                 410                 415

Ser Gly Tyr Ser Phe Thr Ser Tyr Trp Ile Gly Trp Val Arg Gln Met
                420                 425                 430

Pro Gly Lys Gly Leu Glu Trp Met Gly Ile Ile Tyr Pro Gly Asp Ser
                435                 440                 445

Asp Thr Arg Tyr Ser Pro Ser Phe Gln Gly Gln Val Thr Ile Ser Ala
450                 455                 460
```

```
Asp Lys Ser Ile Ser Thr Ala Tyr Leu Gln Trp Ser Leu Lys Ala
465                 470                 475                 480

Ser Asp Thr Ala Met Tyr Cys Ala Arg Ser Met Gly Ser Ser Leu
                485                 490                 495

Tyr Ala Ser Ser Asp Val Trp Gly Gln Gly Thr Leu Val Thr Val Ser
            500                 505                 510

Ser Glu Gln Lys Leu Ile Ser Glu Glu Asp Leu Ala Ala Ala Ile Glu
        515                 520                 525

Val Met Tyr Pro Pro Tyr Leu Asp Asn Glu Lys Ser Asn Gly Thr
    530                 535                 540

Ile Ile His Val Lys Gly Lys His Leu Cys Pro Ser Pro Leu Phe Pro
545                 550                 555                 560

Gly Pro Ser Lys Pro Phe Trp Val Leu Val Val Gly Gly Val Leu
                565                 570                 575

Ala Cys Tyr Ser Leu Leu Val Thr Val Ala Phe Ile Ile Phe Trp Val
            580                 585                 590

Arg Ser Lys Arg Ser Arg Leu Leu His Ser Asp Tyr Met Asn Met Thr
        595                 600                 605

Pro Arg Arg Pro Gly Pro Thr Arg Lys His Tyr Gln Pro Tyr Ala Pro
    610                 615                 620

Pro Arg Asp Phe Ala Ala Tyr Arg Ser
625                 630

<210> SEQ ID NO 186
<211> LENGTH: 623
<212> TYPE: PRT
<213> ORGANISM: Artificial Sequence
<220> FEATURE:
<223> OTHER INFORMATION: Synthetic Construct

<400> SEQUENCE: 186

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Met Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Met Lys
    130                 135                 140

Lys Pro Gly Glu Ser Leu Lys Ile Ser Cys Lys Gly Ser Gly Tyr Asn
145                 150                 155                 160

Phe Ala Ser Tyr Trp Val Gly Trp Val Arg Gln Met Pro Gly Lys Gly
                165                 170                 175

Leu Glu Trp Met Gly Thr Ile Tyr Pro Asp Asp Ser Asp Thr Arg Tyr
            180                 185                 190
```

```
Gly Pro Ala Phe Gln Gly Gln Val Thr Ile Ser Ala Asp Lys Ser Ile
            195                 200                 205

Ser Thr Ala Tyr Leu Gln Trp Ser Ser Leu Lys Ala Ser Asp Thr Ala
    210                 215                 220

Met Tyr Tyr Cys Ala Arg Asp Ser Tyr Gly Ile Asp Val Trp Gly
225                 230                 235                 240

Gln Gly Thr Leu Val Thr Val Ser Ser Gly Gly Gly Ser Gly Gly
                245                 250                 255

Gly Gly Ser Gln Ser Val Leu Thr Gln Pro Pro Ser Val Ser Gly Ala
            260                 265                 270

Pro Gly Gln Arg Val Thr Ile Ser Cys Thr Gly Ser Ser Ser Asn Ile
            275                 280                 285

Gly Ala Gly Tyr Asp Val His Trp Tyr Gln Gln Leu Pro Gly Thr Ala
290                 295                 300

Pro Lys Leu Leu Ile Tyr Gly Asn Ser Asn Arg Pro Ser Gly Val Pro
305                 310                 315                 320

Asp Arg Phe Ser Gly Ser Lys Ser Gly Thr Ser Ala Ser Leu Ala Ile
            325                 330                 335

Thr Gly Leu Gln Ala Glu Asp Glu Ala Asp Tyr Tyr Cys Gln Ser Tyr
            340                 345                 350

Asp Ser Ser Leu Ser Gly Tyr Val Phe Gly Thr Gly Thr Lys Val Thr
            355                 360                 365

Val Leu Gly Ser Arg Gly Gly Gly Ser Gly Gly Gly Gly Ser Gly
370                 375                 380

Gly Gly Ser Leu Glu Met Ala Glu Val Gln Leu Val Gln Ser Gly
385                 390                 395                 400

Ala Glu Val Lys Lys Pro Gly Glu Ser Leu Lys Ile Ser Cys Lys Gly
            405                 410                 415

Ser Gly Tyr Ser Phe Thr Ser Tyr Trp Ile Gly Trp Val Arg Gln Met
            420                 425                 430

Pro Gly Lys Gly Leu Glu Trp Met Gly Ile Ile Tyr Pro Gly Asp Ser
            435                 440                 445

Asp Thr Arg Tyr Ser Pro Ser Phe Gln Gly Gln Val Thr Ile Ser Ala
450                 455                 460

Asp Lys Ser Ile Ser Thr Ala Tyr Leu Gln Trp Ser Ser Leu Lys Ala
465                 470                 475                 480

Ser Asp Thr Ala Met Tyr Tyr Cys Ala Arg Ser Met Gly Ser Ser Leu
            485                 490                 495

Tyr Ala Ser Ser Asp Val Trp Gly Gln Gly Thr Leu Val Thr Val Ser
            500                 505                 510

Ser Ala Ala Ala Ile Glu Val Met Tyr Pro Pro Pro Tyr Leu Asp Asn
            515                 520                 525

Glu Lys Ser Asn Gly Thr Ile Ile His Val Lys Gly Lys His Leu Cys
            530                 535                 540

Pro Ser Pro Leu Phe Pro Gly Pro Ser Lys Pro Phe Trp Val Leu Val
545                 550                 555                 560

Val Val Gly Gly Val Leu Ala Cys Tyr Ser Leu Leu Val Thr Val Ala
            565                 570                 575

Phe Ile Ile Phe Trp Val Arg Ser Lys Arg Ser Arg Leu Leu His Ser
            580                 585                 590
```

```
Asp Tyr Met Asn Met Thr Pro Arg Arg Pro Gly Pro Thr Arg Lys His
            595                 600                 605
Tyr Gln Pro Tyr Ala Pro Pro Arg Asp Phe Ala Ala Tyr Arg Ser
    610             615                 620
```

CONSTRUCTS TARGETING PROSTATE-SPECIFIC MEMBRANE ANTIGEN (PSMA) AND USES THEREOF

CROSS-REFERENCE TO RELATED APPLICATION

This application is a U.S. national phase application under 35 U.S.C. § 371 of International Application No. PCT/US2019/037534, filed on Jun. 17, 2019, which claims priority to U.S. Provisional Application No. 62/686,605, filed on Jun. 18, 2018, the contents of each of which are hereby incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 750042001500SEQLIST.TXT, date recorded: Dec. 11, 2020, size: 487 KB).

FIELD OF THE INVENTION

The present disclosure pertains to polypeptide constructs that specifically bind Prostate-Specific Membrane Antigen (PSMA), and uses thereof including treating and diagnosing diseases.

BACKGROUND OF THE INVENTION

Prostate cancer is the second most common cancer and the second leading cause of cancer-related deaths in American men. There are over 27,000 deaths from prostate cancer every year in United States (American Cancer Society). Between 35-61% of prostate cancer patients undergoing radical prostatectomy or radical radiotherapy eventually relapse. These patients may respond transiently to androgen deprivation therapy, but a majority will subsequently progress to hormone-refractory disease for which curative systemic therapies are lacking (Perambakam S, et al., *Clin. Dev. Immunol.* 2010; Epub 2011 Jan. 5).

Prostate-Specific Membrane Antigen (PSMA), is a 750 amino acid type II transmembrane glycoprotein that is highly expressed on the surface of prostate tumor cells at all tumor stages and is known to be upregulated in castrate-resistant and metastatic prostate cancers (Afshar-Oromieh, A. et al., *J. Nucl. Med.* 2016, 57: 79S). In other solid tumors including colon, ovarian, breast, and kidney cancers, elevated PSMA expression has been observed on tumor neovasculature, but not normal vasculature, suggesting a role for PSMA in angiogenesis. Most PSMA expression appears to be restricted to the prostate, but lower-level expression is seen in the brain, kidneys, salivary glands, and small intestine.

Small molecule PSMA ligands have been used in imaging studies in the detection of metastasis of prostate cancers in lymph nodes and bone. Given the expression pattern of PSMA, it has also been explored as a therapeutic target. Current immunotherapy approaches to target PSMA include peptide, cell, vector or DNA-based vaccines, administration of monoclonal antibodies (mAb) or expression of a DNA-encoded mAb against PSMA (Muthumani, K. et al., *Cancer Immunol. Immunother.* 2017, 66: 1577) and chimeric antigen receptor (CAR)-modified T cells (Junghans, R P et al., *Prostate.* 2016, 76: 1257). Despite the reported expression of PSMA in normal tissues, anti-PSMA toxicities were not observed in the Phase I clinical study using anti-PSMA CAR T cells.

Accordingly, there remains a need in the art for agents (such as polypeptide constructs) that target PSMA for the diagnosis and/or treatment of cancer. The present application addresses these and other needs.

The disclosures of all publications, patents, patent applications and published patent applications referred to herein are hereby incorporated herein by reference in their entirety.

BRIEF SUMMARY OF THE INVENTION

In some embodiments, provided is an anti-prostate specific membrane antigen (PSMA) construct comprising an antibody moiety specifically recognizing an extracellular domain of a cell surface-bound PSMA that comprises an amino acid sequence set forth in SEQ ID NO: 44. In some embodiments according to (or as applied to) any of the embodiments above, the PSMA is expressed on the surface of a cancer cell. In some embodiments according to (or as applied to) any of the embodiments above, the cancer cell is a prostate cancer cell, a renal cell cancer cell, a uterine cancer cell, or a liver cancer cell. In some embodiments according to (or as applied to) any of the embodiments above, the cancer cell is a prostate cancer cell. In some embodiments according to (or as applied to) any of the embodiments above, the prostate cancer cell is a hormone refractory prostate cancer cell or a metastatic prostate cancer cell. In some embodiments according to (or as applied to) any of the embodiments above, the cancer cell is a renal cancer cell. In some embodiments according to (or as applied to) any of the embodiments above, the renal cancer cell is a clear cell renal cell carcinoma (CCRCC) cell. In some embodiments according to (or as applied to) any of the embodiments above, the PSMA is expressed on the surface of a cell selected from the group consisting of: LNCaP, MDA PCa 2b, VCaP, 22Rv1, Caki-1; HCC1482; and HuH-7.

In some embodiments according to (or as applied to) any of the embodiments above, the antibody moiety comprises: i) a heavy chain variable domain ($V_H$) comprising a CDR-H1 comprising the amino acid sequence of any one of SEQ ID NOs: 1-2, or a variant thereof comprising up to about 5 amino acid substitutions, a CDR-H2 comprising the amino acid sequence of any one of SEQ ID NOs: 3-4, or a variant thereof comprising up to about 5 amino acid substitutions, and a CDR-H3 comprising the amino acid sequence of any one of SEQ ID NOs: 5-6, or a variant thereof comprising up to about 5 amino acid substitutions; and ii) a light chain variable domain ($V_L$) comprising a CDR-L1 comprising the amino acid sequence of any one of SEQ ID NOs: 7-8, or a variant thereof comprising up to about 5 amino acid substitutions, a CDR-L2 comprising the amino acid sequence GNS or SSN, or a variant thereof comprising about 2 amino acid substitutions, and a CDR-L3 comprising the amino acid sequence of any one of SEQ ID NOs: 9-10, or a variant thereof comprising up to about 5 amino acid substitutions. In some embodiments according to (or as applied to) any of the embodiments above, the antibody moiety comprises: i) a $V_H$ comprising a CDR-H1 comprising the amino acid sequence of any one of SEQ ID NOs: 1-2, a CDR-H2 comprising the amino acid sequence of any one of SEQ ID NOs: 3-4, and a CDR-H3 comprising the amino acid sequence of any one of SEQ ID NOs: 5-6; and ii) a $V_L$ comprising a CDR-L1 comprising the amino acid sequence of any one of SEQ ID NOs: 7-8, a CDR-L2 comprising the amino acid sequence of GNS or SNN, and a CDR-L3 comprising the amino acid sequence of any one of SEQ ID NOs: 9-10. In some embodiments according to (or as applied to) any of the embodiments above, the antibody moiety comprises i) a $V_H$ comprising a CDR-H1 comprising the amino acid sequence of SEQ ID NO: 1, a CDR-H2 comprising the amino acid sequence of SEQ ID NO: 3, and a CDR-H3 comprising the amino acid sequence of SEQ ID NO: 5; and ii) a light chain variable domain ($V_L$) comprising a CDR-L1 comprising the amino acid sequence of SEQ ID NO: 7, a CDR-L2 comprising the amino acid sequence GNS, and a CDR-L3 comprising the amino acid sequence of SEQ ID NO: 9. In some embodiments according to (or as applied to) any of the embodiments above, the antibody moiety comprises i) a $V_H$ comprising a CDR-H1 comprising the amino acid sequence of SEQ ID NO: 2, a CDR-H2 comprising the amino acid sequence of SEQ ID NO: 4, and a CDR-H3 comprising the amino acid sequence of SEQ ID NO: 6; and ii) a $V_L$ comprising a CDR-L1 comprising the amino acid sequence of SEQ ID NO: 8, a CDR-L2 comprising the amino acid sequence SNN, and a CDR-L3 comprising the amino acid sequence of SEQ ID NO: 10.

In some embodiments according to (or as applied to) any of the embodiments above, the antibody moiety comprises a CDR-H1, a CDR-H2, and a CDR-H3 of a heavy chain variable domain ($V_H$) set forth in SEQ ID NO: 16 or 17 and a CDR-L1, a CDR-L2, and a CDR-L3 of a light chain variable domain ($V_L$) set forth in SEQ ID NO: 18 or 19. In some embodiments according to (or as applied to) any of the embodiments above, the antibody moiety comprises the CDR-H1, CDR-H2, and CDR-H3 of the $V_H$ set forth in SEQ ID NO: 16 and the CDR-L1, the CDR-L2, and the CDR-L3 of the $V_L$ set forth in SEQ ID NO: 18. In some embodiments according to (or as applied to) any of the embodiments above, the antibody moiety comprises the CDR-H1, CDR-H2, and CDR-H3 of the $V_H$ set forth in SEQ ID NO: 17 and the CDR-L1, the CDR-L2, and the CDR-L3 of the $V_L$ set forth in SEQ ID NO: 19. In some embodiments according to (or as applied to) any of the embodiments above, the antibody moiety comprises: i) a $V_H$ comprising an amino acid sequence having at least about 85% sequence identity to SEQ ID NO: 16 or 17 and ii) a $V_L$ comprising an amino acid sequence having at least about 85% sequence identity to SEQ ID NO: 18 or 19. In some embodiments according to (or as applied to) any of the embodiments above, the antibody moiety comprises: i) a $V_H$ comprising an amino acid sequence having at least about 90% sequence identity to SEQ ID NO: 16 or 17 and ii) a $V_L$ comprising an amino acid sequence having at least about 90% sequence identity to SEQ ID NO: 18 or 19. In some embodiments according to (or as applied to) any of the embodiments above, the antibody moiety comprises: i) a $V_H$ comprising an amino acid sequence having at least about 95% sequence identity to SEQ ID NO: 16 or 17 and ii) a $V_L$ comprising an amino acid sequence having at least about 95% sequence identity to SEQ ID NO: 18 or 19. In some embodiments according to (or as applied to) any of the embodiments above, the antibody moiety comprises: a $V_H$ comprising an amino acid sequence of SEQ ID NO: 16 and a $V_L$ comprising the amino acid sequence of SEQ ID NO: 18. In some embodiments according to (or as applied to) any of the embodiments above, the antibody moiety comprises: a $V_H$ comprising an amino acid sequence of SEQ ID NO: 17; and a $V_L$ comprising the amino acid sequence of SEQ ID NO: 19. In some embodiments according to (or as applied to) any of the embodiments above, the antibody moiety comprises: i) a heavy chain variable domain ($V_H$) comprising the amino acid sequences of SEQ ID NOs: 1, 3, and 5, and a light chain variable domain ($V_L$) comprising the amino acid sequence of SEQ ID NO: 7, GNS, and SEQ ID NO: 9; or ii) a $V_H$ comprising the amino acid sequences of SEQ ID NOs: 2, 4, and 6, and a $V_L$ comprising the amino acid sequence of SEQ ID NO: 8, SSN, and SEQ ID NO: 10.

In some embodiments according to (or as applied to) any of the embodiments above, the antibody moiety specifically recognizing PSMA is chimeric, human, partially humanized, fully humanized, or semi-synthetic. In some embodiments according to (or as applied to) any of the embodiments above, the antibody moiety specifically recognizing PSMA is a full-length antibody, a Fab, a Fab', a F(ab')$_2$, an Fv, or a single chain Fv (scFv). In some embodiments according to (or as applied to) any of the embodiments above antibody moiety specifically recognizing PSMA is an scFv. In some embodiments according to (or as applied to) any of the embodiments above, the scFv comprises an amino acid sequence set forth in SEQ ID NO: 20. In some embodiments according to (or as applied to) any of the embodiments above, the scFv comprises an amino acid sequence set forth in SEQ ID NO: 21. In some embodiments according to (or as applied to) any of the embodiments above, the antibody moiety specifically recognizing PSMA is a Fab or Fab'. In some embodiments according to (or as applied to) any of the embodiments above, the antibody moiety specifically recognizing PSMA is fused to an Fc fragment optionally via a linker. In some embodiments according to (or as applied to) any of the embodiments above, the Fc fragment is a human IgG Fc fragment. In some embodiments according to (or as applied to) any of the embodiments above, the human IgG is an IgG1, IgG2, IgG3, or IgG4. In some embodiments according to (or as applied to) any of the embodiments above, the anti-PSMA antibody moiety is a full-length antibody. In some embodiments according to (or as applied to) any of the embodiments above, the full-length antibody comprises a heavy chain comprising an amino acid sequence set forth in SEQ ID NO: 39 and a light chain comprising an amino acid sequence set forth in SEQ ID NO: 40. In some embodiments according to (or as applied to) any of the embodiments above, the full-length antibody comprises a heavy chain comprising an amino acid sequence set forth in SEQ ID NO: 41 and a light chain comprising an amino acid sequence set forth in SEQ ID NO: 42. In some embodiments according to (or as applied to) any of the embodiments above, the anti-PSMA construct is monospecific. In some embodiments according to (or as applied to) any of the embodiments above the anti-PSMA construct is multispecific. In some embodiments according to (or as applied to) any of the embodiments above the anti-PSMA construct is bispecific. In some embodiments according to (or as applied to) any of the embodiments above the anti-PSMA construct is a tandem scFv, a diabody (Db), a single chain diabody (scDb), a dual-affinity retargeting (DART) antibody, a F(ab')2, a dual variable domain (DVD) antibody, a knob-into-hole (KiH) antibody, a dock and lock (DNL) antibody, a chemically cross-linked antibody, a heteromultimeric antibody, or a heteroconjugate antibody.

In some embodiments according to (or as applied to) any of the embodiments above the anti-PSMA construct is a tandem scFv comprising two scFvs linked by a peptide linker. In some embodiments according to (or as applied to) any of the embodiments above the anti-PSMA construct further comprises a second antibody moiety specifically recognizing a second antigen. In some embodiments according to (or as applied to) any of the embodiments above, the second antigen is an antigen on the surface of a T cell. In some embodiments according to (or as applied to) any of the embodiments above, the T cell is selected from the group consisting of a cytotoxic T cell, a helper T cell, and a natural killer T cell. In some embodiments according to (or as applied to) any of the embodiments above, the second antigen is selected from the group consisting of CD3γ, CD3δ, CD3ε, CD3ζ, CD28, OX40, GITR, CD137, CD27, CD40L, and HVEM. In some embodiments according to (or as applied to) any of the embodiments above, the second antigen is CD3ε. In some embodiments according to (or as applied to) any of the embodiments above, the anti-PSMA construct is a tandem scFv comprising an N-terminal scFv specifically recognizing PSMA and a C-terminal scFv specifically recognizing CD3ε. In some embodiments according to (or as applied to) any of the embodiments above, the anti-PSMA construct comprises an amino acid sequence set forth in SEQ ID NO: 25 or 26. In some embodiments according to (or as applied to) any of the embodiments above, the anti-PSMA construct comprises an amino acid sequence set forth in SEQ ID NO: 27 or 28. In some embodiments according to (or as applied to) any of the embodiments above, the expression of the anti-PSMA construct is induced by the activation of an engineered T cell. In some embodiments according to (or as applied to) any of the embodiments above, the engineered T cell is a T cell comprising a chimeric antigen receptor (CAR). In some embodiments according to (or as applied to) any of the embodiments above, the CAR specifically binds to PSMA. In some embodiments according to (or as applied to) any of the embodiments above, the CAR binds to an antigen other than PSMA. In some embodiments according to (or as applied to) any of the embodiments above, the engineered T cell is a T cell comprising a chimeric antibody-T cell receptor (TCR) construct (caTCR). In some embodiments according to (or as applied to) any of the embodiments above, the caTCR specifically binds to PSMA. In some embodiments according to (or as applied to) any of the embodiments above, the caTCR binds to an antigen other than PSMA. In some embodiments according to (or as applied to) any of the embodiments above, the second antigen bound by the second antibody moiety of the anti-PSMA construct is an antigen on the surface of a B cell, a natural killer cell, a dendritic cell, a macrophage, a monocyte, or a neutrophil.

In some embodiments according to (or as applied to) any of the embodiments above, the anti-PSMA construct is a CAR comprising: (a) an extracellular domain comprising the anti-PSMA antibody moiety; (b) a transmembrane domain; and (c) an intracellular signaling domain. In some embodiments according to (or as applied to) any of the embodiments above, the intracellular signaling domain comprises a primary immune cell signaling sequence derived from CD3ζ, TCRζ, FcRγ, FcRβ, CD3γ, CD3δ, CD3ε, CD5, CD22, CD79a, CD79b, or CD66d. In some embodiments according to (or as applied to) any of the embodiments above, the intracellular signaling domain further comprises a costimulatory signaling sequence derived from CD28, 4-1BB, ICOS, or OX40. In some embodiments according to (or as applied to) any of the embodiments above, the intracellular signaling domain comprises a CD3ζ intracellular signaling sequence and a CD28 intracellular signaling sequence. In some embodiments according to (or as applied to) any of the embodiments above, the anti-PSMA construct comprises an amino acid sequence set forth in SEQ ID NO: 29. In some embodiments according to (or as applied to) any of the embodiments above, the anti-PSMA construct comprises an amino acid sequence set forth in SEQ ID NO: 30.

In some embodiments according to (or as applied to) any of the embodiments above, the anti-PSMA construct is a caTCR comprising: (a) an extracellular domain comprising the anti-PSMA antibody moiety; and (b) a T cell receptor module (TCRM) comprising a first TCR domain (TCRD) comprising a first TCR transmembrane domain (TCR-TM) and a second TCRD comprising a second TCR-TM, wherein the TCRM facilitates recruitment of at least one TCR-associated signaling molecule. In some embodiments according to (or as applied to) any of the embodiments above, the first TCR-TM is derived from one of the transmembrane domains of a first naturally occurring TCR and the second TCR-TM is derived from the other transmembrane domain of the first naturally occurring TCR. In some embodiments according to (or as applied to) any of the embodiments above, the at least one of the TCR-TMs is non-naturally occurring. In some embodiments according to (or as applied to) any of the embodiments above, the TCRM comprising the at least one non-naturally occurring TCR-TM allows for enhanced recruitment of the at least one TCR-associated signaling molecule as compared to a TCRM comprising the first naturally occurring T cell receptor transmembrane domains. In some embodiments according to (or as applied to) any of the embodiments above, the first and second TCR-TMs are naturally occurring. In some embodiments according to (or as applied to) any of the embodiments above, the first naturally occurring TCR is a γ/δ TCR. In some embodiments according to (or as applied to) any of the embodiments above, the anti-PSMA construct comprises a first polypeptide chain comprising an amino acid sequence set forth in SEQ ID NO: 31 and a second polypeptide chain comprising an amino acid sequence set forth in SEQ ID NO: 32. In some embodiments according to (or as applied to) any of the embodiments above, the anti-PSMA construct comprises a first polypeptide chain comprising an amino acid sequence set forth in SEQ ID NO: 34 and a second polypeptide chain comprising an amino acid sequence set forth in SEQ ID NO: 35. In some embodiments according to (or as applied to) any of the embodiments above, the first naturally occurring TCR is an α/β TCR. In some embodiments according to (or as applied to) any of the embodiments above, the TCR-associated signaling molecule is selected from the group consisting of CD3δε, CD3γε, and CD3ζζ. In some embodiments according to (or as applied to) any of the embodiments above, the caTCR lacks a functional primary immune cell signaling domain. In some embodiments according to (or as applied to) any of the embodiments above, the caTCR lacks any primary immune cell signaling sequences.

In some embodiments according to (or as applied to) any of the embodiments above, the anti-PSMA construct is a chimeric signaling receptor (CSR) comprising: i) a ligand-binding module that is capable of binding or interacting with PSMA; ii) a transmembrane module; and iii) a co-stimulatory immune cell signaling module that is capable of providing a co-stimulatory signal to the effector cell, wherein the ligand-binding module and the co-stimulatory immune cell signaling module are not derived from the same molecule, and wherein the CSR lacks a functional primary immune cell signaling domain. In some embodiments according to (or as applied to) any of the embodiments above, the CSR lacks any primary immune cell signaling sequences. In some embodiments according to (or as applied to) any of the embodiments above, the ligand-binding module comprises the anti-PSMA construct of any one of claims 1-23. In some embodiments according to (or as applied to) any of the embodiments above, the transmembrane module of the CSR comprises transmembrane domains derived from CD28, CD3ε, CD3ζ, CD45, CD4, CD5, CD8, CD9, CD16, CD22, CD33, CD37, CD64, CD80, CD86, CD134, CD137, or CD154. In some embodiments according to (or as applied to) any of the embodiments above, the co-stimulatory immune cell signaling module is derived from the intracellular domain of a co-stimulatory receptor of a TCR. In some embodiments according to (or as applied to) any of the embodiments above, the co-stimulatory receptor is selected from the group consisting of CD28, 4-1BB, OX40, ICOS, CD27, and CD40. In some embodiments according to (or as applied to) any of the embodiments above, the expression of the CSR is inducible upon activation of an engineered T cell. In some embodiments according to (or as applied to) any of the embodiments above, the engineered T cell is a T cell comprising a CAR. In some embodiments according to (or as applied to) any of the embodiments above, the CAR specifically binds to PSMA. In some embodiments according to (or as applied to) any of the embodiments above, the CAR binds to an antigen other than PSMA. In some embodiments according to (or as applied to) any of the embodiments above, the engineered T cell is a T cell comprising a caTCR. In some embodiments according to (or as applied to) any of the embodiments above, the caTCR specifically binds to PSMA. In some embodiments according to (or as applied to) any of the embodiments above, the caTCR binds to an antigen other than PSMA. In some embodiments according to (or as applied to) any of the embodiments above, the anti-PSMA construct comprises an amino acid sequence set forth in SEQ ID NO 37. In some embodiments according to (or as applied to) any of the embodiments above, the anti-PSMA construct comprises an amino acid sequence set forth in SEQ ID NO 38.

In some embodiments according to (or as applied to) any of the embodiments above, the anti-PSMA construct is conjugated to an effector molecule. In some embodiments according to (or as applied to) any of the embodiments above, the effector molecule is a therapeutic agent selected from the group consisting of: a drug, a toxin, a radioisotope, a protein, a peptide, and a nucleic acid. In some embodiments according to (or as applied to) any of the embodiments above, the therapeutic agent is a drug or a toxin. In some embodiments according to (or as applied to) any of the embodiments above, the effector molecule is a detectable label.

In another aspect of the current invention, provided is an effector cell that has been genetically modified with one or more nucleic acids encoding the anti-PSMA CAR according to (or as applied to) any of the embodiments above or the anti-PSMA caTCR according to (or as applied to) any of the embodiments above. In some embodiments according to (or as applied to) any of the embodiments above, the one or more nucleic acids encoding the anti-PSMA CAR or anti-PSMA caTCR also encode a CSR comprising a ligand binding module that binds a target antigen. In some embodiments according to (or as applied to) any of the embodiments above, the effector cell has been genetically modified with one or more additional nucleic acids encoding a CSR comprising a ligand binding module that binds a target antigen. In some embodiments according to (or as applied to) any of the embodiments above, the target antigen is PSMA. In some embodiments according to (or as applied to) any of the embodiments above, the target antigen is an antigen other than PSMA. In some embodiments according to (or as applied to) any of the embodiments above, the one or more nucleic acids encoding the anti-PSMA CAR or anti-PSMA caTCR also encode a tandem scFv that comprises a first scFv that binds a target antigen. In some embodiments according to (or as applied to) any of the embodiments above, the effector cell has been genetically modified with one or more additional nucleic acids encoding a tandem scFv that comprises a first scFv that binds a target antigen. In some embodiments according to (or as applied to) any of the embodiments above, the target antigen is PSMA. In some embodiments according to (or as applied to) any of the embodiments above, the target is an antigen other than PSMA. In some embodiments according to (or as applied to) any of the embodiments above, provided is an effector cell that has been genetically modified with one or more nucleic acids encoding the anti-PSMA tandem scFv according to (or as applied to) any of the embodiments above or the anti-PSMA CSR according to (or as applied to) any of the embodiments above. In some embodiments according to (or as applied to) any of the embodiments above, the one or more nucleic acids encoding the anti-PSMA tandem scFv or anti-PSMA CSR also encode a CAR. In some embodiments according to (or as applied to) any of the embodiments above, the effector cell has been genetically modified with one or more additional nucleic acids encoding a CAR. In some embodiments according to (or as applied to) any of the embodiments above, the CAR specifically binds PSMA. In some embodiments according to (or as applied to) any of the embodiments above, the CAR specifically binds an antigen other than PSMA. In some embodiments according to (or as applied to) any of the embodiments above, the one or more nucleic acids encoding the anti-PSMA tandem scFv or anti-PSMA CSR also encode a caTCR. In some embodiments according to (or as applied to) any of the embodiments above, the effector cell has been genetically modified with one or more additional nucleic acids encoding a caTCR. In some embodiments according to (or as applied to) any of the embodiments above, the caTCR specifically binds PSMA. In some embodiments according to (or as applied to) any of the embodiments above, the caTCR specifically binds an antigen other than PSMA. In some embodiments according to (or as applied to) any of the embodiments above, the effector cell is an immune cell. In some embodiments according to (or as applied to) any of the embodiments above, the immune cell is a T cell. In some embodiments according to (or as applied to) any of the embodiments above, the T cell is a cytotoxic T cell, a helper T cell, or a natural killer T cell.

In another aspect of the current invention, provided is a method of producing an effector cell, comprising genetically modifying a cell with one or more nucleic acids encoding the anti-PSMA CAR according to (or as applied to) any of the embodiments above, or the anti-PSMA caTCR according to (or as applied to) any of the embodiments above. In some embodiments according to (or as applied to) any of the embodiments above, the one or more nucleic acids encoding the anti-PSMA CAR or anti-PSMA caTCR also encode a CSR comprising a ligand binding module that binds a target antigen. In some embodiments according to (or as applied to) any of the embodiments above, the method comprises further genetically modifying the cell with one or more additional nucleic acids encoding a CSR comprising a ligand binding module that binds a target antigen. In some embodiments according to (or as applied to) any of the embodiments above, the target antigen is PSMA. In some embodiments according to (or as applied to) any of the embodiments above, the target antigen is an antigen other than PSMA. In some embodiments according to (or as applied to) any of the embodiments above, the one or more nucleic acids encoding the anti-PSMA CAR or anti-PSMA caTCR also encode a tandem scFv that comprises a first scFv that binds a target antigen. In some embodiments according to (or as applied to) any of the embodiments above, the method comprises further genetically modifying the cell with one or more additional nucleic acids encoding a tandem scFv that comprises a first scFv that binds a target antigen. In some embodiments according to (or as applied to) any of the embodiments above, the target antigen is PSMA. In some embodiments according to (or as applied to) any of the embodiments above, the target is an antigen other than PSMA. In some embodiments according to (or as applied to) any of the embodiments above, provided is a method of producing an effector cell, comprising genetically modifying a cell with one or more nucleic acids encoding the anti-PSMA tandem scFv according to (or as applied to) any of the embodiments above, or the anti-PSMA CSR according to (or as applied to) any of the embodiments above. In some embodiments according to (or as applied to) any of the embodiments above, the one or more nucleic acids encoding the anti-PSMA tandem scFv or anti-PSMA CSR also encode a CAR. In some embodiments according to (or as applied to) any of the embodiments above, the method comprises further genetically modifying the cell with one or more additional nucleic acids encoding a CAR. In some embodiments according to (or as applied to) any of the embodiments above, the CAR specifically binds PSMA. In some embodiments according to (or as applied to) any of the embodiments above, the CAR specifically binds an antigen other than PSMA. In some embodiments according to (or as applied to) any of the embodiments above, the one or more nucleic acids encoding the anti-PSMA CAR or anti-PSMA caTCR also encode a caTCR. In some embodiments according to (or as applied to) any of the embodiments above, the method comprises further genetically modifying the cell with one or more additional nucleic acids encoding a caTCR. In some embodiments according to (or as applied to) any of the embodiments above, the caTCR specifically binds PSMA. In some embodiments according to (or as applied to) any of the embodiments above, the caTCR specifically binds an antigen other than PSMA. In some embodiments according to (or as applied to) any of the embodiments above, the effector cell is an immune cell. In some embodiments according to (or as applied to) any of the embodiments above, the immune cell is a T cell. In some embodiments according to (or as applied to) any of the embodiments above, the T cell is a cytotoxic T cell, a helper T cell, or a natural killer T cell.

In another aspect of the current invention, provided is nucleic acid encoding the polypeptide portion(s) of the anti-PSMA construct according to (or as applied to) any of the embodiments above. Also provided is a vector comprising the nucleic acid according to (or as applied to) any of the embodiments above. Also provided is a host cell comprising the nucleic acid or the vector according to (or as applied to) any of the embodiments above.

Also provided is a method of producing the anti-PSMA construct according to (or as applied to) any of the embodiments above, comprising culturing the host cell according to (or as applied to) any of the embodiments above under conditions where the anti-PSMA construct is expressed, and recovering the anti-PSMA construct produced by the host cell.

In another aspect of the current invention, provided is a pharmaceutical composition comprising the anti-PSMA construct according to (or as applied to) any of the embodiments above, the effector cell according to (or as applied to) any of the embodiments above, the nucleic acid according to (or as applied to) any of the embodiments above, or the vector according to (or as applied to) any of the embodiments above, and a pharmaceutical acceptable carrier.

In another aspect of the current invention, provided is a kit comprising the anti-PSMA construct of according to (or as applied to) any of the embodiments above, the effector cell according to (or as applied to) any of the embodiments above, the nucleic acid according to (or as applied to) any of the embodiments above, the vector according to (or as applied to) any of the embodiments above and/or the host cell of according to (or as applied to) any of the embodiments above.

Another aspect of the current invention provides a method of detecting PSMA in a sample, comprising contacting the sample with the anti-PSMA construct according to (or as applied to) any of the embodiments above conjugated to a detectable label, and detecting the presence of the label. In some embodiments according to (or as applied to) any of the embodiments above, provided the sample comprises cells expressing PSMA.

Another aspect of the current invention provides a method of treating an individual having a PSMA-associated disease or disorder, comprising administering to the individual an effective amount of the pharmaceutical composition according to (or as applied to) any of the embodiments above. In some embodiments according to (or as applied to) any of the embodiments above, provided is a method of treating an individual having a PSMA-associated disease or disorder, comprising administering to the individual an effector cell that has been genetically modified with one or more nucleic acids that encode the anti-PSMA CAR according to (or as applied to) any of the embodiments above, or the anti-PSMA caTCR according to (or as applied to) any of the embodiments above. In some embodiments according to (or as applied to) any of the embodiments above, the method comprises genetically modifying the effector cell with the one or more nucleic acids prior to administration. In some embodiments according to (or as applied to) any of the embodiments above, the one or more nucleic acids that encode the anti-PSMA CAR or the anti-PSMA caTCR also encode a CSR or a tandem scFv. In some embodiments according to (or as applied to) any of the embodiments above, the method comprises further genetically modifying the effector cell with one or more additional nucleic acids encoding a CSR or a tandem scFv. In some embodiments according to (or as applied to) any of the embodiments above, the tandem scFv specifically binds PSMA. In some embodiments according to (or as applied to) any of the embodiments above, the tandem scFv specifically binds an antigen other than PSMA. In some embodiments according to (or as applied to) any of the embodiments above, the CSR specifically binds PSMA. In some embodiments according to (or as applied to) any of the embodiments above, the CSR specifically binds an antigen other than PSMA. In some embodiments according to (or as applied to) any of the embodiments above, provided is a method of treating an individual having a PSMA-associated disease or disorder, comprising administering to the individual an effector cell that has been genetically modified with one or more nucleic acids that encode the anti-PSMA tandem scFv according to (or as applied to) any of the embodiments above, or anti-PSMA CSR according to (or as applied to) any of the embodiments above. In some embodiments according to (or as applied to) any of the embodiments above, the method comprises genetically modifying the effector cell with the one or more nucleic acids prior to administration. In some embodiments according to (or as applied to) any of the embodiments above, the one or more nucleic acids that encode the anti-PSMA CSR or anti-PSMA tandem scFv also encode a CAR or a caTCR. In some embodiments according to (or as applied to) any of the embodiments above, the method comprises further genetically modifying the effector cell with one or more additional nucleic acids encoding a CAR or a caTCR. In some embodiments according to (or as applied to) any of the embodiments above, the CAR specifically binds PSMA. In some embodiments according to (or as applied to) any of the embodiments above, the CAR specifically binds an antigen other than PSMA. In some embodiments according to (or as applied to) any of the embodiments above, the caTCR specifically binds PSMA. In some embodiments according to (or as applied to) any of the embodiments above, the caTCR specifically binds an antigen other than PSMA. In some embodiments according to (or as applied to) any of the embodiments above, the effector cell is an immune cell. In some embodiments according to (or as applied to) any of the embodiments above, the immune cell is a T cell. In some embodiments according to (or as applied to) any of the embodiments above, the T cell is a cytotoxic T cell, a helper T cell, or a natural killer T cell. In some embodiments according to (or as applied to) any of the embodiments above, the method further comprises obtaining an effector cell from an individual prior to genetically modifying and administering the effector cell. In some embodiments according to (or as applied to) any of the embodiments above, the individual from whom the effector cell is obtained is the individual to whom the genetically modified effector cell is administered. In some embodiments according to (or as applied to) any of the embodiments above, the individual from whom the effector cell is obtained is not the individual to whom the genetically modified effector cell is administered. In some embodiments according to (or as applied to) any of the embodiments above, the genetically modified effector cell is allogenic with respect to the individual to whom the genetically modified effector cell is administered. In some embodiments according to (or as applied to) any of the embodiments above, the genetically modified effector cell is syngeneic with respect to the individual to whom the genetically modified effector cell is administered. In some embodiments according to (or as applied to) any of the embodiments above, the genetically modified effector cell is xenogeneic respect to the individual to whom the genetically modified effector cell is administered. In some embodiments according to (or as applied to) any of the embodiments above, the method of treating the individual having the PSMA-associated disease or disorder comprises administering an additional therapy to the individual. In some embodiments according to (or as applied to) any of the embodiments above, the PSMA-associated disease or disorder is cancer. In some embodiments according to (or as applied to) any of the embodiments above, the cancer is selected from the group consisting of: prostate cancer, renal cancer cell, uterine cancer, and liver cancer. In some embodiments according to (or as applied to) any of the embodiments above, the cancer is prostate cancer. In some embodiments according to (or as applied to) any of the embodiments above, the prostate cancer is hormone-refractory prostate cancer or metastatic prostate cancer. In some embodiments according to (or as applied to) any of the embodiments above, the cancer is renal cancer. In some embodiments according to (or as applied to) any of the embodiments above, the renal cancer is clear cell renal cell cancer (CCRCC). In some embodiments according to (or as applied to) any of the embodiments above, the individual having the PSMA-associated disease or disorder is a mammal. In some embodiments according to (or as applied to) any of the embodiments above, the mammal is a human.

Another aspect of the current invention provides a method of diagnosing an individual suspected of having a PSMA-associated disease or disorder, comprising: a) administering an effective amount of the anti-PSMA construct according to (or as applied to) any of the embodiments above conjugated to a detectable label to the individual; and b) determining the level of the label in the individual, wherein a level of the label above a threshold level indicates that the individual has the PSMA-associated disease or disorder. In some embodiments according to (or as applied to) any of the embodiments above, provided is a method of diagnosing an individual suspected of having a PSMA-associated disease or disorder, comprising: a) contacting a sample derived from the individual with the anti-PSMA construct according to (or as applied to) any of the embodiments above conjugated to a detectable label; and b) determining the number of cells bound with the anti-PSMA construct in the sample, wherein a value for the number of cells bound with the anti-PSMA construct above a threshold level indicates that the individual has the PSMA-associated disease or disorder. In some embodiments according to (or as applied to) any of the embodiments above, the PSMA-associated disease or disorder is cancer. In some embodiments according to (or as applied to) any of the embodiments above, the cancer is selected from the group consisting of: prostate cancer, renal cancer cell, uterine cancer, and liver cancer. In some embodiments according to (or as applied to) any of the embodiments above, the cancer is prostate cancer. In some embodiments according to (or as applied to) any of the embodiments above, the prostate cancer is hormone-refractory prostate cancer or metastatic prostate cancer. In some embodiments according to (or as applied to) any of the embodiments above, the cancer is renal cancer. In some embodiments according to (or as applied to) any of the embodiments above, the renal cancer is clear cell renal cell cancer (CCRCC). In some embodiments according to (or as applied to) any of the embodiments above, the individual suspected of having a disease or disorder associated with expression, aberrant expression, and/or aberrant activity of PSMA is a mammal. In some embodiments according to (or as applied to) any of the embodiments above, the mammal is a human.

DETAILED DESCRIPTION OF THE INVENTION

Figure 1:
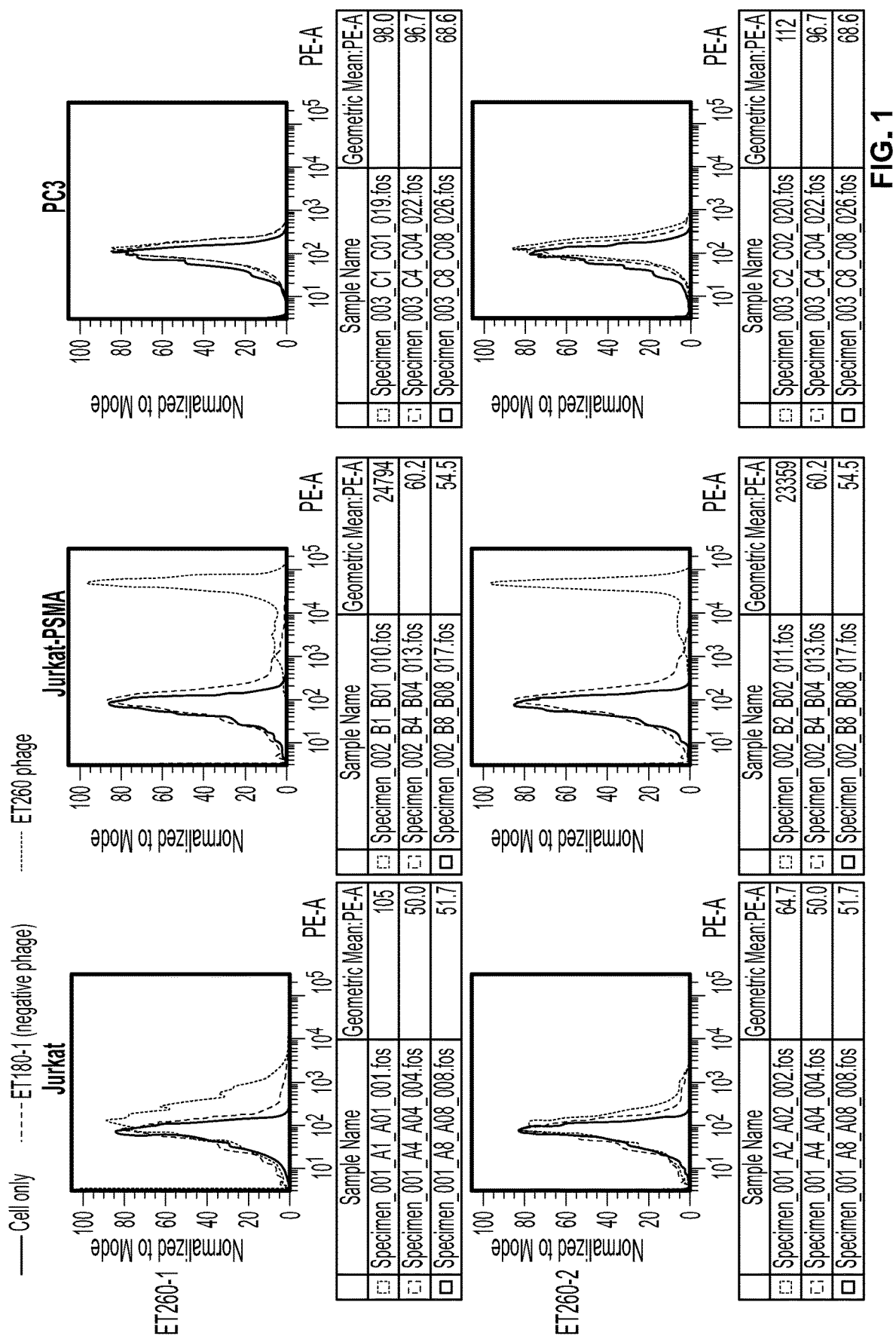
FIG. 1 shows the results of flow cytometry experiments that were performed to assess the binding phage clones A and B to PSMA-positive and PSMA-negative cells.
Figure 1:
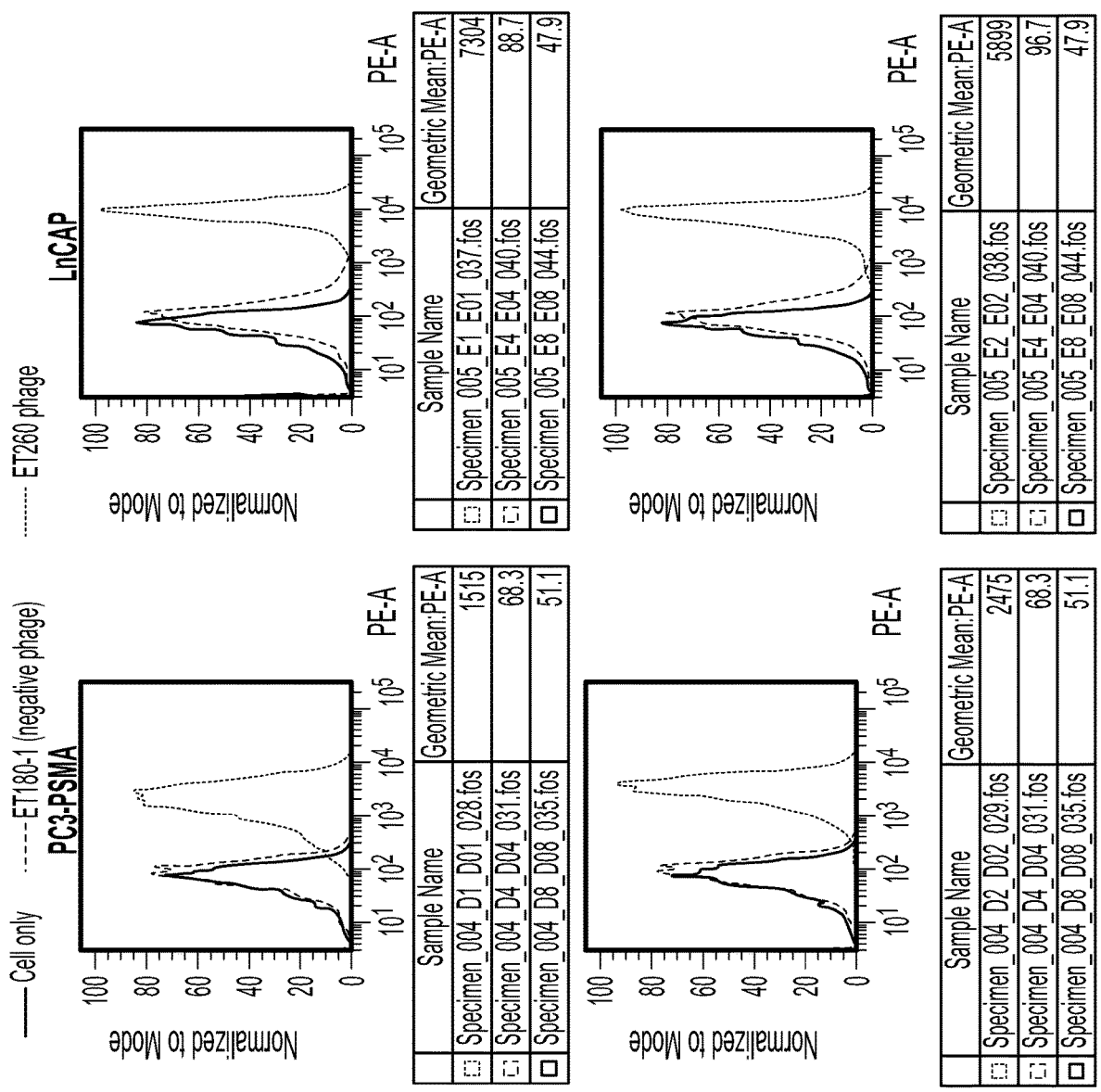

The present application provides isolated constructs (referred to herein as "anti-PSMA constructs") that comprise an antibody moiety (referred to herein as an "anti-PSMA antibody moiety") that specifically binds to prostate specific membrane antigen, or "PSMA" (e.g., PSMA, such as human PSMA) expressed on the surface of a cell, such as a cancer cell). The anti-PSMA constructs allow for specific targeting of cells expressing PSMA (e.g., cells expressing PSMA on their surfaces), such as disease cells expressing (or overexpressing) PSMA. When present in a chimeric antigen receptor (CAR) or chimeric antibody-T cell receptor construct (caTCR) expressed by a T cell, the anti-PSMA antibody moiety specifically redirects human T cells to kill target cells (e.g., cancer cells) expressing PSMA. Furthermore, when fused to a detectable label, the anti-PSMA antibody moiety may be used to visualize changes in the number and localization of PSMA-expressing cells. Such information can, in turn, be used to diagnose and/or prognose PSMA-associated diseases or disorders.

The present application provides constructs (such as isolated constructs) comprising an antibody moiety that specifically binds to PSMA (e.g., PSMA expressed on the surface of a cell, such as a cancer cell). Exemplary constructs include, but are not limited to, e.g., full-length anti-PSMA antibodies, multispecific anti-PSMA constructs (such as a bispecific anti-PSMA antibodies), anti-PSMA chimeric antigen receptors ("CARs"), anti-PSMA chimeric antibody-T cell receptor constructs (caTCRs), anti-PSMA chimeric signaling receptors (CSRs), an anti-PSMA immunoconjugates, as well as other constructs, as described in further detail below. Each of the constructs described herein demonstrates high specificity for human PSMA in native form (e.g., expressed on the surface of a cell, such as a cancer cell).

The present application also provides nucleic acids that encode the anti-PSMA constructs described herein (or the polypeptide portion(s) thereof).

Also provided herein are compositions (such as pharmaceutical compositions or formulations) comprising an anti-PSMA construct described herein or an effector cell expressing or associated with anti-PSMA construct described herein (such as a T cell expressing an anti-PSMA CAR, an anti-PSMA caTCR, or an anti-PSMA chimeric signaling receptor (CSR)).

The present application also provides methods of making and using the anti-PSMA constructs (or effector cells expressing or associated with the anti-PSMA constructs) for treatment, for diagnostic purposes, for prognostic purposes, and for inclusion into kits and articles of manufacture useful for the treatment, diagnosis, and/or prognosis of PSMA-associated diseases and disorders.

Definitions

Before describing the disclosed embodiments in detail, it is to be understood that the present disclosure is not limited to particular compositions or biological systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

As used herein "prostate specific membrane antigen" or "PSMA" refers to any native PSMA from any vertebrate source, including mammals such as primates (e.g., humans, non-human primates (e.g., cynomolgus or rhesus monkeys)) and rodents (e.g., mice and rats), unless otherwise indicated. The term encompasses "full-length," unprocessed PSMA as well as any form of PSMA that results from processing in the cell. The term also encompasses naturally occurring variants of PSMA, e.g., splice variants, allelic variants, and isoforms. PSMA is a type II membrane protein originally characterized by the murine monoclonal antibody (mAb) 7E11-C5.3 and is expressed in all forms of prostate tissue (including carcinoma). The PSMA protein has a 3-part structure: a 19-amino-acid internal portion, a 24-amino-acid transmembrane portion, and a 707-amino-acid external portion (e.g., the extracellular domain. An exemplary amino acid sequence for human PSMA is (SEQ ID NO: 43)
MWNLLHETDSAVATARRPRWLCAGALVLAGGFFLL

GFLFGWFIKSSNEATNITPKHNMKAFLDELKAENI

KKFLYNFTQIPHLAGTEQNFQLAKQIQSQWKEFGL

DSVELAHYDVLLSYPNKTHPNYISIINEDGNEIFN

TSLFEPPPPGYENVSDIVPPFSAFSPQGMPEGDLV

YVNYARTEDFFKLERDMKINCSGKIVIARYGKVFR

GNKVKNAQLAGAKGVILYSDPADYFAPGVKSYPDG

WNLPGGGVQRGNILNLNGAGDPLTPGYPANEYAYR

RGIAEAVGLPSIPVHPIGYYDAQKLLEKMGGSAPP

DSSWRGSLKVPYNVGPGFTGNFSTQKVKMHIHSTN

EVTRIYNVIGTLRGAVEPDRYVILGGHRDSWVFGG

IDPQSGAAVVHEIVRSFGTLKKEGWRPRRTILFAS

WDAEEFGLLGSTEWAEENSRLLQERGVAYINADSS

IEGNYTLRVDCTPLMYSLVHNLTKELKSPDEGFEG

KSLYESWTKKSPSPEFSGMPRISKLGSGNDFEVFF

QRLGIASGRARYTKNWETNKFSGYPLYHSVYETYE

LVEKFYDPMFKYHLTVAQVRGGMVFELANSIVLPF

DCRDYAVVLRKYADKIYSISMKHPQEMKTYSVSFD

```
SLFSAVKNFTEIASKFSERLQDFDKSNPIVLRMMN

DQLMFLERAFIDPLGLPDRPFYRHVIYAPSSHNKY

AGESFPGIYDALFDIESKVDPSKAWGEVKRQIYVA

AFTVQAAAETLSEVA.
```

An exemplary amino acid sequence for the extracellular domain of human PSMA is

```
                                          (SEQ ID NO: 44)
KSSNEATNITPKHNMKAFLDELKAENIKKFLYNFT

QIPHLAGTEQNFQLAKQIQSQWKEFGLDSVELAHY

DVLLSYPNKTHPNYISIINEDGNEIFNTSLFEPPP

PGYENVSDIVPPFSAFSPQGMPEGDLVYVNYARTE

DFFKLERDMKINCSGKIVIARYGKVFRGNKVKNAQ

LAGAKGVILYSDPADYFAPGVKSYPDGWNLPGGGV

QRGNILNLNGAGDPLTPGYPANEYAYRRGIAEAVG

LPSIPVHPIGYYDAQKLLEKMGGSAPPDSSWRGSL

KVPYNVGPGFTGNFSTQKVKMHIHSTNEVTRIYNV

IGTLRGAVEPDRYVILGGHRDSWVFGGIDPQSGAA

VVHEIVRSFGTLKKEGWRPRRTILFASWDAEEFGL

LGSTEWAEENSRLLQERGVAYINADSSIEGNYTLR

VDCTPLMYSLVHNLTKELKSPDEGFEGKSLYESWT

KKSPSPEFSGMPRISKLGSGNDFEVFFQRLGIASG

RARYTKNWETNKFSGYPLYHSVYETYELVEKFYDP

MFKYHLTVAQVRGGMVFELANSIVLPFDCRDYAVV

LRKYADKIYSISMKHPQEMKTYSVSFDSLFSAVKN

FTEIASKFSERLQDFDKSNPIVLRMMNDQLMFLER

AFIDPLGLPDRPFYRHVIYAPSSHNKYAGESFPGI

YDALFDIESKVDPSKAWGEVKRQIYVAAFTVQAAA

ETLSEVA.
```

As used herein, "treatment" or "treating" is an approach for obtaining beneficial or desired results, including clinical results. For purposes of the present application, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods provided herein contemplate any one or more of these aspects of treatment.

The terms "recurrence," "relapse" or "relapsed" refers to the return of a cancer or disease after clinical assessment of the disappearance of disease. A diagnosis of distant metastasis or local recurrence can be considered a relapse.

The term "refractory" or "resistant" refers to a cancer or disease that has not responded to treatment.

"Activation," as used herein in relation to T cells, refers to the state of a T cell that has been sufficiently stimulated to induce detectable cellular proliferation. Activation can also be associated with induced cytokine production, and detectable effector functions.

The term "antibody moiety" includes full-length antibodies and antigen-binding fragments thereof. A full-length antibody comprises two heavy chains and two light chains. The variable regions of the light and heavy chains are responsible for antigen binding. The variable regions in each chain generally comprise three highly variable loops called the complementarity determining regions (CDRs) (light chain (LC) CDRs including CDR-L1, CDR-L2, and CDR-L3, heavy chain (HC) CDRs including CDR-H1, CDR-H2, and CDR-H3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γI heavy chain), IgG2 (γ2 heavy chain), IgG3 (γ3 heavy chain), IgG4 (γ4 heavy chain), IgA1 (α1 heavy chain), or IgA2 (α2 heavy chain).

The term "antigen-binding fragment" as used herein refers to an antibody fragment including, but not limited to, e.g., a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain antibody molecule (scFv), an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

The term "epitope" as used herein refers to the specific group of atoms or amino acids on an antigen to which an antibody or antibody moiety binds. Two antibodies or antibody moieties may bind the same epitope (or overlapping epitopes) within an antigen if they exhibit competitive binding for the antigen.

As used herein, a first antibody moiety "competes" for binding to PSMA with a second antibody moiety when the first antibody moiety inhibits binding of the second antibody moiety to PSMA by at least about 50% (such as at least about any of 55%, 60%, 65%, 70%, 75%, 80%, 85%, 90%, 95%, 98% or 99%) in the presence of an equimolar concentration of the first antibody moiety, or vice versa. A high throughput process for "binning" antibodies based upon their cross-competition is described in PCT Publication No. WO 03/48731.

As use herein, the term "specifically binds" or "is specific for" refers to measurable and reproducible interactions (such as binding between a target and an antibody or an antibody moiety) that are determinative of the presence of the target in the presence of a heterogeneous population of molecules, including biological molecules. For example, an antibody or antibody moiety that specifically binds to a target (which can be an epitope) is an antibody or antibody moiety that binds the target with greater affinity, avidity, more readily, and/or with greater duration than it binds to other targets. In some embodiments, an antibody or antibody moiety that specifically binds to an antigen reacts with one or more antigenic determinants of the antigen (for example an epitope on the extracellular domain of PSMA) with a binding affinity that is at least about 10 times its binding affinity for other targets.

An "isolated" anti-PSMA construct as used herein refers to an anti-PSMA construct that (1) is not associated with proteins found in nature, (2) is free of other proteins from the same source, (3) is expressed by a cell from a different species, or, (4) does not occur in nature.

The term "isolated nucleic acid" as used herein is intended to mean a nucleic acid of genomic, cDNA, or synthetic origin or some combination thereof, which by virtue of its origin the "isolated nucleic acid" (1) is not associated with all or a portion of a polynucleotide in which the "isolated nucleic acid" is found in nature, (2) is operably linked to a polynucleotide which it is not linked to in nature, or (3) does not occur in nature as part of a larger sequence.

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

| | CDR Definitions | | | | |
|---|---|---|---|---|---|
| | Kabat[1] | Chothia[2] | MacCallum[3] | IMGT[4] | AHo[5] |
| $V_H$ CDR1 | 31-35 | 26-32 | 30-35 | 27-38 | 25-40 |
| $V_H$ CDR2 | 50-65 | 53-55 | 47-58 | 56-65 | 58-77 |
| $V_H$ CDR3 | 95-102 | 96-101 | 93-101 | 105-117 | 109-137 |

TABLE 1-continued

| | CDR Definitions | | | | |
|---|---|---|---|---|---|
| | Kabat[1] | Chothia[2] | MacCallum[3] | IMGT[4] | AHo[5] |
| $V_L$ CDR1 | 24-34 | 26-32 | 30-36 | 27-38 | 25-40 |
| $V_L$ CDR2 | 50-56 | 50-52 | 46-55 | 56-65 | 58-77 |
| $V_L$ CDR3 | 89-97 | 91-96 | 89-96 | 105-117 | 109-137 |

[1]Residue numbering follows the nomenclature of Kabat et al., J. Biol. Chem. 252: 6609-6616 (1977); Kabat et al., U.S. Dept. of Health and Human Services, "Sequences of proteins of immunological interest" (1991).
[2]Residue numbering follows the nomenclature of Chothia et al., J. Mol. Biol. 196: 901-917 (1987); Al-Lazikani B. et al., J. Mol. Biol., 273: 927-948 (1997).
[3]Residue numbering follows the nomenclature of MacCallum et al., J. Mol. Biol. 262: 732-745 (1996); Abhinandan and Martin, Mol. Immunol., 45: 3832-3839 (2008).
[4]Residue numbering follows the nomenclature of Lefranc M. P. et al., Dev. Comp. Immunol., 27: 55-77 (2003); and Honegger and Plückthun, J. Mol. Biol., 309: 657-670 (2001).
[5]Residue numbering follows the nomenclature of Honegger and Plückthun, J. Mol. Biol., 309: 657-670 (2001).

The term "chimeric antibodies" refer to antibodies in which a portion of the heavy and/or light chain is identical or homologous to corresponding sequences in antibodies derived from a particular species or belonging to a particular antibody class or subclass, while the remainder of the chain(s) is identical or homologous to corresponding sequences in antibodies derived from another species or belonging to another antibody class or subclass, as well as fragments of such antibodies, so long as they exhibit a biological activity of interest (e.g., binding to PSMA, such as human PSMA, on the surface of a cell, e.g., a cancer cell) (see U.S. Pat. No. 4,816,567; and Morrison et al., Proc. Natl. Acad. Sci. USA, 81:6851-6855 (1984)).

The term "semi-synthetic" in reference to an antibody or antibody moiety means that the antibody or antibody moiety has one or more naturally occurring sequences and one or more non-naturally occurring (i.e., synthetic) sequences or amino acids.

"Fv" is the minimum antibody fragment which contains a complete antigen-recognition and antigen-binding site. This fragment consists of a dimer of one heavy- and one light-chain variable region domain in tight, non-covalent association. From the folding of these two domains emanate six hypervariable loops (3 loops each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv," also abbreviated as "sFv" or "scFv," are antibody fragments that comprise the $V_H$ and $V_L$ antibody domains connected into a single polypeptide chain. In some embodiments, the scFv polypeptide further comprises a polypeptide linker between the $V_H$ and $V_L$ domains which permits the scFv to form the desired structure for antigen binding. For a review of scFv, see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments prepared by constructing scFv fragments (see preceding paragraph) typically with short linkers (such as about 5 to about 10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" scFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA*, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a complementarity determining region (CDR) of the recipient are replaced by residues from a CDR of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance (e.g., affinity for the target antigen). In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., *Nucleic Acids Research* 32(5):1792-1797, 2004; Edgar, R. C., *BMC Bioinformatics* 5(1):113, 2004).

The terms "Fc receptor" or "FcR" are used to describe a receptor that binds to the Fc region of an antibody. In some embodiments, an FcR is one that binds an IgG antibody (a γ receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daeron, *Annu. Rev. Immunol.* 15:203-234 (1997)). The term includes allotypes, such as FcγRIIIA allotypes: FcγRIIIA-Phe158, FcγRIIIA-Val158, FcγRIIA-R131 and/or FcγRIIA-H131.

FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

The term "FcRn" refers to the neonatal Fc receptor (FcRn). FcRn is structurally similar to major histocompatibility complex (MHC) and consists of an α-chain noncovalently bound to P2-microglobulin. The multiple functions of the neonatal Fc receptor FcRn are reviewed in Ghetie and Ward (2000) *Annu. Rev. Immunol.* 18, 739-766. FcRn plays a role in the passive delivery of immunoglobulin IgGs from mother to young and the regulation of serum IgG levels. FcRn can act as a salvage receptor, binding and transporting pinocytosed IgGs in intact form both within and across cells, and rescuing them from a default degradative pathway.

The "CH1 domain" of a human IgG Fc region (also referred to as "C1" of "H1" domain) usually extends from about amino acid 118 to about amino acid 215 (EU numbering system).

The "hinge region" is generally defined as stretching from Glu216 to Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions.

The "CH2 domain" of a human IgG Fc region (also referred to as "C2" of "H2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec Immunol.* 22:161-206 (1985).

The "CH3 domain" (also referred to as "C2" or "H3" domain) comprises the stretch of residues C-terminal to a CH2 domain in an Fc region (i.e. from about amino acid residue 341 to the C-terminal end of an antibody sequence, typically at amino acid residue 446 or 447 of an IgG).

A "functional Fc fragment" possesses an "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art.

An antibody with a variant IgG Fc with "altered" FcR binding affinity or ADCC activity is one which has either enhanced or diminished FcR binding activity (e.g., FcγR or FcRn) and/or ADCC activity compared to a parent polypeptide or to a polypeptide comprising a native sequence Fc region. The variant Fc which "exhibits increased binding" to an FcR binds at least one FcR with higher affinity (e.g., lower apparent $K_d$ or $IC_{50}$ value) than the parent polypeptide or a native sequence IgG Fc. According to some embodiments, the improvement in binding compared to a parent polypeptide is about 3 fold, such as about any of 5, 10, 25, 50, 60, 100, 150, 200, or up to 500 fold, or about 25% to 1000% improvement in binding. The polypeptide variant which "exhibits decreased binding" to an FcR, binds at least one FcR with lower affinity (e.g., higher apparent $K_d$ or higher $IC_{50}$ value) than a parent polypeptide. The decrease in binding compared to a parent polypeptide may be about 40% or more decrease in binding.

"Antibody-dependent cell-mediated cytotoxicity" or "ADCC" refers to a form of cytotoxicity in which secreted Ig bound to Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

The polypeptide comprising a variant Fc region which "exhibits increased ADCC" or mediates ADCC in the presence of human effector cells more effectively than a polypeptide having wild type IgG Fc or a parent polypeptide is one which in vitro or in vivo is substantially more effective at mediating ADCC, when the amounts of polypeptide with variant Fc region and the polypeptide with wild type Fc region (or the parent polypeptide) in the assay are essentially the same. Generally, such variants will be identified using any in vitro ADCC assay known in the art, such as assays or methods for determining ADCC activity, e.g. in an animal model etc. In some embodiments, the variant is from about 5 fold to about 100 fold, e.g. from about 25 to about 50 fold, more effective at mediating ADCC than the wild type Fc (or parent polypeptide).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., *J. Immunol. Methods* 202:163 (1996), may be performed. Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared times 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

An "effective amount" of an anti-PSMA construct or composition as disclosed herein, is an amount sufficient to carry out a specifically stated purpose. An "effective amount" can be determined empirically and by known methods relating to the stated purpose.

The term "therapeutically effective amount" refers to an amount of an anti-PSMA construct or composition as disclosed herein, effective to "treat" a disease or disorder in an individual. In the case of cancer, the therapeutically effective amount of the anti-PSMA construct or composition as disclosed herein can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the anti-PSMA construct or composition as disclosed herein can prevent growth and/or kill existing cancer cells, it can be cytostatic and/or cytotoxic. In some embodiments, the therapeutically effective amount is a growth inhibitory amount. In some embodiments, the therapeutically effective amount is an amount that extends the survival of a patient. In some embodiments, the therapeutically effective amount is an amount that improves progression free survival of a patient.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

The term "label" when used herein refers to a detectable compound or composition which can be conjugated directly or indirectly to the anti-PSMA antibody moiety. The label may be detectable by itself (e.g., radioisotope labels or fluorescent labels) or, in the case of an enzymatic label, may catalyze chemical alteration of a substrate compound or composition which is detectable.

The term "chimeric antigen receptor (CAR)" refers to an artificially constructed hybrid single-chain protein or single-chain polypeptide containing a single-chain variable fragment (scFv) as a part of the extracellular antigen-binding domain, linked directly or indirectly to a transmembrane domain (e.g., a TCR transmembrane domain), which is in turn linked directly or indirectly to an intracellular immune cell (e.g., T cell or NK cell) signaling domain. The intracellular signaling domain (ISD) comprises a primary signaling sequence, or primary immune cell signaling sequence, from an antigen-dependent, TCR-associated T cell activation molecule, e.g., a portion of the intracellular domain of CD3ζ, TCRζ, FcRγ, FcRβ, CD3γ, CD3δ, CD3ε, CD5, CD22, CD79a, CD79b, or CD66d). The ISD can further comprise a co-stimulatory signaling sequence; e.g., a portion of the intracellular domain of an antigen-independent, co-stimulatory molecule such as CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, or the like. Characteristics of CARs include their ability to redirect immune cell (e.g., T cell or NK cell) specificity and reactivity toward a selected target in either MHC-restricted (in cases of TCR-mimic antibodies) or non-MHC-restricted (in cases of antibodies against cell surface proteins) manners, exploiting the antigen-binding properties of monoclonal antibodies. The non-MHC-restricted antigen recognition gives immune cells (e.g., T cells or NK cells) expressing CARs the ability to recognize antigen independent of antigen processing, thus bypassing a major mechanism of tumor escape.

There are currently three generations of CARs. The "first generation" CARs are typically single-chain polypeptides composed of a scFv as the antigen-binding domain fused to a transmembrane domain fused to the cytoplasmic/intracellular domain, which comprises a primary immune cell signaling sequence, of a molecule from the T cell receptor (TCR) complex, i.e., an antigen-dependent, TCR-associated T cell activation molecule such as CD3ζ, TCRζ, FcRγ, FcRβ, CD3γ, CD3δ, CD3ε, CD5, CD22, CD79a, CD79b, or CD66d. The "first generation" CARs typically have the intracellular domain from the CD3ζ chain, which is the primary transmitter of signals from endogenous TCRs. The "first generation" CARs can provide de novo antigen recognition and cause activation of both $CD4^+$ and $CD8^+$ T cells through their CD3ζ chain signaling domain in a single fusion molecule, independent of HLA-mediated antigen presentation. The "second generation" CARs add intracellular domains from various co-stimulatory molecules (e.g., CD28, 4-1BB, ICOS, OX40) to the primary immune cell signaling sequence of the CAR to provide additional signals to the T cell. "Second generation" CARs comprise fragments that provide co-stimulation (e.g., CD28 or 4-IBB) and activation (e.g., CD3ζ). Preclinical studies have indicated that the "second generation" CARs can improve the antitumor activity of T cells. For example, robust efficacy of the "second generation" CAR modified T cells was demonstrated in clinical trials targeting the CD19 molecule in patients with chronic lymphoblastic leukemia (CLL) and acute lymphoblastic leukemia (ALL). The "third generation" CARs comprise those that provide multiple co-stimulation (e.g., CD28 and 4-1BB) and activation (e.g., CD3ζ).

As used herein, the term "chimeric antibody-T cell receptor construct" (or caTCR) refers to a functional polypeptide complex comprising two separate polypeptide chains, one including an antibody heavy chain variable region ($V_H$) and an antibody heavy chain constant region ($C_H$), and the other including an antibody light chain variable region ($V_L$) and an antibody light chain constant region ($C_L$). A caTCR as defined herein is therefore a 2-subunit construct, each subunit substantially resembling a cell membrane-anchored antibody heavy chain or light chain that is fused to a transmembrane domain (e.g., a TCR transmembrane domain) and an intracellular immune cell signaling domain. In some embodiments, a caTCR does not include a co-stimulatory domain (e.g., a portion of the intracellular domain of CD3γ, CD3δ, CD3ε, or CD3ζ). In some embodiments, a caTCR comprises a) an extracellular domain comprising an antibody moiety and b) a T cell receptor module (TCRM) capable of recruiting at least one TCR-associated signaling module. In some embodiments, an anti-PSMA caTCR comprises a) an extracellular domain comprising an anti-PSMA antibody moiety that specifically binds to an extracellular region of PSMA or a portion thereof (e.g., SEQ ID NO: 44 or a portion thereof) and b) a T cell receptor module (TCRM) capable of recruiting at least one TCR-associated signaling module.

A caTCR as defined herein comprises a first polypeptide chain and a second polypeptide chain, in which the first polypeptide chain comprises an antibody $V_H$ fused to an antibody $C_H$ fused to a transmembrane domain and an intracellular immune cell signaling domain, and the second polypeptide comprises an antibody $V_L$ fused to an antibody $C_L$ fused to a transmembrane domain and an intracellular immune cell signaling domain. In some embodiments, the first and second polypeptide chains are linked, such as by a covalent linkage (e.g., peptide or other chemical linkage) or non-covalent linkage. In some embodiments, the anti-PSMA caTCR is a heterodimer comprising the first polypeptide chain and the second polypeptide chain. In some embodiments, the first polypeptide chain and the second polypeptide chain are linked by at least one disulfide bond. The specificity of the anti-PSMA caTCR derives from an antibody moiety that confers binding specificity to an extracellular region of PSMA or a portion thereof (e.g., SEQ ID NO: 44 or a portion thereof).

The terms "chimeric antibody-T cell receptor (caTCR)" and "antibody-TCR chimeric molecule or construct (abTCR or AbTCR)" are used interchangeably herein. Further descriptions and examples of caTCR and abTCR may be found in, e.g., WO 2017/070608 and PCT/US2018/029217 (now published as WO 2018/200582), the contents of which are incorporated by reference herein in their entirety.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

Anti-PSMA Constructs

Provided herein are constructs that specifically bind to prostate specific membrane antigen (PSMA) that comprise an antibody moiety that specifically binds to PSMA (e.g., PSMA expressed on the surface of a cell, such as a cancer cell). Such constructs are also referred to herein as "anti- PSMA constructs." The specificity of the anti-PSMA construct for PSMA is derived from the anti-PSMA antibody moiety (such as a full-length antibody or antigen-binding fragment thereof) that specifically binds to cell surface-bound PSMA. In some embodiments, the extracellular domain of PSMA comprises the amino acid sequence set forth in SEQ ID NO: 44.

Anti-PSMA constructs within the scope of the present application include, without limitation, e.g., full-length anti-PSMA antibodies, multispecific anti-PSMA constructs, anti-PSMA CARs, anti-PSMA chimeric antibody-T cell receptor constructs (caTCRs), anti-PSMA chimeric signaling receptors (CSRs), anti-PSMA immunoconjugates, and others, as described herein below.

For example, in some embodiments, the anti-PSMA construct (such as an isolated anti-PSMA construct) comprises an anti-PSMA antibody moiety that specifically binds to PSMA (e.g., PSMA expressed on the surface of a cell, such as a cancer cell). In some embodiments, the extent of binding of the anti-PSMA antibody to a non-target polypeptide is less than about 10% of the binding of the anti-PSMA antibody moiety to PSMA as determined by methods known in the art, such as ELISA, fluorescence activated cell sorting (FACS) analysis, or radioimmunoprecipitation (RIA). Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of nonlabeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a $K_D$ for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or less. In one embodiment, the term "specific binding" refers to binding where a molecule binds to a particular polypeptide (e.g., PSMA) or epitope on a particular polypeptide (e.g., PSMA) without substantially binding to any other polypeptide or polypeptide epitope.

In some embodiments, the anti-PSMA construct comprises an anti-PSMA antibody moiety that specifically binds to PSMA (e.g., PSMA expressed on the surface of a cell, such as a cancer cell) and competes for binding to PSMA with a second anti-PSMA antibody (or antibody moiety) that specifically binds PSMA (e.g., PSMA expressed on the surface of a cell, such as a cancer cell) and comprises: (a) a CDR-H1 comprising an amino acid sequence set forth in SEQ ID NO: 1 or 2; (b) a CDR-H2 comprising an amino acid sequence set forth in SEQ ID NO: 3 or 4; (c) a CDR-H3 comprising an amino acid sequence set forth in SEQ ID NO: 5 or 6; (d) a CDR-L1 comprising an amino acid sequence set forth in SEQ ID NO: 7 or 8; (e) a CDR-L2 comprising the amino acid sequence GNS or SNN; and (f) a CDR-L3 comprising an amino acid sequence set forth in SEQ ID NO: 9 or 10. In some embodiments, the anti-PSMA construct comprises an anti-PSMA antibody moiety that specifically binds to the same epitope of PSMA (e.g., PSMA expressed on the surface of a cell, such as a cancer cell) as a second anti-PSMA antibody (or antibody moiety) that specifically binds PSMA (e.g., PSMA expressed on the surface of a cell, such as a cancer cell) and comprises (a) a CDR-H1 comprising an amino acid sequence set forth in SEQ ID NO: 1 or 2; (b) a CDR-H2 comprising an amino acid sequence set forth in SEQ ID NO: 3 or 4; (c) a CDR-H3 comprising an amino acid sequence set forth in SEQ ID NO: 5 or 6; (d) a CDR-L1 comprising an amino acid sequence set forth in SEQ ID NO: 7 or 8; (e) a CDR-L2 comprising the amino acid sequence GNS or SNN; and (f) a CDR-L3 comprising an amino acid sequence set forth in SEQ ID NO: 9 or 10.

In some embodiments, the anti-PSMA construct comprises an anti-PSMA antibody moiety that comprises one, two, three, four, five, or six complementarity determining region (CDR) sequences selected from the group consisting of: (a) a CDR-H1 comprising an amino acid sequence set forth in $GYX_1FX_2SYW$ (SEQ ID NO: 11), wherein $X_1$ is S or N; and $X_2$ is T or A; (b) a CDR-H2 comprising an amino acid sequence set forth in IYPXIDSDT (SEQ ID NO: 12), wherein $X_1$ is G or D; (c) a CDR-H3 comprising an amino acid sequence set forth in $ARX_1X_2X_3X_4X_5X_6YX_7X_8X_9DV$ (SEQ ID NO: 13), wherein $X_1$ is S or no amino acid; $X_2$ is M or no amino acid; $X_3$ is G or no amino acid; $X_4$ is S or no amino acid; $X_5$ is S or D; $X_6$ is L or S; $X_7$ is A or Y; $X_8$ is S or G; and $X_9$ is S or I; (d) a CDR-L1 comprising an amino acid sequence set forth in $SSNIGX_1X_2X_3X_4$ (SEQ ID NO: 14), wherein $X_1$ is A or S; $X_2$ is G or N; $X_3$ is Y or T; and $X_4$ is D or no amino acid; (e) a CDR-L2 comprising the amino acid sequence $X_1NX_2$, wherein $X_1$ is G or S; and $X_2$ is S or N; and (f) a CDR-L3 comprising an amino acid sequence set forth in $X_1X_2X_3DX_4SLX_5GYV$ (SEQ ID NO: 15), wherein $X_1$ is Q or A; $X_2$ is S or A; $X_3$ is Y or W; $X_4$ is S or D; and $X_5$ is S or N.

In some embodiments, the anti-PSMA construct comprises an anti-PSMA antibody moiety that comprises one, two, three, four, five, or six complementarity determining region (CDR) sequences selected from the group consisting of: (a) a CDR-H1 comprising an amino acid sequence set forth in SEQ ID NO: 1 or 2, or a variant thereof comprising up to about 5 (such as about any of 1, 2, 3, 4, or 5) amino acid substitutions; (b) a CDR-H2 comprising an amino acid sequence set forth in SEQ ID NO:3 or 4, or a variant thereof comprising up to about 5 (such as about any of 1, 2, 3, 4, or 5) amino acid substitutions (c) a CDR-H3 comprising an amino acid sequence set forth in SEQ ID NO: 5 or 6, or a variant thereof comprising up to about 5 (such as about any of 1, 2, 3, 4, or 5) amino acid substitutions; (d) a CDR-L1 comprising an amino acid sequence set forth in SEQ ID NO: 7 or 8, or a variant thereof comprising up to about 5 (such as about any of 1, 2, 3, 4, or 5) amino acid substitutions; (e) a CDR-L2 comprising the amino acid sequence GNS or SNN, or a variant thereof comprising up to about 3 (such as about any of 1, 2, or 3) amino acid substitutions; and (f) a CDR-L3 comprising an amino acid sequence set forth in SEQ ID NO: 9 or 10, or a variant thereof comprising up to about 5 (such as about any of 1, 2, 3, 4, or 5) amino acid substitutions.

In some embodiments, the anti-PSMA construct comprises an anti-PSMA antibody moiety that comprises (a) a CDR-H1 comprising an amino acid sequence set forth in SEQ ID NO: 1 or 2, or a variant thereof comprising up to about 5 (such as about any of 1, 2, 3, 4, or 5) amino acid substitutions; (b) a CDR-H2 comprising an amino acid sequence set forth in SEQ ID NO:3 or 4, or a variant thereof comprising up to about 5 (such as about any of 1, 2, 3, 4, or 5) amino acid substitutions (c) a CDR-H3 comprising an amino acid sequence set forth in SEQ ID NO: 5 or 6, or a variant thereof comprising up to about 5 (such as about any of 1, 2, 3, 4, or 5) amino acid substitutions; (d) a CDR-L1 comprising an amino acid sequence set forth in SEQ ID NO: 7 or 8, or a variant thereof comprising up to about 5 (such as about any of 1, 2, 3, 4, or 5) amino acid substitutions; (e) a CDR-L2 comprising the amino acid sequence GNS or SNN, or a variant thereof comprising up to about 3 (such as about any of 1, 2, or 3) amino acid substitutions; and (f) a CDR-L3 comprising an amino acid sequence set forth in SEQ ID NO: 9 or 10, or a variant thereof comprising up to about 5 (such as about any of 1, 2, 3, 4, or 5) amino acid substitutions.

In some embodiments, the anti-PSMA construct comprises an anti-PSMA antibody moiety that comprises one, two, three, four, five, or six complementarity determining region (CDR) sequences selected from the group consisting of: (a) a CDR-H1 comprising an amino acid sequence set forth in SEQ ID NO: 1 or 2; (b) a CDR-H2 comprising an amino acid sequence set forth in SEQ ID NO: 3 or 4; (c) a CDR-H3 comprising an amino acid sequence set forth in SEQ ID NO: 5 or 6; (d) a CDR-L1 comprising an amino acid sequence set forth in SEQ ID NO: 7 or 8; (e) a CDR-L2 comprising the amino acid sequence GNS or SNN; and (f) a CDR-L3 comprising an amino acid sequence set forth in SEQ ID NO: 9 or 10.

In some embodiments, the anti-PSMA construct comprises an anti-PSMA antibody moiety that comprises a) a CDR-H1 comprising an amino acid sequence set forth in SEQ ID NO: 1 or 2; (b) a CDR-H2 comprising an amino acid sequence set forth in SEQ ID NO: 3 or 4; (c) a CDR-H3 comprising an amino acid sequence set forth in SEQ ID NO: 5 or 6; (d) a CDR-L1 comprising an amino acid sequence set forth in SEQ ID NO: 7 or 8; (e) a CDR-L2 comprising the amino acid sequence GNS or SNN; and (f) a CDR-L3 comprising an amino acid sequence set forth in SEQ ID NO: 9 or 10. In some embodiments, the CDRs are human CDRs.

The amino acid sequences of SEQ ID NOs: 1-10 are provided in Table 2 below.

TABLE 2

| GYSFTSYW (SEQ ID NO: 1) | IYPDDSDT (SEQ ID NO: 4) | SSNIGAGYD (SEQ ID NO: 7) | AAWDDSLNGYV (SEQ ID NO: 10) |
|---|---|---|---|
| GYNFASYW (SEQ ID NO: 2) | ARSMGSSLYASSDV (SEQ ID NO: 5) | SSNIGSNT (SEQ ID NO: 8) | |
| IYPGDSDT (SEQ ID NO: 3) | ARDSYYGIDV (SEQ ID NO: 6) | QSYDSSLSGYV (SEQ ID NO: 9) | |

In some embodiments, the anti-PSMA construct comprises an anti-PSMA antibody moiety that comprises one, two, or three CDRs of an antibody heavy chain variable domain ($V_H$) comprising an amino acid sequence that is at least about 95%, 96%, 97%, 98%, 99%, or 100% identical to an amino acid sequence set forth SEQ ID NOs: 16 or 17. Additionally or alternatively, in some embodiments, the anti-PSMA construct comprises an anti-PSMA antibody moiety that comprises one, two, or three CDRs of a light chain variable domain ($V_L$) comprising an amino acid sequence that is at least about 95%, 96%, 97%, 98%, 99%, or 100% identical to an amino acid sequence set forth in SEQ ID NO: 18 or 19.

In some embodiments, the anti-PSMA construct comprises an anti-PSMA antibody moiety that comprises a heavy chain variable domain ($V_H$) comprising an amino acid sequence that is at least about 95%, 96%, 97%, 98%, 99%, or 100% identical to an amino acid sequence set forth SEQ ID NOs: 16 or 17 and/or a light chain variable domain ($V_L$) comprising an amino acid sequence that is at least about 95%, 96%, 97%, 98%, 99%, or 100% identical to an amino acid sequence set forth in SEQ ID NO: 18 or 19. The amino acid sequences of SEQ ID NOs: 16-19 are provided in Table 3 below. The CDR sequences are in underlined bold type.

TABLE 3

```
EVQLVQSGAE VKKPGESLKI SCKGSGYSFT SYWIGWVRQM
PGKGLEWMGI IYPGDSDTRY SPSFQGQVTI SADKSISTAY
LQWSSLKASD TAMYYCARSM GSSLYASSDV WGQGTLVTVS
S (SEQ ID NO: 16)

EVQLVQSGAE MKKPGESLKI SCKGSGYNFA SYWVGWVRQM
PGKGLEWMGT IYPDDSDTRY GPAFQGQVTI SADKSISTAY
LQWSSLKASD TAMYYCARDS YYGIDVWGQG TLVTVSS
(SEQ ID NO: 17)

QSVLTQPPSV SGAPGQRVTI SCTGSSSNIG AGYDVHWYQQ
LPGTAPKLLI YGNSNRPSGV PDRFSGSKSG TSASLAITGL
QAEDEADYYC QSYDSSLSGY VFGTGTKVTV LG
(SEQ ID NO: 18)

QAVLTQPPSA SGTPGQRVTI SCSGSSSNIG SNTVNWYQQL
PGTAPKLLMY SNNQRPSGVP DRFSGSKSGT SASLAISGLQ
SEDEADYYCA AWDDSLNGYV FGTGTKVTVL G
(SEQ ID NO: 19)
```

The heavy and light chain variable domains can be combined in pair-wise combinations to generate additional anti-PSMA antibody moieties that can be incorporated into and/or used with the anti-PSMA constructs of the present disclosure.

In certain embodiments, the anti-PSMA construct comprises an anti-PSMA antibody moiety that comprises: (a) a CDR-H1 comprising GYSFTSYW (SEQ ID NO: 1) or a variant thereof comprising up to about 5 (such as about any of 1, 2, 3, 4, or 5) amino acid substitutions, (b) a CDR-H2 comprising IYPGDSDT (SEQ ID NO: 3) or a variant thereof comprising up to about 5 (such as about any of 1, 2, 3, 4, or 5) amino acid substitutions, (c) a CDR-H3 comprising ARSMGSSLYASSDV (SEQ ID NO: 5) or a variant thereof comprising up to about 5 (such as about any of 1, 2, 3, 4, or 5) amino acid substitutions, (d) a CDR-L1 comprising SSNIGAGYD (SEQ ID NO: 7) or a variant thereof comprising up to about 5 (such as about any of 1, 2, 3, 4, or 5) amino acid substitutions, (e) a CDR-L2 comprising GNS or a variant thereof comprising up to about 3 (such as about any of 1, 2, or 3) amino acid substitutions, and (f) a CDR-L3 comprising QSYDSSLSGYV (SEQ ID NO: 9) or a variant thereof comprising up to about 5 (such as about any of 1, 2, 3, 4, or 5) amino acid substitutions. In certain embodiments, the anti-PSMA construct comprises an anti-PSMA antibody moiety that comprises: (a) a CDR-H1 comprising GYSFTSYW (SEQ ID NO: 1), (b) a CDR-H2 comprising 1YPGDSDT (SEQ ID NO: 3), (c) a CDR-H3 comprising ARSMGSSLYASSDV (SEQ ID NO: 5); (d) a CDR-L1 comprising SSNIGAGYD (SEQ ID NO: 7), (e) a CDR-L2 comprising GNS, and (f) a CDR-L3 comprising QSYDSSLSGYV (SEQ ID NO: 9). In some embodiments, the CDRs are human CDRs. In certain embodiments, the anti-PSMA construct comprises an anti-PSMA antibody moiety that comprises one, two, or three CDRs of a $V_H$ domain comprising SEQ ID NO: 16 and one, two, or three CDRs of a $V_L$ domain comprising SEQ ID NO: 18. In certain embodiments, the anti-PSMA construct comprises an anti-PSMA antibody moiety that comprises a $V_H$ domain comprising an amino acid sequence that is at least about 85%

(e.g., at least about any one of 85%, 86%, 87%, 88%, 89%, 90%, 91%, 92%, 93%, 94%, 95%, 96%, 97%, 98%, 99% or 100%) identical to SEQ ID NO: 16 and/or a $V_L$ domain comprising an amino acid sequence that is at least about 85% (e.g., at least about any one of 85%, 86%, 87%, 88%, 89%, 90%, 91%, 92%, 93%, 94%, 95%, 96%, 97%, 98%, 99% or 100%) identical to SEQ ID NO: 18. In certain embodiments, the anti-PSMA construct comprises an anti-PSMA antibody moiety that comprises a $V_H$ domain comprising SEQ ID NO: 16 and a $V_L$ domain comprising SEQ ID NO: 18. An anti-PSMA antibody moiety comprising SEQ ID NO: 16 and SEQ ID NO: 18 is alternatively referred to herein as a "Clone A anti-PSMA antibody moiety".

In certain embodiments, the anti-PSMA construct comprises an anti-PSMA antibody moiety that comprises: (a) a CDR-H1 comprising GYNFASYW (SEQ ID NO: 2) or a variant thereof comprising up to about 5 (such as about any of 1, 2, 3, 4, or 5) amino acid substitutions, (b) a CDR-H2 comprising IYPDDSDT (SEQ ID NO: 4) or a variant thereof comprising up to about 5 (such as about any of 1, 2, 3, 4, or 5) amino acid substitutions, (c) a CDR-H3 comprising ARDSYYGIDV (SEQ ID NO: 6) or a variant thereof comprising up to about 5 (such as about any of 1, 2, 3, 4, or 5) amino acid substitutions, (d) a CDR-L1 comprising SSNIGSNT (SEQ ID NO: 8) or a variant thereof comprising up to about 5 (such as about any of 1, 2, 3, 4, or 5) amino acid substitutions, (e) a CDR-L2 comprising SNN or a variant thereof comprising up to about 3 (such as about any of 1, 2, or 3) amino acid substitutions, and (f) a CDR-L3 comprising AAWDDSLNGYV (SEQ ID NO: 10) or a variant thereof comprising up to about 5 (such as about any of 1, 2, 3, 4, or 5) amino acid substitutions. In certain embodiments, the anti-PSMA construct comprises an anti-PSMA antibody moiety that comprises: (a) a CDR-H1 comprising GYNFASYW (SEQ ID NO: 2), (b) a CDR-H2 comprising IYPDDSDT (SEQ ID NO: 4), (c) a CDR-H3 comprising ARDSYYGIDV (SEQ ID NO: 6); (d) a CDR-L1 comprising SSNIGSNT (SEQ ID NO: 8), (e) a CDR-L2 comprising SNN, and (f) a CDR-L3 comprising AAWDDSLNGYV (SEQ ID NO: 10). In some embodiments, the CDRs are human CDRs. In certain embodiments, the anti-PSMA construct comprises an anti-PSMA antibody moiety that comprises one, two, or three CDRs of a $V_H$ domain comprising SEQ ID NO: 17 and one, two, or three CDRs of a $V_L$ domain comprising SEQ ID NO: 19. In certain embodiments, the anti-PSMA construct comprises an anti-PSMA antibody moiety that comprises a $V_H$ domain comprising an amino acid sequence that is at least about 85% (e.g., at least about any one of 85%, 86%, 87%, 88%, 89%, 90%, 91%, 92%, 93%, 94%, 95%, 96%, 97%, 98%, 99% or 100%) identical to SEQ ID NO: 17 and/or a $V_L$ domain comprising an amino acid sequence that is at least about 85% (e.g., at least about any one of 85%, 86%, 87%, 88%, 89%, 90%, 91%, 92%, 93%, 94%, 95%, 96%, 97%, 98%, 99% or 100%) identical to SEQ ID NO: 19. In some embodiments, the anti-PSMA construct comprises an anti-PSMA antibody moiety that comprises a $V_H$ domain comprising SEQ ID NO: 17 and a $V_L$ domain comprising SEQ ID NO: 19. An anti-PSMA antibody moiety comprising SEQ ID NO: 17 and SEQ ID NO: 19 is alternatively referred to herein as a "Clone B anti-PSMA antibody moiety".

In some embodiments, the anti-PSMA antibody moiety of the anti-PSMA construct is a full-length antibody. In some embodiments, the anti-PSMA antibody moiety of the anti-PSMA construct is an antigen-binding fragment of an anti-PSMA antibody, for example an antigen-binding fragment selected from the group consisting of a Fab, a Fab', a F(ab')2, an Fv fragment, a disulfide stabilized Fv fragment (dsFv), and a single-chain antibody molecule (scFv). In some embodiments, the anti-PSMA antibody moiety of the anti-PSMA construct is an scFv. In some embodiments, the anti-PSMA antibody moiety is human, humanized, or semi-synthetic.

The amino acid sequences of two exemplary anti-PSMA scFvs are provided Table 4 below. The $V_L$ in each scFv is in plain text (i.e., no underline), the $V_H$ in each scFv is underlined, and the linker is in italic type. The CDRs are in bold type and underlined bold type.

TABLE 4

```
Clone A anti-PSMA scFv
QSVLTQPPSV SGAPGQRVTI SCTGSSSNIG AGYDVHWYQQ
LPGTAPKLLI YGNSNRPSGV PDRFSGSKSG TSASLAITGL
QAEDEADYYC QSYDSSLSGY VFGTGTKVTV LGSRGGGGSG
GGGSGGGGSL EMAEVQLVQS GAEVKKPGES LKISCKGSGY
SFTSYWIGWV RQMPGKGLEW MGIIYPGDSD TRYSPSFQGQ
VTISADKSIS TAYLQWSSLK ASDTAMYYCA RSMGSSLYAS
SDVWGQGTLV TVSS
(SEQ ID NO: 20)

Clone B Anti-PSMA scFv
QAVLTQPPSA SGTPGQRVTI SCSGSSSNIG SNTVNWYQQL
PGTAPKLLMY SNNQRPSGVP DRFSGSKSGT SASLAISGLQ
SEDEADYYCA AWDDSLNGYV FGTGTKVTVL GSRGGGGSGG
GGGSGGGGSLE MAEVQLVQSG AEMKKPGESL KISCKGSGYN
FASYWVGWVR QMPGKGLEWM GTIYPDDSDT RYGPAFQGQV
TISADKSIST AYLQWSSLKA SDTAMYYCAR DSYYGIDVWG
QGTLVTVSS
(SEQ ID NO: 21)
```

In some embodiments, the anti-PSMA scFv comprises an amino acid sequence that has at least about 85% (e.g., at least about any one of 85%, 86%, 87%, 88%, 89%, 91%, 92%, 93%, 94%, 95%, 96%, 97%, 98%, or 99%) sequence identity to SEQ ID NO: 20 or SEQ ID NO: 21.

In some embodiments, the anti-PSMA construct comprises an anti-PSMA antibody moiety that binds human PSMA, mouse PSMA, rat PSMA, cynomolgus monkey PSMA, and/or rhesus PSMA. In some embodiments, the anti-PSMA construct comprises an anti-PSMA antibody moiety that specifically binds human PSMA. In some embodiments, the anti-PSMA construct comprises an anti-PSMA antibody moiety that specifically binds to PSMA present on or expressed on the surface of a cell. In some embodiments, the cell is a cancer cell. In some embodiments, the cell expresses abnormally high levels of PSMA, as compared to a reference cell. In some embodiments, the reference cell is a cell obtained from or derived from non-diseased (such as non-cancerous) tissue. In some embodiments, the cell that expresses abnormally high levels of PSMA is a cancer cell. In some embodiments, the cancer cell is in a solid tumor. In some embodiments, the cancer cell is a prostate cancer cell, a renal cell cancer cell, a uterine cancer cell, or a liver cancer cell. In some embodiments, the cancer cell is a metastatic cancer cell.

Anti-PSMA Constructs Comprising Anti-PSMA Antibody Moiety Sequence Variants

In some embodiments, anti-PSMA constructs of the present application comprise variants (such as amino acid sequence variants) of the anti-PSMA antibody moieties described herein. For example, it may be desirable to improve the binding affinity and/or other biological properties of the anti-PSMA antibody moiety of an anti-PSMA construct. Amino acid sequence variants of an anti-PSMA antibody moiety may be prepared by introducing appropriate modifications into the nucleotide sequence encoding the antibody moiety, or by peptide synthesis. Such modifications include, for example, deletions from, insertions into, and/or substitutions of residues within the amino acid sequences of the anti-PSMA antibody moiety. Any combination of deletion(s), insertion(s), and substitution(s) can be made to arrive at the final anti-PSMA antibody moiety, provided that the final antibody moiety possesses the desired characteristics, e.g., binding to PSMA (such as PSMA expressed on the surface of a cell, e.g., a cancer cell).

In some embodiments, an anti-PSMA antibody moiety sequence variant comprises one or more amino acid substitutions. Sites of interest for substitutional mutagenesis include the CDRs and/or the framework regions (FRs). Amino acid substitutions may be introduced into an anti-PSMA antibody moiety of interest and the products screened for a desired activity, e.g., retained/improved binding to PSMA (e.g., cell surface-bound PSMA), decreased immunogenicity, or improved ADCC or CDC, etc. Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-PSMA antibody moiety with an N-terminal methionyl residue. Other insertional variants of the anti-PSMA antibody moiety include the fusion to the N- or C-terminus of the antibody moiety to an enzyme (e.g. for ADEPT) or a polypeptide which increases the serum half-life of the anti-PSMA antibody moiety.

In some embodiments, an anti-PSMA antibody moiety sequence variant comprises one or more conservative amino acid substitutions, as shown in Table 5 below.

TABLE 5

Conservative Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties:

| | |
|---|---|
| a) Hydrophobic: | Norleucine, Met, Ala, Val, Leu, Ile; |
| b) Neutral hydrophilic: | Cys, Ser, Thr, Asn, Gln; |
| c) Acidic: | Asp, Glu; |
| d) Basic: | His, Lys, Arg; |
| e) Residues that influence chain orientation: | Gly, Pro; |
| f) Aromatic: | Trp, Tyr, Phe. |

Non-conservative substitutions entail exchanging a member of one of these classes for another class.

An exemplary substitutional variant is an affinity matured antibody moiety, which may be conveniently generated, e.g., using phage display-based affinity maturation techniques. Briefly, one or more CDR residues are mutated and the variant antibody moieties displayed on phage and screened for a particular biological activity (e.g. binding affinity). Alterations (e.g., substitutions) may be made in CDRs, e.g., to improve antibody moiety affinity. Such alterations may be made in CDR "hotspots," i.e., residues encoded by codons that undergo mutation at high frequency during the somatic maturation process (see, e.g., Chowdhury, *Methods Mol. Biol.* 207:179-196 (2008)), and/or specificity determining residues (SDRs), with the resulting variant $V_H$ or $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).)

In some embodiments, one or more CDR sequences provided herein is either is unaltered, or contains no more than one, two, three, four, or five amino acid substitutions. In some embodiments a $V_H$ and/or $V_L$ sequence provided herein is either is unaltered, or contains no more than one, two, three, four, or five amino acid substitutions. In some embodiments one or more CDR sequences within a $V_H$ and/or $V_L$ sequence provided herein is either is unaltered, or contains no more than one, two, three, four, or five amino acid substitutions.

Diversity may be introduced into the variable genes chosen for maturation by any of a variety of methods (e.g., error-prone PCR, chain shuffling, or oligonucleotide-directed mutagenesis). A secondary library is then created. The library is then screened to identify any antibody moiety variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

The anti-PSMA antibodies or anti-PSMA antibody moieties may also be identified by screening combinatorial libraries for antibodies with the desired activity or activities. For example, a variety of methods are known in the art for generating polypeptide display libraries and screening such libraries for antibodies possessing the desired binding characteristics. Such methods are reviewed, e.g., in Hoogenboom et al., *Methods in Molecular Biology* 178:1-37 (O'Brien et al., ed., Human Press, Totowa, N.J., 2001) and further described, e.g., in McCafferty et al., *Nature* 348:552-554; Clackson et al., *Nature* 352: 624-628 (1991); Marks et al., *J Mol. Biol.* 222: 581-597 (1992); Marks and Bradbury, *Methods in Molecular Biology* 248:161-175 (Lo, ed., Human Press, Totowa, N.J., 2003); Sidhu et al., *J Mol. Biol.* 338(2): 299-310 (2004); Lee et al., *J Mol. Biol.* 340(5): 1073-1093 (2004); Fellouse, *Proc. Natl. Acad. Sci. USA* 101(34): 12467-12472 (2004); and Lee et al., *J Immunol. Methods* 284(1-2): 119-132(2004).

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self as well as self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Anti-PSMA antibody moiety sequence variants can be prepared using phage display to screen libraries for antibodies specific to PSMA (e.g., a cell surface-bound PSMA). The library can be a human scFv phage display library having a diversity of at least $1\times10^9$ (such as at least about any one of $1\times10^9$, $2.5\times10^9$, $5\times10^9$, $7.5\times10^9$, $1\times10^{10}$, $2.5\times10^{10}$, $5\times10^{10}$, $7.5\times10^{10}$, or $1\times10^{11}$) unique human antibody fragments. In some embodiments, the library is a naïve human library constructed from DNA extracted from human PMBCs and spleens from healthy donors, encompassing all human heavy and light chain subfamilies. In some embodiments, the library is a naïve human library constructed from DNA extracted from PBMCs isolated from patients with various diseases, such as patients with autoimmune diseases, cancer patients, and patients with infectious diseases. In some embodiments, the library is a semi-synthetic human library, wherein heavy chain CDR3 is completely randomized, with all amino acids (with the exception of cysteine) equally likely to be present at any given position (see, e.g., Hoet, R. M. et al., *Nat. Biotechnol.* 23(3):344-348, 2005). In some embodiments, the heavy chain CDR3 of the semi-synthetic human library has a length from about 5 to about 24 amino acids (such as about any of 5, 6, 7, 8, 9, 10, 11, 12, 13, 14, 15, 16, 17, 18, 19, 20, 21, 22, 23, or 24 amino acids). In some embodiments, the library is a non-human phage display library.

Phage clones that bind to PSMA (e.g., a cell surface-bound human PSMA) with high affinity can be selected by iterative binding of phage to PSMA, which is bound to a solid support (such as, for example, beads for solution panning or mammalian cells for cell panning), followed by removal of non-bound phage and by elution of specifically bound phage. In an example of solution panning, the PSMA can be biotinylated for immobilization to a solid support. The biotinylated PSMA is mixed with the phage library and a solid support, such as streptavidin-conjugated Dynabeads M-280, and then PSMA-phage-bead complexes are isolated. The bound phage clones are then eluted and used to infect an appropriate host cell, such as *E. coli* XL1-Blue, for expression and purification.

In another example of cell panning, mammalian cells expressing cell surface-bound PSMA (such as Jurkat cells expressing human PSMA) are mixed with the phage library, after which the cells are collected and the bound clones are eluted and used to infect an appropriate host cell for expression and purification. The panning can be performed for multiple (such as about any of 2, 3, 4, 5, 6 or more) rounds via solution panning, cell panning, or a combination of both, to enrich for phage clones binding specifically to the PSMA.

Enriched phage clones can be tested for specific binding to PSMA by any methods known in the art, including for example ELISA and FACS.

A useful method of identification of residues or regions of an anti-PSMA antibody moiety that may be targeted for mutagenesis is called "alanine scanning mutagenesis" as described by Cunningham and Wells (1989) *Science*, 244: 1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody moiety with antigen is affected. Further substitutions may be introduced at the amino acid locations demonstrating functional sensitivity to the initial substitutions. Alternatively, or additionally, a crystal structure of an antigen-antibody moiety complex can be determined to identify contact points between the antibody moiety and antigen. Such contact residues and neighboring residues may be targeted or eliminated as candidates for substitution. Variants may be screened to determine whether they contain the desired properties.

An anti-PSMA antibody moiety provided herein may additionally comprise one or more peptide tag sequences, peptide linker sequences (including self-cleaving linkers), cleavage sites, or other peptide sequences (e.g., signal peptides). An exemplary signal peptide sequence is METDTLLLWVLLLWVPGSTG (SEQ ID NO: 128). Exemplary peptide linker sequences, cleavage sites, and peptide tag sequences are shown in Tables 6A and 6B below.

TABLE 6A

Exemplary Peptide Linkers and Cleavage Sites

| | | | |
|---|---|---|---|
| SRGGGGSG GGGSGGGG SLEMA (SEQ ID NO: 24) | GGGGS (SEQ ID NO:140) | SGGG (SEQ ID NO: 147) | GGSGGSGG SGGS (SEQ ID NO: 154) |
| RAKRS (SEQ ID NO: 129) | GGGGSGGG GS (SEQ ID NO: 141) | GSGS (SEQ ID NO: 148) | GGSG (SEQ ID NO: 155) |
| GSGAPVKQ TLNFDLLK LAGDVESN PGP (SEQ ID NO: 130) | GGGGSGGG GSGGGGS (SEQ ID NO: 142) | GSGSGS (SEQ ID NO: 149) | GGSGGGSG (SEQ ID NO: 156) |
| RAKRSGSG APVKQTLN FDLLKLAG DVESNPGP (SEQ ID NO: 131) | AAATG (SEQ ID NO: 143) | GSGSGSGS (SEQ ID NO: 150) | GGSGGGSG GGSG (SEQ ID NO: 157) |
| GSGATNFS LLKQAGDV EENPGP (SEQ ID NO: 132) | TPLGDTTH TSG (SEQ ID NO: 144) | GSGSGSGS GS (SEQ ID NO: 151) | |
| RAKRSGSG ATNFSLLK QAGDVEEN PGP (SEQ ID NO: 133) | AAA (SEQ ID NO: 145) | GGSGGS (SEQ ID NO: 152) | |

TABLE 6A-continued

Exemplary Peptide Linkers and Cleavage Sites

| | | |
|---|---|---|
| GSRGGGGS GGGGSGGG GSLEMA (SEQ ID NO: 139) | GGSG (SEQ ID NO: 146) | GGSGGSGG S (SEQ ID NO: 153) |

TABLE 6B

Exemplary Peptide Tags

| | |
|---|---|
| EQKLISEEDL (SEQ ID NO: 136) | HHHHHH (SEQ ID NO: 158) |
| DYKDHDGDYKDHDIDYKDDDDK (SEQ ID NO: 137) | YPYDVPDYA (SEQ ID NO: 159) |
| DYKDDDDK (SEQ ID NO 138) | YPYDVPDYAS (SEQ ID NO: 160) |

Full-Length Anti-PSMA Antibodies

In some embodiments, the anti-PSMA construct provided herein is or comprises a full-length antibody, e.g., a full-length antibody comprising an anti-PSMA antibody moiety, also referred to herein as a "full-length anti-PSMA antibody." In some embodiments, the full-length antibody is a monoclonal antibody, as described in further detail elsewhere herein.

In some embodiments, the full-length anti-PSMA antibody comprises an Fc sequence from an immunoglobulin, e.g., a human immunoglobulin such as IgA, IgD, IgE, IgG, or IgM. In some embodiments, the full-length anti-PSMA antibody comprises an Fc sequence of IgG, e.g., a human IgG, such as any of IgG1, IgG2, IgG3, or IgG4. In some embodiments, the full-length anti-PSMA antibody comprises an Fc sequence of a rabbit, rat, or mouse immunoglobulin. In some embodiments, the full-length anti-PSMA antibody comprises an Fc sequence of a non-human primate (e.g., a rhesus monkey or cynomolgus monkey). In some embodiments, the full-length anti-PSMA antibody comprises an Fc sequence that has been altered or otherwise changed so that it has enhanced antibody dependent cellular cytotoxicity (ADCC) function and/or enhanced complement dependent cytotoxicity (CDC) effector function, as described in further detail elsewhere herein.

The amino acid sequences of exemplary full length anti-PSMA antibodies that comprise an human IgG1 Fc region are provided in Table 7 below. The V$_L$ in each light chain is underlined, and the V$_H$ in each heavy chain is underlined. The CDRs are in bold type.

TABLE 7

Exemplary full length Clone A anti-PSMA antibody comprising a human IgG1 Fc E2212EL
Heavy chain:
EVQLVQSGAEVKKPGESLKISCKGSGYSFTSYWIG
WVRQMPGKGLEWMGITYPGDSDTRYSPSFQGQVTI
SADKSISTAYLQWSSLKASDTAMYYCARSMGSSLY
ASSDVWGQGTLVTVSSASTKGPSVFPLAPSSKSTS
GGTAALGCLVKDYFPEPVTVSWNSGALTSGVHTFP
AVLQSSGLYSLSSVVTVPSSSLGTQTYICNVNHKP
SNTKVDKKVEPKSCDKTHTCPPCPAPELLGGPSVF
LFPPKPKDTLMISRTPEVTCVVVDVSHEDPEVKFN
WYVDGVEVHNAKTKPREEQYNSTYRVVSVLTVLHQ

TABLE 7-continued

DWLNGKEYKCKVSNKALPAPIEKTISKAKGQPREP
QVYTLPPSREEMTKNQVSLTCLVKGFYPSDIAVEW
ESNGQPENNYKTTPPVLDSDGSFFLYSKLTVDKSR
WQQGNVFSCSVMHEALHNHYTQKSLSLSPGK
(SEQ ID NO: 39)

Light Chain:
QSVLTQPPSVSGAPGQRVTISCTGSSSNIGAGYDV
HWYQQLPGTAPKLLIYGNSNRPSGVPDRFSGSKSG
TSASLAITGLQAEDEADYYCQSYDSSLSGYVFGTG
TKVTVLGQPKANPTVTLFPPSSEELQANKATLVCL
ISDFYPGAVTVAWKADGSPVKAGVETTKPSKQSNN
KYAASSYLSLTPEQWKSHRSYSCQVTHEGSTVEKT
VAPTECS
(SEQ ID NO: 40)

Exemplary full length Clone B anti-PSMA antibody comprising a human IgG1 Fc E2.912LU
Heavy chain:
EVQLVQSGAEMKKPGESLKISCKGSGYNFASYWVG
WVRQMPGKGLEWMGTIYPDDSDTRYGPAFQGQVTI
SADKSISTAYLQWSSLKASDTAMYYCARDSYYGID
VWGQGTLVTVSSASTKGPSVFPLAPSSKSTSGGTA
ALGCLVKDYFPEPVTVSWNSGALTSGVHTFPAVLQ
SSGLYSLSSVVTVPSSSLGTQTYICNVNHKPSNTK
VDKKVEPKSCDKTHTCPPCPAPELLGGPSVFLFPP
KPKDTLMISRTPEVTCVVVDVSHEDPEVKFNWYVD
GVEVHNAKTKPREEQYNSTYRVVSVLTVLHQDWLN
GKEYKCKVSNKALPAPIEKTISKAKGQPREPQVYT
LPPSREEMTKNQVSLTCLVKGFYPSDIAVEWESNG
QPENNYKTTPPVLDSDGSFFLYSKLTVDKSRWQQG
NVFSCSVMHEALHNHYTQKSLSLSPGK
(SEQ ID NO: 41)

Light Chain:
QAVLTQPPSASGTPGQRVTISCSGSSSNIGSNTVN
WYQQLPGTAPKLLMYSNNQRPSGVPDRFSGSKSGT
SASLAISGLQSEDEADYYCAAWDDSLNGYVFGTGT
KVTVLGQPKANPTVTLFPPSSEELQANKATLVCLI
SDFYPGAVTVAWKADGSPVKAGVETTKPSKQSNNK
YAASSYLSLTPEQWKSHRSYSCQVTHEGSTVEKTV
APTECS
(SEQ ID NO: 42)

In some embodiments, the full length anti-PSMA IgG1 antibody comprises a heavy chain that comprises a V$_H$ described herein and a light chain that comprises a V$_L$ described herein. In some embodiments, the full length anti-PSMA IgG1 antibody comprises a heavy chain that comprises an amino acid sequence that has at least about 85% (e.g., at least about any one of 85%, 86%, 87%, 88%, 89%, 90%, 91%, 92%, 93%, 94%, 95%, 96%, 97%, 98%, or 99%) sequence identity to SEQ ID NO: 39 and a light chain that comprises an amino acid sequence that has at least about 850% (e.g., at least about any one of 85%, 86%, 87%, 88%, 89%, 90%, 91%, 92%, 93%, 94%, 95%, 96%, 97%, 98%, or 99%) sequence identity to SEQ ID NO: 40. In some embodiments, the full-length anti-PSMA IgG1 antibody comprises a heavy chain that comprises an amino acid sequence that has at least about 85% (e.g., at least about any one of 85%, 86%, 87%, 88%, 89%, 90%, 91%, 92%, 93%, 94%, 95%, 96%, 970, 980%, or 990%) sequence identity to SEQ ID NO: 41 and a light chain that comprises an amino acid sequence that has at least about 85% (e.g., at least about any one of 85%, 86%, 87%, 88%, 89%, 90%, 91%, 92%, 93%, 94%, 95%, 96%, 97%, 98%, or 99%) sequence identity to SEQ ID NO: 42.

Human and Humanized Anti-PSMA Antibodies and Antibody Moieties

In some embodiments, the anti-PSMA construct comprises an anti-PSMA antibody moiety that is a human or humanized. Humanized forms of non-human (e.g., murine)

antibody moieties are chimeric immunoglobulins, immunoglobulin chains, or fragments thereof (such as Fv, Fab, Fab', F(ab')$_2$, scFv, or other antigen-binding subsequences of full-length antibodies that typically contain minimal sequence derived from non-human immunoglobulin. Humanized antibody moieties include human immunoglobulins (recipient antibodies) in which residues from one or more CDRs of the recipient are replaced by residues (import residues) from a CDR of a non-human species (donor antibody) such as a mouse, rat, or rabbit antibody having the desired specificity, affinity, and capacity. In some instances, Fv framework residues of the human immunoglobulin are replaced by corresponding non-human residues. Humanized antibodies can also comprise residues that are found neither in the recipient antibody nor in the imported CDR or framework sequences. In general, the humanized antibody can comprise substantially all of at least one, and typically two, variable domains, in which all or substantially all of the CDR regions correspond to those of a non-human immunoglobulin, and all or substantially all of the FR regions are those of a human immunoglobulin consensus sequence. In some embodiments, the humanized antibody will comprise at least a portion of an immunoglobulin constant region (Fc), typically that of a human immunoglobulin. See, e.g., Jones et al., *Nature,* 321: 522-525 (1986); Riechmann et al., *Nature,* 332: 323-329 (1988); Presta, *Curr. Op. Struct. Biol.,* 2:593-596 (1992), Verhoeyen et al., *Science,* 239: 1534-1536 (1988), and U.S. Pat. No. 4,816,567.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *PNAS USA,* 90:2551 (1993); Jakobovits et al., *Nature,* 362:255-258 (1993); Bruggemann et al., *Year in Immunol.,* 7:33 (1993); U.S. Pat. Nos. 5,545, 806, 5,569,825, 5,591,669; 5,545,807; and WO 97/17852. Alternatively, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; and 5,661,016, and Marks et al., *Bio Technology,* 10: 779-783 (1992); Lonberg et al., *Nature,* 368: 856-859 (1994); Morrison, *Nature,* 368: 812-813 (1994); Fishwild et al., *Nature Biotechnology,* 14: 845-851 (1996); Neuberger, *Nature Biotechnology,* 14: 826 (1996); Lonberg and Huszar, *Intern. Rev. Immunol.,* 13: 65-93 (1995).

Human antibodies may also be generated by in vitro activated B cells (see U.S. Pat. Nos. 5,567,610 and 5,229, 275) or by using various techniques known in the art, including phage display libraries. Hoogenboom and Winter, *J. Mol. Biol.,* 227:381 (1991); Marks et al., *J. Mol. Biol.,* 222:581 (1991). The techniques of Cole et al. and Boerner et al. are also available for the preparation of human monoclonal antibodies. Cole et al., *Monoclonal Antibodies and Cancer Therapy,* Alan R. Liss, p. 77 (1985) and Boerner et al., *J. Immunol.,* 147(1): 86-95 (1991).

Monoclonal Anti-PSMA Antibodies and Antibody Moieties

In some embodiments, an anti-PSMA construct of the present disclosure comprises a monoclonal anti-PSMA antibody or a monoclonal anti-PSMA antibody moiety. Monoclonal antibodies can be prepared, e.g., using hybridoma methods, such as those described by Kohler and Milstein, *Nature,* 256:495 (1975) and Sergeeva et al., *Blood,* 117(16): 4262-4272, using the phage display methods described herein and in the Examples below, or using recombinant DNA methods (see, e.g., U.S. Pat. No. 4,816,567).

In a hybridoma method, a hamster, mouse, or other appropriate host animal is typically immunized with an immunizing agent to elicit lymphocytes that produce or are capable of producing antibodies that will specifically bind to the immunizing agent. Alternatively, the lymphocytes can be immunized in vitro. The immunizing agent can include a polypeptide or a fusion protein of the protein of interest, or a complex comprising at least two molecules. Generally, peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. See, e.g., Goding, Monoclonal Antibodies: Principles and Practice (New York: Academic Press, 1986), pp. 59-103. Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which prevents the growth of HGPRT-deficient cells.

In some embodiments, the immortalized cell lines fuse efficiently, support stable high-level expression of antibody by the selected antibody-producing cells, and are sensitive to a medium such as HAT medium. In some embodiments, the immortalized cell lines are murine myeloma lines, which can be obtained, for instance, from the Salk Institute Cell Distribution Center, San Diego, California and the American Type Culture Collection, Manassas, Virginia Human myeloma and mouse-human heteromyeloma cell lines also have been described for the production of human monoclonal antibodies. Kozbor, *J. Immunol.,* 133:3001 (1984); Brodeur et al. Monoclonal Antibody Production Techniques and Applications (Marcel Dekker, Inc.: New York, 1987) pp. 51-63.

The culture medium in which the hybridoma cells are cultured can then be assayed for the presence of monoclonal antibodies directed against the polypeptide. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones can be sub cloned by limiting dilution procedures and grown by standard methods. Goding, supra. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the sub clones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

In certain embodiments, the anti-PSMA antibody or antibody moiety is monovalent. Methods for preparing monovalent antibodies are known in the art. One exemplary method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using any method known in the art.

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. In some embodiments, the first heavy-chain constant region (CH1) containing the site necessary for light-chain binding is present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies, see, for example, Suresh et al., *Methods in Enzymology*, 121: 210 (1986).

Monoclonal antibodies can also be made by recombinant DNA methods, such as those described in U.S. Pat. No. 4,816,567. DNA encoding the monoclonal anti-PSMA antibodies can be readily isolated and sequenced using conventional procedures (e.g., by using oligonucleotide probes that are capable of binding specifically to genes encoding the heavy and light chains of murine antibodies). Hybridoma cells as described above or PSMA-specific phage clones can serve as a source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy- and light-chain constant domains and/or framework regions in place of the homologous non-human sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an anti-PSMA antibody, or can be substituted for the variable domains of one antigen-combining site of an anti-PSMA antibody to create a chimeric bivalent antibody.

Multispecific Anti-PSMA Constructs

In some embodiments, the anti-PSMA construct is multispecific. Multispecific anti-PSMA constructs provided herein demonstrate binding specificities for at least two different antigens or two different epitopes (e.g., two different epitopes on the same antigen). Multispecific constructs comprising more than two valencies and/or antigen specificities are also contemplated. For example, trispecific antibodies can be prepared. See, e.g., Tutt et al. *J. Immunol.* 147: 60 (1991). Thus, in some embodiments, the multispecific anti-PSMA construct comprises an anti-PSMA antibody moiety and at least one additional binding moiety, such as an antigen-binding moiety, e.g., an antibody moiety.

In some embodiments, the multispecific (e.g., bispecific) anti-PSMA construct comprises a) an anti-PSMA antibody moiety (such as described herein) that specifically binds to PSMA (e.g., a cell surface-bound PSMA), and b) a second binding moiety (such as an antigen-binding moiety). In some embodiments, the second binding moiety specifically binds to an epitope on PSMA (e.g., PSMA expressed on the surface of a cell, such as a cancer cell) that does not overlap with the epitope bound by the anti-PSMA antibody moiety. In some embodiments, the second binding moiety specifically binds to a different antigen (i.e., an antigen other than PSMA). In some embodiments, the second binding moiety specifically binds to an antigen on the surface of a cell, such as a cancer cell or an immune cell. In some embodiments, the second binding moiety specifically binds to an antigen on the surface of a lymphocyte, such as a T cell, an NK cell, a neutrophil, a monocyte, a macrophage, or a dendritic cell. In some embodiments, the second binding moiety specifically binds to an effector T cell, such as a cytotoxic T cell (also known as cytotoxic T lymphocyte (CTL) or T killer cell). In some embodiments, the second binding moiety is an antibody moiety.

In some embodiments, the multispecific anti-PSMA construct comprises a) an anti-PSMA antibody moiety (such as described herein) that specifically binds to PSMA (e.g., PSMA expressed on the surface of a cell, such as a cancer cell), and b) a second binding moiety that binds specifically to CD3. In some embodiments, the second binding moiety is an antibody moiety that binds CD3. In some embodiments, the second antigen-binding moiety is a human, humanized, or semi-synthetic antibody moiety. In some embodiments, the second binding moiety specifically binds to CD3ε. In some embodiments, the second binding moiety specifically binds to an agonistic epitope of CD3ε. In some embodiments, the term "agonistic epitope" refers to an epitope that, upon binding of the multispecific molecule, optionally upon binding of several multispecific molecules on the same cell, allows said multispecific molecules to activate TCR signaling and induce T cell activation. In some embodiments, the term "agonistic epitope" refers to an epitope that is solely composed of amino acid residues of the epsilon chain of CD3 and is accessible for binding by the multispecific molecule, when presented in its natural context on T cells (i.e. surrounded by the TCR, the CD3γ chain, etc.). In some embodiments, the term "agonistic epitope" refers to an epitope that, upon binding of the multispecific molecule, does not lead to stabilization of the spatial position of CD3ε relative to CD3γ. In some embodiments, the multispecific anti-PSMA construct further comprises at least one (such as at least about any of 2, 3, 4, 5, or more) additional antigen-binding moieties.

In some embodiments, the multispecific anti-PSMA construct comprises a) an anti-PSMA antibody moiety (such as described herein) that specifically binds to PSMA (e.g., PSMA expressed on the surface of a cell, such as a cancer cell), and b) a second binding moiety that binds specifically to an antigen on the surface of an effector cell, including for example CD3γ, CD3δ, CD3ε, CD3ζ, CD28, CD16a, CD56, CD68, and GDS2D. In some embodiments, the second binding moiety is an antibody moiety. In some embodiments, the second antigen-binding moiety is a human, humanized, or semi-synthetic antibody moiety. In some embodiments, the multispecific anti-PSMA construct further comprises at least one (such as at least about any of 2, 3, 4, 5, or more) additional antigen-binding moieties.

In some embodiments, the multispecific anti-PSMA construct comprises a) an anti-PSMA antibody moiety (such as described herein) that specifically binds to PSMA (e.g., PSMA expressed on the surface of a cell, such as a cancer cell), and b) a second binding moiety that binds specifically to a component of the complement system, such as C1q. C1q is a subunit of the C1 enzyme complex that activates the serum complement system. In some embodiments, the second binding moiety is an antibody moiety. In some embodiments, the second antigen-binding moiety is a human, humanized, or semi-synthetic antibody moiety. In some embodiments, the multispecific anti-PSMA construct further comprises at least one (such as at least about any of 2, 3, 4, 5, or more) additional antigen-binding moieties.

In some embodiments, the multispecific anti-PSMA construct comprises a) an anti-PSMA antibody moiety (such as described herein) that specifically binds to PSMA (e.g., PSMA expressed on the surface of a cell, such as a cancer cell), and b) a second binding moiety that specifically binds to an Fc receptor, e.g., an Fcγ receptor (FcγR). The FcγR may be an FcγRIII present on the surface of natural killer (NK) cells or one of FcγRI, FcγRIIA, FcγRIIBI, FcγRIIB2, and FcγRIIIB present on the surface of macrophages, monocytes, neutrophils and/or dendritic cells. In some embodiments, the second binding moiety is an antibody moiety. In some embodiments, the second antigen-binding moiety is a human, humanized, or semi-synthetic antibody moiety. In some embodiments, the second binding moiety that is an Fc region or functional fragment thereof. In some embodiments, "functional fragment" refers to a fragment of an antibody Fc region that is still capable of binding to an FcR, in particular to an FcγR, with sufficient specificity and affinity to allow an FcγR bearing effector cell, in particular a macrophage, a monocyte, a neutrophil and/or a dendritic cell, to kill the target cell by cytotoxic lysis or phagocytosis. A functional Fc fragment is capable of competitively inhibiting the binding of the original, full-length Fc portion to an FcR such as FcγRI, FcγRIIA, FcγRIIBI, FcγRIIB2, or FcγRIIIB. In some embodiments, a functional Fc fragment retains at least 30%, 40%, 50%, 60%, 70%, 80%, 90% or 95% of its affinity to an FcγR, such as an activating FcγR. In some embodiments, the Fc region or functional fragment thereof is an enhanced Fc region or functional fragment thereof. As used herein, "enhanced Fc region" refers to an Fc region that is modified to enhance Fc receptor-mediated effector-functions, in particular antibody-dependent cell-mediated cytotoxicity (ADCC), complement-dependent cytotoxicity (CDC), and antibody-mediated phagocytosis. For example, an Fc region can be altered in a way that leads to an increased affinity for an activating receptor (e.g. FcγRIIIA (CD16A) expressed on natural killer (NK) cells) and/or a decreased binding to an inhibitory receptor (e.g. FcγRIIB1/B2 (CD32B)). In some embodiments, the second antigen-binding moiety is an antibody or antigen-binding fragment thereof that specifically binds to an FcR, in particular to an FcγR, with sufficient specificity and affinity to allow an FcγR bearing effector cell, in particular a macrophage, a monocyte, a neutrophil and/or a dendritic cell, to kill the target cell by cytotoxic lysis or phagocytosis. In some embodiments, the multispecific anti-PSMA construct further comprises at least one (such as at least about any of 2, 3, 4, 5, or more) additional antigen-binding moieties.

In some embodiments, the multispecific anti-PSMA construct allows killing of target cells (such as cancer cells) expressing PSMA on their surfaces. In some embodiments, the multispecific anti-PSMA construct effectively redirects cytotoxic T lymphocytes (CTLs) to lyse target cells (such as cancer cells) expressing (such as overexpressing) PSMA on their surfaces. In some embodiments, the multispecific (e.g., bispecific) anti-PSMA construct has an in vitro $EC_{50}$ value ranging from 10 to 500 ng/ml. In some embodiments, the multispecific (e.g., bispecific) anti-PSMA construct capable of inducing redirected lysis of about 50% of the target cells through CTLs at a ratio of CTLs:target cells of from about 1:1 to about 50:1 (such as from about 1:1 to about 15:1, or from about 2:1 to about 10:1).

In some embodiments, the multispecific (e.g., bispecific) anti-PSMA construct is capable of cross-linking a stimulated or unstimulated CTL and the target cell (such as a cancer cell) in such a way that the target cell is lysed. This offers the advantage that no generation of target-specific T cell clones or common antigen presentation by dendritic cells is required for the multispecific anti-PSMA construct to exert its desired activity. In some embodiments, a multispecific anti-PSMA construct provided herein is capable of redirecting CTLs to lyse the target cells (such as cancer cells) in the absence of other activating signals. In some embodiments, the second antigen-binding moiety of the multispecific anti-PSMA construct specifically binds to CD3 (e.g., CD3R), and signaling through CD28 and/or IL-2 is not required for redirecting CTLs to lyse the target cells (e.g., cancer cells).

Methods for measuring the preference of the multispecific anti-PSMA construct to simultaneously bind to two antigens (e.g., two different antigens on two different cells or, alternatively two different antigens of the same cell) are within the capabilities of a person of ordinary skill in the art. For example, when the second binding moiety of a multispecific anti-PSMA construct specifically binds to CD3, the multispecific anti-PSMA construct may be contacted with a mixture of $CD3^+/PSMA^-$ cells and $CD3^-/PSMA^+$ cells. The number of single cells bound by the multispecific anti-PSMA constructs and the number of cross-linked cells bound by the multispecific anti-PSMA constructs may then be assessed by fluorescence microscopy, fluorescence-activated cell sorting (FACS), and/or other methods known in the art.

In some embodiments, the multispecific anti-PSMA construct is, for example, a bispecific antibody, a diabody (Db), a single-chain diabody (scDb), a tandem scDb (Tandab), a linear dimeric scDb (LD-scDb), a circular dimeric scDb (CD-scDb), a di-diabody, a tandem scFv, a tandem di-scFv, a tandem tri-scFv, a tri(a)body, a bispecific Fab2, a di-miniantibody, a tetrabody, an scFv-Fc-scFv fusion, a dual-affinity retargeting (DART) antibody, a dual variable domain (DVD) antibody, an IgG-scFab, an scFab-ds-scFv, an Fv2-Fc, an IgG-scFv fusion, a dock and lock (DNL) antibody, a knob-into-hole (KiH) antibody (bispecific IgG prepared by the KiH technology), a DuoBody (bispecific IgG prepared by the Duobody technology), a heteromultimeric antibody, or a heteroconjugate antibody. In some embodiments, the multispecific anti-PSMA molecule is a tandem scFv (e.g., a tandem di-scFv). It is to be appreciated that one of ordinary skill in the art could select appropriate features of various multispecific constructs known in the art and combine them with one another to form a further multispecific anti-PSMA construct within the scope of this disclosure.

Suitable methods for making multispecific constructs (e.g., bispecific antibodies) are well known in the art. For example, the production of bispecific antibodies can based on the co-expression of two immunoglobulin heavy-chain/light-chain pairs, where the two pairs each have different specificities, and upon association result in a heterodimeric antibody (see, e.g., Milstein and Cuello, *Nature*, 305: 537-539 (1983); WO 93/08829, and Traunecker et al., *EMBO J.* 10: 3655 (1991)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829 and in Traunecker et al., *EMBO*, 10: 3655-3659 (1991). Alternatively, the combining of heavy and light chains can be directed by taking advantage of species-restricted pairing (see, e.g., Lindhofer et al., *J. Immunol.*, 155:219-225 (1995)) and the pairing of heavy chains can be directed by use of "knob-into hole" engineering of CH3 domains (see, e.g., U.S. Pat. No. 5,731,168; Ridgway et al., *Protein Eng.*, 9(7):617-621 (1996)). Multispecific antibodies may also be made by engineering electrostatic steering effects for making antibody Fc-heterodimeric molecules (see, e.g., WO 2009/089004A1). In yet another method, stable bispecific antibodies can be generated by controlled Fab-arm exchange, where two parental antibodies having distinct antigen specificity and matched point mutations in the CH3 domains are mixed in reducing condition to allow for separation, reassembly, and reoxidation to form highly pure bispecific antibodies. Labrigin et al., *Proc. Natl. Acad. Sci.*, 110(13):5145-5150 (2013). Such antibodies, comprising a mixture of heavy-chain/light-chain pairs, are also referred to herein as "heteromultimeric antibodies."

Antibodies or antigen-binding fragments thereof having different specificities can also be chemically cross-linked to generate multispecific heteroconjugate antibodies. For example, two F(ab')2 molecules, each having specificity for a different antigen, can be chemically linked. Pullarkat et al., *Trends Biotechnol.*, 48:9-21 (1999). Such antibodies have, for example, been proposed to target immune-system cells to unwanted cells (U.S. Pat. No. 4,676,980), and for treatment of HIV infection. WO 91/00360; WO 92/200373; EP 03089. It is contemplated that the antibodies can be prepared in vitro using known methods in synthetic protein chemistry, including those involving crosslinking agents. For example, immunotoxins can be constructed using a disulfide-exchange reaction or by forming a thioether bond. Examples of suitable reagents for this purpose include iminothiolate and methyl-4-mercaptobutyrimidate and those disclosed, for example, in U.S. Pat. No. 4,676,980.

In some embodiments, multispecific anti-PSMA constructs can be prepared using recombinant DNA techniques. For example, a bispecific antibody can be engineered by fusing two scFvs, such as by fusing them through a peptide linker, resulting in a tandem scFv (such as a tandem di-scFv). The terms "anti-PSMA tandem di-scFv" and "bispecific anti-PSMA antibody" are used interchangeably herein. In some embodiments, the tandem scFv comprises an anti-CD3 scFv to an scFv comprising an anti-PSMA binding moiety described herein, resulting in the redirection of T cells to target cells that express (such as overexpress) PSMA. Additional details regarding the construction and expression of tandem scFvs are provided in, e.g., Mack et al., *Proc. Natl. Acad. Sci.*, 92:7021-7025 (1995); Brischwein et al., *Mol. Immunol.*, 43(8):1129-1143 (2006). Additional details regarding tandem scFvs of the present disclosure are provided elsewhere herein.

By shortening the length of a peptide linker between two variable domains, the variable domains can be prevented from self-assembling and forced to pair with domains on a second polypeptide, resulting in a compact bispecific antibody called a diabody (Db). Holliger et al., *Proc. Natl. Acad. Sci.*, 90:6444-6448 (1993). The two polypeptides of a Db each comprise a $V_H$ connected to a $V_L$ by a linker which is too short to allow pairing between the two domains on the same chain. Accordingly, the $V_H$ and $V_L$ domains of one polypeptide are forced to pair with the complementary $V_L$ and $V_H$ domains of another polypeptide, thereby forming two antigen-binding sites. In a modification of this format, the two polypeptides are linked by another peptide linker, resulting in a single chain diabody (scDb). In yet another modification of the Db format, dual-affinity retargeting (DART) bispecific antibodies can be generated by introducing a disulfide linkage between cysteine residues at the C-terminus of each polypeptide, optionally including domains prior to the C-terminal cysteine residues that drive assembly of the desired heterodimeric structure. Veri et al., *Arthritis Rheum.*, 62(7):1933-1943 (2010). Dual-variable-domain immunoglobulins (DVD-Ig™), in which the target-binding variable domains of two monoclonal antibodies are combined via naturally occurring linkers to yield a tetravalent, bispecific antibody, are also known in the art. Gu and Ghayur, *Methods Enzymol.*, 502:25-41 (2012). In yet another format, Dock and Lock (DNL), bispecific antibodies are prepared by taking advantage of the dimerization of a peptide (DDD2) derived from the regulatory subunit of human cAMP-dependent protein kinase (PKA) with a peptide (AD2) derived from the anchoring domains of human A kinase anchor proteins (AKAPs). Rossi et al., *Proc. Natl. Acad. Sci.*, 103:6841-6846 (2006).

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). This method can also be utilized for the production of antibody homodimers.

Tandem scFv Constructs

In some embodiments, the multispecific anti-PSMA construct is a tandem scFv construct ("anti-PSMA tandem scFv") comprising a first scFv that comprises an anti-PSMA antibody moiety (such as described herein) and a second scFv that binds to a second target. In some embodiments, the tandem scFv is a di-scFv (comprising two scFv) or a tandem tri-scFv (comprising three scFv). In some embodiments, the anti-PSMA tandem scFv further comprises at least 3, 4, 5, 6, 7, 8, 9, 10, or more scFv. In some embodiments, the second scFv specifically binds to PSMA (such as an epitope that does not overlap the epitope bound by the anti-PSMA antibody moiety of the first scFv. In some embodiments, the second scFv specifically binds to another antigen (i.e., an antigen other than PSMA). In some embodiments, the second scFv specifically binds to an antigen on the surface of a cell, such as a cell that expresses PSMA (e.g., a cancer cell). In some embodiments, the second scFv specifically binds to an antigen on the surface of a cell that does not express PSMA. In some embodiments, the second scFv specifically binds to an antigen on the surface of a cytotoxic cell. In some embodiments, the second scFv specifically binds to an antigen on the surface of a lymphocyte, such as a T cell, an NK cell, a neutrophil, a monocyte, a macrophage, or a dendritic cell. In some embodiments, the second scFv specifically binds to an antigen on the surface of an effector T cell, such as a cytotoxic T cell. In some embodiments, the second scFv specifically binds to an antigen on the surface of an effector cell, including for example CD3γ, CD3δ, CD3ε, CD3ζ, CD28, CD16a, CD56, CD68, and GDS2D. In some embodiments, the first scFv and/or the second scFv is human, humanized, or semi-synthetic.

In some embodiments, the anti-PSMA tandem scFv comprises a) a first scFv that comprises an anti-PSMA antibody moiety (such as described herein) that specifically binds to PSMA (e.g., a cell surface-bound PSMA), and b) a second scFv that specifically binds to an antigen on the surface of a T cell. In some embodiments, the second scFv specifically binds to an antigen on the surface of an effector T cell, such as a cytotoxic T cell. In some embodiments, the second scFv specifically binds to, e.g., CD3γ, CD3δ, CD3ε, CD3ζ, CD28, OX40, GITR, CD137, CD27, CD40L, or HVEM. In some embodiments, the second scFv specifically binds to an agonistic epitope on an antigen on the surface of a T cell, wherein the binding of the second scFv to the agonistic epitope enhances T cell activation. In some embodiments, the first scFv and/or the second scFv is human, humanized, or semi-synthetic.

In some embodiments, the anti-PSMA tandem scFv comprises a) a first scFv that comprises an anti-PSMA antibody moiety (such as described herein) that specifically binds to PSMA (e.g., a cell surface-bound PSMA), and b) a second scFv that specifically binds to CD3ε. In some embodiments, the first scFv is fused to the second scFv via a peptide linker. In some embodiments, the peptide linker is between about 5 to about 20 amino acids in length (such as about any of 5, 10, 15, or 20, including any ranges between these values). In some embodiments, the peptide linker comprises (such as consists of or consists essentially of) the amino acid sequence GGGGS (SEQ ID NO: 140), although alternative linkers (such as those in Table 6A) may be used. In some embodiments, the first scFv and/or the second scFv is human, humanized, or semi-synthetic.

In some embodiments, the PSMA-binding scFv of an anti-PSMA tandem scFv provided herein binds to PSMA (e.g., a cell surface-bound PSMA) with a $K_d$ between about 0.1 pM to about 500 nM (such as about any one of 0.1 pM, 2.5 pM, 1.0 pM, 5 pM, 10 pM, 25 pM, 50 pM, 75 pM, 100 pM, 250 pM, 500 pM, 750 pM, 1 nM, 5 nM, 10 nM, 25 nM, 50 nM, 75 nM, 100 nM, 250 nM, or 500 nM, including any ranges between these values). In some embodiments, the PSMA-binding scFv of an anti-PSMA tandem scFv provided herein binds to PSMA (e.g., a cell surface-bound PSMA) with a $K_d$ between about 1 nM to about 500 nM (such as about any of 1, 5, 10, 25, 50, 75, 100, 150, 200, 250, 300, 350, 400, 450, or 500 nM, including any ranges between these values).

The amino acid sequences of exemplary anti-PSMA anti-CD3 tandem di-scFvs are provided in Table 8 below. The anti-PSMA scFv in each tandem di-scFv is in plain text (i.e., not underlined). The anti-CD3 scFv in each tandem di-scFv is underlined. The linker connecting the anti-PSMA scFv and the anti-CD3 scFv is in bold italic type.

TABLE 8

Clone A anti-PSMA anti-CD3 tandem
di-scFv (with His tag):
QSVLTQPPSVSGAPGQRVTISCTGSSSNIGAGYDV
HWYQQLPGTAPKLLIYGNSNRPSGVPDRFSGSKSG
TSASLAITGLQAEDEADYYCQSYDSSLSGYVFGTG
TKVTVLGSRGGGGSGGGGSGGGGSLEMAEVQLVQS TABLE 8 -continued GAEVKKPGESLKISCKGSGYSFTSYWIGWVRQMPG
KGLEWMGITYPGDSDTRYSPSFQGQVTISADKSIS
TAYLQWSSLKASDTAMYYCARSMGSSLYASSDVWG
QGTLVTVSS*TSGGGGS*DVQLVQSGAEVKKPGASVK
VSCKASGYTFTRYTMHWVRQAPGQGLEWIGYINPS
RGYTNYADSVKGRFTITTDKSTSTAYMELSSLRSE
DTATYYCARYYDDHYCLDYWGQGTTVTVSSGEGTS
TGSGGSGGSGGADDIVLTQSPATLSLSPGERATLS
CRASQSVSYMNWYQQKPGKAPKRWIYDTSKVASGV
PARFSGSGSGTDYSLTINSLEAEDAATYYCQQWSS
NPLTFGGGTKVEIKHHHHHH
(SEQ ID NO: 25)

Clone A anti-PSMA anti-CD3 tandem
di-scFv:
QSVLTQPPSVSGAPGQRVTISCTGSSSNIGAGYDV
HWYQQLPGTAPKLLIYGNSNRPSGVPDRFSGSKSG
TSASLAITGLQAEDEADYYCQSYDSSLSGYVFGTG
TKVTVLGSRGGGGSGGGGSGGGGSLEMAEVQLVQS
GAEVKKPGESLKISCKGSGYSFTSYWIGWVRQMPG
KGLEWMGITYPGDSDTRYSPSFQGQVTISADKSIS
TAYLQWSSLKASDTAMYYCARSMGSSLYASSDVWG
QGTLVTVSS*TSGGGGS*DVQLVQSGAEVKKPGASVK
VSCKASGYTFTRYTMHWVRQAPGQGLEWIGYINPS
RGYTNYADSVKGRFTITTDKSTSTAYMELSSLRSE
DTATYYCARYYDDHYCLDYWGQGTTVTVSSGEGTS
TGSGGSGGSGGADDIVLTQSPATLSLSPGERATLS
CRASQSVSYMNWYQQKPGKAPKRWIYDTSKVASGV
PARFSGSGSGTDYSLTINSLEAEDAATYYCQQWSS
NPLTFGGGTKVEIK
(SEQ ID NO: 26)

Clone B anti-PSMA anti-CD3 tandem
di-scEv (with His tag):
QAVLTQPPSASGTPGQRVTISCSGSSSNIGSNTVN
WYQQLPGTAPKLLMYSNNQRPSGVPDRFSGSKSGT
SASLAISGLQSEDEADYYCAAWDDSLNGYVFGTGT
KVTVLGSRGGGGSGGGGSGGGGSLEMAEVQLVQSG
AEMKKPGESLKISCKGSGYNFASYWVGWVRQMPGK
GLEWMGTIYPDDSDTRYGPAFQGQVTISADKSIST
AYLQWSSLKASDTAMYYCARDSYYGIDVWGQGTLV
TVSS*TSGGGGS*DVQLVQSGAEVKKPGASVKVSCKA
SGYTFTRYTMHWVRQAPGQGLEWIGYINPSRGYTN
YADSVKGRFTITTDKSTSTAYMELSSLRSEDTATY
YCARYYDDHYCLDYWGQGTTVTVSSGEGTSTGSGG
SGGSGGADDIVLTQSPATLSLSPGERATLSCRASQ
SVSYMNWYQQKPGKAPKRWIYDTSKVASGVPARFS
GSGSGTDYSLTINSLEAEDAATYYCQQWSSNPLTF
GGGTKVEIKHHHHHH
(SEQ ID NO: 27)

Clone B anti-PSMA anti-CD3 tandem
di-scFv:
QAVLTQPPSASGTPGQRVTISCSGSSSNIGSNTVN
WYQQLPGTAPKLLMYSNNQRPSGVPDRFSGSKSGT
SASLAISGLQSEDEADYYCAAWDDSLNGYVFGTGT
KVTVLGSRGGGGSGGGGSGGGGSLEMAEVQLVQSG
AEMKKPGESLKISCKGSGYNFASYWVGWVRQMPGK
GLEWMGTIYPDDSDTRYGPAFQGQVTISADKSIST
AYLQWSSLKASDTAMYYCARDSYYGIDVWGQGTLV
TVSS*TSGGGGS*DVQLVQSGAEVKKPGASVKVSCKA
SGYTFTRYTMHWVRQAPGQGLEWIGYINPSRGYTN
YADSVKGRFTITTDKSTSTAYMELSSLRSEDTATY
YCARYYDDHYCLDYWGQGTTVTVSSGEGTSTGSGG
SGGSGGADDIVLTQSPATLSLSPGERATLSCRASQ
SVSYMNWYQQKPGKAPKRWIYDTSKVASGVPARFS
GSGSGTDYSLTINSLEAEDAATYYCQQWSSNPLTF
GGGTKVEIK
(SEQ ID NO: 28)

Although the sequences in Table 8 comprise specific peptide linkers and peptide tags, any linker or tag (see, e.g., Tables 6A and 6B) may be used.

In some embodiments, the anti-PSMA anti-CD3 tandem di-scFv comprises an amino acid sequence that has at least about 85% (e.g., at least about any one of 85%, 86%, 87%, 88%, 89%, 90%, 91%, 92%, 93%, 94%, 95%, 96%, 97%, 98%, or 99%) sequence identity to SEQ ID NO: 25, 26, 27, or 28.

Anti-PSMA Chimeric Antigen Receptors (Anti-PSMA CARs)

In some embodiments, the anti-PSMA construct provided herein in is a chimeric antigen receptor (CAR) (also referred to herein as an "anti-PSMA CAR") comprising an anti-PSMA antibody moiety (such as an anti-PSMA antibody moiety described herein). As described in further detail elsewhere herein, the present disclosure also provides CAR effector cells (e.g., T cells) that comprise, express, or as associated with an anti-PSMA CAR. Such effector cells are also referred to herein as an "anti-PSMA CAR effector cells", e.g., "anti-PSMA CAR immune cells" or "anti-PSMA CAR T cells").

In some embodiments, an anti-PSMA CAR comprises a) an extracellular domain comprising an anti-PSMA antibody moiety (such as described herein) that specifically binds to PSMA (e.g., a cell surface-bound PSMA) and b) an intracellular signaling domain. In some embodiments, the anti-PSMA CAR comprises a transmembrane domain between the extracellular domain and the intracellular domain. In some embodiments, the anti-PSMA CAR further comprises a spacer. In some embodiments, the spacer connects the extracellular domain and the transmembrane domain of the anti-PSMA CAR. In some embodiments, the spacer connects the intracellular domain and the transmembrane domain of the anti-PSMA CAR. In some embodiments, the spacer domain is any oligo- or polypeptide that functions to link the transmembrane domain to the extracellular domain or the intracellular domain in the polypeptide chain. For example, a spacer domain may comprise up to about 300 amino acids, including for example between about 10 and about 100 amino acids, or between about 25 and about 50 amino acids.

The transmembrane domain of the anti-PSMA CAR may be derived from a natural source or a synthetic source. Where the source is natural, the domain may be derived from any membrane-bound or transmembrane protein. For example, in some embodiments, the anti-PSMA CAR comprises a transmembrane domain (e.g., at least one transmembrane domain or at least one transmembrane region) derived from, without limitation, the α, β, δ, or γ chain of the T-cell receptor, CD28, CD3ε, CD3ζ, CD45, CD4, CD5, CD8, CD9, CD16, CD22, CD33, CD37, CD64, CD80, CD86, CD134, CD137, or CD154. In some embodiments, the anti-PSMA CAR comprises a synthetic transmembrane domain, in which case the transmembrane domain may comprise predominantly hydrophobic residues such as leucine and valine. In some embodiments, a triplet of phenylalanine, tryptophan and valine may be found at each end of a synthetic transmembrane domain. In some embodiments, a short oligo- or polypeptide linker, having a length of, e.g., between about 2 and about 10 amino acids in length (such as about any of 2, 3, 4, 5, 6, 7, 8, 9, or 10 amino acids in length) may form the linkage between the transmembrane domain and the intracellular signaling domain of the anti-PSMA CAR. In some embodiments, the linker is a glycine-serine doublet.

In some embodiments, the anti-PSMA CAR comprises transmembrane domain that naturally is associated with one of the sequences in the anti-PSMA CAR's intracellular domain of. For example, if an anti-PSMA CAR intracellular domain comprises a CD28 co-stimulatory sequence, the transmembrane domain of the anti-PSMA CAR is derived from the CD28 transmembrane domain. In some embodiments, the anti-PSMA CAR comprises a transmembrane domain that has been selected or modified by amino acid substitution to minimize interactions with other members of the receptor complex and/or to avoid binding to the transmembrane domains of the same or different surface membrane proteins.

The intracellular signaling domain of the anti-PSMA CAR is responsible for activation of at least one of the normal effector functions of the immune cell in which the anti-PSMA CAR is expressed. Effector function of a T cell, for example, may be cytolytic activity or helper activity, including the secretion of cytokines. Thus, in some embodiments, the term "intracellular signaling domain" refers to the portion of an anti-PSMA CAR that transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. In some embodiments, the term "intracellular signaling sequence" refers to any truncated portion of the intracellular signaling domain sufficient to transduce the effector function signal.

In some embodiments, the anti-PSMA CAR comprises an intracellular signaling that comprises the cytoplasmic sequences of the T cell receptor (TCR) and co-receptors that act in concert to initiate signal transduction following antigen receptor engagement. In some embodiments, the anti-PSMA CAR comprises an intracellular signaling domain that comprises a derivative or variant of the T cell receptor (TCR) and co-receptors, and/or any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of intracellular signaling sequences: those that initiate antigen-dependent primary activation through the TCR (primary signaling sequences or primary immune cell signaling sequences) and those that act in an antigen-independent manner to provide a secondary or co-stimulatory signal (co-stimulatory signaling sequences).

Primary signaling sequences, or primary immune cell signaling sequences, regulate primary activation of the TCR complex in a stimulatory way or in an inhibitory way. Primary signaling sequences that act in a stimulatory manner may contain signaling motifs which are known as immunoreceptor tyrosine-based activation motifs (or ITAMs). Thus, in some embodiments, the anti-PSMA CAR comprises one or more ITAMs. In some embodiments, the anti-PSMA CAR comprises a primary immune cell signaling sequence derived from, without limitation, TCRζ, FcRγ, FcRO, CD3γ, CD3δ, CD3ε, CD5, CD22, CD79a, CD79b, and CD66d. In some embodiments, the anti-PSMA CAR further comprises a costimulatory signaling sequence. In some embodiments, the costimulatory signaling sequence is a portion of the intracellular domain of a costimulatory molecule including, for example, CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, and the like. In some embodiments, the anti-PSMA CAR comprises more than one costimulatory signaling sequence.

In some embodiments, the anti-PSMA CAR comprises a primary immune cell signaling sequence derived from CD3ζ. In some embodiments, the anti-PSMA CAR comprises a primary immune cell signaling sequence derived from CD3ζ by itself or combined with any other desired intracellular signaling sequence(s) useful in the context of the anti-PSMA CAR provided herein. For example, in some embodiments, the anti-PSMA CAR comprises an intracellular domain that comprises a primary immune cell signaling sequence derived from CD3ζ and a costimulatory signaling sequence. In some embodiments, the costimulatory signaling sequence is a portion of the intracellular domain of a costimulatory molecule including, for example, CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, and the like. In some embodiments, the costimulatory signaling sequence is derived from, e.g., CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, and the like. In some embodiments, the anti-PSMA CAR comprises more than one costimulatory signaling sequence.

In some embodiments, the anti-PSMA CAR comprises the intracellular signaling domain that comprises a primary immune cell signaling sequence derived from CD3ζ and a costimulatory signaling sequence derived from CD28. In some embodiments, the anti-PSMA CAR comprises the intracellular signaling domain that comprises a primary immune cell signaling sequence derived from CD3ζ and a costimulatory signaling sequence derived from 4-1BB. In some embodiments, the intracellular signaling domain of the anti-PSMA CAR comprises a primary immune cell signaling sequence derived from CD3ζ and costimulatory signaling sequences derived from CD28 and 4-1BB.

In some embodiments, the anti-PSMA CAR comprises a) an extracellular domain comprising an anti-PSMA antibody moiety (such as described herein) that specifically binds to PSMA (e.g., a cell surface-bound PSMA), b) a transmembrane domain, and c) an intracellular signaling domain capable of activating an immune cell. In some embodiments, the intracellular signaling domain comprises a primary immune cell signaling sequence and a co-stimulatory signaling sequence. In some embodiments, the primary immune cell signaling sequence comprises a CD3ζ intracellular signaling sequence. In some embodiments, the co-stimulatory signaling sequence comprises a CD28 or 4-1BB intracellular signaling sequence. In some embodiments, the intracellular domain comprises a CD3ζ intracellular signaling sequence and a CD28 or 4-1BB intracellular signaling sequence. In some embodiments, the anti-PSMA CAR comprises the anti-PSMA antibody moiety (such as described herein) fused to the amino acid sequence of SEQ ID NO: 22 (see below) which comprises a CD3ζ intracellular signaling sequence and a CD28 intracellular signaling sequence. In some embodiments, the anti-PSMA CAR comprises the anti-PSMA antibody moiety (such as described herein) fused to the amino acid sequence of SEQ ID NO: 23 (see below) which comprises a CD3ζ intracellular signaling sequence and a 4-1BB intracellular signaling sequence.

```
                                        (SEQ ID NO: 22)
AAAIEVMYPP PYLDNEKSNG TIIHVKGKHL CPSPLFPGPS

KPFWVLVVVG GVLACYSLLV TVAFIIFWVR SKRSRLLHSD

YMNMTPRRPG PTRKHYQPYA PPRDFAAYRS RVKFSRSADA
```

```
-continued
PAYQQGQNQL YNELNLGRRE EYDVLDKRRG RDPEMGGKPR

RKNPQEGLYN ELQKDKMAEA YSEIGMKGER RRGKGHDGLY

QGLSTATKDT YDALHMQALP PR (SED ID NO: 23)
TGTTTPAPRP PTPAPTIASQ PLSLRPEACR PAAGGAVHTR

GLDFACDIYI WAPLAGTCGV LLLSLVITLY CKRGRKKLLY

IFKQPFMRPV QTTQEEDGCS CRFPEEEEGG CELRVKFSRS

ADAPAYQQGQ NQLYNELNLG RREEYDVLDK RRGRDPEMGG

KPRRKNPQEG LYNELQKDKM AEAYSEIGMK GERRRGKGHD

GLYQGLSTAT KDTYDALHMQ ALPPR
```

In some embodiments, the anti-PSMA antibody moiety is an scFv (such as a multispecific anti-PSMA scFv, e.g., an anti-PSMA tandem di-scFv). In some embodiments, the scFv comprises heavy and light chain variable regions linked by a peptide linker, including, but not limited to, a peptide linker comprising the amino acid sequence of SRGGGGSGGGGSGGGGSLEMA (SEQ ID NO: 24).

The amino acid sequences of exemplary anti-PSMA CARs are provided Table 9 below. Each CAR comprises (sequentially, from the N-terminus to the C-terminus) an anti-PSMA scFv (plain text, i.e., no underline), a myc tag (bold underlined), a linker (bold italic type), sequences derived from CD28 (underlined), and sequences derived from CD3ζ (bold type and underlined).

TABLE 9

```
Clone A anti-PSMA CAR:
QSVLTQPPSVSGAPGQRVTISCTGSSSNIGAGYDVHWYQQ
LPGTAPKLLIYGNSNRPSGVPDRFSGSKSGTSASLAITGL
QAEDEADYYCQSYDSSLSGYVFGTGTKVTVLGSRGGGGSG
GGGSGGGGSLEMAEVQLVQSGAEVKKPGESLKISCKGSGY
SFTSYWIGWVRQMPGKGLEWMGITYPGDSDTRYSPSFQGQ
VTISADKSISTAYLQWSSLKASDTAMYYCARSMGSSLYAS
SDVWGQGTLVTVSSEQKLISEEDLAAAIEVMYPPPYLDNE
KSNGTIIHVKGKHLCPSPLFPGPSKPFWVLVVVGGVLACY
SLLVTVAFTIFWVRSKRSRLLHSDYMNMTPRRPGPTRKHY
QPYAPPRDFAAYRSRVKFSRSADAPAYQQGQNQLYNELNL
GRREEYDVLDKRRGRDPEMGGKPRRKNPQEGLYNELQKDK
MAEAYSEIGMKGERRRGKGHDGLYQGLSTATKDTYDALHM
QALPPR
(SEQ ID NO: 29)

Clone B anti-PSMA CAR:
QAVLTQPPSASGTPGQRVTISCSGSSSNIGSNTVNWYQQL
PGTAPKLLMYSNNQRPSGVPDRFSGSKSGTSASLAISGLQ
SEDEADYYCAAWDDSLNGYVFGTGTKVTVLGSRGGGGSGG
GGSGGGGSLEMAEVQLVQSGAEMKKPGESLKISCKGSGYN
FASYWVGWVRQMPGKGLEWMGTIYPDDSDTRYGPAFQGGV
TISADKSISTAYLQWSSLKASDTAMYYCARDSYYGIDVWG
QGTLVTVSSEQKLISEEDLAAAIEVMYPPPYLDNEKSNGT
IIHVKGKHLCPSPLFPGPSKPFWVLVVVGGVLACYSLLVT
VAFIIFWVRSKRSRLLHSDYMNMTPRRPGPTRKHYQPYAP
PRDFAAYRSRVKFSRSADAPAYQQGQNQLYNELNLGRREE
YDVLDKRRGRDPEMGGKPRRKNPQEGLYNELQKDKMAEAY
SEIGMKGERRRGKGHDGLYQGLSTATKDTYDALHMQALPP
R
(SEQ ID NO: 30)
```

Although the sequences in Table 9 comprise specific peptide linkers and peptide tags, any linker or tag (see, e.g., Tables 6A and 6B) may be used.

In some embodiments, the anti-PSMA CAR comprises an amino acid sequence that has at least about 85% (e.g., at least about any one of 85%, 86%, 87%, 88%, 89%, 90%, 91%, 92%, 93%, 94%, 95%, 96%, 97%, 98%, or 99%) sequence identity to SEQ ID NO: 29 or 30.

Anti-PSMA Chimeric Antibody-T Cell Receptor (TCR) Constructs (caTCRs)

In some embodiments, the anti-PSMA construct is a chimeric antibody-T cell receptor construct (caTCR) comprising an anti-PSMA antibody moiety (such as an anti-PSMA antibody moiety described herein). Such construct is also referred to herein as an "anti-PSMA caTCR." Exemplary caTCRs are discussed in PCT/US2016/058305 (now published as WO 2017/070608), the contents of which are incorporated herein by reference in their entirety. In some embodiments, the anti-PSMA caTCR specifically bind to PSMA (such as PSMA expressed on the surface of a cell, e.g., a cancer cell) and is capable of recruiting at least one TCR-associated signaling molecule (such as CD3δε, CD3γε, and/or CD3ζζ).

As described in further detail below, the present disclosure also provides an effector cell (e.g., T cell) that comprises, expresses, or is associated with an anti-PSMA-caTCR. Such effector cells are also referred to herein as an "anti-PSMA caTCR effector cells" e.g., "anti-PSMA caTCR T cells").

In some embodiments, the anti-PSMA caTCR comprises a) an antigen-binding module comprising an anti-PSMA antibody moiety (such as described herein) that specifically recognizes PSMA (e.g., cell surface-bound human PSMA), and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or CD3ζζ), and wherein the antibody moiety is linked to the first and/or second TCRDs. In some embodiments, the first TCR-TM and the second TCR-TM are derived from a γ/δ TCR. In some embodiments, the first TCR-TM is derived from a TCR γ chain and the second TCR-TM is derived from a TCR δ chain. In some embodiments, the first TCR-TM is derived from a TCR δ chain and the second TCR-TM is derived from a TCR γ chain. In some embodiments, the first TCR-TM and the second TCR-TM are derived from an α/β TCR. In some embodiments, the first TCR-TM is derived from a TCR α chain and the second TCR-TM is derived from a TCR β chain. In some embodiments, the first TCR-TM is derived from a TCR β chain and the second TCR-TM is derived from a TCR α chain. In some embodiments, the anti-PSMA caTCR comprises naturally occurring TCR domains. In some embodiments, the anti-PSMA caTCR comprises at least one non-naturally occurring TCR domain. For example, the γ/δ TCR, the α/β TCR, the TCR γ chain, the TCR δ chain, the TCR α chain, and/or the TCR β chain may ne naturally occurring or non-naturally occurring. The antigen-binding module of the anti-PSMA caTCR provides the antigen specificity and a TCRM that allows for CD3 recruitment and signaling. In some embodiments, the antigen-binding module is not a naturally occurring T cell receptor antigen-binding moiety. In some embodiments, the antigen-binding module is linked to the N-terminus of a polypeptide chain in the TCRM. In some embodiments, the antigen binding module is an anti-PSMA antibody moiety selected from the group consisting of: a Fab, a Fab', a F(ab')2, an Fv, or an scFv. The TCRM comprises a transmembrane module derived from the transmembrane domains of one or more TCRs (TCR-TMs), such as an αβ and/or γδ TCR, and optionally further comprises one or both of the connecting peptides or fragments thereof of a TCR and/or one or more TCR intracellular domains or fragments thereof. In some embodiments, the TCRM comprises two polypeptide chains, each polypeptide chain comprising, from N-terminus to C-terminus, a connecting peptide, a transmembrane domain, and optionally a TCR intracellular domain. In some embodiments, the TCRM comprises one or more non-naturally occurring TCR domains. For example, in some embodiments, the TCRM comprises one or two non-naturally occurring TCR transmembrane domains. A non-naturally occurring TCR domain may be a corresponding domain of a naturally occurring TCR modified by substitution of one or more amino acids, and/or by replacement of a portion of the corresponding domain with a portion of an analogous domain from another TCR. In some embodiments, the anti-PSMA caTCR comprises a first polypeptide chain and a second polypeptide chain, wherein the first and second polypeptide chains together form the antigen-binding module and the TCRM. In some embodiments, the first and second polypeptide chains are separate polypeptide chains, and the caTCR is a multimer, such as a dimer. In some embodiments, the first and second polypeptide chains are covalently linked, such as by a peptide linkage, or by another chemical linkage, such as a disulfide linkage. In some embodiments, the first polypeptide chain and the second polypeptide chain are linked by at least one disulfide bond. In some embodiments, the anti-PSMA caTCR further comprises one or more T cell co-stimulatory signaling sequences. The one or more co-stimulatory signaling sequences can be, individually, all or a portion of the intracellular domain of a co-stimulatory molecule including, for example, CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like. In some embodiments, the one or more co-stimulatory signaling sequences are between the first TCR-TM and the first TCR intracellular domain and/or between the second TCR-TM and the second TCR intracellular domain. In some embodiments, the one or more co-stimulatory signaling sequences are C-terminal to the first TCRD and/or the second TCRD. In some embodiments, the anti-PSMA caTCR lacks a T cell co-stimulatory signaling sequence. In some embodiments, the caTCR lacks a functional primary immune cell signaling domain. In some embodiments, the caTCR lacks any primary immune cell signaling sequences. In some embodiments, the anti-PSMA caTCR further comprises a stabilization module comprising a first stabilization domain and a second stabilization domain, wherein the first and second stabilization domains have a binding affinity for each other that stabilizes the anti-PSMA caTCR. In some embodiments, the stabilization module is located between the antigen-binding module and the TCRM. In some embodiments, the anti-PSMA caTCR further comprises a spacer module between any two caTCR modules or domains. In some embodiments, the spacer module comprises one or more peptide linkers connecting two caTCR modules or domains.

In some embodiments, the anti-PSMA caTCR comprises: a) a first polypeptide chain comprising a first antigen-binding domain comprising $V_H$ and $C_H1$ antibody domains and a first T cell receptor domain (TCRD) comprising a first transmembrane domain of a first TCR subunit; and b) a second polypeptide chain comprising a second antigen-binding domain comprising $V_L$ and $C_L$ antibody domains and a second TCRD comprising a second transmembrane domain of a second TCR subunit, wherein the $V_H$ and $C_H1$ domains of the first antigen-binding domain and the $V_L$ and $C_L$ domains of the second antigen-binding domain form an antigen-binding module that specifically binds to PSMA, and wherein the first TCRD and the second TCRD form a T cell receptor module (TCRM) that is capable of recruiting at least one TCR-associated signaling module. In some embodiments, the antigen-binding module comprises a disulfide bond between a residue in the $C_H1$ domain and a residue in the $C_L$ domain.

In some embodiments, the anti-PSMA caTCR comprises: a) a first polypeptide chain comprising a first antigen-binding domain comprising a $V_H$ antibody domain and a first TCRD comprising a first transmembrane domain of a first TCR subunit; and b) a second polypeptide chain comprising a second antigen-binding domain comprising a $V_L$ antibody domains and a second TCRD comprising a second transmembrane domain of a second TCR subunit, wherein the $V_H$ domain of the first antigen-binding domain and the $V_L$ domain of the second antigen-binding domain form an antigen-binding module that specifically binds to PSMA, wherein the first TCRD and the second TCRD form a T cell receptor module (TCRM) that is capable of recruiting at least one TCR-associated signaling module.

In some embodiments, the anti-PSMA caTCR comprises a TCRM that comprises a) a first T cell receptor domain (TCRD) comprising a first TCR transmembrane domain (TCR-TM) and b) a second TCRD comprising a second TCR-TM, wherein the TCRM facilitates recruitment of at least one TCR-associated signaling molecule. In some embodiments, both of the TCR-TMs are naturally occurring. In some embodiments, at least one of the TCR-TMs is non-naturally occurring. In some embodiments, both of the TCR-TMs are non-naturally occurring. In some embodiments, the first TCR-TM is derived from one of the transmembrane domains of a T cell receptor (such as an αβ TCR or a γδ TCR) and the second TCR-TM is derived from the other transmembrane domain of the T cell receptor. In some embodiments, the TCRM allows for enhanced recruitment of the at least one TCR-associated signaling molecule as compared to a TCRM comprising the transmembrane domains of the T cell receptor. Recruitment of TCR-associated signaling molecules can be determined by methods known in the art, such as FACS analysis for TCR-CD3 complex surface expression or co-immunoprecipitation of CD3 subunits with the caTCR.

In some embodiments, the anti-PSMA caTCR comprises an antigen-binding module that comprises a first antigen-binding domain comprising a $V_H$ antibody domain (e.g., a $V_H$ antibody domain described herein) and a second antigen-binding domain comprising a $V_L$ antibody domain (e.g., a $V_L$ antibody domain described herein). In some embodiments, the $V_H$ antibody domain and $V_L$ antibody domain CDRs are derived from the same anti-PSMA antibody moiety. In some embodiments, some of the $V_H$ antibody domain and $V_L$ antibody domain CDRs are derived from different anti-PSMA antibody moieties. In some embodiments, the $V_H$ antibody domain and/or $V_L$ antibody domain are human, humanized, chimeric, semi-synthetic, or fully synthetic.

In some embodiments, the anti-PSMA caTCR comprises an antigen-binding module described herein linked to a TCRM described herein, optionally including a stabilization module. For example, in the some embodiments, the anti-PSMA caTCR comprises the antigen-binding module linked to the N-terminus of one or both of the TCRDs. In some embodiments, the anti-PSMA caTCR comprises a stabilization module between a TCRM and an antigen-binding module. In some embodiments, the anti-PSMA caTCR further comprises a spacer module between any two anti-PSMA caTCR modules or domains. In some embodiments, the spacer module comprises one or more peptide linkers between about 5 to about 70 (such as about any of 5, 10, 15, 20, 25, 30, 35, 40, 45, 50, 55, 60, 65, or 70, including any ranges between these values) amino acids in length. In some embodiments, the anti-PSMA caTCR further comprises one or more accessory intracellular domains. In some embodiments, the one or more accessory intracellular domains are carboxy-terminal to the first and/or second TCRD. In some embodiments, the one or more accessory intracellular domains are between the first TCR-TM and the first TCR intracellular domain and/or between the second TCR-TM and the second TCR intracellular domain. In some embodiments, the one or more accessory intracellular domains comprise, individually, a TCR co-stimulatory domain. In some embodiments, the TCR co-stimulatory domain comprises all or a portion of the intracellular domain of an immune co-stimulatory molecule (such as CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like).

In some embodiments, the anti-PSMA caTCR comprises a) an antigen-binding module comprising an antibody moiety (such as described herein) that recognizes a cell surface-bound PSMA, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or CD3ζζ), and wherein the antibody moiety is linked to the first and/or second TCRDs.

In some embodiments, the anti-PSMA caTCR comprises: a) a first polypeptide chain comprising a first antigen-binding domain comprising $V_H$ and $C_H1$ antibody domains and a first T cell receptor domain (TCRD) comprising a first transmembrane domain of a first TCR subunit; and b) a second polypeptide chain comprising a second antigen-binding domain comprising $V_L$ and $C_L$ antibody domains and a second TCRD comprising a second transmembrane domain of a second TCR subunit, wherein the $V_H$ and $C_H1$ domains of the first antigen-binding domain and the $V_L$ and $C_L$ domains of the second antigen-binding domain form an antigen-binding module that specifically binds to PSMA (e.g., cell surface bound-PSMA), and wherein the first TCRD and the second TCRD form a T cell receptor module (TCRM) that is capable of recruiting at least one TCR-associated signaling module. In some embodiments, the anti-PSMA caTCR comprises an antigen-binding module that comprises a disulfide bond between a residue in the $C_H1$ domain and a residue in the $C_L$ domain.

In some embodiments, the anti-PSMA caTCR comprises: a) a first polypeptide chain comprising a first antigen-binding domain comprising a $V_H$ antibody domain and a first TCRD comprising a first transmembrane domain of a first TCR subunit; and b) a second polypeptide chain comprising a second antigen-binding domain comprising a $V_L$ antibody domain and a second TCRD comprising a second transmembrane domain of a second TCR subunit, wherein the $V_H$ domain of the first antigen-binding domain and the $V_L$ domain of the second antigen-binding domain form an antigen-binding module that specifically binds to PSMA (e.g., cell surface bound-PSMA), wherein the first TCRD and the second TCRD form a T cell receptor module (TCRM) that is capable of recruiting at least one TCR-associated signaling module.

The amino acid sequences of exemplary anti-PSMA caTCRs are provided in Table 10A below. The anti-PSMA $V_H/C_H$ sequence in each Chain 1 is in plain text (i.e., no underlining). The TCR delta chain sequence in each Chain 1 is underlined. The anti-PSMA $V_L/C_L$ sequence in each Chain 2 is bold underlined. The TCR gamma chain sequence in each Chain 2 is in italic type.

TABLE 10A

Clone A anti-PSMA caTCR Clone A
Chain 1:
EVQLVQSGAEVKKPGESLKISCKGSGYSFTSYWIGWVRQMP
GKGLEWMGITYPGDSDTRYSPSFQGQVTISADKSISTAYL
QWSSLKASDTAMYYCARSMGSSLYASSDVWGQGTLVTVSSA
STKGPSVFPLAPSSKSTSGGTAALGCLVKDYFPEPVTVSW
NSGALTSGVHTFPAVLQSSGLYSLSSVVTVPSSSLGTQTYI
CNVNHKPSNTKVDKRVEPKSCEVKTDSTDHVKPKETENTK
QPSKSCHKPKAIVHTEKVNMMSLTVLGLRMLFAKTVAVNFL
LTAKLFFL
(SEQ ID NO: 31)

Chain 2:
<u>QSVLTQPPSVSGA</u>*PGQRVTISCTGSSSNIGAGYDVHWYQQLP*
*GTAPKLLIYGNSNRPSGVPDRFSGSKSGTSASLAITGLQ*
*AEDEADYYCQSYDS*<u>SLSGYVFGTGTKVTV</u>LGQPKANPTVTLF
PPSSEELQANKATLVCLISDFYPGAVTVAWKADGSPVKA
GVETTKPSKQSNNKYAASSYLSLTPEQWKSHRSYSCQVTHEG
STVEKTVAPTECS*PIKTDVITMDPEDNCSKDANDTLLLQ*
*LTNTSAYYMYLLLLLKSVVYFAIITCCLLRRTA*
*FCCNGEKS*
(SEQ ID NO: 32)

Clone B anti-PSMA caTCR
Chain 1:
EVQLVQSGAEMKKPGESLKISCKGSGYNFASYWVGWVRQMP
GKGLEWMGTIYPDDSDTRYGPAFQGQVTISADKSISTAYL
QWSSLKASDTAMYYCARDSYYGIDVWGQGTLVTVSSASTKG
PSVFPLAPSSKSTSGGTAALGCLVKDYFPEPVTVSWNSGA
LTSGVHTFPAVLQSSGLYSLSSVVTVPSSSLGTQTYICNVN
HKPSNTKVDKRVEPKSCEVKTDSTDHVKPKETENTKQPSK
SCHKPKAIVHTEKVNMMSLTVLGLRMLFAKTVAVNFLLTAK
LFFL
(SEQ ID NO: 34)

Chain 2:
<u>QAVLTQPPSASGT</u>*PGQRVTISCSGSSSNIGSNTVNWYQQL*
*PGTAPKLLMYSNNQRPSGVPDRFSGSKSGTSASLAISGLQS*
*EDEADYYCAAWDDSLNGYVFGTGTKVYVL*GQPKANPTVTLF
PPSSEELQANKATLVCLISDFYPGAVTVAWKADGSPVKAG
VETTKPSKQSNNKYAASSYLSLTPEQWKSHRSYSCQVTH
EGSTVEKTVAPTECS*PIKTDVITMDPKDNCSEDANDTLLLQL*
*TNTSAYYMYLLLLLKSVVYFAIITCCLLRRIA*
*FCCNGEKS*
(SEQ ID NO: 35)

In some embodiments, the anti-PSMA caTCR comprises a Chain 1 that has at least about 85% (e.g., at least about any one of 85%, 86%, 87%, 88%, 89%, 90%, 91%, 92%, 93%, 94%, 95%, 96%, 97%, 98%, or 99%) sequence identity to SEQ ID NO: 31 and a Chain 2 that has at least about 85% (e.g., at least about any one of 85%, 86%, 87%, 88%, 89%, 90%, 91%, 92%, 93%, 94%, 95%, 96%, 97%, 98%, or 99%) sequence identity to SEQ ID NO: 32. In some embodiments, the anti-PSMA caTCR comprises a Chain 1 that has at least about 85% (e.g., at least about any one of 85%, 86%, 87%, 88%, 89%, 90%, 91%, 92%, 93%, 94%, 95%, 96%, 97%, 98%, or 99%) sequence identity to SEQ ID NO: 34 and a Chain 2 that has at least about 85% (e.g., at least about any one of 85%, 86%, 87%, 88%, 89%, 90%, 91%, 92%, 93%, 94%, 95%, 96%, 97%, 98%, or 99%) sequence identity to SEQ ID NO: 35.

In some embodiments, a nucleic acid encoding exemplary anti-PSMA caTCR Clone A expresses a polypeptide comprising the amino acid sequence (with markings corresponding to those shown in Table 9):

(SEQ ID NO: 33)
METDTLLLWVLLLWVPGSTGEVQLVQSGAEVKKPGESLKISC

KGSGYSFTSYWIGWVRQMPGKGLEWMGIIYPGDSDTRYSPSF

QGQVTISADKSISTAYLQWSSLKASDTAMYYCARSMGSSLYA

SSDVWGQGTLVTVSSASTKGPSVFPLAPSSKSTSGGTAALGC

LVKDYFPEPVTVSWNSGALTSGVHTFPAVLQSSGLYSLSSVV

TVPSSSLGTQTYICNVNHKPSNTKVDKRVEPKSCEVKTDSTD

HVKPKETENTKQPSKSCHKPKAIVHTEKVNMMSLTVLGLRML

FAKTVAVNFLLTAKLFFLRAKRSGSGAPVKQTLNFDLLKLAG

DVESNPGPMETDTLLLWVLLLWVPGSTG<u>QSVLTQPPSVSGA</u>

<u>PGQRVTISCTGSSSNIGAGYDVHWYQQLPGTAPKLLIY</u>

<u>GNSNRPSGVPDRFSGSKSGTSASLAITGLQAEDEADYYC</u>

<u>QSYDSSLSGYVFGTGTKVTVLGQPKANPTVTLFPPS</u>

<u>SEELQANKATLVCLISDFYPGAVTVAWKADGS</u>

<u>PVKAGVETTKPSKQSNNKYAASSYISLTPEQWKSHR</u>

<u>SYSCQVTHEGSTVEKTVAPTECS</u>*PIKTDVITMDPRDNCS*

*KDANDTLLLQLTNTSAYYMYLLLLLKSVVYFAIITCCLLRR*

*TAFCCNGEKS*

In some embodiments, a nucleic acid encoding exemplary anti-PSMA caTCR Clone B expresses a polypeptide comprising the amino acid sequence (with markings corresponding to those shown in Table 9):

(SEQ ID NO: 36)
METDTLLLWVLLLWVPGSTGEVQLVQSGAEMKKPGESLKISCKGSGYNF

ASYWVGWVRQMPGKGLEWMGTIYPDDSDTRYGPAFQGQVTISADKSIST

AYLQWSSLKASDTAMYYCARDSYYGIDVWGQGTLVTVSSASTKGPSVFP

LAPSSKSTSGGTAALGCLVKDYFPEPVTVSWNSGALTSGVHTFPAVLQS

SGLYSLSSVVTVPSSSLGTQTYICNVNHKPSNTKVDKRVEPKSCEVKTD

STDHVKPKETENTKQPSKSCHKPKAIVHTEKVNMMSLTVLGLRMLFAKT

VAVNFLLTAKLFFLRAKRSGSGAPVKQTLNFDLLKLAGDVESNPGPMET

DTLLLWVLLLWVPGSTG<u>QAVLTQPPSASGTPGQRVTISCSGSSSNIGSN</u>

<u>TVNWYQQLPGTAPKLLMYSNNQRPSGVPDRFSGSKSGTSASLAISGLQS</u>

<u>EDEADYYCAAWDDSLNGYVFGTGTKVTVLGQPKANPTVTLFPPSSEELQ</u>

<u>ANKATLVCLISDFYPGAVTVAWKADGSPVKAGVETTKPSKQSNNKYAAS</u>

<u>SYLSLTPEQWKSHRSYSCQVTHEGSTVEKTVAPTECS</u>*PIKTDVITMDPK*

*DNCSRDANDTLLLQQLTNTSAYYMYLLLLLKSVVYFAIITCCLLRRTAF*

*CCNGEKS*

The sequences in bold type in SEQ ID NOs: 33 and 36 correspond to signal peptides and/or self-cleaving peptides. Although SEQ ID NOs: 33 and 36 comprise specific peptide linkers any cleavable linker (see, e.g., Table 6A) may be used.

In some embodiments, the nucleic acid encoding an anti-PSMA caTCR expresses a polypeptide that has at least about 85% (e.g., at least about any one of 85%, 86%, 87%, 88%, 89%, 90%, 91%, 92%, 93%, 94%, 95%, 96%, 97%, 98%, or 99%) sequence identity to SEQ ID NO: 33 or SEQ ID NO: 36.

In some embodiments, the anti-PSMA caTCR is a bivalent caTCR. In some embodiments, the bivalent anti-PSMA caTCR is a homobivalent anti-PSMA caTCR that comprises two anti-PSMA antibody moieties that comprise identical $V_H$ sequences and identical $V_L$ sequences. The amino acid sequences of exemplary homobivalent anti-PSMA caTCRs are provided in Table 10B below. SEQ ID NO: 165 comprises a Clone A scFv and a Clone A $V_H$-$C_H$1, and SEQ ID NO: 166 comprises a Clone A $V_L$-CL. SEQ ID NO: 167 comprises a Clone A $V_H$ and Clone A $V_H$-$C_H$1, and SEQ ID NO: 168 comprises a Clone A $V_L$ and a Clone A $V_L$-CL. SEQ ID NO: 169 comprises a Clone B scFv and a Clone B $V_H$-$C_H$1, and SEQ ID NO: 170 comprises a Clone A $V_L$-CL. SEQ ID NO: 171 comprises a Clone B $V_H$ and Clone B $V_H$-$C_H$1, and SEQ ID NO: 168 comprises a Clone B $V_L$ and a Clone B $V_L$-CL.

TABLE 10B

Exemplary homobivalent Clone A anti-PSMA caTCR #1

Chain 1:
QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGSRGGGGSGGGGSGGGGSLEMAEVQLVQSGAEVKKPGESLKISCKGSGYSF
TSYWIGWVRQMPGKGLEWMGITYPGDSDTRYSPSFQGQVTISADKSISTAYLQWSSLKASDTAMYYCARSMGSSLYASSDV
WGQGTLVTVSSGGGGSEVQLVQSGAEVKKPGESLKISCKGSGYSFTSYWIGWVRQMPGKGLEWMGITYPGDSDTRYSPSFQ
GQVTISADKSISTAYLQWSSLKASDTAMYYCARSMGSSLYASSDVWGQGTLVTVSSASTKGPSVFPLAPSSKSTSGGTAAL
GCLVKDYFPEPVTVSWNSGALTSGVHTFPAVLQSSGLYSLSSVVTVPSSSLGTQTYICNVNHKPSNTKVDKRVEPKSCEVK
TDSTDHVKPKETENTKQPSKSCHKPKAIVHTEKVNMMSLTVLGLRMLFAKTVAVNFLLTAKLFFL (SEQ ID NO:
165)

Chain 2:
QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGQPKANPTVTLFPPSSEELQANKATLVCLISDFYPGAVTVAWKADGSPVKA
GVETTKPSKQSNNKYAASSYLSLTPEQWKSHRSYSCQVTHEGSTVEKTVAPTECSPIKTDVITMDPKDNCSKDANDTLLLQ
LTNTSAYYMYLLLLLKSVVYFAIITCCLLRRTAFCCNGEKS (SEQ ID NO: 166)

Exemplary homobivalent Clone A anti-PSMA caTCR #2

Chain 1:
EVQLVQSGAEVKKPGESLKISCKGSGYSFTSYWIGWVRQMPGKGLEWMGITYPGDSDTRYSPSFQGQVTISADKSISTAYL
QWSSLKASDTAMYYCARSMGSSLYASSDVWGQGTLVTVSSGGGGSGGGGSEVQLVQSGAEVKKPGESLKISCKGSGYSFTS
YWIGWVRQMPGKGLEWMGITYPGDSDTRYSPSFQGQVTISADKSISTAYLQWSSLKASDTAMYYCARSMGSSLYASSDVWG
QGTLVTVSSASTKGPSVFPLAPSSKSTSGGTAALGCLVKDYFPEPVTVSWNSGALTSGVHTFPAVLQSSGLYSLSSVVTVP
SSSLGTQTYICNVNHKPSNTKVDKRVEPKSCEVKTDSTDHVKPKETENTKQPSKSCHKPKAIVHTEKVNMMSLTVLGLRML
FAKTVAVNFLLTAKLFFL (SEQ ID NO: 167)

Chain 2:
QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGGGGGSGGGGSQSVLTQPPSVSGAPGQRVTISCTGSSSNIGAGYDVHWYQQ
LPGTAPKLLIYGNSNRPSGVPDRFSGSKSGTSASLAITGLQAEDEADYYCQSYDSSLSGYVFGTGTKVTVLGQPKANPTVT
LFPPSSEELQANKATLVCLISDFYPGAVTVAWKADGSPVKAGVETTKPSKQSNNKYAASSYLSLTPEQWKSHRSYSCQVTH
EGSTVEKTVAPTECSPIKTDVITMDPKDNCSKDANDTLLLQLTNTSAYYMYLLLLLKSVVYFAIITCCLLRRTAFCCNGEK
S (SEQ ID NO: 168)

Exemplary homobivalent Clone B anti-PSMA caTCR #1

Chain 1:
QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGSRGGGGSGGGGSGGGGSLEMAEVQLVQSGAEMKKPGESLKISCKGSGYNFA
SYWVGWVRQMPGKGLEWMGTIYPDDSDTRYGPAFQGQVTISADKSISTAYLQWSSLKASDTAMYYCARDSYYGIDVWGQGT
LVTVSSGGGGSEVQLVQSGAEMKKPGESLKISCKGSGYNFASYWVGWVRQMPGKGLEWMGTIYPDDSDTRYGPAFQGQVTI
SADKSISTAYLQWSSLKASDTAMYYCARDSYYGIDVWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICNVNHKPSNTKVDKRVEPKSCEVKTDSTDHVKP
KETENTKQPSKSCHKPKAIVHTEKVNMMSLTVLGLRMLFAKTVAVNFLLTAKLFFL (SEQ ID NO: 169)

Chain 2:
QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGQPKANPTVTLFPPSSEELQANKATLVCLISDFYPGAVTVAWKADGSPVKAG
VETTKPSKQSNNKYAASSYLSLTPEQWKSHRSYSCQVTHEGSTVEKTVAPTECSPIKTDVITMDPKDNCSKDANDTLLLQL
TNTSAYYMYLLLLLKSVVYFAIITCCLLRRTAFCCNGEKS (SEQ ID NO: 170)

Exemplary homobivalent Clone B anti-PSMA caTCR #2

Chain 1:
EVQLVQSGAEMKKPGESLKISCKGSGYNFASYWVGWVRQMPGKGLEWMGTIYPDDSDTRYGPAFQGQVTISADKSISTAYL
QWSSLKASDTAMYYCARDSYYGIDVWGQGTLVTVSSGGGGSGGGGSEVQLVQSGAEMKKPGESLKISCKGSGYNFASYWVG
WVRQMPGKGLEWMGTIYPDDSDTRYGPAFQGQVTISADKSISTAYLQWSSLKASDTAMYYCARDSYYGIDVWGQGTLVTVS
SASTKGPSVFPLAPSSKSTSGGTAALGCLVKDYFPEPVTVSWNSGALTSGVHTFPAVLQSSGLYSLSSVVTVPSSSLGTQT
YICNVNHKPSNTKVDKRVEPKSCEVKTDSTDHVKPKETENTKQPSKSCHKPKAIVHTEKVNMMSLTVLGLRMLFAKTVAVN
FLLTAKLFFL (SEQ ID NO: 171)

TABLE 10B-continued

Chain 2:
QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGGGGGSGGGGSQAVLTQPPSASGTPGQRVTISCSGSSSNIGSNTVNWYQQLP
GTAPKLLMYSNNQRPSGVPDRFSGSKSGTSASLAISGLQSEDEADYYCAAWDDSLNGYVFGTGTKVTVLGQPKANPTVTLF
PPSSEELQANKATLVCLISDFYPGAVTVAWKADGSPVKAGVETTKPSKQSNNKYAASSYLSLTPEQWKSHRSYSCQVTHEG
STVEKTVAPTECSPIKTDVITMDPKDNCSKDANDTLLLQLTNTSAYYMYLLLLLKSVVYFAIITCCLLRRTAFCCNGEKS
(SEQ ID NO: 172)

In some embodiments, the anti-PSMA caTCR comprises a Chain 1 that has at least about 85% (e.g., at least about anyone of 85%, 86%, 87%, 88%, 89%, 90%, 91%, 92%, 93%, 94%, 95%, 96%, 97%, 98%, or 99%) sequence identity to SEQ ID NO: 165 and a Chain 2 that has at least about 85% (e.g., at least about any one of 85%, 86%, 87%, 88%, 89%, 90%, 91%, 92%, 93%, 94%, 95%, 96%, 97%, 98%, or 99%) sequence identity to SEQ ID NO: 166. In some embodiments, the anti-PSMA caTCR comprises a Chain 1 that has at least about 85% (e.g., at least about any one of 85%, 86%, 87%, 88%, 89%, 90%, 91%, 92%, 93%, 94%, 95%, 96%, 97%, 98%, or 99%) sequence identity to SEQ ID NO: 167 and a Chain 2 that has at least about 85% (e.g., at least about any one of 85%, 86%, 87%, 88%, 89%, 90%, 91%, 92%, 93%, 94%, 95%, 96%, 97%, 98%, or 99%) sequence identity to SEQ ID NO: 168. In some embodiments, the anti-PSMA caTCR comprises a Chain 1 that has at least about 85% (e.g., at least about any one of 85%, 86%, 87%, 88%, 89%, 90%, 91%, 92%, 93%, 94%, 95%, 96%, 97%, 98%, or 99%) sequence identity to SEQ ID NO: 169 and a Chain 2 that has at least about 85% (e.g., at least about any one of 85%, 86%, 87%, 88%, 89%, 90%, 91%, 92%, 93%, 94%, 95%, 96%, 97%, 98%, or 99%) sequence identity to SEQ ID NO: 170. In some embodiments, the anti-PSMA caTCR comprises a Chain 1 that has at least about 85% (e.g., at least about any one of 85%, 86%, 87%, 88%, 89%, 90%, 91%, 92%, 93%, 94%, 95%, 96%, 97%, 98%, or 99%) sequence identity to SEQ ID NO: 171 and a Chain 2 that has at least about 85% (e.g., at least about any one of 85%, 86%, 87%, 88%, 89%, 90%, 91%, 92%, 93%, 94%, 95%, 96%, 97%, 98%, or 99%) sequence identity to SEQ ID NO: 172.

In some embodiments, a nucleic acid encoding exemplary homobivalent Clone A anti-PSMA caTCR #1 expresses a polypeptide comprising SEQ ID NO: 47.

(SEQ ID NO: 47)
METDTLLLWVLLLWVPGSTGQSVLTQPPSVSGAPGQRVTISCTGSSSNI
GAGYDVHWYQQLPGTAPKLLIYGNSNRPSGVPDRFSGSKSGTSASLAIT
GLQAEDEADYYCQSYDSSLSGYVFGTGTKVTVLGSRGGGGSGGGGSGGG
GSLEMAEVQLVQSGAEVKKPGESLKISCKGSGYSFTSYWIGWVRQMPGK
GLEWMGIIYPGDSDTRYSPSFQGQVTISADKSISTAYLQWSSLKASDTA
MYYCARSMGSSLYASSDVWGQGTLVTVSSGGGGSEVQLVQSGAEVKKPG
ESLKISCKGSGYSFTSYWIGWVRQMPGKGLEWMGIIYPGDSDTRYSPSF
QGQVTISADKSISTAYLQWSSLKASDTAMYYCARSMGSSLYASSDVWGQ
GTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPS
NTKVDKRVEPKSCEVKTDSTDHVKPKETENTKQPSKSCHKPKAIVHTEK

VNMMSLTVLGLRMLFAKTVAVNFLLTAKLFFLRAKRSGSGAPVKQTLNF

DLLKLAGDVESNPGPMETDTLLLWVLLLWVPGSTGQSVLTQPPSVSGAP

GQRVTISCTGSSSNIGAGYDVHWYQQLPGTAPKLLIYGNSNRPSGVPDR

FSGSKSGTSASLAITGLQAEDEADYYCQSYDSSLSGYVFGTGTKVTVLG

QPKANPTVTLFPPSSEELQANKATLVCLISDFYPGAVTVAWKADGSPVK

AGVETTKPSKQSNNKYAASSYLSLTPEQWKSHRSYSCQVTHEGSTVEKT

VAPTECSPIKTDVITMDPKDNCSKDANDTLLLQLTNTSAYYMYLLLLLK

SVVYFAIITCCLLRRTAFCCNGEKS

In some embodiments, a nucleic acid encoding exemplary homobivalent Clone A anti-PSMA caTCR #2 expresses a polypeptide comprising SEQ ID NO: 48.

(SEQ ID NO: 48)
METDTLLLWVLLLWVPGSTGEVQLVQSGAEVKKPGESLKISCKGSGYSF

TSYWIGWVRQMPGKGLEWMGITYPGDSDTRYSPSFQGQVTISADKSIST

AYLQWSSLKASDTAMYYCARSMGSSLYASSDVWGQGTLVTVSSGGGGSG

GGGSEVQLVQSGAEVKKPGESLKISCKGSGYSFTSYWIGWVRQMPGKGL

EWMGITYPGDSDTRYSPSFQGQVTISADKSISTAYLQWSSLKASDTAMY

YCARSMGSSLYASSDVWGQGTLVTVSSASTKGPSVFPLAPSSKSTSGGT

AALGCLVKDYFPEPVTVSWNSGALTSGVHTFPAVLQSSGLYSLSSVVTV

PSSSLGTQTYICNVNHKPSNTKVDKRVEPKSCEVKTDSTDHVKPKETEN

TKQPSKSCHKPKAIVHTEKVNMMSLTVLGLRMLFAKTVAVNFLLTAKLF

FLRAKRSGSGAPVKQTLNFDLLKLAGDVESNPGPMETDTLLLWVLLLWV

PGSTGQSVLTQPPSVSGAPGQRVTISCTGSSSNIGAGYDVHWYQQLPGT

APKLLIYGNSNRPSGVPDRFSGSKSGTSASLAITGLQAEDEADYYCQSY

DSSLSGYVFGTGTKVTVLGGGGGSGGGGSQSVLTQPPSVSGAPGQRVTI

SCTGSSSNIGAGYDVHWYQQLPGTAPKLLIYGNSNRPSGVPDRFSGSKS

GTSASLAITGLQAEDEADYYCQSYDSSLSGYVFGTGTKVTVLGQPKANP

TVTLFPPSSEELQANKATLVCLISDFYPGAVTVAWKADGSPVKAGVETT

KPSKQSNNKYAASSYLSLTPEQWKSHRSYSCQVTHEGSTVEKTVAPTEC

SPIKTDVITMDPKDNCSKDANDTLLLQLTNTSAYYMYLLLLLKSVVYFA

IITCCLLRRTAFCCNGEKS

In some embodiments, a nucleic acid encoding exemplary homobivalent Clone B anti-PSMA caTCR #1 expresses a polypeptide comprising SEQ ID NO: 49.

(SEQ ID NO: 49)
METDTLLLWVLLLWVPGSTGQAVLTQPPSASGTPGQRVTISCSGSSSNI
GSNTVNWYQQLPGTAPKLLMYSNNQRPSGVPDRFSGSKSGTSASLAISG
LQSEDEADYYCAAWDDSLNGYVFGTGTKVTVLGSRGGGGSGGGGSGGGG
SLEMAEVQLVQSGAEMKKPGESLKISCKGSGYNFASYWVGWVRQMPGKG
LEWMGTIYPDDSDTRYGPAFQGQVTISADKSISTAYLQWSSLKASDTAM
YYCARDSYYGIDVWGQGTLVTVSSGGGGSEVQLVQSGAEMKKPGESLKI
SCKGSGYNFASYWVGWVRQMPGKGLEWMGTIYPDDSDTRYGPAFQGQVT
ISADKSISTAYLQWSSLKASDTAMYYCARDSYYGIDVWGQGTLVTVSSA
STKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVE
PKSCEVKTDSTDHVKPKETENTKQPSKSCHKPKAIVHTEKVNMMSLTVL
GLRMLFAKTVAVNFLLTAKLFFLRAKRSGSGAPVKQTLNFDLLKLAGDV
ESNPGPMETDTLLLWVLLLWVPGSTGQAVLTQPPSASGTPGQRVTISCS
GSSSNIGSNTVNWYQQLPGTAPKLLMYSNNQRPSGVPDRFSGSKSGTSA
SLAISGLQSEDEADYYCAAWDDSLNGYVFGTGTKVTVLGQPKANPTVTL
FPPSSEELQANKATLVCLISDFYPGAVTVAWKADGSPVKAGVETTKPSK
QSNNKYAASSYLSLTPEQWKSHRSYSCQVTHEGSTVEKTVAPTECSPIK
TDVITMDPKDNCSKDANDTLLLQLTNTSAYYMYLLLLLKSVVYFAIITC
CLLRRTAFCCNGEKS

In some embodiments, a nucleic acid encoding exemplary homobivalent Clone B anti-PSMA caTCR #1 expresses a polypeptide comprising SEQ ID NO: 50.

(SEQ ID NO: 50)
METDTLLLWVLLLWVPGSTGEVQLVQSGAEMKKPGESLKISCKGSGYNF
ASYWVGWVRQMPGKGLEWMGTIYPDDSDTRYGPAFQGQVTISADKSIST
AYLQWSSLKASDTAMYYCARDSYYGIDVWGQGTLVTVSSGGGGSGGGGS
EVQLVQSGAEMKKPGESLKISCKGSGYNFASYWVGWVRQMPGKGLEWMG

-continued
TIYPDDSDTRYGPAFQGQVTISADKSISTAYLQWSSLKASDTAMYYCAR
DSYYGIDVWGQGTLVTVSSASTKGPSVFPLAPSSKSTSGGTAALGCLVK
DYFPEPVTVSWNSGALTSGVHTFPAVLQSSGLYSLSSVVTVPSSSLGTQ
TYICNVNHKPSNTKVDKRVEPKSCEVKTDSTDHVKPKETENTKQPSKSC
HKPKAIVHTEKVNMMSLTVLGLRMLFAKTVAVNFLLTAKLFFLRAKRSG
SGAPVKQTLNFDLLKLAGDVESNPGPMETDTLLLWVLLLWVPGSTGQAV
LTQPPSASGTPGQRVTISCSGSSSNIGSNTVNWYQQLPGTAPKLLMYSN
NQRPSGVPDRFSGSKSGTSASLAISGLQSEDEADYYCAAWDDSLNGYVF
GTGTKVTVLGGGGSGGGGSQAVLTQPPSASGTPGQRVTISCSGSSSNI
GSNTVNWYQQLPGTAPKLLMYSNNQRPSGVPDRFSGSKSGTSASLAISG
LQSEDEADYYCAAWDDSLNGYVFGTGTKVTVLGQPKANPTVTLFPPSSE
ELQANKATLVCLISDFYPGAVTVAWKADGSPVKAGVETTKPSKQSNNKY
AASSYLSLTPEQWKSHRSYSCQVTHEGSTVEKTVAPTECSPIKTDVITM
DPKDNCSKDANDTLLLQLTNTSAYYMYLLLLLKSVVYFAIITCCLLRRT
AFCCNGEKS Although SEQ ID NOs: 47-50 comprise specific peptide linkers, any linker (see, e.g., Table 6A) may be used.

In some embodiments, the nucleic acid encoding a homobivalent anti-PSMA caTCR expresses a polypeptide that has at least about 85% (e.g., at least about any one of 85%, 86%, 87%, 88%, 89%, 90%, 91%, 92%, 93%, 94%, 95%, 96%, 97%, 98%, or 99%) sequence identity to any one of SEQ ID NOs: 47-50.

In some embodiments, the bivalent anti-PSMA caTCR is a heterobivalent anti-PSMA caTCR that comprises two anti-PSMA antibody moieties, where each anti-PSMA antibody moiety comprises a different $V_H$ sequence and/or different VL sequence. The amino acid sequences of exemplary heterobivalent anti-PSMA caTCRs are provided in Table #1C below. SEQ ID NO 173 comprises a Clone A scFv and a Clone B $V_H$-$C_H$1, and SEQ ID NO: 174 comprises a Clone B $V_L$-CL. SEQ ID NO: 175 comprises a Clone B $V_L$-CL, and SEQ ID NO: 176 comprises a Clone A scFv and a Clone B $V_H$-$C_H$1. SEQ ID NO 177 comprises a Clone A $V_H$ and a Clone B $V_H$-$C_H$1, and SEQ ID NO: 178 comprises a Clone A $V_L$ and a Clone B $V_L$-CL. SEQ ID NO 179 comprises a Clone A $V_L$ and a Clone B $V_L$-CL, and SEQ ID NO: 178 comprises a Clone A $V_H$ and a Clone B $V_H$-CH1.

TABLE 10C

Exemplary heterobivalent Clone A/Clone B anti-PSMA caTCR #1

Chain 1:
QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGSRGGGGSGGGGSGGGGSLEMAEVQLVQSGAEVKKPGESLKISCKGSGYSF
TSYWIGWVRQMPGKGLEWMGITYPGDSDTRYSPSFQGQVTISADKSISTAYLQWSSLKASDTAMYYCARSMGSSLYASSDV
WGQGTLVTVSSGGGGSEVQLVQSGAEMKKPGESLKISCKGSGYNFASYWVGWVRQMPGKGLEWMGTIYPDDSDTRYGPAFQ
GQVTISADKSISTAYLQWSSLKASDTAMYYCARDSYYGIDVWGQGTLVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKRVEPKSCEVKTDST
DHVKPKETENTKQPSKSCHKPKAIVHTEKVNMMSLTVLGLRMLFAKTVAVNFLLTAKLFFL (SEQ ID NO: 173)

Chain 2:
QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGQPKANPTVTLFPPSSEELQANKATLVCLISDFYPGAVTVAWKADGSPVKAG
VETTKPSKQSNNKYAASSYLSLTPEQWKSHRSYSCQVTHEGSTVEKTVAPTECSPIKTDVITMDPKDNCSKDANDTLLLQL
TNTSAYYMYLLLLLKSVVYFAIITCCLLRRTAFCCNGEKS (SEQ ID NO: 174)

TABLE 10C-continued

Exemplary heterobivalent Clone B/Clone A anti-PSMA caTCR #1

Chain 1:
QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGQPKANPTVTLFPPSSEELQANKATLVCLISDFYPGAVTVAWKADGSPVKAG
VETTKPSKQSNNKYAASSYLSLTPEQWKSHRSYSCQVTHEGSTVEKTVAPTECSEVKTDSTDHVKPKETENTKQPSKSCHK
PKAIVHTEKVNMMSLTVLGLRMLFAKTVAVNFLLTAKLFFL (SEQ ID NO: 175)

Chain 2:
QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGSRGGGGSGGGGSGGGGSLEMAEVQLVQSGAEVKKPGESLKISCKGSGYSF
TSYWIGWVRQMPGKGLEWMGITYPGDSDTRYSPSFQGQVTISADKSISTAYLQWSSLKASDTAMYYCARSMGSSLYASSDV
WGQGTLVTVSSGGGGSEVQLVQSGAEMKKPGESLKISCKGSGYNFASYWVGWVRQMPGKGLEWMGTIYPDDSDTRYGPAFQ
GQVTISADKSISTAYLQWSSLKASDTAMYYCARDSYYGIDVWGQGTLVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKRVEPKSCPIKTDVI
TMDPKDNCSKDANDTLLLQLTNTSAYYMYLLLLLKSVVYFAIITCCLLRRTAFCCNGEKS (SEQ ID NO: 176)

Exemplary heterobivalent Clone A/Clone B anti-PSMA caTCR #2

Chain 1:
EVQLVQSGAEVKKPGESLKISCKGSGYSFTSYWIGWVRQMPGKGLEWMGIIYPGDSDTRYSPSFQGQVTISADKSISTAYL
QWSSLKASDTAMYYCARSMGSSLYASSDVWGQGTLVTVSSGGGGSGGGGSEVQLVQSGAEMKKPGESLKISCKGSGYNFAS
YWVGWVRQMPGKGLEWMGTIYPDDSDTRYGPAFQGQVTISADKSISTAYLQWSSLKASDTAMYYCARDSYYGIDVWGQGTL
VTVSSASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKRVEPKSCEVKTDSTDHVKPKETENTKQPSKSCHKPKAIVHTEKVNMMSLTVLGLRMLFAKT
VAVNFLLTAKLFFL (SEQ ID NO: 177)

Chain 2:
QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGGGGGSGGGGSQAVLTQPPSASGTPGQRVTISCSGSSSNIGSNTVNWYQQL
PGTAPKLLMYSNNQRPSGVPDRFSGSKSGTSASLAISGLQSEDEADYYCAAWDDSLNGYVFGTGTKVTVLGQPKANPTVTL
FPPSSEELQANKATLVCLISDFYPGAVTVAWKADGSPVKAGVETTKPSKQSNNKYAASSYLSLTPEQWKSHRSYSCQVTHE
GSTVEKTVAPTECSPIKTDVITMDPKDNCSKDANDTLLLQLTNTSAYYMYLLLLLKSVVYFAIITCCLLRRTAFCCNGEKS
(SEQ ID NO: 178)

Exemplary heterobivalent Clone B/Clone A anti-PSMA caTCR #2

Chain 1:
QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGGGGGSGGGGSQAVLTQPPSASGTPGQRVTISCSGSSSNIGSNTVNWYQQL
PGTAPKLLMYSNNQRPSGVPDRFSGSKSGTSASLAISGLQSEDEADYYCAAWDDSLNGYVFGTGTKVTVLGQPKANPTVTL
FPPSSEELQANKATLVCLISDFYPGAVTVAWKADGSPVKAGVETTKPSKQSNNKYAASSYLSLTPEQWKSHRSYSCQVTHE
GSTVEKTVAPTECSEVKTDSTDHVKPKETENTKQPSKSCHKPKAIVHTEKVNMMSLTVLGLRMLFAKTVAVNFLLTAKLFF
L (SEQ ID NO: 179)

Chain 2:
EVQLVQSGAEVKKPGESLKISCKGSGYSFTSYWIGWVRQMPGKGLEWMGITYPGDSDTRYSPSFQGQVTISADKSISTAYL
QWSSLKASDTAMYYCARSMGSSLYASSDVWGQGTLVTVSSGGGGSGGGGSEVQLVQSGAEMKKPGESLKISCKGSGYNFAS
YWVGWVRQMPGKGLEWMGTIYPDDSDTRYGPAFQGQVTISADKSISTAYLQWSSLKASDTAMYYCARDSYYGIDVWGQGTL
VTVSSASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKRVEPKSCPIKTDVITMDPKDNCSKDANDTLLLQLTNTSAYYMYLLLLLKSVVYFAIITCCL
LRRTAFCCNGEKS (SEQ ID NO: 180)

In some embodiments, the anti-PSMA caTCR comprises a Chain 1 that has at least about 85% (e.g., at least about any one of 85%, 86%, 87%, 88%, 89%, 90%, 91%, 92%, 93%, 94%, 95%, 960%, 970, 980%, or 990%) sequence identity to SEQ ID NO: 173 and a Chain 2 that has at least about 85% (e.g., at least about any one of 85%, 86%, 87%, 88%, 89%, 90%, 91%, 92%, 93%, 94%, 95%, 96%, 97%, 98%, or 99%) sequence identity to SEQ ID NO: 174. In some embodiments, the anti-PSMA caTCR comprises a Chain 1 that has at least about 85% (e.g., at least about any one of 850%, 86%, 87%, 88%, 89%, 90%, 91%, 92%, 93%, 94%, 95%, 96%, 97%, 98%, or 99%) sequence identity to SEQ ID NO: 175 and a Chain 2 that has at least about 850% (e.g., at least about any one of 85%, 86%, 87%, 88%, 89%, 90%, 91%, 92%, 93%, 94%, 95%, 96%, 97%, 98%, or 99%) sequence identity to SEQ ID NO: 176. In some embodiments, the anti-PSMA caTCR comprises a Chain 1 that has at least about 85%, 86%, 87%, 88%, 89%, 90%, 91%, 92%, 93%, 94%, 95%, 96%, 97%, 98%, or 99%) sequence identity to SEQ ID NO: 177 and a Chain 2 that has at least about 85% (e.g., at least about any one of 85%, 86%, 87%, 88%, 89%, 90%, 91%, 92%, 93%, 940, 950%, 960%, 970, 980%, or 990%) sequence identity to SEQ ID NO: 178. In some embodiments, the anti-PSMA caTCR comprises a Chain 1 that has at least about 850% (e.g., at least about any one of 85%, 86%, 87%, 88%, 89%, 90%, 91%, 92%, 93%, 94%, 95%, 96%, 97%, 98%, or 99%) sequence identity to SEQ ID NO: 179 and a Chain 2 that has at least about 850% (e.g., at least about any one of 85%, 86%, 87%, 88%, 89%, 90%, 91%, 92%, 93%, 94%, 95%, 96%, 97%, 98%, or 99%) sequence identity to SEQ ID NO: 180.

In some embodiments, a nucleic acid encoding exemplary heterobivalent Clone A/Clone B anti-PSMA caTCR #1 expresses a polypeptide comprising SEQ ID NO: 91.

(SEQ ID NO: 91)
METDTLLLWVLLLWVPGSTGQSVLTQPPSVSGAPGQRVTISCTGSSSNI
GAGYDVHWYQQLPGTAPKLLIYGNSNRPSGVPDRFSGSKSGTSASLAIT
GLQAEDEADYYCQSYDSSLSGYVFGTGTKVTVLGSRGGGGSGGGGSGGG
GSLEMAEVQLVQSGAEVKKPGESLKISCKGSGYSFTSYWIGWVRQMPGK
GLEWMGIIYPGDSDTRYSPSFQGQVTISADKSISTAYLQWSSLKASDTA
MYYCARSMGSSLYASSDVWGQGTLVTVSSGGGGSEVQLVQSGAEMKKPG
ESLKISCKGSGYNFASYWVGWVRQMPGKGLEWMGTIYPDDSDTRYGPAF
QGQVTISADKSISTAYLQWSSLKASDTAMYYCARDSYYGIDVWGQGTLV
TVSSASTKGPSVFPLAPSSKSTSGGTAALGCLVKDYFPEPVTVSWNSGA
LTSGVHTFPAVLQSSGLYSLSSVVTVPSSSLGTQTYICNVNHKPSNTKV
DKRVEPKSCEVKTDSTDHVKPKETENTKQPSKSCHKPKAIVHTEKVNMM
SLTVLGLRMLFAKTVAVNFLLTAKLFFLRAKRSGSGAPVKQTLNFDLLK
LAGDVESNPGPMETDTLLLWVLLLWVPGSTGQAVLTQPPSASGTPGQRV
TISCSGSSSNIGSNTVNWYQQLPGTAPKLLMYSNNQRPSGVPDRFSGSK
SGTSASLAISGLQSEDEADYYCAAWDDSLNGYVFGTGTKVTVLGQPKAN
PTVTLFPPSSEELQANKATLVCLISDFYPGAVTVAWKADGSPVKAGVET
TKPSKQSNNKYAASSYLSLTPEQWKSHRSYSCQVTHEGSTVEKTVAPTE
CSPIKTDVITMDPKDNCSKDANDTLLLQLTNTSAYYMYLLLLLKSVVYF
AIITCCLLRRTAFCCNGEKS

In some embodiments, a nucleic acid encoding exemplary heterobivalent Clone B/Clone A anti-PSMA caTCR #1 expresses a polypeptide comprising SEQ ID NO: 181.

(SEQ ID NO: 181)
METDTLLLWVLLLWVPGSTGQAVLTQPPSASGTPGQRVTISCSGSSSNI
GSNTVNWYQQLPGTAPKLLMYSNNQRPSGVPDRFSGSKSGTSASLAISG
LQSEDEADYYCAAWDDSLNGYVFGTGTKVTVLGQPKANPTVTLFPPSSE
ELQANKATLVCLISDFYPGAVTVAWKADGSPVKAGVETTKPSKQSNNKY
AASSYLSLTPEQWKSHRSYSCQVTHEGSTVEKTVAPTECSPIKTDVITM
DPKDNCSKDANDTLLLQLTNTSAYYMYLLLLLKSVVYFAIITCCLLRRT
AFCCNGEKSRAKRSGSGAPVKQTLNFDLLKLAGDVESNPGPMETDTLLL
WVLLLWVPGSTGQSVLTQPPSVSGAPGQRVTISCTGSSSNIGAGYDVHW
YQQLPGTAPKLLIYGNSNRPSGVPDRFSGSKSGTSASLAITGLQAEDEA
DYYCQSYDSSLSGYVFGTGTKVTVLGSRGGGGSGGGGSGGGGSLEMAEV
QLVQSGAEVKKPGESLKISCKGSGYSFTSYWIGWVRQMPGKGLEWMGII
YPGDSDTRYSPSFQGQVTISADKSISTAYLQWSSLKASDTAMYYCARSM
GSSLYASSDVWGQGTLVTVSSGGGGSEVQLVQSGAEMKKPGESLKISCK
GSGYNFASYWVGWVRQMPGKGLEWMGTIYPDDSDTRYGPAFQGQVTISA
DKSISTAYLQWSSLKASDTAMYYCARDSYYGIDVWGQGTLVTVSSASTK
GPSVFPLAPSSKSTSGGTAALGCLVKDYFPEPVTVSWNSGALTSGVHTF
PAVLQSSGLYSLSSVVTVPSSSLGTQTYICNVNHKPSNTKVDKRVEPKS
CEVKTDSTDHVKPKETENTKQPSKSCHKPKAIVHTEKVNMMSLTVLGLR
MLFAKTVAVNFLLTAKLFFL

In some embodiments, a nucleic acid encoding exemplary heterobivalent Clone A/Clone B anti-PSMA caTCR #2 expresses a polypeptide comprising the amino acid sequence SEQ ID NO: 92.

(SED ID NO: 92)
METDTLLLWVLLLWVPGSTGEVQLVQSGAEVKKPGESLKISCKGSGYSF
TSYWIGWVRQMPGKGLEWMGITYPGDSDTRYSPSFQGQVTISADKSIST
AYLQWSSLKASDTAMYYCARSMGSSLYASSDVWGQGTLVTVSSGGGGSG
GGGSEVQLVQSGAEMKKPGESLKISCKGSGYNFASYWVGWVRQMPGKGL
EWMGTIYPDDSDTRYGPAFQGQVTISADKSISTAYLQWSSLKASDTAMY
YCARDSYYGIDVWGQGTLVTVSSASTKGPSVFPLAPSSKSTSGGTAALG
CLVKDYFPEPVTVSWNSGALTSGVHTFPAVLQSSGLYSLSSVVTVPSSS
LGTQTYICNVNHKPSNTKVDKRVEPKSCEVKTDSTDHVKPKETENTKQP
SKSCHKPKAIVHTEKVNMMSLTVLGLRMLFAKTVAVNFLLTAKLFFLRA
KRSGSGAPVKQTLNFDLLKLAGDVESNPGPMETDTLLLWVLLLWVPGST
GQSVLTQPPSVSGAPGQRVTISCTGSSSNIGAGYDVHWYQQLPGTAPKL
LIYGNSNRPSGVPDRFSGSKSGTSASLAITGLQAEDEADYYCQSYDSSL
SGYVFGTGTKVTVLGGGGSGGGGSQAVLTQPPSASGTPGQRVTISCSG
SSSNIGSNTVNWYQQLPGTAPKLLMYSNNQRPSGVPDRFSGSKSGTSAS
LAISGLQSEDEADYYCAAWDDSLNGYVFGTGTKVTVLGQPKANPTVTLF
PPSSEELQANKATLVCLISDFYPGAVTVAWKADGSPVKAGVETTKPSKQ
SNNKYAASSYLSLTPEQWKSHRSYSCQVTHEGSTVEKTVAPTECSPIKT
DVITMDPKDNCSKDANDTLLLQLTNTSAYYMYLLLLLKSVVYFAIITCC
LLRRTAFCCNGEKS

In some embodiments, a nucleic acid encoding exemplary heterobivalent Clone B/Clone A anti-PSMA caTCR #2 expresses a polypeptide comprising the amino acid sequence SEQ ID NO: 182.

(SED ID NO: 182)
METDTLLLWVLLLWVPGSTGQSVLTQPPSVSGAPGQRVTISCTGSSSNI
GAGYDVHWYQQLPGTAPKLLIYGNSNRPSGVPDRFSGSKSGTSASLAIT
GLQAEDEADYYCQSYDSSLSGYVFGTGTKVTVLGGGGSGGGGSQAVLT
QPPSASGTPGQRVTISCSGSSSNIGSNTVNWYQQLPGTAPKLLMYSNNQ
RPSGVPDRFSGSKSGTSASLAISGLQSEDEADYYCAAWDDSLNGYVFGT
GTKVTVLGQPKANPTVTLFPPSSEELQANKATLVCLISDFYPGAVTVAW
KADGSPVKAGVETTKPSKQSNNKYAASSYLSLTPEQWKSHRSYSCQVTH
EGSTVEKTVAPTECSPIKTDVITMDPKDNCSKDANDTLLLQLTNTSAYY
MYLLLLLKSVVYFAIITCCLLRRTAFCCNGEKSRAKRSGSGAPVKQTLN
FDLLKLAGDVESNPGPMETDTLLLWVLLLWVPGSTGEVQLVQSGAEVKK
PGESLKISCKGSGYSFTSYWIGWVRQMPGKGLEWMGITYPGDSDTRYSP

-continued

```
SFQGQVTISADKSISTAYLQWSSLKASDTAMYYCARSMGSSLYASSDVW

GQGTLVTVSSGGGGSGGGGSEVQLVQSGAEMKKPGESLKISCKGSGYNF

ASYWVGWVRQMPGKGLEWMGTIYPDDSDTRYGPAFQGQVTISADKSIST

AYLQWSSLKASDTAMYYCARDSYYGIDVWGQGTLVTVSSASTKGPSVFP

LAPSSKSTSGGTAALGCLVKDYFPEPVTVSWNSGALTSGVHTFPAVLQS

SGLYSLSSVVTVPSSSLGTQTYICNVNHKPSNTKVDKRVEPKSCEVKTD

STDHVKPKETENTKQPSKSCHKPKAIVHTEKVNMMSLTVLGLRMLFAKT

VAVNFLLTAKLFFL
```

Although SEQ ID NOs: 91-92 and 181-182 comprise specific peptide linkers, any linker (see, e.g., Table 6A) may be used.

In some embodiments, the nucleic acid encoding a heterobivalent anti-PSMA caTCR expresses a polypeptide that has at least about 85% (e.g., at least about any one of 85%, 86%, 87%, 88%, 89%, 90%, 91%, 92%, 93%, 94%, 95%, 96%, 97%, 98%, or 99%) sequence identity any one of SEQ ID NOs: 91-92 and 181-182.

While the exemplary caTCRs discussed above that comprise a CH1 sequence comprise the CH1 sequence set forth in ASTKGPSVFPLAPSSKSTSGGTAALGCLVKDYFPEPVTVSWNSGALTSGVHTFPAVLQSSGLYSLSSVVTVPSSSLGTQTYIC NVNHKPSNTKVDKRVEPKSC (SEQ ID NO: 122), alternative CH1 sequences may be used. For example, ASTKGPSVFPLAPSSKSTSGGTAALGCLVKDYFPEPVTVSWNSGALTSGVHTFPAVLQSSGLYELVSVVTVPSSSLGTQTYIC NVNHKPSNTKVDKRVEPKSC (SEQ ID NO 123), which comprises S64E and S66V mutations (EU numbering) may be used. While the exemplary caTCRs discussed above that comprise a CL sequence comprise the CL sequence set forth in GQPKANPTVTLFPPSSEELQANKATLVCLISDFYPGAVTVAWKADGSPVKAGVETTKPSKQSNNKYAAS-SYLSLTPEQWKSHR SYSCQVTHEGSTVEKTVAPTECS (SEQ ID NO: 124), i.e., the constant region of a λ light chain, alternative CL sequences may be used. For example, TVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC (SEQ ID NO: 125), i.e., the constant region of the κ light chain, or TVAAPSVFIFPPSDEQLKSGTASVVCLLNNFYPREAKVQWKVDNALQSGNSQESVTEQDSKDSTYSLLSSLTLSKADYEKHKV YACEVTHQGLSSPVTKSFNRGEC (SEQ ID NO: 126), the constant region of the κ light chain that comprises S69L and T71S mutations (EU numbering) may be used.

Anti-PSMA Chimeric Co-Stimulatory Receptor Constructs (CSRs)

Also provided herein are PSMA-specific chimeric co-stimulatory receptor constructs, which are alternatively referred to herein as chimeric signaling receptor constructs (i.e., "anti-PSMA CSRs"). Exemplary CSRs are discussed in PCT/US2018/029218 (now published as WO 2018/200583), the contents of which are incorporated herein by reference in their entirety. In some embodiments, the anti-PSMA CSR is expressed on the surface of an immune cell (such as a T cell). The anti-PSMA CSR binds to PSMA expressed on or associated with the surface of a cell (such as a cancer cell) and, upon binding to PSMA, is capable of stimulating the immune cell on which the anti-PSMA CSR is expressed. An anti-PSMA CSR comprises a PSMA-binding module (e.g. that comprises an anti-PSMA antibody moiety described herein), a transmembrane (TM) module, and a co-stimulatory immune cell signaling module that allows for stimulating the immune cell in or on which the anti-PSMA CSR is expressed. In some embodiments, the anti-PSMA CSR lacks a functional primary immune cell signaling sequence. In some embodiments, the anti-PSMA CSR lacks a primary immune cell signaling sequence. In some embodiments, the anti-PSMA CSR comprises a single polypeptide chain comprising the PSMA-binding module (e.g. that comprises an anti-PSMA antibody moiety described herein), transmembrane module, and co-stimulatory signaling module. In some embodiments, the anti-PSMA CSR comprises a first polypeptide chain and a second polypeptide chain, wherein the first and second polypeptide chains together form the PSMA-binding module (e.g. that comprises an anti-PSMA antibody moiety described herein), the transmembrane module, and the co-stimulatory signaling module. In some embodiments, the first and second polypeptide chains are separate polypeptide chains, and the anti-PSMA CSR is a multimer, such as a dimer. In some embodiments, the first and second polypeptide chains are covalently linked, such as by a peptide linkage, or by another chemical linkage, such as a disulfide linkage. In some embodiments, the first polypeptide chain and the second polypeptide chain are linked by at least one disulfide bond.

Also provided are effector cells (such as T cells) expressing an anti-PSMA CSR of the present disclosure. Such effector cells (such as T cells) are produced by introducing (e.g., transducing or transfecting) a nucleic acid encoding an anti-PSMA CSR described herein (or a vector comprising such a nucleic acid) into the effector cell (e.g., T cell).

Examples of co-stimulatory immune cell signaling domains for use in an anti-PSMA CSR include, but are not limited to, the cytoplasmic sequences of co-receptors of the T cell receptor (TCR), which can act in concert with a caTCR to initiate signal transduction following caTCR engagement, as well as any derivative or variant of these sequences and any synthetic sequence that has the same functional capability. Thus, in some embodiments provided is an effector cell (such as a T cell) that expresses a caTCR and an anti-PSMA CSR. Effector cells (such as T cells) expressing a caTCR and an anti-PSMA CSR (i.e., "caTCR plus anti-PSMA CSR effector cells") are described in further detail below.

It is known that signals generated through the TCR alone are insufficient for full activation of the T cell and that a secondary or co-stimulatory signal is also required. Thus, T cell activation can be said to be mediated by two distinct classes of intracellular (IC) signaling sequence: those that initiate antigen-dependent primary activation through the TCR (referred to herein as "primary T cell signaling sequences") and those that act in an antigen-independent manner to provide a secondary or co-stimulatory signal (referred to herein as "co-stimulatory T cell signaling sequences").

Primary immune cell signaling sequences that act in a stimulatory manner may contain signaling motifs which are known as immunoreceptor tyrosine-based activation motifs or ITAMs. Examples of ITAM-containing primary immune cell signaling sequences include those derived from CD3ζ, TCRζ, FcRγ, FcRβ, CD3γ, CD3δ, CD3ε, CD5, CD22, CD79a, CD79b, and CD66d. A "functional" primary immune cell signaling sequence is a sequence that is capable of transducing an immune cell activation signal when operably coupled to an appropriate receptor. "Non-functional" primary immune cell signaling sequences, which may comprise fragments or variants of primary immune cell signaling sequences, are unable to transduce an immune cell activation signal. Thus, in some embodiments, an anti-PSMA CSRs described herein lacks a functional primary immune cell signaling sequence, such as a functional signaling sequence comprising an ITAM. In some embodiments, the anti-PSMA CSR described herein lack any primary immune cell signaling sequence.

In some embodiments, the anti-PSMA CSR comprises a co-stimulatory signaling module that comprises (such as consists of or consists essentially of) all or a portion of the intracellular (IC) domain of an immune cell co-stimulatory molecule including, for example, CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like. In some embodiments, the CSR comprises a fragment of an immune cell co-stimulatory molecule (fCSM), wherein the fCSM comprises the CSR transmembrane (TM) domain and CSR intracellular (IC) co-stimulatory signaling domain. Exemplary IC co-stimulatory immune cell signaling module sequences are provided below:

```
4-1BB IC signaling sequence:
                                                              (SEQ ID NO: 100)
KRGRKKLLYIFKQPFMRPVQTTQEEDGCSCRFPEEEEGGCEL CD27 IC signaling sequence:
                                                              (SEQ ID NO: 101)
QRRKYRSNKGESPVEPAEPCRYSCPREEEGSTIPIQEDYRKPEPACSP CD28 IC signaling sequence:
                                                              (SEQ ID NO: 102)
RSKRSRLLHSDYMNMTPRRPGPTRKHYQPYAPPRDFAAYRS CD30 IC signaling sequence:
                                                              (SEQ ID NO: 183)
HRRACRKRIRQKLHLCYPVQTSQPKLELVDSRPRRSSTQLRSGASVTEPVAEERGLMSQPLMETCHSVGAAYLESLPLQDASP AGGPSSPRDLPEPRVSTEHTNNKIEKIYIMKADTVIVGTVKAELPEGRGLAGPAEPELEEELEADHTPHYPEQETEPPLGSCS

DVMLSVEEEGKEDPLPTAASGK

OX40 IC signaling sequence:
                                                              (SEQ ID NO: 103)
ALYLLRRDQRLPPDAHKPPGGGSFRTPIQEEQADAHSTLAKI myc tag + truncated CD28 sequence:
                                                              (SEQ ID NO: 104)
EQKLISEEDLAAAIEVMYPPPYLDNEKSNGTIIHVKGKHLCPSPLFPGPSKPFWVLVVVGGVLACYSLLVTVAFIIFWVRSKR

SRLLHSDYMNMTPRRPGPTRKHYQPYAPPRDFAAYRS truncated CD28 sequence:
                                                              (SEQ ID NO: 105)
IEVMYPPPYLDNEKSNGTIIHVKGKHLCPSPLFPGPSKPFWVLVVVGGVLACYSLLVTVAFTIFWVRSKRSRLLHSDYMNMTP

RRPGPTRKHYQPYAPPRDFAAYRS myc tag + truncated 4-1BB sequence:
                                                              (SEQ ID NO: 106)
EQKLISEEDLAAATGPADLSPGASSVTPPAPAREPGHSPQIISFFLALTSTALLFLLFFLTLRFSVVKRGRKKLLYIFKQPFM

RPVQTTQEEDGCSCRFPEEEEGGCEL truncated 4-1BB sequence:
                                                              (SEQ ID NO: 107)
AAATGPADLSPGASSVTPPAPAREPGHSPQIISFFLALTSTALLFLLFFLTLRFSVVKRGRKKLLYIFKQPFMRPVQTTQEED

GCSCRFPEEEEGGCEL myc tag + truncated CD27 sequence:
                                                              (SEQ ID NO: 108)
EQKLISEEDLAAATGPTHLPYVSEMLEARTAGHMQTLADFRQLPARTLSTHWPPQRSLCSSDFIRILVIFSGMFLVFTLAGAL

FLHQRRKYRSNKGESPVEPAEPCRYSCPREEEGSTIPIQEDYRKPEPACSP truncated CD27 sequence:
                                                              (SEQ ID NO: 109)
AAATGPTHLPYVSEMLEARTAGHMQTLADFRQLPARTLSTHWPPQRSLCSSDFIRILVIFSGMFLVFTLAGALFLHQRRKYRS

NKGESPVEPAEPCRYSCPREEEGSTIPIQEDYRKPEPACSP myc tag + truncated CD30 sequence:
                                                              (SEQ ID NO: 110)
EQKLISEEDLAAATGAPPLGTQPDCNPTPENGEAPASTSPTQSLLVDSQASKTLPIPTSAPVALSSTGKPVLDAGPVLFWVIL VLVVVVGSSAFLLCHRRACRKRIRQKLHLCYPVQTSQPKLELVDSRPRRSSTQLRSGASVTEPVAEERGLMSQPLMETCHSVG
```

-continued

AAYLESLPLQDASPAGGPSSPRDLPEPRVSTEHTNNKIEKIYIMKADTVIVGTVKAELPEGRGLAGPAEPELEEELEADHTPH

YPEQETEPPLGSCSDVMLSVEEEGKEDPLPTAASGK truncated CD30 sequence:
(SEQ ID NO: 111)
AAATGAPPLGTQPDCNPTPENGEAPASTSPTQSLLVDSQASKTLPIPTSAPVALSSTGKPVLDAGPVLFWVILVLVVVGSSA FLLCHRRACRKRIRQKLHLCYPVQTSQPKLELVDSRPRRSSTQLRSGASVTEPVAEERGLMSQPLMETCHSVGAAYLESLPLQ DASPAGGPSSPRDLPEPRVSTEHTNNKIEKIYIMKADTVIVGTVKAELPEGRGLAGPAEPELEEELEADHTPHYPEQETEPPL

GSCSDVMLSVEEEGKEDPLPTAASGK myc tag + truncated OX40 sequence:
(SEQ ID NO: 112)
EQKLISEEDLAAATGDRDPPATQPQETQGPPARPITVQPTEAWPRTSQGPSTRPVEVPGGRAVAAILGLGLVLGLLGPLAILL

ALYLLRRDQRLPPDAHKPPGGGSFRTPIQEEQADAHSTLAKI truncated OX40 sequence:
(SEQ ID NO: 113)
AAATGDRDPPATQPQETQGPPARPITVQPTEAWPRTSQGPSTRPVEVPGGRAVAAILGLGLVLGLLGPLAILLALYLLRRDQR

LPPDAHKPPGGGSFRTPIQEEQADAHSTLAKI myc tag + CD8 TM sequence and CD27 IC signaling sequence:
(SEQ ID NO: 114)
EQKLISEEDLAAATGTTTPAPRPPTPAPTIASQPLSLRPEACRPAAGGAVHTRGLDFACDIYIWAPLAGTCGVLLLSLVITLY

CQRRKYRSNKGESPVEPAEPCRYSCPREEEGSTIPIQEDYRKPEPACSP

CD8 TM sequence and CD27 IC signaling sequence:
(SEQ ID NO: 115)
AAATGTTTPAPRPPTPAPTIASQPLSLRPEACRPAAGGAVHTRGLDFACDIYIWAPLAGTCGVLLLSLVITLYCQRRKYRSNK

GESPVEPAEPCRYSCPREEEGSTIPIQEDYRKPEPACSP myc tag + CD8 TM sequence and CD30 IC signaling sequence:
(SEQ ID NO: 116)
EQKLISEEDLAAATGTTTPAPRPPTPAPTIASQPLSLRPEACRPAAGGAVHTRGLDFACDIYIWAPLAGTCGVLLLSLVITLY CHRRACRKRIRQKLHLCYPVQTSQPKLELVDSRPRRSSTQLRSGASVTEPVAEERGLMSQPLMETCHSVGAAYLESLPLQDAS PAGGPSSPRDLPEPRVSTEHTNNKIEKIYIMKADTVIVGTVKAELPEGRGLAGPAEPELEEELEADHTPHYPEQETEPPLGSC

SDVMLSVEEEGKEDPLPTAASGK

CD8 TM sequence and CD30 IC signaling sequence:
(SEQ ID NO: 117)
AAATGTTTPAPRPPTPAPTIASQPLSLRPEACRPAAGGAVHTRGLDFACDIYIWAPLAGTCGVLLLSLVITLYCHRRACRKRI RQKLHLCYPVQTSQPKLELVDSRPRRSSTQLRSGASVTEPVAEERGLMSQPLMETCHSVGAAYLESLPLQDASPAGGPSSPRD LPEPRVSTEHTNNKIEKIYIMKADTVIVGTVKAELPEGRGLAGPAEPELEEELEADHTPHYPEQETEPPLGSCSDVMLSVEEE

GKEDPLPTAASGK myc tag + CD8 TM sequence and OX40 IC signaling sequence:
(SEQ ID NO: 118)
EQKLISEEDLAAATGTTTPAPRPPTPAPTIASQPLSLRPEACRPAAGGAVHTRGLDFACDIYIWAPLAGTCGVLLLSLVITLY

CALYLLRRDQRLPPDAHKPPGGGSFRTPIQEEQADAHSTLAKI

CD8 TM sequence and OX40 IC signaling sequence:
(SEQ ID NO: 119)
AAATGTTTPAPRPPTPAPTIASQPLSLRPEACRPAAGGAVHTRGLDFACDIYIWAPLAGTCGVLLLSLVITLYCALYLLRRDQ

RLPPDAHKPPGGGSFRTPIQEEQADAHSTLAKI myc tag + CD8 TM sequence and 4-1BB IC signaling sequence:
(SEQ ID NO: 120)
EQKLISEEDLAAATGTTTPAPRPPTPAPTIASQPLSLRPEACRPAAGGAVHTRGLDFACDIYIWAPLAGTCGVLLLSLVITLY

CKRGRKKLLYIFKQPFMRPVQTTQEEDGCSCRFPEEEEGGCEL

CD8 TM sequence and 4-1BB IC signaling sequence:
(SEQ ID NO: 121)
AAATGTTTPAPRPPTPAPTIASQPLSLRPEACRPAAGGAVHTRGLDFACDIYIWAPLAGTCGVLLLSLVITLYCKRGRKKLLY

IFKQPFMRPVQTTQEEDGCSCRFPEEEEGGCEL

In some embodiments, the PSMA-binding module of an anti-PSMA CSR of the present disclosure is an anti-PSMA antibody moiety. In some embodiments, the anti-PSMA antibody moiety is a Fab, a Fab', a (Fab')2, an Fv, or a single chain Fv (scFv). In some embodiments, the anti-PSMA antibody moiety comprises the CDRs or variables domains ($V_H$ and/or $V_L$ domains) of an antibody moiety specific for PSMA (e.g., PSMA expressed on or associated with the surface of a cell, e.g., a cancer cell), such as any of anti-PSMA antibody moieties described elsewhere herein.

In some embodiments, the transmembrane module of an anti-PSMA CSR of the present disclosure comprises one or more transmembrane domains derived from, for example, CD28, CD3ε, CD3ζ, CD45, CD4, CD5, CD8, CD9, CD16, CD22, CD33, CD37, CD64, CD80, CD86, CD134, CD137, or CD154. In some embodiments, the CSR comprises a fragment of a transmembrane protein (fTMP), wherein the fTMP comprises the CSR transmembrane domain. Exemplary transmembrane domain (TM) sequences are provided below:

CD8 TM sequence:
(SEQ ID NO: 94)
IYIWAPLAGTCGVLLLSLVIT 4-1BB TM sequence:
(SEQ ID NO: 95)
IISFFLALTSTALLFLLFFLTLRFSVV CD27 TM sequence:
(SEQ ID NO: 96)
ILVIFSGMFLVFTLAGALFLH CD28 TM sequence:
(SEQ ID NO: 97)
FWVLVVVGGVLACYSLLVTVAFIIFWV CD30 TM sequence:
(SEQ ID NO: 98)
PVLDAGPVLFWVILVLVVVVGSSAFLLC OX40 TM sequence:
(SEQ ID NO: 99)
VAAILGLGLVLGLLGPLAILL In some embodiments, the anti-PSMA CSR further comprises a spacer module between any of the ligand-binding module, the transmembrane module, and the co-stimulatory signaling module. In some embodiments, the spacer module comprises one or more peptide linkers connecting two CSR modules. In some embodiments, the spacer module comprises one or more peptide linkers between about 5 to about 70 (such as about any of 5, 10, 15, 20, 25, 30, 35, 40, 45, 50, 55, 60, 65, or 70, including any ranges between these values) amino acids in length.

The amino acid sequences of exemplary anti-PSMA CSRs are provided in Table 11 below. The anti-PSMA sequences are in plain text (i.e., no underline), and sequences derived from CD28 (see SEQ ID NOs: 37-38, 51-55, and 70), 4-1BB (see SEQ ID NOs: 56, 57, 71, and 72), CD27 (see SEQ ID NOs: 58, 59, 73, and 74), CD30 (see SEQ ID NOs: 60, 61, 75, and 76), OX40 (see SEQ ID NOs: 62, 63, 77, and 78), CD8 and CD27 (see SEQ ID NO: 64, 65, 79, and 80), CD8 and CD30 (see SEQ ID NOs: 66, 67, 81, and 82), CD8 and OX40 (see SEQ ID NOs: 68, 69, 83, and 84), are underlined.

TABLE 11

QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGSRGGGGSGGGGSGGGGSLEMAEVQLVQSGAEVKKPGESLKISCKGSGYSF
TSYWIGWVRQMPGKGLEWMGITYPGDSDTRYSPSFQGQVTISADKSISTAYLQWSSLKASDTAMYYCARSMGSSLYASSDV
WGQGTLVTVSSAAAIEVMYPPPYLDNEKSNGTIIHVKGKHLCPSPLFPGPSKPFWVLVVVGGVLACYSLLVTVAFTIFWVR
SKRSRLLHSDYMNMTPRRPGPTRKHYQPYAPPRDFAAYRS (SEQ ID NO: 37)

QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGSRGGGGSGGGGSGGGGSLEMAEVQLVQSGAEMKKPGESLKISCKGSGYNFA
SYWVGWVRQMPGKGLEWMGTIYPDDSDTRYGPAFQGQVTISADKSISTAYLQWSSLKASDTAMYYCARDSYYGIDVWGQGT
LVTVSSAAAIEVMYPPPYLDNEKSNGTIIHVKGKHLCPSPLFPGPSKPFWVLVVVGGVLACYSLLVTVAFTIFWVRSKRSR
LLHSDYMNMTPRRPGPTRKHYQPYAPPRDFAAYRS (SEQ ID NO: 38)

*METDTLLLWVLLLWVPGSTG*QSVLTQPPSVSGAPGQRVTISCTGSSSNIGAGYDVHWYQQLPGTAPKLLIYGNSNRPSGVP
DRFSGSKSGTSASLAITGLQAEDEADYYCQSYDSSLSGYVFGTGTKVTVLGSRGGGGSGGGGSGGGGSLEMAEVQLVQSGA
EVKKPGESLKISCKGSGYSFTSYWIGWVRQMPGKGLEWMGITYPGDSDTRYSPSFQGQVTISADKSISTAYLQWSSLKASD
TAMYYCARSMGSSLYASSDVWGQGTLVTVSSEQKLISEEDLAAAIEVMYPPPYLDNEKSNGTIIHVKGKHLCPSPLFPGPS
KPFWVLVVVGGVLACYSLLVTVAFTIFWVRSKRSRLLHSDYMNMTPRRPGPTRKHYQPYAPPRDFAAYRS (SEQ ID
NO: 51)

*METDTLLLWVLLLWVPGSTG*QSVLTQPPSVSGAPGQRVTISCTGSSSNIGAGYDVHWYQQLPGTAPKLLIYGNSNRPSGVP
DRFSGSKSGTSASLAITGLQAEDEADYYCQSYDSSLSGYVFGTGTKVTVLGSRGGGGSGGGGSGGGGSLEMAEVQLVQSGA
EVKKPGESLKISCKGSGYSFTSYWIGWVRQMPGKGLEWMGITYPGDSDTRYSPSFQGQVTISADKSISTAYLQWSSLKASD
TAMYYCARSMGSSLYASSDVWGQGTLVTVSSAAAIEVMYPPPYLDNEKSNGTIIHVKGKHLCPSPLFPGPSKPFWVLVVVG
GVLACYSLLVTVAFTIFWVRSKRSRLLHSDYMNMTPRRPGPTRKHYQPYAPPRDFAAYRS (SEQ ID NO: 52)

*METDTLLLWVLLLWVPGSTG*QAVLTQPPSASGTPGQRVTISCSGSSSNIGSNTVNWYQQLPGTAPKLLMYSNNQRPSGVPD
RFSGSKSGTSASLAISGLQSEDEADYYCAAWDDSLNGYVFGTGTKVTVLGSRGGGGSGGGGSGGGGSLEMAEVQLVQSGAE
MKKPGESLKISCKGSGYNFASYWVGWVRQMPGKGLEWMGTIYPDDSDTRYGPAFQGQVTISADKSISTAYLQWSSLKASDT
AMYYCARDSYYGIDVWGQGTLVTVSSEQKLISEEDLAAAIEVMYPPPYLDNEKSNGTIIHVKGKHLCPSPLFPGPSKPFWV
LVVVGGVLACYSLLVTVAFTIFWVRSKRSRLLHSDYMNMTPRRPGPTRKHYQPYAPPRDFAAYRS (SEQ ID NO:
53)

*METDTLLLWVLLLWVPGSTG*QAVLTQPPSASGTPGQRVTISCSGSSSNIGSNTVNWYQQLPGTAPKLLMYSNNQRPSGVPD
RFSGSKSGTSASLAISGLQSEDEADYYCAAWDDSLNGYVFGTGTKVTVLGSRGGGGSGGGGSGGGGSLEMAEVQLVQSGAE
MKKPGESLKISCKGSGYNFASYWVGWVRQMPGKGLEWMGTIYPDDSDTRYGPAFQGQVTISADKSISTAYLQWSSLKASDT
AMYYCARDSYYGIDVWGQGTLVTVSSAAAIEVMYPPPYLDNEKSNGTIIHVKGKHLCPSPLFPGPSKPFWVLVVVGGVLAC
YSLLVTVAFTIFWVRSKRSRLLHSDYMNMTPRRPGPTRKHYQPYAPPRDFAAYRS (SEQ ID NO: 54)

TABLE 11-continued

QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGSRGGGGSGGGGSGGGGSLEMAEVQLVQSGAEVKKPGESLKISCKGSGYSF
TSYWIGWVRQMPGKGLEWMGITYPGDSDTRYSPSFQGQVTISADKSISTAYLQWSSLKASDTAMYYCARSMGSSLYASSDV
WGQGTLVTVSSEQKLISEEDLAAAIEVMYPPPYLDNEKSNGTIIHVKGKHLCPSPLFPGPSKPFWVLVVVGGVLACYSLLV
TVAFTIFWVRSKRSRLLHSDYMNMTPRRPGPTRKHYQPYAPPRDFAAYRS (SEQ ID NO: 55)

QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGSRGGGGSGGGGSGGGGSLEMAEVQLVQSGAEVKKPGESLKISCKGSGYSF
TSYWIGWVRQMPGKGLEWMGITYPGDSDTRYSPSFQGQVTISADKSISTAYLQWSSLKASDTAMYYCARSMGSSLYASSDV
WGQGTLVTVSSEQKLISEEDLAAATGPADLSPGASSVTPPAPAREPGHSPQIISFFLALTSTALLFLLFFLTLRFSVVKRG
RKKLLYIFKQPFMRPVQTTQEEDGCSCRFPEEEEGGCEL (SEQ ID NO: 56)

QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGSRGGGGSGGGGSGGGGSLEMAEVQLVQSGAEVKKPGESLKISCKGSGYSF
TSYWIGWVRQMPGKGLEWMGITYPGDSDTRYSPSFQGQVTISADKSISTAYLQWSSLKASDTAMYYCARSMGSSLYASSDV
WGQGTLVTVSSAAATGPADLSPGASSVTPPAPAREPGHSPQIISFFLALTSTALLFLLFFLTLRFSVVKRGRKKLLYIFKQ
PFMRPVQTTQEEDGCSCRFPEEEEGGCEL (SEQ ID NO: 57)

QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGSRGGGGSGGGGSGGGGSLEMAEVQLVQSGAEVKKPGESLKISCKGSGYSF
TSYWIGWVRQMPGKGLEWMGITYPGDSDTRYSPSFQGQVTISADKSISTAYLQWSSLKASDTAMYYCARSMGSSLYASSDV
WGQGTLVTVSSEQKLISEEDLAAATGPTHLPYVSEMLEARTAGHMQTLADFRQLPARTLSTHWPPQRSLCSSDFIRILVIF
SGMFLVFTLAGALFLHQRRKYRSNKGESPVEPAEPCRYSCPREEEGSTIPIQEDYRKPEPACSP (SEQ ID NO: 58)

QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGSRGGGGSGGGGSGGGGSLEMAEVQLVQSGAEVKKPGESLKISCKGSGYSF
TSYWIGWVRQMPGKGLEWMGITYPGDSDTRYSPSFQGQVTISADKSISTAYLQWSSLKASDTAMYYCARSMGSSLYASSDV
WGQGTLVTVSSAAATGPTHLPYVSEMLEARTAGHMQTLADFRQLPARTLSTHWPPQRSLCSSDFIRILVIFSGMFLVFTLA
GALFLHQRRKYRSNKGESPVEPAEPCRYSCPREEEGSTIPIQEDYRKPEPACSP (SEQ ID NO: 59)

QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGSRGGGGSGGGGSGGGGSLEMAEVQLVQSGAEVKKPGESLKISCKGSGYSF
TSYWIGWVRQMPGKGLEWMGITYPGDSDTRYSPSFQGQVTISADKSISTAYLQWSSLKASDTAMYYCARSMGSSLYASSDV
WGQGTLVTVSSEQKLISEEDLAAATGAPPLGTQPDCNPTPENGEAPASTSPTQSLLVDSQASKTLPIPTSAPVALSSTGKP
VLDAGPVLFWVILVLVVVGSSAFLLCHRRACRKRIRQKLHLCYPVQTSQPKLELVDSRPRRSSTQLRSGASVTEPVAEER
GLMSQPLMETCHSVGAAYLESLPLQDASPAGGPSSPRDLPEPRVSTEHTNNKIEKIYIMKADTVIVGTVKAELPEGRGLAG
PAEPELEEELEADHTPHYPEQETEPPLGSCSDVMLSVEEEGKEDPLPTAASGK (SEQ ID NO: 60)

QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGSRGGGGSGGGGSGGGGSLEMAEVQLVQSGAEVKKPGESLKISCKGSGYSF
TSYWIGWVRQMPGKGLEWMGITYPGDSDTRYSPSFQGQVTISADKSISTAYLQWSSLKASDTAMYYCARSMGSSLYASSDV
WGQGTLVTVSSAAATGAPPLGTQPDCNPTPENGEAPASTSPTQSLLVDSQASKTLPIPTSAPVALSSTGKPVLDAGPVLFW
VILVLVVVGSSAFLLCHRRACRKRIRQKLHLCYPVQTSQPKLELVDSRPRRSSTQLRSGASVTEPVAEERGLMSQPLMET
CHSVGAAYLESLPLQDASPAGGPSSPRDLPEPRVSTEHTNNKIEKIYIMKADTVIVGTVKAELPEGRGLAGPAEPELEEEL
EADHTPHYPEQETEPPLGSCSDVMLSVEEEGKEDPLPTAASGK (SEQ ID NO: 61)

QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGSRGGGGSGGGGSGGGGSLEMAEVQLVQSGAEVKKPGESLKISCKGSGYSF
TSYWIGWVRQMPGKGLEWMGITYPGDSDTRYSPSFQGQVTISADKSISTAYLQWSSLKASDTAMYYCARSMGSSLYASSDV
WGQGTLVTVSSEQKLISEEDLAAATGDRDPPATQPQETQGPPARPITVQPTEAWPRTSQGPSTRPVEVPGGRAVAAILGLG
LVLGLLGPLAILLALYLLRRDQRLPPDAHKPPGGGSFRTPIQEEQADAHSTLAKI (SEQ ID NO: 62)

QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGSRGGGGSGGGGSGGGGSLEMAEVQLVQSGAEVKKPGESLKISCKGSGYSF
TSYWIGWVRQMPGKGLEWMGITYPGDSDTRYSPSFQGQVTISADKSISTAYLQWSSLKASDTAMYYCARSMGSSLYASSDV
WGQGTLVTVSSAAATGDRDPPATQPQETQGPPARPITVQPTEAWPRTSQGPSTRPVEVPGGRAVAAILGLGLVLGLLGPLA
ILLALYLLRRDQRLPPDAHKPPGGGSFRTPIQEEQADAHSTLAKI (SEQ ID NO: 63)

QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGSRGGGGSGGGGSGGGGSLEMAEVQLVQSGAEVKKPGESLKISCKGSGYSF
TSYWIGWVRQMPGKGLEWMGITYPGDSDTRYSPSFQGQVTISADKSISTAYLQWSSLKASDTAMYYCARSMGSSLYASSDV
WGQGTLVTVSSEQKLISEEDLAAATGTTTPAPRPPTPAPTIASQPLSLRPEACRPAAGGAVHTRGLDFACDIYIWAPLAGT
CGVLLLSLVITLYCQRRKYRSNKGESPVEPAEPCRYSCPREEEGSTIPIQEDYRKPEPACSP (SEQ ID NO: 64)

QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGSRGGGGSGGGGSGGGGSLEMAEVQLVQSGAEVKKPGESLKISCKGSGYSF
TSYWIGWVRQMPGKGLEWMGITYPGDSDTRYSPSFQGQVTISADKSISTAYLQWSSLKASDTAMYYCARSMGSSLYASSDV
WGQGTLVTVSSAAATGTTTPAPRPPTPAPTIASQPLSLRPEACRPAAGGAVHTRGLDFACDIYIWAPLAGTCGVLLLSLVI
TLYCQRRKYRSNKGESPVEPAEPCRYSCPREEEGSTIPIQEDYRKPEPACSP (SEQ ID NO: 65)

QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGSRGGGGSGGGGSGGGGSLEMAEVQLVQSGAEVKKPGESLKISCKGSGYSF
TSYWIGWVRQMPGKGLEWMGITYPGDSDTRYSPSFQGQVTISADKSISTAYLQWSSLKASDTAMYYCARSMGSSLYASSDV
WGQGTLVTVSSEQKLISEEDLAAATGTTTPAPRPPTPAPTIASQPLSLRPEACRPAAGGAVHTRGLDFACDIYIWAPLAGT
CGVLLLSLVITLYCHRRACRKRIRQKLHLCYPVQTSQPKLELVDSRPRRSSTQLRSGASVTEPVAEERGLMSQPLMETCHS
VGAAYLESLPLQDASPAGGPSSPRDLPEPRVSTEHTNNKIEKIYIMKADTVIVGTVKAELPEGRGLAGPAEPELEEELEAD
HTPHYPEQETEPPLGSCSDVMLSVEEEGKEDPLPTAASGK (SEQ ID NO: 66)

TABLE 11-continued

```
QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGSRGGGGSGGGGSGGGGSLEMAEVQLVQSGAEVKKPGESLKISCKGSGYSF
TSYWIGWVRQMPGKGLEWMGITYPGDSDTRYSPSFQGQVTISADKSISTAYLQWSSLKASDTAMYYCARSMGSSLYASSDV
WGQGTLVTVSSAAATGTTTPAPRPPTPAPTIASQPLSLRPEACRPAAGGAVHTRGLDFACDIYIWAPLAGTCGVLLLSLVI
TLYCHRRACRKRIRQKLHLCYPVQTSQPKLELVDSRPRRSSTQLRSGASVTEPVAEERGLMSQPLMETCHSVGAAYLESLP
LQDASPAGGPSSPRDLPEPRVSTEHTNNKIEKIYIMKADTVIVGTVKAELPEGRGLAGPAEPELEEELEADHTPHYPEQET
EPPLGSCSDVMLSVEEEGKEDPLPTAASGK (SEQ ID NO: 67)

QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGSRGGGGSGGGGSGGGGSLEMAEVQLVQSGAEVKKPGESLKISCKGSGYSF
TSYWIGWVRQMPGKGLEWMGITYPGDSDTRYSPSFQGQVTISADKSISTAYLQWSSLKASDTAMYYCARSMGSSLYASSDV
WGQGTLVTVSSEQKLISEEDLAAATGTTTPAPRPPTPAPTIASQPLSLRPEACRPAAGGAVHTRGLDFACDIYIWAPLAGT
CGVLLLSLVITLYCALYLLRRDQRLPPDAHKPPGGGSFRTPIQEEQADAHSTLAKI (SEQ ID NO: 68)

QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGSRGGGGSGGGGSGGGGSLEMAEVQLVQSGAEVKKPGESLKISCKGSGYSF
TSYWIGWVRQMPGKGLEWMGITYPGDSDTRYSPSFQGQVTISADKSISTAYLQWSSLKASDTAMYYCARSMGSSLYASSDV
WGQGTLVTVSSAAATGTTTPAPRPPTPAPTIASQPLSLRPEACRPAAGGAVHTRGLDFACDIYIWAPLAGTCGVLLLSLVI
TLYCALYLLRRDQRLPPDAHKPPGGGSFRTPIQEEQADAHSTLAKI (SEQ ID NO: 69)

QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGSRGGGGSGGGGSGGGGSLEMAEVQLVQSGAEMKKPGESLKISCKGSGYNFA
SYWVGWVRQMPGKGLEWMGTIYPDDSDTRYGPAFQGQVTISADKSISTAYLQWSSLKASDTAMYYCARDSYYGIDVWGQGT
LVTVSSEQKLISEEDLAAAIEVMYPPPYLDNEKSNGTIIHVGKHLCPSPLFPGPSKPFWVLVVVGGVLACYSLLVTVAFI
IFWVRSKRSRLLHSDYMNMTPRRPGPTRKHYQPYAPPRDFAAYRS (SEQ ID NO: 70)

QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGSRGGGGSGGGGSGGGGSLEMAEVQLVQSGAEMKKPGESLKISCKGSGYNFA
SYWVGWVRQMPGKGLEWMGTIYPDDSDTRYGPAFQGQVTISADKSISTAYLQWSSLKASDTAMYYCARDSYYGIDVWGQGT
LVTVSSEQKLISEEDLAAATGPADLSPGASSVTPPAPAREPGHSPQIISFFLALTSTALLFLLFFLTLRFSVVKRGRKKLL
YIFKQPFMRPVQTTQEEDGCSCRFPEEEEGGCEL (SEQ ID NO: 71)

QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGSRGGGGSGGGGSGGGGSLEMAEVQLVQSGAEMKKPGESLKISCKGSGYNFA
SYWVGWVRQMPGKGLEWMGTIYPDDSDTRYGPAFQGQVTISADKSISTAYLQWSSLKASDTAMYYCARDSYYGIDVWGQGT
LVTVSSAAATGPADLSPGASSVTPPAPAREPGHSPQIISFFLALTSTALLFLLFFLTLRFSVVKRGRKKLLYIFKQPFMRP
VQTTQEEDGCSCRFPEEEEGGCEL (SEQ ID NO: 72)

QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGSRGGGGSGGGGSGGGGSLEMAEVQLVQSGAEMKKPGESLKISCKGSGYNFA
SYWVGWVRQMPGKGLEWMGTIYPDDSDTRYGPAFQGQVTISADKSISTAYLQWSSLKASDTAMYYCARDSYYGIDVWGQGT
LVTVSSEQKLISEEDLAAATGPTHLPYVSEMLEARTAGHMQTLADFRQLPARTLSTHWPPQRSLCSSDFIRILVIFSGMFL
VFTLAGALFLHQRRKYRSNKGESPVEPAEPCRYSCPREEEGSTIPIQEDYRKPEPACSP (SEQ ID NO: 73)

QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGSRGGGGSGGGGSGGGGSLEMAEVQLVQSGAEMKKPGESLKISCKGSGYNFA
SYWVGWVRQMPGKGLEWMGTIYPDDSDTRYGPAFQGQVTISADKSISTAYLQWSSLKASDTAMYYCARDSYYGIDVWGQGT
LVTVSSAAATGPTHLPYVSEMLEARTAGHMQTLADFRQLPARTLSTHWPPQRSLCSSDFIRILVIFSGMFLVFTLAGALFL
HQRRKYRSNKGESPVEPAEPCRYSCPREEEGSTIPIQEDYRKPEPACSP (SEQ ID NO: 74)

YYCAAWDDSLNGYVFGTGTKVTVLGSRGGGGSGGGGSGGGGSLEMAEVQLVQSGAEMKKPGESLKISCKGSGYNFASYWVG
WVRQMPGKGLEWMGTIYPDDSDTRYGPAFQGQVTISADKSISTAYLQWSSLKASDTAMYYCARDSYYGIDVWGQGTLVTVS
SEQKLISEEDLAAATGAPPLGTQPDCNPTPENGEAPASTSPTQSLLVDSQASKTLPIPTSAPVALSSTGKPVLDAGPVLFW
VILVLVVVVGSSAFLLCHRRACRKRIRQKLHLCYPVQTSQPKLELVDSRPRRSSTQLRSGASVTEPVAEERGLMSQPLMET
CHSVGAAYLESLPLQDASPAGGPSSPRDLPEPRVSTEHTNNKIEKIYIMKADTVIVGTVKAELPEGRGLAGPAEPELEEEL
EADHTPHYPEQETEPPLGSCSDVMLSVEEEGKEDPLPTAASGK (SEQ ID NO: 75)

QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGSRGGGGSGGGGSGGGGSLEMAEVQLVQSGAEMKKPGESLKISCKGSGYNFA
SYWVGWVRQMPGKGLEWMGTIYPDDSDTRYGPAFQGQVTISADKSISTAYLQWSSLKASDTAMYYCARDSYYGIDVWGQGT
LVTVSSAAATGAPPLGTQPDCNPTPENGEAPASTSPTQSLLVDSQASKTLPIPTSAPVALSSTGKPVLDAGPVLFWVILVL
VVVVGSSAFLLCHRRACRKRIRQKLHLCYPVQTSQPKLELVDSRPRRSSTQLRSGASVTEPVAEERGLMSQPLMETCHSVG
AAYLESLPLQDASPAGGPSSPRDLPEPRVSTEHTNNKIEKIYIMKADTVIVGTVKAELPEGRGLAGPAEPELEEELEADHT
PHYPEQETEPPLGSCSDVMLSVEEEGKEDPLPTAASGK (SEQ ID NO: 76)

QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGSRGGGGSGGGGSGGGGSLEMAEVQLVQSGAEMKKPGESLKISCKGSGYNFA
SYWVGWVRQMPGKGLEWMGTIYPDDSDTRYGPAFQGQVTISADKSISTAYLQWSSLKASDTAMYYCARDSYYGIDVWGQGT
LVTVSSEQKLISEEDLAAATGDRDPPATQPQETQGPPARPITVQPTEAWPRTSQGPSTRPVEVPGGRAVAAILGLGLVLGL
LGPLAILLALYLLRRDQRLPPDAHKPPGGGSFRTPIQEEQADAHSTLAKI (SEQ ID NO: 77)

QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGSRGGGGSGGGGSGGGGSLEMAEVQLVQSGAEMKKPGESLKISCKGSGYNFA
SYWVGWVRQMPGKGLEWMGTIYPDDSDTRYGPAFQGQVTISADKSISTAYLQWSSLKASDTAMYYCARDSYYGIDVWGQGT
LVTVSSAAATGDRDPPATQPQETQGPPARPITVQPTEAWPRTSQGPSTRPVEVPGGRAVAAILGLGLVLGLLGPLAILLAL
YLLRRDQRLPPDAHKPPGGGSFRTPIQEEQADAHSTLAKI (SEQ ID NO: 78)

QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGSRGGGGSGGGGSGGGGSLEMAEVQLVQSGAEMKKPGESLKISCKGSGYNFA
```

TABLE 11-continued

```
SYWVGWVRQMPGKGLEWMGTIYPDDSDTRYGPAFQGQVTISADKSISTAYLQWSSLKASDTAMYYCARDSYYGIDVWGQGT
LVTVSSEQKLISEEDLAAATGTTTPAPRPPTPAPTIASQPLSLRPEACRPAAGGAVHTRGLDFACDIYIWAPLAGTCGVLL
LSLVITLYCQRRKYRSNKGESPVEPAEPCRYSCPREEEGSTIPIQEDYRKPEPACSP (SEQ ID NO: 79)

QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGSRGGGGSGGGGSGGGGSLEMAEVQLVQSGAEMKKPGESLKISCKGSGYNFA
SYWVGWVRQMPGKGLEWMGTIYPDDSDTRYGPAFQGQVTISADKSISTAYLQWSSLKASDTAMYYCARDSYYGIDVWGQGT
LVTVSSAAATGTTTPAPRPPTPAPTIASQPLSLRPEACRPAAGGAVHTRGLDFACDIYIWAPLAGTCGVLLLSLVITLYCQ
RRKYRSNKGESPVEPAEPCRYSCPREEEGSTIPIQEDYRKPEPACSP (SEQ ID NO: 80)

QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGSRGGGGSGGGGSGGGGSLEMAEVQLVQSGAEMKKPGESLKISCKGSGYNFA
SYWVGWVRQMPGKGLEWMGTIYPDDSDTRYGPAFQGQVTISADKSISTAYLQWSSLKASDTAMYYCARDSYYGIDVWGQGT
LVTVSSEQKLISEEDLAAATGTTTPAPRPPTPAPTIASQPLSLRPEACRPAAGGAVHTRGLDFACDIYIWAPLAGTCGVLL
LSLVITLYCHRRACRKRIRQKLHLCYPVQTSQPKLELVDSRPRRSSTQLRSGASVTEPVAEERGLMSQPLMETCHSVGAAY
LESLPLQDASPAGGPSSPRDLPEPRVSTEHTNNKIEKIYIMKADTVIVGTVKAELPEGRGLAGPAEPELEEELEADHTPHY
PEQETEPPLGSCSDVMLSVEEEGKEDPLPTAASGK (SEQ ID NO: 81)

QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGSRGGGGSGGGGSGGGGSLEMAEVQLVQSGAEMKKPGESLKISCKGSGYNFA
SYWVGWVRQMPGKGLEWMGTIYPDDSDTRYGPAFQGQVTISADKSISTAYLQWSSLKASDTAMYYCARDSYYGIDVWGQGT
LVTVSSAAATGTTTPAPRPPTPAPTIASQPLSLRPEACRPAAGGAVHTRGLDFACDIYIWAPLAGTCGVLLLSLVITLYCH
RRACRKRIRQKLHLCYPVQTSQPKLELVDSRPRRSSTQLRSGASVTEPVAEERGLMSQPLMETCHSVGAAYLESLPLQDAS
PAGGPSSPRDLPEPRVSTEHTNNKIEKIYIMKADTVIVGTVKAELPEGRGLAGPAEPELEEELEADHTPHYPEQETEPPLG
SCSDVMLSVEEEGKEDPLPTAASGK (SEQ ID NO: 82)

QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGSRGGGGSGGGGSGGGGSLEMAEVQLVQSGAEMKKPGESLKISCKGSGYNFA
SYWVGWVRQMPGKGLEWMGTIYPDDSDTRYGPAFQGQVTISADKSISTAYLQWSSLKASDTAMYYCARDSYYGIDVWGQGT
LVTVSSEQKLISEEDLAAATGTTTPAPRPPTPAPTIASQPLSLRPEACRPAAGGAVHTRGLDFACDIYIWAPLAGTCGVLL
LSLVITLYCALYLLRRDQRLPPDAHKPPGGGSFRTPIQEEQADAHSTLAKI (SEQ ID NO: 83)

QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGSRGGGGSGGGGSGGGGSLEMAEVQLVQSGAEMKKPGESLKISCKGSGYNFA
SYWVGWVRQMPGKGLEWMGTIYPDDSDTRYGPAFQGQVTISADKSISTAYLQWSSLKASDTAMYYCARDSYYGIDVWGQGT
LVTVSSAAATGTTTPAPRPPTPAPTIASQPLSLRPEACRPAAGGAVHTRGLDFACDIYIWAPLAGTCGVLLLSLVITLYCA
LYLLRRDQRLPPDAHKPPGGGSFRTPIQEEQADAHSTLAKI (SEQ ID NO: 84)
```

The sequences in bold type in Table 11 correspond to the myc tag EQKLISEEDL (SEQ ID NO: 136). The sequences in bold italic type in Table 11 correspond to the signal peptide METDTLLLWVLLLWVPGSTG (SEQ ID NO: 128).

In some embodiments, the CSR is a bivalent anti-PSMA CSR that comprises two anti-PSMA antibody moieties. In some embodiments, the bivalent anti-PSMA CSR is homobivalent, e.g., comprising two anti-PSMA antibody moieties that comprise identical $V_H$ sequences and identical $V_L$ sequences. In some embodiments, the bivalent anti-PSMA CSR is heterobivalent, e.g., comprising two different anti-PSMA antibody moieties, where each anti-PSMA antibody moiety comprises a different VH sequence and/or different VL sequence. The amino acid sequences of four exemplary heterobivalent anti-PSMA CSRs are shown below (i.e., SEQ ID NO: 93 and SEQ ID NOs: 183-185). The Clone A anti-PSMA scFv sequence is in plain text (i.e., no underlining), the Clone B anti-PSMA scFv is underlined, a linker sequence is in bold text, a myc tag sequence (when present) is in bold text and underlined, and sequences derived from CD28 are italicized.

```
                                                            (SEQ ID NO: 93)
QSVLTQPPSVSGAPGQRVTISCTGSSSNIGAGYDVHWYQQLPGTAPKLLIYGNSNRPSGVPDRFSGSKSGTSASLAITGLQAE

DEADYYCQSYDSSLSGYVFGTGTKVTVLGSRGGGGSGGGGSGGGGSLEMAEVQLVQSGAEVKKPGESLKISCKGSGYSFTSYW

IGWVRQMPGKGLEWMGITYPGDSDTRYSPSFQGQVTISADKSISTAYLQWSSLKASDTAMYYCARSMGSSLYASSDVWGQGTL

VTVSSGGGGSGGGGSQAVLTQPPSASGTPGQRVTISCSGSSSNIGSNTVNWYQQLPGTAPKLLMYSNNQRPSGVPDRFSGSKS

GTSASLAISGLQSEDEADYYCAAWDDSLNGYVFGTGTKVTVLGSRGGGGSGGGGSGGGGSLEMAEVQLVQSGAEMKKPGESLK

ISCKGSGYNFASYWVGWVRQMPGKGLEWMGTIYPDDSDTRYGPAFQGQVTISADKSISTAYLQWSSLKASDTAMYYCARDSYY

GIDVWGQGTLVTVSSEQKLISEEDLAAAIEVMYPPPYLDNEKSNGTIIHVKGKHLCPSPLFPGPSKPFWVLVVVGGVLACYSL

LVTVAFIIFWVRSERSRLLHSDYMNMTPRRPGPTREHYQPYAPPRDFAAYRS (SEQ ID NO: 185)
QSVLTQPPSVSGAPGQRVTISCTGSSSNIGAGYDVHWYQQLPGTAPKLLIYGNSNRPSGVPDRFSGSKSGTSASLAITGLQAE

DEADYYCQSYDSSLSGYVFGTGTKVTVLGSRGGGGSGGGGSGGGGSLEMAEVQLVQSGAEVKKPGESLKISCKGSGYSFTSYW

IGWVRQMPGKGLEWMGITYPGDSDTRYSPSFQGQVTISADKSISTAYLQWSSLKASDTAMYYCARSMGSSLYASSDVWGQGTL
```

-continued

VTVSSGGGGSGGGGSQAVLTQPPSASGTPGQRVTISCSGSSSNIGSNTVNWYQQLPGTAPKLLMYSNNQRPSGVPDRFSGSKS

GTSASLAISGLQSEDEADYYCAAWDDSLNGYVFGTGTKVTVLGSRGGGGSGGGGSGGGGSLEMAEVQLVQSGAEMKKPGESLK

ISCKGSGYNFASYWVGWVRQMPGKGLEWMGTIYPDDSDTRYGPAFQGQVTISADKSISTAYLQWSSLKASDTAMYYCARDSYY

GIDVWGQGTLVTVS*SAAAIEVMYPPPYLDNEKSNGTIIHVKGKHLCPSPLFPGPSKPFWVLVVVGGVLACYSLLVTVAFIIFW*

*VRSERSRLLHSDYMNMTPRRPGPTREHYQPYAPPRDFAAYRS*

(SEQ ID NO: 184)
QAVLTQPPSASGTPGQRVTISCSGSSSNIGSNTVNWYQQLPGTAPKLLMYSNNQRPSGVPDRFSGSKSGTSASLAISGLQSED

EADYYCAAWDDSLNGYVFGTGTKVTVLGSRGGGGSGGGGSGGGGSLEMAEVQLVQSGAEMKKPGESLKISCKGSGYNFASYWV

GWVRQMPGKGLEWMGTIYPDDSDTRYGPAFQGQVTISADKSISTAYLQWSSLKASDTAMYYCARDSYYGIDVWGQGTLVTVSS

GGGGSGGGGSQSVLTQPPSVSGAPGQRVTISCTGSSSNIGAGYDVHWYQQLPGTAPKLLIYGNSNRPSGVPDRFSGSKSGTSA

SLAITGLQAEDEADYYCQSYDSSLSGYVFGTGTKVTVLGSRGGGGSGGGGSGGGGSLEMAEVQLVQSGAEVKKPGESLKISCK

GSGYSFTSYWIGWVRQMPGKGLEWMGITYPGDSDTRYSPSFQGQVTISADKSISTAYLQWSSLKASDTAMYYCARSMGSSLYA

SSDVWGQGTLVTVSSEQKLISEEDLAAA*IEVMYPPPYLDNEKSNGTIIHVKGKHLCPSPLFPGPSKPFWVLVVVGGVLACYSL*

*LVITAFIIFWVRSERSRLLHSDYMNMTPRRPGPTREHYQPYAPPRDFAAYRS*

(SEQ ID NO: 186)
QAVLTQPPSASGTPGQRVTISCSGSSSNIGSNTVNWYQQLPGTAPKLLMYSNNQRPSGVPDRFSGSKSGTSASLAISGLQSED

EADYYCAAWDDSLNGYVFGTGTKVTVLGSRGGGGSGGGGSGGGGSLEMAEVQLVQSGAEMKKPGESLKISCKGSGYNFASYWV

GWVRQMPGKGLEWMGTIYPDDSDTRYGPAFQGQVTISADKSISTAYLQWSSLKASDTAMYYCARDSYYGIDVWGQGTLVTVSS

GGGGSGGGGSQSVLTQPPSVSGAPGQRVTISCTGSSSNIGAGYDVHWYQQLPGTAPKLLIYGNSNRPSGVPDRFSGSKSGTSA

SLAITGLQAEDEADYYCQSYDSSLSGYVFGTGTKVTVLGSRGGGGSGGGGSGGGGSLEMAEVQLVQSGAEVKKPGESLKISCK

GSGYSFTSYWIGWVRQMPGKGLEWMGITYPGDSDTRYSPSFQGQVTISADKSISTAYLQWSSLKASDTAMYYCARSMGSSLYA

SSDVWGQGTLVTVS*SAAAIEVMYPPPYLDNEKSNGTIIHVKGKHLCPSPLFPGPSKPFWVLVVVGGVLACYSLLVTVAFIIFW*

*VRSERSRLLHSDYMNMTPRRPGPTREHYQPYAPPRDFAAYRS*

In some embodiments, any one of SEQ ID NOs: 37-38, 55-84 and 93 further comprises an N-terminal signal peptide, e.g., the signal peptide of SEQ ID NO: 128. In some embodiments, any one of SEQ ID NOs: 37-38, 51-84, and 93 further comprises a peptide linker and/or peptide tag (see, e.g. Tables 6A and 6B). In some embodiments, the anti-PSMA CSR comprises an amino acid sequence that has at least about 85% (e.g., at least about any one of 85%, 86%, 87%, 88%, 89%, 90%, 91%, 92%, 93%, 94%, 95%, 96%, 97%, 98%, or 99%) sequence identity to any one of SEQ ID NOs: 37-38, 51-84, and 93.

The present disclosure also provides effector cells (such as T cells) that express a caTCR or a CAR and an anti-PSMA CSR (such as an anti-PSMA CSR described herein). Such effector cells are also referred to herein as "caTCR plus anti-PSMA CSR effector cells." In some embodiments, the caTCR plus anti-PSMA CSR effector cell (such as a T cell) comprises a nucleic acid sequence encoding the anti-PSMA CSR operably linked to an inducible promoter, including any of the inducible promoters described herein. In some embodiments, the expression of the anti-PSMA CSR in the caTCR plus anti-PSMA CSR effector cell (such as a T cell) is inducible upon signaling through the caTCR. In some such embodiments, the caTCR plus anti'-PSMA CSR effector cell (such as a T cell) comprises a nucleic acid sequence encoding the anti-PSMA CSR operably linked to a promoter or regulatory element that is responsive to signaling through the caTCR. In some embodiments, the nucleic acid sequence encoding the anti-PSMA CSR is operably linked to a nuclear-factor of the activated T-cell (NFAT)-derived promoter. In some embodiments, the NFAT-derived promoter is an NFAT-derived minimal promoter (see for example Durand, D. et. al., *Molec. Cell. Biol.* 8, 1715-1724 (1988); Clipstone, N A, Crabtree, G R. *Nature.* 1992 357(6380): 695-7; Chmielewski, M., et al. *Cancer research* 71.17 (2011): 5697-5706; and Zhang, L., et al. *Molecular therapy* 19.4 (2011): 751-759). In some embodiments, the caTCR expressed by the caTCR plus anti-PSMA CSR effector cell (such as a T cell) is an anti-PSMA caTCR. In some embodiments the caTCR expressed by the caTCR plus anti-PSMA CSR effector cell (such as a T cell) is not an anti-PSMA caTCR and targets a different antigen. Further description of CSRs may be found in U.S. Application No. 62/490,578, filed Apr. 26, 2017, which is incorporated by reference herein in its entirety.

Construct Combinations

Also provided are construct combinations that comprise at least two different anti-PSMA constructs described herein. In some embodiments, the at least two different anti-PSMA constructs are the same format, e.g., at least two different antibodies (e.g., two different full-length IgG antibodies or two different bispecific antibodies), at least two different CARs, at least two different caTCRs, or at least two different CSRs. In some embodiments, the at least two different anti-PSMA constructs are different formats, e.g., an antibody and a CAR; an antibody and a caTCR; a CAR and a CSR; a caTCR and a CSR, etc.

In some embodiments, the construct combination comprises an anti-PSMA caTCR and an anti-PSMA CSR (i.e., an "anti-PSMA caTCR+anti-PSMA CSR construct combination"), wherein the anti-PSMA caTCR comprises a Chain 1 that comprises:

an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 31 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 32;

an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 34 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 35;

an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 165 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 166;

an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 167 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 168;

an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 169 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 170;

an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 171 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 172;

an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 173 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 174;

an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 175 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 176;

an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 177 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 178;

an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 179 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 180;

and wherein the anti-PSMA CSR comprises an amino acid sequence that has at least 85% (e.g., at least about any one of 85%, 86%, 87%, 88%, 89%, 90%, 91%, 92%, 93%, 94%, 95%, 96%, 97%, 98%, 99% or 100%) sequence identity to any one of SEQ ID NOs: 37-38, 55-84, and 93.

In some embodiments, the anti-PSMA caTCR comprises a Chain 1 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 31 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 32, and the anti-PSMA CSR comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 55. In some embodiments, the anti-PSMA caTCR comprises a Chain 1 that comprises SEQ ID NO: 31 and a Chain 2 that comprises SEQ ID NO: 32, and the anti-PSMA CSR comprises the amino acid sequence of SEQ ID NO: 55.

In some embodiments, the anti-PSMA caTCR comprises a Chain 1 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 31 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 32, and the anti-PSMA CSR comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 70. In some embodiments, the anti-PSMA caTCR comprises a Chain 1 that comprises SEQ ID NO: 31 and a Chain 2 that comprises SEQ ID NO: 32, and the anti-PSMA CSR comprises the amino acid sequence of SEQ ID NO: 70.

In some embodiments, the anti-PSMA caTCR comprises a Chain 1 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 34 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 35, and the anti-PSMA CSR comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 55. In some embodiments, the anti-PSMA caTCR comprises a Chain 1 that comprises SEQ ID NO: 34 and a Chain 2 that comprises SEQ ID NO: 35, and the anti-PSMA CSR comprises the amino acid sequence of SEQ ID NO: 55.

In some embodiments, the anti-PSMA caTCR comprises a Chain 1 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 34 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 35, and the anti-PSMA CSR comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 70. In some embodiments, the anti-PSMA caTCR comprises a Chain 1 that comprises SEQ ID NO: 34 and a Chain 2 that comprises SEQ ID NO: 35, and the anti-PSMA CSR comprises the amino acid sequence of SEQ ID NO: 70.

In some embodiments, the anti-PSMA caTCR is a homobivalent anti-PSMA caTCR that comprises a Chain 1 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 165 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 166, and the anti-PSMA CSR comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 70. In some embodiments, the anti-PSMA caTCR comprises a Chain 1 that comprises SEQ ID NO: 165 and a Chain 2 that comprises SEQ ID NO: 166, and the anti-PSMA CSR comprises the amino acid sequence of SEQ ID NO: 70.

In some embodiments, the anti-PSMA caTCR is a homobivalent anti-PSMA caTCR that comprises a Chain 1 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 165 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 166, and the anti-PSMA CSR that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) identity to any one of SEQ ID NOs: 38 and 70-84. In some embodiments, the anti-PSMA caTCR comprises a Chain 1 that comprises SEQ ID NO: 165 and a Chain 2 that comprises SEQ ID NO: 166, and the anti-PSMA CSR comprises the amino acid sequence of any one of SEQ ID NOs: 38 and 70-84.

In some embodiments, the anti-PSMA caTCR is a homobivalent anti-PSMA caTCR that comprises a Chain 1 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 169 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 170, and the anti-PSMA CSR comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 55. In some embodiments, the anti-PSMA caTCR comprises a Chain 1 that comprises SEQ ID NO: 169 and a Chain 2 that comprises SEQ ID NO: 170, and the anti-PSMA CSR comprises the amino acid sequence of SEQ ID NO: 55.

In some embodiments, the anti-PSMA caTCR is a homobivalent anti-PSMA caTCR that comprises a Chain 1 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 169 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 170, and the anti-PSMA CSR that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) identity to any one of SEQ ID NOs: 37 and 55-69. In some embodiments, the anti-PSMA caTCR comprises a Chain 1 that comprises SEQ ID NO: 169 and a Chain 2 that comprises SEQ ID NO: 170, and the anti-PSMA CSR comprises the amino acid sequence of any one of SEQ ID NOs: 37 and 55-69.

In some embodiments, the anti-PSMA caTCR is a homobivalent anti-PSMA caTCR that comprises a Chain 1 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 167 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 168, and the anti-PSMA CSR that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) identity to any one of SEQ ID NOs: 38 and 70-84. In some embodiments, the anti-PSMA caTCR comprises a Chain 1 that comprises SEQ ID NO: 167 and a Chain 2 that comprises SEQ ID NO: 168, and the anti-PSMA CSR comprises the amino acid sequence of any one of SEQ ID NOs: 38 and 70-84.

In some embodiments, the anti-PSMA caTCR is a homobivalent anti-PSMA caTCR that comprises a Chain 1 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 171 and a Chain 2 that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) sequence identity to SEQ ID NO: 172, and the anti-PSMA CSR that comprises an amino acid sequence that has at least 85% (e.g., at least about any one of 85%, 86%, 87%, 88%, 89%, 90%, 91%, 92%, 93%, 94%, 95%, 96%, 97%, 98%, 99%, or 100%) identity to any one of SEQ ID NOs: 37 and 55-69. In some embodiments, the anti-PSMA caTCR comprises a Chain 1 that comprises SEQ ID NO: 171 and a Chain 2 that comprises SEQ ID NO: 172, and the anti-PSMA CSR comprises the amino acid sequence of any one of SEQ ID NOs: 37 and 55-69.

In some embodiments, the anti-PSMA caTCR and the anti-PSMA CSR of a construct combination provided herein are encoded on separate nucleic acids. In some embodiments, the separate nucleic acids are each expressed (e.g., separately) and translated (e.g., separately) in a cell (such as an anti-PSMA effector cell, which is described in further detail elsewhere herein). In some embodiments, the anti-PSMA caTCR and the anti-PSMA CSR of a construct combination provided herein are encoded on the same nucleic acid (e.g., a single nucleic acid). In some embodiments, the single nucleic acid encoding the anti-PSMA caTCR and anti-PSMA CSR construct combination is expressed and translated to generate a single polypeptide which is subsequently processed (e.g., such as cleaved during or following translation) into separate polypeptides, e.g., the anti-PSMA caTCR polypeptide(s) and anti-PSMA CSR polypeptide.

In some embodiments, a single nucleic acid encoding an anti-PSMA caTCR+anti-PSMA CSR construct combination expresses a polypeptide comprising any one of SEQ ID NOs: 85-90, the amino acid sequences of which are provided below:

(SEQ ID NO: 85)
METDTLLLWVLLLWVPGSTGEVQLVQSGAEVKKPGESLKISCKGSGYSF

TSYWIGWVRQMPGKGLEWMGIIYPGDSDTRYSPSFQGQVTISADKSIST

AYLQWSSLKASDTAMYYCARSMGSSLYASSDVWGQGTLVTVSSASTKGP

SVFPLAPSSKSTSGGTAALGCLVKDYFPEPVTVSWNSGALTSGVHTFPA

VLQSSGLYSLSSVVTVPSSSLGTQTYICNVNHKPSNTKVDKRVEPKSCE

VKTDSTDHVKPKETENTKQPSKSCHKPKAIVHTEKVNMMSLTVLGLRML

FAKTVAVNFLLTAKLFFLRAKRSGSGAPVKQTLNFDLLKLAGDVESNPG

PMETDTLLLWVLLLWVPGSTGQSVLTQPPSVSGAPGQRVTISCTGSSSN

IGAGYDVHWYQQLPGTAPKLLIYGNSNRPSGVPDRFSGSKSGTSASLAI

TGLQAEDEADYYCQSYDSSLSGYVFGTGTKVTVLGQPKANPTVTLFPPS

SEELQANKATLVCLISDFYPGAVTVAWKADGSPVKAGVETTKPSKQSNN

KYAASSYLSLTPEQWKSHRSYSCQVTHEGSTVEKTVAPTECSPIKTDVI

TMDPKDNCSKDANDTLLLQLTNTSAYYMLLLLLKSVVYFAIITCCLLR

RTAFCCNGEKSGSGATNFSLLKQAGDVEENPGPMETDTLLLWVLLLWVP

GSTGQSVLTQPPSVSGAPGQRVTISCTGSSSNIGAGYDVHWYQQLPGTA

PKLLIYGNSNRPSGVPDRFSGSKSGTSASLAITGLQAEDEADYYCQSYD

SSLSGYVFGTGTKVTVLGSRGGGGSGGGGSGGGGSLEMAEVQLVQSGAE

VKKPGESLKISCKGSGYSFTSYWIGWVRQMPGKGLEWMGITYPGDSDTR

YSPSFQGQVTISADKSISTAYLQWSSLKASDTAMYYCARSMGSSLYASS

DVWGQGTLVTVSSEQKLISEEDLAAAIEVMYPPPYLDNEKSNGTIIHVK

GKHLCPSPLFPGPSKPFWVLVVVGGVLACYSLLVTVAFTIFWVRSKRSR

LLHSDYMNMTPRRPGPTRKHYQPYAPPRDFAAYRS (SEQ ID NO: 86)
METDTLLLWVLLLWVPGSTGEVQLVQSGAEVKKPGESLKISCKGSGYSF

TSYWIGWVRQMPGKGLEWMGITYPGDSDTRYSPSFQGQVTISADKSIST

AYLQWSSLKASDTAMYYCARSMGSSLYASSDVWGQGTLVTVSSASTKGP

SVFPLAPSSKSTSGGTAALGCLVKDYFPEPVTVSWNSGALTSGVHTFPA

VLQSSGLYSLSSVVTVPSSSLGTQTYICNVNHKPSNTKVDKRVEPKSCE

VKTDSTDHVKPKETENTKQPSKSCHKPKAIVHTEKVNMMSLTVLGLRML

FAKTVAVNFLLTAKLFFLRAKRSGSGAPVKQTLNFDLLKLAGDVESNPG

PMETDTLLLWVLLLWVPGSTGQSVLTQPPSVSGAPGQRVTISCTGSSSN

IGAGYDVHWYQQLPGTAPKLLIYGNSNRPSGVPDRFSGSKSGTSASLAI

TGLQAEDEADYYCQSYDSSLSGYVFGTGTKVTVLGQPKANPTVTLFPPS

SEELQANKATLVCLISDFYPGAVTVAWKADGSPVKAGVETTKPSKQSNN

KYAASSYLSLTPEQWKSHRSYSCQVTHEGSTVEKTVAPTECSPIKTDVI

TMDPKDNCSKDANDTLLLQLTNTSAYYMLLLLLKSVVYFAIITCCLLR

RTAFCCNGEKSGSGATNFSLLKQAGDVEENPGPMETDTLLLWVLLLWVP

GSTGQAVLTQPPSASGTPGQRVTISCSGSSSNIGSNTVNWYQQLPGTAP

KLLMYSNNQRPSGVPDRFSGSKSGTSASLAISGLQSEDEADYYCAAWDD

SLNGYVFGTGTKVTVLGSRGGGGSGGGGSGGGGSLEMAEVQLVQSGAEM

KKPGESLKISCKGSGYNFASYWVGWVRQMPGKGLEWMGTIYPDDSDTRY

GPAFQGQVTISADKSISTAYLQWSSLKASDTAMYYCARDSYYGIDVWGQ

GTLVTVSSEQKLISEEDLAAAIEVMYPPPYLDNEKSNGTIIHVKGKHLC

PSPLFPGPSKPFWVLVVVGGVLACYSLLVTVAFTIFWVRSKRSRLLHSD

YMNMTPRRPGPTRKHYQPYAPPRDFAAYRS (SEQ ID NO: 87)
METDTLLLWVLLLWVPGSTGEVQLVQSGAEMKKPGESLKISCKGSGYNF

ASYWVGWVRQMPGKGLEWMGTIYPDDSDTRYGPAFQGQVTISADKSIST

AYLQWSSLKASDTAMYYCARDSYYGIDVWGQGTLVTVSSASTKGPSVFP

LAPSSKSTSGGTAALGCLVKDYFPEPVTVSWNSGALTSGVHTFPAVLQS

SGLYSLSSVVTVPSSSLGTQTYICNVNHKPSNTKVDKRVEPKSCEVKTD

STDHVKPKETENTKQPSKSCHKPKAIVHTEKVNMMSLTVLGLRMLFAKT

VAVNFLLTAKLFFLRAKRSGSGAPVKQTLNFDLLKLAGDVESNPGPMET

DTLLLWVLLLWVPGSTGQAVLTQPPSASGTPGQRVTISCSGSSSNIGSN

TVNWYQQLPGTAPKLLMYSNNQRPSGVPDRFSGSKSGTSASLAISGLQS

EDEADYYCAAWDDSLNGYVFGTGTKVTVLGQPKANPTVTLFPPSSEELQ

ANKATLVCLISDFYPGAVTVAWKADGSPVKAGVETTKPSKQSNNKYAAS

SYLSLTPEQWKSHRSYSCQVTHEGSTVEKTVAPTECS*PIKTDVITMDPE*

*DNCSKDANDTLLLQLTNTSAYYMYLLLLLKSVVYFAIITCCLLRRTAFC*

*CNGEKSGSGATNFSLLKQAGDVEENPGPMETDTLLLWVLLLWVPGSTGQ*

SVLTQPPSVSGAPGQRVTISCTGSSSNIGAGYDVHWYQQLPGTAPKLLI

YGNSNRPSGVPDRFSGSKSGTSASLAITGLQAEDEADYYCQSYDSSLSG

YVFGTGTKVTVLGSRGGGGSGGGGSGGGGSLEMAEVQLVQSGAEVKKPG

ESLKISCKGSYSFTSYWIGWVRQMPGKGLEWMGITYPGDSDTRYSPSF
QGQVTISADKSISTAYLQWSSLKASDTAMYYCARSMGSSLYASSDVWGQ
GTLVTVSSEQKLISEEDLAAAIEVMYPPPYLDNEKSNGTIIHVKGKHLC
PSPLFPGPSKPFWVLVVVGGVLACYSLLVTVAFTIFWVRSKRSLLHSD
YMNMTPRRPGPTRKHYQPYAPPRDFAAYRS (SEQ ID NO: 88)
METDTLLLWVLLLWVPGSTGEVQLVQSGAEMKKPGESLKISCKGSGYNF
ASYWVGWVRQMPGKGLEWMGTIYPDDSDTRYGPAFQGQVTISADKSIST
AYLQWSSLKASDTAMYYCARDSYYGIDVWGQGTLVTVSSASTKGPSVFP
LAPSSKSTSGGTAALGCLVKDYFPEPVTVSWNSGALTSGVHTFPAVLQS
SGLYSLSSVVTVPSSSLGTQTYICNVNHKPSNTKVDKRVEPKSCEVKTD
STDHVKPKETENTKQPSKSCHKPKAIVHTEKVNMMSLTVLGLRMLFAKT
VAVNFLLTAKLFFLRAKRSGSGAPVKQTLNFDLLKLAGDVESNPGPMET
DTLLLWVLLLWVPGSTGQAVLTQPPSASGTPGQRVTISCSGSSSNIGSN
TVNWYQQLPGTAPKLLMYSNNQRPSGVPDRFSGSKSGTSASLAISGLQS
EDEADYYCAAWDDSLNGYVFGTGTKVTVLGQPKANPTVTLFPPSSEELQ
ANKATLVCLISDFYPGAVTVAWKADGSPVKAGVETTKPSKQSNNKYAAS
SYLSLTPEQWKSHRSYSCQVTHEGSTVEKTVAPTECS*PIKTDVITMDPK*
*DNCSRDANDTLLLQLTNTSAYYMLLLLLKSVVYFAIITCCLLRRTAFC*
*CNGEKS*GSGATNFSLLKQAGDVEENPGPMETDTLLLWVLLLWVPGSTGQ
AVLTQPPSASGTPGQRVTISCSGSSSNIGSNTVNWYQQLPGTAPKLLMY
SNNQRPSGVPDRFSGSKSGTSASLAISGLQSEDEADYYCAAWDDSLNGY
VFGTGTKVTVLGSRGGGSGGGGSGGGGSLEMAEVQLVQSGAEMKKPGE
SLKISCKGSGYNFASYWVGWVRQMPGKGLEWMGTIYPDDSDTRYGPAFQ
GQVTISADKSISTAYLQWSSLKASDTAMYYCARDSYYGIDVWGQGTLVT
VSSEQKLISEEDLAAAIEVMYPPPYLDNEKSNGTIIHVKGKHLCPSPLF
PGPSKPFWVLVVVGGVLACYSLLVTVAFTIFWVRSKRSLLHSDYMNMT
PRRPGPTRKHYQPYAPPRDFAAYRS (SEQ ID NO: 89)
METDTLLLWVLLLWVPGSTGQSVLTQPPSVSGAPGQRVTISCTGSSSNI
GAGYDVHWYQQLPGTAPKLLIYGNSNRPSGVPDRFSGSKSGTSASLAIT
GLQAEDEADYYCQSYDSSLSGYVFGTGTKVTVLGSRGGGGSGGGGSGGG
GSLEMAEVQLVQSGAEVKKPGESLKISCKGSGYSFTSYWIGWVRQMPGK
GLEWMGITYPGDSDTRYSPSFQGQVTISADKSISTAYLQWSSLKASDTA
MYYCARSMGSSLYASSDVWGQGTLVTVSSGGGGSEVQLVQSGAEVKKPG
ESLKISCKGSGYSFTSYWIGWVRQMPGKGLEWMGITYPGDSDTRYSPSF
QGQVTISADKSISTAYLQWSSLKASDTAMYYCARSMGSSLYASSDVWGQ
GTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPS
NTKVDKRVEPKSCEVKTDSTDHVKPKETENTKQPSKSCHKPKAIVHTEK
VNMMSLTVLGLRMLFAKTVAVNFLLTAKLFFLRAKRSGSGAPVKQTLNF
DLLKLAGDVESNPGPMETDTLLLWVLLLWVPGSTGQSVLTQPPSVSGAP

GQRVTISCTGSSSNIGAGYDVHWYQQLPGTAPKLLIYGNSNRPSGVPDR
FSGSKSGTSASLAITGLQAEDEADYYCQSYDSSLSGYVFGTGTKVTVLG
QPKANPTVTLFPPSSEELQANKATLVCLISDFYPGAVTVAWKADGSPVK
AGVETTKPSKQSNNKYAASSYLSLTPEQWKSHRSYSCQVTHEGSTVEKT
VAPTECSPIKTDVITMDPKDNCSKDANDTLLLQLTNTSAYYMYLLLLLK
SVVYFAIITCCLLRRTAFCCNGEKSGSGATNFSLLKQAGDVEENPGPME
TDTLLLWVLLLWVPGSTGQAVLTQPPSASGTPGQRVTISCSGSSSNIGS
NTVNWYQQLPGTAPKLLMYSNNQRPSGVPDRFSGSKSGTSASLAISGLQ
SEDEADYYCAAWDDSLNGYVFGTGTKVTVLGSRGGGGSGGGGSGGGGSL
EMAEVQLVQSGAEMKKPGESLKISCKGSGYNFASYWVGWVRQMPGKGLE
WMGTIYPDDSDTRYGPAFQGQVTISADKSISTAYLQWSSLKASDTAMYY
CARDSYYGIDVWGQGTLVTVSSEQKLISEEDLAAAIEVMYPPPYLDNEK
SNGTIIHVKGKHLCPSPLFPGPSKPFWVLVVVGGVLACYSLLVTVAFTI
FWVRSKRSLLHSDYMNMTPRRPGPTRKHYQPYAPPRDFAAYRS (SEQ ID NO: 90)
METDTLLLWVLLLWVPGSTGQAVLTQPPSASGTPGQRVTISCSGSSSNI
GSNTVNWYQQLPGTAPKLLMYSNNQRPSGVPDRFSGSKSGTSASLAISG
LQSEDEADYYCAAWDDSLNGYVFGTGTKVTVLGSRGGGGSGGGGSGGGG
SLEMAEVQLVQSGAEMKKPGESLKISCKGSGYNFASYWVGWVRQMPGKG
LEWMGTIYPDDSDTRYGPAFQGQVTISADKSISTAYLQWSSLKASDTAM
YYCARDSYYGIDVWGQGTLVTVSSGGGGSEVQLVQSGAEMKKPGESLKI
SCKGSGYNFASYWVGWVRQMPGKGLEWMGTIYPDDSDTRYGPAFQGQVT
ISADKSISTAYLQWSSLKASDTAMYYCARDSYYGIDVWGQGTLVTVSSA
STKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVE
PKSCEVKTDSTDHVKPKETENTKQPSKSCHKPKAIVHTEKVNMMSLTVL
GLRMLFAKTVAVNFLLTAKLFFLRAKRSGSGAPVKQTLNFDLLKLAGDV
ESNPGPMETDTLLLWVLLLWVPGSTGQAVLTQPPSASGTPGQRVTISCS
GSSSNIGSNTVNWYQQLPGTAPKLLMYSNNQRPSGVPDRFSGSKSGTSA
SLAISGLQSEDEADYYCAAWDDSLNGYVFGTGTKVTVLGQPKANPTVTL
FPPSSEELQANKATLVCLISDFYPGAVTVAWKADGSPVKAGVETTKPSK
QSNNKYAASSYLSLTPEQWKSHRSYSCQVTHEGSTVEKTVAPTECSPIK
TDVITMDPKDNCSKDANDTLLLQLTNTSAYYMLLLLLKSVVYFAIITC
CLLRRTAFCCNGEKSGSGATNFSLLKQAGDVEENPGPMETDTLLLWVLL
LWVPGSTGQSVLTQPPSVSGAPGQRVTISCTGSSSNIGAGYDVHWYQQL
PGTAPKLLIYGNSNRPSGVPDRFSGSKSGTSASLAITGLQAEDEADYYC
QSYDSSLSGYVFGTGTKVTVLGSRGGGGSGGGGSGGGGSLEMAEVQLVQ
SGAEVKKPGESLKISCKGSGYSFTSYWIGWVRQMPGKGLEWMGITYPGD
SDTRYSPSFQGQVTISADKSISTAYLQWSSLKASDTAMYYCARSMGSSL
YASSDVWGQGTLVTVSSEQKLISEEDLAAAIEVMYPPPYLDNEKSNGTI

-continued

IHVKGKHLCPSPLFPGPSKPFWVLVVVGGVLACYSLLVTVAFTIFWVRS

KRSRLLHSDYMNMTPRRPGPTRKHYQPYAPPRDFAAYRS

In some embodiments, the single nucleic acid encoding an anti-PSMA caTCR+anti-PSMA CSR construct combination expresses a polypeptide that has at least about 85% (e.g., at least about any one of 85%, 86%, 87%, 88%, 89%, 90%, 91%, 92%, 93%, 94%, 95%, 96%, 97%, 98%, or 99%) sequence identity to any one of SEQ ID NOs: 91-92 and 181-182.

In some embodiments, a single nucleic acid encoding an anti-PSMA caTCR+anti-PSMA CSR construct combination expresses a polypeptide comprising (from N-terminus to C-terminus) the amino acid sequence(s) of an anti-PSMA caTCR construct, a peptide linker, and the amino acid sequence of an anti-PSMA CSR construct. In some embodiments, a single nucleic acid encoding anti-PSMA caTCR+anti-PSMA CSR construct combination expresses a polypeptide comprising (from N-terminus to C-terminus) the amino acid sequence of an anti-PSMA CSR construct, a peptide linker, and the amino acid sequence(s) of an anti-PSMA caTCR construct. In some embodiments, the nucleic acid further encodes, e.g., one or more peptide linkers, peptide spacers, peptide tags, signal peptides and/or other amino acid sequences (see, e.g., Tables 6A and 6B for exemplary linker sequences and tag sequences).

In some embodiments, the single nucleic acid encoding an anti-PSMA caTCR+anti-PSMA CSR construct combination expresses a polypeptide comprising the sequences listed in each of rows 1-128 in Table 12 below.

TABLE 12

| | caTCR + CSR Combination Encoded by Nucleic Acid | Order of Components (from N-Terminus to C-Terminus) in Polypeptide encoded by the Nucleic Acid | Exemplary anti-PSMA caTCR | Exemplary anti-PSMA CSR | Exemplary Linker |
|---|---|---|---|---|---|
| 1 | Ax2-caTCR-1 + B-CSR-1A | caTCR-linker-CSR (see, e.g., SEQ ID NO: 89) | Ax2-caTCR-1 (SEQ ID NO: 47) | B-CSR-1A (SEQ ID NO: 70) | P2A self-cleaving peptide (SEQ ID NO: 132) |
| 2 | B-CSR-1A + Ax2-caTCR-1 | CSR-linker-caTCR (see, e.g., paragraph [0441]) | Ax2-caTCR-1 (SEQ ID NO: 47) | B-CSR-1A (SEQ ID NO: 70) | furin cleavage site + P2A self-cleaving peptide (SEQ ID NO: 133) |
| 3 | Ax2-caTCR-1 + B-CSR-1B | caTCR-linker-CSR (see, e.g., paragraph [0442]) | Ax2-caTCR-1 (SEQ ID NO: 47) | B-CSR-1B (SEQ ID NO: 38) | P2A self-cleaving peptide (SEQ ID NO: 132) |
| 4 | B-CSR-1B + Ax2-caTCR-1 | CSR-linker-caTCR (see, e.g., paragraph [0443]) | Ax2-caTCR-1 (SEQ ID NO: 47) | B-CSR-1B (SEQ ID NO: 38) | furin cleavage site + P2A self-cleaving peptide (SEQ ID NO: 133) |
| 5 | Ax2-caTCR-1 + B-CSR-2A | caTCR-linker-CSR | Ax2-caTCR-1 (SEQ ID NO: 47) | B-CSR-2A (SEQ ID NO: 71) | P2A self-cleaving peptide (SEQ ID NO: 132) |
| 6 | B-CSR-2A + Ax2-caTCR-1 | CSR-linker-caTCR | Ax2-caTCR-1 (SEQ ID NO: 47) | B-CSR-2A (SEQ ID NO: 71) | furin cleavage site + P2A self-cleaving peptide (SEQ ID NO: 133) |
| 7 | Ax2-caTCR-1 + B-CSR-2B | caTCR-linker-CSR | Ax2-caTCR-1 (SEQ ID NO: 47) | B-CSR-2B (SEQ ID NO: 72) | P2A self-cleaving peptide (SEQ ID NO: 132) |
| 8 | B-CSR-2B + Ax2-caTCR-1 | CSR-linker-caTCR | Ax2-caTCR-1 (SEQ ID NO: 47) | B-CSR-2B (SEQ ID NO: 72) | furin cleavage site + P2A self-cleaving peptide (SEQ ID NO: 133) |
| 9 | Ax2-caTCR-1 + B-CSR-3A | caTCR-linker-CSR | Ax2-caTCR-1 (SEQ ID NO: 47) | B-CSR-3A (SEQ ID NO: 73) | P2A self-cleaving peptide (SEQ ID NO: 132) |
| 10 | B-CSR-3A + Ax2-caTCR-1 | CSR-linker-caTCR | Ax2-caTCR-1 (SEQ ID NO: 47) | B-CSR-3A (SEQ ID NO: 73) | furin cleavage site + P2A self-cleaving peptide (SEQ ID NO: 133) |
| 11 | Ax2-caTCR-1 + B-CSR-3B | caTCR-linker-CSR | Ax2-caTCR-1 (SEQ ID NO: 47) | B-CSR-3B (SEQ ID NO: 74) | P2A self-cleaving peptide (SEQ ID NO: 132) |
| 12 | B-CSR-3B + Ax2-caTCR-1 | CSR-linker-caTCR | Ax2-caTCR-1 (SEQ ID NO: 47) | B-CSR-3B (SEQ ID NO: 74) | furin cleavage site + P2A self-cleaving peptide (SEQ ID NO: 133) |
| 13 | Ax2-caTCR-1 + B-CSR-4A | caTCR-linker-CSR | Ax2-caTCR-1 (SEQ ID NO: 47) | B-CSR-4A (SEQ ID NO: 75) | P2A self-cleaving peptide (SEQ ID NO: 132) |
| 14 | B-CSR-4A + Ax2-caTCR-1 | CSR-linker-caTCR | Ax2-caTCR-1 (SEQ ID NO: 47) | B-CSR-4A (SEQ ID NO: 75) | furin cleavage site + P2A self-cleaving peptide (SEQ ID NO: 133) |

TABLE 12-continued

| | caTCR + CSR Combination Encoded by Nucleic Acid | Order of Components (from N-Terminus to C-Terminus) in Polypeptide encoded by the Nucleic Acid | Exemplary anti-PSMA caTCR | Exemplary anti-PSMA CSR | Exemplary Linker |
|---|---|---|---|---|---|
| 15 | Ax2-caTCR-1 + B-CSR-4B | caTCR-linker-CSR | Ax2-caTCR-1 (SEQ ID NO: 47) | B-CSR-4B (SEQ ID NO: 76) | P2A self-cleaving peptide (SEQ ID NO: 132) |
| 16 | B-CSR-4B + Ax2-caTCR-1 | CSR-linker-caTCR | Ax2-caTCR-1 (SEQ ID NO: 47) | B-CSR-4B (SEQ ID NO: 76) | furin cleavage site + P2A self-cleaving peptide (SEQ ID NO: 133) |
| 17 | Ax2-caTCR-1 + B-CSR-5A | caTCR-linker-CSR | Ax2-caTCR-1 (SEQ ID NO: 47) | B-CSR-5A (SEQ ID NO: 77) | P2A self-cleaving peptide (SEQ ID NO: 132) |
| 18 | B-CSR-5A + Ax2-caTCR-1 | CSR-linker-caTCR | Ax2-caTCR-1 (SEQ ID NO: 47) | B-CSR-5A (SEQ ID NO: 77) | furin cleavage site + P2A self-cleaving peptide (SEQ ID NO: 133) |
| 19 | Ax2-caTCR-1 + B-CSR-5B | caTCR-linker-CSR | Ax2-caTCR-1 (SEQ ID NO: 47) | B-CSR-5B (SEQ ID NO: 78) | P2A self-cleaving peptide (SEQ ID NO: 132) |
| 20 | B-CSR-5B + Ax2-caTCR-1 | CSR-linker-caTCR | Ax2-caTCR-1 (SEQ ID NO: 47) | B-CSR-5B (SEQ ID NO: 78) | furin cleavage site + P2A self-cleaving peptide (SEQ ID NO: 133) |
| 21 | Ax2-caTCR-1 + B-CSR-6A | caTCR-linker-CSR | Ax2-caTCR-1 (SEQ ID NO: 47) | B-CSR-6A (SEQ ID NO: 79) | P2A self-cleaving peptide (SEQ ID NO: 132) |
| 22 | B-CSR-6A + Ax2-caTCR-1 | CSR-linker-caTCR | Ax2-caTCR-1 (SEQ ID NO: 47) | B-CSR-6A (SEQ ID NO: 79) | furin cleavage site + P2A self-cleaving peptide (SEQ ID NO: 133) |
| 23 | Ax2-caTCR-1 + B-CSR-6B | caTCR-linker-CSR | Ax2-caTCR-1 (SEQ ID NO: 47) | B-CSR-6B (SEQ ID NO: 80) | P2A self-cleaving peptide (SEQ ID NO: 132) |
| 24 | B-CSR-6B + Ax2-caTCR-1 | CSR-linker-caTCR | Ax2-caTCR-1 (SEQ ID NO: 47) | B-CSR-6B (SEQ ID NO: 80) | furin cleavage site + P2A self-cleaving peptide (SEQ ID NO: 133) |
| 25 | Ax2-caTCR-1 + B-CSR-7A | caTCR-linker-CSR | Ax2-caTCR-1 (SEQ ID NO: 47) | B-CSR-7A (SEQ ID NO: 81) | P2A self-cleaving peptide (SEQ ID NO: 132) |
| 26 | B-CSR-7A + Ax2-caTCR-1 | CSR-linker-caTCR | Ax2-caTCR-1 (SEQ ID NO: 47) | B-CSR-7A (SEQ ID NO: 81) | furin cleavage site + P2A self-cleaving peptide (SEQ ID NO: 133) |
| 27 | Ax2-caTCR-1 + B-CSR-7B | caTCR-linker-CSR | Ax2-caTCR-1 (SEQ ID NO: 47) | B-CSR-7B (SEQ ID NO: 82) | P2A self-cleaving peptide (SEQ ID NO: 132) |
| 28 | B-CSR-7B + Ax2-caTCR-1 | CSR-linker-caTCR | Ax2-caTCR-1 (SEQ ID NO: 47) | B-CSR-7B (SEQ ID NO: 82) | furin cleavage site + P2A self-cleaving peptide (SEQ ID NO: 133) |
| 29 | Ax2-caTCR-1 + B-CSR-8A | caTCR-linker-CSR | Ax2-caTCR-1 (SEQ ID NO: 47) | B-CSR-8A (SEQ ID NO: 83) | P2A self-cleaving peptide (SEQ ID NO: 132) |
| 30 | B-CSR-8A + Ax2-caTCR-1 | CSR-linker-caTCR | Ax2-caTCR-1 (SEQ ID NO: 47) | B-CSR-8A (SEQ ID NO: 83) | furin cleavage site + P2A self-cleaving peptide (SEQ ID NO: 133) |
| 31 | Ax2-caTCR-1 + B-CSR-8B | caTCR-linker-CSR | Ax2-caTCR-1 (SEQ ID NO: 47) | B-CSR-8B (SEQ ID NO: 84) | P2A self-cleaving peptide (SEQ ID NO: 132) |
| 32 | B-CSR-8B + Ax2-caTCR-1 | CSR-linker-caTCR | Ax2-caTCR-1 (SEQ ID NO: 47) | B-CSR-8B (SEQ ID NO: 84) | furin cleavage site + P2A self-cleaving peptide (SEQ ID NO: 133) |
| 33 | Bx2-caTCR-1 + A-CSR-1A | caTCR-linker-CSR (e.g., SEQ ID NO: 90) | Bx2-caTCR-1 (SEQ ID NO: 49) | A-CSR-1A (SEQ ID NO: 55) | P2A self-cleaving peptide (SEQ ID NO: 132) |
| 34 | A-CSR-1A + Bx2-caTCR-1 | CSR-linker-caTCR | Bx2-caTCR-1 (SEQ ID NO: 49) | A-CSR-1A (SEQ ID NO: 55) | furin cleavage site + P2A self-cleaving peptide (SEQ ID NO: 133) |

TABLE 12-continued

| | caTCR + CSR Combination Encoded by Nucleic Acid | Order of Components (from N-Terminus to C-Terminus) in Polypeptide encoded by the Nucleic Acid | Exemplary anti-PSMA caTCR | Exemplary anti-PSMA CSR | Exemplary Linker |
|---|---|---|---|---|---|
| 35 | Bx2-caTCR-1 + A-CSR-1B | caTCR-linker-CSR | Bx2-caTCR-1 (SEQ ID NO: 49) | A-CSR-1B (SEQ ID NO: 37) | P2A self-cleaving peptide (SEQ ID NO: 132) |
| 36 | A-CSR-1B + Bx2-caTCR-1 | CSR-linker-caTCR | Bx2-caTCR-1 (SEQ ID NO: 49) | A-CSR-1B (SEQ ID NO: 37) | furin cleavage site + P2A self-cleaving peptide (SEQ ID NO: 133) |
| 37 | Bx2-caTCR-1 + A-CSR-2A | caTCR-linker-CSR | Bx2-caTCR-1 (SEQ ID NO: 49) | A-CSR-2A (SEQ ID NO: 56) | P2A self-cleaving peptide (SEQ ID NO: 132) |
| 38 | A-CSR-2A + Bx2-caTCR-1 | CSR-linker-caTCR | Bx2-caTCR-1 (SEQ ID NO: 49) | A-CSR-2A (SEQ ID NO: 56) | furin cleavage site + P2A self-cleaving peptide (SEQ ID NO: 133) |
| 39 | Bx2-caTCR-1 + A-CSR-2B | caTCR-linker-CSR | Bx2-caTCR-1 (SEQ ID NO: 49) | A-CSR-2B (SEQ ID NO: 57) | P2A self-cleaving peptide (SEQ ID NO: 132) |
| 40 | A-CSR-2B + Bx2-caTCR-1 | CSR-linker-caTCR | Bx2-caTCR-1 (SEQ ID NO: 49) | A-CSR-2B (SEQ ID NO: 57) | furin cleavage site + P2A self-cleaving peptide (SEQ ID NO: 133) |
| 41 | Bx2-caTCR-1 + A-CSR-3A | caTCR-linker-CSR | Bx2-caTCR-1 (SEQ ID NO: 49) | A-CSR-3A (SEQ ID NO: 58) | P2A self-cleaving peptide (SEQ ID NO: 132) |
| 42 | A-CSR-3A + Bx2-caTCR-1 | CSR-linker-caTCR | Bx2-caTCR-1 (SEQ ID NO: 49) | A-CSR-3A (SEQ ID NO: 58) | furin cleavage site + P2A self-cleaving peptide (SEQ ID NO: 133) |
| 43 | Bx2-caTCR-1 + A-CSR-3B | caTCR-linker-CSR | Bx2-caTCR-1 (SEQ ID NO: 49) | A-CSR-3B (SEQ ID NO: 59) | P2A self-cleaving peptide (SEQ ID NO: 132) |
| 44 | A-CSR-3B + Bx2-caTCR-1 | CSR-linker-caTCR | Bx2-caTCR-1 (SEQ ID NO: 49) | A-CSR-3B (SEQ ID NO: 59) | furin cleavage site + P2A self-cleaving peptide (SEQ ID NO: 133) |
| 45 | Bx2-caTCR-1 + A-CSR-4A | caTCR-linker-CSR | Bx2-caTCR-1 (SEQ ID NO: 49) | A-CSR-4A (SEQ ID NO: 60) | P2A self-cleaving peptide (SEQ ID NO: 132) |
| 46 | A-CSR-4A + Bx2-caTCR-1 | CSR-linker-caTCR | Bx2-caTCR-1 (SEQ ID NO: 49) | A-CSR-4A (SEQ ID NO: 60) | furin cleavage site + P2A self-cleaving peptide (SEQ ID NO: 133) |
| 47 | Bx2-caTCR-1 + A-CSR-4B | caTCR-linker-CSR | Bx2-caTCR-1 (SEQ ID NO: 49) | A-CSR-4B (SEQ ID NO: 61) | P2A self-cleaving peptide (SEQ ID NO: 132) |
| 48 | A-CSR-4B + Bx2-caTCR-1 | CSR-linker-caTCR | Bx2-caTCR-1 (SEQ ID NO: 49) | A-CSR-4B (SEQ ID NO: 61) | furin cleavage site + P2A self-cleaving peptide (SEQ ID NO: 133) |
| 49 | Bx2-caTCR-1 + A-CSR-5A | caTCR-linker-CSR | Bx2-caTCR-1 (SEQ ID NO: 49) | A-CSR-5A (SEQ ID NO: 62) | P2A self-cleaving peptide (SEQ ID NO: 132) |
| 50 | A-CSR-5A + Bx2-caTCR-1 | CSR-linker-caTCR | Bx2-caTCR-1 (SEQ ID NO: 49) | A-CSR-5A (SEQ ID NO: 62) | furin cleavage site + P2A self-cleaving peptide (SEQ ID NO: 133) |
| 51 | Bx2-caTCR-1 + A-CSR-5B | caTCR-linker-CSR | Bx2-caTCR-1 (SEQ ID NO: 49) | A-CSR-5B (SEQ ID NO: 63) | P2A self-cleaving peptide (SEQ ID NO: 132) |
| 52 | A-CSR-5B + Bx2-caTCR-1 | CSR-linker-caTCR | Bx2-caTCR-1 (SEQ ID NO: 49) | A-CSR-5B (SEQ ID NO: 63) | furin cleavage site + P2A self-cleaving peptide (SEQ ID NO: 133) |
| 53 | Bx2-caTCR-1 + A-CSR-6A | caTCR-linker-CSR | Bx2-caTCR-1 (SEQ ID NO: 49) | A-CSR-6A (SEQ ID NO: 64) | P2A self-cleaving peptide (SEQ ID NO: 132) |

TABLE 12-continued

| | caTCR + CSR Combination Encoded by Nucleic Acid | Order of Components (from N-Terminus to C-Terminus) in Polypeptide encoded by the Nucleic Acid | Exemplary anti-PSMA caTCR | Exemplary anti-PSMA CSR | Exemplary Linker |
|---|---|---|---|---|---|
| 54 | A-CSR-6A + Bx2-caTCR-1 | CSR-linker-caTCR | Bx2-caTCR-1 (SEQ ID NO: 49) | A-CSR-6A (SEQ ID NO: 64) | furin cleavage site + P2A self-cleaving peptide (SEQ ID NO: 133) |
| 55 | Bx2-caTCR-1 + A-CSR-6B | caTCR-linker-CSR | Bx2-caTCR-1 (SEQ ID NO: 49) | A-CSR-6B (SEQ ID NO: 65) | P2A self-cleaving peptide (SEQ ID NO: 132) |
| 56 | A-CSR-6B + Bx2-caTCR-1 | CSR-linker-caTCR | Bx2-caTCR-1 (SEQ ID NO: 49) | A-CSR-6B (SEQ ID NO: 65) | furin cleavage site + P2A self-cleaving peptide (SEQ ID NO: 133) |
| 57 | Bx2-caTCR-1 + A-CSR-7A | caTCR-linker-CSR | Bx2-caTCR-1 (SEQ ID NO: 49) | A-CSR-7A (SEQ ID NO: 66) | P2A self-cleaving peptide (SEQ ID NO: 132) |
| 58 | A-CSR-7A + Bx2-caTCR-1 | CSR-linker-caTCR | Bx2-caTCR-1 (SEQ ID NO: 49) | A-CSR-7A (SEQ ID NO: 66) | furin cleavage site + P2A self-cleaving peptide (SEQ ID NO: 133) |
| 59 | Bx2-caTCR-1 + A-CSR-7B | caTCR-linker-CSR | Bx2-caTCR-1 (SEQ ID NO: 49) | A-CSR-7B (SEQ ID NO: 67) | P2A self-cleaving peptide (SEQ ID NO: 132) |
| 60 | A-CSR-7B + Bx2-caTCR-1 | CSR-linker-caTCR | Bx2-caTCR-1 (SEQ ID NO: 49) | A-CSR-7B (SEQ ID NO: 67) | furin cleavage site + P2A self-cleaving peptide (SEQ ID NO: 133) |
| 61 | Bx2-caTCR-1 + A-CSR-8A | caTCR-linker-CSR | Bx2-caTCR-1 (SEQ ID NO: 49) | A-CSR-8A (SEQ ID NO: 68) | P2A self-cleaving peptide (SEQ ID NO: 132) |
| 62 | A-CSR-8A + Bx2-caTCR-1 | CSR-linker-caTCR | Bx2-caTCR-1 (SEQ ID NO: 49) | A-CSR-8A (SEQ ID NO: 68) | furin cleavage site + P2A self-cleaving peptide (SEQ ID NO: 133) |
| 63 | Bx2-caTCR-1 + A-CSR-8B | caTCR-linker-CSR | Bx2-caTCR-1 (SEQ ID NO: 49) | A-CSR-8B (SEQ ID NO: 69) | P2A self-cleaving peptide (SEQ ID NO: 132) |
| 64 | A-CSR-8B + Bx2-caTCR-1 | CSR-linker-caTCR | Bx2-caTCR-1 (SEQ ID NO: 49) | A-CSR-8B (SEQ ID NO: 69) | furin cleavage site + P2A self-cleaving peptide (SEQ ID NO: 133) |
| 65 | Ax2-caTCR-2 + B-CSR-1A | caTCR-linker-CSR | Ax2-caTCR-2 (SEQ ID NO: 48) | B-CSR-1A (SEQ ID NO: 70) | P2A self-cleaving peptide (SEQ ID NO: 132) |
| 66 | B-CSR-1A + Ax2-caTCR-2 | CSR-linker-caTCR | Ax2-caTCR-2 (SEQ ID NO: 48) | B-CSR-1A (SEQ ID NO: 70) | furin cleavage site + P2A self-cleaving peptide (SEQ ID NO: 133) |
| 67 | Ax2-caTCR-2 + B-CSR-1B | caTCR-linker-CSR | Ax2-caTCR-2 (SEQ ID NO: 48) | B-CSR-1B (SEQ ID NO: 38) | P2A self-cleaving peptide (SEQ ID NO: 132) |
| 68 | B-CSR-1B + Ax2-caTCR-2 | CSR-linker-caTCR | Ax2-caTCR-2 (SEQ ID NO: 48) | B-CSR-1B (SEQ ID NO: 38) | furin cleavage site + P2A self-cleaving peptide (SEQ ID NO: 133) |
| 69 | Ax2-caTCR-2 + B-CSR-2A | caTCR-linker-CSR | Ax2-caTCR-2 (SEQ ID NO: 48) | B-CSR-2A (SEQ ID NO: 71) | P2A self-cleaving peptide (SEQ ID NO: 132) |
| 70 | B-CSR-2A + Ax2-caTCR-2 | CSR-linker-caTCR | Ax2-caTCR-2 (SEQ ID NO: 48) | B-CSR-2A (SEQ ID NO: 71) | furin cleavage site + P2A self-cleaving peptide (SEQ ID NO: 133) |
| 71 | Ax2-caTCR-2 + B-CSR-2B | caTCR-linker-CSR | Ax2-caTCR-2 (SEQ ID NO: 48) | B-CSR-2B (SEQ ID NO: 72) | P2A self-cleaving peptide (SEQ ID NO: 132) |
| 72 | B-CSR-2B + Ax2-caTCR-2 | CSR-linker-caTCR | Ax2-caTCR-2 (SEQ ID NO: 48) | B-CSR-2B (SEQ ID NO: 72) | furin cleavage site + P2A self-cleaving peptide (SEQ ID NO: 133) |
| 73 | Ax2-caTCR-2 + B-CSR-3A | caTCR-linker-CSR | Ax2-caTCR-2 (SEQ ID NO: 48) | B-CSR-3A (SEQ ID NO: 73) | P2A self-cleaving peptide (SEQ ID NO: 132) |

TABLE 12-continued

| caTCR + CSR Combination Encoded by Nucleic Acid | Order of Components (from N-Terminus to C-Terminus) in Polypeptide encoded by the Nucleic Acid | Exemplary anti-PSMA caTCR | Exemplary anti-PSMA CSR | Exemplary Linker |
|---|---|---|---|---|
| 74 B-CSR-3A + Ax2-caTCR-2 | CSR-linker-caTCR | Ax2-caTCR-2 (SEQ ID NO: 48) | B-CSR-3A (SEQ ID NO: 73) | furin cleavage site + P2A self-cleaving peptide (SEQ ID NO: 133) |
| 75 Ax2-caTCR-2 + B-CSR-3B | caTCR-linker-CSR | Ax2-caTCR-2 (SEQ ID NO: 48) | B-CSR-3B (SEQ ID NO: 74) | P2A self-cleaving peptide (SEQ ID NO: 132) |
| 76 B-CSR-3B + Ax2-caTCR-2 | CSR-linker-caTCR | Ax2-caTCR-2 (SEQ ID NO: 48) | B-CSR-3B (SEQ ID NO: 74) | furin cleavage site + P2A self-cleaving peptide (SEQ ID NO: 133) |
| 77 Ax2-caTCR-2 + B-CSR-4A | caTCR-linker-CSR | Ax2-caTCR-2 (SEQ ID NO: 48) | B-CSR-4A (SEQ ID NO: 75) | P2A self-cleaving peptide (SEQ ID NO: 132) |
| 78 B-CSR-4A + Ax2-caTCR-2 | CSR-linker-caTCR | Ax2-caTCR-2 (SEQ ID NO: 48) | B-CSR-4A (SEQ ID NO: 75) | furin cleavage site + P2A self-cleaving peptide (SEQ ID NO: 133) |
| 79 Ax2-caTCR-2 + B-CSR-4B | caTCR-linker-CSR | Ax2-caTCR-2 (SEQ ID NO: 48) | B-CSR-4B (SEQ ID NO: 76) | P2A self-cleaving peptide (SEQ ID NO: 132) |
| 80 B-CSR-4B + Ax2-caTCR-2 | CSR-linker-caTCR | Ax2-caTCR-2 (SEQ ID NO: 48) | B-CSR-4B (SEQ ID NO: 76) | furin cleavage site + P2A self-cleaving peptide (SEQ ID NO: 133) |
| 81 Ax2-caTCR-2 + B-CSR-5A | caTCR-linker-CSR | Ax2-caTCR-2 (SEQ ID NO: 48) | B-CSR-5A (SEQ ID NO: 77) | P2A self-cleaving peptide (SEQ ID NO: 132) |
| 82 B-CSR-5A + Ax2-caTCR-2 | CSR-linker-caTCR | Ax2-caTCR-2 (SEQ ID NO: 48) | B-CSR-5A (SEQ ID NO: 77) | furin cleavage site + P2A self-cleaving peptide (SEQ ID NO: 133) |
| 83 Ax2-caTCR-2 + B-CSR-5B | caTCR-linker-CSR | Ax2-caTCR-2 (SEQ ID NO: 48) | B-CSR-5B (SEQ ID NO: 78) | P2A self-cleaving peptide (SEQ ID NO: 132) |
| 84 B-CSR-5B + Ax2-caTCR-2 | CSR-linker-caTCR | Ax2-caTCR-2 (SEQ ID NO: 48) | B-CSR-5B (SEQ ID NO: 78) | furin cleavage site + P2A self-cleaving peptide (SEQ ID NO: 133) |
| 85 Ax2-caTCR-2 + B-CSR-6A | caTCR-linker-CSR | Ax2-caTCR-2 (SEQ ID NO: 48) | B-CSR-6A (SEQ ID NO: 79) | P2A self-cleaving peptide (SEQ ID NO: 132) |
| 86 B-CSR-6A + Ax2-caTCR-2 | CSR-linker-caTCR | Ax2-caTCR-2 (SEQ ID NO: 48) | B-CSR-6A (SEQ ID NO: 79) | furin cleavage site + P2A self-cleaving peptide (SEQ ID NO: 133) |
| 87 Ax2-caTCR-2 + B-CSR-6B | caTCR-linker-CSR | Ax2-caTCR-2 (SEQ ID NO: 48) | B-CSR-6B (SEQ ID NO: 80) | P2A self-cleaving peptide (SEQ ID NO: 132) |
| 88 B-CSR-6B + Ax2-caTCR-2 | CSR-linker-caTCR | Ax2-caTCR-2 (SEQ ID NO: 48) | B-CSR-6B (SEQ ID NO: 80) | furin cleavage site + P2A self-cleaving peptide (SEQ ID NO: 133) |
| 89 Ax2-caTCR-2 + B-CSR-7A | caTCR-linker-CSR | Ax2-caTCR-2 (SEQ ID NO: 48) | B-CSR-7A (SEQ ID NO: 81) | P2A self-cleaving peptide (SEQ ID NO: 132) |
| 90 B-CSR-7A + Ax2-caTCR-2 | CSR-linker-caTCR | Ax2-caTCR-2 (SEQ ID NO: 48) | B-CSR-7A (SEQ ID NO: 81) | furin cleavage site + P2A self-cleaving peptide (SEQ ID NO: 133) |
| 91 Ax2-caTCR-2 + B-CSR-7B | caTCR-linker-CSR | Ax2-caTCR-2 (SEQ ID NO: 48) | B-CSR-7B (SEQ ID NO: 82) | P2A self-cleaving peptide (SEQ ID NO: 132) |
| 92 B-CSR-7B + Ax2-caTCR-2 | CSR-linker-caTCR | Ax2-caTCR-2 (SEQ ID NO: 48) | B-CSR-7B (SEQ ID NO: 82) | furin cleavage site + P2A self-cleaving peptide (SEQ ID NO: 133) |

TABLE 12-continued

| caTCR + CSR Combination Encoded by Nucleic Acid | Order of Components (from N-Terminus to C-Terminus) in Polypeptide encoded by the Nucleic Acid | Exemplary anti-PSMA caTCR | Exemplary anti-PSMA CSR | Exemplary Linker |
|---|---|---|---|---|
| 93 Ax2-caTCR-2 + B-CSR-8A | caTCR-linker-CSR | Ax2-caTCR-2 (SEQ ID NO: 48) | B-CSR-8A (SEQ ID NO: 83) | P2A self-cleaving peptide (SEQ ID NO: 132) |
| 94 B-CSR-8A + Ax2-caTCR-2 | CSR-linker-caTCR | Ax2-caTCR-2 (SEQ ID NO: 48) | B-CSR-8A (SEQ ID NO: 83) | furin cleavage site + P2A self-cleaving peptide (SEQ ID NO: 133) |
| 95 Ax2-caTCR-2 + B-CSR-8B | caTCR-linker-CSR | Ax2-caTCR-2 (SEQ ID NO: 48) | B-CSR-8B (SEQ ID NO: 84) | P2A self-cleaving peptide (SEQ ID NO: 132) |
| 96 B-CSR-8B + Ax2-caTCR-2 | CSR-linker-caTCR | Ax2-caTCR-2 (SEQ ID NO: 48) | B-CSR-8B (SEQ ID NO: 84) | furin cleavage site + P2A self-cleaving peptide (SEQ ID NO: 133) |
| 97 Bx2-caTCR-2 + A-CSR-1A | caTCR-linker-CSR | Bx2-caTCR-2 (SEQ ID NO: 50) | A-CSR-1A (SEQ ID NO: 55) | P2A self-cleaving peptide (SEQ ID NO: 132) |
| 98 A-CSR-1A + Bx2-caTCR-2 | CSR-linker-caTCR | Bx2-caTCR-2 (SEQ ID NO: 50) | A-CSR-1A (SEQ ID NO: 55) | furin cleavage site + P2A self-cleaving peptide (SEQ ID NO: 133) |
| 99 Bx2-caTCR-2 + A-CSR-1B | caTCR-linker-CSR | Bx2-caTCR-2 (SEQ ID NO: 50) | A-CSR-1B (SEQ ID NO: 37) | P2A self-cleaving peptide (SEQ ID NO: 132) |
| 100 A-CSR-1B + Bx2-caTCR-2 | CSR-linker-caTCR | Bx2-caTCR-2 (SEQ ID NO: 50) | A-CSR-1B (SEQ ID NO: 37) | furin cleavage site + P2A self-cleaving peptide (SEQ ID NO: 133) |
| 101 Bx2-caTCR-2 + A-CSR-2A | caTCR-linker-CSR | Bx2-caTCR-2 (SEQ ID NO: 50) | A-CSR-2A (SEQ ID NO: 56) | P2A self-cleaving peptide (SEQ ID NO: 132) |
| 102 A-CSR-2A + Bx2-caTCR-2 | CSR-linker-caTCR | Bx2-caTCR-2 (SEQ ID NO: 50) | A-CSR-2A (SEQ ID NO: 56) | furin cleavage site + P2A self-cleaving peptide (SEQ ID NO: 133) |
| 103 Bx2-caTCR-2 + A-CSR-2B | caTCR-linker-CSR | Bx2-caTCR-2 (SEQ ID NO: 50) | A-CSR-2B (SEQ ID NO: 57) | P2A self-cleaving peptide (SEQ ID NO: 132) |
| 104 A-CSR-2B + Bx2-caTCR-2 | CSR-linker-caTCR | Bx2-caTCR-2 (SEQ ID NO: 50) | A-CSR-2B (SEQ ID NO: 57) | furin cleavage site + P2A self-cleaving peptide (SEQ ID NO: 133) |
| 105 Bx2-caTCR-2 + A-CSR-3A | caTCR-linker-CSR | Bx2-caTCR-2 (SEQ ID NO: 50) | A-CSR-3A (SEQ ID NO: 58) | P2A self-cleaving peptide (SEQ ID NO: 132) |
| 106 A-CSR-3A + Bx2-caTCR-2 | CSR-linker-caTCR | Bx2-caTCR-2 (SEQ ID NO: 50) | A-CSR-3A (SEQ ID NO: 58) | furin cleavage site + P2A self-cleaving peptide (SEQ ID NO: 133) |
| 107 Bx2-caTCR-2 + A-CSR-3B | caTCR-linker-CSR | Bx2-caTCR-2 (SEQ ID NO: 50) | A-CSR-3B (SEQ ID NO: 59) | P2A self-cleaving peptide (SEQ ID NO: 132) |
| 108 A-CSR-3B + Bx2-caTCR-2 | CSR-linker-caTCR | Bx2-caTCR-2 (SEQ ID NO: 50) | A-CSR-3B (SEQ ID NO: 59) | furin cleavage site + P2A self-cleaving peptide (SEQ ID NO: 133) |
| 109 Bx2-caTCR-2 + A-CSR-4A | caTCR-linker-CSR | Bx2-caTCR-2 (SEQ ID NO: 50) | A-CSR-4A (SEQ ID NO: 60) | P2A self-cleaving peptide (SEQ ID NO: 132) |
| 110 A-CSR-4A + Bx2-caTCR-2 | CSR-linker-caTCR | Bx2-caTCR-2 (SEQ ID NO: 50) | A-CSR-4A (SEQ ID NO: 60) | furin cleavage site + P2A self-cleaving peptide (SEQ ID NO: 133) |
| 111 Bx2-caTCR-2 + A-CSR-4B | caTCR-linker-CSR | Bx2-caTCR-2 (SEQ ID NO: 50) | A-CSR-4B (SEQ ID NO: 61) | P2A self-cleaving peptide (SEQ ID NO: 132) |
| 112 A-CSR-4B + Bx2-caTCR-2 | CSR-linker-caTCR | Bx2-caTCR-2 (SEQ ID NO: 50) | A-CSR-4B (SEQ ID NO: 61) | furin cleavage site + P2A self-cleaving peptide (SEQ ID NO: 133) |

TABLE 12-continued

| caTCR + CSR Combination Encoded by Nucleic Acid | Order of Components (from N-Terminus to C-Terminus) in Polypeptide encoded by the Nucleic Acid | Exemplary anti-PSMA caTCR | Exemplary anti-PSMA CSR | Exemplary Linker |
|---|---|---|---|---|
| 113 Bx2-caTCR-2 + A-CSR-5A | caTCR-linker-CSR | Bx2-caTCR-2 (SEQ ID NO: 50) | A-CSR-5A (SEQ ID NO: 62) | P2A self-cleaving peptide (SEQ ID NO: 132) |
| 114 A-CSR-5A + Bx2-caTCR-2 | CSR-linker-caTCR | Bx2-caTCR-2 (SEQ ID NO: 50) | A-CSR-5A (SEQ ID NO: 62) | furin cleavage site + P2A self-cleaving peptide (SEQ ID NO: 133) |
| 115 Bx2-caTCR-2 + A-CSR-5B | caTCR-linker-CSR | Bx2-caTCR-2 (SEQ ID NO: 50) | A-CSR-5B (SEQ ID NO: 63) | P2A self-cleaving peptide (SEQ ID NO: 132) |
| 116 A-CSR-5B + Bx2-caTCR-2 | CSR-linker-caTCR | Bx2-caTCR-2 (SEQ ID NO: 50) | A-CSR-5B (SEQ ID NO: 63) | furin cleavage site + P2A self-cleaving peptide (SEQ ID NO: 133) |
| 117 Bx2-caTCR-2 + A-CSR-6A | caTCR-linker-CSR | Bx2-caTCR-2 (SEQ ID NO: 50) | A-CSR-6A (SEQ ID NO: 64) | P2A self-cleaving peptide (SEQ ID NO: 132) |
| 118 A-CSR-6A + Bx2-caTCR-2 | CSR-linker-caTCR | Bx2-caTCR-2 (SEQ ID NO: 50) | A-CSR-6A (SEQ ID NO: 64) | furin cleavage site + P2A self-cleaving peptide (SEQ ID NO: 133) |
| 119 Bx2-caTCR-2 + A-CSR-6B | caTCR-linker-CSR | Bx2-caTCR-2 (SEQ ID NO: 50) | A-CSR-6B (SEQ ID NO: 65) | P2A self-cleaving peptide (SEQ ID NO: 132) |
| 120 A-CSR-6B + Bx2-caTCR-2 | CSR-linker-caTCR | Bx2-caTCR-2 (SEQ ID NO: 50) | A-CSR-6B (SEQ ID NO: 65) | furin cleavage site + P2A self-cleaving peptide (SEQ ID NO: 133) |
| 121 Bx2-caTCR-2 + A-CSR-7A | caTCR-linker-CSR | Bx2-caTCR-2 (SEQ ID NO: 50) | A-CSR-7A (SEQ ID NO: 66) | P2A self-cleaving peptide (SEQ ID NO: 132) |
| 122 A-CSR-7A + Bx2-caTCR-2 | CSR-linker-caTCR | Bx2-caTCR-2 (SEQ ID NO: 50) | A-CSR-7A (SEQ ID NO: 66) | furin cleavage site + P2A self-cleaving peptide (SEQ ID NO: 133) |
| 123 Bx2-caTCR-2 + A-CSR-7B | caTCR-linker-CSR | Bx2-caTCR-2 (SEQ ID NO: 50) | A-CSR-7B (SEQ ID NO: 67) | P2A self-cleaving peptide (SEQ ID NO: 132) |
| 124 A-CSR-7B + Bx2-caTCR-2 | CSR-linker-caTCR | Bx2-caTCR-2 (SEQ ID NO: 50) | A-CSR-7B (SEQ ID NO: 67) | furin cleavage site + P2A self-cleaving peptide (SEQ ID NO: 133) |
| 125 Bx2-caTCR-2 + A-CSR-8A | caTCR-linker-CSR | Bx2-caTCR-2 (SEQ ID NO: 50) | A-CSR-8A (SEQ ID NO: 68) | P2A self-cleaving peptide (SEQ ID NO: 132) |
| 126 A-CSR-8A + Bx2-caTCR-2 | CSR-linker-caTCR | Bx2-caTCR-2 (SEQ ID NO: 50) | A-CSR-8A (SEQ ID NO: 68) | furin cleavage site + P2A self-cleaving peptide (SEQ ID NO: 133) |
| 127 Bx2-caTCR-2 + A-CSR-8B | caTCR-linker-CSR | Bx2-caTCR-2 (SEQ ID NO: 50) | A-CSR-8B (SEQ ID NO: 69) | P2A self-cleaving peptide (SEQ ID NO: 132) |
| 128 A-CSR-8B + Bx2-caTCR-2 | CSR-linker-caTCR | Bx2-caTCR-2 (SEQ ID NO: 50) | A-CSR-8B (SEQ ID NO: 69) | furin cleavage site + P2A self-cleaving peptide (SEQ ID NO: 133) |

In some embodiments, the single nucleic acid encoding the anti-PSMA caTCR+anti-PSMA CSR of any one of rows 1-128 in Table 12 further encodes a signal peptide (e.g., upstream of the sequence(s) encoding Chain 1 and/or Chain 2 of the caTCR and/or upstream of the sequence encoding the anti-PSMA CSR). In some embodiments, the signal peptide comprises the amino acid sequence of SEQ ID NO: 128. Although specific linkers are listed in rows 1-128 in Table 12, an alternative linker may be use (see e.g., Table 6A) may be used. In some embodiments, the single nucleic acid encoding the anti-PSMA caTCR+anti-PSMA CSR of any one of rows 1-128 in Table 12 further encodes one or more peptide linkers (e.g., cleavable linkers) and/or peptide tags (see e.g., Tables 6A and 6B).

Anti-PSMA Effector Cells

Provided herein is an effector cell (e.g., an immune cell, such as a T cell, e.g., an αβ T cell, a γδ T cell, a cytotoxic T cell, a helper T cell, or a natural killer T cell) that comprises, expresses, or is associated with an anti-PSMA CAR, an anti-PSMA caTCR, an anti-PSMA multispecific construct (e.g., a tandem scFv, such as a tandem di-scFv), an anti-PSMA CSR, or an anti-PSMA construct combination described herein. Such cells are also referred to as "anti-PSMVA effector cells."

In some embodiments, the anti-PSMA effector cells (also referred to herein as "anti-PSMA immune cells" or "anti-PSMA T cells") of the present disclosure are able to replicate in vivo, resulting in long-term persistence that can lead to sustained control of a disease associated with PSMA (such as cancer, e.g., prostate cancer (such as hormone-refractory or metastatic prostate cancer), renal cell cancer cell (such as clear cell renal cell cancer), uterine cancer, or liver cancer).

In some embodiments, the anti-PSMA effector cell (such as a lymphocyte, e.g., a T cell) comprises (such as expresses) is an anti-PSMA CAR effector cell that comprises, expresses, or is associated with an anti-PSMA CAR described herein. In some embodiments, the anti-PSMA CAR effector cell further comprises (such as expresses) a multispecific construct. Such effector cells are referred to herein as "anti-PSMA CAR plus multispecific construct effector cells." In some embodiments, the expression of the multispecific construct is inducible. In some embodiments, the expression of the multispecific construct is inducible upon signaling by the anti-PSMA CAR. In some embodiments, the multispecific construct is selected from the group consisting of a tandem scFv, a diabody (Db), a single chain diabody (scDb), a dual-affinity retargeting (DART) antibody, and a dual variable domain (DVD) antibody. In some embodiments, the multispecific construct is a tandem scFv. Such effector cells are also referred to herein as "anti-PSMA CAR plus tandem scFv effector cells." In some embodiments the tandem scFv is a tandem di-scFv, e.g., a tandem di-scFv comprising a first scFv and a second scFv, optionally connected by a peptide linker. In some embodiments, the first scFv targets a T cell surface antigen (e.g., CD3 or CD16a), a soluble immunosuppressive agent (e.g., TGF-β 1 to 4, IL-4, or IL-10), or an immune checkpoint inhibitor. In some embodiments, the second scFv targets a disease-associated antigen. In some embodiments, the disease-associated antigen is an antigen other than PSMA. In some embodiments, the disease-associated antigen is PSMA. In some embodiments, the tandem di-scFv is an anti-PSMA anti-CD3 tandem di-scFv that comprises an antibody moiety (such as described herein) that specifically binds PSMA (such as PSMA expressed on the surface of a cell, e.g., a cancer cell) and a second binding moiety that specifically binds CD3. In some embodiments, the anti-PSMA anti-CD3 tandem di-scFv comprises an amino acid sequence set forth in any one of SEQ ID NOs: 25-28. In some embodiments, the anti-PSMA anti-CD3 tandem di-scFv is encoded by a nucleic acid that is operably linked to an NFAT-derived promoter. In some embodiments, the NFAT-derived promoter is an NFAT-derived minimal promoter. In some embodiments, the anti-PSMA anti-CD3 tandem di-scFv is encoded by a nucleic acid that is operably linked to an IL-2 promoter.

In some embodiments, the anti-PSMA CAR effector cell further comprises (such as expresses) a CSR (see, e.g., U.S. Application No. 62/490,578, filed Apr. 26, 2017, which is incorporated by reference herein in its entirety). Such effector cells are referred to as "anti-PSMA CAR plus CSR effector cells." In some embodiments, the CSR is an anti-PSMA CSR (i.e., a CSR that comprises a PSMA-binding module), e.g., such as described herein. In some embodiments, the CSR binds to a target ligand other than PSMA.

In some embodiments, the anti-PSMA effector cell (such as a lymphocyte, e.g., a T cell) comprises (such as expresses) is an anti-PSMA caTCR effector cell that comprises, expresses, or is associated with an anti-PSMA caTCR described herein. In some embodiments, the anti-PSMA caTCR effector cell comprises (such as expresses) a multispecific construct. Such effector cells are referred to herein as "anti-PSMA caTCR plus multispecific construct effector cells." In some embodiments, the expression of the multispecific construct is inducible. In some embodiments, the expression of the multispecific construct is inducible upon signaling by the anti-PSMA caTCR. In some embodiments, the multispecific construct is selected from the group consisting of a tandem scFv, a diabody (Db), a single chain diabody (scDb), a dual-affinity retargeting (DART) antibody, and a dual variable domain (DVD) antibody. In some embodiments, the multispecific construct is a tandem scFv. Such effector cells are also referred to herein as "anti-PSMA caTCR plus tandem scFv effector cells." In some embodiments the tandem scFv is a tandem di-scFv, e.g., a tandem di-scFv comprising a first scFv and a second scFv, optionally connected by a peptide linker. In some embodiments, the first scFv targets a T cell surface antigen (e.g., CD3 or CD16a), a soluble immunosuppressive agent (e.g., TGF-β 1 to 4, IL-4, or IL-10), or an immune checkpoint inhibitor. In some embodiments, the second scFv targets a disease-associated antigen. In some embodiments, the disease-associated antigen is an antigen other than PSMA. In some embodiments, the disease-associated antigen is PSMA. In some embodiments, the tandem di-scFv is an anti-PSMA anti-CD3 tandem di-scFv that comprises an antibody moiety (such as described herein) that specifically binds PSMA (such as PSMA expressed on the surface of a cell, e.g., a cancer cell) and a second binding moiety that specifically binds CD3. In some embodiments, the anti-PSMA anti-CD3 tandem di-scFv comprises an amino acid sequence set forth in any one of SEQ ID NOs: 25-28. In some embodiments, the anti-PSMA anti-CD3 tandem di-scFv is encoded by a nucleic acid that is operably linked to an NFAT-derived promoter. In some embodiments, the NFAT-derived promoter is an NFAT-derived minimal promoter. In some embodiments, the anti-PSMA anti-CD3 tandem di-scFv is encoded by a nucleic acid that is operably linked to an IL-2 promoter.

In some embodiments, the anti-PSMA caTCR effector cell comprises (such as expresses) a CSR (see, e.g., U.S. Application No. 62/490,578, filed Apr. 26, 2017, which is incorporated by reference herein in its entirety). Such effector cells are referred to as "anti-PSMA caTCR plus CSR effector cells." In some embodiments, the CSR is an anti-PSMA CSR (i.e., a CSR that comprises a PSMA-binding module), e.g., such as described herein. In some embodiments, the CSR binds to a target ligand other than PSMA. In some embodiments, the anti-PSMA caTCR plus CSR effector cell comprises (such as expresses) any of the anti-PSMA caTCR plus anti-PSMA CSR construct combinations described elsewhere herein.

In some embodiments, the effector cell (such as a lymphocyte, e.g., a T cell) comprises a CAR or a caTCR that does not target PSMA and anti-PSMA multispecific construct (i.e., an anti-PSMA tandem scFv, e.g., an anti-PSMA tandem di-scFv), e.g., such as described herein. In some embodiments, the effector cell referred to as a "CAR plus anti-PSMA tandem scFv effector cell" or "caTCR plus anti-PSMA tandem scFv effector cell."

In some embodiments, the effector cell (such as a lymphocyte, e.g., a T cell) comprises a CAR or a caTCR that does not target PSMA and anti-PSMA CSR (i.e., a CSR that comprises a PSMA-binding module), e.g., such as described herein. In some embodiments, the effector cell referred to as a "CAR plus anti-PSMA CSR effector cell" or "caTCR plus anti-PSMA CSR effector cell."

Also provided herein are methods of producing the effector cells described herein.

For example, provided is a method of producing an anti-PSMA CAR effector cell, e.g., an anti-PSMA CAR immune cell or an anti-PSMA CAR T cell that comprises genetically modifying (i.e., transducing or transfecting) a cell (e.g., a T cell, such as an αβ T cell, a γδ T cell, a cytotoxic T cell, a helper T cell, or a natural killer T cell) with a nucleic acid, a set of nucleic acids, a vector, or a set of vectors encoding an anti-PSMA CAR.

In some embodiments, the method comprises genetically modifying an anti-PSMA CAR effector cell with a further nucleic acid, a set of nucleic acids, a vector, or a set of vectors encoding a multispecific construct. In some embodiments, the method of producing an anti-PSMA CAR plus multispecific construct effector cell (such as an "anti-PSMA CAR plus tandem scFv effector cell") comprises genetically modifying (i.e., transducing or transfecting) a cell (e.g., a T cell, such as an αβ T cell, a γδ T cell, a cytotoxic T cell, a helper T cell, or a natural killer T cell) with a nucleic acid, a set of nucleic acids, a vector, or a set of vectors that encode the anti-PSMA caTCR and the multispecific construct. In some embodiments, the expression of the multispecific construct is inducible. In some embodiments, the expression of the multispecific construct is inducible upon signaling by the anti-PSMA CAR. In some embodiments, the multispecific construct is selected from the group consisting of a tandem scFv, a diabody (Db), a single chain diabody (scDb), a dual-affinity retargeting (DART) antibody, and a dual variable domain (DVD) antibody. In some embodiments, the multispecific construct is a tandem scFv. Such effector cells are also referred to herein as "anti-PSMA caTCR plus tandem scFv effector cells." In some embodiments the tandem scFv is a tandem di-scFv, e.g., a tandem di-scFv comprising a first scFv and a second scFv, optionally connected by a peptide linker. In some embodiments, the first scFv targets a T cell surface antigen (e.g., CD3 or CD16a), a soluble immunosuppressive agent (e.g., TGF-β 1 to 4, IL-4, or IL-10), or an immune checkpoint inhibitor. In some embodiments, the second scFv targets a disease-associated antigen. In some embodiments, the disease-associated antigen is an antigen other than PSMA. In some embodiments, the disease-associated antigen is PSMA. In some embodiments, the tandem di-scFv is an anti-PSMA anti-CD3 tandem di-scFv that comprises an antibody moiety (such as described herein) that specifically binds PSMA (such as PSMA expressed on the surface of a cell, e.g., a cancer cell) and a second binding moiety that specifically binds CD3. In some embodiments, the anti-PSMA anti-CD3 tandem di-scFv comprises an amino acid sequence set forth in any one of SEQ ID NOs: 25-28. In some embodiments, the anti-PSMA anti-CD3 tandem di-scFv is encoded by a nucleic acid that is operably linked to an NFAT-derived promoter. In some embodiments, the NFAT-derived promoter is an NFAT-derived minimal promoter. In some embodiments, the anti-PSMA anti-CD3 tandem di-scFv is encoded by a nucleic acid that is operably linked to an IL-2 promoter.

In some embodiments, the method comprises genetically modifying an anti-PSMA CAR effector cell with a further nucleic acid, a set of nucleic acids, a vector, or a set of vectors encoding a CSR that comprises ligand-binding domain that specifically binds to a target ligand and a costimulatory signaling domain capable of providing a stimulatory signal to the immune cell. In some embodiments, the method of producing an anti-PSMA CAR plus CSR effector cell comprises genetically modifying (i.e., transducing or transfecting) a cell (e.g., a T cell, such as an αβ T cell, a γδ T cell, a cytotoxic T cell, a helper T cell, or a natural killer T cell) with a nucleic acid, a set of nucleic acids, a vector, or a set of vectors that encode the anti-PSMA CAR and the CSR. Further details regarding CSRs are described in U.S. Application No. 62/490,578, filed Apr. 26, 2017, which is incorporated by reference herein in its entirety. In some embodiments, expression of the CSR is inducible upon signaling through the anti-PSMA CAR. In some embodiments, CSR is an anti-PSMA CSR (i.e., a CSR that comprises a PSMA-binding module), e.g., such as described herein. In some embodiments, the CSR binds to a target ligand other than PSMA.

Also provided is a method of producing an anti-PSMA caTCR effector cell, e.g., an anti-PSMA caTCR immune cell or an anti-PSMA caTCR T cell that comprises genetically modifying (i.e., transducing or transfecting) a cell (e.g., a T cell, such as an αβ T cell, a γδ T cell, a cytotoxic T cell, a helper T cell, or a natural killer T cell) with a nucleic acid, a set of nucleic acids, a vector, or a set of vectors encoding an anti-PSMA caTCR.

In some embodiments, the method comprises genetically modifying an anti-PSMA caTCR effector cell with a further nucleic acid, a set of nucleic acids, a vector, or a set of vectors encoding a multispecific construct. In some embodiments, the method of producing an anti-PSMA caTCR plus multispecific construct effector cell (such as an "anti-PSMA caTCR plus tandem scFv effector cell") comprises genetically modifying (i.e., transducing or transfecting) a cell (e.g., a T cell, such as an αβ T cell, a γδ T cell, a cytotoxic T cell, a helper T cell, or a natural killer T cell) with a nucleic acid, a set of nucleic acids, a vector, or a set of vectors that encode the anti-PSMA caTCR and the multispecific construct. In some embodiments, the expression of the multispecific construct is inducible. In some embodiments, the expression of the multispecific construct is inducible upon signaling by the anti-PSMA caTCR. In some embodiments, the multispecific construct is selected from the group consisting of a tandem scFv, a diabody (Db), a single chain diabody (scDb), a dual-affinity retargeting (DART) antibody, and a dual variable domain (DVD) antibody. In some embodiments, the multispecific construct is a tandem scFv. Such effector cells are also referred to herein as "anti-PSMA caTCR plus tandem scFv effector cells." In some embodiments the tandem scFv is a tandem di-scFv, e.g., a tandem di-scFv comprising a first scFv and a second scFv, optionally connected by a peptide linker. In some embodiments, the first scFv targets a T cell surface antigen (e.g., CD3 or CD16a), a soluble immunosuppressive agent (e.g., TGF-β 1 to 4, IL-4, or IL-10), or an immune checkpoint inhibitor. In some embodiments, the second scFv targets a disease-associated antigen. In some embodiments, the disease-associated antigen is an antigen other than PSMA. In some embodiments, the disease-associated antigen is PSMA. In some embodiments, the tandem di-scFv is an anti-PSMA anti-CD3 tandem di-scFv that comprises an antibody moiety (such as described herein) that specifically binds PSMA (such as PSMA expressed on the surface of a cell, e.g., a cancer cell) and a second binding moiety that specifically binds CD3. In some embodiments, the anti-PSMA anti-CD3 tandem di-scFv comprises an amino acid sequence set forth in any one of SEQ ID NOs: 25-28. In some embodiments, the anti-PSMA anti-CD3 tandem di-scFv is encoded by a nucleic acid that is operably linked to an NFAT-derived promoter. In some embodiments, the NFAT-derived promoter is an NFAT-derived minimal promoter. In some embodiments, the anti-PSMA anti-CD3 tandem di-scFv is encoded by a nucleic acid that is operably linked to an IL-2 promoter.

In some embodiments, the method comprises genetically modifying an anti-PSMA caTCR effector cell with a further nucleic acid, a set of nucleic acids, a vector, or a set of vectors encoding a CSR that comprises ligand-binding domain that specifically binds to a target ligand and a costimulatory signaling domain capable of providing a stimulatory signal to the immune cell. In some embodiments, the method of producing an anti-PSMA caTCR plus CSR effector cell comprises genetically modifying (i.e., transducing or transfecting) a cell (e.g., a T cell, such as an $\alpha\beta$ T cell, a $\gamma\delta$ T cell, a cytotoxic T cell, a helper T cell, or a natural killer T cell) with a nucleic acid, a set of nucleic acids, a vector, or a set of vectors that encode the anti-PSMA caTCR and the CSR. Further details regarding CSRs are described in U.S. Application No. 62/490,578, filed Apr. 26, 2017, which is incorporated by reference herein in its entirety. In some embodiments, expression of the CSR is inducible upon signaling through the anti-PSMA caTCR. In some embodiments, CSR is an anti-PSMA CSR (i.e., a CSR that comprises a PSMA-binding module), e.g., such as described herein. In some embodiments, the CSR binds to a target ligand other than PSMA.

In some embodiments, the method comprises genetically modifying an effector cell (such as a lymphocyte, e.g., a T cell) that comprises nucleic acid, a set of nucleic acids, a vector, or a set of vectors encoding a CAR or a caTCR that does not target PSMA and with an additional nucleic acid, a set of nucleic acids, a vector, or a set of vectors that encodes an anti-PSMA multispecific construct (i.e., an anti-PSMA tandem scFv, e.g., an anti-PSMA tandem di-scFv), e.g., such as described herein. In some embodiments, the method comprises genetically modifying an effector cell with a nucleic acid, a set of nucleic acids, a vector, or a set of vectors that encode the CAR or caTCR that does not target PSMA and the anti-PSMA multispecific construct (i.e., an anti-PSMA tandem scFv, e.g., an anti-PSMA tandem di-scFv).

In some embodiments, the method comprises genetically modifying an effector cell (such as a lymphocyte, e.g., a T cell) that comprises nucleic acid, a set of nucleic acids, a vector, or a set of vectors encoding a CAR or a caTCR that does not target PSMA and with an additional nucleic acid, a set of nucleic acids, a vector, or a set of vectors that encodes an anti-PSMA CSR (i.e., a CSR that comprises a PSMA-binding module), e.g., such as described herein. In some embodiments, the method comprises genetically modifying an effector cell with a nucleic acid, a set of nucleic acids, a vector, or a set of vectors that encode the CAR or caTCR that does not target PSMA and the anti-PSMA CSR.

Briefly, prior to expansion and genetic modification of the cells (such as T cells), a source of cells is obtained from a subject. For example, T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available in the art may be used. In some embodiments, T cells can be obtained from a unit of blood collected from a subject using any number of techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In some embodiments, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells may be resuspended in a variety of biocompatible buffers, such as $Ca^{2+}$-free, $Mg^{2+}$-free PBS, PlasmaLyte A, or other saline solutions with or without buffer. Alternatively, the undesirable components of the apheresis sample may be removed and the cells directly resuspended in culture media.

In some embodiments, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in some embodiments, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In some embodiments, the time period is about 30 minutes. In some embodiments, the time period ranges from 30 minutes to 36 hours or longer and all integer values there between. In some embodiments, the time period is at least one, 2, 3, 4, 5, or 6 hours. In some embodiments, the time period is 10 to 24 hours. In some embodiments, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such as in isolating tumor infiltrating lymphocytes (TIL) from tumor tissue or from immune-compromised individuals. Further, use of longer incubation times can increase the efficiency of capture of $CD8^+$ T cells. Thus, by simply shortening or lengthening the time T cells are allowed to bind to the CD3/CD28 beads and/or by increasing or decreasing the ratio of beads to T cells, subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used. In some embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD 14, CD20, CD11b, CD 16, HLA-DR, and CD8. In some embodiments, it may be desirable to enrich for or positively select for regulatory T cells which typically express CD4$^+$, CD25$^+$, CD62Lhi, GITR$^+$, and FoxP3$^+$. Alternatively, in some embodiments, T regulatory cells are depleted by anti-CD25 conjugated beads or other similar methods of selection.

For isolation of a desired population of cells by positive or negative selection, the concentration of cells and surface (e.g., particles such as beads) can be varied. In some embodiments, it may be desirable to significantly decrease the volume in which beads and cells are mixed together (i.e., increase the concentration of cells), to ensure maximum contact of cells and beads. For example, in some embodiments, a concentration of about 2 billion cells/ml is used. In some embodiments, a concentration of about 1 billion cells/ml is used. In some embodiments, greater than about 100 million cells/ml is used. In some embodiments, a concentration of cells of about any of 10, 15, 20, 25, 30, 35, 40, 45, or 50 million cells/ml is used. In some embodiments, a concentration of cells of about any of 75, 80, 85, 90, 95, or 100 million cells/ml is used. In some embodiments, a concentration of about 125 or about 150 million cells/ml is used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8$^+$ T cells that normally have weaker CD28 expression.

In some embodiments, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present disclosure to collect blood cells, including T cells, dendritic cells, or other cells of the hematopoietic lineage, during this recovery phase. Further, in some embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Whether prior to or after genetic modification of the T cells to express, e.g., an anti-PSMA CAR or an anti-PSMA caTCR, optionally with a CSR (such as an anti-PSMA CSR) or a tandem scFv (such as an anti-PSMA tandem scFv), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the genetically modified cells (such as T cells, such as αβ T cells, γδ T cells, cytotoxic T cells, helper T cells, or natural killer T cells) described herein are expanded by contact with a surface having attached thereto an agent that stimulates a CD3/TCR complex associated signal and a ligand that stimulates a co-stimulatory molecule on the surface of the T cells. In particular, T cell populations may be stimulated, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4$^+$ T cells or CD8$^+$ T cells, an anti-CD3 antibody and an anti-CD28 antibody. Examples of an anti-CD28 antibody include 9.3, B-T3, XR-CD28 (Diaclone, Besangon, France) can be used as can other methods commonly known in the art (Berg et al., *Transplant Proc.* 30(8):3975-3977, 1998; Haanen et al., *J. Exp. Med.* 190(9):13191328, 1999; Garland et al., *J. Immunol. Meth.* 227(1-2):53-63, 1999).

Immunoconjugates and Preparation Thereof

Also provided herein are immunoconjugates ("anti-PSMA immunoconjugates") that comprise an anti-PSMA construct (such as described herein) attached to an effector molecule. In some embodiments the effector molecule is a therapeutic agent, such as a cancer therapeutic agent (or a chemotherapeutic agent), or a toxin that is cytotoxic, cytostatic, and/or otherwise provides some therapeutic benefit. In some embodiments, the effector molecule is a label (e.g., a label that directly or indirectly produces a detectable signal.)

Anti-PSMA immunoconjugates comprising a therapeutic agent (also referred to as "antibody-drug conjugates" or "ADCs") may be used for the local delivery of cytotoxic or cytostatic agents, i.e., drugs to kill or inhibit proliferation tumor cells during treatment for cancer. Targeted delivery of the drug moiety to cells (such as cancer cells) that express or overexpress PSMA permit the intracellular accumulation of the therapeutic agent. See, e.g., Syrigos and Epenetos, *Anticancer Research* 19:605-614 (1999); Niculescu-Duvaz and Springer, *Adv. Drg. Del. Rev.* 26:151-172 (1997); U.S. Pat. No. 4,975,278. By contrast, systemic administration of unconjugated therapeutic agents may result in unacceptable levels of toxicity to normal cells as well as the target cells sought to be eliminated (Baldwin et al., *Lancet* (Mar. 15, 1986):603-605 (1986); Thorpe, (1985) "Antibody Carriers Of Cytotoxic Agents In Cancer Therapy: A Review," in Monoclonal Antibodies '84: Biological And Clinical Applications, A. Pinchera et al. (eds.), pp. 475-506). Maximal efficacy with minimal toxicity is sought thereby.

In some embodiments, the anti-PSMA immunoconjugate comprises an anti-PSMA antibody moiety (such as described herein) and a chemotherapeutic agent such as (but not limited to), e.g., daunomycin, doxorubicin, methotrexate, or vindesine (Rowland et al., *Cancer Immunol. Immunother.* 21:183-187 (1986)). In some embodiments, the anti-PSMA immunoconjugate comprises a bacterial toxin (such as diphtheria toxin), a plant toxin (such as ricin), a small molecule toxin (such as geldanamycin (Mandler et al., *J. Nat. Cancer Inst.* 92(19):1573-1581 (2000); Mandler et al., *Bioorganic & Med. Chem. Letters* 10:1025-1028 (2000); Mandler et al., *Bioconjugate Chem.* 13:786-791 (2002)), a maytansinoid (EP 1391213; Liu et al., *Proc. Natl. Acad. Sci. USA* 93:8618-8623 (1996)), a calicheamicin (Lode et al., *Cancer Res.* 58:2928 (1998); Hinman et al., *Cancer Res.* 53:3336-3342

(1993)), a dolastatin, an aurostatin, a trichothecene, CC1065, or a derivative thereof that exhibits toxin activity.

In some embodiments, the anti-PSMA immunoconjugate comprises an anti-PSMA antibody moiety (such as described herein) and an enzymatically active toxin (or a fragment thereof that exhibits toxin activity). Such enzymatic toxins include, but are not limited to, e.g., a diphtheria A chain, a nonbinding active fragment of diphtheria toxin, exotoxin A chain (from *Pseudomonas aeruginosa*), ricin A chain, abrin A chain, modeccin A chain, α-sarcin, an Aleuritesfordii protein, a dianthin protein, a *Phytolaca americana* protein (such as PAPI, PAPII, and PAP-S), aMomordica *charantia* inhibitor, curcin, crotin, a *Sapaonaria officinalis* inhibitor, gelonin, mitogellin, restrictocin, phenomycin, enomycin, or a tricothecene. See, e.g., WO 93/21232 published Oct. 28, 1993.

In some embodiments, the anti-PSMA immunoconjugate comprises an anti-PSMA antibody moiety (such as described herein) and a therapeutic agent that has an intracellular activity. In some embodiments, the anti-PSMA immunoconjugate is internalized and the therapeutic agent that has an intracellular activity is a cytotoxin that blocks the protein synthesis in a cell, thus leading to cell death. Exemplary toxins that block protein synthesis (such as by inactivating ribosomes) include, without limitation, e.g., gelonin, bouganin, saporin, ricin, ricin A chain, bryodin, diphtheria toxin, restrictocin, *Pseudomonas* exotoxin A and variants thereof. In some embodiments, the anti-PSMA immunoconjugate that comprises a cytotoxin that blocks protein synthesis in a cell must be internalized upon binding to the target cell in order for the protein to be cytotoxic to the cells.

In some embodiments, the anti-PSMA immunoconjugate comprises an anti-PSMA antibody moiety (such as described herein) and a therapeutic agent inhibits the synthesis of DNA. Exemplary therapeutic agents that inhibit DNA synthesis/DNA replication include, without limitation, e.g., enediyne (e.g., calicheamicin and esperamicin) and non-enediyne small molecule agents (e.g., bleomycin, methidiumpropyl-EDTA-Fe(II)). Other cancer therapeutic agents useful in accordance with the present application include, without limitation, daunorubicin, doxorubicin, distamycin A, cisplatin, mitomycin C, ecteinascidins, duocarmycin/CC-1065, and bleomycin/pepleomycin. In some embodiments, the anti-PSMA immunoconjugate comprises an anti-PSMA antibody moiety described herein and a compound with nucleolytic activity (e.g., a ribonuclease or a DNA endonuclease such as a deoxyribonuclease; DNase).

In some embodiments, the anti-PSMA immunoconjugate comprises an anti-PSMA antibody moiety described herein and an agent that binds microtubules or tubulin. In some embodiments, the agent that binds microtubules or tubulin stabilizes the microtubule cytoskeleton against depolymerization. Alternatively, in some embodiments, the agent that binds microtubules or tubulin inhibits tubulin polymerization. Such therapeutic agents include, without limitation, e.g., rhizoxin/maytansine, paclitaxel, vincristine and vinblastine, colchicine, auristatin dolastatin 10 MMAE, and peloruside A.

In some embodiments, the anti-PSMA immunoconjugate comprises an anti-PSMA antibody moiety (such as described herein) and an alkylating agent such as, without limitation, e.g., Asaley NSC 167780, AZQ NSC 182986, BCNU NSC 409962, Busulfan NSC 750, carboxyphthalatoplatinum NSC 271674, CBDCA NSC 241240, CCNU NSC 79037, CHIP NSC 256927, chlorambucil NSC 3088, chlorozotocin NSC 178248, cis-platinum NSC 119875, clomesone NSC 338947, cyanomorpholinodoxorubicin NSC 357704, cyclodisone NSC 348948, dianhydrogalactitol NSC 132313, fluorodopan NSC 73754, hepsulfam NSC 329680, hycanthone NSC 142982, melphalan NSC 8806, methyl CCNU NSC 95441, mitomycin C NSC 26980, mitozolamide NSC 353451, nitrogen mustard NSC 762, PCNU NSC 95466, piperazine NSC 344007, piperazinedione NSC 135758, pipobroman NSC 25154, porfiromycin NSC 56410, spirohydantoin mustard NSC 172112, teroxirone NSC 296934, tetraplatin NSC 363812, thio-tepa NSC 6396, triethylenemelamine NSC 9706, uracil nitrogen mustard NSC 34462, and Yoshi-864 NSC 102627.

In some embodiments, the anti-PSMA immunoconjugate comprises an anti-PSMA antibody moiety described herein and antimitotic agent such as, without limitation, e.g., allo-colchicine NSC 406042, Halichondrin B NSC 609395, colchicine NSC 757, colchicine derivative NSC 33410, dolastatin 10 NSC 376128 (NG-auristatin derived), maytansine NSC 153858, rhizoxin NSC 332598, taxol NSC 125973, taxol derivative NSC 608832, thiocolchicine NSC 361792, trityl cysteine NSC 83265, vinblastine sulfate NSC 49842, and vincristine sulfate NSC 67574.

In some embodiments, the anti-PSMA immunoconjugate comprises an anti-PSMA antibody moiety (such as described herein) and a topoisomerase I inhibitor such as, e.g., camptothecin NSC 94600, camptothecin, Na salt NSC 100880, aminocamptothecin NSC 603071, camptothecin derivative NSC 95382, camptothecin derivative NSC 107124, camptothecin derivative NSC 643833, camptothecin derivative NSC 629971, camptothecin derivative NSC 295500, camptothecin derivative NSC 249910, camptothecin derivative NSC 606985, camptothecin derivative NSC 374028, camptothecin derivative NSC 176323, camptothecin derivative NSC 295501, camptothecin derivative NSC 606172, camptothecin derivative NSC 606173, camptothecin derivative NSC 610458, camptothecin derivative NSC 618939, camptothecin derivative NSC 610457, camptothecin derivative NSC 610459, camptothecin derivative NSC 606499, camptothecin derivative NSC 610456, camptothecin derivative NSC 364830, camptothecin derivative NSC 606497, and morpholinodoxorubicin NSC 354646.

In some embodiments, the anti-PSMA immunoconjugate comprises an anti-PSMA antibody moiety (such as described herein) and a topoisomerase II inhibitor such as, without limitation, e.g., doxorubicin NSC 123127, amonafide NSC 308847, m-AMSA NSC 249992, anthrapyrazole derivative NSC 355644, pyrazoloacridine NSC 366140, bisantrene HCL NSC 337766, daunorubicin NSC 82151, deoxydoxorubicin NSC 267469, mitoxantrone NSC 301739, menogaril NSC 269148, N,N-dibenzyl daunomycin NSC 268242, oxanthrazole NSC 349174, rubidazone NSC 164011, VM-26 NSC 122819, and VP-16 NSC 141540.

In some embodiments, the anti-PSMA immunoconjugate comprises an anti-PSMA antibody moiety (such as described herein) and an RNA or DNA antimetabolite such as, without limitation, e.g., L-alanosine NSC 153353, 5-azacytidine NSC 102816, 5-fluorouracil NSC 19893, acivicin NSC 163501, aminopterin derivative NSC 132483, aminopterin derivative NSC 184692, aminopterin derivative NSC 134033, an antifol NSC 633713, an antifol NSC 623017, Baker's soluble antifol NSC 139105, dichlorallyl lawsone NSC 126771, brequinar NSC 368390, ftorafur (pro-drug) NSC 148958, 5,6-dihydro-5-azacytidine NSC 264880, methotrexate NSC 740, methotrexate derivative NSC 174121, N-(phosphonoacetyl)-L-aspartate (PALA) NSC 224131, pyrazofurin NSC 143095, trimetrexate NSC 352122, 3-HP NSC 95678, 2'-deoxy-5-fluorouridine NSC 27640, 5-HP NSC 107392, α-TGDR NSC 71851, aphidicolin glycinate NSC 303812, ara-C NSC 63878, 5-aza-2'-deoxycytidine NSC 127716, β-TGDR NSC 71261, cyclocytidine NSC 145668, guanazole NSC 1895, hydroxyurea NSC 32065, inosine glycodialdehyde NSC 118994, macbecin II NSC 330500, pyrazoloimidazole NSC 51143, thioguanine NSC 752, and thiopurine NSC 755.

In some embodiments, the anti-PSMA immunoconjugate comprises an anti-PSMA antibody moiety (such as described herein) and a radioactive isotope. A variety of radioactive isotopes are well known in the art and used for the production of radioconjugated polypeptide. Examples include, without limitation, e.g., $^{211}$At, $^{131}$I, $^{125}$I, $^{90}$Y, $^{86}$Re, $^{188}$Re, $^{153}$Sm, $^{212}$Bi, $^{32}$P, $^{212}$Pb and radioactive isotopes of Lu.

In some embodiments, the anti-PSMA immunoconjugate comprises an anti-PSMA antibody moiety (such as described herein) and a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., any one or more of the cytotoxic agents described herein or known in the art).

In some embodiments, the anti-PSMA immunoconjugate comprises an anti-PSMA antibody moiety (such described herein) and a prodrug-activating enzyme. In some embodiments, the prodrug-activating enzyme converts a prodrug (e.g., a peptidyl chemotherapeutic agent, see WO 81/01145) to an active drug, such as an anti-cancer drug. In some embodiments, the anti-PSMA immunoconjugate comprising the prodrug-activating enzyme is used in antibody-dependent enzyme-mediated prodrug therapy ("ADEPT"). In some embodiments, the anti-PSMA immunoconjugate comprises an anti-PSMA antibody moiety (such as described herein) and alkaline phosphatase, which converts phosphate-containing prodrugs into free drugs; an arylsulfatase, which converts sulfate-containing prodrugs into free drugs; a cytosine deaminase, which converts non-toxic 5-fluorocytosine into the anti-cancer drug 5-fluorouracil; a protease (e.g., serratia protease, thermolysin, subtilisin, a carboxypeptidas or a cathepsin (such as cathepsin B and L)), which converts peptide-containing prodrugs into free drugs; a D-alanylcarboxypeptidase, which converts prodrugs that contain D-amino acid substituents; a carbohydrate-cleaving enzyme (such as β-galactosidase and neuraminidase), which converts glycosylated prodrugs into free drugs; β-lactamase, which converts drugs derivatized with β-lactams into free drugs; or a penicillin amidase (such as penicillin V amidase or penicillin G amidase), which converts drugs derivatized at their amine nitrogens with phenoxyacetyl or phenylacetyl groups, respectively, into free drugs. In some embodiments, the prodrug-activating enzyme is covalently attached to anti-PSMA antibody moiety. In some embodiments, provided is a nucleic acid that encodes an anti-PSMA immunoconjugate that comprises anti-PSMA antibody moiety (such as described herein) and an enzyme (such as a prodrug activating enzyme). See, e.g., Neuberger et al., *Nature* 312:604-608. Producing such immunoconjugate entails transforming, transfecting, or transducing a host cell with the nucleic acid, culturing the host cell under conditions wherein the immunoconjugate is expressed, and harvesting the immunoconjugate.

In some embodiments, the anti-PSMA immunoconjugate comprises an anti-PSMA antibody moiety (such as described herein) and a nucleic acid, such as, but are not limited to, e.g., an anti-sense RNA, a gene, or other polynucleotide. In some embodiments, the polynucleotide conjugated to the anti-PSMA antibody moiety comprises one or more nucleic acid analogs, such as thioguanine and thiopurine.

In some embodiments, the anti-PSMA immunoconjugate comprises an anti-PSMA antibody moiety (such as described herein) and a label that generates a detectable signal, either directly or indirectly. Such anti-PSMA immunoconjugates can be used for research or diagnostic applications including, e.g., the in vivo or in vitro detection of cancer cells (e.g., in an individual having or suspected of having cancer or in a sample obtained from such an individual). In some embodiments, the label is radio-opaque. In some embodiments, the label is a radioisotope, e.g., without limitation, $^{3}$H, $^{14}$C, $^{32}$P, $^{35}$S, $^{123}$I, $^{125}$I, $^{131}$I. In some embodiments, the label is a fluorescent compound (fluorophore) or a chemiluminescent compound (chromophore), such as, e.g., fluorescein isothiocyanate, rhodamine or luciferin. In some embodiments, the label is an enzyme, such as alkaline phosphatase, β-galactosidase or horseradish peroxidase. In some embodiments, the label is an imaging agent or a metal ion. In some embodiments, the label is a radioactive atom for scintigraphic studies, for example $^{99}$Tc or $^{123}$I, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

In some embodiments, the anti-PSMA immunoconjugate comprises an anti-PSMA antibody moiety (such as described herein) and a label that produces an indirectly detectable signal. For example, a secondary antibody that is specific for the anti-PSMA immunoconjugate and comprises a detectable label can be used to detect the anti-PSMA immunoconjugate.

Anti-PSMA immunoconjugates may be prepared using any methods known in the art. See, e.g., WO 2009/067800, WO 2011/133886, and U.S. Patent Application Publication No. 2014322129, incorporated by reference herein in their entirety.

The anti-PSMA antibody moiety of an anti-PSMA immunoconjugate may be "attached to" the effector molecule by any means by which the anti-PSMA antibody moiety can be associated with, or linked to, the effector molecule. In some embodiments, the anti-PSMA immunoconjugate comprise an anti-PSMA antibody moiety described herein and a label or therapeutic agent, wherein the label or the therapeutic agent molecule is covalently attached to the anti-PSMA antibody moiety. The anti-PSMA antibody moiety of an anti-PSMA immunoconjugate may be attached to the effector molecule by chemical or recombinant means. Chemical means for preparing fusions or conjugates are known in the art and can be used to prepare the anti-PSMA immunoconjugate. The method used to conjugate the anti-PSMA antibody moiety and effector molecule (i.e., the label or therapeutic agent) must be capable of joining the binding protein with the effector molecule without interfering with the ability of the anti-PSMA antibody moiety to bind to PSMA expressed on the target cell.

In some embodiments, the anti-PSMA immunoconjugate comprises an anti-PSMA antibody moiety (such as described herein) that is indirectly linked to the effector molecule (i.e., the label or therapeutic agent). For example, the anti-PSMA antibody moiety of an anti-PSMA immunoconjugate may be directly linked to a liposome containing the effector molecule (i.e., the label or therapeutic agent). The effector molecule(s) and/or the anti-PSMA antibody moiety may also be bound to a solid surface.

In some embodiments, the anti-PSMA antibody moiety of an anti-PSMA immunoconjugate and the effector molecule (i.e., the label or therapeutic agent) are both proteins and can be conjugated using techniques well known in the art. A variety of crosslinkers that can conjugate two proteins are well known in the art. (See for example "Chemistry of Protein Conjugation and Crosslinking". 1991, Shans Wong, CRC Press, Ann Arbor). The crosslinker is generally chosen based on the reactive functional groups available or inserted on the anti-PSMA antibody moiety and/or effector molecule (i.e., the label or therapeutic agent). In addition, if there are no reactive groups, a photoactivatable crosslinker can be used. In certain instances, it may be desirable to include a spacer between the anti-PSMA antibody moiety and the effector molecule. Crosslinking agents known to the art include the homobifunctional agents: glutaraldehyde, dimethyladipimidate and Bis(diazobenzidine) and the heterobifunctional agents: m-Maleimidobenzoyl-N-Hydroxysuccinimide and Sulfo-m Maleimidobenzoyl-N-Hydroxysuccinimide.

In some embodiments, the anti-PSMA antibody moiety of an anti-PSMA immunoconjugate may be engineered with specific residues for chemical attachment of the effector molecule (i.e., the label or therapeutic agent). Specific residues used for chemical attachment of molecule known to the art include lysine and cysteine. The crosslinker is chosen based on the reactive functional groups inserted on the anti-PSMA antibody moiety, and available on the effector molecule.

An anti-PSMA immunoconjugate may also be prepared using recombinant DNA techniques. In such a case a DNA sequence encoding the anti-PSMA antibody moiety is fused to a DNA sequence encoding the effector molecule, resulting in a chimeric DNA molecule. The chimeric DNA sequence is transfected into a host cell that expresses the fusion protein. The fusion protein can be recovered from the cell culture and purified using techniques known in the art.

Exemplary methods of attaching a detectable label to a binding molecule (such as an anti-PSMA antibody moiety) are described in Hunter, et al., *Nature* 144:945 (1962); David, et al., *Biochemistry* 13:1014 (1974); Pain, et al., *J. Immunol. Meth.* 40:219 (1981); Nygren, *J. Histochem. and Cytochem.* 30:407 (1982); Wensel and Meares, *Radioimmunoimaging And Radioimmunotherapy*, Elsevier, N.Y. (1983); and Colcher et al., "Use Of Monoclonal Antibodies As Radiopharmaceuticals For The Localization Of Human Carcinoma Xenografts In Athymic Mice", *Meth. Enzymol.*, 121:802-16 (1986).

Radiolabels (or other labels) may be incorporated in the immunoconjugate in known ways. For example, the anti-PSMA antibody moiety may be biosynthesized or may be synthesized by chemical amino acid synthesis using suitable amino acid precursors involving, for example, fluorine-19 in place of hydrogen. Labels such as $^{99}$Tc or $^{123}$I, $^{86}$Re, $^{188}$Re and $^{111}$In can be attached via a cysteine residue in the anti-PSMA antibody moiety. Yttrium-90 can be attached via a lysine residue. The IODOGEN method (Fraker et al., *Biochem. Biophys. Res. Commun.* 80:49-57 (1978)) can be used to incorporate iodine-123. "Monoclonal Antibodies in Immunoscintigraphy" (Chatal, CRC Press 1989) describes other methods in detail.

Anti-PSMA immunoconjugates may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCI), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene tnaminepentaacetic acid (MX-DTPA) is an exemplary chelating agent for conjugation of radionuclide to the anti-PSMA antibody moiety of the anti-PSMA immunoconjugate. See, e.g., WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208,020) may be used.

The anti-PSMA immunoconjugates of the present disclosure include, are not limited to, those prepared using BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), i.e., cross-linking reagents that are commercially available (e.g., from Pierce Biotechnology, Inc., Rockford, IL, U.S.A.). See pages 467-498, 2003-2004 Applications Handbook and Catalog.

Nucleic Acids, Vectors, Host Cells, and Methods of Making Anti-PSMA Constructs

Also provided are nucleic acid molecules (including sets of nucleic acid molecules) that encode the polypeptide portions of the anti-PSMA constructs described herein. In some embodiments, the nucleic acid (or a set of nucleic acids) encodes a full-length anti-PSMA antibody. In some embodiments, the nucleic acid (or a set of nucleic acids) encodes a multispecific anti-PSMA molecule (e.g., a multispecific anti-PSMA antibody, a bispecific anti-PSMA antibody, or a tandem di-scFv that comprises an anti-PSMA antibody moiety), or polypeptide portion thereof. In some embodiments, the nucleic acid (or a set of nucleic acids) encodes an anti-PSMA CAR. In some embodiments, the nucleic acid (or set of nucleic acids) encodes an anti-PSMA caTCR. In some embodiments, the two chains of the anti-PSMA caTCR are encoded on the same nucleic acid. In some embodiments, the two chains of the anti-PSMA caTCR are encoded on separate nucleic acids. In some embodiments, the nucleic acid encodes an anti-PSMA CSR. In some embodiments, the nucleic acid (or a set of nucleic acids) encodes an anti-PSMA immunoconjugate, or polypeptide portion thereof.

Nucleic acid sequence variants that encode the polypeptide portions of the anti-PSMA constructs described herein are also provided. For example, the variants include nucleotide sequences that hybridize to the nucleic acid sequences encoding an anti-PSMA construct or anti-PSMA antibody moiety described herein under at least moderately stringent hybridization conditions.

Also provided are vectors (such as expression vectors) comprising one or more nucleic acids described herein.

An anti-PSMA construct described herein, or polypeptide portion thereof, e.g., an anti-PSMA CAR can be expressed from a natural or synthetic nucleic acid encoding the anti-PSMA construct or polypeptide portion thereof. Briefly, the nucleic acid may be inserted into an appropriate expression vector, such that the nucleic acid is operably linked to 5' and 3' regulatory elements, including for example a promoter (e.g., a lymphocyte-specific promoter) and a 3' untranslated region (UTR). The vectors are preferable suitable for replication and integration in eukaryotic host cells. Typical cloning and expression vectors contain transcription and translation terminators, initiation sequences, and promoters useful for regulation of the expression of the desired nucleic acid sequence.

The nucleic acids described herein may also be used for nucleic acid immunization and gene therapy, using standard gene delivery protocols. Methods for gene delivery are known in the art. See, e.g., U.S. Pat. Nos. 5,399,346; 5,580,859; and 5,589,466; which are incorporated by reference herein in their entireties. In some embodiments, the provided a gene therapy vector.

The nucleic acids described herein may be cloned into any of a variety of vectors known in the art. For example, the nucleic acid (or set of nucleic acids) can be cloned into, e.g., a plasmid, a phagemid, a phage derivative, an animal virus, and/or a cosmid. Vectors of particular interest include expression vectors, replication vectors, probe generation vectors, and sequencing vectors.

In some embodiments, the expression vector comprising a nucleic acid encoding an anti-PSMA construct or anti-PSMA antibody moiety described herein is a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, the viral vector is an adenovirus vectors. A number of adenovirus vectors are known in the art. In some embodiments, the viral vector is a lentivirus vector. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells. They also have the added advantage of low immunogenicity.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the expression of anti-PSMA constructs described herein should not be limited to the use of constitutive promoters. Inducible promoters are also contemplated. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Exemplary selectable markers include, but are not limited to, e.g., antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, β-galactosidase, chloramphenicol acetyl transferase, secreted alkaline phosphatase, or the green fluorescent protein gene (e.g., Ui-Tel et al., 2000 *FEBS Letters* 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). In some embodiments, the introduction of a polynucleotide into a host cell is carried out by calcium phosphate transfection.

Biological methods for introducing a polynucleotide of interest into a host cell include the use of DNA and RNA vectors. Viral vectors, and especially retroviral vectors, have become the most widely used method of inserting genes into mammalian, e.g., human cells. Other viral vectors can be derived from lentivirus, poxviruses, herpes simplex virus 1, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Another exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the present disclosure.

Anti-PSMA Constructs Comprising Fc Region Variants

In some embodiments, one or more amino acid modifications may be introduced into the Fc region of an anti-PSMA construct provided herein (e.g., a full-length anti-PSMA antibody), thereby generating an Fc region variant. In some embodiments, the Fc region variant has enhanced antibody dependent cellular cytotoxicity (ADCC) effector function, often related to binding to Fc receptors (FcRs). In some embodiments, the Fc region variant has decreased ADCC effector function. There are many examples of changes or mutations to Fc sequences that can alter effector function. For example, WO 00/42072 and Shields et al. *J Biol. Chem.* 9(2): 6591-6604 (2001) describe antibody variants with improved or diminished binding to FcRs. The contents of those publications are specifically incorporated herein by reference.

Antibody-Dependent Cell-Mediated Cytotoxicity (ADCC) is a mechanism of action of therapeutic antibodies against tumor cells. ADCC is a cell-mediated immune defense whereby an effector cell of the immune system actively lyses a target cell (e.g., a cancer cell), whose membrane-surface antigens have been bound by specific antibodies (e.g., an anti-PSMA antibody). The typical ADCC involves activation of NK cells by antibodies. An NK cell expresses CD16 which is an Fc receptor. This receptor recognizes, and binds to, the Fc portion of an antibody bound to the surface of a target cell. The most common Fc receptor on the surface of an NK cell is called CD16 or FcγRIII. Binding of the Fc receptor to the Fc region of an antibody results in NK cell activation, release of cytolytic granules and consequent target cell apoptosis. The contribution of ADCC to tumor cell killing can be measured with a specific test that uses NK-92 cells that have been transfected with a high-affinity FcR. Results are compared to wild-type NK-92 cells that do not express the FcR.

In some embodiments, provided is an anti-PSMA construct comprising a variant Fc region that possesses some but not all effector functions, which makes it a desirable candidate for applications in which the half-life of the anti-PSMA construct in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC (i.e., NK cells) express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166: 1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CytoTox 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J Immunol. Methods* 202: 163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J Biol. Chem.* 9(2): 6591-6604 (2001).)

In some embodiments, the anti-PSMA construct (e.g., a full-length anti-PSMA antibody) comprises a variant Fc region comprising one or more amino acid substitutions which improve ADCC. In some embodiments, the variant Fc region comprises one or more amino acid substitutions which improve ADCC, wherein the substitutions are at positions 298, 333, and/or 334 of the variant Fc region (EU numbering of residues). In some embodiments, the anti-PSMA construct (e.g., a full-length anti-PSMA antibody) comprises the following amino acid substitutions in its variant Fc region: S298A, E333A, and K334A.

In some embodiments, alterations are made in the Fc region of the anti-PSMA construct (e.g., a full-length anti-PSMA antibody) hat result in altered (i.e., either improved or diminished) C1q binding and/or Complement Dependent Cytotoxicity (CDC), e.g., as described in U.S. Pat. No. 6,194,551, WO 99/51642, and Idusogie et al., *J. Immunol.* 164: 4178-4184 (2000).

In some embodiments, the anti-PSMA construct (e.g., a full-length anti-PSMA antibody) comprising a variant Fc region comprises one or more amino acid substitutions which increase half-life and/or improve binding to the neonatal Fc receptor (FcRn). Antibodies with increased half-lives and improved binding to FcRn are described in US2005/0014934A1 (Hinton et al.). Such antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

Anti-PSMA constructs (such as full-length anti-PSMA antibodies) comprising any of the Fc variants described herein, or combinations thereof, are contemplated.

Glycosylation Variants of Anti-PSMA Constructs

In some embodiments, an anti-PSMA construct provided herein is altered to increase or decrease the extent to which the anti-PSMA construct is glycosylated. Addition or deletion of glycosylation sites to an anti-PSMA construct may be conveniently accomplished by altering the amino acid sequence of the anti-PSMA construct or polypeptide portion thereof such that one or more glycosylation sites is created or removed.

Where the anti-PSMA construct comprises an Fc region, the carbohydrate attached thereto may be altered. Native antibodies produced by mammalian cells typically comprise a branched, biantennary oligosaccharide that is generally attached by an N-linkage to Asn297 of the $C_H2$ domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-PSMA construct described herein may be made in order to create anti-PSMA construct glycosylation variants with certain improved properties.

In some embodiments, the anti-PSMA construct (such as a full-length anti-PSMA antibody) comprises an Fc region wherein a carbohydrate structure attached to the Fc region has reduced fucose or lacks fucose, which may improve ADCC function. In some embodiments, the anti-PSMA construct (such as full-length anti-PSMA antibody) has reduced fucose relative to the amount of fucose on the same anti-PSMA construct (e.g., the full-length anti-PSMA antibody) produced in a wild-type CHO cell (e.g., a CHO cell that produce a native glycosylation pattern, such as, a CHO cell containing a native FUT8 gene). In some embodiments, the anti-PSMA construct is one wherein less than about 50%, 40%, 30%, 20%, 10%, or 5% of the N-linked glycans thereon comprise fucose. For example, the amount of fucose in such an anti-PSMA construct may be from 1% to 80%, from 1% to 65%, from 5% to 65% or from 20% to 40%. In some embodiments, the anti-PSMA construct is one wherein none of the N-linked glycans thereon comprise fucose, i.e., wherein the anti-PSMA construct is completely without fucose, or has no fucose or is afucosylated. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as α-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

In some embodiments, the anti-PSMA construct (such as a full-length anti-PSMA antibody) is a glycosylation variant comprising bisected oligosaccharides, e.g., in which a biantennary oligosaccharide attached to the Fc region of the anti-PSMA construct is bisected by GlcNAc. Such anti-PSMA construct (e.g., a full-length anti-PSMA antibody) glycosylation variants may have reduced fucosylation and/or improved ADCC function. Examples of such antibody variants are described, e.g., in WO 2003/011878 (Jean-Mairet et al.); U.S. Pat. No. 6,602,684 (Umana et al.); US 2005/0123546 (Umana et al.), and Ferrara et al., *Biotechnology and Bioengineering*, 93(5): 851-861 (2006). In some embodiments, the anti-PSMA construct (such as a full-length anti-PSMA antibody) is a glycosylation variant comprising at least one galactose residue in the oligosaccharide attached to the Fc region. Such anti-PSMA construct glycosylation variants may have improved CDC function. Such glycosylation variants are described, e.g., in WO 1997/30087 (Patel et al.); WO 1998/58964 (Raju, S.); and WO 1999/22764 (Raju, S.).

In some embodiments, the anti-PSMA construct (such as full-length anti-PSMA antibody) glycosylation variant comprises an Fc region capable of binding to an FcγRIII. In some embodiments, the anti-PSMA construct (such as full-length anti-PSMA antibody) glycosylation variant comprises an Fc region have ADCC activity in the presence of human effector cells or have increased ADCC activity in the presence of human effector cells compared to an anti-PSMA construct (such as a full-length anti-PSMA antibody) comprising a human wild-type IgG1 Fc region.

Cysteine Engineered Variants of Anti-PSMA Constructs

In some embodiments, the anti-PSMA construct (such as a full-length anti-PSMA antibody) has been engineered such that one or more amino acid residues are substituted with cysteine residues. In some embodiments, the substituted residues occur at the surface of and/or at solvent-accessible sites of the anti-PSMA construct. By substituting those residues with cysteine, reactive thiol groups are thereby positioned at accessible sites of the anti-PSMA construct and may be used to conjugate the anti-PSMA construct to other moieties, such as drug moieties or linker-drug moieties, to create anti-PSMA immunoconjugates (which are described in further detail elsewhere herein). Cysteine engineered anti-PSMA constructs (such as full-length anti-PSMA antibodies) may be generated as described, e.g., in U.S. Pat. No. 7,521,541.

Derivatized Anti-PSMA Constructs

In some embodiments, the anti-PSMA construct has been further modified to contain additional nonproteinaceous moieties that are known in the art and readily available. The moieties suitable for derivatization of an anti-PSMA construct of the present disclosure include, but are not limited to, water soluble polymers. Non-limiting examples of water soluble polymers include, without limitation, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to a derivatized anti-PSMA construct may vary, and if more than one polymer is attached, the polymers can be the same or different molecules. In general, the number and/or type of polymers used for derivatization can be determined based on considerations including, but not limited to, the particular properties or functions of the anti-PSMA construct to be improved, whether the anti-PSMA construct derivative will be used in a therapy under defined conditions, etc.

In some embodiments, conjugates of an anti-PSMA construct and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the anti-PSMA construct-nonproteinaceous moiety are killed.

Pharmaceutical Compositions

Also provided herein are compositions (such as pharmaceutical compositions, also referred to herein as "pharmaceutical formulations" or "formulations") comprising an anti-PSMA construct or anti-PSMA construct combination described herein. In some embodiments, the composition further comprises a cell (such as an effector cell, e.g., a T cell) associated with the anti-PSMA construct or anti-PSMA construct combination. In some embodiments, the pharmaceutical composition comprises an anti-PSMA construct or anti-PSMA construct combination and a pharmaceutically acceptable carrier. In some embodiments, the pharmaceutical composition further comprises a cell (such as an effector cell, e.g., a T cell) associated with the anti-PSMA construct or anti-PSMA construct combination. In yet other embodiments, the pharmaceutic composition comprises a nucleic acid encoding an anti-PSMA construct or anti-PSMA construct combination.

Suitable formulations of the anti-PSMA constructs or construct combinations are obtained by mixing an anti-PSMA construct or construct combination having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary formulations are described in WO98/56418, expressly incorporated herein by reference. Lyophilized formulations adapted for subcutaneous administration are described in WO97/04801. Such lyophilized formulations may be reconstituted with a suitable diluent to a high protein concentration and the reconstituted formulation may be administered subcutaneously to the individual to be treated herein. Lipofectins or liposomes can be used to deliver the anti-PSMA constructs or construct combinations described herein into cells.

In some embodiments, the pharmaceutical composition comprises one or more active compounds in addition to the anti-PSMA construct or construct combination as necessary for the particular indication being treated. Preferably, the active compounds in the pharmaceutical composition do not adversely affect each others' activities. In some embodiments, the one or more active compounds is an anti-neoplastic agent, a growth inhibitory agent, a cytotoxic agent, or a chemotherapeutic agent, i.e., in addition to the anti-PSMA construct or construct combination. Such molecules are suitably present in combination in amounts that are effective for the purpose intended. The effective amount of such other agents depends on the amount of anti-PSMA construct or construct combination present in the formulation, the type of disease or disorder or treatment, and other factors discussed elsewhere herein. These are generally used in the same dosages and with administration routes as described herein or about from 1 to 99% of the heretofore employed dosages.

The anti-PSMA constructs or construct combinations may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in *Remington's Pharmaceutical Sciences* 16th edition, Osol, A. Ed. (1980). Sustained-release preparations may be prepared.

Sustained-release preparations of the anti-PSMA constructs or construct combinations can be prepared. Suitable examples of sustained-release preparations include semipermeable matrices of solid hydrophobic polymers containing the antibody (or fragment thereof), which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydro gels release proteins for shorter time periods. When encapsulated antibodies remain in the body for a long time, they can denature or aggregate as a result of exposure to moisture at 37° C., resulting in a loss of biological activity and possible changes in immunogenicity. Rational strategies can be devised for stabilization of anti-PSMA constructs or construct combinations depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

In some embodiments, the anti-PSMA construct or construct combination is formulated in a buffer comprising a citrate, NaCl, acetate, succinate, glycine, polysorbate 80 (Tween 80), or any combination of the foregoing. In some embodiments, the anti-PSMA construct or construct combination is formulated in a buffer comprising about 100 mM to about 150 mM glycine. In some embodiments, the anti-PSMA construct or construct combination is formulated in a buffer comprising about 50 mM to about 100 mM NaCl. In some embodiments, the anti-PSMA construct or construct combination is formulated in a buffer comprising about 10 mM to about 50 mM acetate. In some embodiments, the anti-PSMA construct is formulated in a buffer comprising about 10 mM to about 50 mM succinate. In some embodiments, the anti-PSMA construct or construct combination is formulated in a buffer comprising about 0.005% to about 0.02% polysorbate 80. In some embodiments, the anti-PSMA construct or construct combination is formulated in a buffer having a pH between about 5.1 and 5.6. In some embodiments, the anti-PSMA construct or construct combination is formulated in a buffer comprising 10 mM citrate, 100 mM NaCl, 100 mM glycine, and 0.010% polysorbate 80, wherein the formulation is at pH 5.5.

The pharmaceutical formulations to be used for in vivo administration must be sterile. This is readily accomplished by, e.g., filtration through sterile filtration membranes.

Methods of Treatment Using Anti-PSMA Constructs

The anti-PSMA constructs, anti-PSMA construct combinations, and/or compositions described herein may be administered to individuals (e.g., mammals such as humans) to treat a PSMA-associated disease or disorder. In some embodiments, the PMSA-associated disease or disorder is characterized by PSMA expression, PSMA overexpression, and/or aberrant PSMA activity. Such diseases or disorders including, for example, PSMA-associated cancer, e.g., prostate cancer (such as hormone-refractory or metastatic prostate cancer), renal cell cancer cell (such as clear cell renal cell cancer), uterine cancer, or liver cancer.

Thus, provided herein is a method of treating a PSMA-associated disease (such as cancer) in an individual, which method comprises administering to the individual an effective amount of a composition (such as a pharmaceutical composition) comprising an anti-PSMA construct or construct combination described herein. In some embodiments, the composition further comprises a cell (such as an effector cell) associated with the anti-PSMA construct or construct combination (such as an effector cell that expresses an anti-PSMA construct or construct combination described herein). In some embodiments, the cancer is, for example, prostate cancer (such as hormone-refractory or metastatic prostate cancer), renal cell cancer cell (such as clear cell renal cell cancer), uterine cancer, or liver cancer. In some embodiments, the individual is human.

In some embodiments, the anti-PSMA construct or construct combination used in the method is non-naturally occurring. In some embodiments, the anti-PSMA construct used in the method is a full-length antibody, a multispecific (such as bispecific) anti-PSMA construct, an anti-PSMA chimeric antigen receptor (CAR), an anti-PSMA chimeric antibody-T cell receptor construct (caTCR), an anti-PSMA chimeric signaling receptors (CSRs), an anti-PSMA immunoconjugate, or any other anti-PSMA construct described in further detail elsewhere herein. In some embodiments, a construct combination comprising anti-PSMA caTCR and an anti-PSMA CSR (e.g., an anti-PSMA caTCR+anti-PSMA CSR construct combination described elsewhere herein) is used in the method. Each of the constructs or construct combinations described herein demonstrates high specificity for human PSMA in native form (e.g., expressed on the surface of a cell, such as a cancer cell). In some embodiments, the pharmaceutical composition used in the method further comprises a cell (such as an effector cell) that expresses or is associated with the anti-PSMA construct or construct combination. In some embodiments, the PSMA-associated disease is cancer. In some embodiments, the cancer is, for example, prostate cancer (such as hormone-refractory or metastatic prostate cancer), renal cell cancer cell (such as clear cell renal cell cancer), uterine cancer, or liver cancer. In some embodiments, the individual is human.

In some embodiments of any of the methods for treating a PSMA-associated disease described herein, the anti-PSMA construct or construct combination is conjugated to a cell (such as an immune cell, e.g., a T cell) prior to being administered to the individual. Thus, provided is a method of treating a PSMA-associated disease in an individual comprising a) conjugating any one of the anti-PSMA constructs or construct combinations described herein to a cell (such as an immune cell, e.g., a T cell) to form an anti-PSMA construct/cell conjugate, and b) administering an effective amount of a composition comprising the anti-PSMA construct/cell conjugate to the individual. In some embodiments, the cell to which the anti-PSMA construct or construct combination is conjugated is derived from the individual being treated. In some embodiments, the cell to which the anti-PSMA construct or construct combination is conjugated is not derived from the individual being treated. In some embodiments, the anti-PSMA construct or construct combination is conjugated to the cell by covalent linkage to a molecule on the surface of the cell. In some embodiments, the anti-PSMA construct or construct combination is conjugated to the cell by non-covalent linkage to a molecule on the surface of the cell. In some embodiments, the anti-PSMA construct or construct combination is conjugated to the cell by insertion of a portion of the anti-PSMA construct or construct combination into the outer membrane of the cell. In some embodiments, the anti-PSMA construct or construct combination is non-naturally occurring. In some embodiments, the anti-PSMA construct used in the method is a full-length antibody, a multispecific (such as bispecific) anti-PSMA construct (such as a tandem di-scFv), an anti-PSMA immunoconjugate, or any other anti-PSMA construct described in further detail elsewhere herein. In some embodiments, a construct combination comprising anti-PSMA caTCR and an anti-PSMA CSR (e.g., an anti-PSMA caTCR+anti-PSMA CSR construct combination described elsewhere herein) is used in the method. In some embodiments, the PSMA-associated disease is cancer. In some embodiments, the cancer is, for example, prostate cancer (such as hormone-refractory or metastatic prostate cancer), renal cell cancer cell (such as clear cell renal cell cancer), uterine cancer, or liver cancer. In some embodiments, the individual is human.

In some embodiments of any of the methods for treating a PSMA-associated disease described herein, treatment comprises administering to a recipient in need a cell (e.g., a T cell, such as an $\alpha\beta$ T cell, a $\gamma\delta$ T cell, a cytotoxic T cell, a helper T cell, or a natural killer T cell) that has been genetically modified (i.e., transduced or transfected, such as in vitro) with a nucleic acid, a set of nucleic acids, a vector, or a set of vectors encoding an anti-PSMA CAR, anti-PSMA caTCR, anti-PSMA tandem multispecific scFv (such as a tandem di-scFv), or anti-PSMA CSR disclosed herein, or an anti-PSMA caTCR+anti-PSMA CSR construct combination disclosed herein. In some embodiments, the genetically modified cell (e.g., a T cell, such as an $\alpha\beta$ T cell, a $\gamma\delta$ T cell, a cytotoxic T cell, a helper T cell, a natural killer T cell, and a suppressor T cell) expresses the anti-PSMA CAR, anti-PSMA caTCR, anti-PSMA tandem multispecific scFv (such as a tandem di-scFv), anti-PSMA CSR, or an anti-PSMA caTCR+anti-PSMA CSR construct combination encoded by the nucleic acid, set of nucleic acids, vector, or set of vectors. In some embodiments, the recipient is a mammal, such as a human, e.g., a human who has or is suspected of having the PSMA-associated disease).

In some embodiments of the methods for treating a PSMA-associated disease, treatment further comprises the step of genetically modifying (i.e., transducing or transfecting, such as in vitro) the cell (e.g., a T cell, such as an $\alpha\beta$ T cell, a $\gamma\delta$ T cell, a cytotoxic T cell, a helper T cell, or a natural killer T cell) with the nucleic acid, the set of nucleic acids, the vector, or the set of vectors encoding the anti-PSMA CAR, the anti-PSMA caTCR, anti-PSMA tandem multispecific scFv (such as a tandem di-scFv), or anti-PSMA CSR prior to administration to the recipient. In some embodiments, the cell (e.g., a T cell, such as an $\alpha\beta$ T cell, a $\gamma\delta$ T cell, a cytotoxic T cell, a helper T cell, or a natural killer T cell) has been genetically modified (i.e., transduced or transfected, such as in vitro) with the nucleic acid, the set of nucleic acids, the vector, or the set of vectors encoding anti-PSMA CAR or anti-PSMA caTCR, and is further genetically modified (i.e., transduced or transfected, such as in vitro) with a nucleic acid, a set of nucleic acids, a vector, or a set of vectors encoding a multispecific scFv (such as a tandem di-scFv) or a CSR. In some embodiments, the multispecific scFv (e.g., a tandem di-scFv) targets PSMA. In some embodiments, the multispecific scFv (e.g., a tandem di-scFv) targets a different antigen (e.g., an antigen other than PSMA). In some embodiments, the CSR targets PSMA. In some embodiments, the CSR targets a different antigen (e.g., an antigen other than PSMA). In some embodiments, the cell (e.g., a T cell, such as an $\alpha\beta$ T cell, a $\gamma\delta$ T cell, a cytotoxic T cell, a helper T cell, or a natural killer T cell) has been genetically modified (i.e., transduced or transfected, such as in vitro) with the nucleic acid, the set of nucleic acids, the vector, or the set of vectors encoding the anti-PSMA tandem multispecific scFv (such as a tandem di-scFv) or the anti-PSMA CSR, and is further genetically modified (i.e., transduced or transfected, such as in vitro) with a nucleic acid, a set of nucleic acids, a vector, or a set of vectors encoding a CAR or caTCR. In some embodiments, the CAR targets PSMA. In some embodiments, the CAR targets a different antigen (e.g., an antigen other than PSMA). In some embodiments, the caTCR targets PSMA. In some embodiments, the caTCR targets a different antigen (e.g., an antigen other than PSMA). In some embodiments, the construct combination comprises an anti-PSMA caTCR and anti-PSMA CSR (e.g., an anti-PSMA caTCR+anti-PSMA CSR construct combination described elsewhere herein).

In some embodiments of the methods for treating a PSMA-associated disease, treatment further comprises the step of obtaining (such as isolating) cells (e.g., T cells, such as $\alpha\beta$ T cells, a $\gamma\delta$ T cells, cytotoxic T cells, helper T cells, or natural killer T cells) from an individual (e.g., a mammal, such as a human, e.g., a human who has or is suspected of having the PSMA-associated disease) prior to the step of genetically modifying (i.e., transducing or transfecting, such as in vitro) the cells with a nucleic acid, a set of nucleic acids, a vector, or a set of vectors encoding the anti-PSMA CAR, the anti-PSMA caTCR, anti-PSMA tandem multispecific scFv (such as a tandem di-scFv), anti-PSMA CSR, or anti-PSMA caTCR+anti-PSMA CSR construct combination, e.g., as described above. In some embodiments, the recipient to whom the genetically modified cells are administered is the individual from whom the cells were obtained. Such a genetically modified immune cell is referred to as an "autologous anti-PSMA effector cell." In some embodiments, the recipient to whom the genetically modified cells are administered is not the individual from whom the cells were obtained. Such a genetically modified immune cell is referred to as a "heterologous anti-PSMA effector cell." In some embodiments, the heterologous anti-PSMA cell is allogeneic, syngeneic, or xenogeneic with respect to the recipient.

In some embodiments, the individual is a mammal (e.g., a human, a non-human primate (such as a rhesus monkey or a cynomolgus monkey), a rat, a mouse, a cow, a horse, a pig, a sheep, a goat, a dog, a cat, etc.). In some embodiments, the individual is a human. In some embodiments, the individual is a clinical patient, a clinical trial volunteer, an experimental animal, etc. In some embodiments, the individual is younger than about 60 years old (including for example younger than about any of 50, 40, 30, 25, 20, 15, or 10 years old). In some embodiments, the individual is older than about 60 years old (including for example older than about any one of 70, 75, 80, 85, 90, 95, 100, or more than 100 years old). In some embodiments, the individual is diagnosed with or genetically prone to one or more of the PSMA-associated diseases or disorders described herein (e.g., prostate cancer (such as hormone-refractory or metastatic prostate cancer), renal cell cancer cell (such as clear cell renal cell cancer), uterine cancer, or liver cancer). In some embodiments, the individual has one or more risk factors associated with one or more PSMA-associated diseases or disorders described herein.

Also provided is a method of delivering an anti-PSMA construct (such as any one of the anti-PSMA constructs described herein) or an anti-PSMA construct combination (such as any one of the anti-PSMA construct combinations described herein) to a cell expressing PSMA (such as cell surface-bound PSMA), the method comprising administering to the individual a composition comprising the anti-PSMA construct or construct combination. In some embodiments, the anti-PSMA construct or construct combination to be delivered is associated with a cell (such as an effector cell, e.g., a T cell).

Many diagnostic methods for PSMA-associated cancer e.g., prostate cancer (such as hormone-refractory or metastatic prostate cancer), renal cell cancer cell (such as clear cell renal cell cancer), uterine cancer, or liver cancer) or any other PSMA-associated disease, e.g., a disease exhibiting PSMA expression and the clinical delineation of those diseases are known in the art. Such methods include, but are not limited to, e.g., immunohistochemistry, PCR, and fluorescent in situ hybridization (FISH).

In some embodiments, the anti-PSMA constructs, anti-PSMA construct combinations, and/or compositions of the present disclosure are administered in combination with a second, third, or fourth agent (including, e.g., an antineoplastic agent, a growth inhibitory agent, a cytotoxic agent, or a chemotherapeutic agent) to treat PSMA-associated diseases or disorders, e.g., diseases involving PSMA expression. In some embodiments, the anti-PSMA construct or construct combination is administered in combination with an agent that increases the expression PSMA on diseased cells (such as cancer cells). In some embodiments, the agent is a chemotherapeutic agent including, for example, topotecan, etoposide, cisplatin, paclitaxel, and vinblastine.

The efficacy of cancer treatments can be evaluated, for example, by a variety of well-known methods including, without limitation, e.g., tumor regression, tumor weight or size shrinkage, time to progression, duration of survival, progression free survival, overall response rate, duration of response, quality of life, PSMA protein expression and/or PSMA activity. Approaches to determining efficacy of the therapy can be employed, including for example, measurement of response through radiological imaging.

In some embodiments, the efficacy of a method of treatment is measured as the percentage tumor growth inhibition (% TGI), calculated using the equation $100-(T/C\times100)$, where T is the mean relative tumor volume of the treated tumor, and C is the mean relative tumor volume of a non-treated tumor. In some embodiments, the % TGI is about any one of 10%, 20%, 30%, 40%, 50%, 60%, 70%, 80%, 90%, 91%, 92%, 93%, 94%, 95%, or more than 95% (e.g., up to 100%), including any range in between these values.

Dosing and Administration of Anti-PSMA Constructs

The dose of a pharmaceutical composition comprising an anti-PSMA construct or construct combination described herein that is administered to an individual (such as a human) may vary with the particular composition, the mode of administration, and the type of disease being treated. In some embodiments, the amount of the pharmaceutical composition is effective to result in an objective response (e.g., in the case of solid tumor, a partial response (PR) or a complete response (CR), e.g., according to RECIST criteria described in Eisenhauer et al. (2009) *European Journal of Cancer*, 45 (2): 228-247 or Therasse et al. (2000) *J. Nat'l. Cancer Inst.* 92(3): 205-216). In some embodiments, the amount a composition comprising the anti-PSMA construct (or construct combination) administered to an individual in need thereof (for example when administered as a single agent) is sufficient to produce an overall response rate of more than about any one of 20%, 25%, 30%, 35%, 40%, 45%, 50%, 55%, 60%, 64%, 65%, 70%, 75%, 80%, 85%, or 90% among a population of individuals treated with a pharmaceutical composition comprising an anti-PSMA construct (or construct combination) described herein. Responses of an individual to the treatment of the methods described herein can be determined, for example, based on RECIST levels.

In some embodiments, the amount of the pharmaceutical composition administered to an individual in need thereof is sufficient to prolong progression-free survival of the individual. In some embodiments, the amount of the composition administered to an individual in need thereof is sufficient to prolong overall survival of the individual. In some embodiments, the amount of the composition administered to an individual in need thereof is sufficient to produce clinical benefit rate of more than about any of 50%, 60%, 70%, or 77% among a population of individuals treated with the anti-PSMA construct composition.

In some embodiments, the amount of the composition administered to an individual in need thereof (e.g., as a single agent or in combination with a second, third, and/or fourth agent), is sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% (including any range in between these values), as compared to the corresponding tumor size, number of cancer cells, or tumor growth rate in the same subject prior to treatment, or as compared to the corresponding activity in other subjects not receiving the treatment. Standard methods can be used to measure the magnitude of this effect, such as in vitro assays with purified enzyme, cell-based assays, animal models, or human testing.

In some embodiments, the amount of the anti-PSMA construct (e.g., full-length anti-PSMA antibody, multispecific anti-PSMA construct, an anti-PSMA CAR, an anti-PSMA chimeric antibody-T cell receptor construct (caTCR), an anti-PSMA chimeric signaling receptors (CSRs), an anti-PSMA immunoconjugate, or any other anti-PSMA construct or construct combination described in further detail elsewhere herein) in the pharmaceutical composition is below the level that induces a toxicological effect. In some embodiments, the amount of the anti-PSMA construct (e.g., full-length anti-PSMA antibody, multispecific anti-PSMA construct, an anti-PSMA CAR, an anti-PSMA chimeric antibody-T cell receptor construct (caTCR), an anti-PSMA chimeric signaling receptors (CSRs), an anti-PSMA immunoconjugate, or any other anti-PSMA construct or construct combination described in further detail elsewhere herein) in the pharmaceutical composition is at a level where a potential side effect can be controlled or tolerated when the composition is administered to the individual.

In some embodiments, the amount of the pharmaceutical composition administered to an individual in need thereof is close to a maximum tolerated dose (MTD) of the composition following the same dosing regimen. In some embodiments, the amount of the composition is more than about any of 80%, 90%, 95%, or 98% of the MTD.

In some embodiments, the amount of an anti-PSMA construct (e.g., full-length anti-PSMA antibody, multispecific anti-PSMA construct, an anti-PSMA CAR, an anti-PSMA chimeric antibody-T cell receptor construct (caTCR), an anti-PSMA chimeric signaling receptors (CSRs), an anti-PSMA immunoconjugate, or any other anti-PSMA construct or construct combination described in further detail elsewhere herein) in the pharmaceutical composition is included in a range of about 0.001 µg to about 1000 µg.

In some embodiments, the effective amount of an anti-PSMA construct (e.g., full-length anti-PSMA antibody, multispecific anti-PSMA construct, an anti-PSMA immunoconjugate, or any other anti-PSMA construct or construct combination described in further detail elsewhere herein) in the composition is in the range of about 0.1 µg/kg to about 100 mg/kg of total body weight.

A pharmaceutical compositions comprising an anti-PSMA construct or construct combination described herein may be administered to an individual (such as human) via any known available route, including, for example, intravenous, intraportal, intra-arterial, intraperitoneal, intrahepatic, hepatic arterial infusion, intrapulmonary, oral, inhalation, intravesicular, intramuscular, intra-tracheal, subcutaneous, intraocular, intrathecal, transmucosal, and transdermal. In some embodiments, a sustained continuous release formulation of a pharmaceutical composition comprising an anti-PSMA construct described herein can be used.

Anti-PSMA Effector Cell Therapy

In some embodiments, a method of treating a PSMA-associated disease or disorder comprises using an anti-PSMA effector cell (e.g., an anti-PSMA CAR effector cell, an anti-PSMA caTCR effector cell, an anti-PSMA caTCR plus tandem di-scFv effector cell, and/or an anti-PSMA caTCR plus CSR effector cell) to redirect the specificity of an effector cell (such as a primary T cell) to PSMA (e.g., PSMA expressed on or associated with the surface of a cell, such as a cancer cell). Thus, provided herein is a method of stimulating an effector cell-mediated response (such as a T cell-mediated immune response) to a target cell population and/or tissue (e.g., a target cell population and/or tissue comprising PSMA-expressing cells) in an individual, which method comprises the step of administering an anti-PSMA effector cell (such as a T cell) described herein to the individual.

Anti-PSMA effector cells (such as T cells), such as those described in further detail elsewhere herein, can be infused to an individual in need thereof (e.g., an individual who has or is suspected of having a PSMA-associated disease or disorder, such as cancer). The infused anti-PSMA effector cell is able to kill PSMA-expressing cells in the individual. Unlike therapeutic antibodies, anti-PSMA effector cells (such as T cells) are able to replicate in vivo, resulting in long-term persistence that can lead to sustained tumor control. In some embodiments, anti-PSMA effector cells (such as T cells) develop into specific memory T cells that can be reactivated to inhibit any additional tumor formation or growth.

The anti-PSMA effector cells (such as T cells) described herein may also serve as a type of vaccine for ex vivo immunization and/or in vivo therapy in an individual. In some embodiments, the individual is a mammal. In some embodiments, the mammal is a human or a non-human primate (such as a rhesus monkey or a cynomolgus monkey).

With respect to ex vivo immunization, of least one of the following occurs in vitro prior to administering the cell into the individual: i) expansion of the cells, ii) introducing a nucleic acid encoding an anti-PSMA CAR or an anti-PSMA caTCR to the cells, and/or iii) cryopreservation of the cells.

Ex vivo procedures are well known in the art and are discussed more fully below. Briefly, cells (e.g., T cells, such as αβ T cells, a γδ T cells, cytotoxic T cells, helper T cells, or natural killer T cells) are isolated from an individual (e.g., a mammal, preferably a human) and genetically modified (i.e., transduced or transfected, such as in vitro) with a nucleic acid, a set of nucleic acids, a vector, or a set of vectors encoding an anti-PSMA CAR, anti-PSMA caTCR, anti-PSMA tandem multispecific scFv (such as an anti-PSMA tandem di-scFv), and/or anti-PSMA CSR disclosed herein.

In some embodiments, the cell (e.g., a T cell, such as an αβ T cell, a γδ T cell, a cytotoxic T cell, a helper T cell, or a natural killer T cell) has been genetically modified (i.e., transduced or transfected, such as in vitro) with the nucleic acid, the set of nucleic acids, the vector, or the set of vectors encoding anti-PSMA CAR or anti-PSMA caTCR, and is further genetically modified (i.e., transduced or transfected, such as in vitro) with a nucleic acid, a set of nucleic acids, a vector, or a set of vectors encoding a multispecific scFv (such as a tandem di-scFv) or a CSR. In some embodiments, the cell (e.g., a T cell, such as an αβ T cell, a γδ T cell, a cytotoxic T cell, a helper T cell, or a natural killer T cell) been genetically modified (i.e., transduced or transfected, such as in vitro) with a nucleic acid, a set of nucleic acids, a vector, or a set of vectors that encode an anti-PSMA CAR or anti-PSMA caTCR and a multispecific scFv (such as a tandem di-scFv). In some embodiments, the cell (e.g., a T cell, such as an αβ T cell, a γδ T cell, a cytotoxic T cell, a helper T cell, or a natural killer T cell) been genetically modified (i.e., transduced or transfected, such as in vitro) with a nucleic acid, a set of nucleic acids, a vector, or a set of vectors that encode an anti-PSMA CAR or anti-PSMA caTCR and a CSR. In some embodiments, the multispecific scFv (e.g., a tandem di-scFv) targets PSMA. In some embodiments, the multispecific scFv (e.g., a tandem di-scFv) targets a different antigen (e.g., an antigen other than PSMA). In some embodiments, the CSR targets PSMA. In some embodiments, the CSR targets a different antigen (e.g., an antigen other than PSMA).

In some embodiments, the cell (e.g., a T cell, such as an αβ T cell, a γδ T cell, a cytotoxic T cell, a helper T cell, or a natural killer T cell) has been genetically modified (i.e., transduced or transfected, such as in vitro) with the nucleic acid, the set of nucleic acids, the vector, or the set of vectors encoding the anti-PSMA tandem multispecific scFv (such as a tandem di-scFv) or the anti-PSMA CSR, and is further genetically modified (i.e., transduced or transfected, such as in vitro) with a nucleic acid, a set of nucleic acids, a vector, or a set of vectors encoding a CAR or caTCR. In some embodiments, the cell (e.g., a T cell, such as an αβ T cell, a γδ T cell, a cytotoxic T cell, a helper T cell, or a natural killer T cell) been genetically modified (i.e., transduced or transfected, such as in vitro) with a nucleic acid, a set of nucleic acids, a vector, or a set of vectors that encode an anti-PSMA tandem multispecific scFv (such as a tandem di-scFv) or anti-PSMA CSR and a CAR. In some embodiments, the cell (e.g., a T cell, such as an αβ T cell, a γδ T cell, a cytotoxic T cell, a helper T cell, or a natural killer T cell) been genetically modified (i.e., transduced or transfected, such as in vitro) with a nucleic acid, a set of nucleic acids, a vector, or a set of vectors that encode an anti-PSMA tandem multispecific scFv (such as a tandem di-scFv) or anti-PSMA CSR and a caTCR. In some embodiments, the CAR targets PSMA. In some embodiments, the CAR targets a different antigen (e.g., an antigen other than PSMA). In some embodiments, the caTCR targets PSMA. In some embodiments, the caTCR targets a different antigen (e.g., an antigen other than PSMA).

In some embodiments, the cells (e.g., T cells, such as αβ T cells, γδ T cells, cytotoxic T cells, helper T cells, or natural killer T cells) that have been genetically modified (i.e., transduced or transfected, such as in vitro) as described above are administered to a recipient. In some embodiments, the recipient is a mammal, such as a human, e.g., a human who has or is suspected of having the PSMA-associated disease. In some embodiments, the recipient to whom the genetically modified cells are administered is the individual from whom the cells were obtained. Such a genetically modified immune cell is referred to as an "autologous anti-PSMA effector cell." In some embodiments, the recipient to whom the genetically modified immune cells are administered is not the individual from whom the cells were obtained. Such a genetically modified immune cell is referred to as a "heterologous anti-PSMA effector cell." In some embodiments, the heterologous anti-PSMA effector cell is allogeneic, syngeneic, or xenogeneic with respect to the recipient.

The procedure for ex vivo expansion of hematopoietic stem and progenitor cells is described in U.S. Pat. No. 5,199,942, incorporated herein by reference in its entirety. Other suitable methods are also known in the art, and the present disclosure is not limited to any particular method of ex vivo expansion of the cells. Briefly, ex vivo culture and expansion of T cells comprises: (1) collecting CD34+ hematopoietic stem and progenitor cells from an individual (e.g., a mammal such as a human) from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present disclosure also provides compositions and methods for in vivo immunization to elicit an immune response directed against an antigen in an individual in need thereof (e.g., an individual who has or is suspected of having a PSMA-associated disease, such as cancer).

The anti-PSMA effector cells (such as T cells) of the present disclosure may be administered either alone, or as a pharmaceutical composition in combination with diluents and/or with other components such as IL-2 or other cytokines or cell populations. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In some embodiments, effector cell (such as T cell) compositions are formulated for intravenous administration.

The precise amount of the anti-PSMA effector cell (such as T cell) of the present disclosure to be administered to an individual in need thereof can be determined by a physician with consideration of the individual's age, weight, tumor size, stage and/or severity of the disease, presence or absence of metastasis, condition of the individual, and other factors. In some embodiments, a pharmaceutical composition comprising anti-PSMA effector cells (such as T cells) of the present disclosure is administered at a dosage of about $10^4$ to about $10^9$ cells/kg body weight, such any of about $10^4$ to about $10^5$, about $10^5$ to about $10^6$, about $10^6$ to about $10^7$, about $10^7$ to about $10^8$, or about $10^8$ to about $10^9$ cells/kg body weight, including all integer values within those ranges. Anti-PSMA effector cell (such as T cell) compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regimen for a particular patient can readily be determined by one skilled in the art of medicine by monitoring the patient for signs of disease and adjusting the treatment accordingly.

In some embodiments, it may be desirable to administer activated anti-PSMA effector cells (such as T cells) described herein to an individual, subsequently redraw blood (or have an apheresis performed), activate the anti-PSMA effector cells (e.g., anti-PSMA T cells) described herein obtained from the redrawn blood, and reinfuse the individual with the activated and expanded anti-PSMA effector cells (e.g., anti-PSMA T cells). In some embodiments, this process is carried out multiple times every few weeks. In some embodiments, the anti-PSMA effector cells (e.g., anti-PSMA T cells) are activated from blood draws of from 10 cc to 400 cc. In some embodiments, the anti-PSMA effector cells (e.g., anti-PSMA T cells) are activated from blood draws of 20 cc, 30 cc, 40 cc, 50 cc, 60 cc, 70 cc, 80 cc, 90 cc, or 100 cc.

The administration anti-PSMA effector cells (e.g., anti-PSMA T cells) described herein may be carried out in any convenient manner, including by aerosol inhalation, injection, ingestion, transfusion, implantation or transplantation. Compositions comprising anti-PSMA effector cells (e.g., anti-PSMA T cells) described herein may be administered to a patient subcutaneously, intradermally, subcutaneously, intratumorally, intranodally, intramedullary, intramuscularly, by intravenous (i.v.) injection, or intraperitoneally. In some embodiments, compositions comprising anti-PSMA effector cells (e.g., anti-PSMA T cells) of the present disclosure are administered by i.v. injection directly into a tumor, lymph node, or site of disease.

Provided are methods of treating a PSMA-associated disease in an individual that comprise administering to the individual an effective amount of a composition comprising an anti-PSMA effector cell (e.g., anti-PSMA T cell) of the present disclosure. In some embodiments, the PSMA-associated disease is cancer. In some embodiments, the cancer is, for example, prostate cancer (such as hormone-refractory or metastatic prostate cancer), renal cell cancer cell (such as clear cell renal cell cancer), uterine cancer, or liver cancer. In some embodiments, the individual is human. In some embodiments, the individual to whom the composition comprising an anti-PSMA effector cell (e.g., anti-PSMA T cell) is administered is an individual who has (e.g., has been diagnosed with) or is suspected of having a PSMA-associated disease. In some embodiments, the PSMA-associated disease is refractory to at least one conventional treatment. In some embodiments, the individual to whom the composition comprising an anti-PSMA effector cell (e.g., anti-PSMA T cell) is administered is an individual who has (e.g., has been diagnosed with) a PSMA-associated disease and has relapsed following at least one conventional treatment for the PSMA-associated diseases.

Cancers

The anti-PSMA constructs and effector cells described herein may be used in the treatment of cancer, e.g., a PSMA-associated cancer. Cancers that may be treated using any of the methods described herein include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the anti-PSMA constructs and effector cells described herein include, but are not limited to, carcinomas, blastomas, and sarcomas, and leukemias or lymphoid malignancies, benign and malignant tumors, and malignancies e.g., melanomas. Adult tumors/cancers and pediatric tumors/cancers are also contemplated.

Hematologic cancers are cancers of the blood or bone marrow. Examples of hematological (or hematogenous) cancers include leukemias, e.g., acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, liver cancer, pancreatic cancer, uterine cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer (e.g., cervical carcinoma and pre-invasive cervical dysplasia), cancer of the anus, anal canal, or anorectum, vaginal cancer, cancer of the vulva (e.g., squamous cell carcinoma, intraepithelial carcinoma, adenocarcinoma, and fibrosarcoma), penile cancer, oropharyngeal cancer, head cancers (e.g., squamous cell carcinoma), neck cancers (e.g., squamous cell carcinoma), testicular cancer (e.g., seminoma, teratoma, embryonal carcinoma, teratocarcinoma, choriocarcinoma, sarcoma, Leydig cell tumor, fibroma, fibroadenoma, adenomatoid tumors, and lipoma), bladder carcinoma, melanoma, cancer of the uterus (e.g., endometrial carcinoma), urothelial cancers (e.g., squamous cell carcinoma, transitional cell carcinoma, adenocarcinoma, ureter cancer, and urinary bladder cancer), and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In some embodiments, the PSMA-overexpression cancer is prostate cancer. In some embodiments, the prostate cancer is an adenocarcinoma. In some embodiments, the prostate cancer is a sarcoma, neuroendocrine tumor, small cell cancer, ductal cancer, or a lymphoma. In some embodiments, the prostate cancer is at any of the four stages, A, B, C, or D, according to the Whitmore-Jewett staging system, the TNM (i.e., Tumors, Nodes, Metastasis) staging system, or the AUA (Modified Whitmore-Jewett) staging system. In some embodiments, the prostate cancer is stage A prostate cancer (e.g., the cancer cannot be felt during a rectal exam). In some embodiments, the prostate cancer is stage B prostate cancer (e.g., the tumor involves more tissue within the prostate, and can be felt during a rectal exam, or is found with a biopsy that is done because of a high PSA level). In some embodiments, the prostate cancer is stage C prostate cancer (e.g., the cancer has spread outside the prostate to nearby tissues). In some embodiments, the prostate cancer is stage D prostate cancer. In some embodiments, the prostate cancer is androgen independent prostate cancer (AIPC). In some embodiments, the prostate cancer is androgen dependent prostate cancer. In some embodiments, the prostate cancer is refractory to hormone therapy.

Cancer treatments can be evaluated, for example, by tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

Methods for Diagnosis and Imaging

Labeled anti-PSMA constructs described herein (e.g., constructs that specifically bind to PSMA expressed on the surface of a cell, such as a cancer cell) may be used for diagnostic purposes to, e.g., detect, diagnose, monitor the progression of a PSMA-associated disease or disorder, e.g., a disease or disorder associated with the expression, aberrant expression and/or activity of PSMA, and/or monitor a patients response to treatment for a PSMA-associated disease. Exemplary PSMA-associated diseases or disorders include any of the diseases and disorders described herein, such as cancer (e.g., prostate cancer (such as hormone-refractory or metastatic prostate cancer), renal cell cancer cell (such as clear cell renal cell cancer), uterine cancer, or liver cancer). For example, the anti-PSMA constructs described herein can be used in in situ, in vivo, ex vivo, and in vitro diagnostic assays or imaging assays.

In some embodiments, provided are methods of diagnosing a disease or disorder associated with expression or aberrant expression of PSMA in an individual (e.g., a mammal, such as a human or a non-human primate, such as a rhesus monkey or a cynomolgus monkey). The methods comprise detecting cells that aberrantly express PSMA in the individual. In some embodiments, provided is a method of diagnosing a PSMA-associated disease or disorder in an individual (e.g., a mammal, such as a human or a non-human primate, such as a rhesus monkey or a cynomolgus monkey) comprising (a) administering an effective amount of a labeled anti-PSMA construct described herein to the individual; and (b) determining the level of the label in the individual, such that a level of the label above a threshold level indicates that the individual has the disease or disorder. The threshold level can be determined by various methods, including, for example, by detecting the label according to the method of diagnosing described herein in a first set of individuals that have the disease or disorder and a second set of individuals that do not have the disease or disorder, and setting the threshold to a level that allows for discrimination between the first and second sets. In some embodiments, the threshold level is zero, and the method comprises determining the presence or absence of the label in the individual. In some embodiments, the method further comprises waiting for a time interval following the administering of step (a) to permit the labeled anti-PSMA construct to preferentially concentrate at sites in the individual where the PSMA is expressed (and for unbound labeled anti-PSMA construct to be cleared). In some embodiments, the method further comprises subtracting a background level of the label. Background level can be determined by various methods, including, for example, by detecting the label in the individual prior to administration of the labeled anti-PSMA construct, or by detecting the label according to the method of diagnosing described herein in an individual that does not have the disease or disorder. In some embodiments, the disease or disorder is cancer. In some embodiments, the cancer is selected, for example, from the group consisting of prostate cancer (such as hormone-refractory or metastatic prostate cancer), renal cell cancer cell (such as clear cell renal cell cancer), uterine cancer, or liver cancer. In some embodiments, the individual is human. In some embodiments, the individual is suspected of having a disease or disorder associated with expression, aberrant expression and/or activity of PSMA.

In some embodiments, provided is a method of diagnosing a PSMA-associated disease or disorder in an individual (e.g., a mammal, such as a human or a non-human primate, such as a rhesus monkey or a cynomolgus monkey), comprising (a) contacting a labeled anti-PSMA construct according to any of the embodiments described herein with a sample (such as homogenized tissue) obtained or derived from the individual; and (b) determining the number of cells bound with the labeled anti-PSMA construct in the sample, such that a value for the number of cells bound with the labeled anti-PSMA construct above a threshold level indicates that the individual has the disease or disorder. The threshold level can be determined by various methods, including, for example, by determining the number of cells bound with the labeled anti-PSMA construct according to the method of diagnosing described herein in a first set of individuals that have the disease or disorder and a second set of individuals that do not have the disease or disorder, and setting the threshold to a level that allows for discrimination between the first and second sets. In some embodiments, the threshold level is zero, and the method comprises determining the presence or absence of cells bound with the labeled anti-PSMA construct in the sample. In some embodiments, the method further comprises subtracting a background level of the number of cells bound with the labeled anti-PSMA construct. Background level can be determined by various methods, including, for example, by determining the number of cells bound with the labeled anti-PSMA construct in the individual prior to administration of the labeled anti-PSMA construct, or by determining the number of cells bound with the labeled anti-PSMA construct according to the method of diagnosing described herein in an individual that does not have the disease or disorder. In some embodiments, the disease or disorder is cancer. In some embodiments, the cancer is selected, for example, from the group consisting of prostate cancer (such as hormone-refractory or metastatic prostate cancer), renal cell cancer cell (such as clear cell renal cell cancer), uterine cancer, or liver cancer. In some embodiments, the cancer is metastatic. In some embodiments, the individual is human. In some embodiments, the individual is suspected of having a PSMA-associated disease or disorder.

In some embodiments, there is provided a method of diagnosing a PSMA-associated cancer in an individual (e.g., a mammal, such as a human or a non-human primate, such as a rhesus monkey or a cynomolgus monkey), comprising (a) contacting a labeled anti-PSMA construct according to any of the embodiments described herein with a tissue sample derived from the individual; and (b) determining the number of cells in the tissue sample bound with the labeled anti-PSMA construct, such that a value for the number of cells in the tissue sample bound with the labeled anti-PSMA construct above a threshold level indicates that the individual has a PSMA-associated cancer. The threshold level can be determined by various methods, including, for example, by determining the number of cells bound with the labeled anti-PSMA construct according to the method of diagnosing described herein in tissue samples from a first set of individuals who have a PSMA-associated and tissue samples from a second set of individuals who do not have a PSMA-associated cancer, and setting the threshold to a level that allows for discrimination between the tissue samples from the first and second sets. In some embodiments, the threshold level is zero, and the method comprises determining the presence or absence of cells in the tissue sample bound with the labeled anti-PSMA antibody moiety. In some embodiments, the method further comprises subtracting a background level of the number of cells bound with the labeled anti-PSMA construct. Background level can be determined by various methods, including, for example, by determining the number of cells in the tissue sample bound with the labeled anti-PSMA construct in the individual prior to contacting with the labeled anti-PSMA construct, or by determining the number of cells in a tissue sample bound with the labeled anti-PSMA construct according to the method of diagnosing described herein, which tissue sample is obtained or derived from an individual that does not have a PSMA-associated cancer. In some embodiments, the PSMA-associated cancer is selected, for example, from the group consisting of prostate cancer (such as hormone-refractory or metastatic prostate cancer), renal cell cancer cell (such as clear cell renal cell cancer), uterine cancer, or liver cancer. In some embodiments, the individual is human. In some embodiments, the individual is suspected of having a PSMA-associated cancer.

The anti-PSMA constructs provided herein may be used to assay levels of PSMA in a biological sample using methods known to those of skill in the art. Suitable labels are known in the art and include enzyme labels, such as, glucose oxidase; radioisotopes, such as iodine ($^{131}$I, $^{125}$I, $^{123}$I, $^{121}$I) carbon ($^{14}$C), sulfur ($^{35}$S), tritium ($^{3}$H), indium ($^{115m}$In, $^{113m}$In, $^{112}$In, $^{111}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon (133Xe), fluorine ($^{18}$F), samarium ($^{153}$Sm), lutetium ($^{77}$Lu), gadolinium ($^{159}$Gd), promethium ($^{149}$Pm), lanthanum ($^{140}$La), ytterbium ($^{75}$Yb), holmium ($^{166}$Ho), yttrium ($^{90}$Y), scandium ($^{47}$Sc), rhenium ($^{186}$Re, $^{188}$Re), praseodymium ($^{142}$Pr), rhodium ($^{105}$Rh), and ruthenium ($^{97}$Ru); luminol; fluorescent labels, such as fluorescein and rhodamine; and biotin.

Techniques known in the art may be applied to labeled anti-PSMA constructs provided herein. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003). Aside from the above assays, various in vivo and ex vivo assays are available to the skilled practitioner. For example, one can expose cells within the body of the subject to an anti-PSMA construct which is optionally labeled with a detectable label, e.g., a radioactive isotope, and binding of the anti-PSMA antibody moiety to the cells can be evaluated, e.g., by external scanning for radioactivity or by analyzing a sample (e.g., a biopsy or other biological sample) derived from a subject previously exposed to the anti-PSMA construct.

Articles of Manufacture and Kits

Provided herein are articles of manufacture that comprise materials useful for the diagnosis or treatment of a PSMA-associated disease, such as cancer (for example prostate cancer (such as hormone-refractory or metastatic prostate cancer), renal cell cancer cell (such as clear cell renal cell cancer), uterine cancer, or liver cancer), for delivering an anti-PSMA construct or construct combination to a cell expressing PSMA on its surface, or for isolation or detection of PSMA-expressing cells in an individual. The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for diagnosing or treating a PSMA-associated disease or disorder described herein, and may have a sterile access port (for example the container may be an intravenous solution bag or a vial having a stopper pierceable by a hypodermic injection needle). At least one active agent in the composition is an anti-PSMA construct or construct combination provided herein. The label or package insert indicates that the composition is used for treating the particular condition. The label or package insert will further comprise instructions for administering the anti-PSMA construct or construct combination (or, e.g., a composition comprising such construct or construct combination) to an individual in need thereof (e.g., an individual having or suspected of having a PSMA-associated disease or disorder. Articles of manufacture and kits comprising combinatorial therapies (e.g., one or more therapeutic agents in addition to an anti-PSMA construct or construct combination described herein) are also contemplated.

A package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating PSMA-associated cancer (e.g., prostate cancer (such as hormone-refractory or metastatic prostate cancer), renal cell cancer cell (such as clear cell renal cell cancer), uterine cancer, or liver cancer).

Additionally, the article of manufacture may further comprise a second container comprising a pharmaceutically-acceptable buffer, such as bacteriostatic water for injection (BWFI), sterile water for injection (SWFI) phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for treatment of a PSMA-associated disease or disorder described herein, for delivering an anti-PSMA construct or construct combination to a cell expressing PSMA on its surface, or for isolation or detection of PSMA-binding cells in an individual, optionally in combination with the articles of manufacture. Kits provided herein include one or more containers comprising a composition comprising an anti-PSMA construct or construct combination (or unit dosage form thereof and/or article of manufacture), and in some embodiments, further comprise another agent (such as the agents described herein) and/or instructions for use in accordance with any of the methods described herein. The kit may further comprise a description of selection of individuals suitable for treatment. Instructions supplied in the kits herein are typically written instructions on a label or package insert (e.g., a paper sheet included in the kit), but machine-readable instructions (e.g., instructions carried on a magnetic or optical storage disk) are also acceptable.

For example, in some embodiments, the kit comprises a composition comprising an anti-PSMA construct (e.g., a full-length anti-PSMA antibody, a mono-specific anti-PSMA construct, a multispecific anti-PSMA construct (such as a bispecific anti-PSMA antibody), or an anti-PSMA immunoconjugate) or an anti-PSMA construct combination (e.g., an anti-PSMA caTCR+anti-PSMA CSR). In some embodiments, the kit comprises a) a composition comprising an anti-PSMA construct or construct combination, and b) an effective amount of at least one other therapeutic agent. In some embodiments, the kit comprises a) a composition comprising an anti-PSMA construct or construct combination, and b) instructions for administering the composition to an individual for treatment of a PSMA-associated disease, including for example prostate cancer (such as hormone-refractory or metastatic prostate cancer), renal cell cancer cell (such as clear cell renal cell cancer), uterine cancer, or liver cancer. The anti-PSMA construct (or construct combination) and the other agent(s) can be present in separate containers or in a single container. For example, the kit may comprise one distinct composition or two or more compositions wherein one composition comprises an anti-PSMA construct or construct combination and another composition comprises another agent.

In some embodiments, the kit comprises a) a composition comprising an anti-PSMA construct (e.g., a full-length anti- PSMA antibody, a mono-specific anti-PSMA construct, a multispecific anti-PSMA construct (such as a bispecific anti-PSMA antibody), an anti-PSMA immunoconjugate, or other anti-PSMA construct described herein) or an anti-PSMA construct combination (e.g., an anti-PSMA caTCR+ anti-PSMA CSR), and b) instructions for combining the anti-PSMA construct or construct combination with cells (such as cells, e.g., immune cells, derived from an individual) to form a composition comprising anti-PSMA construct-cell conjugates and administering the anti-PSMA construct-cell conjugate composition to the individual for treatment of a PSMA-associated disease (including for example prostate cancer (such as hormone-refractory or metastatic prostate cancer), renal cell cancer cell (such as clear cell renal cell cancer), uterine cancer, or liver cancer). In some embodiments, the kit comprises a) a composition comprising an anti-PSMA construct or construct combination (such as described herein), and b) a cell (such as a cytotoxic cell). In some embodiments, the kit comprises a) a composition comprising an anti-PSMA construct or construct combination (such as described herein), b) a cell (such as a cytotoxic cell), and c) instructions for combining the anti-PSMA construct or construct combination with the cell to form a composition comprising anti-PSMA construct-cell conjugates and administering the anti-PSMA construct-cell conjugate composition to an individual for the treatment of a PSMA-associated disease, including for example prostate cancer (such as hormone-refractory or metastatic prostate cancer), renal cell cancer cell (such as clear cell renal cell cancer), uterine cancer, or liver cancer. In some embodiments, the kit comprises a composition comprising an anti-PSMA construct or construct combination (such as described herein) in association with a cell (such as a cytotoxic cell). In some embodiments, the kit comprises a) a composition comprising an anti-PSMA construct or construct combination (such as described herein) in association with a cell (such as a cytotoxic cell), and b) instructions for administering the composition to an individual for the treatment of a PSMA-associated disease, including for example prostate cancer (such as hormone-refractory or metastatic prostate cancer), renal cell cancer cell (such as clear cell renal cell cancer), uterine cancer, or liver cancer. In some embodiments, the association is by conjugation of the anti-PSMA construct or construct combination to a molecule on the surface of the cell. In some embodiments, the association is by insertion of a portion of the anti-PSMA construct or construct combination into the outer membrane of the cell.

In some embodiments, the kit comprises a nucleic acid (or set of nucleic acids) encoding an anti-PSMA construct (e.g., a full-length anti-PSMA antibody, a mono-specific anti-PSMA construct, a multispecific anti-PSMA construct, e.g., a bispecific anti-PSMA construct (such as a bispecific anti-PSMA antibody, e.g., anti-PSMA tandem di-scFv), an anti-PSMA CAR, an anti-PSMA immunoconjugate, or other anti-PSMA construct described herein), an anti-PSMA construct combination described herein, or the polypeptide portion(s) thereof. In some embodiments, the kit comprises a) a nucleic acid (or set of nucleic acids) encoding an anti-PSMA construct (or construct combination) or polypeptide portion(s) thereof, and b) a host cell (such as an effector cell, e.g., a T cell) for expressing the nucleic acid (or set of nucleic acids). In some embodiments, the kit comprises a) a nucleic acid (or set of nucleic acids) encoding an anti-PSMA construct (or construct combination) or polypeptide portion(s) thereof, and b) instructions for i) expressing the anti-PSMA construct (or construct combination) in a host cell (such as an effector cell, e.g., a T cell), ii) preparing a composition comprising the anti-PSMA construct (or construct combination) or the host cell (e.g., effector cell, e.g., T cell) expressing the anti-PSMA construct (or construct combination), and iii) administering the composition comprising the anti-PSMA construct (or construct combination) or the host cell expressing the anti-PSMA construct (or construct combination) to an individual for the treatment of a PSMA-associated disease, including for example prostate cancer (such as hormone-refractory or metastatic prostate cancer), renal cell cancer cell (such as clear cell renal cell cancer), uterine cancer, or liver cancer. In some embodiments, the host cell (e.g., effector cell, such as a T cell) is derived from the individual. In some embodiments, the kit comprises a) a nucleic acid (or set of nucleic acids) encoding an anti-PSMA construct (or construct combination) or polypeptide portion(s) thereof, b) a host cell (such as an effector cell, e.g., a T cell) for expressing the nucleic acid (or set of nucleic acids), and c) instructions for i) expressing the anti-PSMA construct (or construct combination) in the host cell, ii) preparing a composition comprising the anti-PSMA construct (or construct combination) or the host cell expressing the anti-PSMA construct (or construct combination), and iii) administering the composition comprising the anti-PSMA construct (or construct combination) or the host cell expressing the anti-PSMA construct (or construct combination) to an individual for the treatment of a PSMA-associated disease, including for example prostate cancer (such as hormone-refractory or metastatic prostate cancer), renal cell cancer cell (such as clear cell renal cell cancer), uterine cancer, or liver cancer.

In some embodiments, the kit comprises a nucleic acid encoding an anti-PSMA CAR. In some embodiments, the kit comprises a vector comprising a nucleic acid encoding an anti-PSMA CAR. In some embodiments, the kit comprises a) a vector comprising a nucleic acid encoding an anti-PSMA CAR, and b) instructions for i) introducing the vector into effector cells, such as T cells derived from an individual, ii) preparing a composition comprising the anti-PSMA CAR effector cells, and iii) administering the anti-PSMA CAR effector cell composition to the individual for treatment of a PSMA-associated disease, including for example prostate cancer (such as hormone-refractory or metastatic prostate cancer), renal cell cancer cell (such as clear cell renal cell cancer), uterine cancer, or liver cancer.

In some embodiments, the kit comprises a nucleic acid encoding an anti-PSMA caTCR. In some embodiments, the kit comprises a vector comprising a nucleic acid encoding an anti-anti-PSMA caTCR. In some embodiments, the kit further comprises nucleic acid(s) encoding a bispecific construct, e.g., a tandem di-scFv (e.g., an anti-PSMA tandem di-scFv) or a CSR (such as an anti-PSMA CSR). In some embodiments, the kit comprises a) a vector comprising a nucleic acid encoding an anti-PSMA caTCR, and b) instructions for i) introducing the vector into effector cells, such as T cells derived from an individual, ii) preparing a composition comprising the anti-PSMA caTCR effector cells, and iii) administering the anti-PSMA caTCR effector cell composition to the individual for treatment of a PSMA-associated disease, including for example prostate cancer (such as hormone-refractory or metastatic prostate cancer), renal cell cancer cell (such as clear cell renal cell cancer), uterine cancer, or liver cancer. In some embodiments, the kit further comprises a) vector(s) comprising a nucleic acid that encodes a bispecific construct, e.g., a tandem di-scFv (such as an anti-PSMA tandem scFv), and b) instructions for i) introducing the vector(s) encoding the tandem di-scFv into the host cell simultaneously or sequentially with the vector encoding the anti-PSMA caTCR, ii) preparing a composition comprising the anti-PSMA caTCR plus tandem di-scFv effector cells, and iii) administering the anti-PSMA caTCR plus tandem di-scFv effector cell composition to the individual for treatment of a PSMA-associated disease, including for example prostate cancer (such as hormone-refractory or metastatic prostate cancer), renal cell cancer cell (such as clear cell renal cell cancer), uterine cancer, or liver cancer. In some embodiments, the kit further comprises a) vector(s) comprising a nucleic acid that encodes a CSR (such as an anti-PSMA CSR), and b) instructions for i) introducing the vector(s) encoding the CSR into the host cell simultaneously or sequentially with the vector encoding the anti-PSMA caTCR, ii) preparing a composition comprising the anti-PSMA caTCR plus CSR effector cells, and iii) administering the anti-PSMA caTCR plus CSR effector cell composition to the individual for treatment of a PSMA-associated disease, including for example prostate cancer (such as hormone-refractory or metastatic prostate cancer), renal cell cancer cell (such as clear cell renal cell cancer), uterine cancer, or liver cancer.

The kits described herein are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of compositions comprising an anti-PSMA construct (or construct combination) generally include information as to dosage, dosing schedule, and route of administration for the intended treatment. The containers may be unit doses, bulk packages (e.g., multi-dose packages) or sub-unit doses. For example, kits may be provided that contain sufficient dosages of an anti-PSMA construct (e.g., a full-length anti-PSMA antibody, a multi-specific anti-PSMA molecule (such as a bispecific anti-PSMA antibody), an anti-PSMA CAR, an anti-PSMA immunoconjugate, or other anti-PSMA construct or construct combination described herein) to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the anti-PSMA construct (or construct combination) and pharmaceutical compositions and instructions for use and packaged in quantities sufficient for storage and use in pharmacies, for example, hospital pharmacies and compounding pharmacies.

Those skilled in the art will recognize that several embodiments are possible within the scope and spirit of this application. The embodiments will now be described in greater detail by reference to the following non-limiting examples. The following examples further illustrate the methods and compositions of the present disclosure but, of course, should not be construed as in any way limiting its scope.

EXAMPLES

Example 1: Materials and Methods

The reagents discussed below are used in Examples 2-9.

The cell lines include: prostate cancer cell lines: LNCaP (ATCC CRL-1740, PSMA positive), PC-3 (ATCC CRL-1438, PSMA negative), PC-3-PSMA (PC-3 engineered to express PSMA by lentiviral transduction), T cell line: Jurkat Clone E61 (ATCC TIB-152) and Jurkat-PSMA (Jurkat engineered to express PSMA by lentiviral transduction). The cell lines were cultured in RPMI 1640 (Hyclone, SH30027.02) supplemented with 10% FBS, 2.05 mM L-glutamine at 37° C./5% $CO_2$.

Additional PSMA-positive human cancer cell lines used in the examples below include MDA PCa 2b, VCaP, 22Rv1, Caki-1, HCC1482, and HuH-7. The following PSMA-negative human cancer cell lines are also used: PrEC LH, PC-3, NCI-H660, and DU 145.

Example 2: Selection and Characterization of scFv Specific for PSMA

Identification of PSMA-Specific Antibodies

A collection of human scFv antibody phage display libraries (diversity=10×10$^{10}$) constructed by Eureka Therapeutics (i.e., the E-ALPHA® phage display library) was used for the selection of human mAbs specific to PSMA. Specifically, the E-ALPHA® phage display library was used to pan against a Jurkat cell line that has been engineered to express PSMA. The parental Jurkat cell line was used for negative selection. Two unique scFv clones isolated in this screen, i.e., Clone A and Clone B, were found to be specific for PSMA by flow cytometry assay. The sequences of Clone A and Clone B are provided in Table 13 below. The V$_L$ in each scFv is underlined, the V$_H$ in each scFv is double underlined, and the linker is in bold italic type. The CDRs are in underlined bold type and double underlined bold type.

TABLE 13

Anti-PSMA scFv Clones

| | |
|---|---|
| Clone A | QSVLTQPPS VSGAPGQRV TISCTGSSS NIGAGYDVH WYQQLPGTA PKLLIYGNS NRPSGVPDR FSGSKSGTS ASLAITGLQ AEDEADYYC QSYDSSLSG YVFGTGTKV TVLG*SRGGG GSGGGGSGG GGSLEMA*EV QLVQSGAEV KKPGESLKI SCKGSGYSF TSYWIGWVR QMPGKGLEW MGIIYPGDS DTRYSPSFQ GQVTISADK SISTAYLQW SSLKASDTA MYYCARSMG SSLYASSDV WGQGTLVTV SS (SEQ ID NO: 20) |
| Clone B | QAVLTQPPS ASGTPGQRV TISCSGSSS NIGSNTVNW YQQLPGTAP KLLMYSNNQ RPSGVPDRF SGSKSGTSA SLAISGLQS EDEADYYCA AWDDSLNGY VFGTGTKVT VLG*SRGGGG SGGGGSGGG GSLEMA*EVQ LVQSGAEMK KPGESLKIS CKGSGYNFA SYWVGWVRQ MPGKGLEWM GTIYPDDSD TRYGPAFQG QVTISADKS ISTAYLQWS SLKASDTAM YYCARDSYY GIDVWGQGT LVTVSS (SEQ ID NO: 21) |

The binding specificities of Clone A and Clone B against PSMA-positive cell lines and PSMA-negative cell lines were evaluated via flow cytometry. The PSMA-positive cell lines included LNCaP, a PSMA-expressing human prostate adenocarcinoma cell line; PC3-PSMA, a PSMA-negative human prostate cancer cell line engineered to express hPSMA; and Jurkat-PSMA, i.e., a PSMA-negative human T lymphocyte cell line engineered to express hPSMA. The PSMA-native cell lines included: PC3 and Jurkat. As shown in FIG. 1, both Clones A and B demonstrated specific binding to PSMA-expressing cell lines.

Example 3: Characterization of T Cells Expressing Anti-PSMA CAR Constructs in Cytotoxicity Assays and Interferon-γ (IFN-γ) Release Assays To evaluate Clone A and Clone B in their abilities to redirect T cells and lead to cellular cytotoxicity and IFN-γ release, nucleic acids encoding Clone A and Clone B ScFvs were cloned into a CD28/CD3ζ chimeric antigen receptor (CAR) construct, and each CAR (i.e., Clone A-CAR and Clone-B CAR) was transduced into primary human T cells. The amino acid sequences of Clone A-CAR and Clone B-CAR are provided in Table 14 below. Each CAR comprises (sequentially, from the N-terminus to the C-terminus) an anti-PSMA scFv (underlined), a myc tag (bold underlined), a linker (bold italic type), sequences derived from CD28 (double underlined), and sequences derived from CD3ζ (bold double underlined).

TABLE 14

| Clone A-CAR |
|---|
| QSVLTQPPSVSGAPGQRVTISCTGSSSNIGAGYDVHWYQQLPGTAPKLLIYGNSNRPSGVPDRFSGSKSGTSASLAITGLQ |
| AEDEADYYCQSYDSSLSGYVFGTGTKVTVLGSRGGGGSGGGSLEMAEVQLVQSGAEVKKPGESLKISCKGSGYSF |
| TSYWIGWVRQMPGKGLEWMGITYPGDSDTRYSPSFQGQVTISADKSISTAYLQWSSLKASDTAMYYCARSMGSSLYASSDV |
| WGQGTLVTVSSEQKLISEEDLAAAIEVMYPPPYLDNEKSNGTIIHVKGKHLCPSPLFPGPSKPFWVLVVVGGVLACYSLLV |
| TVAFTIFWVRSKRSRLLHSDYMNMTPRRPGPTRKHYQPYAPPRDFAAYRSRVKFSRSADAPAYQQGQNQLYNELNLGRREE |
| YDVLDKRRGRDPEMGGKPRRKNPQEGLYNELQKDKMAEAYSEIGMKGERRRGKGHDGLYQGLSTATKDTYDALHMQALPPR |
| (SEQ ID NO: 29) |

| Clone B-CAR |
|---|
| QAVLTQPPSASGTPGQRVTISCSGSSSNIGSNTVNWYQQLPGTAPKLLMYSNNQRPSGVPDRFSGSKSGTSASLAISGLQS |
| EDEADYYCAAWDDSLNGYVFGTGTKVTVLGSRGGGGSGGGGSGGGGSLEMAEVQLVQSGAEMKKPGESLKISCKGSGYNFA |
| SYWVGWVRQMPGKGLEWMGTIYPDDSDTRYGPAFQGQVTISADKSISTAYLQWSSLKASDTAMYYCARDSYYGIDVWGQGT |
| LVTVSSEQKLISEEDLAAAIEVMYPPPYLDNEKSNGTIIHVKGKHLCPSPLFPGPSKPFWVLVVVGGVLACYSLLVTVAFI |
| IFWVRSKRSRLLHSDYMNMTPRRPGPTRKHYQPYAPPRDFAAYRSRVKFSRSADAPAYQQGQNQLYNELNLGRREEYDVLD |
| KRRGRDPEMGGKRRRKNPQEGLYNEIQKDKMAEAYSEIGMKGERRRGKGHDGLYQGLSTATKDTYDALHMQALPPR |
| (SEQ ID NO: 30) |

Mock and CAR-encoding-nucleic-acid-transduced T cells were incubated for 16 hours at a 1:1 effector cell to target cell (E:T) ratio. The target cells used in these assays included: LNCaP (PSMA+), PC3 (PSMA−), PC3-PSMA (PSMA+), Jurkat (PSMA−), and Jurkat-PSMA (PSMA+).

Figure 2:
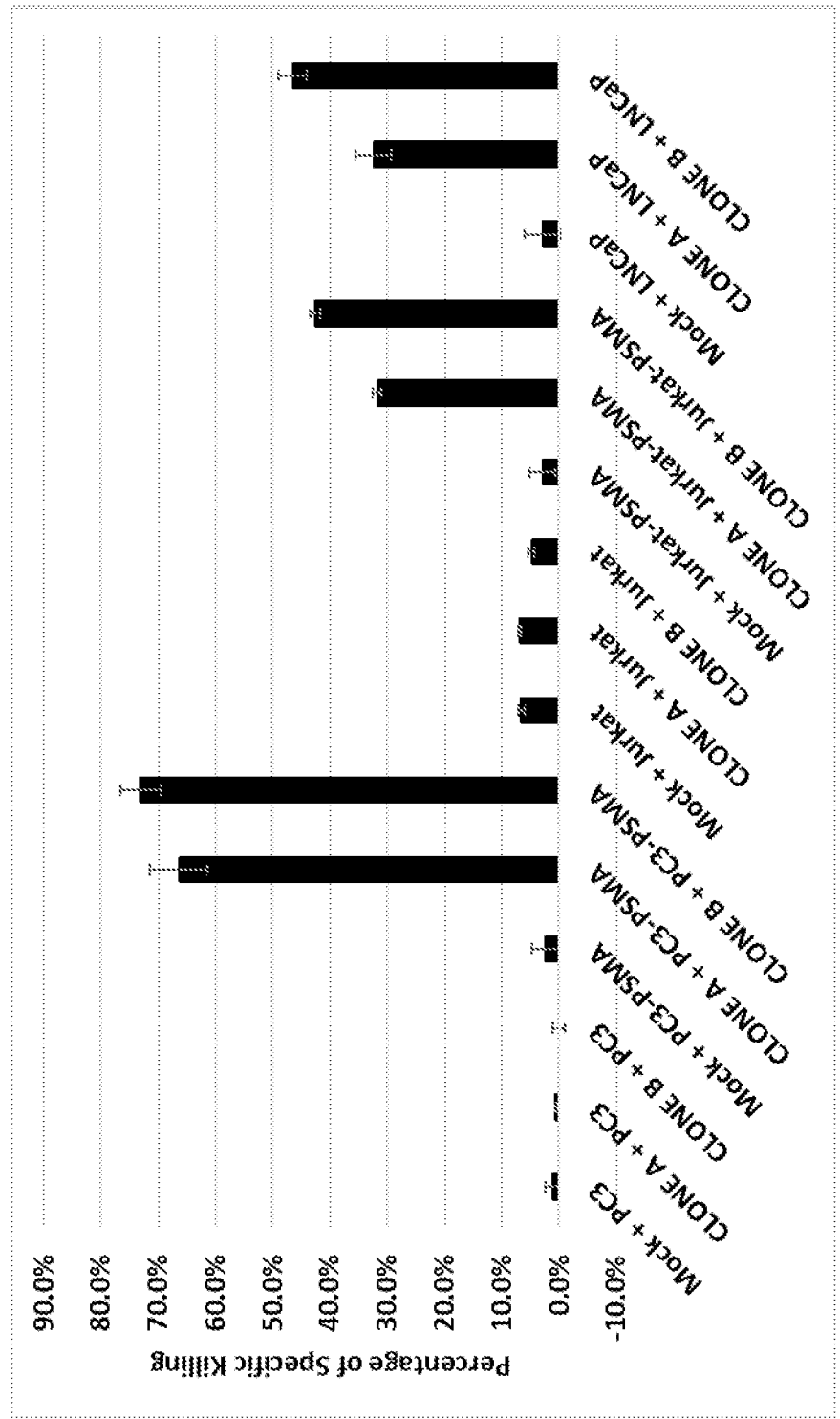
FIG. 2 shows the results experiments that were performed to assess specific killing of target cells by T cells expressing a CAR comprising an scFv moiety derived from Clone A or Clone B.

Cellular cytotoxicity was assessed using the LDH Cytotoxicity Assay (Promega, G1780). As shown in FIG. 2, specific killing of target cells was observed when effector cells expressing Clone A-CAR or Clone B-CAR construct were incubated with PSMA-expressing cells. No specific killing was observed with mock effector cells (i.e., mock T cells that do not express a CAR that targets PSMA) or with PSMA-negative target cells.

Figure 3:
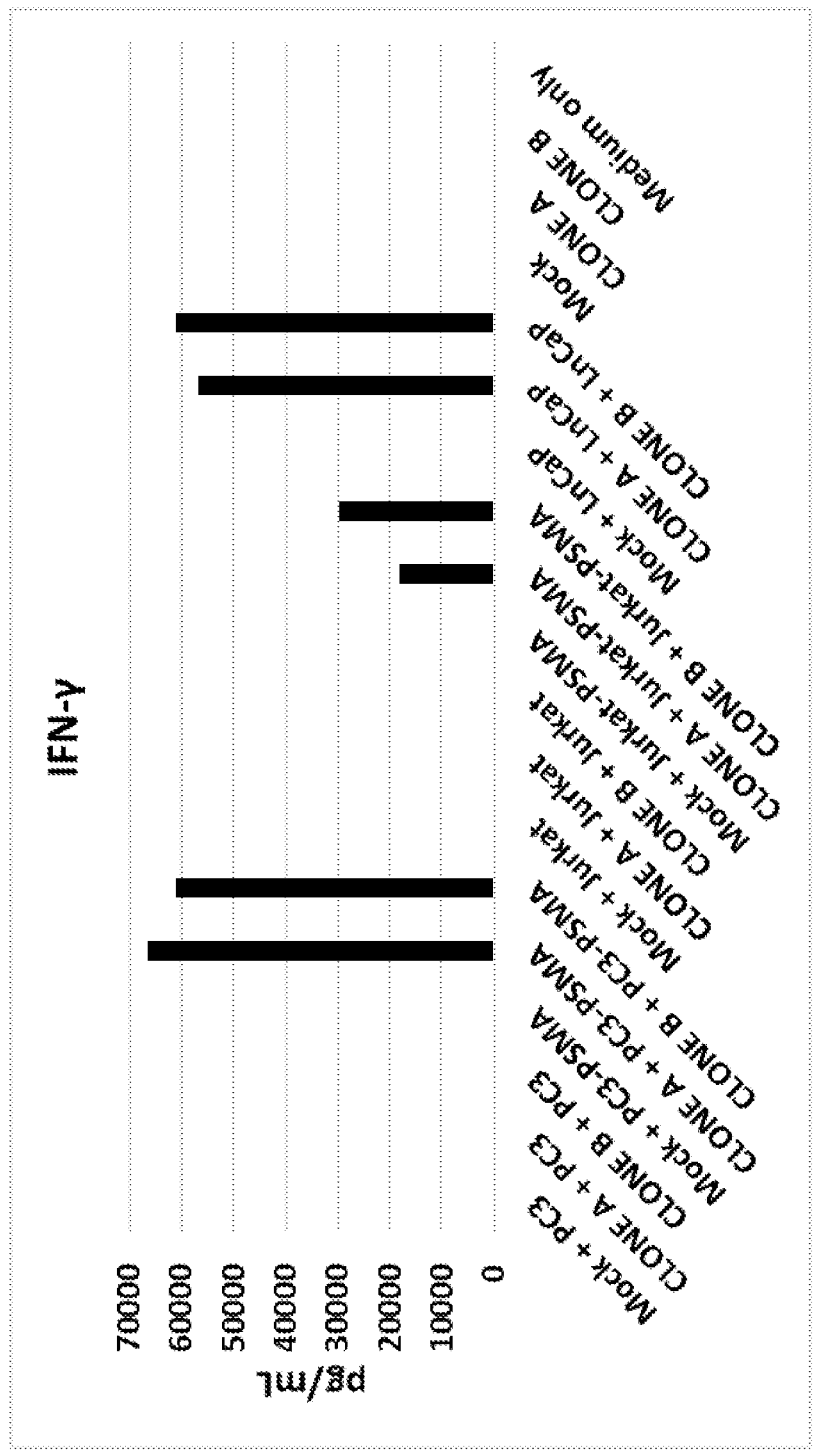
FIG. 3 shows the results experiments that were performed to assess specific IFN gamma release by T cells expressing a CAR comprising an scFv moiety derived from Clone A or Clone B.

Target-dependent activation of T cells expressing Clone A-CAR or Clone B-CAR was assessed by measuring IFN-γ release. Briefly, mock and transduced T cells were incubated for 16 hours at a 1:1 effector cell to target cell (E:T) ratio, as described above. IFN-γ levels in the culture supernatants were measured using the Bio-Plex Pro human cytokine 8-plex Assay (Bio-Rad, M50000007A). As shown in FIG. 3, specific release of IFN-γ was detected when Clone A-CAR or Clone B-CAR expressing T cells were incubated with PSMA-expressing cells. No specific release was observed with mock effector cells (i.e., mock T cells that do not express a CAR that targets PSMA) or with PSMA-negative target cells.

Example 4: Affinity Maturation of Anti-PSMA scFv Clones

DNA encoding the Clone A and Clone B scFvs is subjected to random mutagenesis using, e.g., GeneMorph II Random Mutagenesis kit (Agilent Technologies). After mutagenesis, DNA sequences are cloned into an scFv-expressing phagemid vector to build variant antibody phage libraries. Separate mutation libraries are built for Clone A and Clone B. Individual phage clones from enriched phage panning pools (e.g., variant clones) are tested for enhanced binding to cell-surface human PSMA compared to their respective parental clones. Further, a competition cell-binding assay is performed to compare the binding affinities of the variant clones to those of the parental clones.

Briefly, the relative binding affinities of the variant clones, as compared to their respective parental clones, are determined through antibody titration flow cytometry using, e.g., LNCaP, PC3, PC3-PSMA, Jurkat, and Jurkat-PSMA cells. $EC_{50}$ and apparent $K_D$ for each variant clone is calculated based on flow cytometry binding signals.

The variant clones are also evaluated for their abilities to redirect T cells and lead to cellular cytotoxicity and IFN-γ release, as described in Example 3. Parental clones, i.e., Clone A and Clone B, are evaluated in parallel as a basis to measure the relative changes in the cellular cytotoxicity and IFN-γ release levels demonstrated by the variant clones.

Example 5: Characterization of the Epitopes Bound by PSMA-Specific scFv Clones Epitope Binding To assess the epitope(s) of PSMA bound by Clone A, Clone B, and affinity-matured variants thereof, a binding competition assay is carried out as follows: Clones A and B are each conjugated to a fluorescent label. PSMA-expressing cell lines are incubated with unlabeled Clone A at 1 ug/ml.

After pre-incubation, increasing concentrations (e.g., 0.001 µg/mL, 0.01 µg/mL, 0.1 µg/mL, 1 µg/mL, 5 µg/mL, and 10 µg/mL) of labeled Clone B is added directly to the sample without washing and incubated for another 30 minutes. After blocking, FACS is used for detection and analysis. The percent binding is determined from the MFI (mean fluorescence intensity) and samples are normalized against the isotype control. A parallel set of experiments is performed in which PSMA-expressing cell lines are incubated with unlabeled Clone B at 1 ug/ml in the presence of increasing concentrations (e.g., 0.001 µg/mL, 0.01 µg/mL, 0.1 µg/mL, 1 µg/mL, 5 µg/mL, and 10 µg/mL) of labeled Clone A. Additional experiments are performed in which PSMA-expressing cell lines are incubated with unlabeled J591 (i.e., a monoclonal murine anti-hPSMA antibody) at 1 ug/ml in the presence of increasing concentrations of labeled Clone A, and, in a separate set of experiments, increasing concentrations of labeled Clone B.

Epitope Mapping

To identify the residues of PSMA that are components of the epitope(s) bound by Clone A and Clone B (as well as affinity matured variants thereof), a variety of mammalian cell lines, each expressing a different PSMA mutant comprising at least one alanine substitution in the extracellular domain, are generated using standard recombinant DNA technology. The expression of the PSMA mutants on the surfaces of each of the mammalian cell lines is confirmed. Clones A and B (and affinity matured variants thereof) are assessed via flow cytometry for binding to cells expressing each different PSMA mutant. KO7 helper phage is assessed in parallel as a negative control. J591, a monoclonal murine anti-hPSMA antibody, is also assessed in parallel.

The tandem di-scFvs are constructed using a single-chain format comprising the $V_L$-$V_H$ scFv sequence of Clone A or Clone B the N-terminus and an anti-human CD3ε mouse monoclonal scFv at the C-terminus (anti-PSMA anti-CD3 tandem di-scFv; e.g., see Brischwein, K. et al., Mol. Immunol. 43:1129-1143, 2006). DNA fragments encoding Clone A scFv, Clone B scFv, and the anti-human CD3ε scFv are synthesized using, e.g., Genewiz or Genscript, and subcloned into a mammalian expression vector such as pQD-T (Eureka Therapeutics, Inc.) using standard recombinant DNA technology. A hexahistidine tag HHHHIH (SEQ ID NO: 158) is inserted at the C-terminus of each tandem di-scFv for purification and detection.

HEK293 cells are transfected with an expression vector encoding the Clone A-tandem di-scFv or the Clone B-tandem di-scFv and cultured for seven days to express the tandem di-scFv. Each tandem di-scFv is purified from HEK293 cell supernatants, e.g., using HisTrap HP column (GE healthcare) by FPLC AKTA system or His GraviTrap columns (GE healthcare) based on the cell culture volume. Molecular weights of the purified tandem di-scFvs are measured under non-reducing conditions by gel electrophoresis. Bands (~98kD) corresponding to each construct (Clone A anti-PSMA anti-CD3 tandem di-scFv and Clone B anti-PSMA anti-CD3 tandem di-scFv) are expected to be observed as the major species on the gel.

The amino acid sequences of Clone A anti-PSMA anti-CD3 tandem di-scFv and Clone B anti-CD3 tandem di-scFv are provided in Table 15 below. The anti-PSMA scFv in each tandem di-scFv is underlined. The anti-CD3 scFv in each tandem di-scFv is double underlined. The linker connecting the anti-PSMA scFv and the anti-CD3 scFv is in bold italic type.

TABLE 15

| Clone A anti-PSMA anti-CD3 tandem di-scFv |
|---|
| QSVLTQPPSVSGAPGQRVTISCTGSSSNIGAGYDVHWYQQLPGTAPKLLIYGNSNRPSGVPDRFSGSKSGTSASLAITGLQ AEDEADYYCQSYDSSLSGYVFGTGTKVTVLGSRGGGGSGGGGSGGGGSLEMAEVQLVQSGAEVKKPGESLKISCKGSGYSF TSYWIGWVRQMPGKGLEWMGITYPGDSDTRYSPSFQGQVTISADKSISTAYLQWSSLKASDTAMYYCARSMGSSLYASSDV WGQGTLVTVSS*TSGGGGS*DVQLVQSGAEVKKPGASVKVSCKASGYTFTRYTMHWVRQAPGQGLEWIGYINPSRGYTNYADS VKGRFTITTDKSTSTAYMELSSLRSEDTATYYCARYYDDHYCLDYWGQGTTVTVSSGEGTSTGSGGSGGSGGADDIVLTQS PATLSLSPGERATLSCRASQSVSYMNWYQQKPGKAPKRWIYDTSKVASGVPARFSGSGSGTDYSLTINSLEAEDAATYYCQ QWSSNPLTFGGGTKVEIKHHHHHH (SEQ ID NO: 25) |

| Clone B anti-PSMA anti-CD3 tandem di-scFv |
|---|
| QAVLTQPPSASGTPGQRVTISCSGSSSNIGSNTVNWYQQLPGTAPKLLMYSNWQRPSGVPDRFSGSKSGTSASLAISGLQS EDEADYYCAAWDDSLNGYVFGTGTKVTVLGSRGGGGSGGGGSGGGGSLEMAEVQLVQSGAEMKKPGESLKISCKGSGYNFA SYWVGWVRQMPGKGLEWMGTIYPDDSDTRYGPAFQGQVTISADKSISTAYLQWSSLKASDTAMYYCARDSYYGIDVWGQGT LVTVSS*TSGGGGS*DVQLVQSGAEVKKPGASVKVSCKASGYTFTRYTMHWVRQAPGQGLEWIGYINPSRGYTNYADSVKGRF TITTDKSTSTAYMELSSLRSEDTATYYCARYYDDHYCLDYWGQGTTVTVSSGEGTSTGSGGSGGSGGADDIVLTQSPATLS LSPGERATLSCRASQSVSYMNWYQQKPGKAPKRWIYDTSKVASGVPARFSGSGSGTDYSLTINSLEAEDAATYYCQQWSSN PLTFGGGTKVEIKHHHHHH (SEQ ID NO: 27) |

The tandem di-scFvs are characterized further, as described below.

Assessing the Binding of Anti-PSMA Bispecific Antibody Constructs to Human Cancer Cell Lines The Clone A anti-PSMA anti-CD3 tandem di-scFv and Clone B anti-PSMA anti-CD3 tandem di-scFv constructs are evaluated for binding to human PSMA-expressing cancer cell lines (including, e.g., prostate cancer cell lines LNCaP, MDA PCa 2b, VCaP, and 22Rv1; renal cancer cell line Caki-1; uterine cancer cell line HCC1482; and liver cancer cell line HuH-7) via flow cytometry. Binding to human cancer cells lines that do not express PSMA (e.g., prostate cancer cell lines PrEC LH, PC-3, NCI-H660, DU 145) is evaluated in parallel. Additional bispecific antibody constructs (comprising e.g., a non-PSMA binding scFv with an Example 6: Anti-PSMA Bispecific Antibodies Generation of Bispecific Antibody Constructs Using Human Anti-PSMA Antibodies This example described the construction of an anti-PSMA bispecific antibody construct (a tandem di-scFv) having a first antibody moiety (e.g., scFv) that binds human PSMA in native format (i.e., cell-surface expressed PSMA) and a second antibody moiety (e.g., scFv) that binds CD3 on T cells. The tandem di-scFvs described herein can be used for directing T cells to kill target cells that express human PSMA.

anti-human CD3ε scFv and/or, e.g., an scFv comprising the PSMA-binding moiety from J591 and an anti-human CD3ε scFv) are tested in parallel.

Figure 4:
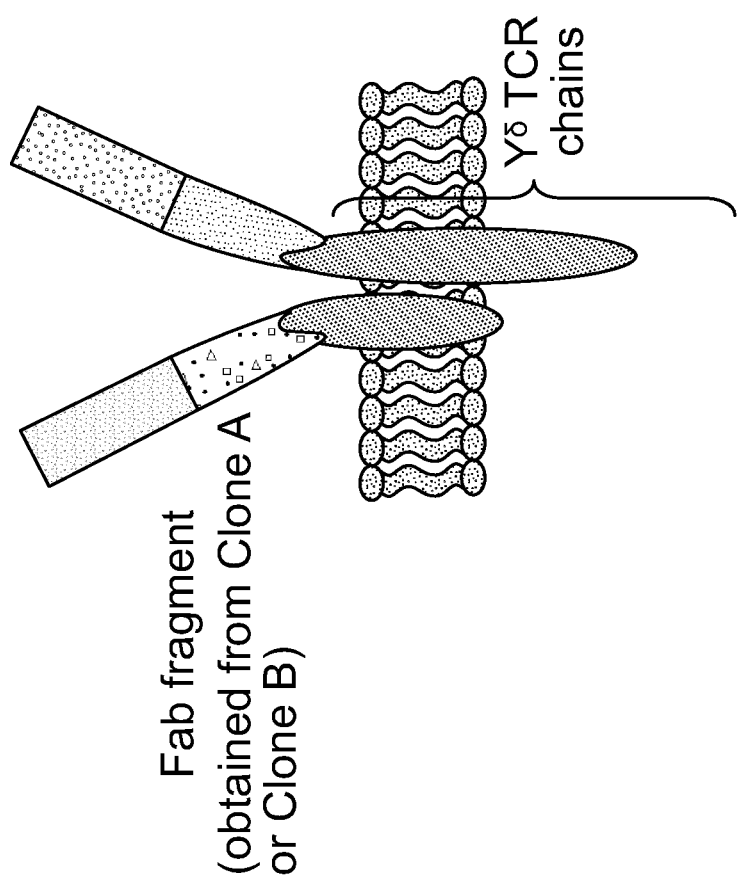
FIG. 4 provides a schematic depiction of an exemplary caTCR. The Fab fragment is derived from Clone A or Clone B.

Example 7: Generation and Characterization of T Cells Expressing Chimeric Antibody-T Cell Receptor (caTCR) Constructs Nucleic acids encoding the $V_H$ and $V_L$ domains from Clone A anti-PSMA scFv or Clone B anti-PSMA scFv are each fused to nucleic acids encoding Ig CH1 and CL constant regions and the transmembrane domain of a γδTCR using standard molecular biological techniques, generating nucleic acids encoding Clone A-caTCR and Clone B-caTCR. A schematic of the Clone A-caTCR and Clone B-caTCR constructs is provided in FIG. 4. The amino acid sequences of Clone A-caTCR and Clone B-caTCR are provided in Table 16 below. The anti-PSMA $V_H/C_H$ sequence in each Chain 1 is underlined. The TCR delta chain sequence in each Chain 1 is double underlined. The anti-PSMA $V_L/C_L$ sequence in each Chain 2 is bold underlined. The TCR gamma chain sequence in each Chain 2 is in italic type.

flow cytometric analysis of Clone A-caTCR-T cells and Clone B-caTCR-T cells is performed to measure the levels of TNFα, IL-2, and IFNγ expressed by CD4$^+$ caTCR$^+$ cells and CD4-CD8$^+$ caTCR$^+$ cells in response to PSMA-expressing cells as compared to PSMA-non expressing cells.

The tumor-killing activities of Clone A-caTCR-T cells and Clone B-caTCR-T cells are assessed as described in Example 3. The percentage of Clone A-caTCR-positive-, Clone B-caTCR-positive-, Clone A-caTCR-negative-, and Clone B-caTCR-negative-T cells are each co-cultured with multiple PSMA-expressing and PSMA-non-expressing cell lines, including, e.g., LNCaP, PC3, PC3-PSMA, Jurkat, and Jurkat-PSMA. Specific lysis of target cells across a range of effector cell: target cell ratios is measured, as described in Example 3.

A fluorescence-based assay is used to assess in vitro proliferation of Clone A-caTCR-T cells and Clone B-caTCR-T cells upon antigen stimulation. Briefly, Clone A-caTCR-T cells or Clone B-caTCR-T are serum starved overnight and then labeled with, e.g., 1 M CFSE (ThermoFisher Scientific), for 5 minutes at room temperature. The labeled cells are re-suspended in serum-free medium and

TABLE 16

Clone A-caTCR

Chain 1:
EVQLVQSGAEVKKPGESLKISCKGSGYSFTSYWIGWVRQMPGKGLEWMGITYPGDSDTRYSPSFQGQVTISADKSISTAYL
QWSSLKASDTAMYYCARSMGSSLYASSDVWGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDKRVEPKSCEVKTDSTDHVKPKETENTK
QPSKSCHKPKAIVHTEKVNMMSLTVLGLRMLFAKTVAVNFLLTAKLFFL (SEQ ID NO: 31)

Chain 2:
QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLQPKANPTVTLFPPSSEELQANKATLVCLISDFYPGAVTVAWKADGSPVKA
GVETTKPSKQSNNKYAASSYLSLTPEQWKSHRSYSCQVTHEGSTVEKTVAPTECS*PIKTDVITMDPEDNCSKDANDTLLLQ
LTNTSAYYMYLLLLLKSVVYFAIITCCLLRRTAFCCNGEKS* (SEQ ID NO: 32)

Clone B-caTCR

Chain 1:
EVQLVQSGAEMKKPGESLKISCKGSGYNFASYWVGWVRQMPGKGLEWMGTIYPDDSDTRYGPAFQGQVTISADKSISTAYL
QWSSLKASDTAMYYCARDSYYGIDVWGQGTLVTVSSASTKGPSVFPLAPSSKSTSGGTAALGCLVKDYFPEPVTVSWNSGA
LTSGVHTFPAVLQSSGLYSLSSVVTVPSSSLGTQTYICNVNHKPSNTKVDKRVEPKSCEVKTDSTDHVKPKETENTKQPSK
SCHKPKAIVHTEKVNMMSLTVLGLRMLFAKTVAVNFLLTAKLFFL (SEQ ID NO: 34)

Chain 2:
QAVLTQPPSASGTPGQRVTISCSGSSSNIGSNTVNWYQQLPGTAPKLLMYSNNQFPSGVPDRFSGSKSGTSASLAISGLQS
EDEADYYCAAWDDSLNGYVFGTGTKVTVIGQPKANPTVTLFPPSSEELQANKATLVCLISDFYPGAVTVAWKADGSPVKAG
VETTKPSKQSNNKYAASSYLSLTPEQWKSHRSYSCQVTHEGSTVEKTVAPTECS*PIKTDVITMDPKDNCSEDANDTLLLQL
TNTSAYYMYLLLLLKSVVYFAIITCCLLRRTAFCCNGEKS* (SEQ ID NO: 35)

Clone A-caTCR T cells and Clone B-caTCR T cells are generated using methods described in WO 2017/070608, PCT/US2018/029217 (now published as WO 2018/200582), and Milone, et al (Molecular Therapy, 17:1453-1464, 2009).

The T-cell phenotypes resulting from activation through each anti-PSMA caTCR are characterized. Clone A-caTCR-T cells are incubated alone, co-incubated with PSMA-expressing LNCaP cells, or co-incubated with LNCaP cells in which PSMA has been knocked out at a ratio of effector cells:target cells of 2:1 in the presence of brefeldin. Parallel sets incubations are performed using Clone B-caTCR-T cells. Following the incubation, Clone A-caTCR-T cells and Clone B-caTCR-T cells are assayed via flow cytometry for the expression of activation markers, including, e.g., CD69 and CD25, and cellular degranulation markers, including, e.g., CD107a. In addition, intracellular co-cultured with target cells (e.g., LNCaP cells, PC3-PSMA cells, or Jurkat-PSMA cells) at an effector cell: target cell ratio of 2:1. To account for differences in transduction efficiency, donor-matched un-transduced T cells are used to normalize the percentage of receptor-positive cells. Cell division is monitored by flow cytometry.

Example 8: Generation and Characterization of Full-Length Anti-PSMA Antibodies Comprising a Human IgG1 Fc Region Clone A and Clone B are reformatted as full-length antibodies comprising a human IgG1 Fc region in, e.g., HEK293 and Chinese hamster ovary (CHO) cell lines, as described (Tomimatsu K. et al., *Biosci. Biotechnol. Biochem.* 73(7):1465-1469, 2009). Briefly, the antibody variable regions Clone A and Clone B are each subcloned into mammalian expression vectors, with matching human lambda or kappa light chain constant region and human IgG1 constant region sequences. Applying the same cloning strategy, chimeric PSMA full-length antibodies with mouse IgG1 heavy chain and light chain constant regions are generated. The molecular weights of purified full length IgG antibodies are measured under both reducing and non-reducing conditions by electrophoresis to assess the purity of the antibody sample. Sample purity is also assessed by performing SDS-PAGE, as follows: 2 µg of each antibody is mixed with 2.5 µL of NuPAGE LDS Sample Buffer (Life Technologies, NP0008) and the volume of each sample is adjusted to 10 µL with deionized water. The samples are heated at 70° C. for 10 minutes, and then loaded onto the gel. Gel electrophoresis is performed at 180V for 1 hour.

Anti-PSMA chimeric IgG1 antibodies comprising the antibody variable regions Clone A or Clone B are each assessed via FACS for binding to Jurkat cells, Jurkat cells expressing PSMA, PC3 cells, PC3 cells expressing PSMA, and to LNCaP human prostate adenocarcinoma cells. 10 µg/mL of each antibody is added to each of the cell lines and incubated on ice. After washing, R-PE conjugated anti-mouse IgG (H+L) (Vector Labs #EI-2007) is added to detect antibody binding. Binding affinity of the anti-PSMA chimeric IgG1 antibodies is determined by ForteBio Octet QK. 5 µg/mL biotinylated PSMA (extracellular domain) is loaded onto a streptavidin biosensor. After washing off excess antigen, 10 µg/mL of each antibody is tested at for association and dissociation kinetics. Binding parameters are calculated using a 1:1 binding site, partial fit model.

The amino acid sequences of the full length Clone A-IgG1 and full length Clone A-IgGlantibodies are provided in Table 17 below. The $V_L$ in each light chain is underlined, and the $V_H$ in each heavy chain is double underlined. The CDRs are in bold type.

Example 9: In Vivo Efficacy Studies

PSMA CAR-T Cell Treatment in Mice

Human PSMA-expressing prostate cancer (s.c.) xenograft models are generated in SCID-beige (no functional T-, B-, NK-cells) mice. Animals are randomized when average s.c. tumor volume reaches 200 mm$^3$. Mice are divided into 6 groups (n=8-10 mice/group) that receive one of the following: (i) no treatment (ii) 10$^7$ mock transduced CAR T cells, 1x/week for 4 weeks (iii) 10$^7$ Clone A-CAR T cells, 1x/week for 4 weeks, (iv) 2×10$^6$ Clone A-CAR T cells, 1x/week for 4 weeks, (v) 107 Clone B-CAR T cells, 1x/week for 4 weeks, or (iv) 2×10$^6$ Clone B-CAR T cells, 1x/week for 4 weeks. The animals in each group are monitored for tumor volume, adverse response, human cytokine profile, histopathology of tumor for human CD3$^+$ cells in tumor and organs for CAR T cell infiltration, PSMA expression on cells from tumor tissue, body weight and general health condition (such as eating, walking, daily activities). The amino acid sequences of Clone A-CAR and Clone B-CAR are provided in Table 13 above.

PSMA caTCR-T Cell Treatment in Mice

Human PSMA-expressing prostate cancer (s.c.) xenograft models are generated in SCID-beige (no functional T-, B-, NK-cells) mice. Animals are randomized when average s.c. tumor volume reaches 200 mm$^3$. Mice are divided into 4 groups (n=8-10 mice/group) that receive one of the following: (i) no treatment, (ii) 10$^7$ mock transduced caTCR T cells, 1x/week for 4 weeks, (iii) 10$^7$ Clone A-caTCR T cells, 1x/week for 4 weeks, (iv) 2×10$^6$ Clone A-caTCR T cells, 1x/week for 4 weeks, (v) 10$^7$ Clone B-caTCR T cells, 1x/week for 4 weeks, or (iv) 2×10$^6$ Clone B-caTCR T cells, 1x/week for 4 weeks. The animals in each group are monitored for tumor volume, adverse response, human cytokine profile, histopathology of tumor for human CD3$^+$ cells in tumor and organs for caTCR-T cell infiltration,

TABLE 17

Full length Clone A IgG1 antibody:

Heavy chain:
EVQLVQSGAEVKKPGESLKISCKGSGYSFTSYWIGWVRQMPGKGLEWMGIIYPGDSDTRYSPSFQGQVTISADKSISTAYL
QWSSLKASDTAMYYCARSMGSSLYASSDVWGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK (SEQ ID NO: 39)

Light Chain:
QSVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSGYVFGTGTKVTVLGQPKANPTVTLFPPSSEELQANKATLVCLISDFYPGAVTVAWKADGSPVKA
GVETTKPSKQSNNKYAASSYLSLTPEQWKSHRSYSCQVTHEGSTVEKTVAPTECS (SEQ ID NO: 40)

Full length Clone B IgG1 antibody:

Heavy chain:
EVQLVQSGAEMKKPGESLKISCKGSGYNFASYWVGWVRQMPGKGLEWMGTIYPDDSDTRYGPAFQGQVTISADKSISTAYL
QWSSLKASDTAMYYCARDSYYGIDVWGQGTLVTVSSASTKGPSVFPLAPSSKSTSGGTAALGCLVKDYFPEPVTVSWNSGA
LTSGVHTFPAVLQSSGLYSLSSVVTVPSSSLGTQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIAVEWESNGQPENNYKTTPPVLDSDGSFF
LYSKLTVDKSRWQQGNVFSCSVMHEALHNHYTQKSLSLSPGK (SEQ ID NO: 41)

Light Chain:
QAVLTQPPSASGTPGQRVTISCSGSSSNIGSNTVNWYQQLPGTAPKLLMYSNNQRPSGVPDRFSGSKSGTSASLAISGLQS
EDEADYYCAAWDDSLNGYVFGTGTKVTVLGQPKANPTVTLFPPSSEELQANKATLVCLISDFYPGAVTVAWKADGSPVKAG
VETTKPSKQSNNKYAASSYLSLTPEQWKSHRSYSCQVTHEGSTVEKTVAPTECS (SEQ ID NO: 42)

PSMA expression on cells from tumor tissue, body weight and general health condition (eating, walking, daily activities). The amino acid sequences of Clone A-caTCR and Clone B-caTCR are provided in Table 15 above.

Example 10: Generation and Characterization of T Cells Expressing Monovalent and Bivalent caTCR Constructs Nucleic acids encoding a monovalent anti-PSMA Clone A caTCR construct and a monovalent anti-PSMA Clone B caTCR construct were generated according to the description in Example 7. SEQ ID NO: 33 is an exemplary amino acid sequence of an anti-PSMA Clone A caTCR construct. Such construct is alternatively referred to herein as Clone A caTCR, anti-PSMA caTCR #1, or Ax1-caTCR. SEQ ID NO: 36 is an exemplary amino acid sequence of an anti-PSMA Clone B caTCR construct. The anti-PSMA Clone B caTCR construct is alternatively referred to herein as Clone B caTCR, anti-PSMA caTCR #2, or Bx1-caTCR.

(SEQ ID NO: 33)
METDTLLLWVLLLWVPGSTGEVQLVQSGAEVKKPGESLKISCKGSGYSF

TSYWIGWVRQMPGKGLEWMGITYPGDSDTRYSPSFQGQVTISADKSIST

AYLQWSSLKASDTAMYYCARSMGSSLYASSDVWGQGTLVTVSSASTKGP

SVFPLAPSSKSTSGGTAALGCLVKDYFPEPVTVSWNSGALTSGVHTFPA

VLQSSGLYSLSSVVTVPSSSLGTQTYICNVNHKPSNTKVDKRVEPKSCE

VKTDSTDHVKPKETENTKQPSKSCHKPKAIVHTEKVNMMSLTVLGLRML

FAKTVAVNFLLTAKLFFLRAKRSGSGAPVKQTLNFDLLKLAGDVESNPG

PMETDTLLLWVLLLWVPGSTGQSVLTQPPSVSGAPGQRVTISCTGSSSN

IGAGYDVHWYQQLPGTAPKLLIYGNSNRPSGVPDRFSGSKSGTSASLAI

TGLQAEDEADYYCQSYDSSLSGYVFGTGTKVTVLGQPKANPTVTLFPPS

SEELQANKATLVCLISDFYPGAVTVAWKADGSPVKAGVETTKPSKQSNN

KYAASSYLSLTPEQWKSHRSYSCQVTHEGSTVEKTVAPTECSPIKTDVI

TMDPKDNCSKDANDTLLLQLTNTSAYYMYLLLLLKSVVYFAIITCCLLR

RTAFCCNGEKS (SEQ ID NO: 36)
METDTLLLWVLLLWVPGSTGEVQLVQSGAEMKKPGESLKISCKGSGYNF

ASYWVGWVRQMPGKGLEWMGTIYPDDSDTRYGPAFQGQVTISADKSIST

AYLQWSSLKASDTAMYYCARDSYYGIDVWGQGTLVTVSSASTKGPSVFP

LAPSSKSTSGGTAALGCLVKDYFPEPVTVSWNSGALTSGVHTFPAVLQS

SGLYSLSSVVTVPSSSLGTQTYICNVNHKPSNTKVDKRVEPKSCEVKTD

STDHVKPKETENTKQPSKSCHKPKAIVHTEKVNMMSLTVLGLRMLFAKT

VAVNFLLTAKLFFLRAKRSGSGAPVKQTLNFDLLKLAGDVESNPGPMET

DTLLLWVLLLWVPGSTGQAVLTQPPSASGTPGQRVTISCSGSSSNIGSN

TVNWYQQLPGTAPKLLMYSNNQRPSGVPDRFSGSKSGTSASLAISGLQS

EDEADYYCAAWDDSLNGYVFGTGTKVTVLGQPKANPTVTLFPPSSEELQ

ANKATLVCLISDFYPGAVTVAWKADGSPVKAGVETTKPSKQSNNKYAAS

SYLSLTPEQWKSHRSYSCQVTHEGSTVEKTVAPTECSPIKTDVITMDPK

-continued

DNCSKDANDTLLLQLTNTSAYYMYLLLLLKSVVYFAIITCCLLRRTAFC

CNGEKS

In an effort to increase the binding of anti-PSMA caTCR to PSMA, bivalent caTCR constructs were designed. In particular, nucleic acids encoding the following "homo" bivalent caTCR constructs were generated.

1. Ax2-caTCR-1 (which is alternatively referred to herein as "Ax2-caTCR" or "Bivalent Clone A caTCR-1") is a bivalent anti-PSMA Clone A caTCR comprising 1 scFv and 1 Fab. See, e.g., SEQ ID NO: 47 below.

(SEQ ID NO: 47)
METDTLLLWVLLLWVPGSTGQSVLTQPPSVSGAPGQRVTISCTGSSSNI

GAGYDVHWYQQLPGTAPKLLIYGNSNRPSGVPDRFSGSKSGTSASLAIT

GLQAEDEADYYCQSYDSSLSGYVFGTGTKVTVLGSRGGGGSGGGGSGGG

GSLEMAEVQLVQSGAEVKKPGESLKISCKGSGYSFTSYWIGWVRQMPGK

GLEWMGIIYPGDSDTRYSPSFQGQVTISADKSISTAYLQWSSLKASDTA

MYYCARSMGSSLYASSDVWGQGTLVTVSSGGGGSEVQLVQSGAEVKKPG

ESLKISCKGSGYSFTSYWIGWVRQMPGKGLEWMGIIYPGDSDTRYSPSF

QGQVTISADKSISTAYLQWSSLKASDTAMYYCARSMGSSLYASSDVWGQ

GTLVTVSSASTKGPSVFPLAPSSKSTSGGTAALGCLVKDYFPEPVTVSW

NSGALTSGVHTFPAVLQSSGLYSLSSVVTVPSSSLGTQTYICNVNHKPS

NTKVDKRVEPKSCEVKTDSTDHVKPKETENTKQPSKSCHKPKAIVHTEK

VNMMSLTVLGLRMLFAKTVAVNFLLTAKLFFLRAKRSGSGAPVKQTLNF

DLLKLAGDVESNPGPMETDTLLLWVLLLWVPGSTGQSVLTQPPSVSGAP

GQRVTISCTGSSSNIGAGYDVHWYQQLPGTAPKLLIYGNSNRPSGVPDR

FSGSKSGTSASLAITGLQAEDEADYYCQSYDSSLSGYVFGTGTKVTVLG

QPKANPTVTLFPPSSEELQANKATLVCLISDFYPGAVTVAWKADGSPVK

AGVETTKPSKQSNNKYAASSYLSLTPEQWKSHRSYSCQVTHEGSTVEKT

VAPTECSPIKTDVITMDPKDNCSKDANDTLLLQLTNTSAYYMYLLLLLK

SVVYFAIITCCLLRRTAFCCNGEKS

2. Ax2-caTCR-2 (which is alternatively referred to herein as "Bivalent Clone A caTCR-2") is a bivalent Anti-PSMA Clone A caTCR comprising 2 Fabs. See, e.g., SEQ ID NO: 48 below.

(SEQ ID NO: 48)
METDTLLLWVLLLWVPGSTGEVQLVQSGAEVKKPGESLKISCKGSGYSF

TSYWIGWVRQMPGKGLEWMGITYPGDSDTRYSPSFQGQVTISADKSIST

AYLQWSSLKASDTAMYYCARSMGSSLYASSDVWGQGTLVTVSSGGGGSG

GGGSEVQLVQSGAEVKKPGESLKISCKGSGYSFTSYWIGWVRQMPGKGL

EWMGITYPGDSDTRYSPSFQGQVTISADKSISTAYLQWSSLKASDTAMY

YCARSMGSSLYASSDVWGQGTLVTVSSASTKGPSVFPLAPSSKSTSGGT

AALGCLVKDYFPEPVTVSWNSGALTSGVHTFPAVLQSSGLYSLSSVVTV

PSSSLGTQTYICNVNHKPSNTKVDKRVEPKSCEVKTDSTDHVKPKETEN

TKQPSKSCHKPKAIVHTEKVNMMSLTVLGLRMLFAKTVAVNFLLTAKLF

FLRAKRSGSGAPVKQTLNFDLLKLAGDVESNPGPMETDTLLLWVLLLWV

PGSTGQSVLTQPPSVSGAPGQRVTISCTGSSSNIGAGYDVHWYQQLPGT

APKLLIYGNSNRPSGVPDRFSGSKSGTSASLAITGLQAEDEADYYCQSY

DSSLSGYVFGTGTKVTVLGGGGSGGGGSQSVLTQPPSVSGAPGQRVTI

SCTGSSSNIGAGYDVHWYQQLPGTAPKLLIYGNSNRPSGVPDRFSGSKS

GTSASLAITGLQAEDEADYYCQSYDSSLSGYVFGTGTKVTVLGQPKANP

TVTLFPPSSEELQANKATLVCLISDFYPGAVTVAWKADGSPVKAGVETT

KPSKQSNNKYAASSYLSLTPEQWKSHRSYSCQVTHEGSTVEKTVAPTEC

SPIKTDVITMDPKDNCSKDANDTLLLQLTNTSAYYMYLLLLLKSVVYFA

IITCCLLRRTAFCCNGEKS

3. Bx2-caTCR-1 (which is alternatively referred to herein as "Bx2-caTCR" or "Bivalent Clone B caTCR-1") is a bivalent anti-PSMA Clone B caTCR comprising 1 scFv and 1 Fab. See, e.g., SEQ ID NO: 49 below.

(SEQ ID NO: 49)
METDTLLLWVLLLWVPGSTGQAVLTQPPSASGTPGQRVTISCSGSSSNI

GSNTVNWYQQLPGTAPKLLMYSNNQRPSGVPDRFSGSKSGTSASLAISG

LQSEDEADYYCAAWDDSLNGYVFGTGTKVTVLGSRGGGGSGGGGSGGGG

SLEMAEVQLVQSGAEMKKPGESLKISCKGSGYNFASYWVGWVRQMPGKG

LEWMGTIYPDDSDTRYGPAFQGQVTISADKSISTAYLQWSSLKASDTAM

YYCARDSYYGIDVWGQGTLVTVSSGGGGSEVQLVQSGAEMKKPGESLKI

SCKGSGYNFASYWVGWVRQMPGKGLEWMGTIYPDDSDTRYGPAFQGQVT

ISADKSISTAYLQWSSLKASDTAMYYCARDSYYGIDVWGQGTLVTVSSA

STKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVE

PKSCEVKTDSTDHVKPKETENTKQPSKSCHKPKAIVHTEKVNMMSLTVL

GLRMLFAKTVAVNFLLTAKLFFLRAKRSGSGAPVKQTLNFDLLKLAGDV

ESNPGPMETDTLLLWVLLLWVPGSTGQAVLTQPPSASGTPGQRVTISCS
GSSSNI

4. Bx2-caTCR-2 (which is alternatively referred to herein as "Bivalent Clone B caTCR-2") is a bivalent anti-PSMA Clone B caTCR comprising 2 Fabs. See, e.g., SEQ ID NO: 50 below.

(SEQ ID NO: 50)
METDTLLLWVLLLWVPGSTGEVQLVQSGAEMKKPGESLKISCKGSGYNF

ASYWVGWVRQMPGKGLEWMGTIYPDDSDTRYGPAFQGQVTISADKSIST

AYLQWSSLKASDTAMYYCARDSYYGIDVWGQGTLVTVSSGGGGSGGGGS

EVQLVQSGAEMKKPGESLKISCKGSGYNFASYWVGWVRQMPGKGLEWMG

TIYPDDSDTRYGPAFQGQVTISADKSISTAYLQWSSLKASDTAMYYCAR

DSYYGIDVWGQGTLVTVSSASTKGPSVFPLAPSSKSTSGGTAALGCLVK

DYFPEPVTVSWNSGALTSGVHTFPAVLQSSGLYSLSSVVTVPSSSLGTQ

TYICNVNHKPSNTKVDKRVEPKSCEVKTDSTDHVKPKETENTKQPSKSC

HKPKAIVHTEKVNMMSLTVLGLRMLFAKTVAVNFLLTAKLFFLRAKRSG

SGAPVKQTLNFDLLKLAGDVESNPGPMETDTLLLWVLLLWVPGSTGQAV

LTQPPSASGTPGQRVTISCSGSSSNIGSNTVNWYQQLPGTAPKLLMYSN

NQRPSGVPDRFSGSKSGTSASLAISGLQSEDEADYYCAAWDDSLNGYVF

GTGTKVTVLGGGGSGGGGSQAVLTQPPSASGTPGQRVTISCSGSSSNI

GSNTVNWYQQLPGTAPKLLMYSNNQRPSGVPDRFSGSKSGTSASLAISG

LQSEDEADYYCAAWDDSLNGYVFGTGTKVTVLGQPKANPTVTLFPPSSE

ELQANKATLVCLISDFYPGAVTVAWKADGSPVKAGVETTKPSKQSNNKY

AASSYLSLTPEQWKSHRSYSCQVTHEGSTVEKTVAPTECSPIKTDVITM

DPKDNCSKDANDTLLLQLTNTSAYYMYLLLLLKSVVYFAIITCCLLRRT

AFCCNGEKS

T cells expressing Ax2-caTCR-1, Ax2-caTCR-2, Bx2-caTCR-1, or Bx2-caTCR-2 were generated by transducing primary human T cells with viruses comprising nucleic acids encoding the caTCR constructs. The features and functions of the transformed T cells were assessed using the methods described in Example 7. Such T cells expressed the encoded caTCR constructs, proliferated well, redirected the T cells' specificity, and showed positive PSMA-specific cellular cytotoxicity/tumor-killing activities.

Figure 6:
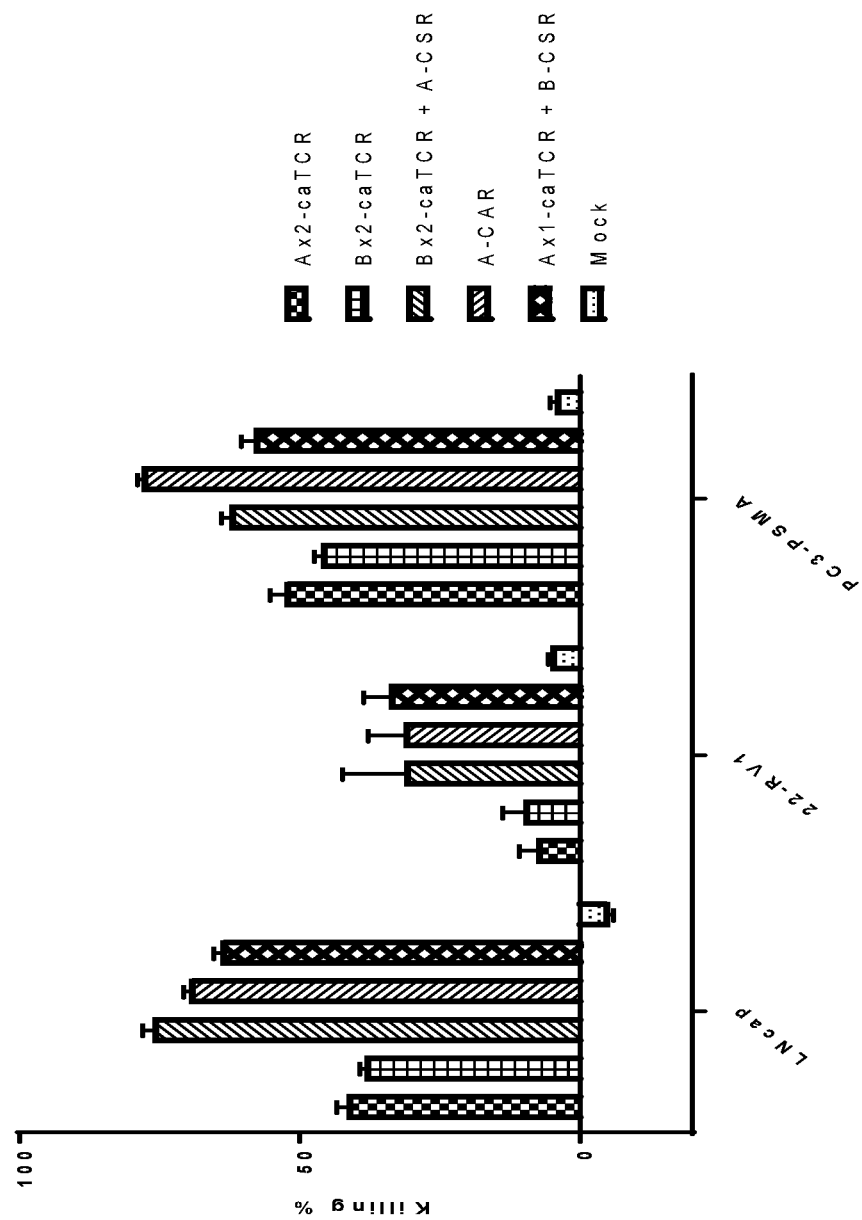
FIG. 6 shows the results of experiments performed to assess the specific killing of three PSMA+ target cell lines by T cells expressing Clone A and/or Clone B in different anti-PSMA construct configurations and construct combinations.
Figure 7:
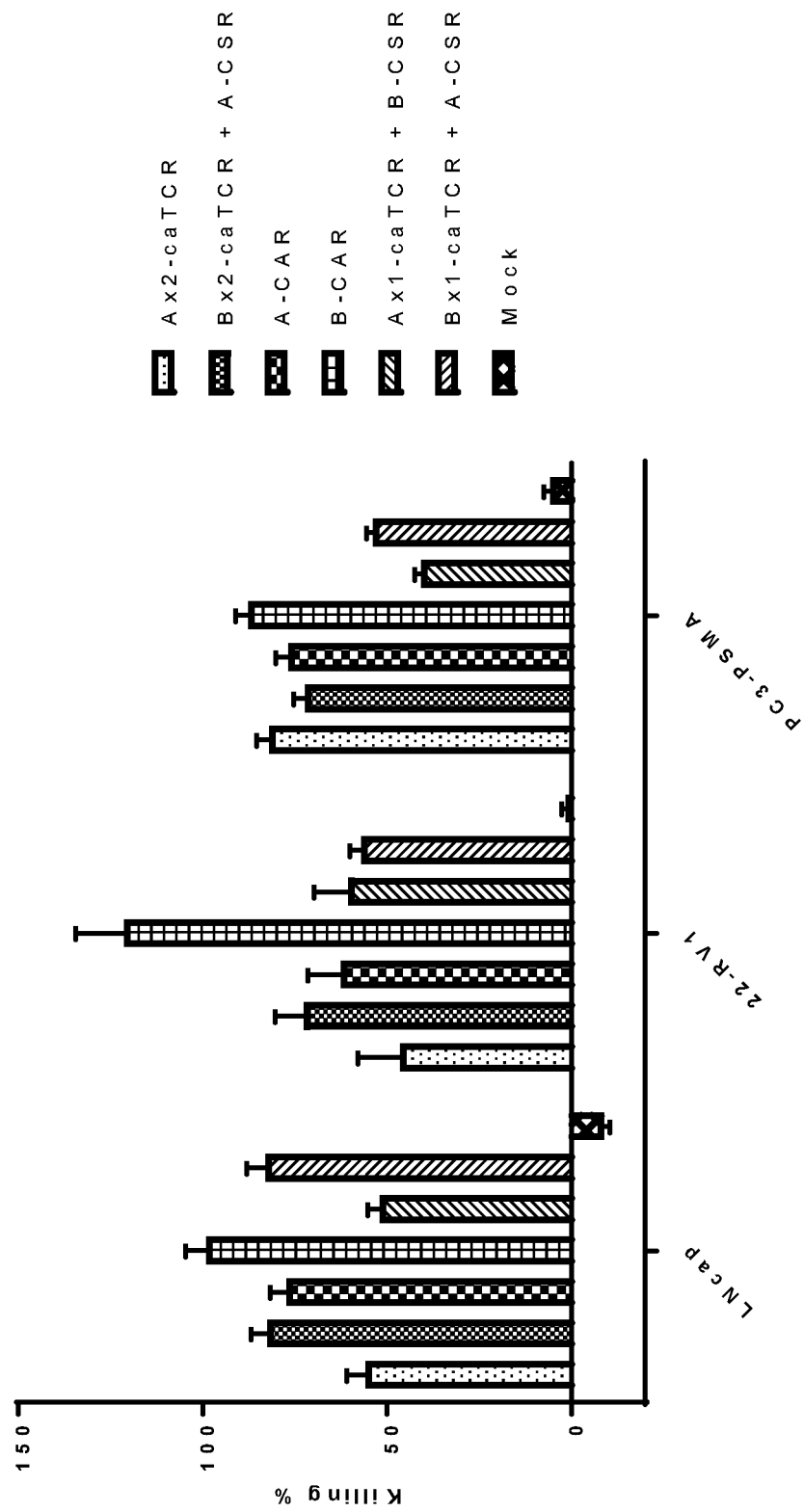
FIG. 7 shows the results of additional experiments performed to assess the specific killing of three PSMA+ target cell lines by T cells expressing Clone A and/or Clone B in different anti-PSMA construct configurations and construct combinations.

In two representative tumor cell killing experiments, T cells expressing Bx2-caTCR (i.e., Bx2-caTCR-1) (see FIG. 6); Ax2-caTCR (i.e., Ax2-caTCR-1) (see FIGS. 6 and 7); Bx2-caTCR+A-CSR (see FIGS. 6 and 7); A-CAR (see FIGS. 6 and 7); Ax1-caTCR+B-CSR (see FIGS. 6 and 7); B-CAR (see FIG. 7); or Bx1-caTCR+A-CSR (see FIG. 7) were generated, and receptor (caTCR or CAR) positive T cell percentages were normalized to 60% with mock-transduced T cells. Next, mock-transduced T cells, caTCR-expressing T cells, and anti-PCMA CAR-expressing T cells were incubated at a 2:1 effector cell to target cell (E:T) ratio (0.2M:0.1M, receptor-positive effector:target ratio 1.2:1) for 16 hours. The following three PSMA$^+$ target cell lines were used: LNCaP, 22RV land PC3-PMSA. The results of the tumor cell killing experiments are shown in FIGS. 6 and 7. Briefly, T cells expressing any one of the constructs listed above were able to cause PSMA-specific target cell lysis, whereas mock-transduced T cells were not.

In addition, nucleic acids encoding the "hetero" bivalent caTCR constructs described below are generated and used to transduce primary human T cells. The transduced caTCR-T cells are characterized using the methods described in Example 7 and in the current Example to assess the whether the transduced T cells express the encoded caTCR constructs, proliferate well, redirect the T cells' specificity, and induce PSMA-specific cellular cytotoxicity/tumor cell killing.

5. Ax1-Bx1-caTCR-1 (alternatively referred to herein as "Clone A Clone B caTCR-1") is an anti-PSMA caTCR comprising a Clone A scFv and a Clone B Fab. See, e.g., SEQ ID NO: 91 below.

(SEQ ID NO: 91)
METDTLLLWVLLLWVPGSTGQSVLTQPPSVSGAPGQRVTISCTGSSSNI

GAGYDVHWYQQLPGTAPKLLIYGNSNRPSGVPDRFSGSKSGTSASLAIT

GLQAEDEADYYCQSYDSSLSGYVFGTGTKVTVLGSRGGGGSGGGGSGGG

GSLEMAEVQLVQSGAEVKKPGESLKISCKGSGYSFTSYWIGWVRQMPGK
GLEWMGIIYPGDSDTRYSPSFQGQVTISADKSISTAYLQWSSLKASDTA
MYYCARSMGSSLYASSDVWGQGTLVTVSSGGGGSEVQLVQSGAEMKKPG
ESLKISCKGSGYNFASYWVGWVRQMPGKGLEWMGTIYPDDSDTRYGPAF
QGQVTISADKSISTAYLQWSSLKASDTAMYYCARDSYYGIDVWGQGTLV
TVSSASTKGPSVFPLAPSSKSTSGGTAALGCLVKDYFPEPVTVSWNSGA
LTSGVHTFPAVLQSSGLYSLSSVVTVPSSSLGTQTYICNVNHKPSNTKV
DKRVEPKSCEVKTDSTDHVKPKETENTKQPSKSCHKPKAIVHTEKVNMM
SLTVLGLRMLFAKTVAVNFLLTAKLFFLRAKRSGSGAPVKQTLNFDLLK
LAGDVESNPGPMETDTLLLWVLLLWVPGSTGQAVLTQPPSASGTPGQRV
TISCSGSSSNIGSNTVNWYQQLPGTAPKLLMYSNNQRPSGVPDRFSGSK
SGTSASLAISGLQSEDEADYYCAAWDDSLNGYVFGTGTKVTVLGQPKAN
PTVTLFPPSSEELQANKATLVCLISDFYPGAVTVAWKADGSPVKAGVET
TKPSKQSNNKYAASSYLSLTPEQWKSHRSYSCQVTHEGSTVEKTVAPTE
CSPIKTDVITMDPKDNCSKDANDTLLLQLTNTSAYYMYLLLLLKSVVYF
AIITCCLLRRTAFCCNGEKS

6. Ax1-Bx1-caTCR-2 (alternatively referred to herein as "Clone A Clone B caTCR-2" is an anti-PSMA caTCR comprising a Clone A Fab and a Clone B Fab. See, e.g., SEQ ID NO: 92 below.

(SEQ ID NO: 92)
METDTLLLWVLLLWVPGSTGEVQLVQSGAEVKKPGESLKISCKGSGYSF
TSYWIGWVRQMPGKGLEWMGIIYPGDSDTRYSPSFQGQVTISADKSIST
AYLQWSSLKASDTAMYYCARSMGSSLYASSDVWGQGTLVTVSSGGGGSG
GGGSEVQLVQSGAEMKKPGESLKISCKGSGYNFASYWVGWVRQMPGKGL
EWMGTIYPDDSDTRYGPAFQGQVTISADKSISTAYLQWSSLKASDTAMY
YCARDSYYGIDVWGQGTLVTVSSASTKGPSVFPLAPSSKSTSGGTAALG
CLVKDYFPEPVTVSWNSGALTSGVHTFPAVLQSSGLYSLSSVVTVPSSS
LGTQTYICNVNHKPSNTKVDKRVEPKSCEVKTDSTDHVKPKETENTKQP
SKSCHKPKAIVHTEKVNMMSLTVLGLRMLFAKTVAVNFLLTAKLFFLRA
KRSGSGAPVKQTLNFDLLKLAGDVESNPGPMETDTLLLWVLLLWVPGST
GQSVLTQPPSVSGAPGQRVTISCTGSSSNIGAGYDVHWYQQLPGTAPKL
LIYGNSNRPSGVPDRFSGSKSGTSASLAITGLQAEDEADYYCQSYDSSL
SGYVFGTGTKVTVLGGGGSGGGGSQAVLTQPPSASGTPGQRVTISCSG
SSSNIGSNTVNWYQQLPGTAPKLLMYSNNQRPSGVPDRFSGSKSGTSAS
LAISGLQSEDEADYYCAAWDDSLNGYVFGTGTKVTVLGQPKANPTVTLF
PPSSEELQANKATLVCLISDFYPGAVTVAWKADGSPVKAGVETTKPSKQ
SNNKYAASSYLSLTPEQWKSHRSYSCQVTHEGSTVEKTVAPTECSPIKT
DVITMDPKDNCSKDANDTLLLQLTNTSAYYMYLLLLLKSVVYFAIITCC
LLRRTAFCCNGEKS

Example 11: Generation and Characterization of T Cells Expressing Construct Combinations with caTCR and CSR Receptors Nucleic acids encoding anti-PSMA Clone A chimeric signaling receptor (CSR) or anti-PSMA Clone B CSR were fused to the nucleic acids encoding monovalent or bivalent anti-PSMA caTCR constructs described in Example 10 to generate full-length nucleic acids encoding various caTCR+CSR construct combinations. Viruses comprising the full-length nucleic acids were used to transduce primary human T cells, so that the caTCR+CSR construct combinations were expressed on the surface of the T cells.

Specifically, nucleic acids encoding the anti-PSMA CSR constructs listed below have been designed, and many have been generated.

```
Clone A-CSR-1A (in order from N-terminus to C-terminus: anti-PSMA Clone A scFv +
myc tag (bold) + sequences derived from CD28 (underlined))
                                                              (SEQ ID NO: 55)
QSVLTQPPSVSGAPGQRVTISCTGSSSNIGAGYDVHWYQQLPGTAPKLLIYGNSNRPSGVPDRFSGSKSGTSASLAITGLQAE DEADYYCQSYDSSLSGYVFGTGTKVTVLGSRGGGGSGGGGSGGGGSLEMAEVQLVQSGAEVKKPGESLKISCKGSGYSFTSYW IGWVRQMPGKGLEWMGITYPGDSDTRYSPSFQGQVTISADKSISTAYLQWSSLKASDTAMYYCARSMGSSLYASSDVWGQGTL VTVSSEQKLISEEDLAAAIEVMYPPPYLDNEKSNGTIIHVKGKHLCPSPLFPGPSKPFWVLVVVGGVLACYSLLVTVAFTIFW

VRSKRSRLLHSDYMNMTPRRPGPTRKHYQPYAPPRDFAAYRS

Clone A-CSR-1B (in order from N-terminus to C-terminus: anti-PSMA Clone A scFv +
sequences derived from CD28 (underlined))
                                                              (SEQ ID NO: 37)
QSVLTQPPSVSGAPGQRVTISCTGSSSNIGAGYDVHWYQQLPGTAPKLLIYGNSNRPSGVPDRFSGSKSGTSASLAITGLQAE DEADYYCQSYDSSLSGYVFGTGTKVTVLGSRGGGGSGGGGSGGGGSLEMAEVQLVQSGAEVKKPGESLKISCKGSGYSFTSYW IGWVRQMPGKGLEWMGITYPGDSDTRYSPSFQGQVTISADKSISTAYLQWSSLKASDTAMYYCARSMGSSLYASSDVWGQGTL VTVSSAAAIEVMYPPPYLDNEKSNGTIIHVKGKHLCPSPLFPGPSKPFWVLVVVGGVLACYSLLVTVAFTIFWVRSKRSRLLH

SDYMNMTPRRPGPTRKHYQPYAPPRDFAAYRS
```

Clone A-CSR-2A (in order from N-terminus to C-terminus: anti-PSMA Clone A scFv +
myc tag (bold) + sequences derived from 4-1BB (underlined))

(SEQ ID NO: 56)
QSVLTQPPSVSGAPGQRVTISCTGSSSNIGAGYDVHWYQQLPGTAPKLLIYGNSNRPSGVPDRFSGSKSGTSASLAITGLQAE

DEADYYCQSYDSSLSGYVFGTGTKVTVLGSRGGGSGGGGSGGGGSLEMAEVQLVQSGAEVKKPGESLKISCKGSGYSFTSYW

IGWVRQMPGKGLEWMGITYPGDSDTRYSPSFQGQVTISADKSISTAYLQWSSLKASDTAMYYCARSMGSSLYASSDVWGQGTL

VTVSSEQKLISEEDLAAATGPADLSPGASSVTPPAPAREPGHSPQIISFFLALTSTALLFLLFFLTLRFSVVKRGRKKLLYIF

KQPFMRPVQTTQEEDGCSCRFPEEEEGGCEL

Clone A-CSR-2B (in order from N-terminus to C-terminus: anti-PSMA Clone A scFv +
sequences derived from 4-1BB (underlined))

(SEQ ID NO: 57)
QSVLTQPPSVSGAPGQRVTISCTGSSSNIGAGYDVHWYQQLPGTAPKLLIYGNSNRPSGVPDRFSGSKSGTSASLAITGLQAE

DEADYYCQSYDSSLSGYVFGTGTKVTVLGSRGGGSGGGGSGGGGSLEMAEVQLVQSGAEVKKPGESLKISCKGSGYSFTSYW

IGWVRQMPGKGLEWMGITYPGDSDTRYSPSFQGQVTISADKSISTAYLQWSSLKASDTAMYYCARSMGSSLYASSDVWGQGTL

VTVSSAAATGPADLSPGASSVTPPAPAREPGHSPQIISFFLALTSTALLFLLFFLTLRFSVVKRGRKKLLYIFKQPFMRPVQT

TQEEDGCSCRFPEEEEGGCEL

Clone A-CSR-3A (in order from N-terminus to C-terminus: anti-PSMA Clone A scFv +
myc tag (bold) + sequences derived from CD27 (underlined))

(SEQ ID NO: 58)
QSVLTQPPSVSGAPGQRVTISCTGSSSNIGAGYDVHWYQQLPGTAPKLLIYGNSNRPSGVPDRFSGSKSGTSASLAITGLQAE

DEADYYCQSYDSSLSGYVFGTGTKVTVLGSRGGGSGGGGSGGGGSLEMAEVQLVQSGAEVKKPGESLKISCKGSGYSFTSYW

IGWVRQMPGKGLEWMGITYPGDSDTRYSPSFQGQVTISADKSISTAYLQWSSLKASDTAMYYCARSMGSSLYASSDVWGQGTL

VTVSSEQKLISEEDLAAATGPTHLPYVSEMLEARTAGHMQTLADFRQLPARTLSTHWPPQRSLCSSDFIRILVIFSGMFLVFT

LAGALFLHQRRKYRSNKGESPVEPAEPCRYSCPREEEGSTIPIQEDYRKPEPACSP

Clone A-CSR-3B (in order from N-terminus to C-terminus: anti-PSMA Clone A scFv +
sequences derived from CD27 (underlined))

(SEQ ID NO: 59)
QSVLTQPPSVSGAPGQRVTISCTGSSSNIGAGYDVHWYQQLPGTAPKLLIYGNSNRPSGVPDRFSGSKSGTSASLAITGLQAE

DEADYYCQSYDSSLSGYVFGTGTKVTVLGSRGGGSGGGGSGGGGSLEMAEVQLVQSGAEVKKPGESLKISCKGSGYSFTSYW

IGWVRQMPGKGLEWMGITYPGDSDTRYSPSFQGQVTISADKSISTAYLQWSSLKASDTAMYYCARSMGSSLYASSDVWGQGTL

VTVSSAAATGPTHLPYVSEMLEARTAGHMQTLADFRQLPARTLSTHWPPQRSLCSSDFIRILVIFSGMFLVFTLAGALFLHQR

RKYRSNKGESPVEPAEPCRYSCPREEEGSTIPIQEDYRKPEPACSP

CLONE A-CSR-4A (in order from N-terminus to C-terminus: anti-PSMA Clone A scFv +
myc tag (bold) + sequences derived from CD30 (underlined))

(SEQ ID NO: 60)
QSVLTQPPSVSGAPGQRVTISCTGSSSNIGAGYDVHWYQQLPGTAPKLLIYGNSNRPSGVPDRFSGSKSGTSASLAITGLQAE

DEADYYCQSYDSSLSGYVFGTGTKVTVLGSRGGGSGGGGSGGGGSLEMAEVQLVQSGAEVKKPGESLKISCKGSGYSFTSYW

IGWVRQMPGKGLEWMGITYPGDSDTRYSPSFQGQVTISADKSISTAYLQWSSLKASDTAMYYCARSMGSSLYASSDVWGQGTL

VTVSSEQKLISEEDLAAATGAPPLGTQPDCNPTPENGEAPASTSPTQSLLVDSQASKTLPIPTSAPVALSSTGKPVLDAGPVL

FWVILVLVVVVGSSAFLLCHRRACRKRIRQKLHLCYPVQTSQPKLELVDSRPRRSSTQLRSGASVTEPVAEERGLMSQPLMET

CHSVGAAYLESLPLQDASPAGGPSSPRDLPEPRVSTEHTNNKIEKIYIMKADTVIVGTVKAELPEGRGLAGPAEPELEEELEA

DHTPHYPEQETEPPLGSCSDVMLSVEEEGKEDPLPTAASGK

CLONE A-CSR-4B (in order from N-terminus to C-terminus: anti-PSMA Clone A scFv +
sequences derived from CD30 (underlined))

(SEQ ID NO: 61)
QSVLTQPPSVSGAPGQRVTISCTGSSSNIGAGYDVHWYQQLPGTAPKLLIYGNSNRPSGVPDRFSGSKSGTSASLAITGLQAE

DEADYYCQSYDSSLSGYVFGTGTKVTVLGSRGGGSGGGGSGGGGSLEMAEVQLVQSGAEVKKPGESLKISCKGSGYSFTSYW

IGWVRQMPGKGLEWMGITYPGDSDTRYSPSFQGQVTISADKSISTAYLQWSSLKASDTAMYYCARSMGSSLYASSDVWGQGTL

VTVSSAAATGAPPLGTQPDCNPTPENGEAPASTSPTQSLLVDSQASKTLPIPTSAPVALSSTGKPVLDAGPVLFWVILVLVVV

-continued

VGSSAFLLCHRRACRKRIRQKLHLCYPVQTSQPKLELVDSRPRRSSTQLRSGASVTEPVAEERGLMSQPLMETCHSVGAAYLE

SLPLQDASPAGGPSSPRDLPEPRVSTEHTNNKIEKIYIMKADTVIVGTVKAELPEGRGLAGPAEPELEEELEADHTPHYPEQE

TEPPLGSCSDVMLSVEEEGKEDPLPTAASGK

CLONE A-CSR-5A (in order from N-terminus to C-terminus: anti-PSMA Clone A scFv +
myc tag (bold) + sequences derived from OX40 (underlined))
(SEQ ID NO: 62)
QSVLTQPPSVSGAPGQRVTISCTGSSSNIGAGYDVHWYQQLPGTAPKLLIYGNSNRPSGVPDRFSGSKSGTSASLAITGLQAE DEADYYCQSYDSSLSGYVFGTGTKVTVLGSRGGGGSGGGGSGGGGSLEMAEVQLVQSGAEVKKPGESLKISCKGSGYSFTSYW IGWVRQMPGKGLEWMGITYPGDSDTRYSPSFQGQVTISADKSISTAYLQWSSLKASDTAMYYCARSMGSSLYASSDVWGQGTL VTVSSEQKLISEEDLAAATGDRDPPATQPQETQGPPARPITVQPTEAWPRTSQGPSTRPVEVPGGRAVAAILGLGLVLGLLGP

LAILLALYLLRRDQRLPPDAHKPPGGGSFRTPIQEEQADAHSTLAKI

CLONE A-CSR-5B (in order from N-terminus to C-terminus: anti-PSMA Clone A scFv +
sequences derived from OX40 (underlined))
(SEQ ID NO: 63)
QSVLTQPPSVSGAPGQRVTISCTGSSSNIGAGYDVHWYQQLPGTAPKLLIYGNSNRPSGVPDRFSGSKSGTSASLAITGLQAE DEADYYCQSYDSSLSGYVFGTGTKVTVLGSRGGGGSGGGGSGGGGSLEMAEVQLVQSGAEVKKPGESLKISCKGSGYSFTSYW IGWVRQMPGKGLEWMGITYPGDSDTRYSPSFQGQVTISADKSISTAYLQWSSLKASDTAMYYCARSMGSSLYASSDVWGQGTL VTVSSAAATGDRDPPATQPQETQGPPARPITVQPTEAWPRTSQGPSTRPVEVPGGRAVAAILGLGLVLGLLGPLAILLALYLL

RRDQRLPPDAHKPPGGGSFRTPIQEEQADAHSTLAKI

CLONE A-CSR-6A (in order from N-terminus to C-terminus: anti-PSMA Clone A scFv +
myc tag (bold) + CD8 MM and CD27 IC (underlined))
(SEQ ID NO: 64)
QSVLTQPPSVSGAPGQRVTISCTGSSSNIGAGYDVHWYQQLPGTAPKLLIYGNSNRPSGVPDRFSGSKSGTSASLAITGLQAE DEADYYCQSYDSSLSGYVFGTGTKVTVLGSRGGGGSGGGGSGGGGSLEMAEVQLVQSGAEVKKPGESLKISCKGSGYSFTSYW IGWVRQMPGKGLEWMGITYPGDSDTRYSPSFQGQVTISADKSISTAYLQWSSLKASDTAMYYCARSMGSSLYASSDVWGQGTL VTVSSEQKLISEEDLAAATGTTTPAPRPPTPAPTIASQPLSLRPEACRPAAGGAVHTRGLDFACDIYIWAPLAGTCGVLLLSL

VITLYCQRRKYRSNKGESPVEPAEPCRYSCPREEEGSTIPIQEDYRKPEPACSP

CLONE A-CSR-6B (in order from N-terminus to C-terminus: anti-PSMA Clone A scFv +
CD8 TM and CD27 IC (underlined))
(SEQ ID NO: 65)
QSVLTQPPSVSGAPGQRVTISCTGSSSNIGAGYDVHWYQQLPGTAPKLLIYGNSNRPSGVPDRFSGSKSGTSASLAITGLQAE DEADYYCQSYDSSLSGYVFGTGTKVTVLGSRGGGGSGGGGSGGGGSLEMAEVQLVQSGAEVKKPGESLKISCKGSGYSFTSYW IGWVRQMPGKGLEWMGITYPGDSDTRYSPSFQGQVTISADKSISTAYLQWSSLKASDTAMYYCARSMGSSLYASSDVWGQGTL VTVSSAAATGTTTPAPRPPTPAPTIASQPLSLRPEACRPAAGGAVHTRGLDFACDIYIWAPLAGTCGVLLLSLVITLYCQRRK

YRSNKGESPVEPAEPCRYSCPREEEGSTIPIQEDYRKPEPACSP

CLONE A-CSR-7A (in order from N-terminus to C-terminus: anti-PSMA Clone A scFv +
myc tag (bold) + CD8 MM and CD30 IC (underlined))
(SEQ ID NO: 66)
QSVLTQPPSVSGAPGQRVTISCTGSSSNIGAGYDVHWYQQLPGTAPKLLIYGNSNRPSGVPDRFSGSKSGTSASLAITGLQAE DEADYYCQSYDSSLSGYVFGTGTKVTVLGSRGGGGSGGGGSGGGGSLEMAEVQLVQSGAEVKKPGESLKISCKGSGYSFTSYW IGWVRQMPGKGLEWMGITYPGDSDTRYSPSFQGQVTISADKSISTAYLQWSSLKASDTAMYYCARSMGSSLYASSDVWGQGTL VTVSSEQKLISEEDLAAATGTTTPAPRPPTPAPTIASQPLSLRPEACRPAAGGAVHTRGLDFACDIYIWAPLAGTCGVLLLSL VITLYCHRRACRKRIRQKLHLCYPVQTSQPKLELVDSRPRRSSTQLRSGASVTEPVAEERGLMSQPLMETCHSVGAAYLESLP LQDASPAGGPSSPRDLPEPRVSTEHTNNKIEKIYIMKADTVIVGTVKAELPEGRGLAGPAEPELEEELEADHTPHYPEQETEP

PLGSCSDVMLSVEEEGKEDPLPTAASGK

CLONE A-CSR-7B (in order from N-terminus to C-terminus: anti-PSMA Clone A scFv +
CD8 TM and CD30 IC (underlined))
(SEQ ID NO: 67)
QSVLTQPPSVSGAPGQRVTISCTGSSSNIGAGYDVHWYQQLPGTAPKLLIYGNSNRPSGVPDRFSGSKSGTSASLAITGLQAE DEADYYCQSYDSSLSGYVFGTGTKVTVLGSRGGGGSGGGGSGGGGSLEMAEVQLVQSGAEVKKPGESLKISCKGSGYSFTSYW

```
IGWVRQMPGKGLEWMGITYPGDSDTRYSPSFQGQVTISADKSISTAYLQWSSLKASDTAMYYCARSMGSSLYASSDVWGQGTL

VTVSSAAATGTTTPAPRPPTPAPTIASQPLSLRPEACRPAAGGAVHTRGLDFACDIYIWAPLAGTCGVLLLSLVITLYCHRRA

CRKRIRQKLHLCYPVQTSQPKLELVDSRPRRSSTQLRSGASVTEPVAEERGLMSQPLMETCHSVGAAYLESLPLQDASPAGGP

SSPRDLPEPRVSTEHTNNKIEKIYIMKADTVIVGTVKAELPEGRGLAGPAEPELEEELEADHTPHYPEQETEPPLGSCSDVML

SVEEEGKEDPLPTAASGK

CLONE A-CSR-8A (in order from N-terminus to C-terminus: anti-PSMA Clone A scFv +
myc tag (bold) + CD8 MM and OX40 IC (underlined))
                                                                (SEQ ID NO: 68)
QSVLTQPPSVSGAPGQRVTISCTGSSSNIGAGYDVHWYQQLPGTAPKLLIYGNSNRPSGVPDRFSGSKSGTSASLAITGLQAE DEADYYCQSYDSSLSGYVFGTGTKVTVLGSRGGGSGGGGSGGGGSLEMAEVQLVQSGAEVKKPGESLKISCKGSGYSFTSYW IGWVRQMPGKGLEWMGITYPGDSDTRYSPSFQGQVTISADKSISTAYLQWSSLKASDTAMYYCARSMGSSLYASSDVWGQGTL VTVSSEQKLISEEDLAAATGTTTPAPRPPTPAPTIASQPLSLRPEACRPAAGGAVHTRGLDFACDIYIWAPLAGTCGVLLLSL

VITLYCALYLLRRDQRLPPDAHKPPGGGSFRTPIQEEQADAHSTLAKI

CLONE A-CSR-8B (in order from N-terminus to C-terminus: anti-PSMA Clone A scFv +
CD8 TM and OX40 IC (underlined))
                                                                (SEQ ID NO: 69)
QSVLTQPPSVSGAPGQRVTISCTGSSSNIGAGYDVHWYQQLPGTAPKLLIYGNSNRPSGVPDRFSGSKSGTSASLAITGLQAE DEADYYCQSYDSSLSGYVFGTGTKVTVLGSRGGGSGGGGSGGGGSLEMAEVQLVQSGAEVKKPGESLKISCKGSGYSFTSYW IGWVRQMPGKGLEWMGITYPGDSDTRYSPSFQGQVTISADKSISTAYLQWSSLKASDTAMYYCARSMGSSLYASSDVWGQGTL VTVSSAAATGTTTPAPRPPTPAPTIASQPLSLRPEACRPAAGGAVHTRGLDFACDIYIWAPLAGTCGVLLLSLVITLYCALYL

LRRDQRLPPDAHKPPGGGSFRTPIQEEQADAHSTLAKI

Clone B-CSR-1A (in order from N-terminus to C-terminus: anti-PSMA Clone B scFv +
myc tag (bold) + sequences derived from CD28 (underlined))
                                                                (SEQ ID NO: 70)
QAVLTQPPSASGTPGQRVTISCSGSSSNIGSNTVNWYQQLPGTAPKLLMYSNNQRPSGVPDRFSGSKSGTSASLAISGLQSED EADYYCAAWDDSLNGYVFGTGTKVTVLGSRGGGSGGGGSGGGGSLEMAEVQLVQSGAEMKKPGESLKISCKGSGYNFASYWV GWVRQMPGKGLEWMGTIYPDDSDTRYGPAFQGQVTISADKSISTAYLQWSSLKASDTAMYYCARDSYYGIDVWGQGTLVTVSS

EQKLISEEDLAAAIEVMYPPPYLDNEKSNGTIIHVKGKHLCPSPLFPGPSKPFWVLVVVGGVLACYSLLVTVAFTIFWVRSKR

SRLLHSDYMNMTPRRPGPTRKHYQPYAPPRDFAAYRS

Clone B-CSR-1B (in order from N-terminus to C-terminus: anti-PSMA Clone B scFv +
sequences derived from CD28 (underlined))
                                                                (SEQ ID NO: 38)
QAVLTQPPSASGTPGQRVTISCSGSSSNIGSNTVNWYQQLPGTAPKLLMYSNNQRPSGVPDRFSGSKSGTSASLAISGLQSED EADYYCAAWDDSLNGYVFGTGTKVTVLGSRGGGSGGGGSGGGGSLEMAEVQLVQSGAEMKKPGESLKISCKGSGYNFASYWV GWVRQMPGKGLEWMGTIYPDDSDTRYGPAFQGQVTISADKSISTAYLQWSSLKASDTAMYYCARDSYYGIDVWGQGTLVTVSS AAAIEVMYPPPYLDNEKSNGTIIHVKGKHLCPSPLFPGPSKPFWVLVVVGGVLACYSLLVTVAFTIFWVRSKRSRLLHSDYMN

MTPRRPGPTRKHYQPYAPPRDFAAYRS

Clone B-CSR-2A (in order from N-terminus to C-terminus: anti-PSMA Clone B scFv +
myc tag (bold) + sequences derived from 4-1BB (underlined))
                                                                (SEQ ID NO: 71)
QAVLTQPPSASGTPGQRVTISCSGSSSNIGSNTVNWYQQLPGTAPKLLMYSNNQRPSGVPDRFSGSKSGTSASLAISGLQSED EADYYCAAWDDSLNGYVFGTGTKVTVLGSRGGGSGGGGSGGGGSLEMAEVQLVQSGAEMKKPGESLKISCKGSGYNFASYWV GWVRQMPGKGLEWMGTIYPDDSDTRYGPAFQGQVTISADKSISTAYLQWSSLKASDTAMYYCARDSYYGIDVWGQGTLVTVSS

EQKLISEEDLAAATGPADLSPGASSVTPPAPAREPGHSPQIISFFLALTSTALLFLLFFLTLRFSVVKRGRKKLLYIFKQPFM

RPVQTTQEEDGCSCRFPEEEEGGCEL
```

CLONE B-CSR-2B (from N-terminus to C-terminus: anti-PSMA Clone B scFv + sequences
derived from 4-1BB (underlined))

(SEQ ID NO: 72)

QAVLTQPPSASGTPGQRVTISCSGSSSNIGSNTVNWYQQLPGTAPKLLMYSNNQRPSGVPDRFSGSKSGTSASLAISGLQSED

EADYYCAAWDDSLNGYVFGTGTKVTVLGSRGGGGSGGGGSGGGGSLEMAEVQLVQSGAEMKKPGESLKISCKGSGYNFASYWV

GWVRQMPGKGLEWMGTIYPDDSDTRYGPAFQGQVTISADKSISTAYLQWSSLKASDTAMYYCARDSYYGIDVWGQGTLVTVSS

AAATGPADLSPGASSVTPPAPAREPGHSPQIISFFLALTSTALLFLLFFLTLRFSVVKRGRKKLLYIFKQPFMRPVQTTQEED

GCSCRFPEEEEGGCEL

Clone B-CSR-3A (in order from N-terminus to C-terminus: anti-PSMA Clone B scFv +
myc tag (bold) + sequences derived from CD27 (underlined))

(SEQ ID NO: 73)

QAVLTQPPSASGTPGQRVTISCSGSSSNIGSNTVNWYQQLPGTAPKLLMYSNNQRPSGVPDRFSGSKSGTSASLAISGLQSED

EADYYCAAWDDSLNGYVFGTGTKVTVLGSRGGGGSGGGGSGGGGSLEMAEVQLVQSGAEMKKPGESLKISCKGSGYNFASYWV

GWVRQMPGKGLEWMGTIYPDDSDTRYGPAFQGQVTISADKSISTAYLQWSSLKASDTAMYYCARDSYYGIDVWGQGTLVTVSS

EQKLISEEDLAAATGPTHLPYVSEMLEARTAGHMQTLADFRQLPARTLSTHWPPQRSLCSSDFIRILVIFSGMFLVFTLAGAL

FLHQRRKYRSNKGESPVEPAEPCRYSCPREEEGSTIPIQEDYRKPEPACSP

Clone B-CSR-3B (in order from N-terminus to C-terminus: anti-PSMA Clone B scFv +
sequences derived from CD27 (underlined))

(SEQ ID NO: 74)

QAVLTQPPSASGTPGQRVTISCSGSSSNIGSNTVNWYQQLPGTAPKLLMYSNNQRPSGVPDRFSGSKSGTSASLAISGLQSED

EADYYCAAWDDSLNGYVFGTGTKVTVLGSRGGGGSGGGGSGGGGSLEMAEVQLVQSGAEMKKPGESLKISCKGSGYNFASYWV

GWVRQMPGKGLEWMGTIYPDDSDTRYGPAFQGQVTISADKSISTAYLQWSSLKASDTAMYYCARDSYYGIDVWGQGTLVTVSS

AAATGPTHLPYVSEMLEARTAGHMQTLADFRQLPARTLSTHWPPQRSLCSSDFIRILVIFSGMFLVFTLAGALFLHQRRKYRS

NKGESPVEPAEPCRYSCPREEEGSTIPIQEDYRKPEPACSP

CLONE B-CSR-4A (in order from N-terminus to C-terminus: anti-PSMA Clone B scFv +
myc tag (bold) + sequences derived from CD30 (underlined))

(SEQ ID NO: 75)

QAVLTQPPSASGTPGQRVTISCSGSSSNIGSNTVNWYQQLPGTAPKLLMYSNNQRPSGVPDRFSGSKSGTSASLAISGLQSED

EADYYCAAWDDSLNGYVFGTGTKVTVLGSRGGGGSGGGGSGGGGSLEMAEVQLVQSGAEMKKPGESLKISCKGSGYNFASYWV

GWVRQMPGKGLEWMGTIYPDDSDTRYGPAFQGQVTISADKSISTAYLQWSSLKASDTAMYYCARDSYYGIDVWGQGTLVTVSS

EQKLISEEDLAAATGAPPLGTQPDCNPTPENGEAPASTSPTQSLLVDSQASKTLPIPTSAPVALSSTGKPVLDAGPVLFWVIL

VLVVVVGSSAFLLCHRRACRKRIRQKLHLCYPVQTSQPKLELVDSRPRRSSTQLRSGASVTEPVAEERGLMSQPLMETCHSVG

AAYLESLPLQDASPAGGPSSPRDLPEPRVSTEHTNNKIEKIYIMKADTVIVGTVKAELPEGRGLAGPAEPELEEELEADHTPH

YPEQETEPPLGSCSDVMLSVEEEGKEDPLPTAASGK

CLONE B-CSR-4B (in order from N-terminus to C-terminus: anti-PSMA Clone B sFv +
sequences derived from CD30 (underlined))

(SEQ ID NO: 76)

QAVLTQPPSASGTPGQRVTISCSGSSSNIGSNTVNWYQQLPGTAPKLLMYSNNQRPSGVPDRFSGSKSGTSASLAISGLQSED

EADYYCAAWDDSLNGYVFGTGTKVTVLGSRGGGGSGGGGSGGGGSLEMAEVQLVQSGAEMKKPGESLKISCKGSGYNFASYWV

GWVRQMPGKGLEWMGTIYPDDSDTRYGPAFQGQVTISADKSISTAYLQWSSLKASDTAMYYCARDSYYGIDVWGQGTLVTVSS

AAATGAPPLGTQPDCNPTPENGEAPASTSPTQSLLVDSQASKTLPIPTSAPVALSSTGKPVLDAGPVLFWVILVLVVVVGSSA

FLLCHRRACRKRIRQKLHLCYPVQTSQPKLELVDSRPRRSSTQLRSGASVTEPVAEERGLMSQPLMETCHSVGAAYLESLPLQ

DASPAGGPSSPRDLPEPRVSTEHTNNKIEKIYIMKADTVIVGTVKAELPEGRGLAGPAEPELEEELEADHTPHYPEQETEPPL

GSCSDVMLSVEEEGKEDPLPTAASGK

CLONE B-CSR-5A (in order from N-terminus to C-terminus: anti-PSMA Clone B scFv +
myc tag (bold) + sequences derived from OX40 (underlined))

(SEQ ID NO: 77)

QAVLTQPPSASGTPGQRVTISCSGSSSNIGSNTVNWYQQLPGTAPKLLMYSNNQRPSGVPDRFSGSKSGTSASLAISGLQSED

EADYYCAAWDDSLNGYVFGTGTKVTVLGSRGGGGSGGGGSGGGGSLEMAEVQLVQSGAEMKKPGESLKISCKGSGYNFASYWV

GWVRQMPGKGLEWMGTIYPDDSDTRYGPAFQGQVTISADKSISTAYLQWSSLKASDTAMYYCARDSYYGIDVWGQGTLVTVSS

EQKLISEEDLAAATGDRDPPATQPQETQGPPARPITVQPTEAWPRTSQGPSTRPVEVPGGRAVAAILGLGLVLGLLGPLAILL

ALYLLRRDQRLPPDAHKPPGGGSFRTPIQEEQADAHSTLAKI

CLONE B-CSR-5B (in order from N-terminus to C-terminus: anti-PSMA Clone B scFv + sequences derived from OX40 (underlined))

(SEQ ID NO: 78)

QAVLTQPPSASGTPGQRVTISCSGSSSNIGSNTVNWYQQLPGTAPKLLMYSNNQRPSGVPDRFSGSKSGTSASLAISGLQSED

EADYYCAAWDDSLNGYVFGTGTKVTVLGSRGGGGSGGGGSGGGGSLEMAEVQLVQSGAEMKKPGESLKISCKGSGYNFASYWV

GWVRQMPGKGLEWMGTIYPDDSDTRYGPAFQGQVTISADKSISTAYLQWSSLKASDTAMYYCARDSYYGIDVWGQGTLVTVSS

AAATGDRDPPATQPQETQGPPARPITVQPTEAWPRTSQGPSTRPVEVPGGRAVAAILGLGLVLGLLGPLAILLALYLLRRDQR

LPPDAHKPPGGGSFRTPIQEEQADAHSTLAKI

CLONE B-CSR-6A (in order from N-terminus to C-terminus: anti-PSMA Clone B scFv + myc tag (bold) + CD8 MM and CD27 IC (underlined))

(SEQ ID NO: 79)

QAVLTQPPSASGTPGQRVTISCSGSSSNIGSNTVNWYQQLPGTAPKLLMYSNNQRPSGVPDRFSGSKSGTSASLAISGLQSED

EADYYCAAWDDSLNGYVFGTGTKVTVLGSRGGGGSGGGGSGGGGSLEMAEVQLVQSGAEMKKPGESLKISCKGSGYNFASYWV

GWVRQMPGKGLEWMGTIYPDDSDTRYGPAFQGQVTISADKSISTAYLQWSSLKASDTAMYYCARDSYYGIDVWGQGTLVTVSS

EQKLISEEDLAAATGTTTPAPRPPTPAPTIASQPLSLRPEACRPAAGGAVHTRGLDFACDIYIWAPLAGTCGVLLLSLVITLY

CQRRKYRSNKGESPVEPAEPCRYSCPREEEGSTIPIQEDYRKPEPACSP

CLONE B-CSR-6B (in order from N-terminus to C-terminus: anti-PSMA Clone B scFv + CD8 TM and CD27 IC (underlined))

(SEQ ID NO: 80)

QAVLTQPPSASGTPGQRVTISCSGSSSNIGSNTVNWYQQLPGTAPKLLMYSNNQRPSGVPDRFSGSKSGTSASLAISGLQSED

EADYYCAAWDDSLNGYVFGTGTKVTVLGSRGGGGSGGGGSGGGGSLEMAEVQLVQSGAEMKKPGESLKISCKGSGYNFASYWV

GWVRQMPGKGLEWMGTIYPDDSDTRYGPAFQGQVTISADKSISTAYLQWSSLKASDTAMYYCARDSYYGIDVWGQGTLVTVSS

AAATGTTTPAPRPPTPAPTIASQPLSLRPEACRPAAGGAVHTRGLDFACDIYIWAPLAGTCGVLLLSLVITLYCQRRKYRSNK

GESPVEPAEPCRYSCPREEEGSTIPIQEDYRKPEPACSP

CLONE B-CSR-7A (in order from N-terminus to C-terminus: anti-PSMA Clone B scFv + myc tag (bold) + CD8 MM and CD30 IC (underlined))

(SEQ ID NO: 81)

QAVLTQPPSASGTPGQRVTISCSGSSSNIGSNTVNWYQQLPGTAPKLLMYSNNQRPSGVPDRFSGSKSGTSASLAISGLQSED

EADYYCAAWDDSLNGYVFGTGTKVTVLGSRGGGGSGGGGSGGGGSLEMAEVQLVQSGAEMKKPGESLKISCKGSGYNFASYWV

GWVRQMPGKGLEWMGTIYPDDSDTRYGPAFQGQVTISADKSISTAYLQWSSLKASDTAMYYCARDSYYGIDVWGQGTLVTVSS

EQKLISEEDLAAATGTTTPAPRPPTPAPTIASQPLSLRPEACRPAAGGAVHTRGLDFACDIYIWAPLAGTCGVLLLSLVITLY

CHRRACRKRIRQKLHLCYPVQTSQPKLELVDSRPRRSSTQLRSGASVTEPVAEERGLMSQPLMETCHSVGAAYLESLPLQDAS

PAGGPSSPRDLPEPRVSTEHTNNKIEKIYIMKADTVIVGTVKAELPEGRGLAGPAEPELEEELEADHTPHYPEQETEPPLGSC

SDVMLSVEEEGKEDPLPTAASGK

CLONE B-CSR-7B (in order from N-terminus to C-terminus: anti-PSMA Clone B scFv + CD8 TM and CD30 IC (underlined))

(SEQ ID NO: 82)

QAVLTQPPSASGTPGQRVTISCSGSSSNIGSNTVNWYQQLPGTAPKLLMYSNNQRPSGVPDRFSGSKSGTSASLAISGLQSED

EADYYCAAWDDSLNGYVFGTGTKVTVLGSRGGGGSGGGGSGGGGSLEMAEVQLVQSGAEMKKPGESLKISCKGSGYNFASYWV

GWVRQMPGKGLEWMGTIYPDDSDTRYGPAFQGQVTISADKSISTAYLQWSSLKASDTAMYYCARDSYYGIDVWGQGTLVTVSS

AAATGTTTPAPRPPTPAPTIASQPLSLRPEACRPAAGGAVHTRGLDFACDIYIWAPLAGTCGVLLLSLVITLYCHRRACRKRI

RQKLHLCYPVQTSQPKLELVDSRPRRSSTQLRSGASVTEPVAEERGLMSQPLMETCHSVGAAYLESLPLQDASPAGGPSSPRD

LPEPRVSTEHTNNKIEKIYIMKADTVIVGTVKAELPEGRGLAGPAEPELEEELEADHTPHYPEQETEPPLGSCSDVMLSVEEE

GKEDPLPTAASGK

-continued

CLONE B-CSR-8A (in order from N-terminus to C-terminus: anti-PSMA Clone B scFv + myc tag (bold) + CD8 MM and OX40 IC (underlined))

(SEQ ID NO: 83)

QAVLTQPPSASGTPGQRVTISCSGSSSNIGSNTVNWYQQLPGTAPKLLMYSNNQRPSGVPDRFSGSKSGTSASLAISGLQSED

EADYYCAAWDDSLNGYVFGTGTKVTVLGSRGGGGSGGGGSGGGGSLEMAEVQLVQSGAEMKKPGESLKISCKGSGYNFASYWV

GWVRQMPGKGLEWMGTIYPDDSDTRYGPAFQGQVTISADKSISTAYLQWSSLKASDTAMYYCARDSYYGIDVWGQGTLVTVSS

EQKLISEEDLAAATGTTTPAPRPPTPAPTIASQPLSLRPEACRPAAGGAVHTRGLDFACDIYIWAPLAGTCGVLLLSLVITLY

CALYLLRRDQRLPPDAHKPPGGGSFRTPIQEEQADAHSTLAKI

CLONE B-CSR-8B (in order from N-terminus to C-terminus: anti-PSMA Clone B scFv + CD8 TM and OX40 IC (underlined))

(SEQ ID NO: 84)

QAVLTQPPSASGTPGQRVTISCSGSSSNIGSNTVNWYQQLPGTAPKLLMYSNNQRPSGVPDRFSGSKSGTSASLAISGLQSED

EADYYCAAWDDSLNGYVFGTGTKVTVLGSRGGGGSGGGGSGGGGSLEMAEVQLVQSGAEMKKPGESLKISCKGSGYNFASYWV

GWVRQMPGKGLEWMGTIYPDDSDTRYGPAFQGQVTISADKSISTAYLQWSSLKASDTAMYYCARDSYYGIDVWGQGTLVTVSS

AAATGTTTPAPRPPTPAPTIASQPLSLRPEACRPAAGGAVHTRGLDFACDIYIWAPLAGTCGVLLLSLVITLYCALYLLRRDQ

RLPPDAHKPPGGGSFRTPIQEEQADAHSTLAKI

Nucleic acids encoding the caTCR+CSR construct combinations listed below have been designed, and many of these nucleic acids have been generated.

Ax1-caTCR + A-CSR-1A (Ax1-caTCR + P2A self-cleaving peptide (bold) + signal sequence (italic) + Clone A-CSR-1A (underlined))

(SEQ ID NO: 85)

*METDTLLLWVLLLWVPGSTG*EVQLVQSGAEVKKPGESLKISCKGSGYSFTSYWIGWVRQMPGKGLEWMGITYPGDSDTRYSPS

FQGQVTISADKSISTAYLQWSSLKASDTAMYYCARSMGSSLYASSDVWGQGTLVTVSSASTKGPSVFPLAPSSKSTSGGTAAL

GCLVKDYFPEPVTVSWNSGALTSGVHTFPAVLQSSGLYSLSSVVTVPSSSLGTQTYICNVNHKPSNTKVDKRVEPKSCEVKTD

STDHVKPKETENTKQPSKSCHKPKAIVHTEKVNMMSLTVLGLRMLFAKTVAVNELLTAKLEFLRAKRSGSGAPVKQTLNFDLL

KLAGDVESNPGP*METDTLLLWVLLLWVPGSTG*QSVLTQPPSVSGAPGQRVTISCTGSSSNIGAGYDVHWYQQLPGTAPKLLIY

GNSNRPSGVPDRFSGSKSGTSASLAITGLQAEDEADYYCQSYDSSLSGYVEGTGTKVTVLGQPKANPTVTLEPPSSEELQANK

ATLVCLISDFYPGAVTVAWKADGSPVKAGVETTKPSKQSNNKYAASSYLSLTPEQWKSHRSYSCQVTHEGSTVEKTVAPTECS

PIKTDVITMDPKDNCSKDANDTLLLQLTNTSAYYMYLLLLLKSVVYFAIITCCLLRRTAFCCNGEKSGSGATNESLLKQAGDV

EENPGP*METDTLLLWVLLLWVPGSTG*QSVLTQPPSVSGAPGQRVTISCTGSSSNIGAGYDVHWYQQLPGTAPKLLIYGNSNRP

SGVPDRFSGSKSGTSASLAITGLQAEDEADYYCQSYDSSLSGYVEGTGTKVTVLGSRGGGGSGGGGSGGGGSLEMAEVQLVQS

GAEVKKPGESLKISCKGSGYSFTSYWIGWVRQMPGKGLEWMGITYPGDSDTRYSPSFQGQVTISADKSISTAYLQWSSLKASD

TAMYYCARSMGSSLYASSDVWGQGTLVTVSSEQKLISEEDLAAAIEVMYPPPYLDNEKSNGTIIHVKGKHLCPSPLFPGPSKP

FWVLVVVGGVLACYSLLVTVAFTIFWVRSKRSRLLHSDYMNMTPRRPGPTRKHYQPYAPPRDFAAYRS

A-CSR-1A + Ax1-caTCR (signal sequence (italic) + Clone A-CSR-1A (underlined) + P2A self-cleaving peptide (italic) + Ax1-caTCR)

(SEQ ID NO: 161)

*METDTLLLWVLLLWVPGSTG*QSVLTQPPSVSGAPGQRVTISCTGSSSNIGAGYDVHWYQQLPGTAPKLLIYGNSNRPSGVPDR

FSGSKSGTSASLAITGLQAEDEADYYCQSYDSSLSGYVEGTGTKVTVLGSRGGGGSGGGGSGGGGSLEMAEVQLVQSGAEVKK

PGESLKISCKGSGYSFTSYWIGWVRQMPGKGLEWMGITYPGDSDTRYSPSFQGQVTISADKSISTAYLQWSSLKASDTAMYYC

ARSMGSSLYASSDVWGQGTLVTVSSEQKLISEEDLAAAIEVMYPPPYLDNEKSNGTIIHVKGKHLCPSPLFPGPSKPFWVLVV

VGGVLACYSLLVTVAFTIFWVRSKRSRLLHSDYMNMTPRRPGPTRKHYQPYAPPRDFAAYRSGSGATNESLLKQAGDVEENPG

P*METDTLLLWVLLLWVPGSTG*EVQLVQSGAEVKKPGESLKISCKGSGYSFTSYWIGWVRQMPGKGLEWMGITYPGDSDTRYSP

SFQGQVTISADKSISTAYLQWSSLKASDTAMYYCARSMGSSLYASSDVWGQGTLVTVSSASTKGPSVFPLAPSSKSTSGGTAA

LGCLVKDYFPEPVTVSWNSGALTSGVHTFPAVLQSSGLYSLSSVVTVPSSSLGTQTYICNVNHKPSNTKVDKRVEPKSCEVKT

-continued

DSTDHVKPKETENTKQPSKSCHKPKAIVHTEKVNMMSLTVLGLRMLFAKTVAVNFLLTAKLFFLRAKRSGSGAPVKQTLNFDL

LKLAGDVESNPGP*METDTLLLWVLLLWVPGST*GQSVLTQPPSVSGAPGQRVTISCTGSSSNIGAYDVHWYQQLPGTAPKLLI

YGNSNRPSGVPDRFSGSKSGTSASLAITGLQAEDEADYYCQSYDSSLSGYVFGTGTKVTVLGQPKANPTVTLFPPSSEELQAN

KATLVCLISDFYPGAVTVAWKADGSPVKAGVETTKPSKQSNNKYAASSYLSLTPEQWKSHRSYSCQVTHEGSTVEKTVAPTEC

SPIKTDVITMDPKDNCSKDANDTLLLQLTNTSAYYMYLLLLLKSVVYFAIITCCLLRRTAFCCNGEKS

Ax1-caTCR + B-CSR-1A (Ax1-caTCR + P2A self-cleaving peptide (bold) + signal
sequence (italic) + Clone B-CSR-1A (underlined))

(SEQ ID NO: 86)

*METDTLLLWVLLLWVPGST*GEVQLVQSGAEVKKPGESLKISCKGSGYSFTSYWIGWVRQMPGKGLEWMGITYPGDSDTRYSPS

FQGQVTISADKSISTAYLQWSSLKASDTAMYYCARSMGSSLYASSDVWGQGTLVTVSSASTKGPSVFPLAPSSKSTSGGTAAL

GCLVKDYFPEPVTVSWNSGALTSGVHTFPAVLQSSGLYSLSSVVTVPSSSLGTQTYICNVNHKPSNTKVDKRVEPKSCEVKTD

STDHVKPKETENTKQPSKSCHKPKAIVHTEKVNMMSLTVLGLRMLFAKTVAVNFLLTAKLFFLRAKRSGSGAPVKQTLNFDLL

KLAGDVESNPGP*METDTLLLWVLLLWVPGST*GQSVLTQPPSVSGAPGQRVTISCTGSSSNIGAYDVHWYQQLPGTAPKLLIY

GNSNRPSGVPDRFSGSKSGTSASLAITGLQAEDEADYYCQSYDSSLSGYVFGTGTKVTVLGQPKANPTVTLFPPSSEELQANK

ATLVCLISDFYPGAVTVAWKADGSPVKAGVETTKPSKQSNNKYAASSYLSLTPEQWKSHRSYSCQVTHEGSTVEKTVAPTECS

PIKTDVITMDPKDNCSKDANDTLLLQLTNTSAYYMYLLLLLKSVVYFAIITCCLLRRTAFCCNGEKSGSGATNESLLKQAGDV

EENPGP*METDTLLLWVLLLWVPGST*GQAVLTQPPSASGTPGQRVTISCSGSSSNIGSNTVNWYQQLPGTAPKLLMYSNNQRPS

GVPDRFSGSKSGTSASLAISGLQSEDEADYYCAAWDDSLNGYVFGTGTKVTVLGSRGGGGSGGGGSGGGGSLEMAEVQLVQSG

AEMKKPGESLKISCKGSGYNFASYWVGWVRQMPGKGLEWMGTIYPDDSDTRYGPAFQGQVTISADKSISTAYLQWSSLKASDT

AMYYCARDSYYGIDVWGQGTLVTVSSEQKLISEEDLAAAIEVMYPPPYLDNEKSNGTIIHVKGKHLCPSPLFPGPSKPFWVLV

VVGGVLACYSLLVTVAFTIFWVRSKRSRLLHSDYMNMTPRRPGPTRKHYQPYAPPRDFAAYRS

B-CSR-1A + Ax1-caTCR (signal sequence (italic) + Clone B-CSR-1A (underlined) + P2A
self-cleaving peptide (italic) + Ax1-caTCR)

(SEQ ID NO: 162)

*METDTLLLWVLLLWVPGST*GQAVLTQPPSASGTPGQRVTISCSGSSSNIGSNTVNWYQQLPGTAPKLLMYSNNQRPSGVPDRF

SGSKSGTSASLAISGLQSEDEADYYCAAWDDSLNGYVFGTGTKVTVLGSRGGGGSGGGGSGGGGSLEMAEVQLVQSGAEMKKP

GESLKISCKGSGYNFASYWVGWVRQMPGKGLEWMGTIYPDDSDTRYGPAFQGQVTISADKSISTAYLQWSSLKASDTAMYYCA

RDSYYGIDVWGQGTLVTVSSEQKLISEEDLAAAIEVMYPPPYLDNEKSNGTIIHVKGKHLCPSPLFPGPSKPFWVLVVVGGVL

ACYSLLVTVAFTIFWVRSKRSRLLHSDYMNMTPRRPGPTRKHYQPYAPPRDFAAYRSGSGATNESLLKQAGDVEENPGP*METD

TLLLWVLLLWVPGST*GEVQLVQSGAEVKKPGESLKISCKGSGYSFTSYWIGWVRQMPGKGLEWMGITYPGDSDTRYSPSFQGQ

VTISADKSISTAYLQWSSLKASDTAMYYCARSMGSSLYASSDVWGQGTLVTVSSASTKGPSVFPLAPSSKSTSGGTAALGCLV

KDYFPEPVTVSWNSGALTSGVHTFPAVLQSSGLYSLSSVVTVPSSSLGTQTYICNVNHKPSNTKVDKRVEPKSCEVKTDSTDH

VKPKETENTKQPSKSCHKPKAIVHTEKVNMMSLTVLGLRMLFAKTVAVNFLLTAKLFFLRAKRSGSGAPVKQTLNFDLLKLAG

DVESNPGP*METDTLLLWVLLLWVPGST*GQSVLTQPPSVSGAPGQRVTISCTGSSSNIGAYDVHWYQQLPGTAPKLLIYGNSN

RPSGVPDRFSGSKSGTSASLAITGLQAEDEADYYCQSYDSSLSGYVFGTGTKVTVLGQPKANPTVTLFPPSSEELQANKATLV

CLISDFYPGAVTVAWKADGSPVKAGVETTKPSKQSNNKYAASSYLSLTPEQWKSHRSYSCQVTHEGSTVEKTVAPTECSPIKT

DVITMDPKDNCSKDANDTLLLQLTNTSAYYMYLLLLLKSVVYFAIITCCLLRRTAFCCNGEKS

Bx1-caTCR + A-CSR-1A (Bx1-caTCR + P2A self-cleaving peptide (bold) + signal
sequence (italic) + Clone A-CSR-1A (underlined))

(SEQ ID NO: 87)

*METDTLLLWVLLLWVPGST*GEVQLVQSGAEMKKPGESLKISCKGSGYNFASYWVGWVRQMPGKGLEWMGTIYPDDSDTRYGPA

FQGQVTISADKSISTAYLQWSSLKASDTAMYYCARDSYYGIDVWGQGTLVTVSSASTKGPSVFPLAPSSKSTSGGTAALGCLV

KDYFPEPVTVSWNSGALTSGVHTFPAVLQSSGLYSLSSVVTVPSSSLGTQTYICNVNHKPSNTKVDKRVEPKSCEVKTDSTDH

VKPKETENTKQPSKSCHKPKAIVHTEKVNMMSLTVLGLRMLFAKTVAVNFLLTAKLFFLRAKRSGSGAPVKQTLNFDLLKLAG

DVESNPGP*METDTLLLWVLLLWVPGST*GQAVLTQPPSASGTPGQRVTISCSGSSSNIGSNTVNWYQQLPGTAPKLLMYSNNQR

-continued

PSGVPDRFSGSKSGTSASLAISGLQSEDEADYYCAAWDDSLNGYVFGTGTKVTVLGQPKANPTVTLFPPSSEELQANKATLVC
LISDFYPGAVTVAWKADGSPVKAGVETTKPSKQSNNKYAASSYLSLTPEQWKSHRSYSCQVTHEGSTVEKTVAPTECSPIKTD
VITMDPKDNCSKDANDTLLLQLTNTSAYYMYLLLLLKSVVYFAIITCCLLRRTAFCCNGEKSGSGATNESLLKQAGDVEENPG
*PMETDTLLLWVLLLWVPGSTG*QSVLTQPPSVSGAPGQRVTISCTGSSSNIGAGYDVHWYQQLPGTAPKLLIYGNSNRPSGVPD
RFSGSKSGTSASLAITGLQAEDEADYYCQSYDSSLSGYVFGTGTKVTVLGSRGGGSGGGGSGGGGSLEMAEVQLVQSGAEVK
KPGESLKISCKGSGYSFTSYWIGWVRQMPGKGLEWMGITYPGDSDTRYSPSFQGQVTISADKSISTAYLQWSSLKASDTAMYY
CARSMGSSLYASSDVWGQGTLVTVSSEQKLISEEDLAAAIEVMYPPPYLDNEKSNGTIIHVKGKHLCPSPLFPGPSKPFWVLV
VVGGVLACYSLLVTVAFTIFWVRSKRSRLLHSDYMNMTPRRPGPTRKHYQPYAPPRDFAAYRS

A-CSR-1A + Bx1-caTCR (signal sequence (italic) + Clone A-CSR-1A (underlined) + P2A
self-cleaving peptide (italic) + Bx1-caTCR)

(SEQ ID NO: 163)
*METDTLLLWVLLLWVPGSTG*QSVLTQPPSVSGAPGQRVTISCTGSSSNIGAGYDVHWYQQLPGTAPKLLIYGNSNRPSGVPDR
FSGSKSGTSASLAITGLQAEDEADYYCQSYDSSLSGYVEGTGTKVTVLGSRGGGSGGGGSGGGGSLEMAEVQLVQSGAEVKK
PGESLKISCKGSGYSFTSYWIGWVRQMPGKGLEWMGITYPGDSDTRYSPSFQGQVTISADKSISTAYLQWSSLKASDTAMYYC
ARSMGSSLYASSDVWGQGTLVTVSSEQKLISEEDLAAAIEVMYPPPYLDNEKSNGTIIHVKGKHLCPSPLFPGPSKPFWVLVV
VGGVLACYSLLVTVAFTIFWVRSKRSRLLHSDYMNMTPRRPGPTRKHYQPYAPPRDFAAYRSGSGATNFSLLKQAGDVEENPG
*METDTLLLWVLLLWVPGSTG*EVQLVQSGAEMKKPGESLKISCKGSGYNFASYWVGWVRQMPGKGLEWMGTIYPDDSDTRYGPA
FQGQVTISADKSISTAYLQWSSLKASDTAMYYCARDSYYGIDVWGQGTLVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKRVEPKSCEVKTDSTDH
VKPKETENTKQPSKSCHKPKAIVHTEKVNMMSLTVLGLRMLFAKTVAVNELLTAKLEFLRAKRSGSGAPVKQTLNFDLLKLAG
DVESNPGP*METDTLLLWVLLLWVPGSTG*QAVLTQPPSASGTPGQRVTISCSGSSSNIGSNTVNWYQQLPGTAPKLLMYSNNQR
PSGVPDRFSGSKSGTSASLAISGLQSEDEADYYCAAWDDSLNGYVEGTGTKVTVLGQPKANPTVTLEPPSSEELQANKATLVC
LISDFYPGAVTVAWKADGSPVKAGVETTKPSKQSNNKYAASSYLSLTPEQWKSHRSYSCQVTHEGSTVEKTVAPTECSPIKTD
VITMDPKDNCSKDANDTLLLQLTNTSAYYMYLLLLLKSVVYFAIITCCLLRRTAFCCNGEKS

Bx1-caTCR + B-CSR-1A (Bx1-caTCR + P2A self-cleaving peptide (bold) + signal
sequence (italic) + Clone B-CSR-1A (underlined))

(SEQ ID NO: 88)
*METDTLLLWVLLLWVPGSTG*EVQLVQSGAEMKKPGESLKISCKGSGYNFASYWVGWVRQMPGKGLEWMGTIYPDDSDTRYGPA
FQGQVTISADKSISTAYLQWSSLKASDTAMYYCARDSYYGIDVWGQGTLVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKRVEPKSCEVKTDSTDH
VKPKETENTKQPSKSCHKPKAIVHTEKVNMMSLTVLGLRMLFAKTVAVNELLTAKLEFLRAKRSGSGAPVKQTLNFDLLKLAG
DVESNPGP*METDTLLLWVLLLWVPGSTG*QAVLTQPPSASGTPGQRVTISCSGSSSNIGSNTVNWYQQLPGTAPKLLMYSNNQR
PSGVPDRFSGSKSGTSASLAISGLQSEDEADYYCAAWDDSLNGYVEGTGTKVTVLGQPKANPTVTLEPPSSEELQANKATLVC
LISDFYPGAVTVAWKADGSPVKAGVETTKPSKQSNNKYAASSYLSLTPEQWKSHRSYSCQVTHEGSTVEKTVAPTECSPIKTD
VITMDPKDNCSKDANDTLLLQLTNTSAYYMYLLLLLKSVVYFAIITCCLLRRTAFCCNGEKSGSGATNESLLKQAGDVEENPG
*PMETDTLLLWVLLLWVPGSTG*QAVLTQPPSASGTPGQRVTISCSGSSSNIGSNTVNWYQQLPGTAPKLLMYSNNQRPSGVPDR
FSGSKSGTSASLAISGLQSEDEADYYCAAWDDSLNGYVEGTGTKVTVLGSRGGGSGGGGSGGGGSLEMAEVQLVQSGAEMKK
PGESLKISCKGSGYNFASYWVGWVRQMPGKGLEWMGTIYPDDSDTRYGPAFQGQVTISADKSISTAYLQWSSLKASDTAMYYC
ARDSYYGIDVWGQGTLVTVSSEQKLISEEDLAAAIEVMYPPPYLDNEKSNGTIIHVKGKHLCPSPLFPGPSKPFWVLVVVGGV
LACYSLLVTVAFTIFWVRSKRSRLLHSDYMNMTPRRPGPTRKHYQPYAPPRDFAAYRS

B-CSR-1A + Bx1-caTCR (signal sequence (italic) + Clone A-CSR-1A (underlined) + P2A
self-cleaving peptide (italic) + Bx1-caTCR)

(SEQ ID NO: 164)
*METDTLLLWVLLLWVPGSTG*QAVLTQPPSASGTPGQRVTISCSGSSSNIGSNTVNWYQQLPGTAPKLLMYSNNQRPSGVPDRF
SGSKSGTSASLAISGLQSEDEADYYCAAWDDSLNGYVFGTGTKVTVLGSRGGGSGGGGSGGGGSLEMAEVQLVQSGAEMKKP

-continued

GESLKISCKGSGYNFASYWVGWVRQMPGKGLEWMGTIYPDDSDTRYGPAFQGQVTISADKSISTAYLQWSSLKASDTAMYYCA

RDSYYGIDVWGQGTLVTVSSEQKLISEEDLAAAIEVMYPPPYLDNEKSNGTIIHVKGKHLCPSPLFPGPSKPFWVLVVVGGVL

ACYSLLVTVAFTIFWVRSKRSRLLHSDYMNMTPRRPGPTRKHYQPYAPPRDFAAYRSGSGATNESLLKQAGDVEENPGPMETD

TLLLWVLLLWVPGSTGEVQLVQSGAEMKKPGESLKISCKGSGYNFASYWVGWVRQMPGKGLEWMGTIYPDDSDTRYGPAFQGQ

VTISADKSISTAYLQWSSLKASDTAMYYCARDSYYGIDVWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYICNVNHKPSNTKVDKRVEPKSCEVKTDSTDHVKPK

ETENTKQPSKSCHKPKAIVHTEKVNMMSLTVLGLRMLFAKTVAVNELLTAKLEFLRAKRSGSGAPVKQTLNFDLLKLAGDVES

NPGPMETDTLLLWVLLLWVPGSTGQAVLTQPPSASGTPGQRVTISCSGSSSNIGSNTVNWYQQLPGTAPKLLMYSNNQRPSGV

PDRFSGSKSGTSASLAISGLQSEDEADYYCAAWDDSLNGYVEGTGTKVTVLGQPKANPTVTLEPPSSEELQANKATLVCLISD

FYPGAVTVAWKADGSPVKAGVETTKPSKQSNNKYAASSYLSLTPEQWKSHRSYSCQVTHEGSTVEKTVAPTECSPIKTDVITM

DPKDNCSKDANDTLLLQLTNTSAYYMYLLLLLKSVVYFAIITCCLLRRTAFCCNGEKS

Ax2-caTCR-1 + B-CSR-1A (from N-terminus to C-terminus: Ax2-caTCR + P2A self-
cleaving peptide (bold) + signal sequence (italic) + Clone A-CSR-1A (underlined))
(SEQ ID NO: 89)
METDTLLLWVLLLWVPGSTGQSVLTQPPSVSGAPGQRVTISCTGSSSNIGAGYDVHWYQQLPGTAPKLLIYGNSNRPSGVPDR FSGSKSGTSASLAITGLQAEDEADYYCQSYDSSLSGYVEGTGTKVTVLGSRGGGGSGGGGSGGGGSLEMAEVQLVQSGAEVKK PGESLKISCKGSGYSFTSYWIGWVRQMPGKGLEWMGITYPGDSDTRYSPSFQGQVTISADKSISTAYLQWSSLKASDTAMYYC ARSMGSSLYASSDVWGQGTLVTVSS<u>GGGGS</u>EVQLVQSGAEVKKPGESLKISCKGSGYSFTSYWIGWVRQMPGKGLEWMGITYP GDSDTRYSPSFQGQVTISADKSISTAYLQWSSLKASDTAMYYCARSMGSSLYASSDVWGQGTLVTVSSASTKGPSVFPLAPSS KSTSGGTAALGCLVKDYFPEPVTVSWNSGALTSGVHTFPAVLQSSGLYSLSSVVTVPSSSLGTQTYICNVNHKPSNTKVDKRV EPKSCEVKTDSTDHVKPKETENTKQPSKSCHKPKAIVHTEKVNMMSLTVLGLRMLFAKTVAVNELLTAKLEFLRAKRSGSGAP VKQTLNFDLLKLAGDVESNPGPMETDTLLLWVLLLWVPGSTGQSVLTQPPSVSGAPGQRVTISCTGSSSNIGAGYDVHWYQQL PGTAPKLLIYGNSNRPSGVPDRFSGSKSGTSASLAITGLQAEDEADYYCQSYDSSLSGYVEGTGTKVTVLGQPKANPTVTLFP PSSEELQANKATLVCLISDFYPGAVTVAWKADGSPVKAGVETTKPSKQSNNKYAASSYLSLTPEQWKSHRSYSCQVTHEGSTV EKTVAPTECSPIKTDVITMDPKDNCSKDANDTLLLQLTNTSAYYMYLLLLLKSVVYFAIITCCLLRRTAFCCNGEKSGSGATN

FSLLKQAGDVEENPGPMETDTLLLWVLLLWVPGSTGQAVLTQPPSASGTPGQRVTISCSGSSSNIGSNTVNWYQQLPGTAPKL

LMYSNNQRPSGVPDRFSGSKSGTSASLAISGLQSEDEADYYCAAWDDSLNGYVFGTGTKVTVLGSRGGGGSGGGGSGGGGSLE

MAEVQLVQSGAEMKKPGESLKISCKGSGYNFASYWVGWVRQMPGKGLEWMGTIYPDDSDTRYGPAFQGQVTISADKSISTAYL

QWSSLKASDTAMYYCARDSYYGIDVWGQGTLVTVSSEQKLISEEDLAAAIEVMYPPPYLDNEKSNGTIIHVKGKHLCPSPLFP

GPSKPFWVLVVVGGVLACYSLLVTVAFIIFWVRSKRSRLLHSDYMNMTPRRPGPTRKHYQPYAPPRDFAAYRS

Nucleic acids encoding the caTCR+CSR construct combinations listed in bold below and in Table 12 (which is reproduced below) are also designed.

A nucleic acid encoding B-CSR-1A+Ax2-caTCR-1 comprises sequences that encode (from 5' to 3') the following main components: B-CSR-1A (SEQ ID NO: 70), the furin cleavage site fused to P2A self-cleaving peptide of SEQ ID NO: 133 (i.e., RAKRSGSGATNFSLLKQAGDVEENPGP), and a polypeptide comprising SEQ ID NO: 47 (Ax2-caTCR-1).

A nucleic acid encoding Ax2-caTCR-1+B-CSR-1B comprises sequences that encode (from 5' to 3'): a polypeptide comprising SEQ ID NO: 47 (Ax2-caTCR-1), the P2A self-cleaving peptide of SEQ ID NO: 132 (GSGATNFSLLKQAGDVEENPGP), and B-CSR-1B (SEQ ID NO: 38). (See also row 3 in Table 12, which is reproduced below.)

A nucleic acid encoding B-CSR-1B+Ax2-caTCR-1 comprises sequences that encode (from 5' to 3'): B-CSR-1B (SEQ ID NO: 38), the furin cleavage site fused to P2A self-cleaving peptide of SEQ ID NO: 133, and a polypeptide comprising SEQ ID NO: 47 (Ax2-caTCR-1). (See also row 4 in Table 12, which is reproduced below.)

TABLE 12

| | caTCR + CSR Combination Encoded by Nucleic Acid | Order of Components (from N-Terminus to C-Terminus) in Polypeptide encoded by the Nucleic Acid | Exemplary anti-PSMA caTCR | Exemplary anti-PSMA CSR | Exemplary Linker |
|---|---|---|---|---|---|
| 1 | Ax2-caTCR-1 + B-CSR-1A | caTCR-linker-CSR (see, e.g., SEQ ID NO: 89) | Ax2-caTCR-1 (SEQ ID NO: 47) | B-CSR-1A (SEQ ID NO: 70) | P2A self-cleaving peptide (SEQ ID NO: 132) |
| 2 | B-CSR-1A + Ax2-caTCR-1 | CSR-linker-caTCR (see, e.g., paragraph [0441]) | Ax2-caTCR-1 (SEQ ID NO: 47) | B-CSR-1A (SEQ ID NO: 70) | furin cleavage site + P2A self-cleaving peptide (SEQ ID NO: 133) |
| 3 | Ax2-caTCR-1 + B-CSR-1B | caTCR-linker-CSR (see, e.g., paragraph [0442]) | Ax2-caTCR-1 (SEQ ID NO: 47) | B-CSR-1B (SEQ ID NO: 38) | P2A self-cleaving peptide (SEQ ID NO: 132) |
| 4 | B-CSR-1B + Ax2-caTCR-1 | CSR-linker-caTCR (see, e.g., paragraph [0443]) | Ax2-caTCR-1 (SEQ ID NO: 47) | B-CSR-1B (SEQ ID NO: 38) | furin cleavage site + P2A self-cleaving peptide (SEQ ID NO: 133) |
| 5 | Ax2-caTCR-1 + B-CSR-2A | caTCR-linker-CSR | Ax2-caTCR-1 (SEQ ID NO: 47) | B-CSR-2A (SEQ ID NO: 71) | P2A self-cleaving peptide (SEQ ID NO: 132) |
| 6 | B-CSR-2A + Ax2-caTCR-1 | CSR-linker-caTCR | Ax2-caTCR-1 (SEQ ID NO: 47) | B-CSR-2A (SEQ ID NO: 71) | furin cleavage site + P2A self-cleaving peptide (SEQ ID NO: 133) |
| 7 | Ax2-caTCR-1 + B-CSR-2B | caTCR-linker-CSR | Ax2-caTCR-1 (SEQ ID NO: 47) | B-CSR-2B (SEQ ID NO: 72) | P2A self-cleaving peptide (SEQ ID NO: 132) |
| 8 | B-CSR-2B + Ax2-caTCR-1 | CSR-linker-caTCR | Ax2-caTCR-1 (SEQ ID NO: 47) | B-CSR-2B (SEQ ID NO: 72) | furin cleavage site + P2A self-cleaving peptide (SEQ ID NO: 133) |
| 9 | Ax2-caTCR-1 + B-CSR-3A | caTCR-linker-CSR | Ax2-caTCR-1 (SEQ ID NO: 47) | B-CSR-3A (SEQ ID NO: 73) | P2A self-cleaving peptide (SEQ ID NO: 132) |
| 10 | B-CSR-3A + Ax2-caTCR-1 | CSR-linker-caTCR | Ax2-caTCR-1 (SEQ ID NO: 47) | B-CSR-3A (SEQ ID NO: 73) | furin cleavage site + P2A self-cleaving peptide (SEQ ID NO: 133) |
| 11 | Ax2-caTCR-1 + B-CSR-3B | caTCR-linker-CSR | Ax2-caTCR-1 (SEQ ID NO: 47) | B-CSR-3B (SEQ ID NO: 74) | P2A self-cleaving peptide (SEQ ID NO: 132) |
| 12 | B-CSR-3B + Ax2-caTCR-1 | CSR-linker-caTCR | Ax2-caTCR-1 (SEQ ID NO: 47) | B-CSR-3B (SEQ ID NO: 74) | furin cleavage site + P2A self-cleaving peptide (SEQ ID NO: 133) |
| 13 | Ax2-caTCR-1 + B-CSR-4A | caTCR-linker-CSR | Ax2-caTCR-1 (SEQ ID NO: 47) | B-CSR-4A (SEQ ID NO: 75) | P2A self-cleaving peptide (SEQ ID NO: 132) |
| 14 | B-CSR-4A + Ax2-caTCR-1 | CSR-linker-caTCR | Ax2-caTCR-1 (SEQ ID NO: 47) | B-CSR-4A (SEQ ID NO: 75) | furin cleavage site + P2A self-cleaving peptide (SEQ ID NO: 133) |
| 15 | Ax2-caTCR-1 + B-CSR-4B | caTCR-linker-CSR | Ax2-caTCR-1 (SEQ ID NO: 47) | B-CSR-4B (SEQ ID NO: 76) | P2A self-cleaving peptide (SEQ ID NO: 132) |
| 16 | B-CSR-4B + Ax2-caTCR-1 | CSR-linker-caTCR | Ax2-caTCR-1 (SEQ ID NO: 47) | B-CSR-4B (SEQ ID NO: 76) | furin cleavage site + P2A self-cleaving peptide (SEQ ID NO: 133) |
| 17 | Ax2-caTCR-1 + B-CSR-5A | caTCR-linker-CSR | Ax2-caTCR-1 (SEQ ID NO: 47) | B-CSR-5A (SEQ ID NO: 77) | P2A self-cleaving peptide (SEQ ID NO: 132) |
| 18 | B-CSR-5A + Ax2-caTCR-1 | CSR-linker-caTCR | Ax2-caTCR-1 (SEQ ID NO: 47) | B-CSR-5A (SEQ ID NO: 77) | furin cleavage site + P2A self-cleaving peptide (SEQ ID NO: 133) |
| 19 | Ax2-caTCR-1 + B-CSR-5B | caTCR-linker-CSR | Ax2-caTCR-1 (SEQ ID NO: 47) | B-CSR-5B (SEQ ID NO: 78) | P2A self-cleaving peptide (SEQ ID NO: 132) |
| 20 | B-CSR-5B + Ax2-caTCR-1 | CSR-linker-caTCR | Ax2-caTCR-1 (SEQ ID NO: 47) | B-CSR-5B (SEQ ID NO: 78) | furin cleavage site + P2A self-cleaving peptide (SEQ ID NO: 133) |

TABLE 12-continued

| | caTCR + CSR Combination Encoded by Nucleic Acid | Order of Components (from N-Terminus to C-Terminus) in Polypeptide encoded by the Nucleic Acid | Exemplary anti-PSMA caTCR | Exemplary anti-PSMA CSR | Exemplary Linker |
|---|---|---|---|---|---|
| 21 | Ax2-caTCR-1 + B-CSR-6A | caTCR-linker-CSR | Ax2-caTCR-1 (SEQ ID NO: 47) | B-CSR-6A (SEQ ID NO: 79) | P2A self-cleaving peptide (SEQ ID NO: 132) |
| 22 | B-CSR-6A + Ax2-caTCR-1 | CSR-linker-caTCR | Ax2-caTCR-1 (SEQ ID NO: 47) | B-CSR-6A (SEQ ID NO: 79) | furin cleavage site + P2A self-cleaving peptide (SEQ ID NO: 133) |
| 23 | Ax2-caTCR-1 + B-CSR-6B | caTCR-linker-CSR | Ax2-caTCR-1 (SEQ ID NO: 47) | B-CSR-6B (SEQ ID NO: 80) | P2A self-cleaving peptide (SEQ ID NO: 132) |
| 24 | B-CSR-6B + Ax2-caTCR-1 | CSR-linker-caTCR | Ax2-caTCR-1 (SEQ ID NO: 47) | B-CSR-6B (SEQ ID NO: 80) | furin cleavage site + P2A self-cleaving peptide (SEQ ID NO: 133) |
| 25 | Ax2-caTCR-1 + B-CSR-7A | caTCR-linker-CSR | Ax2-caTCR-1 (SEQ ID NO: 47) | B-CSR-7A (SEQ ID NO: 81) | P2A self-cleaving peptide (SEQ ID NO: 132) |
| 26 | B-CSR-7A + Ax2-caTCR-1 | CSR-linker-caTCR | Ax2-caTCR-1 (SEQ ID NO: 47) | B-CSR-7A (SEQ ID NO: 81) | furin cleavage site + P2A self-cleaving peptide (SEQ ID NO: 133) |
| 27 | Ax2-caTCR-1 + B-CSR-7B | caTCR-linker-CSR | Ax2-caTCR-1 (SEQ ID NO: 47) | B-CSR-7B (SEQ ID NO: 82) | P2A self-cleaving peptide (SEQ ID NO: 132) |
| 28 | B-CSR-7B + Ax2-caTCR-1 | CSR-linker-caTCR | Ax2-caTCR-1 (SEQ ID NO: 47) | B-CSR-7B (SEQ ID NO: 82) | furin cleavage site + P2A self-cleaving peptide (SEQ ID NO: 133) |
| 29 | Ax2-caTCR-1 + B-CSR-8A | caTCR-linker-CSR | Ax2-caTCR-1 (SEQ ID NO: 47) | B-CSR-8A (SEQ ID NO: 83) | P2A self-cleaving peptide (SEQ ID NO: 132) |
| 30 | B-CSR-8A + Ax2-caTCR-1 | CSR-linker-caTCR | Ax2-caTCR-1 (SEQ ID NO: 47) | B-CSR-8A (SEQ ID NO: 83) | furin cleavage site + P2A self-cleaving peptide (SEQ ID NO: 133) |
| 31 | Ax2-caTCR-1 + B-CSR-8B | caTCR-linker-CSR | Ax2-caTCR-1 (SEQ ID NO: 47) | B-CSR-8B (SEQ ID NO: 84) | P2A self-cleaving peptide (SEQ ID NO: 132) |
| 32 | B-CSR-8B + Ax2-caTCR-1 | CSR-linker-caTCR | Ax2-caTCR-1 (SEQ ID NO: 47) | B-CSR-8B (SEQ ID NO: 84) | furin cleavage site + P2A self-cleaving peptide (SEQ ID NO: 133) |
| 33 | Bx2-caTCR-1 + A-CSR-1A | caTCR-linker-CSR (e.g., SEQ ID NO:90) | Bx2-caTCR-1 (SEQ ID NO: 49) | A-CSR-1A (SEQ ID NO: 55) | P2A self-cleaving peptide (SEQ ID NO: 132) |
| 34 | A-CSR-1A + Bx2-caTCR-1 | CSR-linker-caTCR | Bx2-caTCR-1 (SEQ ID NO: 49) | A-CSR-1A (SEQ ID NO: 55) | furin cleavage site + P2A self-cleaving peptide (SEQ ID NO: 133) |
| 35 | Bx2-caTCR-1 + A-CSR-1B | caTCR-linker-CSR | Bx2-caTCR-1 (SEQ ID NO: 49) | A-CSR-1B (SEQ ID NO: 37) | P2A self-cleaving peptide (SEQ ID NO: 132) |
| 36 | A-CSR-1B + Bx2-caTCR-1 | CSR-linker-caTCR | Bx2-caTCR-1 (SEQ ID NO: 49) | A-CSR-1B (SEQ ID NO: 37) | furin cleavage site + P2A self-cleaving peptide (SEQ ID NO: 133) |
| 37 | Bx2-caTCR-1 + A-CSR-2A | caTCR-linker-CSR | Bx2-caTCR-1 (SEQ ID NO: 49) | A-CSR-2A (SEQ ID NO: 56) | P2A self-cleaving peptide (SEQ ID NO: 132) |
| 38 | A-CSR-2A + Bx2-caTCR-1 | CSR-linker-caTCR | Bx2-caTCR-1 (SEQ ID NO: 49) | A-CSR-2A (SEQ ID NO: 56) | furin cleavage site + P2A self-cleaving peptide (SEQ ID NO: 133) |
| 39 | Bx2-caTCR-1 + A-CSR-2B | caTCR-linker-CSR | Bx2-caTCR-1 (SEQ ID NO: 49) | A-CSR-2B (SEQ ID NO: 57) | P2A self-cleaving peptide (SEQ ID NO: 132) |
| 40 | A-CSR-2B + Bx2-caTCR-1 | CSR-linker-caTCR | Bx2-caTCR-1 (SEQ ID NO: 49) | A-CSR-2B (SEQ ID NO: 57) | furin cleavage site + P2A self-cleaving peptide (SEQ ID NO: 133) |

TABLE 12-continued

| | caTCR + CSR Combination Encoded by Nucleic Acid | Order of Components (from N-Terminus to C-Terminus) in Polypeptide encoded by the Nucleic Acid | Exemplary anti-PSMA caTCR | Exemplary anti-PSMA CSR | Exemplary Linker |
|---|---|---|---|---|---|
| 41 | Bx2-caTCR-1 + A-CSR-3A | caTCR-linker-CSR | Bx2-caTCR-1 (SEQ ID NO: 49) | A-CSR-3A (SEQ ID NO: 58) | P2A self-cleaving peptide (SEQ ID NO: 132) |
| 42 | A-CSR-3A + Bx2-caTCR-1 | CSR-linker-caTCR | Bx2-caTCR-1 (SEQ ID NO: 49) | A-CSR-3A (SEQ ID NO: 58) | furin cleavage site + P2A self-cleaving peptide (SEQ ID NO: 133) |
| 43 | Bx2-caTCR-1 + A-CSR-3B | caTCR-linker-CSR | Bx2-caTCR-1 (SEQ ID NO: 49) | A-CSR-3B (SEQ ID NO: 59) | P2A self-cleaving peptide (SEQ ID NO: 132) |
| 44 | A-CSR-3B + Bx2-caTCR-1 | CSR-linker-caTCR | Bx2-caTCR-1 (SEQ ID NO: 49) | A-CSR-3B (SEQ ID NO: 59) | furin cleavage site + P2A self-cleaving peptide (SEQ ID NO: 133) |
| 45 | Bx2-caTCR-1 + A-CSR-4A | caTCR-linker-CSR | Bx2-caTCR-1 (SEQ ID NO: 49) | A-CSR-4A (SEQ ID NO: 60) | P2A self-cleaving peptide (SEQ ID NO: 132) |
| 46 | A-CSR-4A + Bx2-caTCR-1 | CSR-linker-caTCR | Bx2-caTCR-1 (SEQ ID NO: 49) | A-CSR-4A (SEQ ID NO: 60) | furin cleavage site + P2A self-cleaving peptide (SEQ ID NO: 133) |
| 47 | Bx2-caTCR-1 + A-CSR-4B | caTCR-linker-CSR | Bx2-caTCR-1 (SEQ ID NO: 49) | A-CSR-4B (SEQ ID NO: 61) | P2A self-cleaving peptide (SEQ ID NO: 132) |
| 48 | A-CSR-4B + Bx2-caTCR-1 | CSR-linker-caTCR | Bx2-caTCR-1 (SEQ ID NO: 49) | A-CSR-4B (SEQ ID NO: 61) | furin cleavage site + P2A self-cleaving peptide (SEQ ID NO: 133) |
| 49 | Bx2-caTCR-1 + A-CSR-5A | caTCR-linker-CSR | Bx2-caTCR-1 (SEQ ID NO: 49) | A-CSR-5A (SEQ ID NO: 62) | P2A self-cleaving peptide (SEQ ID NO: 132) |
| 50 | A-CSR-5A + Bx2-caTCR-1 | CSR-linker-caTCR | Bx2-caTCR-1 (SEQ ID NO: 49) | A-CSR-5A (SEQ ID NO: 62) | furin cleavage site + P2A self-cleaving peptide (SEQ ID NO: 133) |
| 51 | Bx2-caTCR-1 + A-CSR-5B | caTCR-linker-CSR | Bx2-caTCR-1 (SEQ ID NO: 49) | A-CSR-5B (SEQ ID NO: 63) | P2A self-cleaving peptide (SEQ ID NO: 132) |
| 52 | A-CSR-5B + Bx2-caTCR-1 | CSR-linker-caTCR | Bx2-caTCR-1 (SEQ ID NO: 49) | A-CSR-5B (SEQ ID NO: 63) | furin cleavage site + P2A self-cleaving peptide (SEQ ID NO: 133) |
| 53 | Bx2-caTCR-1 + A-CSR-6A | caTCR-linker-CSR | Bx2-caTCR-1 (SEQ ID NO: 49) | A-CSR-6A (SEQ ID NO: 64) | P2A self-cleaving peptide (SEQ ID NO: 132) |
| 54 | A-CSR-6A + Bx2-caTCR-1 | CSR-linker-caTCR | Bx2-caTCR-1 (SEQ ID NO: 49) | A-CSR-6A (SEQ ID NO: 64) | furin cleavage site + P2A self-cleaving peptide (SEQ ID NO: 133) |
| 55 | Bx2-caTCR-1 + A-CSR-6B | caTCR-linker-CSR | Bx2-caTCR-1 (SEQ ID NO: 49) | A-CSR-6B (SEQ ID NO: 65) | P2A self-cleaving peptide (SEQ ID NO: 132) |
| 56 | A-CSR-6B + Bx2-caTCR-1 | CSR-linker-caTCR | Bx2-caTCR-1 (SEQ ID NO: 49) | A-CSR-6B (SEQ ID NO: 65) | furin cleavage site + P2A self-cleaving peptide (SEQ ID NO: 133) |
| 57 | Bx2-caTCR-1 + A-CSR-7A | caTCR-linker-CSR | Bx2-caTCR-1 (SEQ ID NO: 49) | A-CSR-7A (SEQ ID NO: 66) | P2A self-cleaving peptide (SEQ ID NO: 132) |
| 58 | A-CSR-7A + Bx2-caTCR-1 | CSR-linker-caTCR | Bx2-caTCR-1 (SEQ ID NO: 49) | A-CSR-7A (SEQ ID NO: 66) | furin cleavage site + P2A self-cleaving peptide (SEQ ID NO: 133) |
| 59 | Bx2-caTCR-1 + A-CSR-7B | caTCR-linker-CSR | Bx2-caTCR-1 (SEQ ID NO: 49) | A-CSR-7B (SEQ ID NO: 67) | P2A self-cleaving peptide (SEQ ID NO: 132) |
| 60 | A-CSR-7B + Bx2-caTCR-1 | CSR-linker-caTCR | Bx2-caTCR-1 (SEQ ID NO: 49) | A-CSR-7B (SEQ ID NO: 67) | furin cleavage site + P2A self-cleaving peptide (SEQ ID NO: 133) |

TABLE 12-continued

| | caTCR + CSR Combination Encoded by Nucleic Acid | Order of Components (from N-Terminus to C-Terminus) in Polypeptide encoded by the Nucleic Acid | Exemplary anti-PSMA caTCR | Exemplary anti-PSMA CSR | Exemplary Linker |
|---|---|---|---|---|---|
| 61 | Bx2-caTCR-1 + A-CSR-8A | caTCR-linker-CSR | Bx2-caTCR-1 (SEQ ID NO: 49) | A-CSR-8A (SEQ ID NO: 68) | P2A self-cleaving peptide (SEQ ID NO: 132) |
| 62 | A-CSR-8A + Bx2-caTCR-1 | CSR-linker-caTCR | Bx2-caTCR-1 (SEQ ID NO: 49) | A-CSR-8A (SEQ ID NO: 68) | furin cleavage site + P2A self-cleaving peptide (SEQ ID NO: 133) |
| 63 | Bx2-caTCR-1 + A-CSR-8B | caTCR-linker-CSR | Bx2-caTCR-1 (SEQ ID NO: 49) | A-CSR-8B (SEQ ID NO: 69) | P2A self-cleaving peptide (SEQ ID NO: 132) |
| 64 | A-CSR-8B + Bx2-caTCR-1 | CSR-linker-caTCR | Bx2-caTCR-1 (SEQ ID NO: 49) | A-CSR-8B (SEQ ID NO: 69) | furin cleavage site + P2A self-cleaving peptide (SEQ ID NO: 133) |
| 65 | Ax2-caTCR-2 + B-CSR-1A | caTCR-linker-CSR | Ax2-caTCR-2 (SEQ ID NO: 48) | B-CSR-1A (SEQ ID NO: 70) | P2A self-cleaving peptide (SEQ ID NO: 132) |
| 66 | B-CSR-1A + Ax2-caTCR-2 | CSR-linker-caTCR | Ax2-caTCR-2 (SEQ ID NO: 48) | B-CSR-1A (SEQ ID NO: 70) | furin cleavage site + P2A self-cleaving peptide (SEQ ID NO: 133) |
| 67 | Ax2-caTCR-2 + B-CSR-1B | caTCR-linker-CSR | Ax2-caTCR-2 (SEQ ID NO: 48) | B-CSR-1B (SEQ ID NO: 38) | P2A self-cleaving peptide (SEQ ID NO: 132) |
| 68 | B-CSR-1B + Ax2-caTCR-2 | CSR-linker-caTCR | Ax2-caTCR-2 (SEQ ID NO: 48) | B-CSR-1B (SEQ ID NO: 38) | furin cleavage site + P2A self-cleaving peptide (SEQ ID NO: 133) |
| 69 | Ax2-caTCR-2 + B-CSR-2A | caTCR-linker-CSR | Ax2-caTCR-2 (SEQ ID NO: 48) | B-CSR-2A (SEQ ID NO: 71) | P2A self-cleaving peptide (SEQ ID NO: 132) |
| 70 | B-CSR-2A + Ax2-caTCR-2 | CSR-linker-caTCR | Ax2-caTCR-2 (SEQ ID NO: 48) | B-CSR-2A (SEQ ID NO: 71) | furin cleavage site + P2A self-cleaving peptide (SEQ ID NO: 133) |
| 71 | Ax2-caTCR-2 + B-CSR-2B | caTCR-linker-CSR | Ax2-caTCR-2 (SEQ ID NO: 48) | B-CSR-2B (SEQ ID NO: 72) | P2A self-cleaving peptide (SEQ ID NO: 132) |
| 72 | B-CSR-2B + Ax2-caTCR-2 | CSR-linker-caTCR | Ax2-caTCR-2 (SEQ ID NO: 48) | B-CSR-2B (SEQ ID NO: 72) | furin cleavage site + P2A self-cleaving peptide (SEQ ID NO: 133) |
| 73 | Ax2-caTCR-2 + B-CSR-3A | caTCR-linker-CSR | Ax2-caTCR-2 (SEQ ID NO: 48) | B-CSR-3A (SEQ ID NO: 73) | P2A self-cleaving peptide (SEQ ID NO: 132) |
| 74 | B-CSR-3A + Ax2-caTCR-2 | CSR-linker-caTCR | Ax2-caTCR-2 (SEQ ID NO: 48) | B-CSR-3A (SEQ ID NO: 73) | furin cleavage site + P2A self-cleaving peptide (SEQ ID NO: 133) |
| 75 | Ax2-caTCR-2 + B-CSR-3B | caTCR-linker-CSR | Ax2-caTCR-2 (SEQ ID NO: 48) | B-CSR-3B (SEQ ID NO: 74) | P2A self-cleaving peptide (SEQ ID NO: 132) |
| 76 | B-CSR-3B + Ax2-caTCR-2 | CSR-linker-caTCR | Ax2-caTCR-2 (SEQ ID NO: 48) | B-CSR-3B (SEQ ID NO: 74) | furin cleavage site + P2A self-cleaving peptide (SEQ ID NO: 133) |
| 77 | Ax2-caTCR-2 + B-CSR-4A | caTCR-linker-CSR | Ax2-caTCR-2 (SEQ ID NO: 48) | B-CSR-4A (SEQ ID NO: 75) | P2A self-cleaving peptide (SEQ ID NO: 132) |
| 78 | B-CSR-4A + Ax2-caTCR-2 | CSR-linker-caTCR | Ax2-caTCR-2 (SEQ ID NO: 48) | B-CSR-4A (SEQ ID NO: 75) | furin cleavage site + P2A self-cleaving peptide (SEQ ID NO: 133) |
| 79 | Ax2-caTCR-2 + B-CSR-4B | caTCR-linker-CSR | Ax2-caTCR-2 (SEQ ID NO: 48) | B-CSR-4B (SEQ ID NO: 76) | P2A self-cleaving peptide (SEQ ID NO: 132) |
| 80 | B-CSR-4B + Ax2-caTCR-2 | CSR-linker-caTCR | Ax2-caTCR-2 (SEQ ID NO: 48) | B-CSR-4B (SEQ ID NO: 76) | furin cleavage site + P2A self-cleaving peptide (SEQ ID NO: 133) |

TABLE 12-continued

| caTCR + CSR Combination Encoded by Nucleic Acid | Order of Components (from N-Terminus to C-Terminus) in Polypeptide encoded by the Nucleic Acid | Exemplary anti-PSMA caTCR | Exemplary anti-PSMA CSR | Exemplary Linker |
|---|---|---|---|---|
| 81 Ax2-caTCR-2 + B-CSR-5A | caTCR-linker-CSR | Ax2-caTCR-2 (SEQ ID NO: 48) | B-CSR-5A (SEQ ID NO: 77) | P2A self-cleaving peptide (SEQ ID NO: 132) |
| 82 B-CSR-5A + Ax2-caTCR-2 | CSR-linker-caTCR | Ax2-caTCR-2 (SEQ ID NO: 48) | B-CSR-5A (SEQ ID NO: 77) | furin cleavage site + P2A self-cleaving peptide (SEQ ID NO: 133) |
| 83 Ax2-caTCR-2 + B-CSR-5B | caTCR-linker-CSR | Ax2-caTCR-2 (SEQ ID NO: 48) | B-CSR-5B (SEQ ID NO: 78) | P2A self-cleaving peptide (SEQ ID NO: 132) |
| 84 B-CSR-5B + Ax2-caTCR-2 | CSR-linker-caTCR | Ax2-caTCR-2 (SEQ ID NO: 48) | B-CSR-5B (SEQ ID NO: 78) | furin cleavage site + P2A self-cleaving peptide (SEQ ID NO: 133) |
| 85 Ax2-caTCR-2 + B-CSR-6A | caTCR-linker-CSR | Ax2-caTCR-2 (SEQ ID NO: 48) | B-CSR-6A (SEQ ID NO: 79) | P2A self-cleaving peptide (SEQ ID NO: 132) |
| 86 B-CSR-6A + Ax2-caTCR-2 | CSR-linker-caTCR | Ax2-caTCR-2 (SEQ ID NO: 48) | B-CSR-6A (SEQ ID NO: 79) | furin cleavage site + P2A self-cleaving peptide (SEQ ID NO: 133) |
| 87 Ax2-caTCR-2 + B-CSR-6B | caTCR-linker-CSR | Ax2-caTCR-2 (SEQ ID NO: 48) | B-CSR-6B (SEQ ID NO: 80) | P2A self-cleaving peptide (SEQ ID NO: 132) |
| 88 B-CSR-6B + Ax2-caTCR-2 | CSR-linker-caTCR | Ax2-caTCR-2 (SEQ ID NO: 48) | B-CSR-6B (SEQ ID NO: 80) | furin cleavage site + P2A self-cleaving peptide (SEQ ID NO: 133) |
| 89 Ax2-caTCR-2 + B-CSR-7A | caTCR-linker-CSR | Ax2-caTCR-2 (SEQ ID NO: 48) | B-CSR-7A (SEQ ID NO: 81) | P2A self-cleaving peptide (SEQ ID NO: 132) |
| 90 B-CSR-7A + Ax2-caTCR-2 | CSR-linker-caTCR | Ax2-caTCR-2 (SEQ ID NO: 48) | B-CSR-7A (SEQ ID NO: 81) | furin cleavage site + P2A self-cleaving peptide (SEQ ID NO: 133) |
| 91 Ax2-caTCR-2 + B-CSR-7B | caTCR-linker-CSR | Ax2-caTCR-2 (SEQ ID NO: 48) | B-CSR-7B (SEQ ID NO: 82) | P2A self-cleaving peptide (SEQ ID NO: 132) |
| 92 B-CSR-7B + Ax2-caTCR-2 | CSR-linker-caTCR | Ax2-caTCR-2 (SEQ ID NO: 48) | B-CSR-7B (SEQ ID NO: 82) | furin cleavage site + P2A self-cleaving peptide (SEQ ID NO: 133) |
| 93 Ax2-caTCR-2 + B-CSR-8A | caTCR-linker-CSR | Ax2-caTCR-2 (SEQ ID NO: 48) | B-CSR-8A (SEQ ID NO: 83) | P2A self-cleaving peptide (SEQ ID NO: 132) |
| 94 B-CSR-8A + Ax2-caTCR-2 | CSR-linker-caTCR | Ax2-caTCR-2 (SEQ ID NO: 48) | B-CSR-8A (SEQ ID NO: 83) | furin cleavage site + P2A self-cleaving peptide (SEQ ID NO: 133) |
| 95 Ax2-caTCR-2 + B-CSR-8B | caTCR-linker-CSR | Ax2-caTCR-2 (SEQ ID NO: 48) | B-CSR-8B (SEQ ID NO: 84) | P2A self-cleaving peptide (SEQ ID NO: 132) |
| 96 B-CSR-8B + Ax2-caTCR-2 | CSR-linker-caTCR | Ax2-caTCR-2 (SEQ ID NO: 48) | B-CSR-8B (SEQ ID NO: 84) | furin cleavage site + P2A self-cleaving peptide (SEQ ID NO: 133) |
| 97 Bx2-caTCR-2 + A-CSR-1A | caTCR-linker-CSR | Bx2-caTCR-2 (SEQ ID NO: 50) | A-CSR-1A (SEQ ID NO: 55) | P2A self-cleaving peptide (SEQ ID NO: 132) |
| 98 A-CSR-1A + Bx2-caTCR-2 | CSR-linker-caTCR | Bx2-caTCR-2 (SEQ ID NO: 50) | A-CSR-1A (SEQ ID NO: 55) | furin cleavage site + P2A self-cleaving peptide (SEQ ID NO: 133) |
| 99 Bx2-caTCR-2 + A-CSR-1B | caTCR-linker-CSR | Bx2-caTCR-2 (SEQ ID NO: 50) | A-CSR-1B (SEQ ID NO: 37) | P2A self-cleaving peptide (SEQ ID NO: 132) |
| 100 A-CSR-1B + Bx2-caTCR-2 | CSR-linker-caTCR | Bx2-caTCR-2 (SEQ ID NO: 50) | A-CSR-1B (SEQ ID NO: 37) | furin cleavage site + P2A self-cleaving peptide (SEQ ID NO: 133) |

TABLE 12-continued

| | caTCR + CSR Combination Encoded by Nucleic Acid | Order of Components (from N-Terminus to C-Terminus) in Polypeptide encoded by the Nucleic Acid | Exemplary anti-PSMA caTCR | Exemplary anti-PSMA CSR | Exemplary Linker |
|---|---|---|---|---|---|
| 101 | Bx2-caTCR-2 + A-CSR-2A | caTCR-linker-CSR | Bx2-caTCR-2 (SEQ ID NO: 50) | A-CSR-2A (SEQ ID NO: 56) | P2A self-cleaving peptide (SEQ ID NO: 132) |
| 102 | A-CSR-2A + Bx2-caTCR-2 | CSR-linker-caTCR | Bx2-caTCR-2 (SEQ ID NO: 50) | A-CSR-2A (SEQ ID NO: 56) | furin cleavage site + P2A self-cleaving peptide (SEQ ID NO: 133) |
| 103 | Bx2-caTCR-2 + A-CSR-2B | caTCR-linker-CSR | Bx2-caTCR-2 (SEQ ID NO: 50) | A-CSR-2B (SEQ ID NO: 57) | P2A self-cleaving peptide (SEQ ID NO: 132) |
| 104 | A-CSR-2B + Bx2-caTCR-2 | CSR-linker-caTCR | Bx2-caTCR-2 (SEQ ID NO: 50) | A-CSR-2B (SEQ ID NO: 57) | furin cleavage site + P2A self-cleaving peptide (SEQ ID NO: 133) |
| 105 | Bx2-caTCR-2 + A-CSR-3A | caTCR-linker-CSR | Bx2-caTCR-2 (SEQ ID NO: 50) | A-CSR-3A (SEQ ID NO: 58) | P2A self-cleaving peptide (SEQ ID NO: 132) |
| 106 | A-CSR-3A + Bx2-caTCR-2 | CSR-linker-caTCR | Bx2-caTCR-2 (SEQ ID NO: 50) | A-CSR-3A (SEQ ID NO: 58) | furin cleavage site + P2A self-cleaving peptide (SEQ ID NO: 133) |
| 107 | Bx2-caTCR-2 + A-CSR-3B | caTCR-linker-CSR | Bx2-caTCR-2 (SEQ ID NO: 50) | A-CSR-3B (SEQ ID NO: 59) | P2A self-cleaving peptide (SEQ ID NO: 132) |
| 108 | A-CSR-3B + Bx2-caTCR-2 | CSR-linker-caTCR | Bx2-caTCR-2 (SEQ ID NO: 50) | A-CSR-3B (SEQ ID NO: 59) | furin cleavage site + P2A self-cleaving peptide (SEQ ID NO: 133) |
| 109 | Bx2-caTCR-2 + A-CSR-4A | caTCR-linker-CSR | Bx2-caTCR-2 (SEQ ID NO: 50) | A-CSR-4A (SEQ ID NO: 60) | P2A self-cleaving peptide (SEQ ID NO: 132) |
| 110 | A-CSR-4A + Bx2-caTCR-2 | CSR-linker-caTCR | Bx2-caTCR-2 (SEQ ID NO: 50) | A-CSR-4A (SEQ ID NO: 60) | furin cleavage site + P2A self-cleaving peptide (SEQ ID NO: 133) |
| 111 | Bx2-caTCR-2 + A-CSR-4B | caTCR-linker-CSR | Bx2-caTCR-2 (SEQ ID NO: 50) | A-CSR-4B (SEQ ID NO: 61) | P2A self-cleaving peptide (SEQ ID NO: 132) |
| 112 | A-CSR-4B + Bx2-caTCR-2 | CSR-linker-caTCR | Bx2-caTCR-2 (SEQ ID NO: 50) | A-CSR-4B (SEQ ID NO: 61) | furin cleavage site + P2A self-cleaving peptide (SEQ ID NO: 133) |
| 113 | Bx2-caTCR-2 + A-CSR-5A | caTCR-linker-CSR | Bx2-caTCR-2 (SEQ ID NO: 50) | A-CSR-5A (SEQ ID NO: 62) | P2A self-cleaving peptide (SEQ ID NO: 132) |
| 114 | A-CSR-5A + Bx2-caTCR-2 | CSR-linker-caTCR | Bx2-caTCR-2 (SEQ ID NO: 50) | A-CSR-5A (SEQ ID NO: 62) | furin cleavage site + P2A self-cleaving peptide (SEQ ID NO: 133) |
| 115 | Bx2-caTCR-2 + A-CSR-5B | caTCR-linker-CSR | Bx2-caTCR-2 (SEQ ID NO: 50) | A-CSR-5B (SEQ ID NO: 63) | P2A self-cleaving peptide (SEQ ID NO: 132) |
| 116 | A-CSR-5B + Bx2-caTCR-2 | CSR-linker-caTCR | Bx2-caTCR-2 (SEQ ID NO: 50) | A-CSR-5B (SEQ ID NO: 63) | furin cleavage site + P2A self-cleaving peptide (SEQ ID NO: 133) |
| 117 | Bx2-caTCR-2 + A-CSR-6A | caTCR-linker-CSR | Bx2-caTCR-2 (SEQ ID NO: 50) | A-CSR-6A (SEQ ID NO: 64) | P2A self-cleaving peptide (SEQ ID NO: 132) |
| 118 | A-CSR-6A + Bx2-caTCR-2 | CSR-linker-caTCR | Bx2-caTCR-2 (SEQ ID NO: 50) | A-CSR-6A (SEQ ID NO: 64) | furin cleavage site + P2A self-cleaving peptide (SEQ ID NO: 133) |
| 119 | Bx2-caTCR-2 + A-CSR-6B | caTCR-linker-CSR | Bx2-caTCR-2 (SEQ ID NO: 50) | A-CSR-6B (SEQ ID NO: 65) | P2A self-cleaving peptide (SEQ ID NO: 132) |
| 120 | A-CSR-6B + Bx2-caTCR-2 | CSR-linker-caTCR | Bx2-caTCR-2 (SEQ ID NO: 50) | A-CSR-6B (SEQ ID NO: 65) | furin cleavage site + P2A self-cleaving peptide (SEQ ID NO: 133) |

TABLE 12-continued

| caTCR + CSR Combination Encoded by Nucleic Acid | Order of Components (from N-Terminus to C-Terminus) in Polypeptide encoded by the Nucleic Acid | Exemplary anti-PSMA caTCR | Exemplary anti-PSMA CSR | Exemplary Linker |
|---|---|---|---|---|
| 121 Bx2-caTCR-2 + A-CSR-7A | caTCR-linker-CSR | Bx2-caTCR-2 (SEQ ID NO: 50) | A-CSR-7A (SEQ ID NO: 66) | P2A self-cleaving peptide (SEQ ID NO: 132) |
| 122 A-CSR-7A + Bx2-caTCR-2 | CSR-linker-caTCR | Bx2-caTCR-2 (SEQ ID NO: 50) | A-CSR-7A (SEQ ID NO: 66) | furin cleavage site + P2A self-cleaving peptide (SEQ ID NO: 133) |
| 123 Bx2-caTCR-2 + A-CSR-7B | caTCR-linker-CSR | Bx2-caTCR-2 (SEQ ID NO: 50) | A-CSR-7B (SEQ ID NO: 67) | P2A self-cleaving peptide (SEQ ID NO: 132) |
| 124 A-CSR-7B + Bx2-caTCR-2 | CSR-linker-caTCR | Bx2-caTCR-2 (SEQ ID NO: 50) | A-CSR-7B (SEQ ID NO: 67) | furin cleavage site + P2A self-cleaving peptide (SEQ ID NO: 133) |
| 125 Bx2-caTCR-2 + A-CSR-8A | caTCR-linker-CSR | Bx2-caTCR-2 (SEQ ID NO: 50) | A-CSR-8A (SEQ ID NO: 68) | P2A self-cleaving peptide (SEQ ID NO: 132) |
| 126 A-CSR-8A + Bx2-caTCR-2 | CSR-linker-caTCR | Bx2-caTCR-2 (SEQ ID NO: 50) | A-CSR-8A (SEQ ID NO: 68) | furin cleavage site + P2A self-cleaving peptide (SEQ ID NO: 133) |
| 127 Bx2-caTCR-2 + A-CSR-8B | caTCR-linker-CSR | Bx2-caTCR-2 (SEQ ID NO: 50) | A-CSR-8B (SEQ ID NO: 69) | P2A self-cleaving peptide (SEQ ID NO: 132) |
| 128 A-CSR-8B + Bx2-caTCR-2 | CSR-linker-caTCR | Bx2-caTCR-2 (SEQ ID NO: 50) | A-CSR-8B (SEQ ID NO: 69) | furin cleavage site + P2A self-cleaving peptide (SEQ ID NO: 133) |

The single nucleic acid encoding the anti-PSMA caTCR+ anti-PSMA CSR of any one of rows 1-128 in Table 12 may further encode one or more signal peptides (e.g., upstream of the sequence(s) encoding Chain 1 and/or Chain 2 of the caTCR and/or upstream of the sequence encoding the anti-PSMA CSR). Although specific linkers are listed in rows 1-128 in Table 12, an alternative linker (see e.g., Table 6A) may be used. The single nucleic acid encoding the anti-PSMA caTCR+anti-PSMA CSR of any one of rows 1-128 in Table 12 may further encode one or more peptide linkers (e.g., cleavable linkers) and/or peptide tags. See, e.g., Tables 6A and 6B.

T cells expressing some of the caTCR+CSR construct combinations described in this Example were generated by transducing primary human T cells with viruses comprising corresponding nucleic acids, and their features and functions were assessed, using the methods described in Examples 3 and 7. The myc tags in the CSR constructs carrying such tags were used as the expression marker. Such T cells expressed the encoded caTCR and CSR constructs, proliferated well, redirected the T cells' specificity, and showed positive PSMA-specific cellular cytotoxicity/tumor-killing activities.

In the two representative tumor cell killing experiments described in Example 10, along with the mock-transduced T cells and the T cells transduced with caTCR-encoding nucleic acids, some primary T cells were transduced with nucleic acids encoding various caTCR+CSR combinations and also normalized to 60% receptor positive and incubated with the same three target cell lines at a 2:1 E:T ratio (receptor-positive effector:target ratio 1.2:1) for 16 hours. The results of these experiments are shown in FIG. 6 and FIG. 7 which demonstrated positive PSMA-specific cellular cytotoxicity of these T cells. Comparing to T cells express- ing caTCR alone, T cells expressing both anti-PSMA caTCR and anti-PSMA CSR killed higher percentages of PSMA$^+$ tumor cells in most cases.

Figure 8:
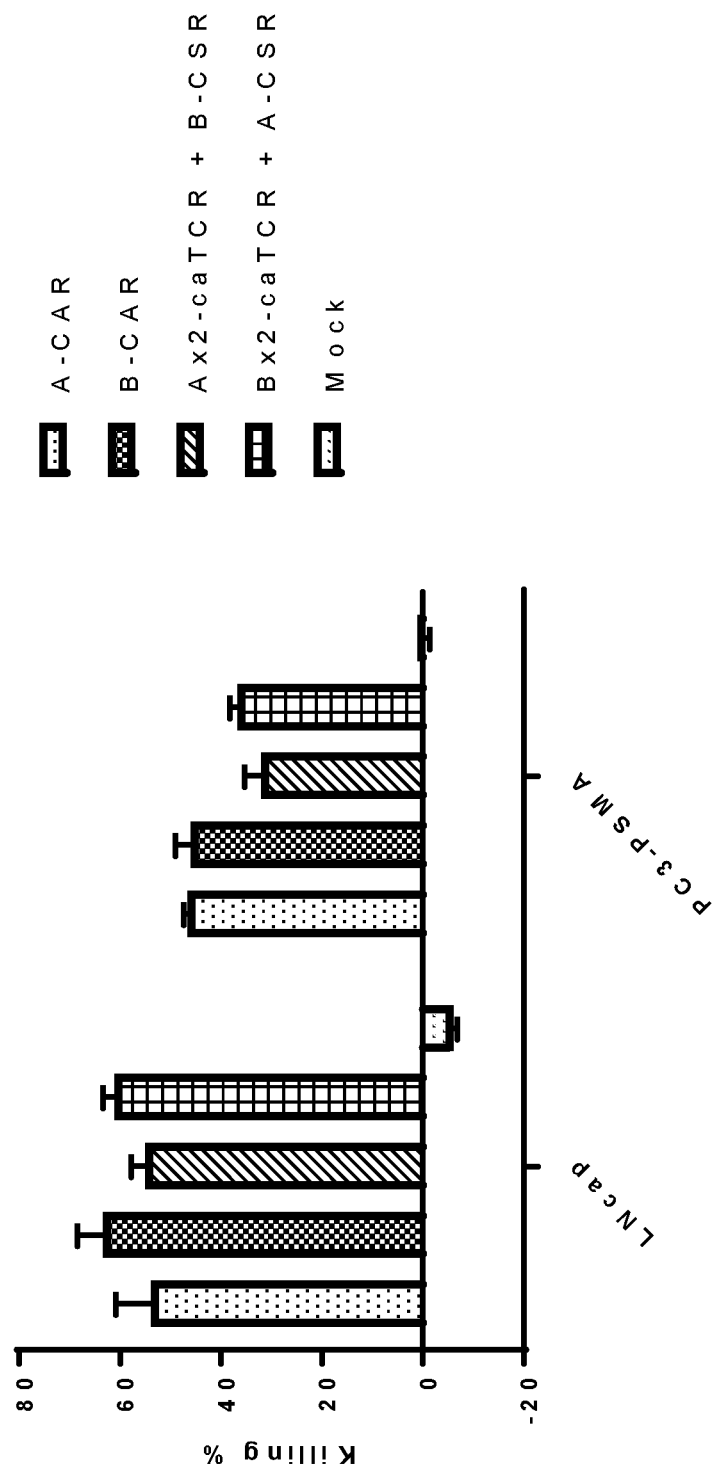
FIG. 8 shows the results of experiments performed to assess the specific killing of two PSMA+ target cell lines by T cells expressing Clone A and/or Clone B in different anti-PSMA construct configurations and construct combinations.

In another representative tumor cell killing experiment, T cells transduced with nucleic acids encoding Ax2-caTCR+ B-CSR or Bx2-caTCR+A-CSR combinations, along with T cells expressing an anti-PSMA CAR construct comprising the amino acid sequence of SEQ ID NO: 29 or an anti-PSMA CAR construct comprising the amino acid sequence of SEQ ID NO: 30 were normalized to 53% receptor positive and incubated with target cells at a 2:1 E:T ratio (0.2M: 0.1M, receptor-positive effector:target ratio 1.06:1) for 16 hours. Two PSMA$^+$ target cell lines were used: LNCaP and PC3-PMSA. The result of this tumor cell killing experiment is shown in FIG. 8, which shows the positive PSMA-specific cellular cytotoxicity of these T cells. In addition, cells in a duplicate experiment of this one were spun down, and supernatants were collected for a Luminex assay to measure release levels of various cytokines, including several inflammatory cytokines such as IL-6. The result shows that the T cells transduced with nucleic acids encoding caTCR+CSR secreted lower levels of inflammatory cytokines including IL-6 than T cells transduced with nucleic acids encoding CAR did (data not shown).

Figure 5:
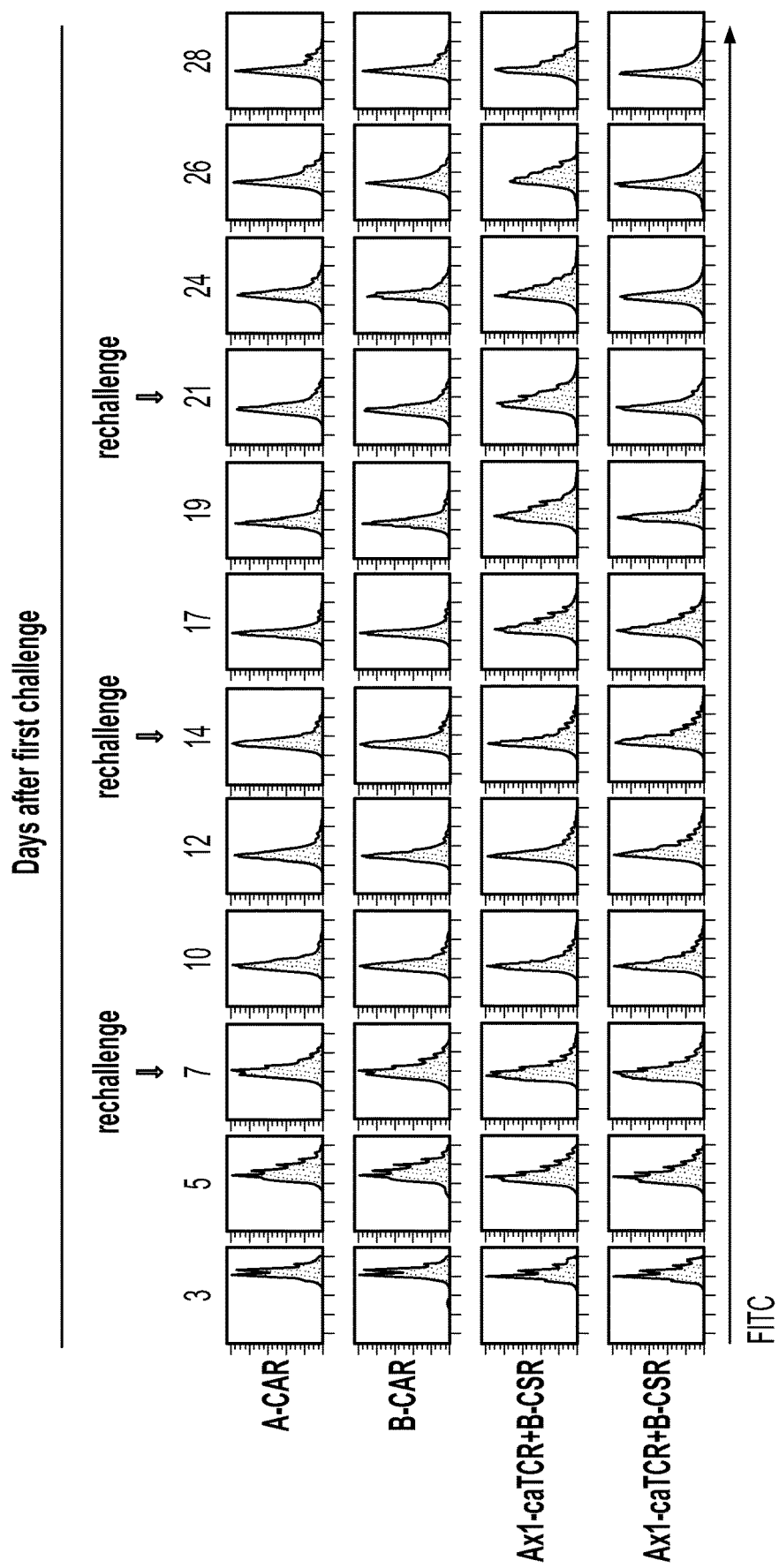
FIG. 5 shows the results of flow cytometry experiments confirming that Clone A and Clone B can be used in multiple receptor configurations (e.g., CAR or caTCR+CSR) to stimulate T-cell proliferation in response to antigen.

In addition to tumor cell killing experiments, a fluorescence-based flow cytometry assay as described in Example 7 was performed with T cells expressing the construct combinations Ax1-caTCR+B-CSR (a.k.a. Ax1-caTCR+B-CSR-1A, SEQ ID NO: 86) or Bx1-caTCR+A-CSR (a.k.a. Bx1-caTCR+A-CSR-1A, SEQ ID NO: 87), along with T cells expressing Clone A CAR (SEQ ID NO: 29) or Clone B CAR (SEQ ID NO: 30), which were all normalized with mock-transduced T cells to 50% receptor positivity, to assess T-cell proliferation. LNCaP was used as the PSMA$^+$ target cell line and the E:T ratio is 2:1 (0.1M/0.05M, receptor-positive effector: target ratio 1:1). T cells were stained with CFSE. T cells were re-challenged with 0.1M target cells every 7 days up to 4 cycles (4 engagements). CFSE signaling were examined by flow cytometry on D3, D5 and D7 of each engagement period. The results are shown in FIG. 5 which demonstrates that both caTCR+CSR construct combinations as well as CARs were able to stimulate T-cell proliferation through antigen recognition.

The experiments described above are repeated using T cells expressing the caTCR+CSR construct combinations shown in Table 12.

LIST OF EMBODIMENTS

1. An anti-prostate specific membrane antigen (PSMA) construct comprising an antibody moiety specifically recognizing an extracellular domain of a cell surface-bound PSMA that comprises an amino acid sequence set forth in SEQ ID NO: 44.
2. The anti-PSMA construct of embodiment 1, wherein the PSMA is expressed on the surface of a cancer cell.
3. The anti-PSMA construct of embodiment 3, wherein the cancer cell is a prostate cancer cell, a renal cell cancer cell, a uterine cancer cell, or a liver cancer cell.
4. The anti-PSMA construct of embodiment 3, wherein the cancer cell is a prostate cancer cell.
5. The anti-PSMA construct of embodiment 4, wherein the prostate cancer cell is a hormone refractory prostate cancer cell or a metastatic prostate cancer cell.
6. The anti-PSMA construct of embodiment 3, wherein the cancer cell is a renal cancer cell.
7. The anti-PSMA construct of embodiment 6, wherein the renal cancer cell is a clear cell renal cell carcinoma (CCRCC) cell.
8. The anti-PSMA construct of any one of embodiments 1-7 wherein the PSMA is expressed on the surface of a cell selected from the group consisting of: LNCaP, MDA PCa 2b, VCaP, 22Rv1, Caki-1; HCC1482; and HuH-7.
9. The anti-PSMA construct of any one of embodiments 1-8, wherein the antibody moiety comprises:
    i) a heavy chain variable domain ($V_H$) comprising a CDR-H1 comprising the amino acid sequence of any one of SEQ ID NOs: 1-2, or a variant thereof comprising up to about 5 amino acid substitutions, a CDR-H2 comprising the amino acid sequence of any one of SEQ ID NOs: 3-4, or a variant thereof comprising up to about 5 amino acid substitutions, and a CDR-H3 comprising the amino acid sequence of any one of SEQ ID NOs: 5-6, or a variant thereof comprising up to about 5 amino acid substitutions; and
    ii) a light chain variable domain ($V_L$) comprising a CDR-L1 comprising the amino acid sequence of any one of SEQ ID NOs: 7-8, or a variant thereof comprising up to about 5 amino acid substitutions, a CDR-L2 comprising the amino acid sequence GNS or SSN, or a variant thereof comprising about 2 amino acid substitutions, and a CDR-L3 comprising the amino acid sequence of any one of SEQ ID NOs: 9-10, or a variant thereof comprising up to about 5 amino acid substitutions.
10. The anti-PSMA construct of embodiment 9, wherein the antibody moiety comprises: i) a $V_H$ comprising a CDR-H1 comprising the amino acid sequence of any one of SEQ ID NOs: 1-2, a CDR-H2 comprising the amino acid sequence of any one of SEQ ID NOs: 3-4, and a CDR-H3 comprising the amino acid sequence of any one of SEQ ID NOs: 5-6; and ii) a $V_L$ comprising a CDR-L1 comprising the amino acid sequence of any one of SEQ ID NOs: 7-8, a CDR-L2 comprising the amino acid sequence of GNS or SNN, and a CDR-L3 comprising the amino acid sequence of any one of SEQ ID NOs: 9-10.
11. The anti-PSMA construct of embodiment 9 or 10, wherein the antibody moiety comprises
    i) a $V_H$ comprising a CDR-H1 comprising the amino acid sequence of SEQ ID NO: 1, a CDR-H2 comprising the amino acid sequence of SEQ ID NO: 3, and a CDR-H3 comprising the amino acid sequence of SEQ ID NO: 5; and
    ii) a light chain variable domain ($V_L$) comprising a CDR-L1 comprising the amino acid sequence of SEQ ID NO: 7, a CDR-L2 comprising the amino acid sequence GNS, and a CDR-L3 comprising the amino acid sequence of SEQ ID NO: 9.
12. The anti-PSMA construct of embodiment 9 or 10, wherein the antibody moiety comprises
    i) a $V_H$ comprising a CDR-H1 comprising the amino acid sequence of SEQ ID NO: 2, a CDR-H2 comprising the amino acid sequence of SEQ ID NO: 4, and a CDR-H3 comprising the amino acid sequence of SEQ ID NO: 6; and
    ii) a $V_L$ comprising a CDR-L1 comprising the amino acid sequence of SEQ ID NO: 8, a CDR-L2 comprising the amino acid sequence SNN, and a CDR-L3 comprising the amino acid sequence of SEQ ID NO: 10.
13. The anti-PSMA construct of any one of embodiments 1-8, wherein the antibody moiety comprises a CDR-H1, a CDR-H2, and a CDR-H3 of a heavy chain variable domain ($V_H$) set forth in SEQ ID NO: 16 or 17 and a CDR-L1, a CDR-L2, and a CDR-L3 of a light chain variable domain ($V_L$) set forth in SEQ ID NO: 18 or 19.
14. The anti-PSMA construct of embodiment 13, wherein the antibody moiety comprises the CDR-H1, CDR-H2, and CDR-H3 of the $V_H$ set forth in SEQ ID NO: 16 and the CDR-L1, the CDR-L2, and the CDR-L3 of the $V_L$ set forth in SEQ ID NO: 18.
15. The anti-PSMA construct of embodiment 13, wherein the antibody moiety comprises the CDR-H1, CDR-H2, and CDR-H3 of the $V_H$ set forth in SEQ ID NO: 17 and the CDR-L1, the CDR-L2, and the CDR-L3 of the $V_L$ set forth in SEQ ID NO: 19.
16. The anti-PSMA construct of any one of embodiments 1-8, wherein the antibody moiety comprises: i) a $V_H$ comprising an amino acid sequence having at least about 85% sequence identity to SEQ ID NO: 16 or 17 and ii) a $V_L$ comprising an amino acid sequence having at least about 85% sequence identity to SEQ ID NO: 18 or 19.
17. The anti-PSMA construct of any one of embodiments 1-16, wherein the antibody moiety comprises: i) a $V_H$ comprising an amino acid sequence having at least about 90% sequence identity to SEQ ID NO: 16 or 17 and ii) a $V_L$ comprising an amino acid sequence having at least about 90% sequence identity to SEQ ID NO: 18 or 19.
18. The anti-PSMA construct of any one of embodiments 1-17, wherein the antibody moiety comprises: i) a $V_H$ comprising an amino acid sequence having at least about 95% sequence identity to SEQ ID NO: 16 or 17 and ii) a $V_L$ comprising an amino acid sequence having at least about 95% sequence identity to SEQ ID NO: 18 or 19.

19. The anti-PSMA construct of embodiment 1-18, wherein the antibody moiety comprises: a $V_H$ comprising an amino acid sequence of SEQ ID NO: 16 and a $V_L$ comprising the amino acid sequence of SEQ ID NO: 18.

20. The anti-PSMA construct of embodiment 1-18, wherein the antibody moiety comprises: a $V_H$ comprising an amino acid sequence of SEQ ID NO: 17; and a $V_L$ comprising the amino acid sequence of SEQ ID NO: 19.

21. The anti-PSMA construct of any one of embodiments 1-8, wherein the antibody moiety comprises:
    i) a heavy chain variable domain ($V_H$) comprising the amino acid sequences of SEQ ID NOs: 1, 3, and 5, and a light chain variable domain ($V_L$) comprising the amino acid sequence of SEQ ID NO: 7, GNS, and SEQ ID NO: 9; or
    ii) a $V_H$ comprising the amino acid sequences of SEQ ID NOs: 2, 4, and 6, and a $V_L$ comprising the amino acid sequence of SEQ ID NO: 8, SSN, and SEQ ID NO: 10.

22. An anti-PSMA construct comprising an antibody moiety that competes with the anti-PSMA construct of embodiment 19 or embodiment 20 for specific binding to PSMA.

23. The anti-PSMA construct of any one of embodiments 1-22, wherein the antibody moiety specifically recognizing PSMA is chimeric, human, partially humanized, fully humanized, or semi-synthetic.

24. The anti-PSMA construct of any one of embodiments 1-23, wherein the antibody moiety specifically recognizing PSMA is a full-length antibody, a Fab, a Fab', a F(ab')$_2$, an Fv, or a single chain Fv (scFv).

25. The anti-PSMA construct of embodiment 24, wherein the antibody moiety specifically recognizing PSMA is an scFv.

26. The anti-PSMA construct of embodiment 25, wherein the scFv comprises the amino acid sequence set forth in SEQ ID NO: 20 or an amino acid sequence that has at least 85%, 90%, or 95% sequence identity to SEQ ID NO: 20.

27. The anti-PSMA construct of embodiment 25, wherein the scFv comprises the amino acid sequence set forth in SEQ ID NO: 21 or an amino acid sequence that has at least 85%, 90%, or 95% sequence identity to SEQ ID NO: 21.

28. The anti-PSMA construct of embodiment 24, wherein the antibody moiety specifically recognizing PSMA is a Fab or Fab'.

29. The anti-PSMA construct of any one of embodiments 1-28, wherein the antibody moiety specifically recognizing PSMA is fused to an Fc fragment optionally via a linker.

30. The anti-PSMA construct of embodiment 29, wherein the Fc fragment is a human IgG Fc fragment.

31. The anti-PSMA construct of embodiment 30, wherein the human IgG is an IgG1, IgG2, IgG3, or IgG4.

32. The anti-PSMA construct of any one of embodiments 1-23, wherein the anti-PSMA antibody moiety is a full-length antibody.

33. The anti-PSMA construct of embodiment 30, wherein the full-length antibody comprises a heavy chain comprising the amino acid sequence of SEQ ID NO: 39 or an amino acid sequence having at least 85% sequence identity to SEQ ID NO: 39 and a light chain comprising the amino acid sequence of SEQ ID NO: 40 or amino acid sequence having at least 85% sequence identity to SEQ ID NO: 40.

34. The anti-PSMA construct of embodiment 30, wherein the full-length antibody comprises a heavy chain comprising an amino acid sequence having at least 90% sequence identity to SEQ ID NO: 39 and a light chain comprising an amino acid sequence having at least 90% sequence identity to SEQ ID NO: 40.

35. The anti-PSMA construct of embodiment 30, wherein the full-length antibody comprises a heavy chain comprising an amino acid sequence having at least 95% sequence identity to SEQ ID NO: 39 and a light chain comprising an amino acid sequence having at least 95% sequence identity to SEQ ID NO: 40.

36. The anti-PSMA construct of embodiment 30, wherein the full-length antibody comprises a heavy chain comprising an amino acid sequence having at least 85% sequence identity to SEQ ID NO: 41 and a light chain comprising an amino acid having at least 85% sequence identity to SEQ ID NO: 42.

37. The anti-PSMA construct of embodiment 30, wherein the full-length antibody comprises a heavy chain comprising an amino acid sequence having at least 90% sequence identity to SEQ ID NO: 41 and a light chain comprising an amino acid having at least 90% sequence identity to SEQ ID NO: 42.

38. The anti-PSMA construct of embodiment 30, wherein the full-length antibody comprises a heavy chain comprising an amino acid sequence having at least 95% sequence identity to SEQ ID NO: 41 and a light chain comprising an amino acid having at least 95% sequence identity to SEQ ID NO: 42.

39. The anti-PSMA construct of any one of embodiments 1-38, wherein the construct is monospecific.

40. The anti-PSMA construct of any one of embodiments 1-38, wherein the construct is multispecific.

41. The anti-PSMA construct of embodiment 40, wherein the construct is bispecific.

42. The anti-PSMA construct of embodiment 40 or 41, wherein the construct is a tandem scFv, a diabody (Db), a single chain diabody (scDb), a dual-affinity retargeting (DART) antibody, a F(ab')2, a dual variable domain (DVD) antibody, a knob-into-hole (KiH) antibody, a dock and lock (DNL) antibody, a chemically cross-linked antibody, a heteromultimeric antibody, or a heteroconjugate antibody.

43. The anti-PSMA construct of embodiment 42, wherein the construct is a tandem scFv comprising two scFvs linked by a peptide linker.

44. The anti-PSMA construct of any one of embodiments 40-43, wherein the construct further comprises a second antibody moiety specifically recognizing a second antigen.

45. The anti-PSMA construct of embodiment 44, wherein the second antigen is an antigen on the surface of a T cell.

46. The anti-PSMA construct of embodiment 45, wherein the second antigen is selected from the group consisting of CD3γ, CD3δ, CD3ε, CD3ζ, CD28, OX40, GITR, CD137, CD27, CD40L, and HVEM.

47. The anti-PSMA construct of embodiment 46, wherein the second antigen is CD3ε.

48. The anti-PSMA construct of embodiment 47, wherein the construct is a tandem scFv comprising an N-terminal scFv specifically recognizing PSMA and a C-terminal scFv specifically recognizing CD3ε.

49. The anti-PSMA construct of embodiment 48, comprising an amino acid sequence that has at least 85%, 90%, 95%, or 100% sequence identity to SEQ ID NO: 25 or 26.

50. The anti-PSMA construct of embodiment 48, comprising an amino acid sequence that has at least 85%, 90%, 95%, or 100% sequence identity to SEQ ID NO: 27 or 28.

51. The anti-PSMA construct of embodiment 45, wherein the T cell is selected from the group consisting of a cytotoxic T cell, a helper T cell, and a natural killer T cell.

52. The anti-PSMA construct of any one of embodiments 45-51, wherein the expression of the anti-PSMA construct is induced by the activation of an engineered T cell.

53. The anti-PSMA construct of embodiment 52, wherein the engineered T cell is a T cell comprising a chimeric antigen receptor (CAR).

54. The anti-PSMA construct of embodiment 53, wherein the CAR specifically binds to PSMA.

55. The anti-PSMA construct of embodiment 53, wherein the CAR binds to an antigen other than PSMA.

56. The anti-PSMA construct of embodiment 52, wherein the engineered T cell is a T cell comprising a chimeric antibody-T cell receptor (TCR) construct (caTCR).

57. The anti-PSMA construct of embodiment 56, wherein the caTCR specifically binds to PSMA.

58. The anti-PSMA construct of embodiment 56, wherein the caTCR binds to an antigen other than PSMA.

59. The anti-PSMA construct of embodiment 44, wherein the second antigen is an antigen on the surface of a B cell, a natural killer cell, a dendritic cell, a macrophage, a monocyte, or a neutrophil.

60. The anti-PSMA construct of any one of embodiments 1-27, wherein the construct is a CAR comprising:
    (a) an extracellular domain comprising the anti-PSMA antibody moiety;
    (b) a transmembrane domain; and
    (c) an intracellular signaling domain.

61. The anti-PSMA construct of embodiment 60, wherein the intracellular signaling domain comprises a primary immune cell signaling sequence derived from CD3ζ, TCRζ, FcRγ, FcRβ, CD3γ, CD3δ, CD3ε, CD5, CD22, CD79a, CD79b, or CD66d.

62. The anti-PSMA construct of embodiment 61, wherein the intracellular signaling domain further comprise a costimulatory signaling sequence derived from CD28, 4-1BB, ICOS, or OX40.

63. The anti-PSMA construct of embodiment 60, 61, or 62, wherein the intracellular signaling domain comprises a primary immune cell signaling sequence derived from CD3ζ and a costimulatory signaling sequence derived from CD28.

64. The anti-PSMA construct of any one of embodiments 60-63, comprising an amino acid sequence that has at least 85%, 90%, 95%, or 100% sequence identity to SEQ ID NO: 29.

65. The anti-PSMA construct of any one of embodiments 60-63, comprising an amino acid sequence that has at least 85%, 90%, 95%, or 100% sequence identity to SEQ ID NO: 30.

66. The anti-PSMA construct of any one of embodiments 1-23, wherein the construct is a caTCR comprising:
    (a) an extracellular domain comprising the anti-PSMA antibody moiety; and
    (b) a T cell receptor module (TCRM) comprising a first TCR domain (TCRD) comprising a first TCR transmembrane domain (TCR-TM) and a second TCRD comprising a second TCR-TM, wherein the TCRM facilitates recruitment of at least one TCR-associated signaling molecule.

67. The anti-PSMA construct of embodiment 66, wherein the first TCR-TM is derived from one of the transmembrane domains of a first naturally occurring TCR and the second TCR-TM is derived from the other transmembrane domain of the first naturally occurring TCR.

68. The anti-PSMA construct of embodiment 67, wherein the at least one of the TCR-TMs is non-naturally occurring.

69. The anti-PSMA construct of embodiment 68, wherein the TCRM comprising the at least one non-naturally occurring TCR-TM allows for enhanced recruitment of the at least one TCR-associated signaling molecule as compared to a TCRM comprising the first naturally occurring T cell receptor transmembrane domains.

70. The anti-PSMA construct of embodiment 66 or 67, wherein the first and second TCR-TMs are naturally occurring.

71. The anti-PSMA construct of any one of embodiments 66-70, wherein the first TCR-TM and the second TCR-TM are derived from a γ/δ TCR,
    optionally wherein the first TCR-TM is derived from a TCR γ chain and the second TCR-TM is derived from a TCR δ chain, or
    optionally wherein the first TCR-TM is derived from a TCR δ chain and the second TCR-TM is derived from a TCR γ chain.

72. The anti-PSMA construct of embodiment 71, wherein the construct comprises a first polypeptide chain comprising an amino acid sequence that has at least 85%, 90%, 95%, or 100% sequence identity to SEQ ID NO: 31 and a second polypeptide chain comprising an amino acid sequence that has at least 85%, 90%, 95%, or 100% sequence identity to SEQ ID NO: 32.

73. The anti-PSMA construct of embodiment 71, wherein the construct comprises a first polypeptide chain comprising an amino acid sequence that has at least 85%, 90%, 95%, or 100% sequence identity to SEQ ID NO: 34 and a second polypeptide chain comprising an amino acid sequence that has at least 85%, 90%, 95%, or 100% sequence identity to SEQ ID NO: 35.

74. The anti-PSMA construct of embodiment 71, wherein the construct comprises a first polypeptide chain comprising an amino acid sequence that has at least 85%, 90%, 95%, or 100% sequence identity to SEQ ID NO: 165 and a second polypeptide chain comprising an amino acid sequence that has at least 85%, 90%, 95%, or 100% sequence identity to SEQ ID NO: 166.

75. The anti-PSMA construct of embodiment 71, wherein the construct comprises a first polypeptide chain comprising an amino acid sequence that has at least 85%, 90%, 95%, or 100% sequence identity to SEQ ID NO: 167 and a second polypeptide chain comprising an amino acid sequence that has at least 85%, 90%, 95%, or 100% sequence identity to SEQ ID NO: 168.

76. The anti-PSMA construct of embodiment 71, wherein the construct comprises a first polypeptide chain comprising an amino acid sequence that has at least 85%, 90%, 95%, or 100% sequence identity to SEQ ID NO: 169 and a second polypeptide chain comprising an amino acid sequence that has at least 85%, 90%, 95%, or 100% sequence identity to SEQ ID NO: 170.

77. The anti-PSMA construct of embodiment 71, wherein the construct comprises a first polypeptide chain comprising an amino acid sequence that has at least 85%, 90%, 95%, or 100% sequence identity to EQ ID NO: 171 and a second polypeptide chain comprising an amino acid sequence that has at least 85%, 90%, 95%, or 100% sequence identity to SEQ ID NO: 172.

78. The anti-PSMA construct of embodiment 71, wherein the construct comprises a first polypeptide chain comprising an amino acid sequence that has at least 85%, 90%, 95%, or 100% sequence identity to SEQ ID NO: 173 and a second polypeptide chain comprising an amino acid sequence that has at least 85%, 90%, 95%, or 100% sequence identity to SEQ ID NO: 174.

79. The anti-PSMA construct of embodiment 71, wherein the construct comprises a first polypeptide chain comprising an amino acid sequence that has at least 85%, 90%, 95%, or 100% sequence identity to SEQ ID NO: 175 and a second polypeptide chain comprising an amino acid sequence that has at least 85%, 90%, 95%, or 100% sequence identity to SEQ ID NO: 176.

80. The anti-PSMA construct of embodiment 71, wherein the construct comprises a first polypeptide chain comprising an amino acid sequence that has at least 85%, 90%, 95%, or 100% sequence identity to SEQ ID NO: 177 and a second polypeptide chain comprising an amino acid sequence that has at least 85%, 90%, 95%, or 100% sequence identity to SEQ ID NO: 178.

81. The anti-PSMA construct of embodiment 71, wherein the construct comprises a first polypeptide chain comprising an amino acid sequence that has at least 85%, 90%, 95%, or 100% sequence identity to SEQ ID NO: 179 and a second polypeptide chain comprising an amino acid sequence that has at least 85%, 90%, 95%, or 100% sequence identity to SEQ ID NO: 180.

82. The anti-PSMA construct of any one of embodiments 66-70, wherein the first TCR-TM and the second TCR-TM are derived from an α/β TCR,
optionally wherein the first TCR-TM is derived from a TCR α chain and the second TCR-TM is derived from a TCR β chain, or
optionally wherein the first TCR-TM is derived from a TCR β chain and the second TCR-TM is derived from a TCR α chain.

83. The anti-PSMA construct of any one of embodiments 66-82, wherein the TCR-associated signaling molecule is selected from the group consisting of CD3δε, CD3γε, and CD3ζζ.

84. The anti-PSMA construct of any one of embodiments 66-83, wherein the caTCR lacks a functional primary immune cell signaling domain.

85. The anti-PSMA construct of any one of embodiments 1-23, wherein the construct is a chimeric signaling receptor (CSR) comprising:
i) a ligand-binding module that is capable of binding or interacting with PSMA;
ii) a transmembrane module; and
iii) a co-stimulatory immune cell signaling module that is capable of providing a co-stimulatory signal to the effector cell,
wherein the ligand-binding module and the co-stimulatory immune cell signaling module are not derived from the same molecule, and wherein the CSR lacks a functional primary immune cell signaling domain.

86. The anti-PSMA construct of embodiment 85, wherein the CSR lacks any primary immune cell signaling sequences.

87. The anti-PSMA construct of embodiment 85 or 86, wherein the ligand-binding module comprises the anti-PSMA construct of any one of embodiments 1-25.

88. The anti-PSMA construct of any one of embodiments 85 to 87, wherein the transmembrane module of the CSR and the co-stimulatory immune cell signaling module of the CSR are from the same molecule.

89. The anti-PSMA construct of embodiment 88, wherein the molecule is selected from the group consisting of CD28, 4-1BB (CD137), OX40, CD30, CD27, CD40, PD-1, ICOS, lymphocyte function-associated antigen-1 (LFA-1), CD2, CD7, LIGHT, NKG2C, B7-H3, and a ligand that specifically binds with CD83.

90. The anti-PSMA construct of embodiment 89, wherein the molecule is selected from the group consisting of CD28, 4-1BB (CD137), OX40, CD30, and CD27

91. The anti-PSMA construct of any one of embodiments 85 to 87, wherein the transmembrane module of the CSR and the co-stimulatory immune cell signaling module of the CSR are from different molecules.

92. The anti-PSMA construct of any one of embodiments 85-91, wherein the transmembrane module of the CSR comprises a transmembrane domain derived from CD28, CD3ε, CD3ζ, CD45, CD4, CD5, CD8, CD9, CD16, CD22, CD27, CD30, CD33, CD37, CD64, CD80, CD86, CD134, CD137, CD154, 4-1BB, OX40, or the α, β, δ, γ, or ζ chain of the T-cell receptor.

93. The anti-PSMA construct of any one of embodiments 85-92, wherein the transmembrane module of the CSR comprises a transmembrane domain derived from CD8, 4-1BB, CD27, CD28, CD30, or OX40.

94. The anti-PSMA construct of embodiment 93, wherein the transmembrane module of the CSR comprises a sequence that has at least 85%, 90%, 95%, or 100% sequence identity to any one of SEQ ID NOS: 94-99.

95. The anti-PSMA construct of any one of embodiments 85-94, wherein the co-stimulatory immune cell signaling module is derived from the intracellular domain of a co-stimulatory receptor of a TCR.

96. The anti-PSMA construct of embodiment 95, wherein the co-stimulatory receptor is selected from the group consisting of 4-1BB, CD27, CD28, CD30, OX40, ICOS, and CD40.

97. The anti-PSMA construct of embodiment 96, wherein the co-stimulatory immune cell signaling module of the CSR comprises a sequence that has at least 85%, 90%, 95%, or 100% sequence identity to any one of SEQ ID NOs: 100-103 and 183.

98. The anti-PSMA construct of any one of embodiments 85-97, wherein the expression of the CSR is inducible upon activation of an engineered T cell.

99. The anti-PSMA construct of embodiment 98, wherein the engineered T cell is a T cell comprising a CAR.

100. The anti-PSMA construct of embodiment 99, wherein the CAR specifically binds to PSMA.

101. The anti-PSMA construct of embodiment 99, wherein the CAR binds to an antigen other than PSMA.

102. The anti-PSMA construct of embodiment 98, wherein the engineered T cell is a T cell comprising a caTCR.

103. The anti-PSMA construct of embodiment 102, wherein the caTCR specifically binds to PSMA.

104. The anti-PSMA construct of embodiment 102, wherein the caTCR binds to an antigen other than PSMA.
105. The anti-PSMA construct of any one of embodiments 85-104, comprising an amino acid sequence that has at least 85%, 90%, 95%, or 100% sequence identity to any one of SEQ ID NOS: 3, 55-69, 93, and 184-186.
106. The anti-PSMA construct of embodiment 105, comprising an amino acid sequence that has at least 85%, 90%, 95%, or 100% sequence identity to SEQ ID NO: 37.
107. The anti-PSMA construct of any one of embodiments 85-104, comprising an amino acid sequence that has at least 85%, 90%, 95%, or 100% sequence identity to any one of SEQ ID NOS: 38, 70-84, 93, and 184-186.
108. The anti-PSMA construct of embodiment 107, comprising an amino acid sequence that has at least 85%, 90%, 95%, or 100% sequence identity to SEQ ID NO 38.
109. The anti-PSMA construct of any one of embodiments 85-108, comprising a signal peptide.
110. The anti-PSMA construct of embodiment 109, wherein the signal peptide comprises the sequence of METDTLLLWVLLLWVPGSTG SEQ ID NO: 128.
111. The anti-PSMA construct of any one of embodiments 1-42, conjugated to an effector molecule.
112. The anti-PSMA construct of embodiment 111, wherein the effector molecule is a therapeutic agent selected from the group consisting of: a drug, a toxin, a radioisotope, a protein, a peptide, and a nucleic acid.
113. The anti-PSMA construct of embodiment 112, wherein the therapeutic agent is a drug or a toxin.
114. The anti-PSMA construct of embodiment 111, wherein the effector molecule is a detectable label.
115. An effector cell that has been genetically modified with one or more nucleic acids encoding the anti-PSMA CAR of any one of embodiments 60-65 or the anti-PSMA caTCR of any one of embodiments 66-84.
116. The effector cell of embodiment 115, wherein the one or more nucleic acids encoding the anti-PSMA CAR or anti-PSMA caTCR also encode a CSR comprising a ligand binding module that binds a target antigen.
117. The effector cell of embodiment 115, which has been genetically modified with one or more additional nucleic acids encoding a CSR comprising a ligand binding module that binds a target antigen.
118. The effector cell of embodiment 116 or 117, wherein the target antigen is PSMA.
119. The effector cell of embodiment 116 or 117, wherein the target antigen is an antigen other than PSMA.
120. The effector cell of embodiment 115, wherein the one or more nucleic acids encoding the anti-PSMA CAR or anti-PSMA caTCR also encode a tandem scFv that comprises a first scFv that binds a target antigen.
121. The effector cell of embodiment 115, which has been genetically modified with one or more additional nucleic acids encoding a tandem scFv that comprises a first scFv that binds a target antigen.
122. The effector cell of embodiment 120 or 121, wherein the target antigen is PSMA.
123. the effector cell of embodiment 120 or 121, wherein the target is an antigen other than PSMA.
124. An effector cell that has been genetically modified with one or more nucleic acids encoding the anti-PSMA tandem scFv of any one of embodiments 43-59 or the anti-PSMA CSR of any one of embodiments 85-110.
125. The effector cell of embodiment 124, wherein the one or more nucleic acids encoding the anti-PSMA tandem scFv or anti-PSMA CSR also encode a CAR.
126. The effector cell of embodiment 124, which has been genetically modified with one or more additional nucleic acids encoding a CAR.
127. The effector cell of embodiment 125 or 126, wherein the CAR specifically binds PSMA.
128. The effector cell of embodiment 125 or 126, wherein the CAR specifically binds an antigen other than PSMA.
129. The effector cell of embodiment 124, wherein the one or more nucleic acids encoding the anti-PSMA tandem scFv or anti-PSMA CSR also encode a caTCR.
130. The effector cell of embodiment 124, which has been genetically modified with one or more additional nucleic acids encoding a caTCR.
131. The effector cell of embodiment 129 or 130, wherein the caTCR specifically binds PSMA.
132. The effector cell of embodiment 129 or 130, wherein the caTCR specifically binds an antigen other than PSMA.
133. The effector cell of any one of embodiments 115-132, wherein the effector cell is an immune cell.
134. The effector cell of embodiment 133, wherein the immune cell is a T cell.
135. The effector cell of embodiment 122, wherein the T cell is a cytotoxic T cell, a helper T cell, or a natural killer T cell.
136. A method of producing an effector cell, comprising genetically modifying a cell with one or more nucleic acids encoding the anti-PSMA CAR of any one of embodiments 60-65 or the anti-PSMA caTCR of any one of embodiments 66-84.
137. The method of embodiment 136, wherein the one or more nucleic acids encoding the anti-PSMA CAR or anti-PSMA caTCR also encode a CSR comprising a ligand binding module that binds a target antigen.
138. The method of embodiment 136, comprising further genetically modifying the cell with one or more additional nucleic acids encoding a CSR comprising a ligand binding module that binds a target antigen.
139. The method of embodiment 137 or 138 wherein the target antigen is PSMA.
140. The method of embodiment 137 or 138, wherein the target antigen is an antigen other than PSMA.
141. The method of embodiment 136, wherein the one or more nucleic acids encoding the anti-PSMA CAR or anti-PSMA caTCR also encode a tandem scFv that comprises a first scFv that binds a target antigen.
142. The method of embodiment 136, comprising further genetically modifying the cell with one or more additional nucleic acids encoding a tandem scFv that comprises a first scFv that binds a target antigen.
143. The method of embodiment 141 or 142, wherein the target antigen is PSMA.
144. The method of embodiment 141 or 142 wherein the target is an antigen other than PSMA.
145. A method of producing an effector cell, comprising genetically modifying a cell with one or more nucleic acids encoding the anti-PSMA tandem scFv of any one of embodiments 37-53 or the anti-PSMA CSR of any one of embodiments 85-110.
146. The method of embodiment 145, wherein the one or more nucleic acids encoding the anti-PSMA tandem scFv or anti-PSMA CSR also encode a CAR.

147. The method of embodiment 145, comprising further genetically modifying the cell with one or more additional nucleic acids encoding a CAR.
148. The method of embodiment 146 or 147, wherein the CAR specifically binds PSMA.
149. The method of embodiment 146 or 147, wherein the CAR specifically binds an antigen other than PSMA.
150. The method of embodiment 145, wherein the one or more nucleic acids encoding the anti-PSMA CAR or anti-PSMA caTCR also encode a caTCR.
151. The method of embodiment 145, comprising further genetically modifying the cell with one or more additional nucleic acids encoding a caTCR.
152. The method of embodiment 150 or 151, wherein the caTCR specifically binds PSMA.
153. The method of embodiment 150 or 151, wherein the caTCR specifically binds an antigen other than PSMA.
154. The method of any one of embodiments 136-153, wherein the effector cell is an immune cell.
155. The method of embodiment 154, wherein the immune cell is a T cell.
156. The method of embodiment 155, wherein the T cell is a cytotoxic T cell, a helper T cell, or a natural killer T cell.
157. A nucleic acid encoding the polypeptide portion(s) of the anti-PSMA construct of any one of embodiments 1-110.
158. A vector comprising the nucleic acid of embodiment 157.
159. A host cell comprising the nucleic acid of embodiment 157, or the vector of 158.
160. A method of producing the anti-PSMA construct of any one of embodiments 1-59, comprising culturing the host cell of embodiment 159 under conditions where the anti-PSMA construct is expressed, and recovering the anti-PSMA construct produced by the host cell.
161. A pharmaceutical composition comprising the anti-PSMA construct of any one of embodiments 1-59 and 111-113 the effector cell of any one of embodiments 115-135, the nucleic acid of embodiment 157, or the vector of embodiment 158 and a pharmaceutical acceptable carrier.
162. A kit comprising the anti-PSMA construct of any one of embodiments 1-59 and 111-113, the effector cell of any one of embodiments 115-135, the nucleic acid of embodiment 157, the vector of embodiment 158 and/or the host cell of embodiment 159.
163. A method of detecting PSMA in a sample, comprising contacting the sample with the anti-PSMA construct of embodiment 114 and detecting the presence of the label.
164. The method of embodiment 163, wherein the sample comprises cells expressing PSMA.
165. A method of treating an individual having a PSMA-associated disease or disorder, comprising administering to the individual an effective amount of the pharmaceutical composition of embodiment 161.
166. A method of treating an individual having a PSMA-associated disease or disorder, comprising administering to the individual an effector cell that has been genetically modified with one or more nucleic acids that encode the anti-PSMA CAR of any one of embodiments 60-65 or the anti-PSMA caTCR of any one of embodiments 66-84.
167. The method of embodiment 166, comprising genetically modifying the effector cell with the one or more nucleic acids prior to administration.
168. The method of embodiment 167, wherein the one or more nucleic acids that encode the anti-PSMA CAR or the anti-PSMA caTCR also encode a CSR or a tandem scFv.
169. The method of embodiment 167, comprising further genetically modifying the effector cell with one or more additional nucleic acids encoding a CSR or a tandem scFv.
170. The method of embodiment 168 or 169, wherein the tandem scFv specifically binds PSMA.
171. The method of embodiment 168 or 169, wherein the tandem scFv specifically binds an antigen other than PSMA.
172. The method of embodiment 168 or 169, wherein the CSR specifically binds PSMA.
173. The method of embodiment 168 or 169, wherein the CSR specifically binds an antigen other than PSMA.
174. A method of treating an individual having a PSMA-associated disease or disorder, comprising administering to the individual an effector cell that has been genetically modified with one or more nucleic acids that encode the anti-PSMA tandem scFv of any one of embodiments 43-59 or anti-PSMA CSR of any one of embodiments 85-110.
175. The method of embodiment 174, comprising genetically modifying the effector cell with the one or more nucleic acids prior to administration.
176. The method of embodiment 175, wherein the one or more nucleic acids that encode the anti-PSMA CSR or anti-PSMA tandem scFv also encode a CAR or a caTCR.
177. The method of embodiment 175, comprising further genetically modifying the effector cell with one or more additional nucleic acids encoding a CAR or a caTCR.
178. The method of embodiment 176 or 177, wherein the CAR specifically binds PSMA.
179. The method of embodiment 176 or 177, wherein the CAR specifically binds an antigen other than PSMA.
180. The method of embodiment 176 or 177, wherein the caTCR specifically binds PSMA.
181. The method of embodiment 176 or 177, wherein the caTCR specifically binds an antigen other than PSMA.
182. The method of any one of embodiments 166-181, wherein the effector cell is an immune cell.
183. The method of embodiment 182, wherein the immune cell is a T cell.
184. The method of embodiment 183, wherein the T cell is a cytotoxic T cell, a helper T cell, or a natural killer T cell.
185. The method of any one of embodiments 166-184, wherein the method further comprises obtaining an effector cell from an individual prior to genetically modifying and administering the effector cell.
186. The method of embodiment 185, wherein the individual from whom the effector cell is obtained is the individual to whom the genetically modified effector cell is administered.
187. The method of embodiment 186, wherein the individual from whom the effector cell is obtained is not the individual to whom the genetically modified effector cell is administered.
188. The method of embodiment 187, wherein the genetically modified effector cell is allogenic with respect to the individual to whom the genetically modified effector cell is administered.

189. The method of embodiment 188, wherein the genetically modified effector cell is syngeneic with respect to the individual to whom the genetically modified effector cell is administered.
190. The method of embodiment 188, wherein the genetically modified effector cell is xenogeneic respect to the individual to whom the genetically modified effector cell is administered.
191. The method of any one of embodiments 165-190, further comprising administering an additional therapy to the individual.
192. The method of any one of embodiments 165-191, wherein the PSMA-associated disease or disorder is cancer.
193. The method of embodiment 192, wherein the cancer is selected from the group consisting of: prostate cancer, renal cancer cell, uterine cancer, and liver cancer.
194. The method of embodiment 193, wherein the cancer is prostate cancer.
195. The method of embodiment 194, wherein the prostate cancer is hormone-refractory prostate cancer or metastatic prostate cancer.
196. The method of embodiment 193, wherein the cancer is renal cancer.
197. The method of embodiment 196, wherein the renal cancer is clear cell renal cell cancer (CCRCC).
198. The method of any one of embodiments 165-197, wherein the individual having the PSMA-associated disease or disorder is a mammal.
199. The method of embodiment 198, wherein the mammal is a human.
200. A method of diagnosing an individual suspected of having a PSMA-associated disease or disorder, comprising:
a) administering an effective amount of the anti-PSMA construct of embodiment 114 to the individual; and
b) determining the level of the label in the individual, wherein a level of the label above a threshold level indicates that the individual has the PSMA-associated disease or disorder.
201. A method of diagnosing an individual suspected of having a PSMA-associated disease or disorder, comprising:
a) contacting a sample comprising cells derived from the individual with the anti-PSMA construct of embodiment 114; and
b) determining the number of cells in the sample bound to the anti-PSMA construct, wherein a value for the number of cells bound to the anti-PSMA construct above a threshold level indicates that the individual has the PSMA-associated disease or disorder
202. The method of embodiment 200 or 201, wherein PSMA-associated disease or disorder is cancer.
203. The method of embodiment 202, wherein the cancer is selected from the group consisting of: prostate cancer, renal cancer cell, uterine cancer, and liver cancer.
204. The method of embodiment 203, wherein the cancer is prostate cancer.
205. The method of embodiment 204, wherein the prostate cancer is hormone-refractory prostate cancer or metastatic prostate cancer.
206. The method of embodiment 203, wherein the cancer is renal cancer.
207. The method of embodiment 206, wherein the renal cancer is clear cell renal cell cancer (CCRCC).
208. The method of any one of embodiments 200-207, wherein the individual suspected of having a disease or disorder associated with expression, aberrant expression, and/or aberrant activity of PSMA is a mammal.
209. The method of embodiment 208, wherein the mammal is a human.

The invention claimed is:

1. An anti-prostate specific membrane antigen (PSMA) construct comprising an anti-PSMA antibody moiety specifically recognizing an extracellular domain of PSMA comprising the amino acid sequence of SEQ ID NO: 44, wherein the anti-PSMA antibody moiety comprises:
 a) a heavy chain variable domain ($V_H$) comprising a heavy chain complementarity determining region (CDR-H) 1 comprising the amino acid sequence of SEQ ID NO: 1, a CDR-H2 comprising the amino acid sequence of SEQ ID NO: 3, and a CDR-H3 comprising the amino acid sequence of SEQ ID NO: 5; and a light chain variable domain ($V_L$) comprising a light chain complementarity determining region (CDR-L) 1 comprising the amino acid sequence of SEQ ID NO: 7, a CDR-L2 comprising the amino acid sequence GNS, and a CDR-L3 comprising the amino acid sequence of SEQ ID NO: 9; or
 b) a $V_H$ comprising a CDR-H1 comprising the amino acid sequence of SEQ ID NO: 2, a CDR-H2 comprising the amino acid sequence of SEQ ID NO: 4, and a CDR-H3 comprising the amino acid sequence of SEQ ID NO: 6; and a $V_L$ comprising a CDR-L1 comprising the amino acid sequence of SEQ ID NO: 8, a CDR-L2 comprising the amino acid sequence SNN, and a CDR-L3 comprising the amino acid sequence of SEQ ID NO: 10.

2. The anti-PSMA construct of claim 1, wherein the anti-PSMA antibody moiety comprises:
 i) a $V_H$ comprising the amino acid sequence of SEQ ID NO: 16, or an amino acid sequence having at least about 85% sequence identity to SEQ ID NO: 16, and a $V_L$ comprising the amino acid sequence of SEQ ID NO: 18, or an amino acid sequence having at least about 85% sequence identity to SEQ ID NO: 18; or
 ii) a Vu comprising the amino acid sequence of SEQ ID NO: 17, or an amino acid sequence having at least about 85% sequence identity to SEQ ID NO: 17, and a $V_L$ comprising the amino acid sequence of SEQ ID NO: 19, or an amino acid sequence having at least about 85% sequence identity to SEQ ID NO: 19.

3. The anti-PSMA construct of claim 1, wherein the anti-PSMA antibody moiety is chimeric, human, humanized, or semi-synthetic.

4. The anti-PSMA construct of claim 1, wherein the anti-PSMA antibody moiety is a full-length antibody, a Fab, a Fab', a F(ab')$_2$, an Fv, or a single chain Fv (scFv).

5. The anti-PSMA construct of claim 4, wherein the anti-PSMA antibody moiety is an scFv.

6. The anti-PSMA construct of claim 5, wherein the scFv comprises:
 i) the amino acid sequence of SEQ ID NO: 20, or an amino acid sequence that has at least about 85% sequence identity to SEQ ID NO: 20; or
 ii) the amino acid sequence of SEQ ID NO: 21, or an amino acid sequence that has at least about 85% sequence identity to SEQ ID NO: 21.

7. The anti-PSMA construct of claim 4, wherein the anti-PSMA moiety is a full-length antibody, and wherein the full-length antibody comprises:
 i) a heavy chain comprising the amino acid sequence of SEQ ID NO: 39 or an amino acid sequence having at least about 85% sequence identity to SEQ ID NO: 39, and a light chain comprising the amino acid sequence of SEQ ID NO: 40 or an amino acid sequence having at least about 85% sequence identity to SEQ ID NO: 40; or
 ii) a heavy chain comprising the amino acid sequence of SEQ ID NO: 41 or an amino acid sequence having at least about 85% sequence identity to SEQ ID NO: 41, and a light chain comprising the amino acid sequence of SEQ ID NO: 42 or an amino acid having at least about 85% sequence identity to SEQ ID NO: 42.

8. The anti-PSMA construct of claim 1, wherein the anti-PSMA construct is monospecific.

9. The anti-PSMA construct of claim 1, wherein the anti-PSMA construct is multi specific.

10. The anti-PSMA construct of claim 9, wherein the anti-PSMA construct is a tandem scFv, a diabody (Db), a single chain diabody (scDb), a dual-affinity retargeting (DART) antibody, a F(ab')$_2$, a dual variable domain (DVD) antibody, a knob-into-hole (KiH) antibody, a dock and lock (DNL) antibody, a chemically cross-linked antibody, a heteromultimeric antibody, or a heteroconjugate antibody.

11. The anti-PSMA construct of claim 9, wherein the anti-PSMA construct further comprises a second antibody moiety specifically recognizing a second antigen.

12. The anti-PSMA construct of claim 11, wherein the second antigen is an antigen on the surface of a B cell, a natural killer cell, a dendritic cell, a macrophage, a monocyte, a neutrophil, or a T cell.

13. The anti-PSMA construct of claim 1, wherein the anti-PSMA construct is a chimeric antigen receptor (CAR) comprising:
 (a) an extracellular domain comprising the anti-PSMA antibody moiety;
 (b) a transmembrane domain; and
 (c) an intracellular signaling domain.

14. The anti-PSMA construct of claim 13, wherein the intracellular signaling domain comprises a primary immune cell signaling sequence of CD3ζ, TCRζ, FcRγ, FcRβ, CD3γ, CD3δ, CD3ε, CD5, CD22, CD79a, CD79b, or CD66d, and/or wherein the intracellular signaling domain further comprise a costimulatory signaling sequence of CD28, 4-1BB, ICOS, or OX40.

15. The anti-PSMA construct of claim 1, wherein the anti-PSMA construct is a chimeric antibody-T cell receptor (TCR) construct (caTCR) comprising:
 (a) an extracellular domain comprising the anti-PSMA antibody moiety; and
 (b) a TCR module (TCRM) comprising a first TCR domain (TCRD) comprising a first TCR transmembrane domain (TCR-TM) and a second TCRD comprising a second TCR-TM, wherein the TCRM facilitates recruitment of at least one TCR-associated signaling molecule.

16. The anti-PSMA construct of claim 15, wherein the first TCR-TM and the second TCR-TM are from a γ/δ TCR.

17. The anti-PSMA construct of claim 2, wherein the anti-PSMA construct comprises:
  i) a first polypeptide chain comprising the amino acid sequence of SEQ ID NO: 31, and a second polypeptide chain comprising the amino acid sequence of SEQ ID NO: 32;
  ii) a first polypeptide chain comprising the amino acid sequence of SEQ ID NO: 34, and a second polypeptide chain comprising the amino acid sequence of SEQ ID NO;
  iii) a first polypeptide chain comprising the amino acid sequence of SEQ ID NO: 165, and a second polypeptide chain comprising the amino acid sequence of SEQ ID NO: 166;
  iv) a first polypeptide chain comprising the amino acid sequence of SEQ ID NO: 167, and a second polypeptide chain comprising the amino acid sequence of SEQ ID NO: 168;
  v) a first polypeptide chain comprising the amino acid sequence of SEQ ID NO: 169, and a second polypeptide chain comprising the amino acid sequence of SEQ ID NO: 170;
  vi) a first polypeptide chain comprising the amino acid sequence of SEQ ID NO: 171, and a second polypeptide chain comprising the amino acid sequence of SEQ ID NO: 172;
  vii) a first polypeptide chain comprising the amino acid sequence of SEQ ID NO: 173, and a second polypeptide chain comprising the amino acid sequence of SEQ ID NO: 174;
  viii) a first polypeptide chain comprising the amino acid sequence of SEQ ID NO: 175, and a second polypeptide chain comprising the amino acid sequence of SEQ ID NO: 176;
  ix) a first polypeptide chain comprising the amino acid sequence of SEQ ID NO: 177, and a second polypeptide chain comprising the amino acid sequence of SEQ ID NO: 178;
  x) a first polypeptide chain comprising the amino acid sequence of SEQ ID NO: 179, and a second polypeptide chain comprising the amino acid sequence of SEQ ID NO: 180;
  xi) a polypeptide chain comprising the amino acid sequence of SEQ ID NO: 29;
  xii) a polypeptide chain comprising the amino acid sequence of SEQ ID NO: 30; or
  xiii) a polypeptide chain comprising the amino acid sequence of any one of SEQ ID NOs: 37, 38, 55-84, 93, and 184-186.

18. The anti-PSMA construct of claim 15, wherein the TCR-associated signaling molecule is selected from the group consisting of CD3δε, CD3γε, and CD3ζζ, and/or wherein the caTCR lacks a functional primary immune cell signaling domain.

19. The anti-PSMA construct of claim 1, wherein the anti-PSMA construct is a chimeric signaling receptor (CSR) comprising:
  i) a ligand-binding module comprising the anti-PSMA antibody moiety;
  ii) a transmembrane module; and
  iii) a co-stimulatory immune cell signaling module that is capable of providing a co-stimulatory signal to an effector cell,
  wherein the CSR lacks a functional primary immune cell signaling domain.

20. The anti-PSMA construct of claim 19, wherein:
  (i) the CSR lacks any primary immune cell signaling sequences;
  (ii) the transmembrane module of the CSR and the co-stimulatory immune cell signaling module of the CSR are from different molecules;
  (iii) the transmembrane module of the CSR comprises a transmembrane domain of CD28, CD3ε, CD3ζ, CD45, CD4, CD5, CD8, CD9, CD16, CD22, CD27, CD30, CD33, CD37, CD64, CD80, CD86, CD134, CD137, CD154, 4-1BB, OX40, or the α, β, δ, or γ chain of a TCR; and/or
  (iv) the co-stimulatory immune cell signaling module is from the intracellular domain of a co-stimulatory receptor of a TCR selected from the group consisting of 4-1BB, CD27, CD28, CD30, OX40, ICOS, and CD40.

21. The anti-PSMA construct of claim 1, wherein the anti-PSMA antibody moiety is conjugated to an effector molecule, wherein the effector molecule is a detectable label or a therapeutic agent selected from the group consisting of a drug, a toxin, a radioisotope, a protein, a peptide, and a nucleic acid.

22. A nucleic acid or a vector encoding the anti-PSMA construct of claim 1.

23. A host cell comprising the nucleic acid or the vector of claim 22.

24. A method of producing an anti-PSMA construct, comprising culturing the host cell of claim 23 under a condition where the anti-PSMA construct is expressed, and recovering the anti-PSMA construct produced by the host cell.

25. A pharmaceutical composition comprising the anti-PSMA construct of claim 1, and a pharmaceutical acceptable carrier.

* * * * *